(12) United States Patent
Yoshikuni et al.

(10) Patent No.: US 8,198,056 B2
(45) Date of Patent: *Jun. 12, 2012

(54) BIOFUEL PRODUCTION

(75) Inventors: Yasuo Yoshikuni, Albany, CA (US); Yuki Kashiyama, Berkeley, CA (US)

(73) Assignee: Bio Architecture Lab, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/072,604

(22) Filed: Mar. 25, 2011

(65) Prior Publication Data

US 2011/0236939 A1 Sep. 29, 2011

Related U.S. Application Data

(63) Continuation of application No. 12/245,537, filed on Oct. 3, 2008.

(60) Provisional application No. 60/977,628, filed on Oct. 4, 2007.

(51) Int. Cl.
*C12P 7/42* (2006.01)

(52) U.S. Cl. .................. 435/146; 435/174; 435/252.33; 502/7

(58) Field of Classification Search .................. 435/146
See application file for complete search history.

(56) References Cited

U.S. PATENT DOCUMENTS

| | | | |
|---|---|---|---|
| 5,000,000 | A | 3/1991 | Ingram et al. |
| 5,028,539 | A | 7/1991 | Ingram et al. |
| 5,162,516 | A | 11/1992 | Ingram et al. |
| 5,298,421 | A | 3/1994 | Davies et al. |
| 5,304,481 | A | 4/1994 | Davies et al. |
| 5,344,771 | A | 9/1994 | Davies et al. |
| 5,424,202 | A | 6/1995 | Ingram et al. |
| 5,455,167 | A | 10/1995 | Voelker et al. |
| 5,482,846 | A | 1/1996 | Ingram et al. |
| 5,487,989 | A | 1/1996 | Fowler et al. |
| 5,554,520 | A | 9/1996 | Fowler et al. |
| 5,667,997 | A | 9/1997 | Voelker et al. |
| 5,821,093 | A | 10/1998 | Ingram et al. |
| 5,916,787 | A | 6/1999 | Ingram et al. |
| 6,102,690 | A | 8/2000 | Ingram et al. |
| 6,107,093 | A | 8/2000 | Ingram et al. |
| 6,197,312 | B1 | 3/2001 | Peak et al. |
| 6,280,986 | B1 | 8/2001 | Hespell et al. |
| 6,495,345 | B1 | 12/2002 | Peak et al. |
| 6,849,434 | B2 | 2/2005 | Ingram et al. |
| 7,129,060 | B1 | 10/2006 | Maurer et al. |
| 7,189,545 | B2 | 3/2007 | Breuer et al. |
| 7,192,772 | B1 | 3/2007 | Ingram et al. |
| 7,439,034 | B2 | 10/2008 | Weiner et al. |
| 7,851,188 | B2 | 12/2010 | Donaldson et al. |
| 2004/0259151 | A1 | 12/2004 | Jose et al. |
| 2009/0139134 | A1 | 6/2009 | Yoshikuni et al. |
| 2009/0155873 | A1 | 6/2009 | Kashiyama et al. |
| 2009/0203089 | A1 | 8/2009 | Kashiyama |

FOREIGN PATENT DOCUMENTS

| | | |
|---|---|---|
| WO | WO-2005/083100 | 9/2005 |
| WO | WO-2005/100582 | 10/2005 |
| WO | WO2005000582 | * 10/2005 |
| WO | WO-2007/018442 | 2/2007 |
| WO | WO-2007/136762 | 11/2007 |
| WO | WO-2009/046370 | 4/2009 |
| WO | WO-2009/046375 | 4/2009 |
| WO | 2009/097346 A2 | 8/2009 |
| WO | 2009/097346 A3 | 9/2009 |
| WO | 2009/046370 A3 | 10/2009 |
| WO | 2010/068921 A2 | 6/2010 |
| WO | WO-2010/068921 | 6/2010 |
| WO | 2011/044279 A2 | 4/2011 |

OTHER PUBLICATIONS

Abbott et al., "Specific Recognition of Saturated and 4,5-Unsaturated Hexuronate Sugars by a Periplasmic Binding Protein Involved in Pectin Catabolism," J Mol. Biol. 369:759-70 (2007).
Alterthum et al., "Efficient Ethanol Production from Glucose, Lactose, and Xylose by Recombinant *Escherichia coli*," Applied & Environ. Microbial. 55(8):1943-48 (Aug. 1989).
Anderson et al., "Purification and Characterization of D-Lyxose Isomerase," J Bio. Chem.240(6):2367-72 (Jun. 1965).
Ashiuchi et al., "Biochemistry and molecular genetics of poly-γ-glutamate synthesis," Appl. Microbiol. Biotechnol. 59(1):9-14 (2002).
Aso et al., "Engineered membrane superchannel improves bioremediation potential of dioxin-degrading bacteria," Nat. Biotechnol. 24(2):188-189 (2006).
Bardiya et al., "Biomethanation of Banana Peel and Pineapple Waste," Bioresource Technology 58(1):73-76 (1996).
Barrett et al., "Quantitative export of a reporter protein, GFP, by the twin-arginine translocation pathway in *Escherichia coli*," Biochemical and Biophysical Research Communications 304(2):279-284 (2003).
Binet et al., "Protein Secretion by Gram-Negative Bacterial ABC Exporters," Folia Microbiol. 42(3):179-183 (1997).
Bird et al., "On the Nature of the Cell Wall Constituents of *Larninaria* spp. Mannuronic Acid," Biochem. XXV:26-2-26-8 (1931). Blaudeck et al., "Specificity of Signal Peptide Recognition in Tat-Dependent Bacterial Protein Translocation," J Bacteriol. 183(2):604-610 (Jan. 2001).
Boynton et al., "Cloning, Sequencing, and Expression of Genes Encoding Phosphotransacetylase and Acetate Kinase from *Clostridium acetobutylicum* ATCC 824," Applied and Environmental Microbiology 62(8):2758-2766 (1996).

(Continued)

*Primary Examiner* — Christopher M Gross

(74) *Attorney, Agent, or Firm* — Morrison & Foerster LLP

(57) ABSTRACT

Methods, enzymes, recombinant microorganism, and microbial systems are provided for converting polysaccharides, such as those derived from biomass, into suitable monosaccharides or oligosaccharides, as well as for converting suitable monosaccharides or oligosaccharides into commodity chemicals, such as biofuels. Commodity chemicals produced by the methods described herein are also provided. Commodity chemical enriched, refinery-produced petroleum products are also provided, as well as methods for producing the same.

5 Claims, 90 Drawing Sheets

OTHER PUBLICATIONS

Causey et al., "Engineering the metabolism of *Escherichia coli* W3110 for the conversion of sugar to redox-neutral and oxidized products: Homoacetate production," PNAS 100(3):825-32 (Feb. 4, 2003).

Chang et al., "Acetate Metabolism in a pta Mutant of *Escherichia coli* W3110: Importance of Maintaining Acetyl Coenzyme a Flux for Growth and Survival," J Bacteriol.181(21):6656-63 (Nov. 1999).

Chang et al., "Engineering *Escherichia coli* for production of functionalized terpenoids using plant P450s," Nat. Chem. Biol. 3(5):274-277 (2007).

Cheesebrough et al., "Microsomal Preparation from an Animal Tissue Catalyzes Release of Carbon Monoxide from a Fatty Aldehyde to Generate an Alkane," J Biol. Chem. 263(6):2738-43 (Feb. 25, 1988).

Choi et al., "Secretory and extracellular production of recombinant proteins using *Escherichia coli*," App. Microbiol. Biotechnol. 64:625-35 (2004).

Cretcher et al., "A New Type of Acid Carbohydrate from Seaweed," Science 67(1743):537-538 (1928).

Dautin et al., "Protein Secretion in Gram-Negative Bacteria via the Autotransporter Pathway," Annu. Rev. Microbial. 61:89-112 (2007).

Dehesh et al., "KAS IV: a 3-ketoacyl-ACP synthase from *Chupea* sp. is a medium chain specific condensing enzyme," Plant J 15(3):383-90 (1998).

Dehesh et al., "Production of high levels of 8:0 and 10:0 fatty acids in transgenic canola by overexpression of Ch FatB2, a thioesterase cDNA from *Cuphea hookeriana*," The Plant J 9(2): 167-72 (1996).

Dehesh et al., "Two Novel Thioesterases Are Key Determinants of the Bimodal Distribution of Acyl Chain Length of *Cuphea palustris* Seed Oil," Plant Physiol. 110:203-10 (1996).

Delisa et al., "Folding quality control in the export of proteins by the bacterial twin-arginine translocation pathway," PNAS 100(10):6115-20 (May 13, 2003).

Dennis et al., "A cobalt-porphyrin enzyme converts a fatty aldehyde to a hydrocarbon and CO," Proc. Natl. Acad. Sci. USA 89:5306-10 (Jun. 1992).

Dittrich et al., "Redistribution of Metabolic Fluxes in the Central Aerobic Metabolic Pathway of *E. coli* Mutant Strains with Deletion of the ackA-pta and poxB Pathways for the Synthesis of Isoamyl Acetate," Biotechnol. Pro~. 21(2):627-631 (2005).

Farmer III et al., "Aldohexuronic Acid Catabolism by a Soil Aeromonas," J Bacteriol. 97(1):97-106 (Jan. 1969).

Fontaine et al., "Molecular Characterization and Transcriptional Analysis of adhE2, the Gene Encoding the NADH-Dependent Aldehyde/Alcohol Dehydrogenase Responsible for Butanol Production in Alcohologenic Cultures of *Clostridium acetobutylicum* ATCC 824," J Bacteriol. 184(3):821-30 (Feb. 2002).

Gentschev et al., "The *E. coli* α-hemolysin secretion system and its use in vaccine development," TRENDS in Microbiology 10(1):39-45 (2002).

González et al., "Benzaldehyde Lyase, a Novel Thiamine PP$_i$-Requiring Enzyme, from *Pseudomonas fluorescens* Biovar I," J Bacteriology 171(5):2401-05 (May 1989).

Görgen et al., "Biosynthesis of I-alkenes in higher plants: stereochemical implications," Eur. J Biochem 185:237-42 (1989).

Graham, "Cuphea: A New Plant Source of Medium-Chain Fatty Acids," Crit. Rev. Food Sci. Nutr. 28(2):139-173 (1989).

Hartmanis M., "Butyrate Kinase from *Clostridium acetobutylicum*," J Biol. Chem. 262(2):617-21 (Jan. 15, 1987).

Hashimoto et al., "Molecular Identification of Oligoalginate Lyase of *Sphingomonas* sp. Strain AI as One of the Enzymes Required for Complete Depolymerization of Alginate," J Bacteriol. 182(16):4572-77 (Aug. 2000).

Hashimoto et al., "Molecular Identification of *Sphingomonas* sp. AI Alginate Lyase (AI-IV') as a Member of Novel Polysaccharide Lyase Family 15 and Implications in Alginate Lyase Evolution," J Bioscience & Bioeng. 99(1):48-54 (2005).

Hashimoto et al., "Structure and Function of Bacterial Super-Biosystem Responsible for Import and Depolymerization of Macromolecules," Biosci. Biotechnol. Biochem. 69(4):673-92 (2005).

He et al., "Cloned *Erwinia chrysanthemi* out genes enable *Escherichia coli* to selectively secrete a diverse family of heterologous proteins into its milieu," Proc. Natl. Acad. Sci. USA 88: 1079-83 (Feb. 1991).

Hinrichsen et al., "Cloning and sequencing of the gene encoding benzaldehyde lyase from *Pseudomonas fluorescens* biovar I," Gene 144(1):137-138 (1994).

Hom et al., "Production of ethanol from mannitol by *Zymobacter palmae*," Journal of Industrial Microbiology & Biotechnology 24(1):51-57 (2000).

Hom, "Bioenergy from Brown Seaweeds," Department of Biotechnology, Norwegian University of Science and Technology, (Nov. 2000).

Hom, "Bioenergy from brown seaweeds," Doctoral Thesis, Dept. of Biotechnology, Norwegian University of Science and Technology NTNU, Trondheim, Norway, Nov. 2000, 93 pages.

Hom, "Production of Ethanol from Mannitol by *Zymobacter palmae*," Journal of Industrial Microbiology and Biotechnology 24:51-57 (2000).

Huang et al., "Identification and Characterization of a Second Butyrate Kinase form *Clostridium acetobutylicum* ATCC 824," J Mol. Microbiol. Biotechnol. 2(1):33-38 (2000).

Hugouvieux-Cotte-Pattat et al., "Identification of TogMNAB, an ABC transporter which mediates the uptake of pectic oligomers in *Erwinia chrysanthemi* 3937," Mol. Microbiol. 41(5):1113-23 (2001).

Hugouvieux-Cotte-Pattat et al., "Two transporters, TogT and TogMNAB, are responsible fo oligogalacturonide uptake in *Erwinia chrysanthemi* 3937," Mol. Microbiol. 41 (5): 1125-1132 (2001).

Hunt et al., "Analysis of the mouse and human acyl-CoA thioesterase (ACOT) gene clusters shows that convergent, functional evolution results in a reduced number of human peroxisomal ACOTs," FASB J 20: 1855-64 (Sep. 2006).

Iwaki et al., "Cloning and Characterization of a Gene Cluster Involved in Cyclopentanol Metabolism in *Comamonas* sp. Strain NCIMB 9872 and Biotransformations Effected by *Escherichia coli*-Expressed Cyclopentanone 1,2-Monooxygenase," Applied & Environ. Microbiol. 68(11):5671-84 (Nov. 2002).

Janzen et al., "Characterization of benzaldehyde lyase from *Pseudomonas fluorescens*: A versatile enzyme for asymmetric C-C bond formation," Bioorg. Chem. 34(6):345-361 (2006).

Jha et al., "Cloning and functional expression of an acyl-ACP thioesterase FatB type from *Diploknema (Madhuca) butyracea* seeds in *Escherichia coli*," Plant Physiol. Biochem. 44(11-12):645-655 (2006).

Jose et al., "Bacterial surface display library screening by target enzyme labeling: Identification of new human cathepsin G inhibitors," Anal. Biochem. 346(2):258-267 (2005).

Jose J., "Autodisplay: efficient bacterial surface display of recombinant proteins," App. Microbiol. Biotechnol. 69:607-14 (2006).

Keen et al., "Molecular Cloning of Pectate Lyase Genes from *Erwinia chrysanthemi* and Their Expression in *Escherichia coli*," J Bacteriol. 159(3):825-831 (1984).

Keshav et al., "Cloning of the *Zymomonas mobilis* Structure Gene Encoding Alcohol Dehydrogenase I (adhA): Sequence Comparison and Expression in *Escherichia coli*," J Bacteriol. 172(5):2491-2497 (1990).

Kneen et al., "Exploring the active site of benzaldehyde lyase by modeling and mutagenesis," Biochim. Biophys. Acta 1753(2):263-271 (2005).

Koronakis, "To1C—the bacterial exit duct for proteins and drugs," FEBS Lett. 555:66-71 (2003).

Lagarde et al., "*Escherichia coli* K-12 Structural kdgT Mutants Exhibiting Thermosensitive 2-Keto-3-Deoxy-D-Gluconate Uptake," J. Bacteriol. 129(2):606-15 (Feb. 1977).

Lawford et al., "Fermentation of Biomass-Derived Glucuronic Acid by pet Expressing Recombinants of *E. coli* B," Applied Biochem. & Biotech. 63-65:221-41 (1997).

Lennarz et al., "A Fatty Acid Synthetase From *E. coli*," Biochem. 48:840-46 (1962).

Leonard et al., "A Cuphea β-ketocyl-ACP synthase shifts the synthesis of fatty acids towards shortel chains in *Arabidopsis* seeds expressing Cuphea FatB thioesterases," Plant J. 13(5):621-28 (1998).

Li et al., "Effect of poxB gene knockout on metabolism in *Escherichia coli* based on growth characteristics and enzyme activities," World J Microbiol. Biotechnol. 23:573-580 (2007).

Lin et al., "Acetyl-CoA synthetase overexpression in *Escherichia coli* demonstrates more efficient acetate assimilation and lower acetate accumulation: a potential tool in metabolic engineering," Appl. Microbiol. Biotechnol. 71(6):870-874 (2006).

Ludwig et al., "A Long-Chain Secondary Alcohol Dehydrogenase from *Rhodococcus erythropolis* ATCC 4277," Applied & Environ. Microbiol. 61(10):3729-33 (Oct. 1995).

Mandrand-Berthelot et al., "Construction and Expression of Hybrid Plasmids Containing the Structural Gene of the *Escherichia coli* K-12 3-Deoxy-2-0xo-D-Gluconate Transport System," J Bacteriol. 160(2):600-606 (Nov. 1984).

Masip et al., "An Engineered Pathway for the Formation of Protein Disulfide Bonds," Science 303: 1185-89 (Feb. 24, 2004).

Mayer et al., "Identification of amino acid residues involved in substrate specificity of plant acyl-ACP thioesterases using a bioinformatics-guided approach," BMC Plant Biol. 7: 1 (Jan. 3, 2007).

McMahon et al., "The protein coded by the PP2216 gene of *Pseudomonas putida* KT2440 is an acyl-CoA dehydrogenase that oxidises only short-chain aliphatic substrates," FEMS Microbiol. Lett.250: 121-27 (2005).

Mergulhão et al., "Recombinant protein secretion in *Escherichia coli*," Biotech. Advances 23: 177-202 (2005).

Miyake et al., "An exotype alginate lyase in *Sphingomonas* sp. A1: overexpression in *Escherichia coli*, purification and characterization of alginate lyase IV (AI-IV)," Protein Expr. Purif 29(1):33-41 (2003).

Miyake et al., "Origin and Diversity of Alginate Lyases of Families PL-5 and -7 in *Sphingomonas* sp. Strain A I," J. Bacteriol. 186(9):2891-96 (May 2004).

Nair et al., "Molecular Characterization of an Aldehyde/Alcohol Dehydrogenase Gene from *Clostridium acetobutylicum* ATCC 824," J. Bacteriol. 176(3):871-85 (Feb. 1994).

Narita et al., "Display of active enzymes on the cell surface of *Escherichia coli* using PgsA anchor protein and their application to bioconversion," Appl. Microbiol. Biotechnol. 70:564-72 (2006).

Ney et al., "Biosynthesis of I-alkenes in higher plants," Eur. J. Biochem. 162:203-11 (1987).

O'Brien et al., "Insight into the Mechanism of the B12-Independent Glycerol Dehydratase from *Clostridium butyricum*: Preliminary Biochemical and Structural Characterization," Biochemistry 43(16):4635-4645 (2004).

Ochiai et al., "A biosystem for alginate metabolism in *Agrobacterium tumefaciens* strain C58: Molecular identification of Atu3025 as an exotype family PL-15 alginate lyase," Research in Microbiology157:642-49 (2006).

Osawa et al., "Crystal Structure of the Alginate (Poly α-L-guluronate) Lyase from *Corynebacterium* sp. at 1.2 A Resolution," J Mol. Biol. 345:1111-1118 (2005).

Park et al., "Isolation and characterization of a bacterium that produces hydrocarbons extracellularly which are equivalent to light oil," Appl. Microbiol. Biotechnol. 56:445-452 (2001).

Park et al., "Production of alternatives to fuel oil from organic waste by the alkaneproducing bacterium, *Vibrio funissii* MI," J Applied Microbiol. 98:324-31 (2005).

Park M., "New Pathway for Long-Chain n-Alkane Synthesis via I-Alcohol in *Vibrio furnissii* MI," J Bacteriol. 187(4):1426-29 (Feb. 2005).

Porra et al., "Haem Synthase and Cobalt Porphyrin Synthase in Various Micro-organisms," Biochem. J 94:557-62 (1965).

Pouyssegur et al., "Genetic Control of the 2-Keto-3-Deoxy-D-Gluconate Metabolism in *Escherichia coli* K-12: kdg Regulon," J Bacteriol. 117(2):641-51 (Feb. 1974).

Preiss et al., "Alginic Acid Metabolism in Bacteria," J Bio. Chem. 237(2):309-16 (Feb. 1962).

Preiss et al., "Alginic Acid Metabolism in Bacteria," J Bio. Chem. 237(2):317-21 (Feb. 1962).

Raynaud et al., "Molecular characterization of the 1,3-propanediol (1,3-PD) operon of *Clostridium butyricum*," PNAS 100(9):4010-15 (Apr. 29, 2003).

Schoeffel et al., "Isolation of α- and β-, d-Mannuronic Acid," J Biol. Chem. 100:397-405 (1933).

Schoeffel et al., "The Preparation of d-Mannuronic Acid Lactone," J Biol. Chem. 95:213-218 (1932).

Schörken et al., "Thiamin-dependent enzymes as catalysts in chemoenzymatic syntheses," Biochimica et Biophysica Acta 1385:229-243 (1998).

Schütt et al., "The role of acyl carrier protein isoforms from *Cuphea lanceolata* seeds in the de-novo biosynthesis of medium-chain fatty acids," Planta 205:263-268 (1998).

Signorell et al., "Projection maps of three members of the KdgM outer membrane protein family," J Struct. Biol. 160:395-403 (2007).

Thompson et al., "Purification and Properties of an Acetoacetyl Coenzyme A-Reacting Phosphotransbutyrylase from *Clostridium beijerinckii* ('*Clostridium butylicum*') NRRL B593," Applied & Environ. Microbiol. 56(3):607-13 (Mar. 1990).

Tobimatsu et al., "Cloning, Sequencing, and High Level Expression of the Genes Encoding Adenosylcobalamin-dependent Glycerol Dehydrase of *Klebsiella pneumoniae*," J Biol. Chem. 271(37):22352-57 (Sep. 13, 1996).

Tobimatsu et al., "Molecular Cloning, Sequencing and Characterization of the Genes for Adenosylcobalamin-dependent Diol Dehydratase of *Klebsiella pneumoniae*," Biosci. Biotechnol. Biochem. 62(9):1774-77 (1998).

Toraya et al., "Substrate Specificity of Coenzyme B12-Dependent Diol Dehydrase: Glycerol as Both a Good Substrate and a Potent Inactivator," Biochemical and Biophysical Research Communications 69(2):475-480 (1976).

Vedadi et al., "Involvement of Cysteine 289 in the Catalytic Activity of an NADP+ -Specific Fatty Aldehyde Dehydrogenase from *Vibrio harvevi*," Biochemistry 34:16725-16732 (1995).

Westin et al., Molecular Cloning and Characterization of Two Mouse Peroxisome Proliferator-activated Receptor a (PPARα)-regulated Peroxisomal Acyl-CoA Thioesterases, J Biol. Chem. 279(21):21841-48 (May 21, 2004).

Westin et al., "The Identification of a Succinyl-CoA Thioesterase Suggests a Novel Pathway for Succinate Production in Peroxisomes," J Biol. Chem. 280(46):38125-32 (Nov. 18, 2005).

Wiberg et al., "The distribution of caprylate, caprate and laurate in lipids from developing and mature seeds of transgenic *Brassica napus* L.," Planta 212:33-40 (2000).

Wiesenborn et al., "Phosphotransbutyrylase from *Clostridium acetobutylicum* ATCC 824 and its Role in Acidogenesis," Applied & Environ. Microbiol. 55(2):371-322 (Feb. 1989).

Wong et al., "Alginate Lyase: Review of Major Sources and Enzyme Characteristics, Structure-Function Analysis, Biological Roles, and Applications," Ann. Rev. Microbiol. 54:289-340 (2000).

Wood et al., "The Genome of the Natural Genetic Engineer *Agrobacterium tumefaciens* C58," Science 294(5550):2317-2323 (2001).

Xie et al., "NAD+-Dependent (S)-Specific Secondary Alcohol Dehydrogenase Involved in Stereoinversion of 3-Pentyn-2-ol Catalyzed by Nocardiafusca AKU 2123," Biosci. Biotechnol. Biochem. 63(10): 1721-29 (1999).

Yamada-Onodera et al., "Purification and Characterization of Alcohol Dehydrogenase Reducing N-Benzyl-3-Pyrrolidinone from *Geotrichum capitatum*," J Bioscience & Bioeng. 103(2):174-78(2007).

Yamada-Onodera et al., "Purification, Characterization, and Gene Cloning of Glycerol Dehydrogenase from *Hansenula ofunaensis*, and Its Expression for Production of Optically Active Diol," J Bioscience & Bioeng 102(6):545-51 (2006).

Yamanishi et al., "The crystal structure of coenzyme B12-dependent glycerol dehydratase in complex with cobalamin and propane-1,2-diol," Eur. J Biochem. 269:4484-94 (2002).

Yamasaki et al., "A Structural Basis for Depolymerization of Alginate by Polysaccharide Lyase Family-7," J Mol. Biol. 352:11-21 (2005).

Yamasaki et al., "Crystallization and preliminary X-ray analysis of alginate lyases AI-II and AI-II' from *Sphingomonas* sp. AI," Acta Cryst. F61:288-290 (2005).

Yan et al., "Coenzyme A-Acylating Aldehyde Dehydrogenase from *Clostridium beijerinckii* NRRL B592," Applied & Environ. Microbial. 56(9):2591-99 (Sep. 1990).

Yomano et al., "Re-engineering *Escherichia coli* for ethanol production," Biotechnol. Lett. 30:2097-2103 (2008).

Yoon et al., "Crystal Structure of Alginate Lyase A1-III Complexed with Trisaccharide Product at 2.0 A Resolution," J Mol. Biol. 307:9-16 (2001).

Yoon et al., "Crystal Structure of Alginate Lyase A1-111 from *Sphingomonas* Species A1 at 1.78 A Resolution," J Mol. Biol. 290:505-514 (1999).

Yoon et al., "Overexpression of *Escherichia coli*, Purification, and Characterization of *Sphingomonas* sp. AI Alginate Lyases," Protein Expression & Purification 19:84-90 (2000).

Yuan et al., "Modification of substrate specificity of an acyl-acyl carrier protein thioesterase by protein engineering," Proc. Nat/. Acad. Sci. USA 92: 10639-634 (Nov. 1995).

Zelinksi et al., "Purification and characterization of a novel carbonyl reductase isolated from *Rhodococcus erythropolis*," Journal of Biotechnology 33:283-292 (1994).

"*Vibrio splendidus* 12B01 1099451319056, whole genome shotgun sequence", XP002530900 retrieved from EBI accession No. EMBL:AAMR01 000010 Database accession No. AAMR01 00'001'0, 2006.

Office Action received for European Patent Application No. 09706304.4, mailed on Jan. 14, 2011, 3 pages.

International Search Report and Written Opinion received for PCT Patent Application No. PCT/US2009/032258, mailed on Jul. 29, 2009, 21 pages.

International Preliminary Report on Patentability received for PCT Patent Application No. PCT/US2009/032258, issued on Aug. 3, 2010, 13 pages.

International Search Report and Written Opinion received for PCT Patent Application No. PCT/US2008/078850, mailed on Aug. 18, 2009, 20 pages.

International Preliminary Report on Patentability received for PCT Patent Application No. PCT/US2008/078850, issued on Apr. 7, 2010, 16 pages.

International Search Report and Written Opinion received for PCT Patent Application No. PCT/US2008/078844, mailed on Sep. 11, 2009, 15 pages.

International Preliminary Report on Patentability received for PCT Patent Application No. PCT/US2008/078844, issued on Apr. 7, 2010, 11 pages.

Invitation to Pay Additional Fees received for PCT Patent Application No. PCT/US2010/051687, mailed on Jun. 24, 2011, 7 page.

International Search Report and Written Opinion received for PCT Patent Application No. PCT/US2010/051687, mailed on Aug. 31, 2011, 14 pages.

Office Action received for New Zealand Patent Application No. 587606, mailed on Mar. 1, 2011, 2 pages.

Non Final Office Action received for U.S. Appl. No. 12/361,293, mailed on Jan. 5, 2011, 16 pages.

Non Final Office Action received for U.S. Appl. No. 12/899,419, mailed on Jul. 14, 2011, 11 pages.

Non Final Office Action received for U.S. Appl. No. 12/245,537, mailed on Oct. 12, 2011, 22 pages.

Non Final Office Action received for U.S. Appl. No. 13/072,562, mailed on Oct. 12, 2011, 18 pages.

Non Final Office Action received for U.S. Appl. No. 13/072,521, mailed on Oct. 13, 2011, 18 pages.

Non Final Office Action received for U.S. Appl. No. 13/072,633, mailed on Oct. 21, 2011, 9 pages.

Kalscheuer, et al., "Microdiesel: *Escherichia coli* engineered for fuel production", Microbiology, vol. 152, See abstract and p. 152, 2006, pp. 2529-2536.

Yasuo et al., Unpublished U.S. Appl. No. 12/899,419, filed Oct. 6, 2010, titled as "Microbial Systems for Producing Commodity Chemicals", 239 pages.

Yasuo et al., Unpublished U.S. Appl. No. 13/072,454, filed Mar. 25, 2011, titled as "Biofuel Production", 266 pages.

Yasuo et al., Unpublished U.S. Appl. No. 13/072,521, filed Mar. 25, 2011, titled as "Biofuel Production", 266 pages.

Yasuo et al., Unpublished U.S. Appl. No. 13/072,562, filed Mar. 25, 2011, titled as "Biofuel Production", 266 pages.

Yasuo et al., Unpublished U.S. Appl. No. 13/072,633, filed Mar. 25, 2011, titled as "Biofuel Production", 266 pages.

Non Final Office Action received for U.S. Appl. No. 13/072,454, mailed on Oct. 12, 2011, 18 pages.

Mexican office action mailed Jul. 28, 2011, for Mexican application No. MX/a/2010/008023 filed Jul. 22, 2010, 8 pages.

Draget et al. (2005) "Alginates from Algae," in Polysaccharides and Polyamides in the Food Industry: Properties, Production, and Patents, Steinbuchel and Rhee (Eds.), 30 pages.

Takase et al. (2010) "Molecular identification of unsaturated uronate reductase prerequisite for alginate metabolism in *Sphingomonas* sp. A1," Biochimica et Biophysica Acta 1804:1925-1936.

Condemine and Robert-Baudouy (May 1987). "2-Keto-3-Deoxygluconate Transport System in *Erwinia chrysanthemi*," J Bacteriology 169(5):1972-1978.

* cited by examiner

E. coli Growing on Alginate

Pyruvate formation from alginate (enzymatic degradation route)

Pyruvate formation from alginate (chemical degradation route).

DEHU hydrogenase activity monitored by NADPH consumption

Mannuronate hydrogenase activity monitored by NADPH consumption

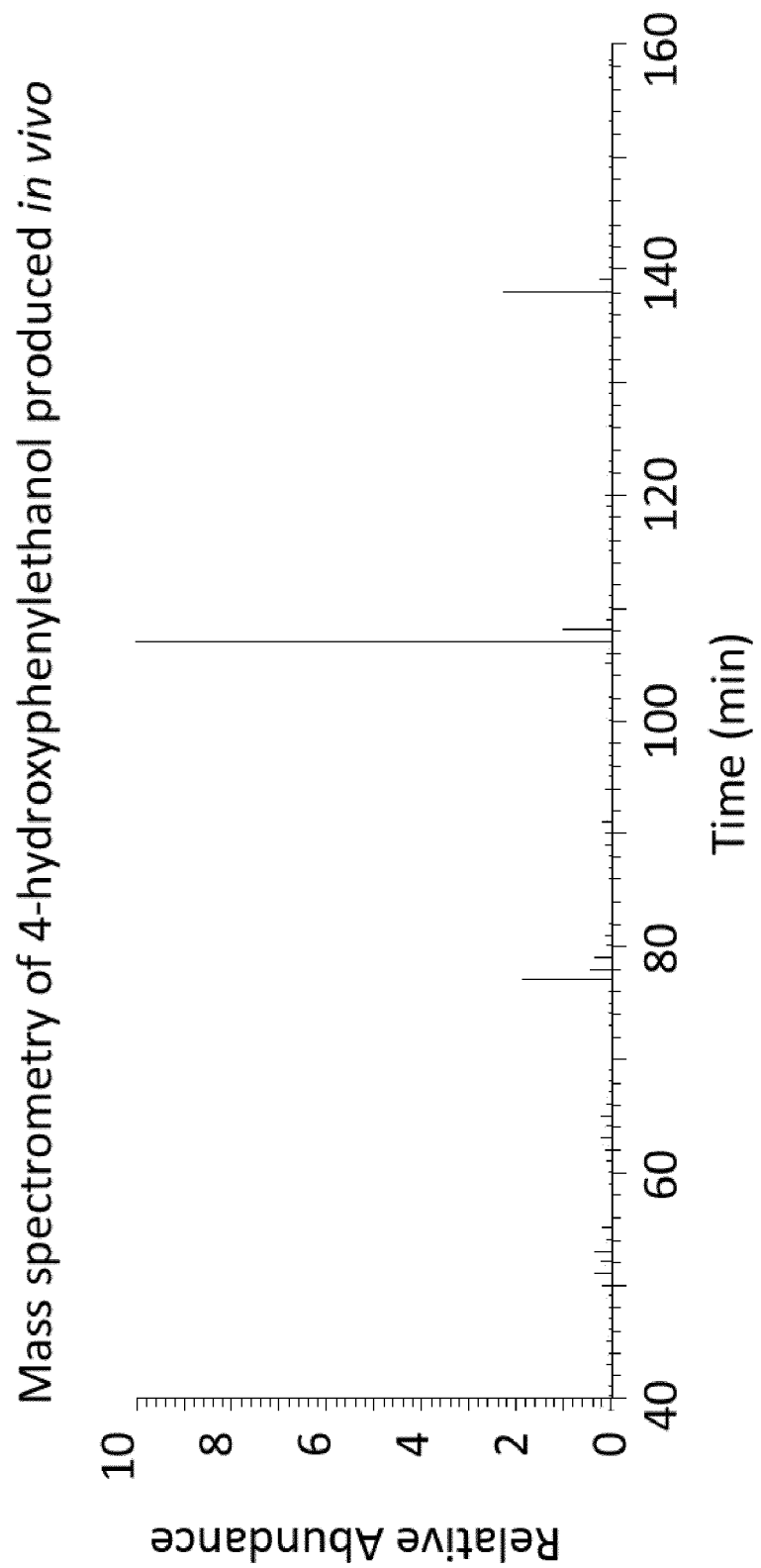

Reduction of butyroin by *ddh*1, *ddh*2, and *ddh*3 monitored by NADH consumption.

Oxidation activity of *ddh*3 towards 1,2-cyclopentanediol and 1,2-cyclohexanediol as measured by NADH production.

Figure 13
- Butyroin: $k_{cat}/K_M = 139\ \text{sec}^{-1}\text{M}^{-1}\ +/-\ 9$ 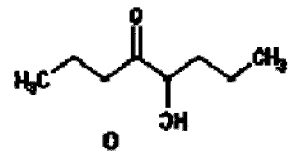
- Propioin: $k_{cat}/K_M - 709\ \text{sec}^{-1}\text{M}^{-1}\ +/-\ 40$ 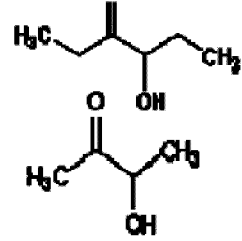
- Acetoin: $k_{cat}/K_M = 1990\ \text{sec}^{-1}\text{M}^{-1}\ +/-\ 210$ 
- meso-2,3-butanediol: $k_{cat}/K_M - 1450\ \text{sec}^{-1}\text{M}^{-1}\ +/-\ 150$ 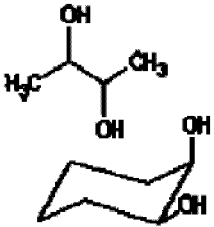
- cis-1,2-cyclohexanediol-: $k_{cat}/K_M = 108\ \text{sec}^{-1}\text{M}^{-1}\ +/-\ 15$ 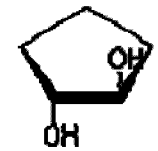
- trans-1,2-cyclopentandiol: $k_{cat}/K_M - 19.1\ \text{sec}^{-1}\text{M}^{-1}\ +/-\ 4.1$ 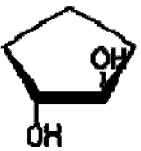

Figure 14A
Nucleotide sequence of diol dehydrogenase DDH1 isolated from *Lactobaccilus brevis* ATCC 367

ATGGCATCAAATGGAAAAGTAGCAATGGTTACCGGTGGCGGACAAGGAATTGGTGAAGC
CATCTCGAAACGGTTAGCTAACGACGGCTTTGCTGTGGCAATTGCTGATTTGAACTTGG
ACAATGCCAACAAGGTCGTTTCTGATATTGAAGCTGCTGGTGGCAAGGCCATTGCGGTC
AAGACCGATGTCTCTGATCGTGATAGCGTGTTTGCTGCGGTTAATGAAGCGGCCGACAA
GCTGGGCGGCTTTGACGTTATCGTTAATAACGCCGGCCTTGGCCCAACCACGCCAATTG
ACACCATCACCCAAGAACAGTTTGATACGGTTTATCACGTTAACGTGGGTGGGGTTCTT
TGGGGCATTCAAGCAGCCCATGCGAAGTTCAAGGAATTGGGTCATGGTGGGAAGATCAT
TTCCGCGACGTCTCAAGCCGGGGTTGTTGGTAACCCGAACTTAGCTCTGTACAGTGGAA
CTAAGTTTGCCATTCGTGGTGTGACCCAAGTTGCGGCGCGTGACTTAGCCGCTGAAGGT
ATCACGGTCAATGCTTATGCACCCGGGATTGTTAAGACACCAATGATGTTTGACATCGC
TCACAAGGTTGGTCAAAATGCTGGTAAAGACGACGAATGGGGGATGCAAACCTTCTCAA
AGGACATCGCTTTATGTCGATTGTCAGAACCAGAAGATGTGGCTAACGGGGTGGCTTTC
TTAGCCGGTCCCGATTCTAACTACATTACGGGTCAAACACTTGAAGTTGATGGTGGGAT
GCAGTTCCACTAA   (SEQ ID NO:97)

Figure 14B
Polypeptide primary sequence of diol dehydrogenase DDH1 isolated from *Lactobaccilus brevis* ATCC 367

MASNGKVAMVTGGGQGIGEAISKRLANDGFAVAIADLNLDNANKVVSDIEAAGGKAIAV
KTDVSDRDSVFAAVNEAADKLGGFDVIVNNAGLGPTTPIDTITQEQFDTVYHVNVGGVL
WGIQAAHAKFKELGHGGKIISATSQAGVVGNPNLALYSGTKFAIRGVTQVAARDLAAEG
ITVNAYAPGIVKTPMMFDIAHKVGQNAGKDDEWGMQTFSKDIALCRLSEPEDVANGVAF
LAGPDSNYITGQTLEVDGGMQFH   (SEQ ID NO:98)

Figure 15A
Nucleotide sequence of diol dehydrogenase DDH2 isolated from *Pseudomonas putida* KT2440

```
ATGAATGACCTGAGCCACACCCACATGCGCGCGGCCGTCTGGCATGGCCGCCACGATAT
TCGTGTCGAACAGGTACCTTTGCCGGCCGACCCTGCGCCGGGCTGGGTGCAGATCAAGG
TGGACTGGTGCGGCATCTGCGGCTCCGACCTGCACGAATATGTTGCCGGCCCGGTGTTC
ATCCCGGTAGAGGCCCCGCACCCGCTGACCGGCATTCAGGGCCAGTGCATCCTCGGCCA
CGAATTCTGCGGCCACATCGCCAAGCTTGGCGAAGGCGTGGAAGGCTATGCCGTAGGCG
ACCCGGTGGCGGCAGACGCGTGCCAGCATTGTGGTACCTGCTATTACTGCACCCATGGC
CTGTACAACATCTGCGAACGCCTGGCGTTCACCGGCCTGATGAACAACGGTGCCTTCGC
CGAGCTGGTCAACGTGCCCGCCAACCTGCTCTACCGGCTGCCGCAGGGCTTCCCTGCCG
AAGCCGGGGCACTGATCGAGCCGCTGGCGGTGGGTATGCACGCGGTGAAAAAGGCCGGC
AGCCTGCTTGGGCAAACCGTTGTAGTGGTTGGGGCCGGCACCATCGGCCTGTGCACCAT
CATGTGCGCCAAGGCTGCAGGTGCGGCACAGGTCATCGCCCTTGAGATGTCCTCTGCGC
GCAAAGCCAAGGCCAAGGAAGCGGGCGCCAACGTGGTGCTGGACCCCAGCCAGTGCGAT
GCCCTGGCGGAAATCCGCGCACTGACTGCTGGGCTGGGCGCCGATGTGAGTTTTGAGTG
CATCGGCAACAAACATACGGCCAAGCTGGCCATCGACACCATCCGCAAAGCAGGCAAGT
GCGTGCTGGTGGGTATTTTCGAAGAGCCCAGCGAGTTCAACTTCTTCGAGCTGGTGTCC
ACCGAGAAGCAAGTGCTGGGGGCGTTGGCGTACAACGGCGAGTTTGCTGACGTGATTGC
CTTCATTGCTGATGGTCGGCTGGATATTCGCCCGCTGGTAACCGGCCGGATCGGATTGG
AGCAGATTGTCGAGCTGGGCTTCGAGGAACTGGTGAACAACAAAGAGGAGAACGTGAAG
ATCATCGTTTCACCAGGTGTGCGCTGA    (SEQ ID NO:99)
```

Figure 15B
Polypeptide sequence of diol dehydrogenase DDH2 isolated from *Pseudomonas putida* KT2440

```
MNDLSHTHMRAAVWHGRHDIRVEQVPLPADPAPGWVQIKVDWCGICGSDLHEYVAGPVF
IPVEAPHPLTGIQGQCILGHEFCGHIAKLGEGVEGYAVGDPVAADACQHCGTCYYCTHG
LYNICERLAFTGLMNNGAFAELVNVPANLLYRLPQGFPAEAGALIEPLAVGMHAVKKAG
SLLGQTVVVGAGTIGLCTIMCAKAAGAAQVIALEMSSARKAKAKEAGANVVLDPSQCD
ALAEIRALTAGLGADVSFECIGNKHTAKLAIDTIRKAGKCVLVGIFEEPSEFNFFELVS
TEKQVLGALAYNGEFADVIAFIADGRLDIRPLVTGRIGLEQIVELGFEELVNNKEENVK
IIVSPGVR    (SEQ ID NO:100)
```

Figure 16A
Nucleotide sequence of diol dehydrogenase DDH3 isolated from *Klebsiella pneumoniae* MGH78578

ATGAAAAAAGTCGCACTTGTTACCGGCGCCGGCCAGGGGATTGGTAAAGCTATCGCCCT
TCGTCTGGTGAAGGATGGATTTGCCGTGGCCATTGCCGATTATAACGACGCCACCGCCA
AAGCGGTCGCCTCGGAAATCAACCAGGCCGGCGGACACGCCGTGGCGGTGAAAGTGGAT
GTCTCCGACCGCGATCAGGTATTTGCCGCCGTTGAACAGGCGCGCAAAACGCTGGGCGG
CTTCGACGTCATCGTCAATAACGCCGGTGTGGCACCGTCTACGCCGATCGAGTCCATTA
CCCCGGAGATTGTCGACAAAGTCTACAACATCAACGTCAAAGGGGTGATCTGGGGTATT
CAGGCGGCGGTCGAGGCCTTTAAGAAAGAGGGGCACGGCGGGAAAATCATCAACGCCTG
TTCCCAGGCCGGCCACGTCGGCAACCCGGAGCTGGCGGTGTATAGCTCCAGTAAATTCG
CGGTACGCGGCTTAACCCAGACCGCCGCTCGCGACCTCGCGCCGCTGGGCATCACGGTC
AACGGCTACTGCCCGGGGATTGTCAAAACGCCAATGTGGGCCGAAATTGACCGCCAGGT
GTCCGAAGCCGCCGGTAAACCGCTGGGCTACGGTACCGCCGAGTTCGCCAAACGCATCA
CTCTCGGTCGTCTGTCCGAGCCGGAAGATGTCGCCGCCTGCGTCTCCTATCTTGCCAGC
CCGGATTCTGATTACATGACCGGTCAGTCGTTGCTGATCGACGGCGGGATGGTATTTAA
CTAA    (SEQ ID NO:101)

Figure 16B
Polypeptide sequence of diol dehydrogenase DDH3 isolated from *Klebsiella pneumoniae* MGH78578

MKKVALVTGAGQGIGKAIALRLVKDGFAVAIADYNDATAKAVASEINQAGGHAVAVKVD
VSDRDQVFAAVEQARKTLGGFDVIVNNAGVAPSTPIESITPEIVDKVYNINVKGVIWGI
QAAVEAFKKEGHGGKIINACSQAGHVGNPELAVYSSSKFAVRGLTQTAARDLAPLGITV
NGYCPGIVKTPMWAEIDRQVSEAAGKPLGYGTAEFAKRITLGRLSEPEDVAACVSYLAS
PDSDYMTGQSLLIDGGMVFN    (SEQ ID NO:102)

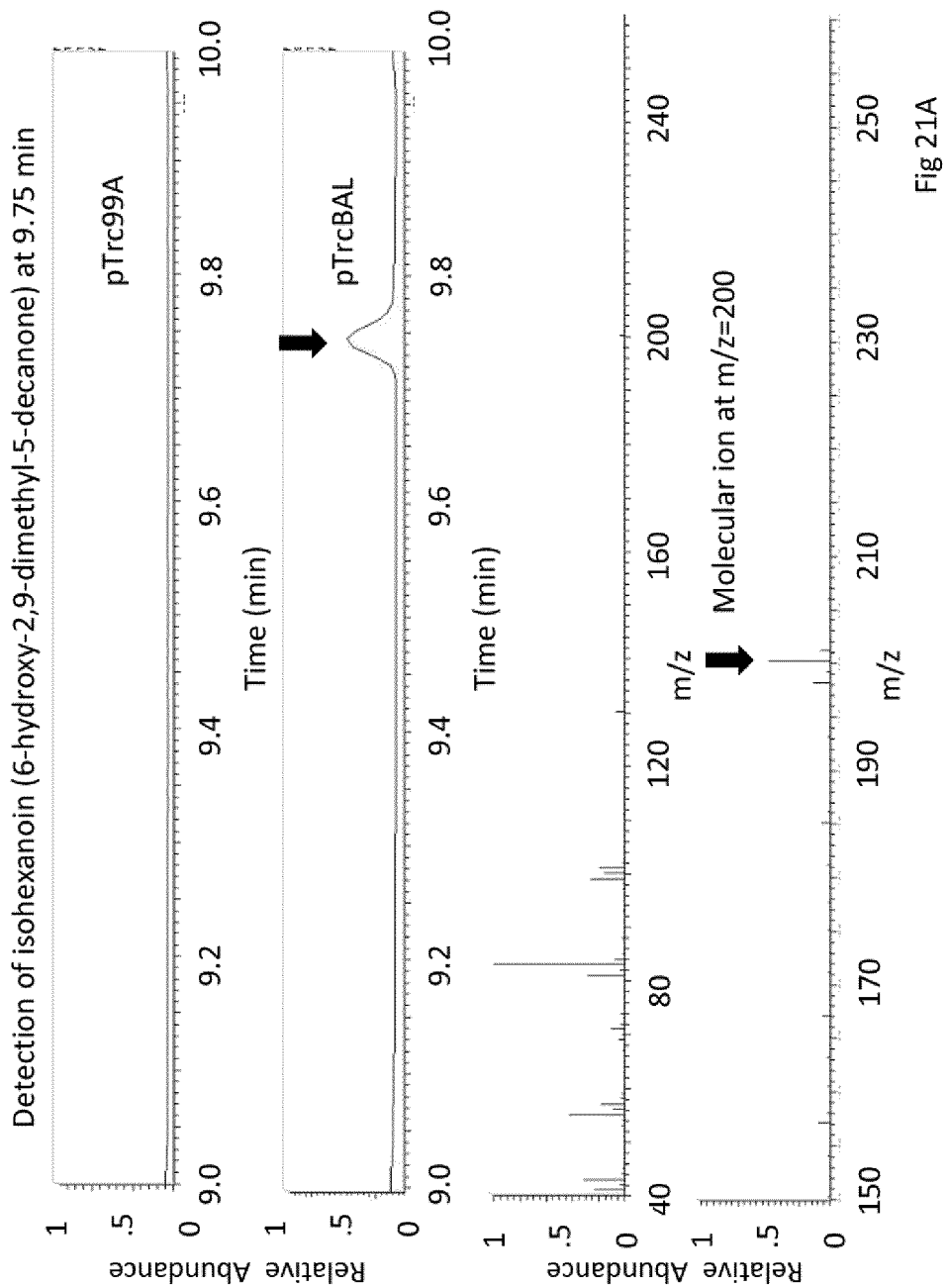

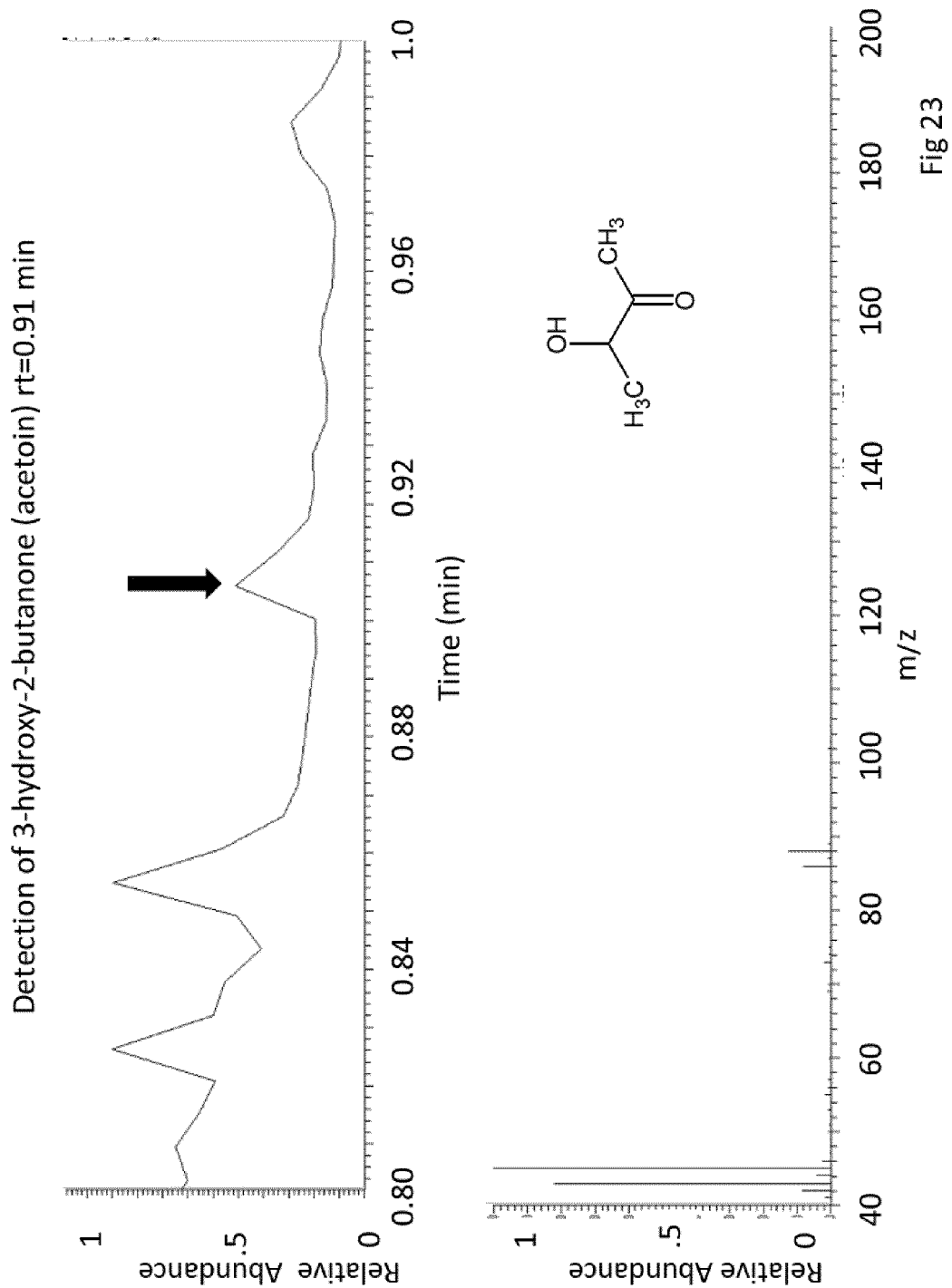

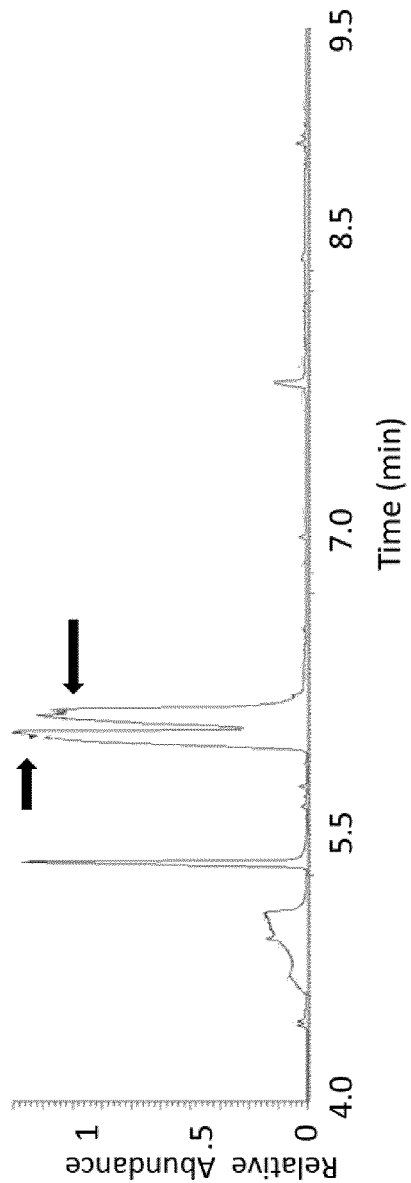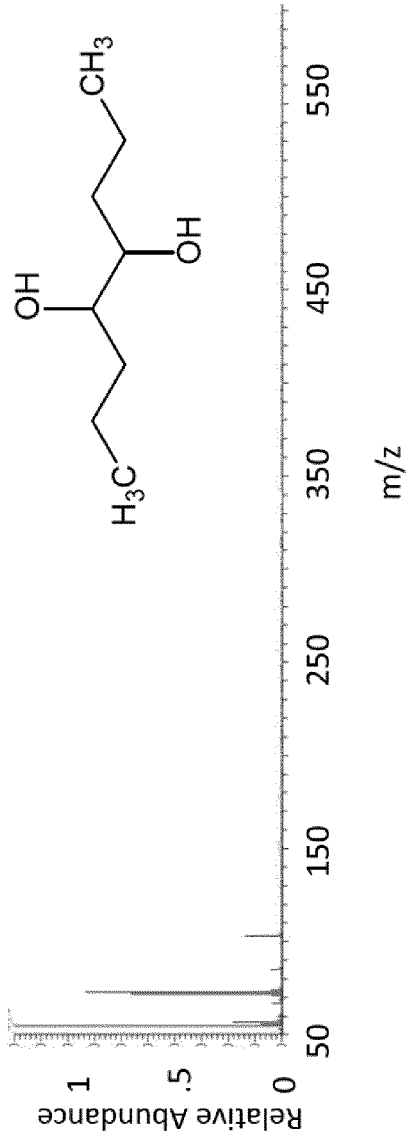
Fig 26A

Figure 28A
Nucleotide sequence of diol dehydratase large subunit (*pduC*) isolated from *Klebsiella pneumoniae* MGH78578

```
ATGAGATCGAAAAGATTTGAAGCACTGGCGAAACGCCCTGTGAATCAGGATGGTTTCGTTAAGGA
GTGGATTGAAGAGGGCTTTATCGCGATGGAAAGCCCTAACGATCCCAAACCTTCTATCCGCATCG
TCAACGGCGCGGTGACCGAACTCGACGATAAACCGGTTGAGCAGTTCGACCTGATTGACCACTTT
ATCGCGCGCTACGGCATTAATCTCGCCCGGGCCGAAGAAGTGATGGCCATGGATTCGGTTAAGCT
CGCCAACATGCTCTGCGACCCGAACGTTAAACGCAGCGACATCGTGCCGCTCACTACCGCGATGA
CCCCGGCGAAAATCGTGGAAGTGGTGTCGCATATGAACGTGGTCGAGATGATGATGGCGATGCAA
AAAATGCGCGCCCGCCGCACGCCGTCCCAGCAGGCGCATGTCACTAATATCAAAGATAATCCGGT
ACAGATTGCCGCCGACGCCGCTGAAGGCGCATGGCGCGGCTTTGACGAGCAGGAGACCACCGTCG
CCGTGGCGCGCTACGCGCCGTTCAACGCCATCGCCCTGCTGGTCGGTTCACAGGTTGGCCGCCCC
GGCGTCCTCACCCAGTGTTCGCTGGAAGAAGCCACCGAGCTGAAACTGGGCATGCTGGGCCACAC
CTGCTATGCCGAAACCATTTCGGTATACGGTACGGAACCGGTGTTTACCGATGGCGATGACACCC
CGTGGTCGAAAGGCTTCCTCGCCTCCTCCTACGCCTCGCGCGGCCTGAAAATGCGCTTTACCTCC
GGTTCCGGCTCGGAGGTGCAGATGGGCTATGCCGAAGGCAAATCGATGCTTTATCTCGAAGCGCG
CTGCATCTACATCACCAAAGCCGCCGGGGTGCAAGGCCTGCAGAATGGCTCCGTCAGCTGTATCG
GCGTGCCGTCCGCCGTGCCGTCCGGGATCCGCGCCGTACTGGCGGAAAACCTGATCTGCTCAGCG
CTGGATCTGGAGTGCGCCTCCAGCAACGATCAAACCTTTACCCACTCGGATATGCGGCGTACCGC
GCGTCTGCTGATGCAGTTCCTGCCAGGTACCGACTTTATCTCCTCCGGTTACTCGGCGGTGCCGA
ACTACGACAACATGTTCGCCGGTTCCAACGAAGATGCCGAAGACTTCGATGACTACAACGTGATC
CAGCGCGACCTGAAGGTCGATGGCGGCCTGCGGCCGGTGCGTGAAGAGGACGTGATCGCCATTCG
CAACAAAGCCGCCCGCGCGCTGCAGGCGGTATTTGCCGGCATGGGTTTGCCGCCTATTACGGATG
AAGAAGTAGAAGCCGCCACCTACGCCCACGGTTCAAAAGATATGCCTGAGCGCAATATCGTCGAG
GACATCAAGTTTGCTCAGGAGATCATCAACAAGAACCGCAACGGCCTGGAGGTGGTGAAAGCCCT
GGCGAAAGGCGGCTTCCCCGATGTCGCCCAGGACATGCTCAATATTCAGAAAGCCAAGCTCACCG
GCGACTACCTGCATACCTCCGCCATCATTGTTGGCGAGGGCCAGGTGCTCTCGGCCGTGAATGAC
GTGAACGATTATGCCGGTCCGGCAACAGGCTACCGCCTGCAAGGCGAGCGCTGGGAAGAGATTAA
AAATATCCCGGGCGCGCTCGATCCCAATGAACTTGGCTAA    (SEQ ID NO:103)
```

Figure 28B
Polypeptide sequence of diol dehydratase large subunit was isolated from *Klebsiella pneumoniae* MGH78578 (*pduC*)

```
MRSKRFEALAKRPVNQDGFVKEWIEEGFIAMESPNDPKPSIRIVNGAVTELDDKPVEQFDLIDHF
IARYGINLARAEEVMAMDSVKLANMLCDPNVKRSDIVPLTTAMTPAKIVEVVSHMNVVEMMMAMQ
KMRARRTPSQQAHVTNIKDNPVQIAADAAEGAWRGFDEQETTVAVARYAPFNAIALLVGSQVGRP
GVLTQCSLEEATELKLGMLGHTCYAETISVYGTEPVFTDGDDTPWSKGFLASSYASRGLKMRFTS
GSGSEVQMGYAEGKSMLYLEARCIYITKAAGVQGLQNGSVSCIGVPSAVPSGIRAVLAENLICSA
LDLECASSNDQTFTHSDMRRTARLLMQFLPGTDFISSGYSAVPNYDNMFAGSNEDAEDFDDYNVI
QRDLKVDGGLRPVREEDVIAIRNKAARALQAVFAGMGLPPITDEEVEAATYAHGSKDMPERNIVE
DIKFAQEIINKNRNGLEVVKALAKGGFPDVAQDMLNIQKAKLTGDYLHTSAIIVGEGQVLSAVND
VNDYAGPATGYRLQGERWEEIKNIPGALDPNELG    (SEQ ID NO:104)
```

Figure 29A
Nucleotide sequence of diol dehydratase medium subunit isolated from *Klebsiella pneumoniae* MGH78578 (*pduD*)

ATGGAAATTAACGAAACGCTGCTGCGCCAGATTATCGAAGAGGTGCTGTCGGAGATGAAATCAGG
CGCAGATAAGCCGGTCTCCTTTAGCGCGCCTGCGGCTTCTGTCGCCTCTGCCGCGCCGGTCGCCG
TTGCGCCTGTGTCCGGCGACAGCTTCCTGACGGAAATCGGCGAAGCCAAACCCGGCACGCAGCAG
GATGAAGTCATTATTGCCGTCGGCCAGCGTTTGGTCTGGCGCAAACCGCCAATATCGTCGGCAT
TCCGCATAAAAATATTCTGCGCGAAGTGATCGCCGGCATTGAGGAAGAAGGCATCAAAGCCCGGG
TGATCCGCTGCTTTAAGTCTTCTGACGTCGCCTTCGTGGCAGTGGAAGGCAACCGCCTGAGCGGC
TCCGGCATCTCGATCGGTATTCAGTCGAAAGGCACCACCGTCATCCACCAGCGCGGCCTGCCGCC
GCTTTCCAATCTGGAACTCTTCCCGCAGGCGCCGCTGCTGACGCTGGAAACCTACCGTCAGATTG
GCAAAAACGCCGCGCGCTACGCCAAACGCGAGTCGCCGCAGCCGGTGCCGACGCTTAACGATCAG
ATGGCTCGTCCCAAATACCAGGCGAAGTCGGCCATTTTGCACATTAAAGAGACCAAATACGTGGT
GACGGGCAAAAACCCGCAGGAACTGCGCGTGGCGCTTTAA    (SEQ ID NO:105)

Figure 29B
Polypeptide sequence of diol dehydratase medium subunit isolated from *Klebsiella pneumoniae* MGH78578 (*pduD*)

MEINETLLRQIIEEVLSEMKSGADKPVSFSAPAASVASAAPVAVAPVSGDSFLTEIGEAKPGTQQ
DEVIIAVGPAFGLAQTANIVGIPHKNILREVIAGIEEEGIKARVIRCFKSSDVAFVAVEGNRLSG
SGISIGIQSKGTTVIHQRGLPPLSNLELFPQAPLLTLETYRQIGKNAARYAKRESPQPVPTLNDQ
MARPKYQAKSAILHIKETKYVVTGKNPQELRVAL    (SEQ ID NO:106)

Figure 29C
Nucleotide sequence of diol dehydratase small subunit isolated from *Klebsiella pneumoniae* MGH78578 (*pduE*)

ATGAATACCGACGCAATTGAATCCATGGTACGCGACGTGCTGAGCCGGATGAACAGCCTACAGGA
CGGGATAACGCCCGCGCCAGCCGCGCCGACAAACGACACCGTTCGCCAGCCAAAAGTTAGCGACT
ACCCGTTAGCGACCCGCCATCCGGAGTGGGTCAAAACCGCTACCAATAAAACGCTCGATGACCTG
ACGCTGGAGAACGTATTAAGCGATCGCGTTACGGCGCAGGACATGCGCATCACTCCGGAAACGCT
GCGTATGCAGGCGGCGATCGCCCAGGATGCCGGACGCGATCGGCTGGCGATGAACTTTGAGCGGG
CCGCAGAGCTCACCGCGGTTCCCGACGACCGAATCCTTGAGATCTACAACGCCCTGCGCCCATAC
CGTTCCACCCAGGCGGAGCTACTGGCGATCGCTGATGACCTCGAGCATCGCTACCAGGCACGACT
CTGTGCCGCCTTTGTTCGGGAAGCGGCCGGGCTGTACATCGAGCGTAAGAAGCTGAAAGGCGACG
ATTAA    (SEQ ID NO:107)

Figure 29D
Polypeptide sequence of diol dehydratase small subunit isolated from *Klebsiella pneumoniae* MGH78578 (*pduE*)

MNTDAIESMVRDVLSRMNSLQDGITPAPAAPTNDTVRQPKVSDYPLATRHPEWVKTATNKTLDDL
TLENVLSDRVTAQDMRITPETLRMQAAIAQDAGRDRLAMNFERAAELTAVPDDRILEIYNALRPY
RSTQAELLAIADDLEHRYQARLCAAFVREAAGLYIERKKLKGDD    (SEQ ID NO:108)

Oxidation of 4-octanol monitored by NADH production (2ADH 1-10)

Oxidation of 4-octanol monitored by NADPH production (2ADH 1-10)

Oxidation of 4-octanol monitored by NADH production (2ADH11-18)

Oxidation of 4-octanol monitored by NADPH production (2ADH 11-18)

Oxidation of 2,7-dimethyl octanol monitored by NADH production (2ADH 11-18)

Oxidation of 2,7-dimethyl octanol monitored by NADPH production (2ADH 11-18)

Reduction of of 2,7-dimethyl octanol monitored by NADPH consumption

Activity of 2ADH11 and 2ADH16 Towards Various Substrates

Oxidation of cyclopentanol catalyzed by 2ADH as monitored by NADH or NADPH formation Reduction of cyclopentanonone catalyzed by 2ADH as monitored by NADPH consumption Figure 35
Calculated Rate Constants for Reduction Reactions of 2ADH16
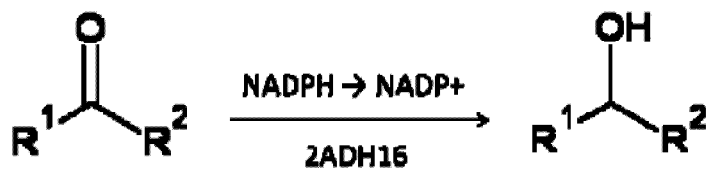
- Reduction Reaction
- 2-methylcyclohexanone: $k_{cat}/K_M$ = 211 sec$^{-1}$M$^{-1}$ +/- 18 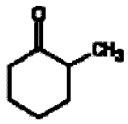
- 4-methylcyclohexanone: $k_{cat}/K_M$ – 17.5 sec$^{-1}$M$^{-1}$ +/- 2.0 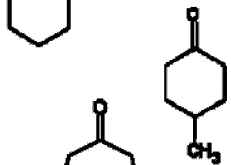
- cycloheptanone: $k_{cat}/K_M$ = 4.08 – sec$^{-1}$M$^{-1}$ +/- 0.62 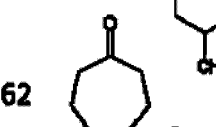
- 4-octanone: $k_{cat}/K_M$ = 44.7 – sec$^{-1}$M$^{-1}$ +/- 3.7 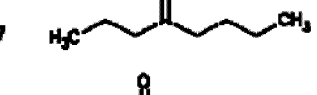
- 4-decanone: $k_{cat}/K_M$ approx 150 sec$^{-1}$M$^{-1}$ 

Figure 36
Calculated Rate Constants for Oxidation Reactions of 2ADH16

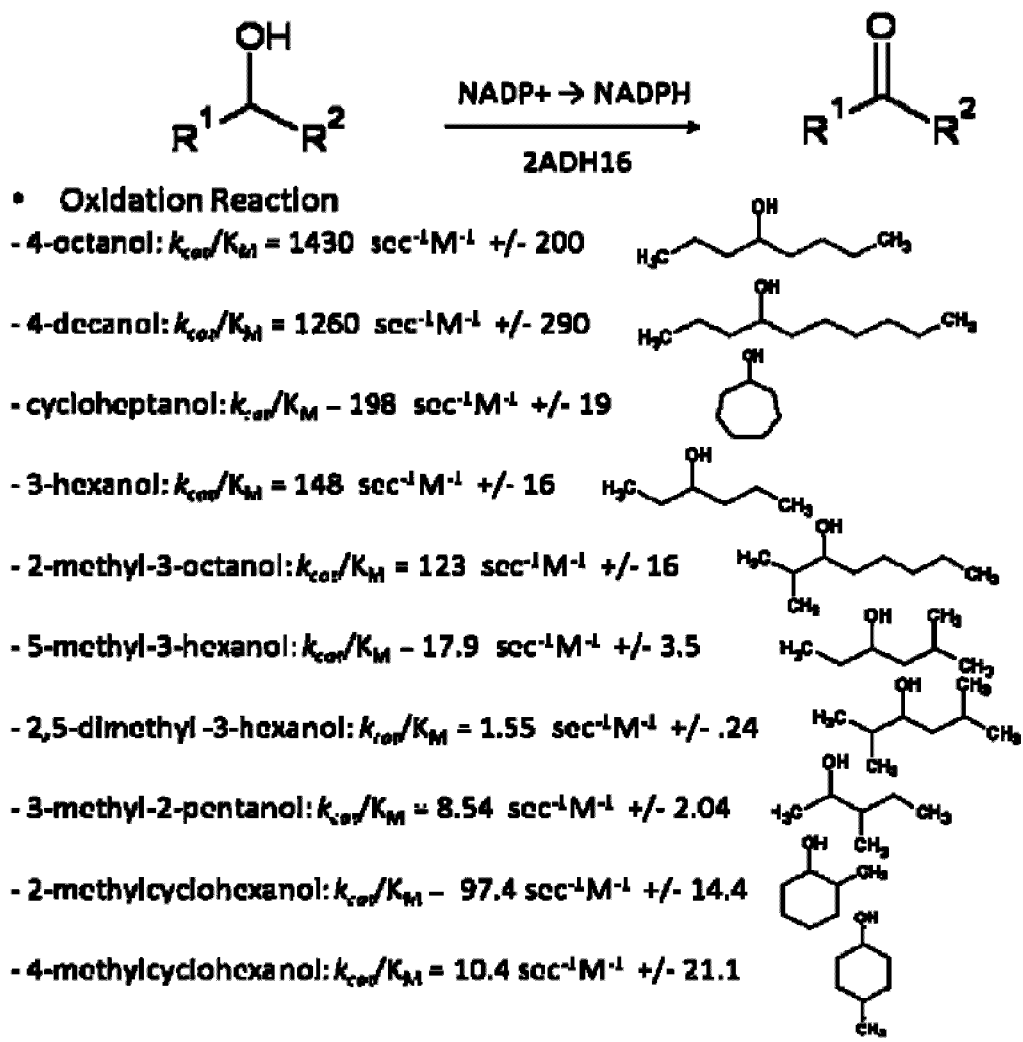

- Oxidation Reaction
- 4-octanol: $k_{cat}/K_M$ = 1430 sec$^{-1}$M$^{-1}$ +/- 200
- 4-decanol: $k_{cat}/K_M$ = 1260 sec$^{-1}$M$^{-1}$ +/- 290
- cycloheptanol: $k_{cat}/K_M$ – 198 sec$^{-1}$M$^{-1}$ +/- 19
- 3-hexanol: $k_{cat}/K_M$ = 148 sec$^{-1}$M$^{-1}$ +/- 16
- 2-methyl-3-octanol: $k_{cat}/K_M$ = 123 sec$^{-1}$M$^{-1}$ +/- 16
- 5-methyl-3-hexanol: $k_{cat}/K_M$ – 17.9 sec$^{-1}$M$^{-1}$ +/- 3.5
- 2,5-dimethyl-3-hexanol: $k_{cat}/K_M$ = 1.55 sec$^{-1}$M$^{-1}$ +/- .24
- 3-methyl-2-pentanol: $k_{cat}/K_M$ = 8.54 sec$^{-1}$M$^{-1}$ +/- 2.04
- 2-methylcyclohexanol: $k_{cat}/K_M$ – 97.4 sec$^{-1}$M$^{-1}$ +/- 14.4
- 4-methylcyclohexanol: $k_{cat}/K_M$ = 10.4 sec$^{-1}$M$^{-1}$ +/- 21.1

Figure 37A
Alginate Lyases

| Protein | Organism | GenBank/ GenPept | |
|---|---|---|---|
| Family 5 | | | |
| alginate lyase (AlgL) | Azotobacter chroococcum ATCC 4412 | AJ223605 | CAA11481.1 |
| | | AF027499 | AAC04567.1 |
| alginate lyase (AlgL) | Azotobacter vinelandii | AF037600 | AAC32313.1 |
| alginate lyase (Alg) | Cobetia marina N-1 | AB018795 | BAA33966.1 |
| alginate lyase (AlgL) | Pseudomonas aeruginosa 8830 | L14597 | AAA71990.1 |
| alginate lyase (AlgL) | Pseudomonas aeruginosa FRD1 | U27829 | AAA91127.1 |
| | Pseudomonas aeruginosa | AE004775 | AAG06935.1 |
| alginate lyase (AlgL;PA3547) | PAO1 | NC_002516 | NP_252237.1 |
| alginate lyase (AlgL) | Pseudomonas sp. QD03 | AY380832 | AAR23929.1 |
| alginate lyase (AlgL) | Pseudomonas sp. QDA | AY163384 | AAN63147.1 |
| alginate lyase (AlgL) | Pseudomonas syringae pv. syringae FF5 | AF222020 | AAF32371.1 |
| alginate lyase (aly;A1-I/PolyG+PolyM;A1-II/PolyG;A1-III/PolyM) | | - | 2009330A |
| | Sphingomonas sp. A1 | AB011415 | BAB03312.1 |
| | | | |
| Family 6 | | | |
| alginate lyase (AlyP) | Pseudomonas sp. OS-ALG-9 | D10336 | BAA01182.1 |
| | | | |
| Family 7 | | | |
| guluronate lyase (alyPG) | Corynebacterium sp. ALY-1 | AB030481 | BAA83339.1 |
| poly(-L-guluronate) lyase (AlyA) | Klebsiella pneumoniae subsp. aerogenes | L19657 | AAA25049.1 |
| alginate lyase / poly-mannuronate lyase (AlxM) | Photobacterium sp. ATCC 43367 | X70036 | CAA49630.1 |
| | | AE004547 | AAG04556.1 |
| alginate lyase (PA1167) | Pseudomonas aeruginosa PAO1 | NC_002516 | NP_249858.1 |
| alginate lyase (A1-II') | Sphingomonas sp. A1 | AB120939 | BAD16656.1 |
| alginate lyase (aly;A1-I/PolyG+PolyM;A1-II/PolyG;A1-III/PolyM) | | - | 2009330A |
| | Sphingomonas sp. A1 | AB011415 | BAB03312.1 |

Figure 37B
Alginate Lyases

| Protein | Organism | GenBank | GenPept |
|---|---|---|---|
| Family 7 | | | |
| poly(a-L-guluronate) lyase (AlyVGI;AlyVG1) | Vibrio halioticoli IAM14596T | AF114039 | AAF22512.1 |
| alginate lyase / poly-mannuronate lyase (AlyVOA) | Vibrio sp. O2 | DQ235160 | ABB36771.1 |
| alginate lyase / poly-mannuronate lyase (AlyVOB) | Vibrio sp. O2 | DQ235161 | ABB36772.1 |
| alginate lyase (AlyVI) | Vibrio sp. QY101 | AY221030 | AAP45155.1 |
| exo-oligoalginate lyase (HdAlex;HdAlex-1) | Haliotis discus hannai | AB234872 | BAE81787.1 |
| alginate lyase (HdAly) | Haliotis discus hannai | AB110094 | BAC87758.1 |
| polysaccharide lyase acting on glucuronic acid (vAL-1) | Chlorella virus CVK2 | AB044791 | BAB19127.1 |
| alginate lyase (AlyII) | Pseudomonas sp. OS-ALG-9 | AB003330 | BAA19848.1 |
| Family18 | | | |
| alginate lyase | Pseudoalteromonas sp. 272 | | |
| alginate lyase (Aly) | Pseudoalteromonas sp. IAM14594 | AF082561 | AAD16034.1 |
| Family15 | | | |
| exotype alginate lyase (Atu3025) | Agrobacterium tumefaciens str. C58 | AE009232 | AAL43841.1 |
| | | NC_003305 | NP_533525.1 |
| exotype alginate lyase (AGR_L_3558p) | Agrobacterium tumefaciens str. C58 (Cereon) | AE008381 | AAK90358.1 |
| | | NC_003063 | NP_357573.1 |
| oligo alginate lyase (A1-IV) | Sphingomonas sp. A1 | AB011415 | BAB03319.1 |
| alginate lyase (A1-IV') | Sphingomonas sp. A1 | AB176667 | BAD90006.1 |

Figure 38A
Pectate Lyases

| Protein | Organism | GenBank/GenPept | |
|---|---|---|---|
| Family1 | | | |
| | | - | AAE59745.1 |
| pectate lyase | Bacillus agaradhaerens | - | AAS29292.1 |
| | | - | AAE59748.1 |
| pectate lyase | Bacillus halodurans | - | AAS29295.1 |
| | | AP001520 | BAB07538.1 |
| pectate lyase (BH3819) | Bacillus halodurans C-125 | NC_002570 | NP_244686.1 |
| | | AP001509 | BAB04417.1 |
| pectate lyase (BH0698) | Bacillus halodurans C-125 | NC_002570 | NP_241564.1 |
| | | - | AAE59746.1 |
| | | - | AAN26179.1 |
| | | AJ517194 | CAD56882.1 |
| pectate lyase (PelA) | Bacillus licheniformis 14A | - | AAS29293.1 |
| | | CP000002 | AAU25568.1 |
| BLi04129 or BL00947 (PelII) | Bacillus licheniformis DSM 13 ATCC 14580 | AE017333 | AAU42942.1 |
| pectate lyase (Pel) | Bacillus licheniformis RN1 | AB428424 | BAG12908.1 |
| pectate lyase (PelB) | Bacillus pumilus DKS1 | EU652988 | ACD11362.1 |
| pectate lyase (fragment) | Bacillus sp. KSM-P7 | AB015043 | BAA76884.1 |
| | | - | AAE59747.1 |
| pectate lyase | Bacillus sp. AAI12 | - | AAS29294.1 |
| | | - | AAE59749.1 |
| | | - | AAR65348.1 |
| pectate lyase | Bacillus sp. I534 | - | AAS29296.1 |
| pectate lyase (Pel-103) | Bacillus sp. KSM-P103 | AB015044 | BAA76885.1 |
| pectate lyase (Pel-34K) | Bacillus sp. P-2850 | AB080666 | BAC11008.1 |
| pectate lyase (Pel-4A) | Bacillus sp. P-4-N | AB041769 | BAA96477.1 |
| pectate lyase (Pel-4B) | Bacillus sp. P-4-N | AB042100 | BAA96478.1 |
| pectate lyase (Pl47) | Bacillus sp. TS-47 | AB045986 | BAB40336.1 |
| pectate lyase (PelK) | Bacillus sp. YA-14 | D26349 | BAA05383.1 |
| | | AX601431 | CAD67509.1 |
| | | AX601436 | CAD67510.1 |
| | | AX601448 | CAD67511.1 |
| pectate lyase | Bacillus subtilis | AX951870 | CAF05441.1 |
| pectate lyase (Pel) | Bacillus subtilis AC327 | D86417 | BAA22313.1 |

Figure 38B
Pectate Lyases

| Protein | Organism | GenBank | GenPept |
|---|---|---|---|
| pectin lyase (Ppr) | Bacillus subtilis IFO 3134 | D83791 | BAA12119.1 |
| pectate lyase (Pel) | Bacillus subtilis SO113 | X74880 | CAA52866.1 |
| | | - | AAR45489.1 |
| | | D86417 | BAA22313.1 |
| | | X74880 | CAA52866.1 |
| pectate lyase (Pel;BSU07560) | Bacillus subtilis subsp. subtilis str. 168 | Z99108 | CAB12585.1 |
| | | NC_000964 | NP_388637.1 |
| pectate lyase (Pel-1;Pel1) | Erwinia carotovora 71 | L32171 | AAA73933.1 |
| Pel9.5 (fragment) | Erwinia carotovora EC14 | X61088 | CAA43402.1 |
| pectin lyase (Pnl) (probable fragment) | Erwinia carotovora ER | M65057 | AAA24857.1 |
| | | M18859 | AAA24845.1 |
| | Erwinia carotovora ER / IAM1068 / atroseptica EC / atroseptica C18 | S51490 | AAC60423.1 |
| | | D00217 | BAA00155.1 |
| pectate lyase 1 (Pel1;PelI) | | X81847 | CAA57439.1 |
| | Erwinia carotovora ER / IAM1068 / atroseptica EC / atroseptica C18 | M17364 | AAA24848.1 |
| | | S51475 | AAC60422.1 |
| pectate lyase 2 (Pel2;PelII) | | X81847 | CAA57440.1 |
| ECA4067 (PelA) | Erwinia carotovora subsp. atroseptica SCRI1043 | BX950851 | CAG76964.1 |
| pectate lyase (PelZ) | Erwinia chrysanthemi 3937 | X97119 | CAA65785.1 |
| pectate lyase A (PelA) | Erwinia chrysanthemi 3937 | M77808 | AAA24846.1 |
| | | | CAA47821.1 |
| pectate lyase B (PelB) | Erwinia chrysanthemi 3937 | X67475 | S25262 |
| pectate lyase (PelD) | Erwinia chrysanthemi 3937 | AJ132101 | CAA10570.1 |
| pectate lyase E (PelE) | Erwinia chrysanthemi 3937 / B374 | M33584 | AAA24854.1 |
| | | X17284 | CAA35175.1 |
| pectate lyase D (PelD) | Erwinia chrysanthemi B374 | X17284 | CAA35176.1 |
| pectate lyase (PelA) | Erwinia chrysanthemi EC16 | M14509 | AAA24843.1 |
| | | M19411 | AAA24849.1 |
| | | - | AAR45490.1 |
| pectate lyase (PelC) | Erwinia chrysanthemi EC16 | - | AAW11900.1 |
| pectate lyase (PelB;PIB) | Erwinia chrysanthemi EC16 | M14510 | AAA24847.1 |
| pectate lyase (PelE) | Erwinia chrysanthemi EC16 | M14509 | AAA24844.1 |

Figure 38C
Pectate Lyases

| Protein | Organism | GenBank | GenPept |
|---|---|---|---|
| pectate lyase C (PelC) | Erwinia chrysanthemi strain 3937 | AJ132325 | CAA10642.1 |
| pectin lyase (PnlA) | Pectobacterium carotovorum Ecc71 | M59909 | AAA24856.1 |
| pectate lyase III (Pel3;PelC) | Pectobacterium carotovorum Er | D10064 | BAA00953.1 |
| pectate lyase B (PelB) | Pseudoalteromonas haloplanktis 505 | AF278705 | AAF86343.1 |
|  |  | AF278705 | AAF86343.2 |
| pectate lyase A | Pseudoalteromonas haloplanktis ANT/505 | AF278706 | AAF86344.2 |
| pectate lyase (Pel) | Pseudomonas fluorescens CY091 | L41673 | AAA93535.1 |
|  |  | L38902 | AAB46399.1 |
| pectin lyase (PnL) (fragment) | Pseudomonas marginalis N6301 | M84971 | AAA92512.1 |
|  |  | D32121 | BAA06847.1 |
| pectate lyase (PeL) | Pseudomonas marginalis N6301 | S65042 | AAC60448.1 |
|  |  | D32122 | BAA06848.1 |
| pectate lyase P (PelP) | Pseudomonas syringae pv. lachrymans | U75414 | AAB17879.1 |
|  |  | L38901 | AAB46398.1 |
|  |  | L38574 | AAC41521.1 |
|  |  | DQ273695 | ABB55454.1 |
| pectate lyase (Pel;Pstru-4) | Pseudomonas viridiflava | D44611 | BAA08077.1 |
| pectate lyase (Pel) | Pseudonocardia sp. | AF002241 | AAC38059.1 |
| pectate lyase (SCO2821;SCBAC17F8.12c) | Streptomyces coelicolor A3(2) | AL596030 | CAC44284.1 |
|  |  | NC_003888 | NP_627050.1 |
| pectate lyase (SCO1880;SCI39.27c) | Streptomyces coelicolor A3(2) | AL591322 | CAC38815.1 |
|  |  | NC_003888 | NP_626147.1 |
| α |  | AE001722 | AAD35518.1 |
| pectate lyase A (PelA;TM0433) | Thermotoga maritima MSB8 | NC_000853 | NP_228243.1 |
| XC_1298 | Xanthomonas campestris pv. campestris str. 8004 | CP000050 | AAY48367.1 |
| XC_3590 | Xanthomonas campestris pv. campestris str. 8004 | CP000050 | AAY50632.1 |
| pectate lyase (Pel;XCC0645) | Xanthomonas campestris pv. campestris str. ATCC 33913 | AE012162 | AAM39961.1 |
|  |  | NC_003902 | NP_636037.1 |
| pectate lyase II (PelB;XCC2815) | Xanthomonas campestris pv. campestris str. ATCC 33913 | AE012393 | AAM42087.1 |
|  |  | NC_003902 | NP_638163.1 |

Figure 38D
Pectate Lyases

| Protein | Organism | GenBank | GenPept |
|---|---|---|---|
| pectate lyase (PelB;Pl;Pstru-3) | Xanthomonas campestris pv. malvacearum strain B414 | L38573 | AAC41522.1 |
| | | DQ490478 | ABF50854.1 |
| pectin lyase (AN2331.2) | Aspergillus nidulans FGSC A4 | AACD01000038 | EAA64442.1 |
| pectin lyase (AN2569.2) | Aspergillus nidulans FGSC A4 | AACD01000043 | EAA64674.1 |
| | | DQ490480 | ABF50856.1 |
| | | U05592 | AAA80568.1 |
| | | DQ490468 | ABF50844.1 |
| | | EF452421 | ABO38859.1 |
| pectate lyase (PelA;AN0741.2) | Aspergillus nidulans FGSC A4 | AACD01000012 | EAA65383.1 |
| pectate lyase (AN7646.2) | Aspergillus nidulans FGSC A4 | AACD01000130 | EAA61832.1 |
| | | DQ490513 | ABF50889.1 |
| pectin lyase A (PelA) - Pl1A | Aspergillus niger CBS 120.49 / N400 | X55784 | CAA39305.1 |
| | | X60724 | CAA43130.1 |
| pectin lyase C (PelC) | Aspergillus niger CBS 120.49 / N400 | AY839647 | AAW03313.1 |
| pectin lyase F (PelF) | Aspergillus niger CBS 120.49 / N400 | AJ489943 | CAD34589.1 |
| pectate lyase A (PlyA) | Aspergillus niger CBS 120.49 / N400 | AJ276331 | CAC33162.1 |
| pectin lyase B (PelB) | Aspergillus niger CBS 120.49 / N400 | A12248 | CAA01023.1 |
| | | X65552 | CAA46521.1 |
| An14g04370 (PelA) | Aspergillus niger CBS 513.88 | AM270321 | CAK48529.1 |
| An03g00190 (PelB) | Aspergillus niger CBS 513.88 | AM270043 | CAK37997.1 |
| An15g07160 (PelF) | Aspergillus niger CBS 513.88 | AM270351 | CAK48551.1 |
| An19g00270 (PelD) | Aspergillus niger CBS 513.88 | AM270415 | CAK47350.1 |
| pectate lyase I (PlyA;An10g00870) | Aspergillus niger CBS 513.88 | AM270216 | CAK40523.1 |
| pectin lyase D (PelD) | Aspergillus niger N756 | M55657 | AAA32701.1 |
| pectin lyase 2 (Pel2) | Aspergillus oryzae KBN616 | AB029323 | BAB82468.1 |
| pectin lyase 1 (Pel1) | Aspergillus oryzae KBN616 | AB029322 | BAB82467.1 |
| pectin lyase 1 (Pel1;AO090010000504) | Aspergillus oryzae RIB 40 | EF452419 | ABO38857.1 |
| | | AP007175 | BAE66352.1 |
| pectin lyase 2 (Pel2;AO090010000030) | Aspergillus oryzae RIB 40 | AP007175 | BAE65949.1 |

Figure 38E
Pectate Lyases

| Protein | Organism | GenBank | GenPept |
|---|---|---|---|
| pectate lyase (PelB) | Colletotrichum gloeosporioides | AF052632 | AAD09857.1 |
| pectin lyase (PnlA) | Colletotrichum gloeosporioides | L22857 | AAA21817.1 |
| pectate lyase 2 (Pel-2) | Colletotrichum gloeosporioides f. sp. malvae | AF156985 | AAD43566.1 |
| pectin lyase (Pnl1;Pnl-1) | Colletotrichum gloeosporioides f. sp. malvae | AF158256 | AAF22244.1 |
| pectin lyase 2 (Pnl2;Pnl-2) | Colletotrichum gloeosporioides f. sp. malvae | AF156984 | AAD43565.1 |
| pectate lyase 1 (Pel-1) | Colletotrichum gloeosporioides f. sp. malvae | AF156983 | AAD43564.1 |
| | | L18911 | AAA33398.1 |
| | | EF026017 | ABM68553.1 |
| pectate lyase (LLP-52) | Lilium longiflorum | Z17328 | CAA78976.1 |
| | | AF206319 | AAF19195.1 |
| pectate lyase (PeII;Pl1;MwPl1;Ban17) | Musa acuminata Williams | DQ663594 | ABG74583.1 |
| | | X92943 | CAA63496.1 |
| | | X61102 | CAA43414.1 |
| | | X67158 | CAA47630.1 |
| pectate lyase | Nicotiana tabacum | X67159 | CAA47631.1 |
| | | Y09541 | CAA70735.1 |
| pectate lyase | Zinnia elegans | AX005936 | CAC05181.1 |

Figure 39A
Rhamnogalacturonases

| Protein | Organism | GenBank/GenPept | |
|---|---|---|---|
| rhamnogalacturonate lyase (RhiE) | Erwinia chrysanthemi 3937 | AJ438339 | CAD27359.1 |
| rhamnogalacturonan lyase (RhgB) | Aspergillus aculeatus KSM 510 | L35500 | AAA64368.1 |
| rhamnogalacturonan lyase (AN6395.2) | Aspergillus nidulans FGSC A4 | AACD01000108 | EAA58417.1 |
| | | DQ490501 | ABF50877.1 |
| rhamnogalacturonan lyase (AN7135.2) | Aspergillus nidulans FGSC A4 | AACD01000122 | EAA61387.1 |
| | | DQ490504 | ABF50880.1 |
| rhamnogalacturonan lyase (YesW;BSU07050) | Bacillus subtilis subsp. subtilis str. 168 | Z99107 | CAB12524.1 |
| | | NC_000964 | NP_388586.1 |
| exo-unsaturated rhamnogalacturonan lyase (YesX;BSU07060) | Bacillus subtilis subsp. subtilis str. 168 | Z99107 | CAB12525.1 |
| | | NC_000964 | NP_388587.1 |
| rhamnogalacturonan lyase - Rgl11A | Cellvibrio japonicus (formerly Pseudomonas cellulosa) | AY026755 | AAK20911.1 |
| CJA_3559 (rhamnogalacturonan lyase) - Rgl11A | Cellvibrio japonicus Ueda107 | CP000934.1 | ACE83155.1 |
| rhamnogalacturonan lyase Y - Rgl11Y | Clostridium cellulolyticum ATCC 35319 | AF316823 | AAG45161.1 |

Figure 39B
Rhamnogalacturonate Hydrolases

| Protein | Organism | GenBank/GenPept | |
|---|---|---|---|
| GH family 105 | | | |
| unsaturated rhamnogalacturonyl hydrolase (BSU30120; YteR) | Bacillus subtilis subsp. subtilis str. 168 | Z99119 | CAB14990.1 |
| unsaturated rhamnogalacturonyl hydrolase (BSU07000; YesR) | Bacillus subtilis subsp. subtilis str. 168 | Z99107 | CAB12519.1 |
| | | NC_000964 | NP_388581.1 |

Figure 40A
Pectate Methyl Esterases

| Protein | Organism | GenBank/GenPept | |
|---|---|---|---|
| Family 8 | | | |
| ECA3253 (PemA) | Erwinia carotovora subsp. atroseptica SCRI1043 | BX950851 | CAG76151.1 |
| ECA0107 (PmeB) | Erwinia carotovora subsp. atroseptica SCRI1043 | BX950851 | CAG73027.1 |
| pectin methylesterase b | Erwinia chrysanthemi 3937 | X84665 | CAA59151.1 |
| | | L07644 | AAA24852.1 |
| pectin methylesterase A (PemA;Pem) | Erwinia chrysanthemi 3937 / B374 | - | AAR64146.1 |
| | | Y00549 | CAA68628.1 |
| pectate lyase A | Pseudoalteromonas haloplanktis ANT/505 | AF278706 | AAF86344.2 |
| | | AC004411 | AAC34240.1 |
| | | AY091768 | AAM10316.1 |
| | | BT001120 | AAN64511.1 |
| | | AY830948 | AAV91508.1 |
| | | AJ250430 | CAB58974.1 |
| pectin methylesterase (Pme5; Vgd1;At2g47040/F14M4.13) | Arabidopsis thaliana | NM_130272 | NP_182227.1 |
| pectin methylesterase (Pme1) | Aspergillus aculeatus | U49378 | AAB42153.1 |
| pectin methyl esterase (AN3390.2) | Aspergillus nidulans FGSC A4 | DQ490489 | ABF50865.1 |
| | | AACD01000055 | EAA63358.1 |
| | | A34997 | CAA02198.1 |
| | | A35006 | CAA02201.1 |
| | | A35008 | CAA02202.1 |
| | | X52902 | CAA37084.1 |
| pectin methylesterase (Pme1) | Aspergillus niger RH 5344 | X54145 | CAA38084.1 |
| pectin methylesterase (PmeA) | Aspergillus oryzae KBN616 | AB011211 | BAA75474.1 |
| pectin methylesterase (PmeA;AO090012000749) | Aspergillus oryzae RIB 40 | AP007161 | BAE60873.1 |
| pectin methylesterase (Bcpme2) | Botryotinia fuckeliana Bd90 | AJ428403 | CAD21438.1 |
| pectin methyl esterase (Bcpme1) | Botryotinia fuckeliana T4 | AJ309701 | CAC29255.1 |
| pectin methylesterase 1.1 (PECS-1.1) | Citrus sinensis | U82973 | AAB57667.1 |
| | | U82976 | AAB57670.1 |

Figure 40B
Pectate Methyl Esterases

| Protein | Organism | GenBank | GenPept |
|---|---|---|---|
| pectin methylesterase (PME1) | Cochliobolus carbonum | AF159252 | AAD43340.1 |
| pectin methylesterase | Daucus carota | | |
| pectinesterase FaPE1 | Fragaria x ananassa | AY324809 | AAQ21124.1 |
| pectin methyl-esterase (Pef1) | Medicago truncatula | AJ249611 | CAB65291.1 |
| pectin methyl-esterase (Per) | Medicago truncatula | AJ249611 | CAB65290.2 |
| pectin methylesterase | Nicotiana benthamiana | AY238968 | AAO85706.1 |
| pectin methylesterase | Nicotiana plumbaginifolia | Z71752 | CAA96434.1 |
| pectin methylesterase (NtPPME1) | Nicotiana tabacum | AY772945 | AAX13972.1 |
| pectin methylesterase | Nicotiana tabacum | AJ401158 | CAB95025.1 |
| pectin methylesterase (PME1) (fragment) | Orobanche cumana | AY072720 | AAL66865.1 |
| pectin methylesterase (fragment) | Orobanche cumana | AF333068 | AAG49395.1 |
| pectin methylesterase | Petunia inflata | L27101 | AAA33714.1 |
| pectin methyl esterase (PttPME1) | Populus tremula x Populus tremuloides | AJ277547 | CAC01624.1 |
| pectin methylesterase PME1 (fragment) | Prunus armeniaca | AF184079 | AAG12248.1 |
| pectin methylesterase (SgPME1) | Salix gilgiana | AB029461 | BAA89480.1 |
| pectin methylesterase | Sitophilus oryzae | AY841894 | AAW28928.1 |
| | | U50985 | AAB67739.1 |
| | | - | AAQ71552.1 |
| | | A15983 | CAA01257.1 |
| | | A17011 | CAA01315.1 |
| | | X07910 | CAA30746.1 |
| pectin methylesterase 2 | Solanum lycopersicum | X74639 | CAA52704.1 |
| | | U49330 | AAD09283.1 |
| pectin methylesterase (PmeU1) | Solanum lycopersicum | AY046596 | AAL02367.1 |
| | | U50986 | AAB67740.1 |
| | | A17010 | CAA01314.1 |
| pectin methylesterase 1 (PME1.9) | Solanum lycopersicum | X74638 | CAA52703.1 |
| pectin methyl esterase (Pest1) | Solanum tuberosum | AF152171 | AAF23891.1 |
| pectin methyl esterase (Pest2) | Solanum tuberosum | AF152172 | AAF23892.1 |
| pectin methylesterase isoform alpha (PME2) (fragment) | Vigna radiata | AF229849 | AAF35897.1 |
| pectin methylesterase (PME) | Vitis riparia | AF178989 | AAD51853.1 |

Figure 41
Pectate Acetyl Esterases

| Protein | Organism | GenBank/GenPept | |
|---|---|---|---|
| Family12 | | | |
| acetyl xylan esterase (Rgae;BH1115) | Bacillus halodurans C-125 | AP001511 | BAB04834.1 |
| | | NC_002570 | NP_241981.1 |
| cephalosporin C deacetylase | Bacillus sp. KCCM10143 | AF184175 | AAF25818.1 |
| acetyl xylan esterase (YesT;BSU07020) | Bacillus subtilis subsp. subtilis str. 168 | Z99107 | CAB12521.1 |
| | | NC_000964 | NP_388583.1 |
| ECA3252 (PaeY) | Erwinia carotovora subsp. atroseptica SCRI1043 | BX950851 | CAG76150.1 |
| pectin acetylesterase (PaeY) | Erwinia chrysanthemi 3937 | Y09828 | CAA70971.1 |
| rhamnogalacturonan acetylesterase (Rha1) | Aspergillus aculeatus KSM 510 | X89714 | CAA61858.1 |
| rhamnogalacturonan acetylesterase (AN2528.2) | Aspergillus nidulans FGSC A4 | DQ490479 | ABF50855.1 |
| | | AACD01000043 | EAA64633.1 |
| pectin acetylesterase | Vigna radiata Wilzeck | X99348 | CAA67728.1 |

Production of 2-phenyl ethanol (24 hrs)

Production of 2-(4-hydroxyphenyl) ethanol (24 hrs)

Production of 2-(indole-3-)ethanol (24 hrs)

Thiobarbituric acid (TBA) Assay

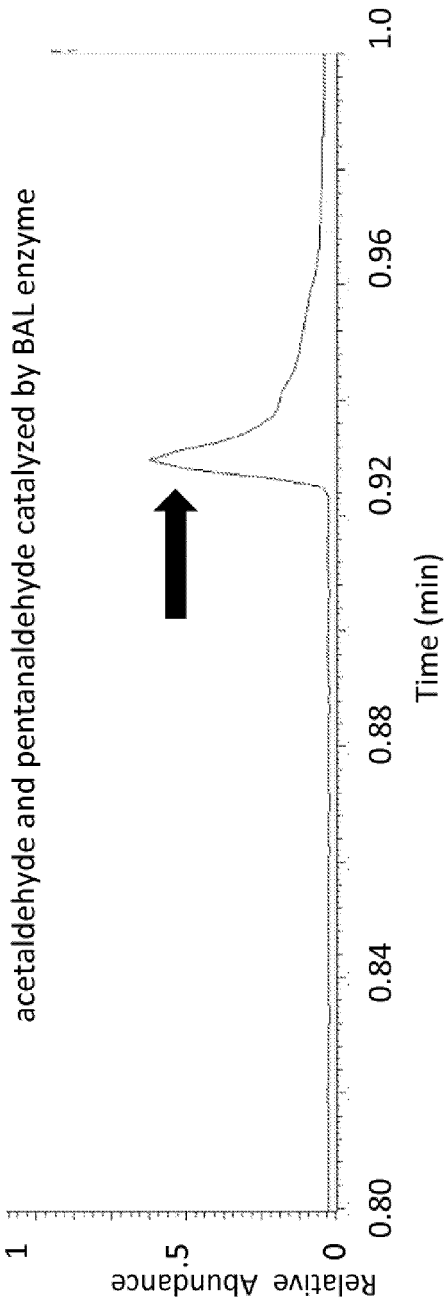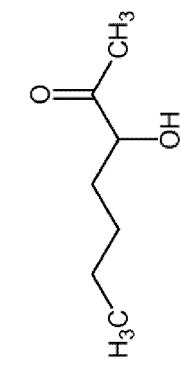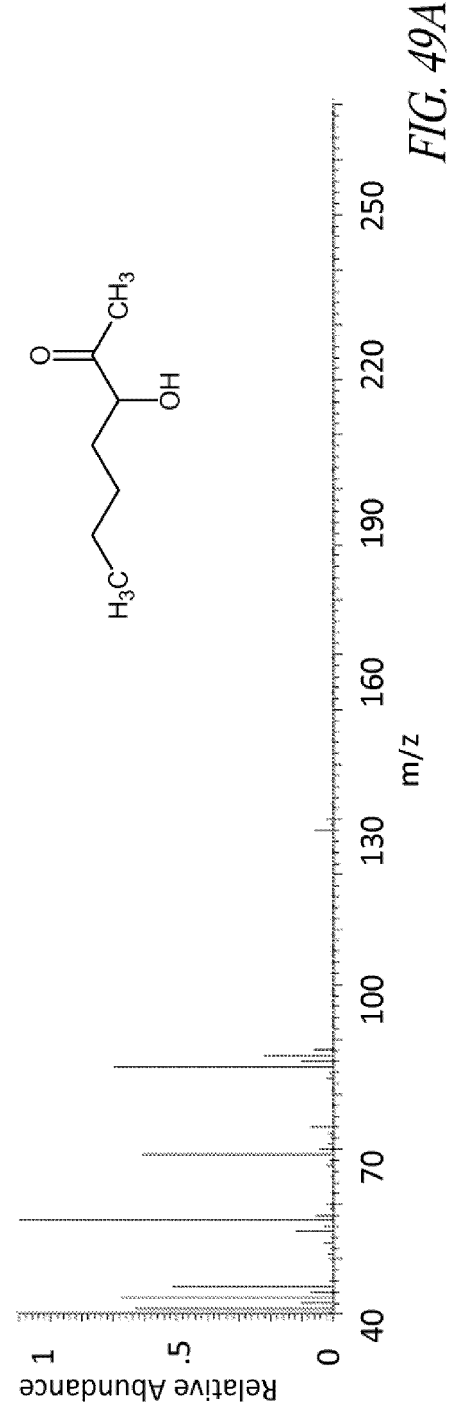
FIG. 49A

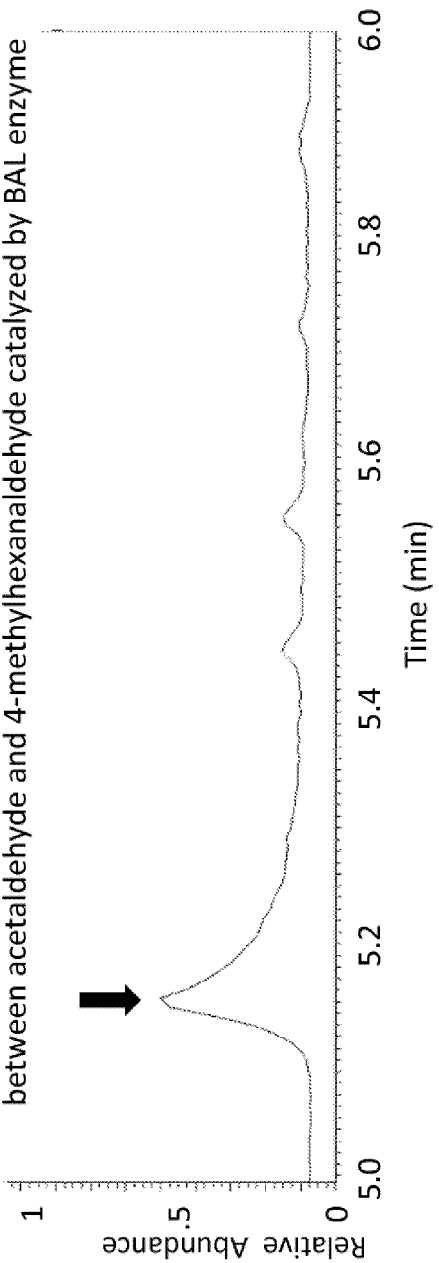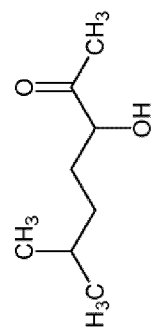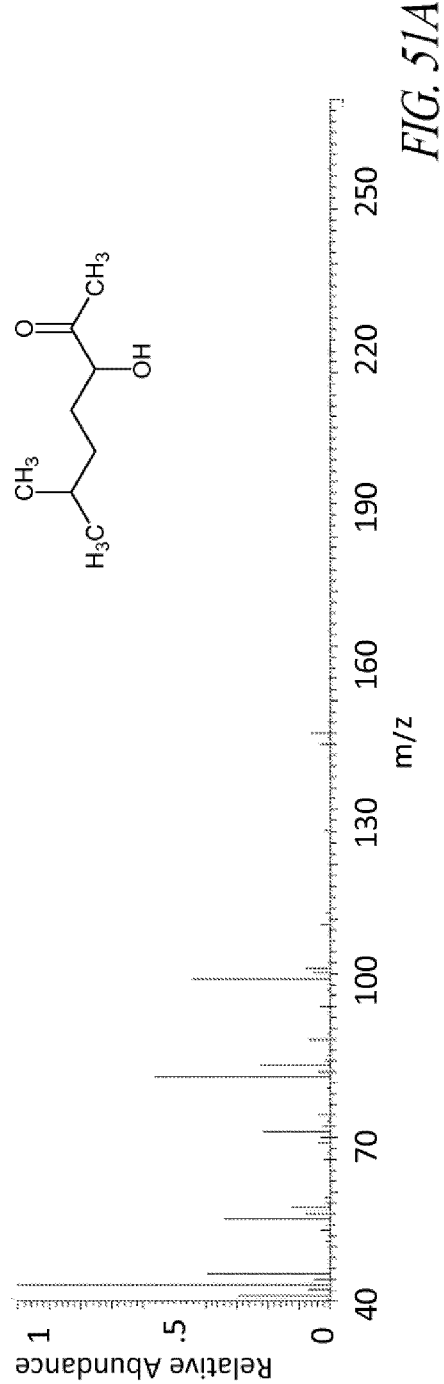
FIG. 51A

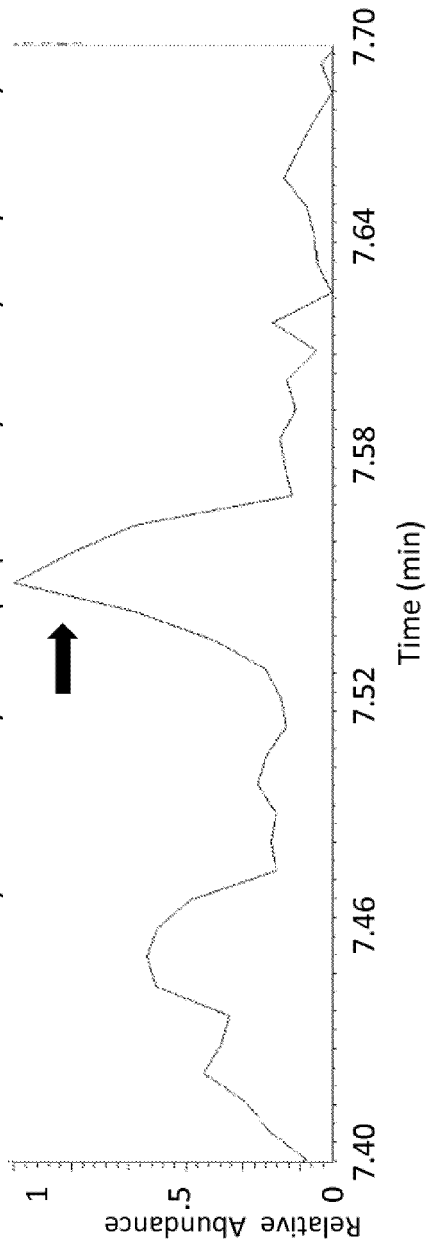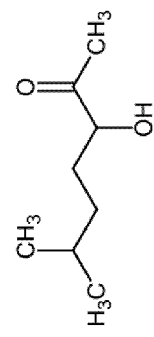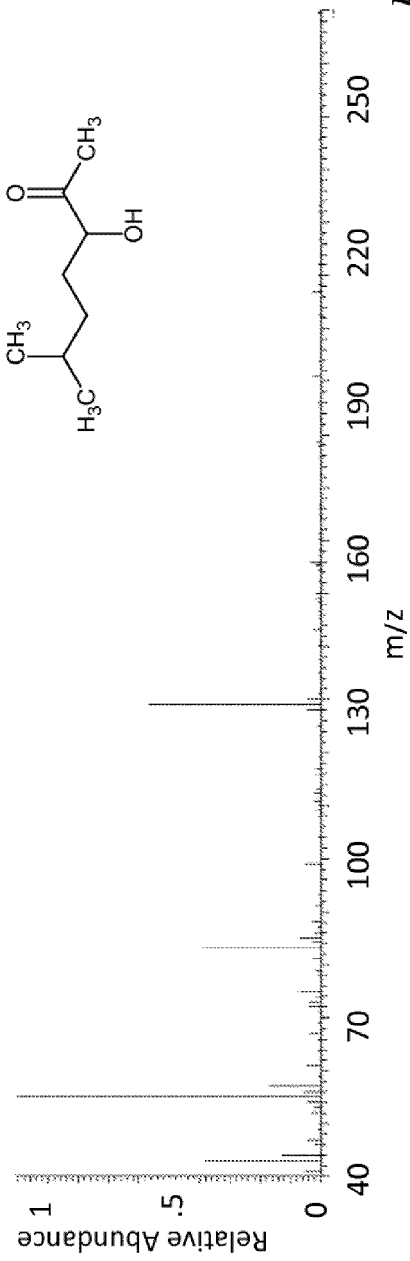
FIG. 51B

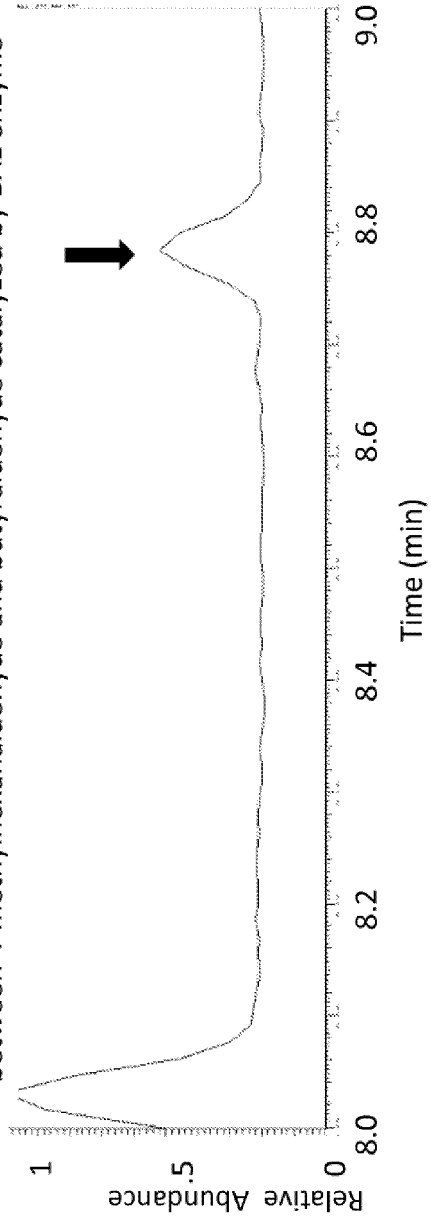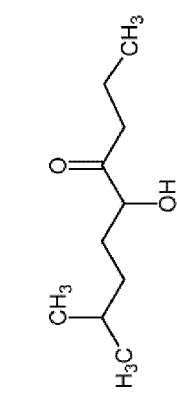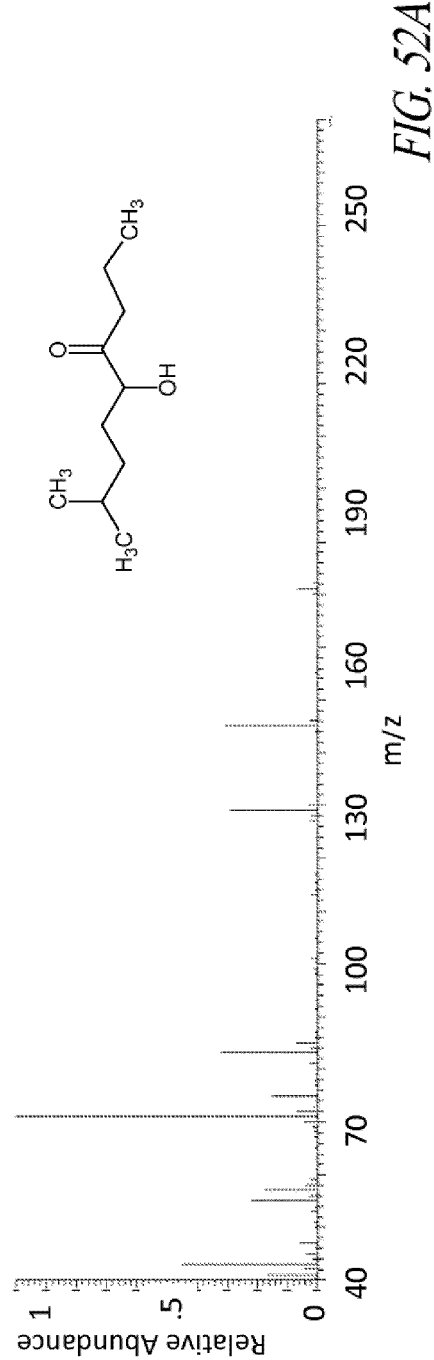
FIG. 52A

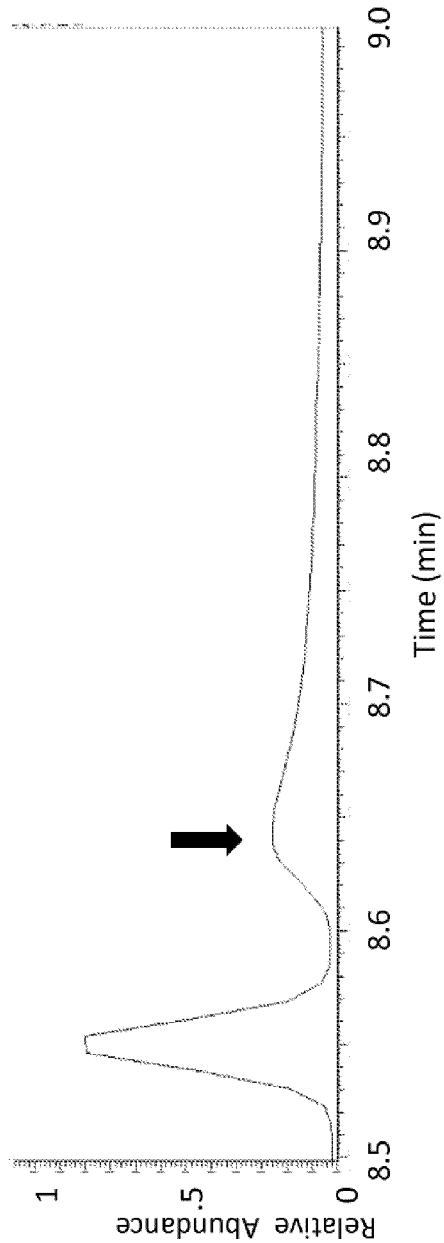
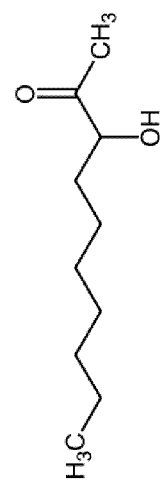
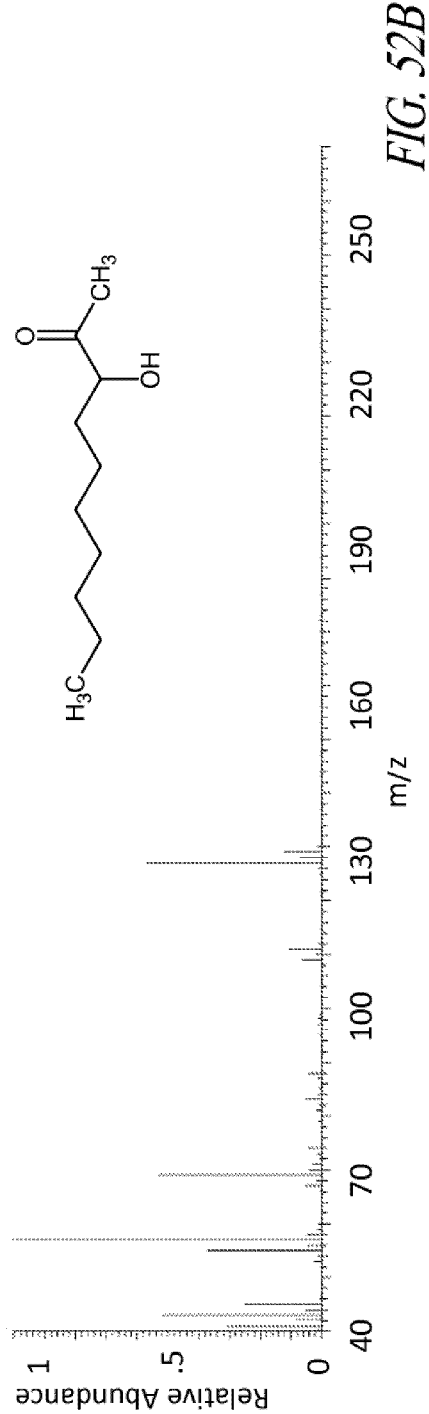
FIG. 52B

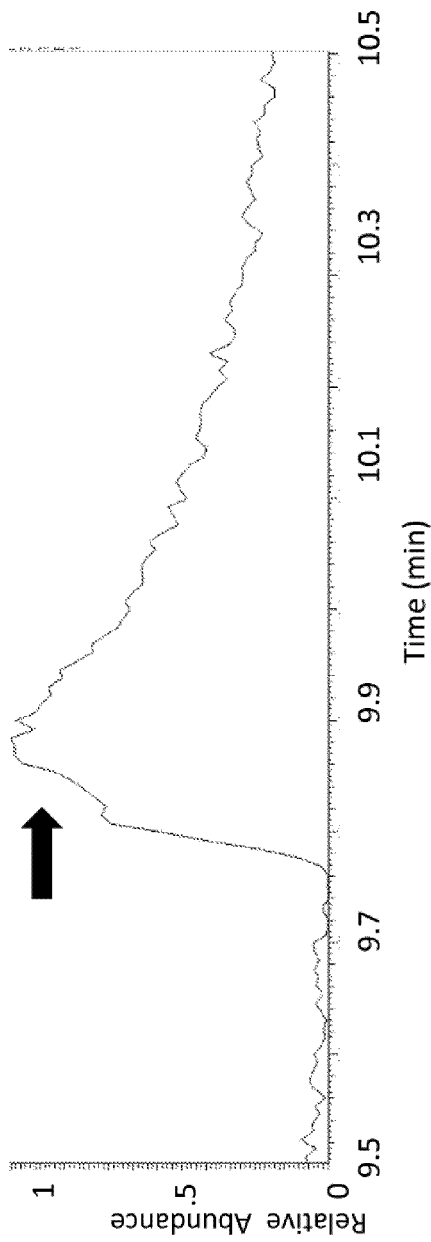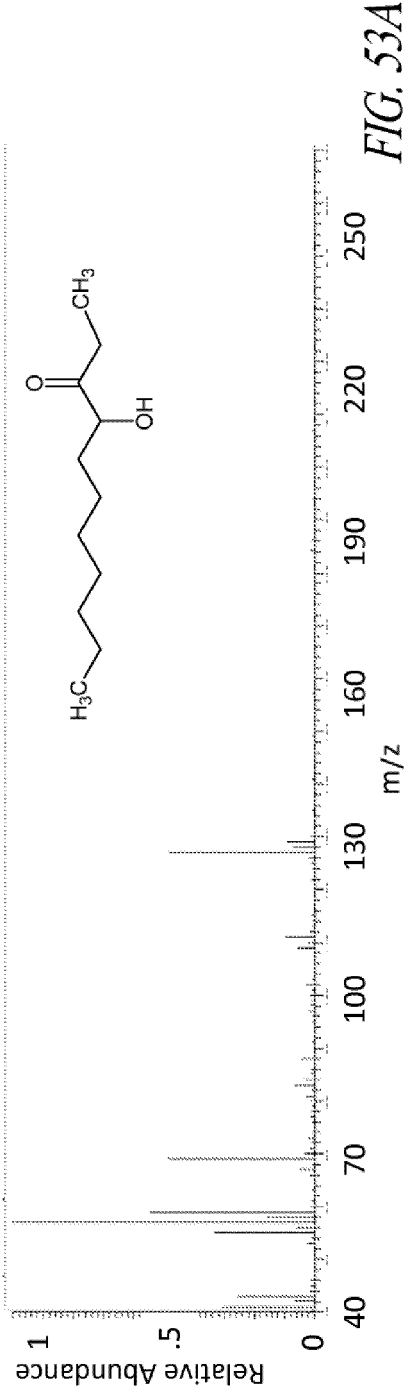
FIG. 53A

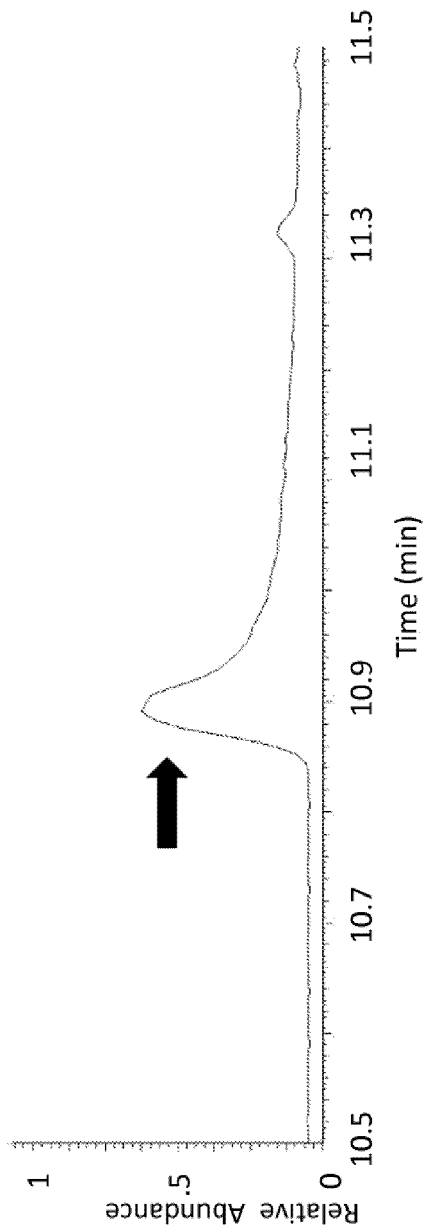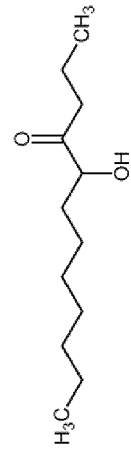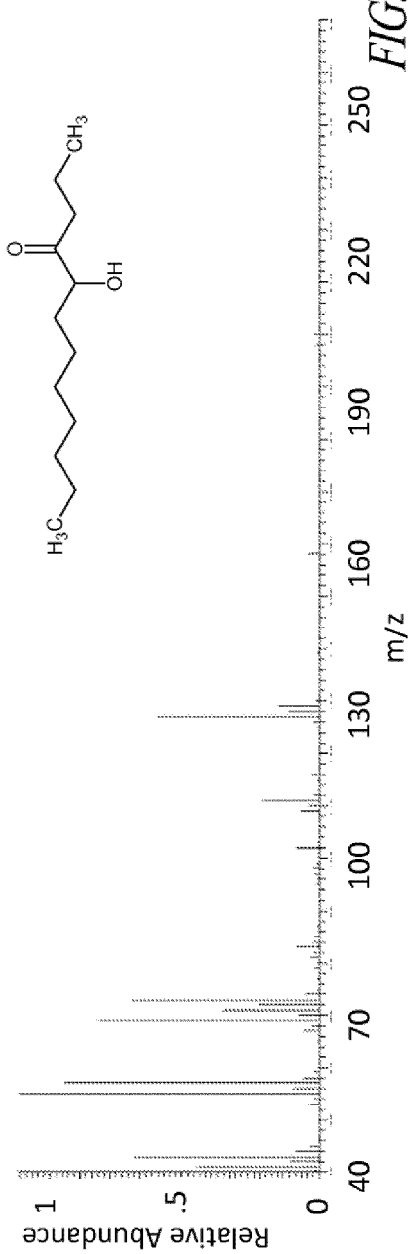
FIG. 53B

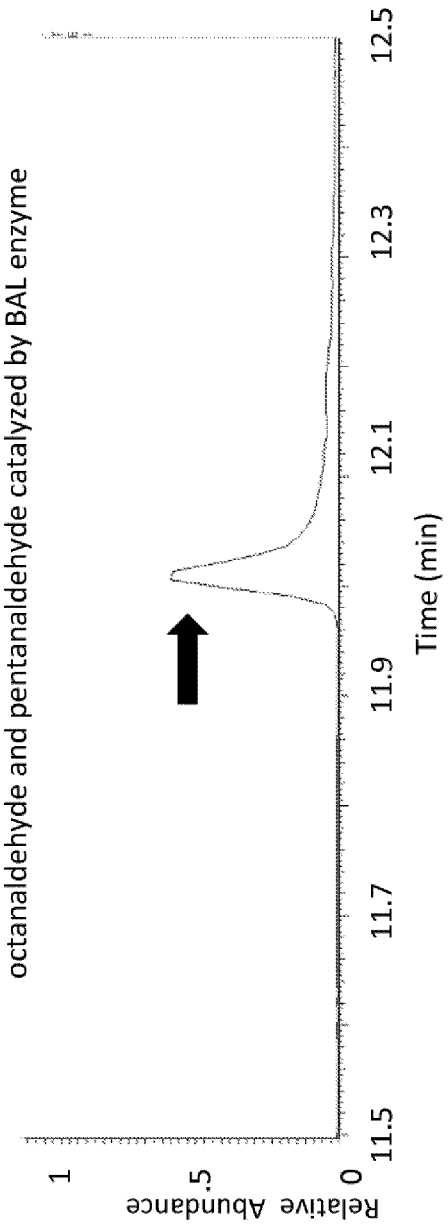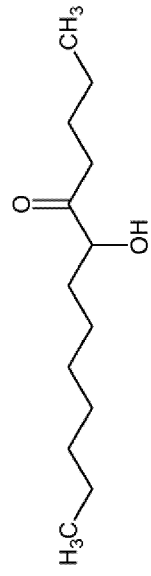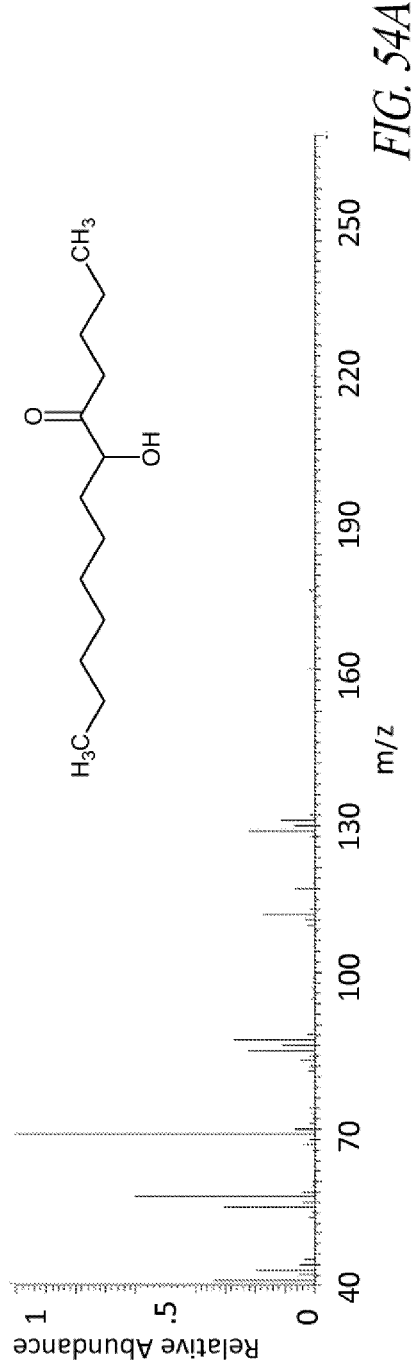
FIG. 54A

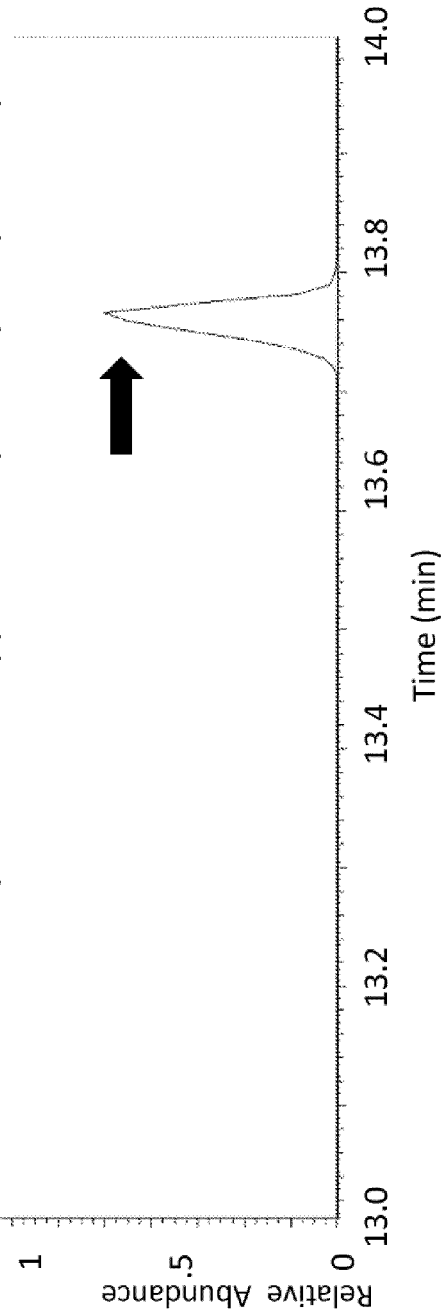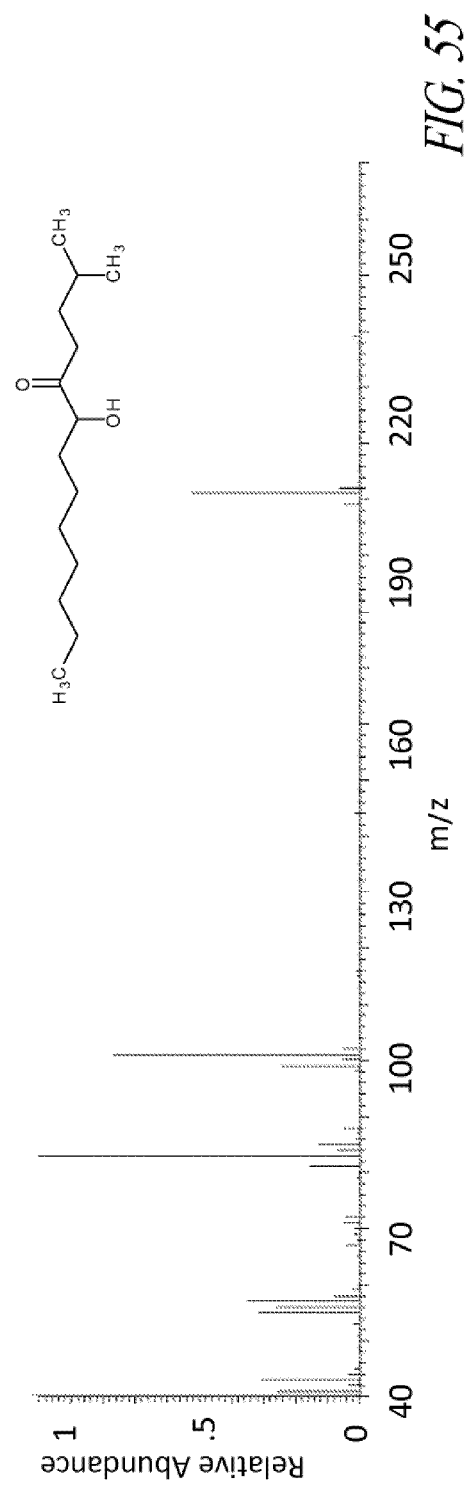
FIG. 55
*In vivo* production 2-methyl-6-hydroxy-5-tridecanone from ligation reaction between octanaldehyde and 4-methylpentanaldehyde catalyzed by BAL enzyme Production of Ethanol from Alginate

SEQUENCE LISTING

<160> NUMBER OF SEQ ID NOS: 333

<210> SEQ ID NO 1
<211> LENGTH: 12066
<212> TYPE: DNA

<213> ORGANISM: Vibrio splendidus

<400> SEQUENCE: 1

```
ggggacaagt tgtacaaaa aagcaggctt gacgcttatc acatttagta gaagcttatg      60
tggaggcgat tggcttttt ttcaaggaag attacaaaat agctcaggta atgccgattt     120
atagatttgc tatgatatag ttcaggatct tatgctttta ataagcagga acagaattta    180
tgaacaaaaa agctgatagt ttagtaggtt acagctttat tcgttataga aagggttagg    240
gaacgtgaac ttttagagc tcaaacttcg catggataac tctccggtgc tgagccgatt     300
tttagagaat ggattttac tccagcagaa actgagcctt gttctttgtt gtgtgttgat     360
cgcagcttct gcatggattt taggacagct tgcatggttt attgaacctg ctgagcaaac    420
cgtcgtgcca tggacagcaa cggcttcctc gtcttcaacg cctcaatcga ctcttgatat    480
ctcttctttg cagcagagca acatgtttgg tgcttataac ccaaccacgc ctgctgtggt    540
tgagcagcaa gttatccaag atgcgccaaa gacgcgactg aacctcgttt tagtgggtgc    600
agtagccagt tctaatccaa agctgagctt ggctgtgatt gccaatcgcg gcacacaagc    660
aacctacggc attaatgaag agatcgaagg tacgcgagct aagttaaaag cggtattagt    720
cgatcgcgtg attattgata actcaggtcg agacgaaacc ttgatgcttg aaggcattga    780
gtacaagcgt ttgtctgtat cagcacctgc gccacctcgt acctcttctt ctgtgcgtgg    840
caacaaccca gcttctgcag aagagaagct agatgaaatt aaagcgaaga taatgaaaga    900
tccgcaacaa atcttccaat atgttcgact gtctcaggtg aaacgcgacg ataaagtgat    960
tggttatcgt gtgagccctg gcaaagattc agaactttt aactctgttg ggctccaaaa   1020
cggagatatt gccactcagt taaatggaca agacctgaca gaccctgctg ctatgggcaa   1080
catattccgt tctatctcag agctgacaga gctaaacctc gtcgtcgaga gagatggtca   1140
acaacatgaa gtgtttattg aatttttagaa ctttgcgtct aacgaaggac gaaagtgtag   1200
gagaagtacg tgaagcattg gtttaagaaa agtgcatggt tattggcagg aagcttaatc   1260
tgcacacccg cagccatcgc gagtgatttt agtgccagct ttaaaggcac tgatattcaa   1320
gagtttatta atattgttgg tcgtaaccta gagaagacga tcatcgttga cccttcggtg   1380
cgcggaaaaa tcgatgtacg cagctacgac gtactcaatg aagagcaata ctacagcttc   1440
ttcctaaacg tattggaagt gtatggctac gcggttgtcg aaatggactc gggtgttctt   1500
aagatcatca aggccaaaga ttcgaaaaca tcggcaattc cagtcgttgg agacagtgac   1560
acgatcaaag cgacaatgt ggtgacacgt gttgtgacgg ttcgtaatgt ctcggtgcgt   1620
gaactttctc ctctgcttcg tcaactaaac gacaatgcag gcgcgggtaa cgttgtgcac   1680
tacgacccag ccaacatcat ccttattaca ggccgagcgg cggtagtaaa ccgtttagct   1740
gaaatcatca agcgtgttga ccaagcgggt gataaagaga ttgaagtcgt tgagctaaag   1800
aatgcttctg cggcagaaat ggtacgtatc gttgatgcgt taagcaaaac cactgatgcg   1860
aaaaacacac ctgcatttct acaacctaaa ttagttgccg atgaacgtac caatgcgatt   1920
cttatctcag cgaccctaa agtacgtagc cgtttaagaa ggctgattga acagcttgat   1980
gttgaaatgg caaccaaggg caataaccaa gttatttacc ttaaatatgc aaaagccgaa   2040
gatctagttg atgtgctgaa aggcgtgtcg gacaacctac aatcagagaa gcagacatca   2100
accaaaggaa gttcatcgca gcgtaaccaa gtgatgatct cagctcacag tgacaccaac   2160
tctttagtga ttaccgcaca gccggacatc atgaatgcgc ttcaagatgt gatcgcacag   2220
ctggatattc gtcgtgctca agtattgatt gaagcactga ttgtcgaaat ggccgaaggt   2280
```

-continued

| | | | | |
|---|---|---|---|---|
| gacggcgtta | accttggtgt | gcagtggggt | aaccttgaaa | cgggtgccat gattcagtac | 2340 |
| agcaacactg | gcgcttccat | tggcggtgtg | atggttggtt | tagaagaagc gaaagacagc | 2400 |
| gaaacgacaa | ccgctgttta | tgattcagac | ggtaaattct | tacgtaatga aaccacgacg | 2460 |
| gaagaaggtg | actattcaac | attagcttcc | gcactttctg | gtgttaatgg tgcggcaatg | 2520 |
| agtgtggtaa | tgggtgactg | gaccgccttg | atcagtgcag | tagcgaccga ttcaaattca | 2580 |
| aatatcctat | cttctccaag | tatcaccgtg | atggataacg | gcgaagcgtc attcattgtg | 2640 |
| ggtgaagagg | tgcctgttct | aaccggttct | acagcaggct | caagtaacga caacccattc | 2700 |
| caaacagttg | aacgtaaaga | agtgggtatc | aagcttaaag | tggtgccgca aatcaatgaa | 2760 |
| ggtgattcgg | ttcaactgca | aatagaacaa | gaagtatcga | acgtattagg cgccaatggt | 2820 |
| gcggttgatg | tgcgttttgc | taagcgacag | ctaaatacat | cagtgattgt tcaagacggt | 2880 |
| caaatgctgg | tgttgggtgg | cttgattgac | gagcgagcat | tggaaagtga atctaaggtg | 2940 |
| ccgttcttgg | gagatattcc | tgtgcttgga | cacttgttca | aatcaaccag tactcaggtt | 3000 |
| gagaaaaaga | acctaatggt | cttcatcaaa | ccaaccatta | ttcgtgatgg tatgacagcc | 3060 |
| gatggtatca | cgcagcgtaa | atacaacttc | atccgtgctg | agcagttgta caaggctgag | 3120 |
| caaggactga | agttaatggc | agacgataac | atcccagtat | tgcctaaatt tggtgccgac | 3180 |
| atgaatcacc | cggctgaaat | tcaagccttc | atcgatcaaa | tggaacaaga ataatggctg | 3240 |
| aattggtagg | ggcggcacgt | acttatcagc | gcttgccgtt | tagctttgcg aatcgctaca | 3300 |
| agatggtgtt | ggaataccaa | catccagagc | gcgcaccgat | actttattat gttgagccac | 3360 |
| tgaaatcggc | ggcgatcatt | gaagtgagtc | gtgttgtgaa | aaatggtttc acgccacaag | 3420 |
| cgattactct | cgatgagttt | gataaaaaac | taaccgatgc | ttatcagcgt gactcgtcag | 3480 |
| aagctcgtca | gctcatggaa | gacattggtg | ctgatagtga | tgatttcttc tcactagcgg | 3540 |
| aagaactgcc | tcaagacgaa | gacttacttg | aatcagaaga | tgatgcacca atcatcaagt | 3600 |
| taatcaatgc | gatgctgggt | gaggcgatca | agagggtgc | ttcggatata cacatcgaaa | 3660 |
| cctttgaaaa | gtcactttgt | atccgttttc | cgagttgatgg | tgtgctgcgt gatgttctag | 3720 |
| cgccaagccg | taaactggct | ccgctattgg | tttcacgtgt | caaggttatg gctaaactgg | 3780 |
| atattgcgga | aaaacgcgtg | ccacaagatg | gtcgtatttc | tctgcgtatt ggtggccgag | 3840 |
| cggttgatgt | tcgtgtttca | accatgcctt | cttcgcatgg | tgagcgtgtg gtaatgcgtc | 3900 |
| tgttggacaa | aaatgccact | cgtctagact | tgcacagttt | aggtatgaca gccgaaaacc | 3960 |
| atgaaaactt | ccgtaagctg | attcagcgcc | cacatgcat | tatcttggtg accggcccga | 4020 |
| caggttcagg | taaatcgacg | accttgtacg | caggtctgca | agaactcaac agcaatgaac | 4080 |
| gaaacatttt | aaccgttgaa | gacccaatcg | aattcgatat | cgatggcatt ggtcaaacac | 4140 |
| aagtgaaccc | taaggttgat | atgacctttg | cgcgtggttt | acgtgccatt cttcgtcaag | 4200 |
| atcctgatgt | tgttatgatt | ggtgagatcc | gtgacttgga | gaccgcagag attgctgtcc | 4260 |
| aggcctcttt | gacaggtcac | ttagttatgt | cgactctgca | taccaatact gccgtcggtg | 4320 |
| cgattacacg | tctacgtgat | atgggcattg | aacctttctt | gatctcttct tcgctgctgg | 4380 |
| gtgttttggc | tcagcgcttg | gttcgtactt | tatgtaacga | atgtaaagaa ccttatgaag | 4440 |
| ccgataaaga | gcagaagaaa | ctgtttgggt | tgaagaagaa | agaaagcttg acgctttacc | 4500 |
| atgccaaagg | ttgtgaagag | tgtggccata | agggttatcg | aggtcgtacg ggtattcatg | 4560 |
| agctgttgat | gattgatgat | tcagtacaag | agctgattca | cagtgaagcg ggtgagcagg | 4620 |
| cgattgataa | agcaattcgt | ggcacaacac | caagtattcg | agatgatggc ttgagcaaag | 4680 |

```
ttctgaaagg ggtaacgtcc ctagaagaag tgatgcgcgt gaccaaggaa gtctagtatg    4740
gcggcatttg aatacaaagc actggatgcc aaaggcaaaa gtaaaaaagg ctcaattgaa    4800
gcagataatg ctcgtcaggc tcgccaaaga ataaagagc ttggcttgat gccggttgag    4860
atgaccgagg ctaaagcaaa aacagcaaaa ggtgctcagc catcgaccag ctttaaacgc    4920
ggcatcagta cgcctgatct tgcgcttatt actcgtcaaa tatccacgct cgttcaatct    4980
ggtatgccgc tagaagagtg tttgaaagcc gttgccgaac agtctgagaa acctcgtatt    5040
cgcaccatgc tactcgcggt gagatctaag gtgactgaag gttattcgtt agcagacagc    5100
ttgtctgatt atccccatat cttcgatgag ctattcagag ccatggttgc tgctggtgag    5160
aagtcagggc atctagatgc ggtattggaa cgattggctg actacgcaga aaaccgtcag    5220
aagatgcgtt ctaagttgct gcaagcgatg atctaccccca tcgtgctggt ggtgtttgcg    5280
gtgacgattg tgtcgttcct actggcaacg gtagtgccga agatcgttga gcctattatc    5340
caaatgggac aagagctccc tcagtcgaca caatttttat tagcatcgag tgaatttatc    5400
cagaattggg gcatccaatt actggtgttg accattggtg tgattgtgtt ggttaagact    5460
gcgctgaaaa agccgggcgt tcgcatgagc tgggatcgca aattattgag catcccgctg    5520
ataggcaaga tagcgaaagg gatcaacacc tctcgttttg cacgaacact ttctatctgt    5580
acctctagtg cgattcctat ccttgaaggg atgaaggtcg cggtagatgt gatgtcgaat    5640
catcacgtga acaacaagt attacaggca tcagatagcg ttagagaagg ggcaagcctg    5700
cgtaaagcgc ttgatcaaac caaactcttt cccccgatga tgctgcatat gatcgccagt    5760
ggtgagcaga gtggccaatt ggaacagatg ctgacaagag cggcagataa tcaggatcaa    5820
agctttgaat cgaccgttaa tatcgcgtta ggcatttta ccccagcgct tattgcgttg    5880
atggctggct tagtgctgtt tatcgtgatg gcgacgctga tgccaatgct tgaaatgaac    5940
aatttaatga gtggttaacc tgccgctcat cagacgttag ttttttggatt atcgagaaga    6000 aggacatcat tccccctcaac tcgctatctg taatttggag aaaataatga aaaataaaat    6060
gaaaaaacaa tcaggctta ccctattaga agtcatggtt gttgtcgtta tccttggtgt    6120
tctagcaagt tttgttgtac ctaacctgtt gggcaacaaa gagaaggcgg atcaacaaaa    6180
agccatcact gatattgtgg cgctagagaa cgcgctcgac atgtacaaac tggataacag    6240
cgtttaccca acaacggatc aaggcctgga cgggttggtg acaaagccaa gcagtccaga    6300
gcctcgtaac taccgagacg gcggttacat caagcgtcta cctaacgacc catggggcaa    6360
tgagtaccaa tacctaagtc ctggtgataa cggcacaatt gatatcttca ctcttggcgc    6420
agatggtcaa gaaggtggtg aaggtattgc tgcagatatc ggcaactgga acatgcagga    6480
cttccaataa gcttcggctt gttgtcggtt gatacgttcc tgttgtttga ttcgttatcg    6540
ttgcttgata cgttattgat ggtagtacgc aaaaaatgga gtctacaagg tgaaaactaa    6600
gcaaacacag ccaggtttca ccttgattga gattctttg gtgttggtat tactgtcagt    6660
atcggcggtc gcggtgatct cgaccatccc taccaatagc aaagatgttg ctaaaaaata    6720
cgctcaaagc ttttatcagc gaattcagct actcaatgaa gaggctattt tgagtggctt    6780 agatttggt gttcgtgttg atgaaaaaaa atcgacttac gttctgatga ctttgaagtc    6840
tgatggctgg caagaaacgg agttcgaaaa gatccctct tcaactgaat taccggaaga    6900
actggcactg tcgctgacat taggtggtgg cgcgtgggaa gacgatgatc ggttgttcaa    6960
tccaggaagc ttatttgatg aagatatgtt tgctgatctt gaagaggaaa agaagccgaa    7020
accaccacag atctacatct tgtcgagtgc tgaaatgacg ccatttgtac tgtcgtttta    7080
```

```
cccaaatacc ggtgacacaa tacaagatgt ttggcgcatt cgagtattgg ataatggtgt    7140
gattcgatta ctcgagccgg gagaagaaga tgaagaagaa taaccgttct ccttatcgtt    7200
ctcgcggtat gcctcttggt tctcgaggaa tgactctgct tgaagtattg gttgcgctgg    7260
ctatcttcgc tacggcggcg atcagtgtga ttcgtgctgt cacccagcac atcaatacgc    7320
tcagttatct cgaagaaaaa accttcgcgg cgatggtcgt tgataatcaa atggccctag    7380
tcatgctaca tcctgagatg cttaaaaaag cgcagggcac gcaagagtta gcgggaagag    7440
aatggttctg gaaggtgact cccatcgata ccagcgataa tttattaaag gcgtttgatg    7500
tgagtgcggc aaccagtaag aaagcgtctc cagtcgttac ggtgcgcagt tatgtggtta    7560
attaagagaa tgtggtcaat taagagcatg ttattaatta agaacagctc gctaactaag    7620
agcgtgtcgc taactaagag catgtcggaa aataagcgta cgccgcgtaa acaaggtcta    7680
ccttcaaaag ggagaggctt taccttaatt gaagtcttgg tctcgattgc tatctttgcc    7740
acgctaagta tggcggctta tcaggtggtt aatcaggtgc agcgaagcaa cgagatctct    7800
attgagcgca gtgctcgttt gaaccaactg caacgcagtt tagtcatttt agataatgat    7860
tttcgccaga tggcggtgcg aaaatttcgt accaacggtg aagaagcatc atctaagctg    7920
atcttaatga aagagtattt attggactcc gacagtgtag gcatcatgtt tactcgtcta    7980
ggttggcaca acccacaaca gcagtttcct cgcggtgaag tcacgaaggt tggctaccgt    8040 attaagaag aaacacttga gcgtgtatgg tggcgttatc ccgatacacc ttcaggccaa    8100
gaaggtgtga ttacccctct gcttgatgat gttgaaagct tggaattcga gttttatgac    8160
ggaagccgct gggggaaaga gtggcaaacc gataaatcac tgccgaaagc ggtgaggctt    8220
aagctgacac tgaaagacta tggtgagata gagcgtgttt atctcactcc cggtggcacc    8280
ctagatcagg ccgatgattc ttcaaacagt gactcttcag gcagtagtga ggggaataat    8340
gactcatcga actaataagc gtttagcgac aaggtcagcc ttgggacgta acaacgtgg    8400 tgtcgcgctg atcattattt tgatgctatt ggcgatcatg gcaaccattg ctggcagcat    8460
gtccgagcgt ttgtttacgc aattcaagcg cgttggtaac caactgaatt accaacaggc    8520
ttactggtac agcattggtg tggaagcgct tgtgcaaaac ggtattaggc aaagttacaa    8580
agacagtgat accgtgaacc taagccaacc atgggcgtta aagagcagg tatacccatt    8640 ggattatggc caagttaagg gccgcattgt tgatgctcag gcatgtttta atcttaatgc    8700
cttagccgga gtggcgacca cttcaagtaa ccagactcct tatttaatca cggtttggca    8760
aaccttattg gaaaaccaag acgttgagcc ttatcaggct gaggttatcg caaattcaac    8820
gtgggaattt gttgatgcgg atacacgaac cacctcttcg tctggtgtag aagacagcac    8880
gtatgaagcg atgaagccct cttatttggc ggcgaatggc ttaatggccg atgaatccga    8940
gctacgagcg gtttatcaag tcactggtga agtgatgaat aaggttcgcc cctttgtttg    9000
cgctctgcca accgatgatt tccgcttgaa tgtgaatact ctcacggaaa acaagcacc    9060 gttattggaa gcgatgtttg cgccaggctt aagtgaatcg gatgccaaac agctgataga    9120
taaacgccca tttgatggct gggatacggt agatgctttc atggctgaac ctgccattgt    9180
tggtgtaagt gccgaagtca gcaagaaagc gaaagcatat ttaactgtag atagcgccta    9240
ttttgagcta gatgcagagg tattagttga gcagtcacgt gtacgtatac ggacgctttt    9300
ctatagtagt aatcgagaaa cagtgacggt agtacgccgt cgttttggag gaatcagtga    9360
gcgagtttct gaccgttcga ctgagtagcg aaccacaaag ccctgtgcag tggttagttt    9420
ggtcgacaag ccaacaagaa gtgatagcaa gcggtgaact gtctagctgg gaacagcttg    9480
```

```
acgagttaac gccttacgct gaaaagcgca gctgtatcgc tttattgccg ggaagtgaat    9540
gcttaattaa gcgtgttgag atcccgaaag gtgctgctcg ccagtttgat tctatgctgc    9600
cgttcttatt agaagacgaa gtcgcacaag atatcgaaga cttacacctg actattttag    9660
ataaagatgc cactcacgct accgtgtgtg gtgtggatcg tgaatggcta aaacaagctt    9720
tagacctgtt tcgcgaagcc aatataatct tccgtaaggt gctaccagat acactagccg    9780 tgcctttga agaacaaggc atcagtgcgt tgcagataga tcagcattgg ttattgcgcc    9840
aaggtcactc tcaacgtcaa ggtcactatc aagccgtatc gatcagtgaa gcatggttac    9900
cgatgttttt gcaaagtgat tgggttgtcg ctggtgagga agagcaagcg acgactatct    9960
tcagctatac cgcgatgccg agcgacgacg ttcaacagca aagcggcctc gagtggcaag   10020
caaagcctgc ggaattggtg atgtctttat tgagtcagca agcgatcaca agcggcgtaa   10080
atttactgac tggcaccttt aaaaccaaat cttcattcag taaatattgg cgtgtttggc   10140
agaaagtggc gattgctgct tgtttgctgg tggccgtgat tgtgactcag caagtgttga   10200
aggttcagca atacgaagcg caagcacaag cctaccgcat ggagagtgag cgtatcttta   10260
gagctgtgct gcctggcaaa caacgcattc cgaccgtgag ttacctcaag cgtcagatga   10320
atgatgaagc taagaaatac ggtggttcag gcgaaggtga ttctttactt ggttggttag   10380
ctttgctgcc tgaaaccta gggcaagtga agacgatcga agttgaaagc attcgctacg   10440
atggcaaccg ttctgaggtt cgactgcagg ctaaaagttc tgacttccaa cactttgaga   10500
ccgcaagggt gaagctcgaa gagaagtttg tcgttgagca agggccattg aaccgtaatg   10560
gcgatgccgt atttggcagt tttactctta acccccatca ataacctgcg taaggagatc   10620
agtgatgaga aatatgattg aaccactcca agcgtggtgg gcttcaataa gtcagcggga   10680
acaacgatta gtcattggtt gttctatttt attgatactg ggcgttgtct attggggatt   10740
aatacaacca cttagccaac gagccgagct tgcacaaagc cgcattcaaa gtgagaagca   10800
acttctggct tgggtaacgg acaaagcgaa tcaagtggtt gaactacgag gcagtggtgg   10860
catcagtgcc agtcagcctt tgaaccaatc tgtgcctgct tctatgcgcc gttttaacat   10920
cgagctgata cgcgtgcaac cacgcggtga gatgctgcaa gtttggatta gcctgtgcc   10980 atttaataag ttcgttgact ggctgacata cctgaaagaa aagcagggtg ttgaggttga   11040
gtttatggat attgatcgct ctgatagccc tggggttatt gagatcaacc gactacagtt   11100
taaacgaggt taatgtgaaa cgcggtttat ctttcaaata cggcctgtta ttcagcgtca   11160
tttttatcgt tttttctcg gtaagcttgt tgctgcattt gcctgccgct tttgctctca   11220
agcatgcacc cgtcgtgcgt ggtttaagca ttgaaggcgt tgagggcacc gtttggcaag   11280
gtcgcgctaa caatatcgcg tggcagcgtg tcaattacgg ctcagtgcag tgggacttcc   11340
agttctctaa actattccaa gccaaagcag aacttgcggt tcgctttggc cgcaacagcg   11400
acatgaactt atcaggtaaa ggacgtgtcg gatatagcat gagtggtgct tacgcggaaa   11460
acttagtggc atcaatgcca gccagcaacg tgatgaaata tgcgccagct atcccagtgc   11520
ctgtgtctat tgcagggcaa gttgaactga cgatcaaaca tgcggttcat gctcaaccett   11580 ggtgtcaatc aggtgaaggt acgcttgctt ggtctggtgc agcagtcgac tcgccagtgg   11640
gttcgttaga ccttggccct gtgattgcgg acataacgtg tgaagacagc acaattgcag   11700
ccaaaggcac tcagaagagc gatcaggtag acagcgagtt ctcagcgagc gtaacaccta   11760
accaacgcta cacctcggca gcatggttta agccaggcgc tgaattcccg ccagcaatgc   11820
agagtcagct taagtggttg ggcaatcctg atagccaagg taaataccaa tttacttatc   11880
```

```
aaggccgctt ttagcccggt atttacttca gagctagtat ctgaagtaaa tttggcgatc    11940
aaatcgcgaa ctataaaaaa cgggcacctc actgaggtgc ccgttttgtt tgttctgaga    12000
atctagagga tatctgacgg ttaaagagag caaactcacc cagctttctt gtacaaagtg    12060
gtcccc                                                               12066

<210> SEQ ID NO 2
<211> LENGTH: 54080
<212> TYPE: DNA
<213> ORGANISM: Vibrio splendidus

<400> SEQUENCE: 2
gtgctttgtg acaacggggg atgtatggat attgaagttt cgcgccaggt tgcggtagtt      60
gaagctacga gtggagatgt cgtcgtagtt aagccagacg gcagcgcaag aaaagtttca     120
gttggcgata ccatccgtga aaatgagatc gtgattacgg ccaacaagtc agagcttgta     180
ttaggcgttc agaatgattc gattccggtt gcagagaatt cgtcggttg tgttgatgaa      240 aacgctgcat gggtagatgc cccaatagct ggtgaggtta attttgactt acagcaagca     300
gacgcagaaa ccttcactga agacgacctt gctgcaattc aagaagccat tttaggtggt     360
gccgatccga ctcaaatctt agaagcaacg gctgctggtg gcggactagg ttctgcaaat     420
gctggctttg tgacgattga ctataactac actgaaactc atccatcgac tttctttgag     480
accgctggtc tagcagaaca aactgttgat gaagacagag aagaattcag atctatcact     540
cgttcatcag gtggccaatc aatcagtgaa acactgactg aaggctccat atctggcaat     600
acctatcccc aatctgtaac aacgacagaa acgattattg ctggtagttt agctctcgcc     660
cctaactctt tcattccaga aactttatcc ctcgcttcac tacttagtga attaaacagc     720
gacattactt caagtggtca gtccgttatc ttcacctatg acgcgacgac taattctatc     780
gttggtgttc aagataccga cgaagtatta cgtatcgaca ttgatgccgt cagtgttggc     840
aataacattg agctttctct aaccacaacg atttcccagc cgattgatca tgtaccgtcg     900
gttggcggtg tcaggttttc ttacactggc gatcaaatag atattgcctt tgatattcaa     960
ggtgaagaca ccgctgggaa cccgctagca cacccgttta cgcacaagt ttcagtgttt    1020 gacgggatag atccgtctgt tgaaagtgtc aatatcacta cgttgaaaac tagcagcgcg    1080
gcaatcgaag gaacgttctc aaatattggt agtgataacc ttcaatcagc cgtatttgat    1140
gcaagtgcac tggaccagtt tgatgggttg ctcagtgata tcaaaacac gcttgcgaga     1200 ctttctgatg atgaacaac gattactctg tccatccaag gtcgaggtga ggttgttctc    1260
actatctctc tagataccga tggcacctat aaattcgagc agtctaatcc gatagaacaa    1320
gtgggtaccg attcactgac gttcgctttg ccaatcacga ttaccgattt tgaccaagat    1380
gttgtaacca atacgatcaa cattgccatt actgatggcg atagccctgt tattactaat    1440
gttgacagta ttgatgttga tgaagcgggc attgttggcg gctcacaaga gggcacggcg    1500
ccagtgtctg gcactggcgg tatcaccgcg gacattttg aaagtgacat cattgaccat    1560
tatgagctag aacccactga atttaatact aatggcacct tggtttcaaa tggcgaggct    1620
gtgctacttg agttgattga tgaaaccaac ggtgtaagaa cttacgaagg ttatgttgag    1680
gtcaatggtt cgagaattac ggtctttgac gttaaaattg atagcccttc attgggcaac    1740
tatgagttta atctttatga agaactttct catcaaggcg ctgaagatgc gctgttaact    1800
tttgcattgc caatttatgc tgttgatgca gatggcgacc gttctgcact gtctggaggt    1860
tcgaacacac cagaagctgc tgagatcctc gttaatgtta aagacgatgt cgttgaatta    1920
```

```
gttgataagg ttgaatcagt caccgagccg accttagcgg gcgatactat tgtttcgtat      1980
aacctgttca attttgaagg cgcagatggt tctacaattc aatcgtttaa ctacgacggt      2040
gttgattact cactcgatca aagcctgctc cccgatgcta cccagatttt cagtttttact     2100 gaaggtgtcg tcactatctc attaaacggt gacttcagtt ttgaagtcgc tcgtgatatc      2160
gaccactcaa gcagtgaaac tatcgtcaaa cagttctcat ttttagccga agatggtgat      2220
ggggatactg atagttcgac gcttgagtta agtattaccg atggccaaga tccgatcatt      2280
gatttgatcc cgcctgtgac tctctctgaa accaaccttta atgacggctc tgctcccagc     2340
ggaagtacag ttagcgcaac cgagacgatt acctttaccg caggcagcga cgatgtagca      2400
agtttccgta ttgaaccaac agagtttaat gtgggcggtg cacttaaatc gaatggatttt    2460 tcggttgaga taaagaaga ttcggctaat ccgggtactt acattggctt tattaccaac       2520
ggttcgggcg ctgaaatccc agtgtttacg attgctttct ctacgagcac attgggtgaa     2580 tacacccttta ctctgcttga agcgttagac catgtagatg gtttagataa gaacgatctg    2640
agctttgatc tgcctatttta tgcggttgat acggacggcg acgattcatt ggtgtctcag    2700
cttaatgtga ctatcggtga tgatgttcaa atcatgcaag acggtacgtt agatatcacc     2760
gagccaaatc ttgctgacgg tacaatcaca accaacacca ttgatgtaat gccaaatcaa     2820
agtgctgatg gcgcgacgat cactcggttc acttatgacg gtgtcgtaaa cacactggat    2880 caaagtatttt caggagaaca gcagttcagc ttcacagaag gcgaactgtt tatcacccctt  2940 gaaggtgaag tgcgctttga gcctaatcgc gatctagacc actcagtgag tgaagatatc    3000
gtgaagtcga ttgtggtgac ttcaagcgac ttcgataacg atccggtgac ttcaaccatt    3060
acgctgacga tcactgatgg tgataacccg acgattgatg ttattccaag tgttacgctt    3120
tctgaaatta acctgagcga tggctctgct ccaagtggca gcgcggtaag ctcgactcaa    3180
actattactt ttaccaatca aagtgatgat gtggttcgtt tccgtattga gtcaacggag    3240
ttcaatacta acgatgatct aaatcgaac ggtttagctg ttgagttacg tgaagacccg      3300
gcagggtcgg gtgactacat tggttttacg accagtgcga cgaacgtaga aactccagta    3360
ttcacattaa gctttaattc tggatcatta ggtgaataca cgttcacact catcgaagcg    3420
ttggaccacc aagatgcccg tggcaacaac gacctcagtt ttgatttacc tgtttacgcg    3480
gtagatagtg atggcgatga ttcattggtg tctccgttaa acgtcactat cggtgatgat    3540
gttcaaatca tgcaagatag tacgttagat atcgtcgagc caaccgtcgc agatttggcc    3600
gctggcacag tgacaactaa caccattgat gtgatgccaa atcaaagtgc cgatggcgca    3660
acggtgacgc aattcactta tgatggccag cttcgaacac ttgaccaaaa tgacaatggt    3720
gagcagcaat ttagcttcac agaaggtgaa ctgttcatca cgcttcaagg tgatgtgcgc    3780
tttgagccta atcgtaatct agaccacaca ctcagcgaag acatcgtgaa atcaatcgtg    3840
gtgacatcta gcgattccga taacgatgtg ttgacctcaa ccgtcactct gaccattacc    3900
gatggtgata tcccaaccat tgataatgtt ccaactgtga acttgtctga aactaatctg    3960
agtgatggct ctgcacctag cggaagcgcg gtgagttcaa ctcaaactat tacttacacc    4020
actcaaagtg atgatgtgac aagcttccgt attgaaccga ctgaatttaa tgttggtggc    4080
gctctcacat caaacggatt ggcagtcgag ttaaagctg atccaaccac accgggtggc     4140
tacatcggtt ttgtgactga tggttcgaac gttgaaacta acgtgttcac gattagcttc    4200
tcagatacca atttaggcca gtacaccttc accttacttg aagcgttaga ccatgtggat    4260
ggtttagcga acaatgatct gacctttgat ctgcctgttt atgcagttga tagcgatggc    4320
```

```
gacgattcac tggtgtctca gttaaatgta accatcggtg atgatgttca aatcatgcaa   4380
ggtggtacgt tagatatcac tgagccaaat cttgcagacg gcacaattac aaccaatacc   4440
atcgatgtga tgccagagca aagcgccgat ggtgcgacga tcactcagtt cacttatgac   4500
ggtcaagttc gaacactgga tcaaacggac aatggtgagc agcaatttag cttcactgaa   4560
ggcgagttgt tcatcactct tcaaggtgac gtgcgtttcg aacccaatcg caacctagat   4620
cacacagcta gcgaagatat cgtgaagtcg atagtggtga cttcaagcga tttagataac   4680
gatgtggtga cgtcaacggt cactctgacg attactgatg gtgatatccc aaccattgat   4740
gcagtgccaa gcgttactct gtctgaaatc aatcttagtg acggctctgc gccaagtggc   4800
actgcagtta gtcaaactga gacgattacc ttcaccaatc aaagtgatga tgtgaccagt   4860
ttccgtattg agccaataga gttcaatgtg ggcggtgcac tgaaatcgaa tggatttgcg   4920
gttgagataa aagaagattc ggctaatccg ggtacttaca ttggctttat taccaacggt   4980
tcgggcgctg aaatcccagt gtttacgatt gctttctcta cgagctcatt gggtgaatac   5040 accttttactc tgcttgaagc gttagaccat gtagatggtt tagataagaa cgatctgagc   5100
ttcgatctgc ctgtttatgc ggtcgatacg gacggcgatg attcattggt gtctcagcta   5160
aacgtgacca tcggtgatga tgtccaaatc atgcaagacg gtacgttaga tatcatcgag   5220
ccaaatctgg ctgatggaac aatcacaacc agcactattg atgtgatgcc aaaccaaagt   5280
gctgatggtg cgacgatcac tcagtttact tatgacggtc agctaagaac gcttgatcaa   5340
aatgacactg gcgaacagca gttcagcttc acagaaggcg agttgtttat caccccttgaa   5400 ggtgaagtgc gctttgagcc aaaccgagac ctagaccaca ccgcgagtga agatattgtt   5460
aagtcgattg tggtcacttc aagtgatttc gataacgact ctctgacttc taccgtaacg   5520
ctgaccatta ctgatggtga taaccctacg atcgacgtca ttccaagcgt tacccttttct   5580 gaaactaatc tgagtgatgg ctctgctcca agtggcagcg cggtaagctc gactcaaact   5640
attactttta ccaatcaaag tgatgatgtg gttcgttttcc gtattgagcc aacggagttc   5700
aatactaacg atgatcttaa atcgaacggt ttagccgttg agttacgtga agacccggct   5760
gggtcgggtg actacattgg ttttactact agtgcgacga atgtcgaaac cacggtattt   5820
acgctgagtt tttctagcac cacattaggt gaatatacct tcactttgct tgaagcgttg   5880
gaccaccaag atgcccgtgg caacaacgac ctcagttttg aactgcctgt ttatgcggta   5940
gacagtgatg gcgatgattc actgatgtct ccgttaaacg tcaccatcgg cgatgatgtt   6000
caaatcatgc aagacggtac gttagatatc gtcgagccaa ccgtcgcaga tttggccgct   6060
ggcattgtga caactaacac cattgatgtg atgccaaatc aaagtgccga tggcgcgacg   6120
atcactcaat tcacttatga tggccaactt cgaacacttg accaaaatga caatggcgaa   6180
caacagttta gcttcacgga aggtgaacta ttcatcactc ttgaaggtga agtgcgcttt   6240
gagcctaatc gtaatctaga ccacacgctg aacgaagaca tcgtgaaatc gatcgtggtg   6300
acgtctagtg actccgataa cgatgtgttg acctcaaccg tcactctgac cattaccgat   6360
ggtgatatcc caaccattga taatgtgcca acagtgagct tgtcagaaac aagtctgagt   6420
gacggctctt caccaagtgg cagcgcagtt agctcaactc aaaccatcac ttacaccact   6480
caaagtgatg atgtaaccag cttccgtatt gaaccgactg agttcaatgt tggcggtgct   6540
ctcaaatcaa atggattggc ggttgagctg aaggccgatc caaccactcc gggcggctac   6600
atcggctttg tgactgatgg ttcgaacgtt gaaactaacg tgttcacgat tagcttctcg   6660
gataccaatt taggtcaata caccttcacc ttgcttgaag cgttggatca tgcggatagc   6720
```

```
cttgcaaata acgatctgag ctttgatctg ccagtctacg ccgtcgatag tgatggcgat    6780
gattcactgg tgtctcaact caatgtaacc atcggtgatg atgttcaaat catgcaaggt    6840
ggtacgttag atatcactga gccaaacctt gcagacggca caaccacaac taacaccatc    6900
gatgtgatgc cagaacaaag tgccgatggt gcgacgatca ctcagtttac gtatgacggg    6960
caagttcgca ctctggatca aactgacaat ggtgagcagc aatttagctt cactgaaggc    7020
gagttgttca tcactcttca aggtgacgtg cgtttcgaac ccaatcgcaa cctagatcac    7080
acagctagcg aagacatcgt gaagtcgata gtggtgactt caagcgattc agataacgat    7140
gtggtgacgt caacggtcac tctgactatt actgatggtg atctcccaac cattgatgca    7200
gtgccaagcg ttactctgtc tgaaactaat cttagtgacg gctctgcgcc aagtggcagc    7260
gcagtcagtc aaactgagac catcaccttt accaatcaaa gtgatgatgt ggcgagtttc    7320
cgtattgagc caaccgagtt taatgtgggc ggtgcactga atcgaatgg gtttgcggtt      7380 gagataaaag aagactctgc taatccgggt acttacattg gctttattgc caatggttcg    7440
agcgctgaaa tcccagtgtt cacgattgct ttctctacga gtacgttggg tgaatacacc    7500
tttactctgc ttgaagcgtt agaccatgcg gatggtttag ataagaacga tctgagcttt    7560
gagcttccgg tttacgcggt tgatacagac ggtgatgatt cattggtatc tcagcttaat    7620
gtgaccattg tgatgatgt tcaaatcatg caagatggta cgttagacgt tatcgagcca      7680
aatcttgcag acggcacaat cacaaccaac accattgatg tgatgcccga gcaaagtgct    7740
gatggtgcga cgatcactca gtttacttat gacggtcagc taagaacgct tgatcaaaat    7800
gacactggtg aacagcagtt cagcttcaca gaaggcgagt tgtttatcac ccttgaaggt    7860
gaagtgcgct ttgaacctaa tcgcgatcta gaccattccg ttagcgaaga catcgtgaag    7920
tcgatagtag tgacttcaag cgacttcgat aacgatccgg tgacttcagc cattacgctg    7980
accattactg atggtgataa tccgactatc gattcggtac cgagcgttgt acttgaagaa    8040
gctgatttaa ctgatggctc atcgccaagt ggcagcgcgg ttagtcaaac ggaaaccatc    8100
actttcacta atcaaagtga cgatgttgag aaattccgtt tagaaccaag tgaatttaat    8160
actaacaacg cgctcaagtc cgatggcttg atcattgaga ttcgagagga accaacagga    8220
tccggcaatt atattggttt cacgaccgat atttcgaatg tcgaaaccac tgtgtttaca    8280
ctcgatttca gcagtaccac tttgggtgag tacaccttca cgcttctgga agcgattgac    8340
cacacgcctg ttcaaggcaa taacgatcta acattcaact tgccagtcta cgcggttgat    8400
agcgacggtg atgattcgct aatgtcatca ctatcggtga cgattactga tgatgttcaa    8460
gtgatggtga gtggttcgct tagtatcgaa gagcctactg ttgccgactt ggctgcaggc    8520
acgccaacaa catcagtatt tgatgtatta acatccgcga gtgctgatgg ggcgaccatt    8580
actcagttca cttatgatgg tggggcggta ttaacgcttg atcaaaacga tacaggtgag    8640
cagaagttcg tggttgctga tgggcatta tatatcactc tgcaaggcga tattcgtttc      8700
gaaccaagtc gtaaccttga ccatactggt ggcgatatcg tcaagtcgat agtcgtaact    8760
tcaagtgatt ccgatagcga tcttgtgtct caacggtaa cgctaaccat tactgatggc      8820
gatatcccaa cgattgacac ggtgccaagc gttactctgt cagaaacgaa tctgagcgac    8880
ggatctgctc cgaatgcaag tgcggtaagt tcaactcaaa ccattacctt tactaaccaa    8940
agtgatgacg tgacgagttt ccgtattgaa ccgactgatt ttaatgttgg tggtgctctg    9000
aaatcgaacg gattggcggt cgaactgaaa gcggacccaa ctacaccggg tggctacatc    9060
ggttttgtga ctgatggttc gaacgttgaa actaacgtgt ttacgattag cttctcggat    9120
```

```
accaatttag gtcaatacac cttcaccctg cttgaagcgt tggatcatgt agatggctta    9180
gtgaagaatg atctgacttt tgatcttcct gtttatgcgg ttgatagcga tggtgatgat    9240
tcactggtgt ctcaactgaa tgtgaccatt ggtgatgatg tacaggtcat gcaaaaccaa    9300
gcgcttaata ttattgagcc aacggttgct gatttggctg caggtactcc gacgacagcc    9360
actgttgatg tgatgcctag ccaaagtgcc gatggcgcga caatcactca gtttacttac    9420
gatggcgggg cggcaataac actcgaccaa aacgacaccg gtgaacagaa gtttgtattt    9480
actgaaggtt cactgtttat caccttgcaa ggtgaagtgc gtttcgagcc aaatcgcaat    9540
ctaaaccaca cagcgagcga agacatcgtg aagtcgattg tggtgacttc aagcgattta    9600
gataacgatg tactgacgtc aacggtcact ctgactatta ctgatggtga tatcccaacc    9660
attgatgcag tgccaagcgt tactctgtct gaaactaatc ttagtgacgg ctcagcgcca    9720
agcagcagtg ctgtaagtca aacagagacg attaccttca tcaatcaaag tgatgatgtg    9780
gcgagtttcc gtattgagcc aacagagttc aatgtgggcg gtgcactgaa atcgaatgga    9840
tttgcggttg agataaaaga agattcggct aatccgggta cttatatcgg ttttattacc    9900
gatggttcga atactgaagt tcctgtattc acgattgctt tctctacaag tacgttgggc    9960
gaatacacct tcaccttact tgaagcgcta gaccatgcaa atggcctaga taagaacgat   10020
ctgagttttg atcttcctgt ttatgcggta gacagtgatg gcgatgattc actggtgtct   10080
caactgaatg tgaccattgg tgatgatgtc caaataatgc aagacggtac gttagatatc   10140
actgagccaa atcttgcaga cggaacaatc acaaccaaca ccattgatgt gatgccaaat   10200
cagagtgccg atggtgcgac gatcactgaa ttctcatttg gcggtattgt caaaacactc   10260
gatcaaagca tcgtaggtga gcagcagttt agtttcaccg aaggtgagct attcatcact   10320
cttcaaggtc aagtgcgctt tgaaccaaat cgtgaccttg accactctgc cagcgaagac   10380
atcgtgaagt cgatagtggt tacttcaagt gattttgata acgatcctgt gacttcaacc   10440
gttacgctga ccattaccga tggtgatatt ccaactatcg atgcggtacc aagtgttacg   10500
ctttcagaaa caaacctagc tgatggttct gcgccaagtg gtagtgcggt tagtcaaacg   10560
gagacgatta cttttaccaa tcaaagtgat gatgtggttc gcttccgtct ggaaccaacc   10620
gagttcaata ctaacgatgc acttaaatcg aatggcttag cggtcgaact gcgcgaagaa   10680
cctcaaggct ctggtcagta cattggcttt accaccagtt cgtctaatgt tgagacaaca   10740
gtatttacgt tggactttaa ctccggaacc ttaggtgaat acacatttac tttaatcgaa   10800
gctctggatc atcaagatgc gcgtggcaac aacgatttaa gctttaatct acctgtgtat   10860
gcggtggata gtgatggcga tgactcgtta gtctctcagc ttggcgtgac cattggcgac   10920
gatgtgcagt tgatgcaaga cggcacaatc accagtcgtg agcctgcagc aagtgttgaa   10980
acatcaaata cctttgatgt gatgccaaac caaagtgctg atggagccaa agtcacttca   11040
tttgttttcg atggtaagac tgcagaaagt cttgatttga atgtgaatgg tgaacaagag   11100
ttcgtcttca cggaaggttc ggtatttatt acgacggaag gtgagatacg attcgagccg   11160
gtacgtaatc aaaatcatgc tggtggtgat attaccaagt cgattgaggt gacgtctgtt   11220
gacctcgatg gcgatattgt cacatcgaca gtgacactga agattgttga tggtgacctt   11280
cctactatcg accttgttcc cggaattacg ttatctgaag tggatctggc cgatggctct   11340
gtgccaaccg gtaatccagt gacaatgaca caaaccatta cctacacagc gggtagtgac   11400
gacgtaagcc atttcagaat tgaccctacg cagttcaata cttcagggg tttgaaatcg   11460 aacggcctag atgtcgaaat aaaagagcag ccagctaatt ctggtaatta cattggcttc   11520
```

```
gtcaaagacg gttctaacgt agaaaccaac gtcttcacga tcagcttctc gacgagcaat   11580
ttagggcaat acacgttcac actacttgaa gcgttagatc atgtagatgg attgcaaaac   11640
aatatactaa gcttcgatgt ccctgtttta gcggttgatg cggatggtga tgattctgca   11700
atgtcgccta tgacggttgc gatcaccgat gacgtacaag gtgttcaaga tggcaccttg   11760
agtatcactg agccttcatt agctgatttg gcatcgggta cgccaccaac gacggcaatc   11820
attgatgtta tgccaacgca gagtgctgat ggcgcgaaag taacacagtt tacttacgat   11880
ggtggcacag ctgtaacgtt agacccaagc atcgccacag aacaagtctt taccgtaacc   11940
gatggcttac tgtacatcac cattgaaggg gaggttcgtt ttgagccgag ccgagatcta   12000
gaccattcat ctggcgatat cgtaagaacg attgtcgtca ccaccagtga ttttgataac   12060
gatacagata ccgcggatgt cactttgacg atcaaagacg gtatcaatcc cgttatcaat   12120
gtggttccag atgttaactt atcggaagtt aatctagcgg atggctcgac gccaagtggt   12180
tctgcagtca gttcgactca cacaatcact tacaccgaag gaagtgatga ttttagtcac   12240
tttagaattg cgaccaacga attcaatcct ggcgatctgt tgaaatcaag tggtcttgtt   12300
gttcaactaa aagaagatcc tgcttctgct ggtgattaca ttggttatac cgatgatggt   12360
atgggtaacg ttaccgatgt atttaccatt agctttgata gtgcaaacaa agctcagttt   12420
acatttacct tgattgaggc gcttgatcac cttgatggtg tgctttacaa cgatcttacg   12480
ttccgtttgc ctatctatgc tgttgataca gatgattctg aatcaacaaa gcgcgatgtg   12540
gtggttacga tagaagatga catccagcaa atgcaagatg gcttcttaac cattaccgag   12600
ccaaattctg gtactccaac aacaactacc gttgatgtga tgccaatacc aagtgcagac   12660
ggtgcgacta ttacgcagtt cacgtatgac ggtggttctc caattactct gaatcaaagc   12720
atcagcggcg aacaagagtt tgttttcact gaaggttcac tgtttgtgac actagatggt   12780
gatgtaaggt ttgagccaaa tagaaacctt gatcactctg cgggcgacat tgttaaatcg   12840
attgtgttca cgtcttcaga ctttgataac gacatcttct catcaaaagt cactctcacc   12900
attgttgatg gtgatgggcc aacaatcgac gttgtgccgg gtgtggcatt gtcagaaagc   12960
ttacttgcgg atggttcgac gcctagcgta aatcccgtga gtatgactca aaccattact   13020
tcacttgcaa gtagtgatga tattgctgaa atagtggtgg aagtcgggtt gttcaatacc   13080
aacggcgcgt tgaagtcgga tggttttgtca ctgagtttac gtgaagaccc tgtaaattca   13140
ggcgactaca ttgcatttac tactaatggt tcgggtgttg agaaagttat cttcactctg   13200
gattttgatg atacgaatcc gagtcaatat acgttactc tgcttgaacg tttagaccat   13260
gttgatggct taggaaataa cgatctgagt tttgatcttt ctgtttatgc agaagatacc   13320
gatggtgata tttcagcgtc taaaccgctt acagtcacca tcaccgatga tgttcagctc   13380
atgcaatccg gtgcgctcaa cattactgag ccaaccacag gaacaccgac tacagcagtc   13440
tttgatgtga tgcctgcgca aagtgcagat ggcgcgacaa tcactaagtt tacctatggc   13500
agccaacctg aagagtctct ggtacaaacc gtcacgggtg agcaagaatt tgtgttcact   13560
gaaggttctc tgtttatcaa tcttgaaggt gatgtacgtt tcgaacctaa ccgtaatctc   13620
gatcattcgg gtggtaacat cgttaagacc attacggtga catcggaaga taaagatggc   13680
gatattgtca cttcaacagt gacgctgact attgtagatg gcgcgccacc agtaatagac   13740
acagtaccaa cggttgcatt ggaagaagcg aatctggtcg acggatcttc accgggttta   13800
cctgttagcc aaactgaaat cattactttc acagcaggaa gtgatgatgt gagccacttc   13860
cgtattgatc cggctcaatt caacacatca ggcgatctga aagcggatgg tttggtggtt   13920
```

```
cagttaaaag aagatcctct aaacagcgat aattatattg gttacgttga aagcggcggt   13980
gtccaaacgg atatcttcac catcacctttt agcagcgtgg ttctaggaga gtacacattc   14040
accttgttgg aagagttaga tcacctgcct gtacaaggta acaatgatca aatcttcacc   14100
ttgccagtga tcgcagtcga caaagacaac actgactcag cggtgaaacc tcttacggtg   14160
accattaccg atgatgttcc aaccattact gacaccaccg gcgccagtac gtttgtggtt   14220
gatgaagatg atttgggcac tctggcacaa gcgacgggtt cgtttgtaac cacagaaggt   14280
gcagatcaag tcgaggttta cgaactacgt aatatatcaa cgttggaagc aacgctatcg   14340
tcgggcagtg aagtattaa gatcactgag atcacaggtg ctgctaacac gaccacctac   14400 caagggcga ccgacccaag tggaacgcca attttcacat tagtgctgac tgatgatggt   14460
gcctacacct ttaccttgct tggccctctc aatcacgcta cgacaccgag taacctcgat   14520
acattaacaa taccatttga tgttgttgcc gttgacggtg atggcgatga ttctaaccaa   14580
tatgtattgc caatcgaggt gctagatgat gtgcctgtaa tgacggcgcc gacgggtgaa   14640
acggttgttg atgaagacga tcttactggc attggttccg atcaatctga agatacaatt   14700
atcaatggac tgttcaccgt tgatgaaggt gcggatggcg ttgtgctgta tgagctggtt   14760
gatgaagatt tggttctgac gggcttaacc tctgatggag aaagcttaga gtggctagct   14820
gtttcacaaa acggcacaac atttacttac gttgctcaaa ctgcaacgag taatgaagcg   14880
gtgttcgaga ttattttcga cacctcggat aacagctacc aatttgaatt atttaagcca   14940
ctgaagcacc ctgacggtgc aaacgagaac gcgatagatc ttgatttctc aatcgttgct   15000
gaagattttg atcaagacca atcggatgcg atcggtctaa aaattacggt aaccgatgat   15060
gttccgttag tgacaactca atcgattact cgtcttgaag gtcaggggta tgcaactct   15120 aaagtcgaca tgtttgccaa tgcaacagat gtgggggctg atggcgcggt actgagtcga   15180
attgagggta tctcaaataa tggtgcagat attgttttcc gtagcgggaa caatgggcca   15240
tatagtagcg gcttcgattt aaacagcggt agccaacaag ttcgagtcta cgagcaaaca   15300
aatggcggtg ctgatactcg tgaacttggc cgtctacgca tcaactcaaa tggtgaggtt   15360
gaattcagag ctaacggcta tctcgatcat gacggtgatg acaccatcga cttctcgatt   15420
aacgtgattg ccacagatgg agatttagac acctctgaaa caccgttaga tattacgatt   15480
actgataggg attctacaag aattgcgctg aaagtgacga ccttcgagga tgcgggtaga   15540
gactcaacca taccttacgc aacaggtgat gagccgactc ttgagaatgt tcaagataac   15600
caaaatggtt tgccgaatgc gccagcgcaa gttgcgctgc aagttagtct gtatgaccaa   15660
gataacgctg aatctattgg gcagttgacg attaaaagcc cgaacggagg tgatagtcat   15720
caaggtactt tttattactt tgatggtgct gactacatag aattagtgcc tgagtcaaat   15780
gggagcatta tatttggctc tcctgaactc gaacaaagct tcgctccaaa cccgagtgaa   15840
ccaagacaaa ctatcgcgac gatagacaac ctgttctttg ttccagacca acacgctagt   15900
tcggatgaaa ctggtgggcg agttcgttat gagcttgaaa ttgagaaaaa tggcagtacg   15960
gatcacaccg ttaattcaaa cttcagaatt gagattgaag ctgtagctga tattgcgact   16020
tgggatgatt ccaacagcac gtatcagtat caagtcaacg aagatgaaga caatgtcacg   16080
ttgcagctga acgcagagtc tcaagataac agtaatactg agacgattac ctatgaactt   16140
gaagccgttc aaggcgacgg gaagtttgag ttacttgatc aaaatggcaa tgtgttaacg   16200
cccgttaatg gtgtttatat catcgcatct gctgatatca atagcaccgt agttaaccct   16260
attgataact tctcagggca gattgagttc aaagcgacgg caattacgga agagacgctt   16320
```

```
aacccatacg atgattcaga caacggtgga gcaaacgata agacgacggc tcgttctgtg  16380
gaacaaagta ttgttattga tgtgaccgca gatgcggacc ctggcacatt cagtgttagt  16440
cgaattcaga tcaacgaaga caatatcgat gatccagatt acgtcgggcc tttggacaat  16500
aaagacgcgt tcacgttaga cgaagtcatc accatgacag ggtcggtcga ttctgacagt  16560
tctgaagaac tgtttgtgcg catcagtaat gttacggaag gagctgtgct ttacttctta  16620
ggcaccacga cagtcgttcc gaccatcacg atcaatggtg tggattatca agaaatcgcg  16680
tattccgatt tggctaacgt tgaggttgtt ccaaccaaac acagtaatgt cgatttcacc  16740
ttcgatgtta cgggagtggt caaagatacg gcaaatctat ccacgggcgc ccaaatcgat  16800
gaggagatac taggaactaa aaccgtcaac gttgaagtca aaggcgttgc cgatactcct  16860
tatggtggaa cgaatggcac ggcttggagt gcaattacag atggcactac atctggtgtt  16920
caaaccacga ttcaagagag ccaaaatggt gatacctttg ctgagcttga tttcaccgtg  16980
ttgtcgggag agaagagacc agatactggc actacaccat tagctgacga tgggtcagaa  17040
tcaataaccg ttattctatc gggtataccc gatggggttg ttctagaaga cggtgacggt  17100
acagtgattg accttaactt tgtcggttat gaaaccggac cgggcggtag tcctgactta  17160
tccaaaccta tctacgaagc gaacattact gaggcgggta aaacttcagg cattcgcatc  17220
agacctgtcg actcttcaac cgagaatatt cacattcaag gtaaagtgat tgtgactgag  17280
aacgatggtc acacgcttac gtttgatcaa gaaattcgag tgcttgttat acctcgaatc  17340
gacacatcag caacttatgt caatacgact aacggtgatg aagatacggc tatcaatatt  17400
gattggcacc ctgaaggcac ggattacatt gatgacgatg agcatttcac taagataact  17460
attaatggaa taccactggg tgttactgca gtagtcaacg gtgatgtgac cgttgatgac  17520
tcaaccccag gaacattgat tataacgcct aaagatgctt cccaaactcc tgaacaattt  17580
actcaaattg cattagctaa taacttcatt caaatgacgc ctccggctga ttctagtgca  17640
gattttacgt tgaccaccga acttaaaatg gaagagcgag atcatgagta tacgtctagc  17700
ggcctagagg atgaagatgg tggttatgtc gaagccgatc cagatataac cggaatcatt  17760
aacgttcaag tacgacctgt ggttgaacct ggagatgccg acaacaagat tgtcgtttca  17820
aacgaagatg gctctggaga tctcactacg attacggctg atgctaatgg tgtcattaaa  17880
tttacaacta acagtgataa ccaaacgact gatactaacg gagacgaaat ctgggacggt  17940
gaatacgtcg tccgatacca agaaacggat ttaagcacag tagaagagca agtcgacgaa  18000
gtgattgttc agctgactaa caccgatgga agcgcgttat ctgatgatat tttagggcaa  18060
cttttagtaa ctggtgcctc ttacgaaggc ggtggccgat gggttgtgac caatgaagat  18120
gcctttagcg tcagtgcgcc caatggatta gatttcaccc ctgccaatga tgcggatgat  18180
gtagctactg atttcaatga tatcaagatg acaattttca ctttggtctc agatcctggt  18240
gatgctaaca atgaaacgtc cgcccaagtg caacgcaccg gagaagtaac gctttcttat  18300
cctgaagtgc tgacggcacc tgacaaagtt gccgcagata ttgcgattgt gccagacagt  18360
gttatcgacg ctgttgagga tactcagctt gatctcggcg cggcactcaa cggcattttg  18420
agcttgacgg gtcgcgatga ttctactgac caagtgacgg tgatcatcga tggcactctg  18480
gtcattgatg ctacaacatc attcccaatt agcctgtcgg gaacaagtga tgttgacttt  18540
gtgaatggga aatatgttta cgagacgact gttgagcagg gcgtagccgt cgattcatcg  18600
ggtttgttat tgaatctgcc accaaactac tctggtgact ttaggttgcc aatgaccatc  18660
gtgaccaaag atttacaatc tggtgatgag aagaccttag tgactgaagt tatcatcaaa  18720
```

```
gtcgcaccag atgctgagac ggatccaacg attgaggtga atgtcgtggg ttcgcttgat    18780
gatgccttta atcctgttga taccgacggt caagctgggc aagatccggt gggttacgaa    18840
gacacctata ttcaactcga cttcaattcg accatttcgg atcaggtttc cggcgtcgaa    18900
ggcggccaag aagcgtttac gtccattact ttaacgttgg acgacccttc tataggtgca    18960
ttctatgaca acacgggtac ttcattaggt acatctgtta cgtttaatca ggctgaaata    19020
gcagcgggtg cactcgataa cgtgctcttt agggcaatcg aaaattaccc aacgggtaat    19080
gatattaacc aagtgcaggt taatgtcagc ggtacagtca cagataccgc aacctataat    19140
gatcctgctt ctcctgcggg tacggcaaca gactcagata cttctctac gagtgtcagc    19200 tttgaagtcg ttcctgtggt cgatgacgtg tctgtcactg gaccgggtag cgatcctgat    19260
gttatcgaga ttactggcaa cgaagaccag ctcatttctt tgtcggggac agggcctgta    19320
tcgattgcac tgactgacct tgatggttca gaacagtttg tatcgattaa gttcacagat    19380
gtccctgatg gcttccaaat gcgtgcagat gctggctcga catataccgt gaaaaataat    19440
ggtaatggag agtggagtgt tcaactgcct caagcttcgg ggttgtcatt cgatttaagt    19500
gagatttcga tcttgccgcc taaaaacttc agtggtaccg ctgagtttgg tgtggaagtc    19560
ttcactcaag aatcgttgct gggtgtgcct actgcggcgg caaacttgcc aagcttcaaa    19620
ctgcatgtgg tacctgttgg tgacgatgtt gataccaatc cgactgattc tgtaacaggc    19680
aacgaaggcc aaaacattga tatcgaaatc aatgcgacta ttttggataa agaattgtct    19740
gcaacaggaa gcgggacgta taccgagaat gcgcccgaaa cgcttcgagt tgaagtggcg    19800
ggtgttcctc aagatgcttc tattttctat ccagatggca cgacattggc tagctacgat    19860
ccggcgacgc agctctggac tctcgatgtt ccagctcagt cgttagataa gatcgtatt    19920 aactctggcg aacataatag tgatacaggc aatgtactgg gtatcaatgg tccactgcag    19980
attacggtac gttcagtaga tactgatgct gataatacag agtacctagg tacgccaacc    20040
agcttcgatg tcgatctggt gattgatcct attaacgatc aaccgatctt tgtgaacgta    20100
acgaatattg aaacatcgga agacatcagt gttgccatcg acaactttag tatctacgac    20160
gtcgacgcaa actttgataa tccagatgct ccgtatgaac tgacgcttaa agtcgaccaa    20220
acactgccgg gagcgcaagg tgtgtttgag tttaccagct ctcctgacgt gacgtttgta    20280
ttgcaacctg acggctcatt ggtgattacc ggtaaagaag ccgacattaa taccgcattg    20340
actaatggag ctgtgacttt caaacccgac ccagaccaga actacctcaa ccagactggt    20400
ttagtcacaa tcaatgcaac gctcgatgat ggtggtaata acggtttgat tgacgcggtt    20460
gatccgaata ccgctcaaac caatcaaact accttcacca ttaaggtgac ggaagtgaat    20520
gacgctcctg tggcgactaa cgttgattta ggctcgattg cggaagacgc tcaaatcgtg    20580
attgttgaga gtgacttgat tgcagccagt tctgatctag aaaaccataa tctcacagta    20640
accggtgtga ctcttactca agggcaaggt cagcttacac gctatgaaaa tgctggtggt    20700
gctgatgacg cagcgattac ggggccattc tggatattca ttgcagataa tgatttcaac    20760
ggcgacgtta aattcaatta ctccattatc gatgatggta ccaccaacgg tgtggatgat    20820
tttaaaaccg atagcgctga atcagccttg tagttactg aagtcaatga ccagccagtg    20880
gcatcgaaca ttgatttggg caccatgctt gaagaaggac agctggtcat taaagaggaa    20940
gacctgattt ccgcaaccac tgatccggaa aacgacacga ttactgtgaa cagtttggtg    21000
ctcgatcaag gtcagggcca attacaacgc tttgagaacg tgggcggtgc tgatgatgct    21060
acgatcactg gcccgtactg ggtatttact gcagccaacg aatacaacgg tgatgttaag    21120
```

```
ttcacttata ccgttgagga cgatggtaca accaacggcg ctgatgattt cttaacagat    21180
accggcgaaa ttagcgttgt ggtaacgaaa gtgaatgatc aaccggtggc aacggatatc    21240
gacttaggaa acatccttga agaagggcag ttgatcatca agaggaaga cttaattgct     21300
gctacgagcg atccggaaaa cgacacgatt accgtgacca atctggtgct cgacgaaggc    21360
caaggccagt tacagcgctt tgagaacgtg ggcggtgctg atgacgctat gattactggc    21420
ccgtactgga tatttacggc tgctgatgaa tacaacggta acgttaagtt cacctatacc    21480
gtcgaggatg atggtacaac caacggcgct aatgatttcc taacggatac tgcagagatc    21540
acagcgattg tcgacggagt gaacgatacg cctgttgtta atggtgacag tgtcactacg    21600
attgttgacg aggatgctgg tcagctattg agtggtatca atgtcagtga cccagattat    21660
gtggatgcat tttctaatga cttgatgaca gtcacgctga cagtggatta cggtacattg    21720
aacgtatcac ttccggcagt gacgacagtg atggtcaacg gcaacaacac tggttcggtt    21780
atcttagttg gtactttgag tgacctgaat gcgctgattg atacgccaac cagtccaaac    21840
ggtgtctacc tcgatgcgag cttgtctcca accaatagca ttggcttaga agtaatcgcc    21900
aaagacagcg gtaacccttc tggtatcgcg attgaaactg caccagtggt ttataatatc    21960
gcagtgacac cagtcgctaa tgcgccaacc ttgtctattg atccggcatt taactatgtg    22020
agaaacatta cgaccagctc atctgtggtc gctaatagtg gagtcgcttt agttggaatt    22080
gtcgctgcat tgacggacat tactgaagag ttaacgttga agatcagcga tgttccggat    22140
ggtgttgatg taaccagtga tgtgggtacg gtttcgttgg tgggtgatac ttggatagcg    22200
accgctgatg cgatcgatag tctcagactc gtagagcagt catcattagg taaaccgttg    22260
acccgggta attacccctt gaaagttgag gcgctatctg aagagactga caacaacgat    22320
attgcgatat ctcaaaacat cgatctgaat ctcaatattg ttgccaatcc aatagatctc    22380
gatctgtctt ctgaaacaga cgatgtgcaa cttttagcga gtaacttga tactaacctc     22440
actggcggaa ctggaaatga ccgacttgta ggtggagcgg gtgacgatac gctggttggc    22500
ggtgacggta acgacacact cattggtggc ggcggttccg atattctaac cggtggcaat    22560
ggtatggatt cgtttgtatg gctcaatatt gaagatggc ttgaagacac cattaccgat      22620
ttcagcctgt ctgaaggaga ccaaatcgac ctacgagaag tattacctga gttgaagaat    22680
acatctccag acatgtctgc attgctacaa cagatagacg cgaaagtgga aggggatgat    22740
attgagctta cgatcaagtc tgatggttta ggcactacgg aacaggtgat tgtggttgaa    22800
gaccttgctc ctcagctaac cttaagtggc accatgcctt cggatatttt ggatgcgtta    22860
gtgcaacaaa atgtcatcac tcacggttaa cgcctaattg gaggctagct attagaatct    22920
aacgattaaa ctaaaagcgg accatttaac cataacgaaa gaggccagca ttgctggcct    22980
cttttttgtc actgtataaa tcgtaaagag ttacttaaga gagttgtgga tcaggaactc    23040
ttcttcgacg ccttcaatt tcatctcatc cataatgaag ttcactgtgt tcaacaagcg     23100
ttgttcacct tttggtatca ggtaaccgaa ttgactgttg gtaaacggtg tttcacagcg    23160
tgccgcttca agacgttcgt ccgtcacttg atagaacaga ccttcaggag tttctgtcac    23220
cattacatca actttacctt ccgcaacggc ttgcggaacg tctaggttgt tctcgtaacg    23280
cgtaaagctc gcgtcttgca agttagcatc cgcaaacatc tcattagtcc caccgatatt    23340
gacgccaaca cgcacagaag agaggttcac tttctcaatg ctgttgtatt gttctgcttt    23400
gcctttcgca actaagaaac acttgccaaa ggtcatgtaa ccttgagttt gttctgcgtt    23460
taactgacgc tgcattttac gcgtgatacc gcccatcgcg atgtcgtatt tatcgctgtc    23520
```

```
tagatcggtc agtagatctt tccatgtggt acgaacaatc tgtaattcaa cgcccaactg  23580
ctctgcaaca tgtttggcta cgtcaatgtc ataaccagag taggttttgc cgtcgaagta  23640
agaaaaaggt tgtagtcgc ctgtggtgcc gacgcgaagt gtgcctgatt tttgaatgtc  23700
ttctagctgg tcagcttgta ctacaccaga aagtgccaga gtaatggaag caagtaatag  23760
tgatgttttt ttcattgtaa ttatctgttg tgtttgtgtt gttattcaaa gtaacagaaa  23820
caatcagaga aagagatcaa accattggaa aggttgtaaa agaagataaa acgagggcag  23880
gagataggta acgctattga tttgtgaaca ttgataaaca tgtgtttcat attccatttt  23940
gataaaccgt agacaaacaa aaagcccatg ttatcgaata acatgggctt cattttggtt  24000
taacttgtta gctgcttatt tagctgctta tttagctgtt tagctgttta gctgtttagc  24060
tacttagcaa ctgactcgtt gttcatctta gccggagctt tagatgcgtt aaccagcagg  24120
ataccaacgg tgagtaccat cgaaccacat agtaggaaca acaagcgtcc tgttggttcg  24180
tttggaatca gagccattgc taggataccg aaacctgctg tgctgataag cttaccaagc  24240
attgaacgct gtttagtatc taggttctgc tgctcttcac cttccgctac tagcggcgta  24300
ttccagttag tgaatagttg gtcaacttct ttctcacgtt caggcgatag gccttttgtag  24360 aagcgagaag ttaggatgaa gtaaccacca gtaaacacta cgtgagcagc taagctaaga  24420
ccaactttca agtcgctcca ttcacggcca gtaagcgctg tttccatacc aaataggtgc  24480
tcgatgtctt ctgcttgaag cgagataccg aagatgtaag aaacgaagcc accaacgatt  24540
aacgtagacc aaccagccca gtcaggcgtc ttacgaatcc acataccaag tagtacaggg  24600
ataagcattg ggaagccaat taacgcacct acgttcatta cgatatcgaa caagctcaaa  24660
tgacgtagag agttaatgaa caagccaatc gcgatgatga taatacccat catgatagtg  24720
gttagcttac ttacaataac cagctctttc tgagttgcgt tttgacgtag aatagggctg  24780
tagaagttca ttacaaagat gccagcgtta cggttcaaac ctgaatccat agaagacatt  24840
gttgcagcga acattgctga cataagaaga ccaaccatac ctgctggcat tacgttctgt  24900
acgaatgcta ggtaagcagc atcaccagct ttatcaccca ttgaagcgta ctccaatgcg  24960
aaatcaggca tgaatgcact tacgtaccaa ggtggtagga accagattag tgggccaaca  25020
accataagga tacatgctag gcctgccgct ttacgtgcgt tttcactgtc tttcgcacat  25080
aggtaacggt aagcgttgat gctgttgttc attcaccga actgcttcac gaagatgaat  25140
acaacccaaa gaacgaagat gctcatgtag tttaggttat tacctaacat gaagtcgccg  25200
tcgaaatttg caacgatgtt agttaggcca ccaccgtgga agtaagctgc aaccgcacaa  25260
gtaatcgtaa ccgccatgat aacaagcatt tgcatgaagt cagaagcaac aaccgcccaa  25320
gagccgcctg ttactgccat caatactaga accatacccg ttaccacaat ggttgcttcc  25380
attgggatgt tgaataccgc tgctacgaag atagctagac catttagcca gatacccgca  25440
gagataaggc tgtcaggcat acctgcccat gtgaagaact gttcagacgt tttaccaaag  25500
cgctgacgaa tagcttcgat cgccgttacc acacgaagtt ggcggaactt tggagcgaag  25560
tacatatagt tcatgaagta gccaaaagca ttggctaaga ataggattac aataacgaaa  25620
ccgtcattga acgcgcgtcc tgcggcacct gtaaacgtcc atgctgaaaa ctgtgtcatg  25680
aaggcggttg caccaaccat ccaccacaac attttgccgc cccctctgaa gtaatcacta  25740
gtcgacgtgg tgaacttacg gaacatccaa ccaatagcga ttaaaagaa gaagtaggcg  25800 agaacaacaa aagtatcgat agtcatcttt tcagccttttt aaatatcata attaactggg  25860
cttagattaa cgcgttcaaa ggtttatttg tactacaata tgtctttagt atgatctagg  25920
```

```
tcgcattgat ttttgggtgc acacgataag ttaatttaac ctactgtttt tattgatttt    25980
aattgttttt atgaattgct ctagatccaa gataaattga agttcaaatg tttatatgta    26040
ttacaatata agtaatgagg ctttagttta ccttatttat aagattttaa ttataaccgt    26100
aacaaatatg ctacaactga gcgtggttgt gcgacgacat tcacgttaat ttggaactct    26160
attctggaaa ttcttgtatt aggatttcaa gtgtagctca ttgttttcac ttcgctattt    26220
tgtgtttgtc tgcggttctg tcgccttttcc atgctattga ttaattttttt cgtgctagag    26280 agacgcgtat ttgaatgtt tgtcactgag tgggcgttaa actggacgac gggacactct    26340
ttcggctcac tttgtctatt gtggtcttca gtgcatgcta tgagaaatgt ttgacgacgt    26400
attgaaaagg aatattgtcg gataaaggga tgggtaagga gctggataag cggtagggag    26460
ccccagtaac gcttcgctag atgcatactg aggttgcttg aaagccttac atcactcgtt    26520
cttgcctgtc ttagtcacgg agctgtacga ggccataggg agaacggtga tagggtatgg    26580
ggaaacagaa cgttgattga gcgtgtttta cggttagtca gcgcaataaa cgccagataa    26640
taaaaagccc caccgaggtg aggctttatc acgaaatcta aaacagatta agcgttaacg    26700
tgatcaactg cgtcacgaac aagcttgcct agttcgtccc acttaccttc atcgataagg    26760
ttagttggaa ccatccaagt accgccacac gcaagaacag aagggatcga taggtattca    26820
tcaacattct tcaagcttac gccaccagta ggcatgaatt taacagggta aactgctgtt    26880
agtgctttaa gcatgccagt accgcctgaa ggctcagcag ggaagaactt caacgtgcga    26940
agacccattt ccattgcttg ctcaactagg cttgggttgt taacacccgg tacgattgca    27000 ataccttat cgatacagta ttgaacagta cgtgggttaa aacctgggct tacgatgaaa    27060
tcaacaccag cttcgataga tgcgtcaact tgctcgttag tcagtacagt acctgaaccg    27120
attagcatgt ctgggaattc tttacgcatg atgcgaatcg cttcgattgc acattctgta    27180
cgtagtgtaa tttctgcaca tggcatgcca ttttcaacca acgctttacc tagagggata    27240
gcgtcttcag cacggttgat cgcgattaca ggaattactt ttaggtttgc tagttgttca    27300
tttaatgtcg tcatgaattc tttctcacgt taaatgtggg cctgctttca actaagcaaa    27360
cccttgatta atagttaaag tgcgtaatta tagagacaga tcaggcgtcg cttctagagg    27420
aatgatagca cctggatgct gaatcacggt tcctgccaca atatgacctg caaatgcagc    27480
atcacgagca ctaccgccgc tcaagcgctt ggccaagaag cctgcactga acgagtcgcc    27540
agcggcagtc gtatcaacga tgttgtctac agggttgggt gcaacgtatt gagcgctttg    27600
gctttcaacc actaagcagt cttttcgcgcc acgtttaatg acgatctctt tcacaccaga    27660
ctctgacgta cgtgtaatac attgttcaat gctttcgtcg ccgtatagct cttgctcatc    27720
atcaaacgtc agcagagccg tatctgtgta cttaagcatt ttcaagtacc aagaaatcgc    27780
ttcttgttgg ctttcccaaa gtttaggtcg gtagttattg tcgaagaata cttggccgcc    27840
ttgagctttg aatttgtcta agaagttgaa tagctgcgtg cgaccatttt ctgtcaagat    27900
tgccagcgta ataccactta agtaaatcgc gtcaaaagag aacagcttat caagaagagc    27960
aggcgtgtct tcctgatcaa acatgaactt cgctgcagca tcactacgcc agtagtggaa    28020
actgcgttca ccagtttcat cggtctcgat gtagtaaagc cctggttgtt tgtggtccag    28080
ctgagcaatt aagctcgtgt cgataccttc cgcttgccaa ttttttaaca tgtcggtact    28140
gaatgggtca gtgcctagtg cagttacgta gctcgtgttg atatcttgct cttttgttaa    28200
gcgtgacaag taaagtgcag tattcagcgt atcgccacca aaactttgct taagcccgtc    28260
ttgtttcttt tgtagctcaa ccatgcactc gccaatgacc gcgatgttta atgatttcat    28320
```

| | |
|---|---|
| atgcttacct tagcaactga ggttgcgcta gttattattt taggaaatct tcacgcgcag | 28380 |
| gattgaagat atcaagaagg atgctgtctt gttctagagc aactgcaccg tgcatcatgt | 28440 |
| gtttacgagc gaagtaagca tcgccttctt taagcacttt cttctcgccg tcgatttcag | 28500 |
| cttcgaagct accacgaaca acataaccga tttggtcgtg aatttcgtga gtatgagggt | 28560 |
| ggccaatcgc gcccttatca aagcataggt gtactgccat tagatcgtca gtgtaagcaa | 28620 |
| cgattttacg cttaatgccg ccaccaagtt cttcccatgg attttcatct aggataaaga | 28680 |
| aagagttcat tgtgtatctc ctaatctgtt taaatctttt aagtgttact aacttgcat | 28740 |
| ccatcataag ggaatgagtt caattgtaat acaatatatc taaatttgtg tgatattgat | 28800 |
| caagcgatag tttatatagc gtaaatgaat caacaactta agaattgctt ggtatctggc | 28860 |
| attagttagc tgcatcaatg gcttacggtg aattatgtga ctctactcat catttggcga | 28920 |
| cgaataggta taattaaagc tcatattgta ttactttata tggagtttga aaatttaatc | 28980 |
| aaagtttaag cagataaact ctttattgag ggtgacaaag aatatgacga ctaaaccagt | 29040 |
| attgttgact gaagctgaaa tcgaacagct tcatcttgaa gtgggccgtt ctagcttaat | 29100 |
| gggcaaaacc attgcagcga acgcgaaaga cctagaagca ttcatgcgtt tacctattga | 29160 |
| tgttccaggt cacggtgaag ctgggggtta cgaacataac cgccacaagc aaaattacac | 29220 |
| gtacatgaac ctagctggtc gcatgttctt gatcactaaa gagcaaaaat acgctgactt | 29280 |
| tgttacagaa ttactagaag agtacgcaga caaatatcta acgtttgatt accacgtaca | 29340 |
| gaaaaacacc aacccaacag gtcgtttgtt ccaccaaatc ctaaacgaac actgctggtt | 29400 |
| aatgttctca agcttagctt attcttgtgt tgcttcaaca ctgacacaag atcagcgtga | 29460 |
| caatattgag tctcgcattt ttgaacccat gctagaaatg ttcacggtta aatacgcaca | 29520 |
| cgacttcgac cgtattcaca atcacggtat ttgggcagta gccgctgtgg gtatctgtgg | 29580 |
| tcttgcttta ggcaaacgtg aatacctaga aatgtcagtg tacggcatcg accgtaatga | 29640 |
| tactggcggt ttcctagcgc aagtttctca gctatttgca ccttctggct actacatgga | 29700 |
| aggtccttac taccatcgtt atgcgattcg cccaacgtgt gtgttcgctg aagtgattca | 29760 |
| ccgtcatatg cctgaagttg atatctacaa ctacaaaggc ggcgtgattg gtaacacagt | 29820 |
| acaagctatg cttgcgacag cgtacccgaa cggcgagttc ccggctctga atgatgcttc | 29880 |
| tcgtactatg ggtatcacag acatgggtgt tcaggttgcg gtcagtgttt acagtaagca | 29940 |
| ttactcttct gaaaacggtg tagaccaaaa cattctgggt atggcgaaga ttcaagacgc | 30000 |
| agtatggatg catccatgtg gtcttgagct atctaaagca tacgaagccg catctgcaga | 30060 |
| gaaagaaatc ggcatgcctt tctggccaag tgttgaattg aatgaaggcc ctcaaggtca | 30120 |
| caacggcgcg caaggcttta tccgtatgca ggataagaaa ggcgacgttt ctcaacttgt | 30180 |
| gatgaactac ggccaacacg gcatgggtca cggcaacttt gatacgctgg gtatttcttt | 30240 |
| ctttaaccgc ggtcaagaag tgctacgtga atacggcttc tgtcgttggg ttaacgttga | 30300 |
| gccaaaattc ggcggccgtt acctagacga aaacaaatct tacgctcgtc aaacgattgc | 30360 |
| tcacaatgca gttacgattg atgaaaaatg tcagaacaac tttgacgttg aacgtgcaga | 30420 |
| ctcagtacat ggtttacctc acttctttaa agtagaagac gatcaaatca acggtatgag | 30480 |
| tgcatttgct aacgatcatt accaaggctt tgacatgcaa cgcagcgtgt tcatgctaaa | 30540 |
| tcttgaagaa ttagaatctc cgttattgtt agacctatac cgcttagatt ctacaaaagg | 30600 |
| cggcgaaggc gagcaccaat acgactattc acaccaatat gcgggtcaga ttgttcgcac | 30660 |
| taacttcgaa taccaagcga acaaagagct aaacactcta ggtgacgatt tcggttacca | 30720 |

```
acatctatgg aacgtcgcaa gcggtgaagt gaagggcaca gcaattgtaa gttggctaca    30780
aaacaacacc tactacacat ggctaggtgc aacgtctaac gataatgctg aagtaatatt    30840
tactcgcact ggcgctaacg acccaagttt caatctacgt tcagagcctg cgttcattct    30900
acgcagcaaa ggcgaaacaa cactgtttgc ttctgttgtt gaaacgcacg gttatttcaa    30960
cgaagaattc gagcaatctg tcaatgcacg tggtgttgtg aaagacatca agtcgtggc     31020
tcacaccaat gtcggttcgg tagttgagat caccacagag aaatcaaacg tgacagtgat    31080
gatcagcaac caacttggcg cgactgacag cactgaacac aaagtagaac tgaacggcaa    31140
agtatacagc tggaaaggct tctactcagt agagacaact ttacaagaaa cgaattcaga    31200
agaacttagc actgcagggc aggggaaata ataatgagct atcaaccact tttacttaac    31260
tttgatgaag cagctgaact tcgtaaagaa cttggcaagg atagcctatt aggtaacgca    31320
ctgactcgcg acattaaaca aactgacgct tacatggctg aagttggcat tgaagtacca    31380
ggtcacggtg aaggcggcgg ttacgagcac aaccgtcata agcaaaacta catccatatg    31440
gatctagcag gccgtttgtt ccttatcact gaggaaacaa ataccgaga ttacatcgtt     31500
gatatgctaa cagcgtacgc gacggtatac ccaacacttg aaagcaacgt aagccgtgac    31560
tctaaccctc cgggtaagct gttccaccaa acgttgaacg agaacatgtg gatgctttac    31620
gcttcttgtg cgtacagctg catctaccac acgatctctg aagagcaaaa gcgtctgatc    31680
gaagacgatc ttcttaagca aatgatcgaa atgttcgttg tgacttacgc acacgacttc    31740
gatatcgtac acaaccacgg cttatgggca gtggcagcag taggtatctg tggttacgca    31800
atcaacgatc aagagtctgt agacaaagca ctatacggcc tgaaactaga caaagtcagc    31860
ggcggtttct tagcgcaact agaccaactg ttttcgccag acggctacta catggaaggt    31920
ccttactacc accgtttctc tctgcgtcca atctacctgt tcgcagaagc gattgaacgt    31980
cgtcagcctg aagttggtat ctatgaattc aacgattcag tgatcaagac aacgtcttac    32040
tctgtattca aaacggcatt cccagacggt acattgcctg ctctgaacga ttcatcgaag    32100
acaatctcta tcaacgatga aggcgttatc atggcaacgt ctgtgtgtta ccaccgttac    32160
gagcaaactg aaactctact tggtatggct aaccaccagc aaaacgtttg ggttcatgct    32220
tcaggtaaaa cactgtctga cgcggttgat gcagcagacg acatcaaagc attcaactgg    32280
ggtagcctgt ttgtaaccga cggccctgaa ggcgaaaaag cggcgtaag catccttcgt     32340
caccgtgacg aacaagatga cgacacgatg gcgttgatct ggtttggtca cacggttct     32400
gatcaccagt accactctgc tctagaccac ggtcactacg atggcctgca cctaagcgta    32460
tttaaccgtg gccacgaagt gctgcacgat ttcggcttcg gtcgctgggt aaacgttgag    32520
cctaagtttg gcggtcgtta catcccagag aacaagtctt actgtaagca gacgttgct     32580
cacaacacag taacggttga tcagaaaacg cagaacaact tcaacacagc attggctgag    32640
tctaagtttg gtcagaagca cttcttcgta gcagacgacc agtctctaca aggcatgagc    32700
ggcacaattt ctgagtacta cactggcgta gacatgcaac gcagcgtgat tcttgctgaa    32760
cttcctgagt tcgagaagcc acttgtaatc gacgtatacc gcatcgaagc tgacgctgaa    32820
caccagtacg acctacccgt tcaccactct ggtcagatca tccgtactga cttcgattac    32880
aacatggaaa aaacgcttaa gccgctaggt gaagacaacg gttaccagca cttatggaac    32940
gtggcttcag gcaaagtgaa cgaagaaggt tctctagtaa gctggctaca tgacagcagc    33000
tactacagcc tagtaaccag cgcgaatgcg ggcagcgaag tgattttgc tcgcactggt      33060
gctaacgatc cagacttcaa ccttaagagt gagcctgcgt tcatcttacg tcagtctggt    33120
```

```
caaaaccacg tgtttgcttc tgtactagaa acgcatggtt actttaacga gtctatcgaa    33180
gcctctgtag gcgctcgtgg tctagttaaa tcagtatctg ttgtgggcca taacagtgtc    33240
gggactgttg ttcgcattca gactacttct ggcaacactt accactacgg tatctcaaac    33300
caagctgaag acacgcagca agcaactcac actgttgagt tcgcgggtga gacatactcg    33360
tgggaaggat catttgctca actgtaaatg attaacatac atgccgttta acgatggcat    33420
gtattgatgt ggtgctttgc gggaacgaag catcacattg aattcagtcg tgattgcaaa    33480
tcgttcgttg ataccaacaa cgactgaata catcgggaat aagtcaaacc gagtaactca    33540
ctgcgagttg ctcggttttt ttatgcgtgc tgcttttata agaaggggga aagaggatgg    33600
ggcaacggag cttcccttt ccttcgaatc ttacagagtg ggctaaagta taatttagga     33660
tttaaaaata aagggattca aggatgaagt ggttattggc aatagttgcg atgtctggtg    33720
tcgcattggc ggcagaaaat aagaatgttg aggtgagcag tgagcatttc gtccgttatc    33780
aataccaaga caaaatcagc tatggaaagc tagacaatga cgcagtgtta ccggtcagcg    33840
gcgatctctt tggcgaatat tcggtagcaa aaaattcgat cccgttagag tcggttgagg    33900
tgttactacc gacaaaacca gagaaagtct tcgccgtcgg gatgaacttc gctagccact    33960
tagcctcacc tgccgatgca ccaccgccga tgtttcttaa acttccttct tctttgattc    34020
tcacgggcga agtgattcaa gtgccaccaa agcaagaaa tgttcatttt gaaggcgagc     34080
tggtggttgt gattggtaga gagctcagtc aagccagtga agaagaagcc gaacaagcga    34140 tctttgggcgt cacggtgggc aacgatatta ctgaaagaag ttggcaaggc gccgatttac    34200
aatggctccg agcgaaagct tccgatggtt ttggcccggt tggcaacaca attgtgcgcg    34260
gcattgatta caacaatatt gagttaacca ctcgtgttaa cggtaaagtg gttcaacaag    34320
aaaatacttc gttcatgatc cacaagccaa gaaaagtcgt gagctatttg agctattatt    34380
ttaccctcaa accgggcgat ctaatttca tgggcacgcc aggtagaact tatgctctgt     34440
ccgacaaaga tcaagtgagt gtcacgattg aaggggtagg gactgtggta aatgaagtgc    34500
ggttctgatg gaattgaatt agcgttggga gctacagagc ttatgtctga atttgcagta    34560
cgtagacgac ttgaacctat taatttgaac taggttaact tgtgtagtga ataaactaac    34620 cgttttcgg ttccattatt ttagcccaat tgagtgatgt ttttggaagc gagcagagaa     34680
aacgagaatg acgaacctac atgctcggcg agggttttgt tagtggtgta acacagtgtt    34740
tctagctaag agaaattaga tgctttctaa gtgtttgatt aattgaataa attaacaggt    34800
actatccgct ttgattttac tcaattggct gtaggtttaa atactgttat agtgttcctt    34860
aaataataca taaacataac atataaataa gcgaacttat ggctagcact tttaattcaa    34920
tttcgggctc gaagcgtagc ctgcacgtgc aagtagcacg cgaaatcgct cgaggaattt    34980
tgtctggtga tctgccgcaa ggttctatta ttcctggtga aatggcgttg tgtgaacagt    35040
ttggtatcag ccgaacggca cttcgtgaag cagttaaact actgacctct aaaggtctgt    35100
tagagtctcg ccctaaaatt ggtactcgcg tagtcgaccg cgcatactgg aacttccttg    35160
atcctcaact gattgaatgg atggacggac taaccgacgt agaccaattc tgttctcagt    35220
ttttaggcct tcgccgtgcg atcgagcctg aagcgtgtgc actggcggca aaatttgcga    35280
cagctgaaca acgtatcgag cttttcagaga tcttccaaaa gatggtcgaa gtggatgaag    35340
ctgaagtgtt tgaccaagaa cgttggacag acattgatac tcgtttccat agcttgatct    35400
tcaatgcgac cggtaacgac ttctatctac cgttcggtaa tattctgact actatgttcg    35460
ttaacttcat agtgcattct tctgaagagg gaagcacatg catcaatgaa caccgcagaa    35520
```

```
tctatgaagc tatcatggcc ggtgattgtg acaaggctag aattgcttct gctgttcact    35580
tgcaagatgc caaccaccgt ttggcaacag cataatagaa atgatttaaa gcgcacctga    35640
gccatctcac atcgagatga acaccctcac gttcggataa acgactttaa aaggtatgcc    35700
tagtgcatgc cttttttggt ttttagaccg cgtgttgcac tatctgtagc actattttgg    35760
gtcagtcttt tcgctacgtc tgttaagcta ttcttccacg ttacaacccg ccttgttttt    35820
aacgtctacg taacaatccc caagcatcgt tctaaacaca tttttagact gtctgtacct    35880
gacaagtagt tatgcgacag ccgggatttt tcacctctca gtattctaaa tctgggatta    35940
aacaaacagg gttctcggat ttaatattta gatatttaaa tcgaattcta atgatattac    36000
ccactcgatt tcgtaaaaaa cactggttta ttgtgtgatg aatgatgtgg gtttggtcaa    36060
ggattctctt ttattatttt tgagaacttt atgtttatat gtgtttgatt gtatttgtta    36120
ataagtgtgc aaagtctcac ttttatttta agttgttgtt tttaatgttt aatttatttt    36180
gagtgtttga tcttttgggt ttttacctaa aaccctaaca atttccttaa tggattagcc    36240
atattccatc ctatgtcata tatataatta acttaatcaa tcaaaataag atcaccatca    36300
cttatttgga ttattgtact acaaataaag agtcgaattt cctatagtcc tcgtaacaaa    36360
ttaaaacgga caaaggatac acgatggaac tcaacacgat tattgtcggc atttatttcc    36420
tattcttgat tgcgataggt tggatgttta gaacatttac aagtactact agtgactact    36480
tccgcggggg cggtaacatg ttgtggtgga tggttggtgc aaccgccttt atgacccagt    36540
ttagtgcatg gacattcacc ggtgcagcag gtaaagcgta taacgatggt ttcgctgtag    36600
cggtcatctt cgtagccaac gcatttggtt acttcatgaa ctacgcgtac ttcgcgccga    36660
aattccgtca acttcgcgtt gttacggtaa tcgaagcgat tcgtatgcgt tttggtgcga    36720
ccaacgaaca agtattcact tggtcttcaa tgccaaactc agtggtatct gcgggtgtgt    36780
ggttaaacgc attggcaatc atcgcttcgg gtatcttcgg tttcgacatg aacatgacta    36840
tctgggtgac tggcctagtg gtattggcaa tgtcggtaac aggtggttca tgggcggtaa    36900
tcgcatctga cttcatgcag atggttatca tcatggcggt aacggtaact tgtgcggttg    36960
tagcggttgt tcaaggtggc ggtgttggtg agattgttaa caacttccca gtacaagatg    37020
gtggttcgtt cctttggggc aacaacatca actacctaag catctttacg atttgggcat    37080
tcttcatctt cgttaagcag ttctcaatca cgaacaacat gcttaactct taccgttacc    37140
tagcggctaa agactcaaag aacgctaaga aagctgcact gcttgcttgt gtgttgatgt    37200
tgtgtggtgt gtttatttgg ttcatgcctt cttggttcat tgcaggccaa ggtgttgatt    37260
tatcagcggc ttacccgaat gcaggtaaaa aagcgggtga cttttgcttac ctatacttcg    37320 tacaagagta catgccagca ggtatggttg gtctattagt tgccgcgatg tttgcagcga    37380
caatgtcttc aatggactca ggtctaaacc gtaactcagg tatttttgtt aagaacttct    37440
acgaaacaat cgttcgtaaa ggtcaagcat cagagaaaga gctagtaacc gtatctaaaa    37500
ttacttcagc ggtatttggt ttcgctatta tcctaatcgc acagttcatc aactcattaa    37560
aaggcttaag cctgtttgat acgatgatgt acgtaggtgc gttaatcggc ttccctatga    37620
cgattcctgc attccttggt ttcttcatca agaagactcc ggactgggct ggttggggaa    37680
cgctagttgt tggtggtatc gtatcttatg tggttggttt tgttatcaac gcggagatgg    37740
tagcagcggc gttttggtctt gatactctaa caggacgtga atggtctgat gttaaagttg    37800
cgattggtct gattgctcac atcacgctaa ccggtggctt cttcgtacta tctacgatgt    37860
tctacaagcc tctatcaaaa gaacgtcaag cggatgttga taagttcttt ggcaacttag    37920
```

```
atacccatt agtagctgaa tcggcagagc aaaaagtgtt ggataacaaa caacgtcaaa   37980
tgcttggtaa actgattgcg gtagcgggtg ttggtattat gctgatggct cttctgacta   38040
acccaatgtg ggggcgccta gtcttcatct tatgtggtgt gatagtgggt ggtgtcggta   38100
ttctacttgt gaaagcggtc gatgacggcg gcaagcaagc gaaagcagta accgaaagct   38160
aatacataga aaacgtttat aatagaatgc gacgactcga aagggcgtcg cattttttat   38220
tctgcggaac tggaaaaccg tcaggtgaaa gatatctgac ctaaatcacg aaaactgtac   38280
aaagtggttc aatcgaatcg aaatatattc aattgtccta caataagacg tatattgttg   38340
ctaattcctt tcaatcaact tgaaaaataa gtgagttaga atgagcgacc aaaaatctct   38400
tgatgcaatc aggaagatga agctggaaaa cgatacttca gcaggtaatc ttgtagacct   38460
actccctatc gaagttcaaa cacgtgactt cgacctatca ttcctagaca ccttgagcga   38520
agcacgtccg cgtcttcttg ttcaagctga tcagctagaa gaattcaaag caaaagtgaa   38580
agctgatcaa gctcactgta tgtttgatga tttctacaac aactctaccg ttaagttcct   38640
tgagactgct cctttcgaag agcctcaagc gtacccagct gagacggtag gtaaagcttc   38700
tctatggcgt cctattggc gtcaaatgta cgttgattgc caaatggcac tgaacgcgac   38760
acgtaaccta gcgattgctg gtgttgtaaa agaagacgaa gcgctcattg cgaaagcaaa   38820
agcttggact ctaaaactgt ctacgtacga tccagaaggc gtgacttctc gtggctataa   38880
cgatgaagcg gctttccgtg ttatcgctgc tatggcttgg ggttacgatt ggctacacgg   38940
ctacttcacc gatgaagaac gccagcaagt tcaagatgct ttgattgagc gtctagacga   39000
aatcatgcac cacctgaaag tgacggttga tctattgaac aacccactaa atagccacgg   39060
tgttcgttct atctcttctg ctatcatccc aacgtgtatc gcgctttacc acgatcaccc   39120
gaaagcaggc gagtacattg catacgcgct agaatactac gcagtacatt acccaccatg   39180
gggcggtgta gacggcggtt gggctgaagg tcctgattac tggaacacgc aaactgcatt   39240
cctaggcgaa gcattcgacc tattgaaagc atactgtggt gtagacatgt taacaaaac   39300 attctacgaa aacacaggtg atttcccgct ttactgcatg ccagttcact ctaagcgcgc   39360
gagcttctgt gaccagtctt caatcggcga tttcccaggt ttaaaactgg cttacaacat   39420
caagcactac gcaggtgtta accagaagcc tgagtacgtt tggtactata accagcttaa   39480
aggccgtgat actgaagcac acaccaaatt ctacaacttc ggttggtggg acttcggtta   39540
tgacgatctt cgttttaact tcctttggga tgcacctgaa gagaaagccc catcgaacga   39600
tccactgttg aaagtattcc caatcacggg ttgggctgca ttccacaaca agatgactga   39660
gcgtgataac catattcaca tggtattcaa atgttctccg tttggctcaa tcagccactc   39720
tcacggtgac caaaacgcat ttacgcttca cgcatttggt gaaacgctag cgtcagtaac   39780
aggttactat ggtggtttcg gtgtagacat gcacacgaaa tggcgtcgtc aaacgttctc   39840
taaaaacctg ccactatttg gcggtaaagg tcagtacggc gagaacaaga acacaggcta   39900
cgaaaaccac caagatcgct tttgtatcga agcgggcggc actatctctg acttcgacac   39960
tgaatctgat gtgaagatgg ttgaaggtga tgcaacggca tcttacaagt acttcgttcc   40020
tgaaatcgaa tcttacaagc gtaaagtctg gttcgttcaa ggtaaagtct tcgtaatgca   40080
agacaaggca acgcttttctg aagagaaaga catgacttgg ctaatgcaca caactttcgc   40140
aaacgaagtg gcagacaagt cttttcactat ccgtggcgaa gttgcgcacc tagacgtaaa   40200
cttcatcaac gagtctgctg ataacatcac gtcagttaag aacgttgaag ctttggcga   40260 agttgaccca tacgagttca aagatcttga gatccaccgt cacgtggaag tggaattcaa   40320
```

```
gccatcgaaa gagcacaaca tcctgacgct tcttgttcct aataagaatg aaggcgagca   40380
agttgaagtg tttcacaagc ttgaaggcaa cacgctactg ctaaatgttg acggcgaaac   40440
ggtttcaatc gaactgtaat ccgctgaagt aacagaagtt agatactaaa aactccgagt   40500
gaaagctcgg agttttttg tttggctagc caattaagtt ggagttggat aagtcagtta    40560
agttgtatta gttgacaacg ttggcaaacc gatcaggttg aaagaaaact taattggcca   40620
gagataaata gcttctcgat gccaagtcag tggctgaggg ctaaatctgg acattgatgc   40680
acataaagac cggcatgtac ttagccacta tgctcaatga aatgtgcagg agtcgtataa   40740
gagactcgta tatatcgctc tgttagaaga acagggcgcc aacgcctgtt tcctagcaat   40800
tgttatgact tacttttccg tgaacagtct tatcactggc tgagtaaggg agtagtgaac   40860
tatacatagg taaaggcgta gcttgttctt actaatcgta tgacatttaa cgtacgttat   40920
tcgttattat aatgaacata taatcataca atactatatt tggagtttga acatgactaa   40980
acctgtaatc ggtttcattg gcctaggtct tatgggcggc aacatggttg aaaacctaca   41040
aaagcgcggc taccacgtaa acgtaatgga tctaagcgct gaagctgttg ctcgcgtaac   41100
agatcgcggc aacgcaactg cattcacttc tgctaaagaa ctagctgctg caagtgacat   41160
cgttcagttt tgtctgacaa cttctgctgt tgttgaaaaa atcgtttacg gcgaagacgg   41220
cgttctagcg ggcatcaaag aaggcgcagt actagtagac ttcggtactt ctatccctgc   41280
ttctactaag aaaatcggcg cagctcttgc tgaaaaaggc gcgggcatga tcgacgcacc   41340
tctaggtcgt actcctgcac acgctaaaga tggtcttctg aacatcatgg ctgctggcga   41400
catggaaact ttcaacaaag ttaaacctgt tcttgaagag caaggcgaaa acgtattcca   41460
cctaggggct ctaggttctg gtcacgtgac taagcttgta aacaacttca tgggtatgac   41520
gactgttgcg actatgtctc aagctttcgc tgttgctcaa cgcgctggtg ttgatggcca   41580
acaactgttt gacatcatgt ctgcaggtcc atctaactct ccgttcatgc aattctgtaa   41640
gttctacgcg gtagacggcg aagagaagct aggtttctct gttgctaacg caaacaaaga   41700
ccttggttac ttccttgcac tttgtgaaga gctaggtact gagtctctaa tcgctcaagg   41760
tactgcaaca agcctacaag ctgctgttga tgcaggcatg gtaacaacg acgtaccagt    41820
aatcttcgac tacttcgcta aactagagaa gtaatcgacg tacgacctcg ctagggtatt   41880
gcttgtcttc taggcggcga tacctcagcg aggttcgttt ttatctgcca tacccaaccc   41940
tttgttccct tgttaaaatc ttctacttct acttctactt ctacttcaat ttcctcagtt   42000
acacctaatc aaaactctgt ttaactctgt tactgcctca attcctattt ttttctatat   42060
ctatttctaa cggtaaattc aaaaccttct agcaccaact cattcactca ttttcctcg    42120
caagctcaaa ctcaacgcgc ttacatgatt gttggtgatg gcttaacacc gctcgtatat   42180
cggtcctgaa aagaaagtaa aaaaaagcc cacacagctg gtgactgtat gggcatgttc    42240
ggacgagccg tctggacaaa caatgagca atagtaagtg aaaaaacgaa taacgagatc    42300
ccccgacagt ttctacgtta acgcgttca atgaccttaa agcggctgct tcaattatca    42360
ctttgaattg aacaaaagca tccagaaaga acttaagtta tgattcaaat acaccatagt   42420
acaagactta ttgtattaca aataaatttt aagattgaat gcctttagtg aatggttagt   42480
tggtagaagt gtgagttaag actcattttt tcactcagct gggtgaggta agaagaaga    42540
gttttcgaaa agatgttatc ggaaaaatga tgagctaatt atctaaaaat cgatctattt   42600
taatgtgtta tgcgtcaatg tttaacttcg aacaaaatcc aaactcataa atgataccta   42660
tgtcacaggg cggttttagc cagttttaat atatcaagat cgctcacaga atgtctggtc   42720
```

```
aattaaacat acaatattaa ttaagttgat ggttgtgacg atggatcggc atgaacaagt    42780
ttcgcttccc gtatcttcga aaatgtaaaa aatggccatt tcattcggat gaaaataata    42840
gacataggtt gatatggatg atgagtttta tgaattcaaa attgtctcta gggtttaaag    42900
gaaaattgat tttaatggta gcggtcgtca gttctagtgc tttggcattt acgaactggt    42960
ttacgcttaa cttggccact gaacaggtaa accaaacgat ttataacgag attgatcact    43020
cgcttacgat agaaatcaat caaatagaaa gtaccgttca gcgcaccatc gataccgtta    43080
actctgttgc acaagagttc atgaaatccc cttaccaagt gccgaatgaa gcactcatgc    43140
attatgccgc taagcttggt ggcattgaca agattgtggt gggttttgac gacggccgtt    43200 cttataccctc tcgcccttca gagtctttcc ctaacggtgt tggaataaaa gaaaaataca    43260
atccaaccac tcgaccttgg tatcaacaag cgaaattgaa atcaggctta tcttttagtg    43320
gtctgttttt cactaagagt actcaagtgc ctatgatcgg tgtgacctac tcataccaag    43380
atcgtgtcat catggccgat atacgctttg acgatttgga aacgcagctt gaacagctgg    43440
acagcatcta cgaagccaaa ggcattatca tcgacgaaaa ggggatggtg gtcgcttcaa    43500
caatcgaaaa cgtgcttccg caaaccaata tatcttctgc agacactcaa atgaaactca    43560
acagtgccat tgaacagcct gatcaattca ttgagggtgt gattgatggt aaccagagaa    43620
tcttgatggc caagaaagtg gatattggca gccagaaaga gtggttcatg atctccagta    43680
ttgaccctga actcgcgctc aatcagctga atggcgtgat gtcgagtgcg cgcatcctta    43740
tcgtcgcttg tgtacttggc tcggtgatat tgatgatttt acttctgaat cgtttctacc    43800
gcccaatcgt gtcactgcgc aaaatcgtcc acgatctatc acaaggtaac ggagacctca    43860
ctcaaaggct tgctgagaag gggaatgatg acttagggca tatcgccaaa gacatcaact    43920
tgttcattat cggcttacaa gagatggtta aggatgtgaa atacaagaac tcggatctcg    43980
ataccaaggt actgagtatt cgcgaaggtt gtaaagaaac cagcgatgta ctgaaagttc    44040
atactgatga aacggttcaa gtggtctctg cgattaacgg cttgtctgaa gcatcaaacg    44100
aagtagagaa gagttctcag tcggcggcag aagcagcaag agaggccgct gtgttcagtg    44160
atgagacgaa acagattaac acggtgacgg aaacctatat cagtgatctt gagaagcaag    44220
tctgcaccac ttctgatgac attcgctcaa tggccaatga acgcagagc atccagtcta    44280 tcgtgtctgt gattggcgga attgcggaac aaactaattt gctggcattg aatgcgtcaa    44340
ttgaagcggc gagggcgggt gaacatggtc gaggtttcgc ggtggttgct gatgaagtcc    44400
gtgcgctagc caaccgaacg caaatcagta cctctgaaat tgatgaagcg ttatctggct    44460
tgcagtctaa atcagatggt ttggttaaat ctattgagtt gaccaaaagt aactgtgaac    44520
tgactcgcgc tcaagttgtt caagctgtaa acatgttggc gaagctaacc gagcagatgg    44580
aaacagtaag tcgtttttaat aatgacattt cgggttcgtc tgttgagcaa aacgcccta    44640 ttcagagcat tgctaagaac atgcataaga ttgaaagctt tgttgaggag cttaataaac    44700
taagccaaga tcagttaact gaatcagcag aaatcaaaac acttaacggt agcgttagtg    44760
aattgatgag cagctttaag gtttaatgtt tctaatattt atacctaaaa atcaacatgt    44820
taagtttagt tgttgatctg aaggccactc aataactgtc gagtttagag tggcttttct    44880
gcgttgttct tgagtctaac tctacgtaat atccgttcat ttcacttcat ttgccgcatc    44940
tcacattctg ataaatagac aattgacata aaatagtaca aatatacatt gtcactctac    45000
tcttatggat aagtgagata aatgtgaata agccaatctt tgtcgtcgta ctcgcttcgc    45060
ttacgtatgg ctgcggtgga agcagctcca gtgactctag tgacccttct gataccaata    45120
```

```
actcaggagc atcttatggt gttgttgctc cctatgatat tgccaagtat caaaacatcc   45180
tttccagctc agatcttcag gtgtctgatc ctaatggaga ggagggcaat aaaacctctg   45240
aagtcaaaga tggtaacttc gatggttatg tcagtgatta tttttatgct gacgaagaga   45300
cggaaaatct gatcttcaaa atggcgaact acaagatgcg ctctgaagtt cgtgaaggag   45360
aaaacttcga tatcaatgaa gcaggcgtaa gacgcagtct acatgcggaa ataagcctac   45420
ctgatattga gcatgtaatg gcgagttctc ccgcagatca cgatgaagtg accgtgctac   45480
agatccacaa taaaggtaca gacgagagtg gcacgggtta tatccctcat ccgctattgc   45540
gtgtggtttg ggagcaagaa cgagatggcc tcacaggtca ctactgggca gtcatgaaaa   45600
ataatgccat tgactgtagc agtgccgctg actcttcgga ttgttatgcc acttcatata   45660
atcgctacga tttgggagag gcggatctcg ataacttcac caagtttgat ctttctgttt   45720
atgaaaatac cctttcgatc aaagtgaacg atgaagttaa agtcgacgaa gacatcacct   45780
actggcagca tctactgagt tactttaaag cgggtatcta caatcaattt gaaaatggtg   45840
aagccacggc tcactttcag gcactgcgat acaccaccac acaggtcaac ggctcaaacg   45900
attgggatat taatgattgg aagttgacga ttcctgcgag taaagacact tggtatggaa   45960
gtgggggtga cagtgcggct gaactagaac ctgagcgctg cgaatcgagc aaagaccttc   46020
tcgccaacga cagtgatgtc tacgacagcg atattggtct ttcttatttc aataccgatg   46080
aagggagagt gcactttaga gcggatatgg gatatggcac ctctaccgaa aattctagct   46140
atattcgctc tgagctcagg gagttgtatc aaagcagtgt tcaaccggat tgtagcacca   46200
gcgatgaaga tacaagttgg tatttggacg acactagaac gaacgctacc agtcacgagt   46260
taaccgcaag cttacgaatt gaagactacc cgaacattaa taaccaagac ccgaaagtgg   46320
tgcttgggca aatacacggt tggaagatca atcaagcatt ggtgaagttg ttatgggaag   46380
gcgagagtaa gccagtaaga gtgatactga actctgattt tgagcgcaac aaccaagact   46440
gtaaccattg tgacccgttc agtgtcgagt taggtactta ttcggcaagt gaagagtggc   46500
gatatacgat tcgagccaat caagacggta tctacttagc gactcatgat ttagatggaa   46560
ctaatacggt ttctcattta atcccttggg gacaagatta cacagataaa gatggggaca   46620
cggtctcgtt gacgtcagat tggacatcga cagacatcgc tttctatttc aaagcgggca   46680
tctacccaca atttaagcct gatagcgact atgcgggtga agtgtttgat gtgagctttta   46740
gttctctaag agcagagcat aactgagttc tctgatgttt ggttagccat gtcggtaatg   46800
aagaagacca tattgatgcc tacaatgtgg tcttttttttg ttttttggaca cttacagtga   46860
tgtgttttga aggacaaatg ttctgctcga atcatgcaaa tacacacgat tacagctcgc   46920
ttgttctgcc cttgctagct catttcgcat tccaaattct tatatattgt cttttatcaa   46980
taggaaatgt gatccagtta aagtatggaa aaatcggaaa gtgttcctag tctcatttat   47040
ccaacgaagt gttttatttg tattataaga ttacgtaata ttttcgtgtt atcgcaaata   47100
ctgataggtg aatcgcctta tagctcgtgt ttgctgattt agctttcact tacgaacgct   47160
gtctttgtat tataataatg gattaaatat gaaacaaatt actctaaaaa ctttactcgc   47220
ttcttctatt ctacttgcgg ttggttgtgc gagcacgagc acgcctactg ctgattttcc   47280
aaataacaaa gaaactggtg aagcgcttct gacgccagtt gctgtttccg ctagtagcca   47340
tgatggtaac ggacctgatc gtctcgttga ccaagaccta actacacgtt ggtcatctgc   47400
gggtgacggc gagtgggcaa cgctagacta tggttcagta caggagtttg acgcggttca   47460
ggcatctttc agtaaaggta atcagcgcca atctaaattt gatatccaag tgagtgttga   47520
```

```
tggcgaaagc tggacaacgg tactagaaaa ccaactaagc tcaggtaaag cgatcggcct    47580
agagcgtttc caatttgagc cagtagtgca agcacgctac gtaagatacg ttggtcacgg    47640
taacaccaaa aacggttgga acagtgtgac tggattagcg gcggttaact gtagcattaa    47700
cgcatgtcct gctagccata tcatcacttc agacgtggtt gcagcagaag ccgtgattat    47760
tgctgaaatg aaagcggcag aaaaagcacg taaagatgcg cgcaaagatc tacgctctgg    47820
taacttcggt gtagcagcgg tttacccttg tgagacgacc gttgaatgtg acactcgcag    47880
tgcacttcca gttccgacag gcctgccagc gacaccagtt gcaggtaact cgccaagcga    47940
aaactttgac atgacgcatt ggtacctatc tcaaccattt gaccatgaca aaaatggcaa    48000
acctgatgat gtgtctgagt ggaaccttgc aaacggttac caacaccctg aaatcttcta    48060
cacagctgat gacggcggcc tagtattcaa agcttacgtg aaaggtgtac gtacctctaa    48120
aaacactaag tacgcgcgta cagagcttcg tgaaatgatg cgtcgtggtg atcagtctat    48180
tagcactaaa ggtgttaata agaataactg ggtattctca agcgctcctg aatctgactt    48240
agagtcggca gcgggtattg acggcgttct agaagcgacg ttgaaaatcg accatgcaac    48300
aacgacgggt aatgcgaatg aagtaggtcg ctttatcatt ggtcagattc acgatcaaaa    48360
cgatgaacca attcgtttgt actaccgtaa actgccaaac caagaaacgg gtgcggttta    48420
cttcgcacat gaaagccaag acgcaactaa agaggacttc taccctctag tgggcgacat    48480
gacggctgaa gtgggtgacg atggtatcgc gcttggcgaa gtgttcagct accgtattga    48540
cgttaaaggc aacacgatga ctgtaacgct aatacgtgaa ggcaaagacg atgttgtaca    48600
agtggttgat atgagcaaca gcggctacga cgcaggcggc aagtacatgt acttcaaagc    48660
cggtgtttac aaccaaaaca tcagcggcga cctagacgat tactcacaag cgactttcta    48720
tcagctagat gtatcgcacg atcaatacaa aaagtaatct aatcgaataa cacttaatat    48780
taaaggtatt gcaatagcct ccagcctag ggttttggagg ctttttttgtg cctgctgttg    48840 gttgggctta agcgtatgat ttaattgagt aggagagggg tagttatcag ttgcacagag    48900
tttaagacat tatcattaag ctcattcagt attaacttta gtcattatca gtcactatta    48960
ccccccaagc gccgatcaca attaacctag ctcatgatta atctcagtta ccaataggct    49020
agcctgtagc ggattcaaac ccaaataatg tcgtgatgtt tatcggaatc accatagctc    49080
gaaaactttg accttgttct caaggctttg ccaatgcacg aacgtattat gtgcgtggtt    49140
tactaataag cgttagctcg gctgactact catactgttc ttgaaaccgt tactcttggg    49200
ttgtttagct agactcctag caacagccat aaatagtgct ctaactcttt cataattaga    49260
agggtagggt tagccattct attggttcca atgctttatg aaatactagg cgggctcaag    49320
tcgatgatca aacgactcta acagcttaag gttatgcgct tttgcgttag ttacctgcag    49380
gccgtaaatg ccctgattgt agttgtacgg tgacgctgaa taataatttg taggattagt    49440
atagaactga gagactttgt ctatctatga tcgatacagg ctttgagagg gctgatcag    49500 tagaaagaca gaatgacaat tagcactaga gttatttgg tttttaatta gagttaataa    49560
aatagatatt tggtttgtta aatttaatcg tgtcataagc tctgtgtttt aaaaaataaa    49620
aaaagccata gcagttgcta tggctttgaa taagtcaggt tctaaggtaa gcaaacagca    49680
agtcaacttg tctgttttga tattcttagt cttagttcaa gatattttct ttacctgccg    49740
cagtgttcac tgcagatggt tgtgcgtaga tggctgtatt tcttatatct ttaccgttgt    49800
cagctgaaag tagggtttg taaccattga acgtattgct ttcaatagtg acattacagc    49860
caaggttatc atcactattc tttatgacgg cactgctaga atcaccaact ttaattccgc    49920
```

```
ccacatcact accaccagag ttaatagtga atgtattatt tgtgatttgt gaaccaaatc    49980
gcccgttgtc actactacag ttaatacgaa ttgcattatt ttggaaactg ccacttaaac    50040
cgacaaattc gctattgtct aatgtaaagt aacctcgaga gaataaccaa cttgctttt     50100 tagtacctag atcatcttcg gtaatgccgt ttgcatcgaa ctttaggttt tcaagtgcta    50160
caggatctga atctttacca attttaccaa taacgatcgc accagtttca ttatctgaag    50220
taccagctga ctccctacca aaacacccgg ccaaattgtc gttagcaaaa gtcatgtttt    50280
tgatacctgc accgggtgca gtgacatcaa taagcatc tccggtaatg gttgctaaac     50340
cagcaccatc aattgtgaca gctttattta gctcaataac accggtatca aacgtacctt    50400
cagatgataa atcaataatc gcgccatctt ctgctgatgc aatcgcagcg ttcacatcat    50460
cgactgattt aggttttcca tcatcggcat tttctaatgc agttataaca gattcatctg    50520
taatctctgt tgctgagtaa gctgtttcta cgtcatcttt ttcacaggtc atatctagct    50580
gttgctcagt cactgtgtaa gtacagtcct taccttcaaa ggaaacaaca ccttcttctt    50640
cagcagtata tattgaactc tcaaaagtga agccattagc tacgtctcca ctgtaaatgc    50700
ttagagcacg agtaccttcc tcattattat caaagcgata tggtgaagtt ccgctgagtg    50760
actgtgcagc aacagcacca cctgtcagat cccaatagac gttttctata gagtaaactt    50820
caacaggttc aacagggtct gttccgcctg gatctgttgg aataggtaaa ccatcactgt    50880
tacaaccaaa taataaacct gtcgaaagag cgacagctgt agcgacttta gaaatttgca    50940
taaaatattc tctttatgat attaaatcca tatgtaaatc acataagaaa tagataatga    51000
atagtcgtta aatatttatt aggatgaagc taattctgat tagaacatcc tattatttaa    51060
aataaagtaa ttaaaatatg cccaaataaa ttacaagagg agagggctat tttatattt     51120 gactatttta ttattagaat gagtaagcaa taccaacacg gtatttagct tcacgatctt    51180
ttgaagatga actgatatca gaagaccaga tttcagcaaa aggtttccaa gaaccgaact    51240
tgtagtttac ctttaagcca gcatcccatt cccagtcatc actattataa agaagtacgt    51300
tatccaaaga ttttacatag tttgcttcgt aagaaaggcc aagcttaggt agagattcaa    51360
ttttgtaaga gcccgtcagt gtaactttag acttttgagc tgattctaaa cgctcgccag    51420
tttcagaatc tttgtcgcca aattgtgtgt ggttacggaa gtcagcatat tcatgacggt    51480
aacgaatagc agttgttaaa cccatatctg ctttatagcc aacgcggaac tgaggttaa     51540 acgtaacctt tttcatcttc cagtcgccat cgttagcatt aggctcatcc caatcccaag    51600
caataggcat acccatttgt agataccaat tattgtctat tttgtatgtc gcagtgttat    51660
cgatctccat accatagatg taccaattgc catcgtaaaa actctggctg tttgctgatt    51720
taacagaacc tgaatcttca tcatagtaag agtcatcacc gtggaactta agttctagac    51780
cagtagagtg cttccacttg tctgacagct taaagctttc acctagctta actcggtgtt    51840
gatggcgagc gtctacgtga gccgtatcac cattagtctt tgtataatcc gtcgcagcac    51900
gatactcgta acgataatca agagatgcac cagcagctgt gcccgctaaa agagtacatg    51960
caacagctgc agcaattttt gtaacagaat tcatacctt gtctcactat tatttttta     52020 ttttggatac atccaatgta cccctgactc acaaaccaat accttacatg gtattaaatt    52080
aatgtatgac aaatatggta tttattccta gggtagattt ctgtgagatc tatcaaaagt    52140
tccgactaat ggcctatttta tatagctaaa tgttatgaat atctcaattt aaggcttacc    52200
aatcaaatca atcatgactc agttctcata ttaacaaacc ttgtaagctc agttggttgt    52260
atgtgttaaa ataatacaaa tataagaata ttcccacact ttcatatcga tgttctagtt    52320
```

```
gttgtggttt aaacataacg gcgcatgttg agggatatag atataaacca ccgccaaatg    52380
tttggtaaaa gttaaaagat ggcgaaatgt aaattctatt tattggttgg tttatttaag    52440
tcgaagagaa aatatttagt actaattcgt gttcaaaagt agtttctgtg ctgagagtgt    52500
actcagtatc tgttaacaat aaaggatgag tcatgtttaa gaaaaacata ttagcagtgg    52560
cgttattagc gactgtgcca atggttactt tcgcaaataa cggtgtttct taccccgtac    52620
ctgccgataa attcgatatg cataattgga aaataaccat accttcagat attaatgaag    52680
atggtcgcgt tgatgaaata gaaggggtcg ctatgatgag ctactcacat agtgatttct    52740
tccatcttga taaagacggc aaccttgtat ttgaagtgca gaaccaagcg attacgacga    52800
aaaactcgaa gaatgcgcgt tctgagttac gccagatgcc aagaggcgca gatttctcta    52860
tcgatacggc tgataaagga aaccagtggg cactgtcgag tcacccagcg gctagtgaat    52920
acagtgctgt gggcggaaca ttagaagcga cattaaaagt gaatcacgtc tcagttaacg    52980
ctaagttccc agaaaaatac ccagctcatt ctgttgtggt tggtcagatt catgctaaaa    53040
aacacaacga gctaatcaaa gctggaaccg gttatgggca tggtaatgaa ccactaaaga    53100
tcttctataa gaagtttcct gaccaagaaa tgggttcagt attctggaac tatgaacgta    53160
acctagagaa aaaagatcct aaccgtgccg atatcgctta tccagtgtgg ggtaacacgt    53220
gggaaaaccc tgcagagccg ggtgaagccg gtattgctct tggtgaagag tttagctaca    53280
aagtggaagt gaaaggcacc atgatgtacc taacgtttga aaccgagcgt cacgataccg    53340
ttaagtatga aatcgacctg agtaagggca tcgatgaact tgactcacca acgggctatg    53400
ctgaagatga ttttttactac aaagcgggcg catacggcca atgtagcgtg agcgattctc    53460
accctgtatg ggggcctggt tgtggcggta ctggcgattt cgctgtcgat aaaaagaatg    53520
gcgattacaa cagtgtgact ttctctgcgc ttaagttaaa cggtaaatag cacatagcat    53580
aaccaatagt ctagctagac gcagtcctta aggaatattt tcgaagacca cttaaccgaa    53640
tgttgagtgg tctttttgtt ttatatgagt tttaagatga acttggtatt aatgtgacct    53700
tggtatcaat gagggtgtac gtgaagccta ccaatgaaag gtacagctaa acaatacaa    53760
ccttgtcaaa agacaaggtt gcattcagaa agcgtaggaa gattttagga cgacaactcg    53820
atacggagtt tagtcataca tcaactcttt ggctttgtcg gcatcaaact ctttaagaga    53880
cttttcgagcc aagtgacgga atgggaaagc tttcacgact tcttcgaatg gttggatggc    53940
aaatgcccaa aagatagaac cgtctaatcc aaagatgatc aatgcacaca atggaattga    54000
aattaccccat tgaccagtaa agttgatttt gaagactgcg gtcgttttte ctagggctct    54060
taatacattc ccatgaaccg                                                54080

<210> SEQ ID NO 3
<211> LENGTH: 22890
<212> TYPE: DNA
<213> ORGANISM: Vibrio splendidus

<400> SEQUENCE: 3
gtgctttgtg acaacggggg atgtatggat attgaagttt cgcgccaggt tgcggtagtt      60
gaagctacga gtggagatgt cgtcgtagtt aagccagacg gcagcgcaag aaaagtttca     120
gttggcgata ccatccgtga aaatgagatc gtgattacgg ccaacaagtc agagcttgta     180
ttaggcgttc agaatgattc gattccggtt gcagagaatt gcgtcggttg tgttgatgaa     240
aacgctgcat gggtagatgc cccaatagct ggtgaggtta ttttgacttt acagcaagca     300
gacgcagaaa ccttcactga agacgacctt gctgcaattc aagaagccat tttaggtggt     360
```

```
gccgatccga ctcaaatctt agaagcaacg gctgctggtg gcggactagg ttctgcaaat    420
gctggctttg tgacgattga ctataactac actgaaactc atccatcgac tttctttgag    480
accgctggtc tagcagaaca aactgttgat gaagacagag aagaattcag atctatcact    540
cgttcatcag gtggccaatc aatcagtgaa acactgactg aaggctccat atctggcaat    600
acctatcccc aatctgtaac aacgacagaa acgattattg ctggtagttt agctctcgcc    660
cctaactctt tcattccaga aactttatcc ctcgcttcac tacttagtga attaaacagc    720
gacattactt caagtggtca gtccgttatc ttcacctatg acgcgacgac taattctatc    780
gttggtgttc aagataccga cgaagtatta cgtatcgaca ttgatgccgt cagtgttggc    840
aataacattg agctttctct aaccacaacg atttcccagc cgattgatca tgtaccgtcg    900
gttggcggtg tcaggtttc ttacactggc gatcaaatag atattgcctt tgatattcaa    960
ggtgaagaca ccgctgggaa cccgctagca acacccgtta acgcacaagt ttcagtgttt   1020
gacgggatag atccgtctgt tgaaagtgtc aatatcacta acgttgaaac tagcagcgcg   1080
gcaatcgaag ggacgttctc aaatattggt agtgataacc ttcaatcagc cgtatttgat   1140
gcaagtgcac tggaccagtt tgatgggttg ctcagtgata tcaaaacac gcttgcgaga   1200 cttttctgatg atggaacaac gattactctg tccatccaag gtcgaggtga ggttgttctc   1260
actatctctc tagataccga tggcacctat aaattcgagc agtctaatcc gatagaacaa   1320
gtgggtaccg attcactgac gttcgctttg ccaatcacga ttaccgattt tgaccaagat   1380
gttgtaacca atacgatcaa cattgccatt actgatggcg atagccctgt tattactaat   1440
gttgacagta ttgatgttga tgaagcgggc attgttggcg gctcacaaga gggcacggcg   1500
ccagtgtctg gcactggcgg tatcaccgcg gacattttg aaagtgacat cattgaccat   1560
tatgagctag aacccactga atttaatact aatggcacct tggtttcaaa tggcgaggct   1620
gtgctacttg agttgattga tgaaaccaac ggtgtaagaa cttacgaagg ttatgttgag   1680
gtcaatggtt cgagaattac ggtctttgac gttaaaattg atagcccttc attgggcaac   1740 tatgagtta atctttatga agaactttct catcaaggcg ctgaagatgc gctgttaact   1800
tttgcattgc caatttatgc tgttgatgca gatggcgacc gttctgcact gtctggaggt   1860
tcgaacacac cagaagctgc tgagatcctc gttaatgtta agacgatgt cgttgaatta   1920 gttgataagg ttgaatcagt caccgagccg accttagcgg gcgatactat tgtttcgtat   1980
aacctgttca attttgaagg cgcagatggt tctacaattc aatcgtttaa ctacgacggt   2040
gttgattact cactcgatca aagcctgctc cccgatgcta cccagatttt cagttttact   2100
gaaggtgtcg tcactatctc attaaacggt gacttcagtt ttgaagtcgc tcgtgatatc   2160
gaccactcaa gcagtgaaac tatcgtcaaa cagttctcat ttttagccga agatggtgat   2220
ggggatactg atagttcgac gcttgagtta agtattaccg atggccaaga tccgatcatt   2280
gatttgatcc cgcctgtgac tctctctgaa accaaccta atgacggctc tgctcccagc   2340
ggaagtacag ttagcgcaac cgagacgatt accttaccg caggcagcga cgatgtagca   2400
agtttccgta ttgaaccaac agagtttaat gtgggcggtg cacttaaatc gaatggatt   2460 tcggttgaga taaaagaaga ttcggctaat ccgggtactt acattggctt tattaccaac   2520
ggttcgggcg ctgaaatccc agtgtttacg attgctttct ctacgagcac attgggtgaa   2580
tacaccttta ctctgcttga agcgttagac catgtagatg gtttagataa gaacgatctg   2640
agctttgatc tgcctatta tgcggttgat acggacggcg acgattcatt ggtgtctcag   2700
cttaatgtga ctatcggtga tgatgttcaa atcatgcaag acggtacgtt agatatcacc   2760
```

```
gagccaaatc ttgctgacgg tacaatcaca accaacacca ttgatgtaat gccaaatcaa    2820
agtgctgatg gcgcgacgat cactcggttc acttatgacg gtgtcgtaaa cacactggat    2880
caaagtattt caggagaaca gcagttcagc ttcacagaag gcgaactgtt tatcaccctt    2940
gaaggtgaag tgcgctttga gcctaatcgc gatctagacc actcagtgag tgaagatatc    3000
gtgaagtcga ttgtggtgac ttcaagcgac ttcgataacg atccggtgac ttcaaccatt    3060
acgctgacga tcactgatgg tgataacccg acgattgatg ttattccaag tgttacgctt    3120
tctgaaatta acctgagcga tggctctgct ccaagtggca gcgcggtaag ctcgactcaa    3180
actattactt ttaccaatca aagtgatgat gtggttcgtt tccgtattga gtcaacggag    3240
ttcaatacta acgatgatct taaatcgaac ggtttagctg ttgagttacg tgaagacccg    3300
gcagggtcgg gtgactacat tggttttacg accagtgcga cgaacgtaga aactccagta    3360
ttcacattaa gctttaattc tggatcatta ggtgaataca cgttcacact catcgaagcg    3420
ttggaccacc aagatgcccg tggcaacaac gacctcagtt ttgatttacc tgtttacgcg    3480
gtagatagtg atggcgatga ttcattggtg tctccgttaa acgtcactat cggtgatgat    3540
gttcaaatca tgcaagatag tacgttagat atcgtcgagc caaccgtcgc agatttggcc    3600
gctggcacag tgacaactaa caccattgat gtgatgccaa atcaaagtgc cgatggcgca    3660
acggtgacgc aattcactta tgatggccag cttcgaacac ttgaccaaaa tgacaatggt    3720
gagcagcaat ttagcttcac agaaggtgaa ctgttcatca cgcttcaagg tgatgtgcgc    3780
tttgagccta tcgtaatctc agaccacaca ctcagcgaag acatcgtgaa atcaatcgtg    3840
gtgacatcta gcgattccga taacgatgtg ttgacctcaa ccgtcactct gaccattacc    3900
gatggtgata tcccaaccat tgataatgtt ccaactgtga acttgtctga aactaatctg    3960
agtgatggct ctgcacctag cggaagcgcg gtgagttcaa ctcaaactat tacttacacc    4020
actcaaagtg atgatgtgac aagcttccgt attgaaccga ctgaatttaa tgttggtggc    4080
gctctcacat caaacggatt ggcagtcgag ttaaaagctg atccaaccac accgggtggc    4140
tacatcggtt ttgtgactga tggttcgaac gttgaaacta cgtgttcac gattagcttc    4200 tcagatacca atttaggcca gtacaccttc accttacttg aagcgttaga ccatgtggat    4260
ggtttagcga acaatgatct gacctttgat ctgcctgttt atgcagttga tagcgatggc    4320
gacgattcac tggtgtctca gttaaatgta accatcggtg atgatgttca aatcatgcaa    4380
ggtggtacgt tagatatcac tgagccaaat cttgcagacg gcacaattac aaccaatacc    4440
atcgatgtga tgccagagca aagcgccgat ggtgcgacga tcactcagtt cacttatgac    4500
ggtcaagttc gaacactgga tcaaacggac aatggtgagc agcaatttag cttcactgaa    4560
ggcgagttgt tcatcactct tcaaggtgac gtgcgtttcg aacccaatcg caacctagat    4620
cacacagcta gcgaagatat cgtgaagtcg atagtggtga cttcaagcga tttagataac    4680
gatgtggtga cgtcaacggt cactctgacg attactgatg gtgatatccc aaccattgat    4740
gcagtgccaa gcgttactct gtctgaaatc aatcttagtg acggctctgc gccaagtggc    4800
actgcagtta gtcaaactga gacgattacc ttcaccaatc aaagtgatga tgtgaccagt    4860
ttccgtattg agccaataga gttcaatgtg ggcggtgcac tgaaatcgaa tggatttgcg    4920
gttgagataa aagaagattc ggctaatccg ggtacttaca ttggctttat taccaacggt    4980
tcgggcgctg aaatcccagt gtttacgatt gctttctcta cgagctcatt gggtgaatac    5040
accttractc tgcttgaagc gttagaccat gtagatggtt tagataagaa cgatctgagc    5100
ttcgatctgc ctgtttatgc ggtcgatacg gacggcgatg attcattggt gtctcagcta    5160
```

```
aacgtgacca tcggtgatga tgtccaaatc atgcaagacg gtacgttaga tatcatcgag   5220
ccaaatctgg ctgatggaac aatcacaacc agcactattg atgtgatgcc aaaccaaagt   5280
gctgatggtg cgacgatcac tcagtttact tatgacggtc agctaagaac gcttgatcaa   5340
aatgacactg gcgaacagca gttcagcttc acagaaggcg agttgtttat cacccttgaa   5400
ggtgaagtgc gctttgagcc aaaccgagac ctagaccaca ccgcgagtga agatattgtt   5460
aagtcgattg tggtcacttc aagtgatttc gataacgact ctctgacttc taccgtaacg   5520
ctgaccatta ctgatggtga taaccctacg atcgacgtca ttccaagcgt taccctttct   5580
gaaactaatc tgagtgatgg ctctgctcca agtggcagcg cggtaagctc gactcaaact   5640 attacttta ccaatcaaag tgatgatgtg gttcgtttcc gtattgagcc aacggagttc   5700
aatactaacg atgatcttaa atcgaacggt ttagccgttg agttacgtga agacccggct   5760
gggtcgggtg actacattgg ttttactact agtgcgacga atgtcgaaac cacggtattt   5820
acgctgagtt tttctagcac cacattaggt gaatatacct tcactttgct tgaagcgttg   5880
gaccaccaag atgcccgtgg caacaacgac ctcagttttg aactgcctgt ttatgcggta   5940
gacagtgatg gcgatgattc actgatgtct ccgttaaacg tcaccatcgg cgatgatgtt   6000
caaatcatgc aagacggtac gttagatatc gtcgagccaa ccgtcgcaga tttggccgct   6060
ggcattgtga caactaacac cattgatgtg atgccaaatc aaagtgccga tggcgcgacg   6120
atcactcaat tcacttatga tggccaactt cgaacacttg accaaaatga caatggcgaa   6180
caacagttta gcttcacgga aggtgaacta ttcatcactc ttgaaggtga agtgcgcttt   6240
gagcctaatc gtaatctaga ccacacgctg aacgaagaca tcgtgaaatc gatcgtggtg   6300
acgtctagtg actccgataa cgatgtgttg acctcaaccg tcactctgac cattaccgat   6360
ggtgatatcc caaccattga taatgtgcca acagtgagct tgtcagaaac aagtctgagt   6420
gacggctctt caccaagtgg cagcgcagtt agctcaactc aaaccatcac ttacaccact   6480
caaagtgatg atgtaaccag cttccgtatt gaaccgactg agttcaatgt tggcggtgct   6540
ctcaaatcaa atggattggc ggttgagctg aaggccgatc caaccactcc gggcggctac   6600
atcggctttg tgactgatgg ttcgaacgtt gaaactaacg tgttcacgat tagcttctcg   6660
gataccaatt taggtcaata caccttcacc ttgcttgaag cgttggatca tgcggatagc   6720
cttgcaaata acgatctgag ctttgatctg ccagtctacg ccgtcgatag tgatggcgat   6780
gattcactgg tgtctcaact caatgtaacc atcggtgatg atgttcaaat catgcaaggt   6840
ggtacgttag atatcactga gccaaaacctt gcagacggca caaccacaac taacaccatc   6900
gatgtgatgc cagaacaaag tgccgatggt gcgacgatca ctcagtttac gtatgacggg   6960
caagttcgca ctctggatca aactgacaat ggtgagcagc aatttagctt cactgaaggc   7020
gagttgttca tcactcttca aggtgacgtg cgtttcgaac ccaatcgcaa cctagatcac   7080
acagctagcg aagacatcgt gaagtcgata tggtgacttt caagcgattc agataacgat   7140
gtggtgacgt caacggtcac tctgactatt actgatggtg atctcccaac cattgatgca   7200
gtgccaagcg ttactctgtc tgaaactaat cttagtgacg gctctgcgcc aagtggcagc   7260
gcagtcagtc aaactgagac catcacccttt accaatcaaa gtgatgatgt ggcgagtttc   7320
cgtattgagc caaccgagtt taatgtgggc ggtgcactga atcgaatgg gtttgcggtt   7380 gagataaaag aagactctgc taatccgggt acttacattg gctttattgc caatggttcg   7440
agcgctgaaa tccagtgtt cacgattgct ttctctacga gtacgttggg tgaatacacc   7500
tttactctgc ttgaagcgtt agaccatgcg gatggtttag ataagaacga tctgagcttt   7560
```

-continued

```
gagcttccgg tttacgcggt tgatacagac ggtgatgatt cattggtatc tcagcttaat    7620
gtgaccattg gtgatgatgt tcaaatcatg caagatggta cgttagacgt tatcgagcca    7680
aatcttgcag acggcacaat cacaaccaac accattgatg tgatgcccga gcaaagtgct    7740
gatggtgcga cgatcactca gtttactat gacggtcagc taagaacgct tgatcaaaat    7800
gacactggtg aacagcagtt cagcttcaca aaggcgagt tgtttatcac ccttgaaggt    7860
gaagtgcgct ttgaacctaa tcgcgatcta gaccattccg ttagcgaaga catcgtgaag    7920
tcgatagtag tgacttcaag cgacttcgat aacgatccgg tgacttcagc cattacgctg    7980
accattactg atggtgataa tccgactatc gattcggtac cgagcgttgt acttgaagaa    8040
gctgatttaa ctgatggctc atcgccaagt ggcagcgcgg ttagtcaaac ggaaaccatc    8100
actttcacta atcaaagtga cgatgttgag aaattccgtt tagaaccaag tgaatttaat    8160
actaacaacg cgctcaagtc cgatggcttg atcattgaga ttcgagagga accaacagga    8220
tccggcaatt atattggttt cacgaccgat atttcgaatg tcgaaaccac tgtgtttaca    8280
ctcgatttca gcagtaccac tttgggtgag tacaccttca cgcttctgga agcgattgac    8340
cacacgcctt tcaaggcaa taacgatcta acattcaact tgccagtcta cgcggttgat    8400
agcgacggtg atgattcgct aatgtcatca ctatcggtga cgattactga tgatgttcaa    8460
gtgatggtga gtggttcgct tagtatcgaa gagcctactg ttgccgactt ggctgcaggc    8520
acgccaacaa catcagtatt tgatgtatta acatccgcga gtgctgatgg ggcgaccatt    8580
actcagttca cttatgatgg tggggcggta ttaacgcttg atcaaaacga tacaggtgag    8640
cagaagttcg tggttgctga tggggcatta tatatcactc tgcaaggcga tattcgtttc    8700
gaaccaagtc gtaaccttga ccatactggt ggcgatatcg tcaagtcgat agtcgtaact    8760
tcaagtgatt ccgatagcga tcttgtgtct tcaacggtaa cgctaaccat tactgatggc    8820
gatatcccaa cgattgacac ggtgccaagc gttactctgt cagaaacgaa tctgagcgac    8880
ggatctgctc cgaatgcaag tgcggtaagt tcaactcaaa ccattacctt tactaaccaa    8940
agtgatgacg tgacgagttt ccgtattgaa ccgactgatt ttaatgttgg tggtgctctg    9000
aaatcgaacg gattggcggt cgaactgaaa gcggacccaa ctacaccggg tggctacatc    9060
ggttttgtga ctgatggttc gaacgttgaa actaacgtgt ttacgattag cttctcggat    9120
accaatttag gtcaatacac cttcaccctg cttgaagcgt tggatcatgt agatggctta    9180
gtgaagaatg atctgacttt tgatcttcct gtttatgcgg ttgatagcga tggtgatgat    9240
tcactggtgt ctcaactgaa tgtgaccatt ggtgatgatg tacaggtcat gcaaaaccaa    9300
gcgcttaata ttattgagcc aacggttgct gatttggctg caggtactcc gacgacagcc    9360
actgttgatg tgatgcctag ccaaagtgcc gatggcgcga caatcactca gtttacttac    9420
gatggcgggg cggcaataac actcgaccaa aacgacaccg gtgaacagaa gtttgtattt    9480
actgaaggtt cactgtttat caccttgcaa ggtgaagtgc gtttcgagcc aaatcgcaat    9540
ctaaaccaca cagcgagcga agacatcgtg aagtcgattg tggtgacttc aagcgattta    9600
gataacgatg tactgacgtc aacggtcact ctgactatta ctgatggtga tatcccaacc    9660
attgatgcag tgccaagcgt tactctgtct gaaactaatc ttagtgacgg ctcagcgcca    9720
agcagcagtg ctgtaagtca aacagagacg attaccttca tcaatcaaag tgatgatgtg    9780
gcgagtttcc gtattgagcc aacagagttc aatgtgggcg gtgcactgaa atcgaatgga    9840
tttgcggttg agataaaaga agattcggct aatccgggta cttatatcgg ttttattacc    9900
gatggttcga atactgaagt tcctgtattc acgattgctt tctctacaag tacgttgggc    9960
```

```
gaatacacct tcaccttact tgaagcgcta gaccatgcaa atggcctaga taagaacgat   10020
ctgagttttg atcttcctgt ttatgcggta gacagtgatg gcgatgattc actggtgtct   10080
caactgaatg tgaccattgg tgatgatgtc caaataatgc aagacggtac gttagatatc   10140
actgagccaa atcttgcaga cggaacaatc acaaccaaca ccattgatgt gatgccaaat   10200
cagagtgccg atggtgcgac gatcactgaa ttctcatttg gcggtattgt caaaacactc   10260
gatcaaagca tcgtaggtga gcagcagttt agtttcaccg aaggtgagct attcatcact   10320
cttcaaggtc aagtgcgctt tgaaccaaat cgtgaccttg accactctgc cagcgaagac   10380
atcgtgaagt cgatagtggt tacttcaagt gattttgata acgatcctgt gacttcaacc   10440
gttacgctga ccattaccga tggtgatatt ccaactatcg atgcggtacc aagtgttacg   10500 cttttcagaaa caaacctagc tgatggttct gcgccaagtg gtagtgcggt tagtcaaacg   10560
gagacgatta cttttaccaa tcaaagtgat gatgtggttc gcttccgtct ggaaccaacc   10620
gagttcaata ctaacgatgc acttaaatcg aatggcttag cggtcgaact gcgcgaagaa   10680
cctcaaggct ctggtcagta cattggcttt accaccagtt cgtctaatgt tgagacaaca   10740
gtatttacgt tggactttaa ctccggaacc ttaggtgaat acacatttac tttaatcgaa   10800
gctctggatc atcaagatgc gcgtggcaac aacgatttaa gctttaatct acctgtgtat   10860
gcggtggata tgatggcga tgactcgtta gtctctcagc ttggcgtgac cattggcgac   10920
gatgtgcagt tgatgcaaga cggcacaatc accagtcgtg agcctgcagc aagtgttgaa   10980
acatcaaata cctttgatgt gatgccaaac caaagtgctg atggagccaa agtcacttca   11040
tttgttttcg atggtaagac tgcagaaagt cttgatttga atgtgaatgg tgaacaagag   11100
ttcgtcttca cggaaggttc ggtatttatt acgacggaag gtgagatacg attcgagccg   11160
gtacgtaatc aaaatcatgc tggtggtgat attaccaagt cgattgaggt gacgtctgtt   11220
gacctcgatg gcgatattgt cacatcgaca gtgacactga agattgttga tggtgacctt   11280
cctactatcg accttgttcc cggaattacg ttatctgaag tggatctggc cgatggctct   11340
gtgccaaccg gtaatccagt gacaatgaca caaaccatta cctacacagc gggtagtgac   11400
gacgtaagcc atttcagaat tgaccctacg cagttcaata cttcagggt tttgaaatcg   11460 aacggcctag atgtcgaaat aaaagagcag ccagctaatt ctggtaatta cattggcttc   11520
gtcaaagacg gttctaacgt agaaaccaac gtcttcacga tcagcttctc gacgagcaat   11580
ttagggcaat acacgttcac actacttgaa gcgttagatc atgtagatgg attgcaaaac   11640
aatatactaa gcttcgatgt ccctgtttta gcggttgatg cggatggtga tgattctgca   11700
atgtcgccta tgacggttgc gatcaccgat gacgtacaag gtgttcaaga tggcaccttg   11760
agtatcactg agccttcatt agctgatttg gcatcgggta cgccaccaac gacggcaatc   11820
attgatgtta tgccaacgca gagtgctgat ggcgcgaaag taacacagtt tacttacgat   11880
ggtggcacag ctgtaacgtt agacccaagc atcgccacag aacaagtctt taccgtaacc   11940
gatggcttac tgtacatcac cattgaaggg gaggttcgtt ttgagccgag ccgagatcta   12000
gaccattcat ctggcgatat cgtaagaacg attgtcgtca ccaccagtga tttgataac   12060 gatacagata ccgcggatgt cactttgacg atcaaagacg gtatcaatcc cgttatcaat   12120
gtggttccag atgttaactt atcggaagtt aatctagcgg atggctcgac gccaagtggt   12180
tctgcagtca gttcgactca cacaatcact tacaccgaag gaagtgatga ttttagtcac   12240
tttagaattg cgaccaacga attcaatcct ggcgatctgt tgaaatcaag tggtcttgtt   12300
gttcaactaa aagaagatcc tgcttctgct ggtgattaca ttggttatac cgatgatggt   12360
```

```
atgggtaacg ttaccgatgt atttaccatt agctttgata gtgcaaacaa agctcagttt    12420
acatttacct tgattgaggc gcttgatcac cttgatggtg tgctttacaa cgatcttacg    12480
ttccgtttgc ctatctatgc tgttgataca gatgattctg aatcaacaaa gcgcgatgtg    12540
gtggttacga tagaagatga catccagcaa atgcaagatg gcttcttaac cattaccgag    12600
ccaaattctg gtactccaac aacaactacc gttgatgtga tgccaatacc aagtgcagac    12660
ggtgcgacta ttacgcagtt cacgtatgac ggtggttctc caattactct gaatcaaagc    12720
atcagcggcg aacaagagtt tgttttcact gaaggttcac tgtttgtgac actagatggt    12780
gatgtaaggt ttgagccaaa tagaaacctt gatcactctg cgggcgacat tgttaaatcg    12840
attgtgttca cgtcttcaga ctttgataac gacatcttct catcaaaagt cactctcacc    12900
attgttgatg tgatgggcc aacaatcgac gttgtgccgg tgtggcatt gtcagaaagc    12960 ttacttgcgg atggttcgac gcctagcgta aatcccgtga gtatgactca aaccattact    13020
tcacttgcaa gtagtgatga tattgctgaa atagtggtgg aagtcgggtt gttcaatacc    13080
aacggcgcgt tgaagtcgga tggtttgtca ctgagtttac gtgaagaccc tgtaaattca    13140
ggcgactaca ttgcatttac tactaatggt tcgggtgttg agaaagttat cttcactctg    13200
gattttgatg atacgaatcc gagtcaatat acgtttactc tgcttgaacg tttagaccat    13260
gttgatggct taggaaataa cgatctgagt tttgatcttt ctgtttatgc agaagatacc    13320
gatggtgata tttcagcgtc taaaccgctt acagtcacca tcaccgatga tgttcagctc    13380
atgcaatccg gtgcgctcaa cattactgag ccaaccacag gaacaccgac tacagcagtc    13440
tttgatgtga tgcctgcgca aagtgcagat ggcgcgacaa tcactaagtt tacctatggc    13500
agccaacctg aagagtctct ggtacaaacc gtcacgggtg agcaagaatt tgtgttcact    13560
gaaggttctc tgtttatcaa tcttgaaggt gatgtacgtt tcgaacctaa ccgtaatctc    13620
gatcattcgg gtggtaacat cgttaagacc attacggtga catcggaaga taaagatggc    13680
gatattgtca cttcaacagt gacgctgact attgtagatg gcgcgccacc agtaatagac    13740
acagtaccaa cggttgcatt ggaagaagcg aatctggtcg acggatcttc accgggttta    13800
cctgttagcc aaactgaaat cattactttc acagcaggaa gtgatgatgt gagccacttc    13860
cgtattgatc cggctcaatt caacacatca ggcgatctga agcggatgg tttggtggtt    13920 cagttaaaag aagatcctct aaacagcgat aattatattg gttacgttga aagcggcggt    13980
gtccaaacgg atatcttcac catcacccttt agcagcgtgg ttctaggaga gtacacattc    14040
accttgttgg aagagttaga tcacctgcct gtacaaggta acaatgatca aatcttcacc    14100
ttgccagtga tcgcagtcga caaagacaac actgactcag cggtgaaacc tcttacggtg    14160
accattaccg atgatgttcc aaccattact gacaccaccg cgccagtac gtttgtggtt    14220 gatgaagatg atttgggcac tctggcacaa gcgacgggtt cgtttgtaac cacagaaggt    14280
gcagatcaag tcgaggttta cgaactacgt aatatatcaa cgttggaagc aacgctatcg    14340
tcgggcagtg aaggtattaa gatcactgag atcacaggtg ctgctaacac gaccacctac    14400
caagggggga ccgacccaag tggaacgcca ttttcacat tagtgctgac tgatgatggt    14460
gcctacacct ttaccttgct tggccctctc aatcacgcta cgacaccgag taacctcgat    14520
acattaacaa taccatttga tgttgttgcc gttgacggtg atggcgatga ttctaaccaa    14580
tatgtattgc caatcgaggt gctagatgat gtgcctgtaa tgacggcgcc gacgggtgaa    14640
acggttgttg atgaagacga tcttactggc attggttccg atcaatctga agatacaatt    14700
atcaatggac tgttcaccgt tgatgaaggt gcggatggcg ttgtgctgta tgagctggtt    14760
```

```
gatgaagatt tggttctgac gggcttaacc tctgatggag aaagcttaga gtggctagct    14820
gtttcacaaa acggcacaac atttacttac gttgctcaaa ctgcaacgag taatgaagcg    14880
gtgttcgaga ttattttcga cacctcggat aacagctacc aatttgaatt atttaagcca    14940
ctgaagcacc ctgacggtgc aaacgagaac gcgatagatc ttgatttctc aatcgttgct    15000
gaagattttg atcaagacca atcggatgcg atcggtctaa aaattacggt aaccgatgat    15060
gttccgttag tgacaactca atcgattact cgtcttgaag gtcaggggta tggcaactct    15120
aaagtcgaca tgtttgccaa tgcaacagat gtggggctg atggcgcggt actgagtcga    15180
attgagggta tctcaaataa tggtgcagat attgttttcc gtagcgggaa caatgggcca    15240
tatagtagcg gcttcgattt aaacagcggt agccaacaag ttcgagtcta cgagcaaaca    15300
aatggcggtg ctgatactcg tgaacttggc cgtctacgca tcaactcaaa tggtgaggtt    15360
gaattcagag ctaacggcta tctcgatcat gacggtgatg acaccatcga cttctcgatt    15420
aacgtgattg ccacagatgg agatttagac acctctgaaa caccgttaga tattacgatt    15480
actgataggg attctacaag aattgcgctg aaagtgacga ccttcgagga tgcgggtaga    15540
gactcaacca taccttacgc aacaggtgat gagccgactc ttgagaatgt tcaagataac    15600
caaaatggtt tgccgaatgc gccagcgcaa gttgcgctgc aagttagtct gtatgaccaa    15660
gataacgctg aatctattgg gcagttgacg attaaaagcc cgaacggagg tgatagtcat    15720
caaggtactt tttattactt tgatggtgct gactacatag aattagtgcc tgagtcaaat    15780
gggagcatta tatttggctc tcctgaactc gaacaaagct tcgctccaaa cccgagtgaa    15840
ccaagacaaa ctatcgcgac gatagacaac ctgttctttg ttccagacca acacgctagt    15900
tcggatgaaa ctggtgggcg agttcgttat gagcttgaaa ttgagaaaaa tggcagtacg    15960
gatcacaccg ttaattcaaa cttcagaatt gagattgaag ctgtagctga tattgcgact    16020
tgggatgatt ccaacagcac gtatcagtat caagtcaacg aagatgaaga caatgtcacg    16080
ttgcagctga acgcagagtc tcaagataac agtaatactg agacgattac ctatgaactt    16140
gaagccgttc aaggcgacgg gaagtttgag ttacttgatc aaaatggcaa tgtgttaacg    16200
cccgttaatg gtgtttatat catcgcatct gctgatatca atagcaccgt agttaaccct    16260
attgataact tctcagggca gattgagttc aaagcgacgg caattacgga agagacgctt    16320
aacccatacg atgattcaga caacggtgga gcaaacgata gacgacggc tcgttctgtg    16380 gaacaaagta ttgttattga tgtgaccgca gatgcggacc ctggcacatt cagtgttagt    16440
cgaattcaga tcaacgaaga caatatcgat gatccagatt acgtcgggcc tttggacaat    16500
aaagacgcgt tcacgttaga cgaagtcatc accatgacag ggtcggtcga ttctgacagt    16560
tctgaagaac tgtttgtgcg catcagtaat gttacgaag gagctgtgct ttacttctta    16620
ggcaccacga cagtcgttcc gaccatcacg atcaatggtg tggattatca agaaatcgcg    16680
tattccgatt tggctaacgt tgaggttgtt ccaaccaaac acagtaatgt cgatttcacc    16740
ttcgatgtta cgggagtggt caaagatacg gcaaatctat ccacgggcgc ccaaatcgat    16800
gaggagatac taggaactaa aaccgtcaac gttgaagtca aaggcgttgc cgatactcct    16860
tatggtggaa cgaatggcac ggcttggagt gcaattacag atggcactac atctggtgtt    16920
caaaccacga ttcaagagag ccaaaatggt gataccttttg ctgagcttga tttcaccgtg    16980
ttgtcgggag agagaagacc agatactggc actacaccat tagctgacga tgggtcagaa    17040
tcaataaccg ttattctatc gggtataccc gatgggggttg ttctagaaga cggtgacggt    17100
acagtgattg accttaactt tgtcggttat gaaaccggac cgggcggtag tcctgactta    17160
```

```
tccaaaccta tctacgaagc gaacattact gaggcgggta aaacttcagg cattcgcatc    17220
agacctgtcg actcttcaac cgagaatatt cacattcaag gtaaagtgat tgtgactgag    17280
aacgatggtc acacgcttac gtttgatcaa gaaattcgag tgcttgttat acctcgaatc    17340
gacacatcag caacttatgt caatacgact aacggtgatg aagatacggc tatcaatatt    17400
gattggcacc ctgaaggcac ggattacatt gatgacgatg agcatttcac taagataact    17460
attaatggaa taccactggg tgttactgca gtagtcaacg gtgatgtgac cgttgatgac    17520
tcaaccccag gaacattgat tataacgcct aaagatgctt cccaaactcc tgaacaattt    17580
actcaaattg cattagctaa taacttcatt caaatgacgc ctccggctga ttctagtgca    17640
gattttacgt tgaccaccga acttaaaatg gaagagcgag atcatgagta cgtctagc     17700 ggcctagagg atgaagatgg tggttatgtc gaagccgatc cagatataac cggaatcatt    17760
aacgttcaag tacgacctgt ggttgaacct ggagatgccg acaacaagat tgtcgtttca    17820
aacgaagatg gctctggaga tctcactacg attacggctg atgctaatgg tgtcattaaa    17880
tttacaacta acagtgataa ccaaacgact gatactaacg gagacgaaat ctgggacggt    17940
gaatacgtcg tccgatacca agaaacggat ttaagcacag tagaagagca agtcgacgaa    18000
gtgattgttc agctgactaa caccgatgga agcgcgttat ctgatgatat tttagggcaa    18060
cttttagtaa ctggtgcctc ttacgaaggc ggtggccgat gggttgtgac caatgaagat    18120
gcctttagcg tcagtgcgcc caatggatta gatttcaccc ctgccaatga tgcggatgat    18180
gtagctactg atttcaatga tatcaagatg acaattttca ctttggtctc agatcctggt    18240
gatgctaaca atgaaacgtc cgcccaagtg caacgcaccg gagaagtaac gctttcttat    18300
cctgaagtgc tgacggcacc tgacaaagtt gccgcagata ttgcgattgt gccagacagt    18360
gttatcgacg ctgttgagga tactcagctt gatctcggcg cggcactcaa cggcattttg    18420
agcttgacgg gtcgcgatga ttctactgac caagtgacgg tgatcatcga tggcactctg    18480
gtcattgatg ctacaacatc attcccaatt agcctgtcgg gaacaagtga tgttgacttt    18540
gtgaatggga aatatgttta cgagacgact gttgagcagg gcgtagccgt cgattcatcg    18600
ggtttgttat tgaatctgcc accaaactac tctggtgact ttaggttgcc aatgaccatc    18660
gtgaccaaag atttacaatc tggtgatgag aagaccttag tgactgaagt tatcatcaaa    18720
gtcgcaccag atgctgagac ggatccaacg attgaggtga atgtcgtggg ttcgcttgat    18780
gatgccttta tcctgttgta taccgacggt caagctgggc aagatccggt gggttacgaa    18840
gacacctata ttcaactcga cttcaattcg accatttcgg atcaggtttc cggcgtcgaa    18900
ggcggccaag aagcgtttac gtccattact ttaacgttgg acgacccttc tataggtgca    18960
ttctatgaca cacgggtac ttcattaggt acatctgtta cgtttaatca ggctgaaata    19020
gcagcgggtg cactcgataa cgtgctcttt agggcaatcg aaaattaccc aacgggtaat    19080
gatattaacc aagtgcaggt taatgtcagc ggtacagtca cagataccgc aacctataat    19140
gatcctgctt ctcctgcggg tacggcaaca gactcagata ctttctctac gagtgtcagc    19200
tttgaagtcg ttcctgtggt cgatgacgtg tctgtcactg gaccgggtag cgatcctgat    19260
gttatcgaga ttactggcaa cgaagaccag ctcatttctt tgtcggggac agggcctgta    19320
tcgattgcac tgactgacct tgatggttca gaacagtttg tatcgattaa gttcacagat    19380
gtccctgatg gcttccaaat gcgtgcagat gctggctcga catataccgt gaaaaataat    19440
ggtaatggag agtggagtgt tcaactgcct caagcttcgg ggttgtcatt cgatttaagt    19500
gagatttcga tcttgccgcc taaaaacttc agtggtaccg ctgagtttgg tgtggaagtc    19560
```

```
ttcactcaag aatcgttgct gggtgtgcct actgcggcgg caaacttgcc aagcttcaaa    19620
ctgcatgtgg tacctgttgg tgacgatgtt gataccaatc cgactgattc tgtaacaggc    19680
aacgaaggcc aaaacattga tatcgaaatc aatgcgacta ttttggataa agaattgtct    19740
gcaacaggaa gcgggacgta taccgagaat gcgcccgaaa cgcttcgagt tgaagtggcg    19800
ggtgttcctc aagatgcttc tattttctat ccagatggca cgacattggc tagctacgat    19860
ccggcgacgc agctctggac tctcgatgtt ccagctcagt cgttagataa gatcgtatt t   19920 aactctggcg aacataatag tgatacaggc aatgtactgg gtatcaatgg tccactgcag    19980
attacggtac gttcagtaga tactgatgct gataatacag agtacctagg tacgccaacc    20040
agcttcgatg tcgatctggt gattgatcct attaacgatc aaccgatctt tgtgaacgta    20100
acgaatattg aaacatcgga agacatcagt gttgccatcg acaactttag tatctacgac    20160
gtcgacgcaa actttgataa tccagatgct ccgtatgaac tgacgcttaa agtcgaccaa    20220
acactgccgg gagcgcaagg tgtgtttgag tttaccagct ctcctgacgt gacgtttgta    20280
ttgcaacctg acggctcatt ggtgattacc ggtaaagaag ccgacattaa taccgcattg    20340
actaatggag ctgtgacttt caaacccgac ccagaccaga actacctcaa ccagactggt    20400
ttagtcacaa tcaatgcaac gctcgatgat ggtggtaata acggtttgat tgacgcggtt    20460
gatccgaata ccgctcaaac caatcaaact accttcacca ttaaggtgac ggaagtgaat    20520
gacgctcctg tggcgactaa cgttgattta ggctcgattg cggaagacgc tcaaatcgtg    20580
attgttgaga gtgacttgat tgcagccagt tctgatctag aaaaccataa tctcacagta    20640
accggtgtga ctcttactca agggcaaggt cagcttacac gctatgaaaa tgctggtggt    20700
gctgatgacg cagcgattac ggggccattc tggatattca ttgcagataa tgatttcaac    20760
ggcgacgtta aattcaatta ctccattatc gatgatggta ccaccaacgg tgtggatgat    20820
tttaaaaccg atagcgctga aatcagcctt gtagttactg aagtcaatga ccagccagtg    20880
gcatcgaaca ttgatttggg caccatgctt gaagaaggac agctggtcat taaagaggaa    20940
gacctgattt ccgcaaccac tgatccggaa aacgacacga ttactgtgaa cagtttggtg    21000
ctcgatcaag gtcagggcca attacaacgc tttgagaacg tgggcggtgc tgatgatgct    21060
acgatcactg gcccgtactg ggtatttact gcagccaacg aatacaacgg tgatgttaag    21120
ttcacttata ccgttgagga cgatggtaca accaacggcg ctgatgattt cttaacagat    21180
accggcgaaa ttagcgttgt ggtaacggaa gtgaatgatc aaccggtggc aacggatatc    21240
gacttaggaa acatccttga agaagggcag ttgatcatca aagaggaaga cttaattgct    21300
gctacgagcg atccggaaaa cgacacgatt accgtgacca atctggtgct cgacgaaggc    21360
caaggccagt tacagcgctt tgagaacgtg ggcggtgctg atgacgctat gattactggc    21420
ccgtactgga tatttacggc tgctgatgaa tacaacggta acgttaagtt cacctatacc    21480
gtcgaggatg atggtacaac caacggcgct aatgatttcc taacggatac tgcagagatc    21540
acagcgattg tcgacggagt gaacgatacg cctgttgtta atggtgacag tgtcactacg    21600
attgttgacg aggatgctgg tcagctattg agtggtatca atgtcagtga cccagattat    21660
gtggatgcat tttctaatga cttgatgaca gtcacgctga cagtggatta cggtacattg    21720
aacgtatcac ttccggcagt gacgacagtg atggtcaacg caacaacac tggttcggtt    21780 atcttagttg gtactttgag tgacctgaat gcgctgattg atacgccaac cagtccaaac    21840
ggtgtctacc tcgatgcgag cttgtctcca accaatagca ttggcttaga agtaatcgcc    21900
aaagacagcg gtaacccttc tggtatcgcg attgaaactg caccagtggt ttataatatc    21960
```

-continued

```
gcagtgacac cagtcgctaa tgcgccaacc ttgtctattg atccggcatt taactatgtg    22020
agaaacatta cgaccagctc atctgtggtc gctaatagtg gagtcgcttt agttggaatt    22080
gtcgctgcat tgacggacat tactgaagag ttaacgttga agatcagcga tgttccggat    22140
ggtgttgatg taaccagtga tgtgggtacg gtttcgttgg tgggtgatac ttggatagcg    22200
accgctgatg cgatcgatag tctcagactc gtagagcagt catcattagg taaaccgttg    22260
accccgggta attacacctt gaaagttgag gcgctatctg aagagactga caacaacgat    22320
attgcgatat ctcaaaacat cgatctgaat ctcaatattg ttgccaatcc aatagatctc    22380
gatctgtctt ctgaaacaga cgatgtgcaa cttttagcga gtaactttga tactaacctc    22440
actggcggaa ctggaaatga ccgacttgta ggtggagcgg gtgacgatac gctggttggc    22500
ggtgacggta acgacacact cattggtggc ggcggttccg atattctaac cggtggcaat    22560
ggtatggatt cgtttgtatg gctcaatatt gaagatggcg ttgaagacac cattaccgat    22620
ttcagcctgt ctgaaggaga ccaaatcgac ctacgagaag tattacctga gttgaagaat    22680
acatctccag acatgtctgc attgctacaa cagatagacg cgaaagtgga aggggatgat    22740
attgagctta cgatcaagtc tgatggttta ggcactacgg aacaggtgat tgtggttgaa    22800
gaccttgctc ctcagctaac cttaagtggc accatgcctt cggatatttt ggatgcgtta    22860
gtgcaacaaa atgtcatcac tcacggttaa                                    22890
```

<210> SEQ ID NO 4
<211> LENGTH: 7629
<212> TYPE: PRT
<213> ORGANISM: Vibrio splendidus

<400> SEQUENCE: 4

```
Met Leu Cys Asp Asn Gly Gly Cys Met Asp Ile Glu Val Ser Arg Gln
1               5                   10                  15

Val Ala Val Glu Ala Thr Ser Gly Asp Val Val Val Lys Pro
            20                  25                  30

Asp Gly Ser Ala Arg Lys Val Ser Val Gly Asp Thr Ile Arg Glu Asn
        35                  40                  45

Glu Ile Val Ile Thr Ala Asn Lys Ser Glu Leu Val Leu Gly Val Gln
    50                  55                  60

Asn Asp Ser Ile Pro Val Ala Glu Asn Cys Val Gly Cys Val Asp Glu
65                  70                  75                  80

Asn Ala Ala Trp Val Asp Ala Pro Ile Ala Gly Glu Val Asn Phe Asp
                85                  90                  95

Leu Gln Gln Ala Asp Ala Glu Thr Phe Thr Glu Asp Leu Ala Ala
            100                 105                 110

Ile Gln Glu Ala Ile Leu Gly Gly Ala Asp Pro Thr Gln Ile Leu Glu
        115                 120                 125

Ala Thr Ala Ala Gly Gly Gly Leu Gly Ser Ala Asn Ala Gly Phe Val
    130                 135                 140

Thr Ile Asp Tyr Asn Tyr Thr Glu Thr His Pro Ser Thr Phe Phe Glu
145                 150                 155                 160

Thr Ala Gly Leu Ala Glu Gln Thr Val Asp Glu Asp Arg Glu Glu Phe
                165                 170                 175

Arg Ser Ile Thr Arg Ser Ser Gly Gly Gln Ser Ile Ser Glu Thr Leu
            180                 185                 190

Thr Glu Gly Ser Ile Ser Gly Asn Thr Tyr Pro Gln Ser Val Thr Thr
        195                 200                 205

Thr Glu Thr Ile Ile Ala Gly Ser Leu Ala Leu Ala Pro Asn Ser Phe
```

```
              210                 215                 220
Ile Pro Glu Thr Leu Ser Leu Ala Ser Leu Leu Ser Glu Leu Asn Ser
225                 230                 235                 240

Asp Ile Thr Ser Ser Gly Gln Ser Val Ile Phe Thr Tyr Asp Ala Thr
                245                 250                 255

Thr Asn Ser Ile Val Gly Val Gln Asp Thr Asp Glu Val Leu Arg Ile
                260                 265                 270

Asp Ile Asp Ala Val Ser Val Gly Asn Asn Ile Glu Leu Ser Leu Thr
                275                 280                 285

Thr Thr Ile Ser Gln Pro Ile Asp His Val Pro Ser Val Gly Gly Gly
290                 295                 300

Gln Val Ser Tyr Thr Gly Asp Gln Ile Asp Ile Ala Phe Asp Ile Gln
305                 310                 315                 320

Gly Glu Asp Thr Ala Gly Asn Pro Leu Ala Thr Pro Val Asn Ala Gln
                325                 330                 335

Val Ser Val Phe Asp Gly Ile Asp Pro Ser Val Glu Ser Val Asn Ile
                340                 345                 350

Thr Asn Val Glu Thr Ser Ser Ala Ala Ile Glu Gly Thr Phe Ser Asn
                355                 360                 365

Ile Gly Ser Asp Asn Leu Gln Ser Ala Val Phe Asp Ala Ser Ala Leu
                370                 375                 380

Asp Gln Phe Asp Gly Leu Leu Ser Asp Asn Gln Asn Thr Leu Ala Arg
385                 390                 395                 400

Leu Ser Asp Asp Gly Thr Thr Ile Thr Leu Ser Ile Gln Gly Arg Gly
                405                 410                 415

Glu Val Val Leu Thr Ile Ser Leu Asp Thr Asp Gly Thr Tyr Lys Phe
                420                 425                 430

Glu Gln Ser Asn Pro Ile Glu Gln Val Gly Thr Asp Ser Leu Thr Phe
                435                 440                 445

Ala Leu Pro Ile Thr Ile Thr Asp Phe Asp Gln Asp Val Val Thr Asn
                450                 455                 460

Thr Ile Asn Ile Ala Ile Thr Asp Gly Asp Ser Pro Val Ile Thr Asn
465                 470                 475                 480

Val Asp Ser Ile Asp Val Asp Glu Ala Gly Ile Val Gly Gly Ser Gln
                485                 490                 495

Glu Gly Thr Ala Pro Val Ser Gly Thr Gly Ile Thr Ala Asp Ile
                500                 505                 510

Phe Glu Ser Asp Ile Ile Asp His Tyr Glu Leu Glu Pro Thr Glu Phe
                515                 520                 525

Asn Thr Asn Gly Thr Leu Val Ser Asn Gly Glu Ala Val Leu Leu Glu
                530                 535                 540

Leu Ile Asp Glu Thr Asn Gly Val Arg Thr Tyr Glu Gly Tyr Val Glu
545                 550                 555                 560

Val Asn Gly Ser Arg Ile Thr Val Phe Asp Val Lys Ile Asp Ser Pro
                565                 570                 575

Ser Leu Gly Asn Tyr Glu Phe Asn Leu Tyr Glu Glu Leu Ser His Gln
                580                 585                 590

Gly Ala Glu Asp Ala Leu Leu Thr Phe Ala Leu Pro Ile Tyr Ala Val
                595                 600                 605

Asp Ala Asp Gly Asp Arg Ser Ala Leu Ser Gly Gly Ser Asn Thr Pro
                610                 615                 620

Glu Ala Ala Glu Ile Leu Val Asn Val Lys Asp Asp Val Val Glu Leu
625                 630                 635                 640
```

-continued

Val Asp Lys Val Glu Ser Val Thr Glu Pro Thr Leu Ala Gly Asp Thr
            645                 650                 655

Ile Val Ser Tyr Asn Leu Phe Asn Phe Glu Gly Ala Asp Gly Ser Thr
            660                 665                 670

Ile Gln Ser Phe Asn Tyr Asp Gly Val Asp Tyr Ser Leu Asp Gln Ser
            675                 680                 685

Leu Leu Pro Asp Ala Thr Gln Ile Phe Ser Phe Thr Glu Gly Val Val
            690                 695                 700

Thr Ile Ser Leu Asn Gly Asp Phe Ser Phe Glu Val Ala Arg Asp Ile
705                 710                 715                 720

Asp His Ser Ser Ser Glu Thr Ile Val Lys Gln Phe Ser Phe Leu Ala
            725                 730                 735

Glu Asp Gly Asp Gly Asp Thr Asp Ser Ser Thr Leu Glu Leu Ser Ile
            740                 745                 750

Thr Asp Gly Gln Asp Pro Ile Ile Asp Leu Ile Pro Pro Val Thr Leu
            755                 760                 765

Ser Glu Thr Asn Leu Asn Asp Gly Ser Ala Pro Ser Gly Ser Thr Val
            770                 775                 780

Ser Ala Thr Glu Thr Ile Thr Phe Thr Ala Gly Ser Asp Asp Val Ala
785                 790                 795                 800

Ser Phe Arg Ile Glu Pro Thr Glu Phe Asn Val Gly Gly Ala Leu Lys
            805                 810                 815

Ser Asn Gly Phe Ser Val Glu Ile Lys Glu Asp Ser Ala Asn Pro Gly
            820                 825                 830

Thr Tyr Ile Gly Phe Ile Thr Asn Gly Ser Gly Ala Glu Ile Pro Val
            835                 840                 845

Phe Thr Ile Ala Phe Ser Thr Ser Thr Leu Gly Glu Tyr Thr Phe Thr
            850                 855                 860

Leu Leu Glu Ala Leu Asp His Val Asp Gly Leu Asp Lys Asn Asp Leu
865                 870                 875                 880

Ser Phe Asp Leu Pro Ile Tyr Ala Val Asp Thr Asp Gly Asp Asp Ser
            885                 890                 895

Leu Val Ser Gln Leu Asn Val Thr Ile Gly Asp Val Gln Ile Met
            900                 905                 910

Gln Asp Gly Thr Leu Asp Ile Thr Glu Pro Asn Leu Ala Asp Gly Thr
            915                 920                 925

Ile Thr Thr Asn Thr Ile Asp Val Met Pro Asn Gln Ser Ala Asp Gly
930                 935                 940

Ala Thr Ile Thr Arg Phe Thr Tyr Asp Gly Val Val Asn Thr Leu Asp
945                 950                 955                 960

Gln Ser Ile Ser Gly Glu Gln Gln Phe Ser Phe Thr Glu Gly Glu Leu
            965                 970                 975

Phe Ile Thr Leu Glu Gly Glu Val Arg Phe Glu Pro Asn Arg Asp Leu
            980                 985                 990

Asp His Ser Val Ser Glu Asp Ile Val Lys Ser Ile Val Val Thr Ser
            995                 1000                1005

Ser Asp Phe Asp Asn Asp Pro Val Thr Ser Thr Ile Thr Leu Thr Ile
            1010                1015                1020

Thr Asp Gly Asp Asn Pro Thr Ile Asp Val Ile Pro Ser Val Thr Leu
1025                1030                1035                1040

Ser Glu Ile Asn Leu Ser Asp Gly Ser Ala Pro Ser Gly Ser Ala Val
            1045                1050                1055

Ser Ser Thr Gln Thr Ile Thr Phe Thr Asn Gln Ser Asp Asp Val Val
            1060                1065                1070

```
Arg Phe Arg Ile Glu Ser Thr Glu Phe Asn Thr Asn Asp Asp Leu Lys
        1075                1080                1085

Ser Asn Gly Leu Ala Val Glu Leu Arg Glu Asp Pro Ala Gly Ser Gly
        1090                1095                1100

Asp Tyr Ile Gly Phe Thr Thr Ser Ala Thr Asn Val Glu Thr Pro Val
1105                1110                1115                1120

Phe Thr Leu Ser Phe Asn Ser Gly Ser Leu Gly Glu Tyr Thr Phe Thr
            1125                1130                1135

Leu Ile Glu Ala Leu Asp His Gln Asp Ala Arg Gly Asn Asn Asp Leu
            1140                1145                1150

Ser Phe Asp Leu Pro Val Tyr Ala Val Asp Ser Asp Gly Asp Asp Ser
            1155                1160                1165

Leu Val Ser Pro Leu Asn Val Thr Ile Gly Asp Val Gln Ile Met
            1170                1175                1180

Gln Asp Ser Thr Leu Asp Ile Val Glu Pro Thr Val Ala Asp Leu Ala
1185                1190                1195                1200

Ala Gly Thr Val Thr Thr Asn Thr Ile Asp Val Met Pro Asn Gln Ser
            1205                1210                1215

Ala Asp Gly Ala Thr Val Thr Gln Phe Thr Tyr Asp Gly Gln Leu Arg
            1220                1225                1230

Thr Leu Asp Gln Asn Asp Asn Gly Glu Gln Gln Phe Ser Phe Thr Glu
            1235                1240                1245

Gly Glu Leu Phe Ile Thr Leu Gln Gly Asp Val Arg Phe Glu Pro Asn
1250                1255                1260

Arg Asn Leu Asp His Thr Leu Ser Glu Asp Ile Val Lys Ser Ile Val
1265                1270                1275                1280

Val Thr Ser Ser Asp Ser Asp Asn Asp Val Leu Thr Ser Thr Val Thr
            1285                1290                1295

Leu Thr Ile Thr Asp Gly Asp Ile Pro Thr Ile Asp Asn Val Pro Thr
            1300                1305                1310

Val Asn Leu Ser Glu Thr Asn Leu Ser Asp Gly Ser Ala Pro Ser Gly
            1315                1320                1325

Ser Ala Val Ser Ser Thr Gln Thr Ile Thr Tyr Thr Thr Gln Ser Asp
            1330                1335                1340

Asp Val Thr Ser Phe Arg Ile Glu Pro Thr Glu Phe Asn Val Gly Gly
1345                1350                1355                1360

Ala Leu Thr Ser Asn Gly Leu Ala Val Glu Leu Lys Ala Asp Pro Thr
            1365                1370                1375

Thr Pro Gly Gly Tyr Ile Gly Phe Val Thr Asp Gly Ser Asn Val Glu
            1380                1385                1390

Thr Asn Val Phe Thr Ile Ser Phe Ser Asp Thr Asn Leu Gly Gln Tyr
            1395                1400                1405

Thr Phe Thr Leu Leu Glu Ala Leu Asp His Val Asp Gly Leu Ala Asn
            1410                1415                1420

Asn Asp Leu Thr Phe Asp Leu Pro Val Tyr Ala Val Asp Ser Asp Gly
1425                1430                1435                1440

Asp Asp Ser Leu Val Ser Gln Leu Asn Val Thr Ile Gly Asp Asp Val
            1445                1450                1455

Gln Ile Met Gln Gly Gly Thr Leu Asp Ile Thr Glu Pro Asn Leu Ala
            1460                1465                1470

Asp Gly Thr Ile Thr Thr Asn Thr Ile Asp Val Met Pro Glu Gln Ser
            1475                1480                1485

Ala Asp Gly Ala Thr Ile Thr Gln Phe Thr Tyr Asp Gly Gln Val Arg
```

```
            1490              1495              1500

Thr Leu Asp Gln Thr Asp Asn Gly Glu Gln Gln Phe Ser Phe Thr Glu
1505                1510                1515                1520

Gly Glu Leu Phe Ile Thr Leu Gln Gly Asp Val Arg Phe Glu Pro Asn
            1525                1530                1535

Arg Asn Leu Asp His Thr Ala Ser Glu Asp Ile Val Lys Ser Ile Val
            1540                1545                1550

Val Thr Ser Ser Asp Leu Asp Asn Asp Val Val Thr Ser Thr Val Thr
            1555                1560                1565

Leu Thr Ile Thr Asp Gly Asp Ile Pro Thr Ile Asp Ala Val Pro Ser
            1570                1575                1580

Val Thr Leu Ser Glu Ile Asn Leu Ser Asp Gly Ser Ala Pro Ser Gly
1585                1590                1595                1600

Thr Ala Val Ser Gln Thr Glu Thr Ile Thr Phe Thr Asn Gln Ser Asp
            1605                1610                1615

Asp Val Thr Ser Phe Arg Ile Glu Pro Ile Glu Phe Asn Val Gly Gly
            1620                1625                1630

Ala Leu Lys Ser Asn Gly Phe Ala Val Glu Ile Lys Glu Asp Ser Ala
            1635                1640                1645

Asn Pro Gly Thr Tyr Ile Gly Phe Ile Thr Asn Gly Ser Gly Ala Glu
            1650                1655                1660

Ile Pro Val Phe Thr Ile Ala Phe Ser Thr Ser Ser Leu Gly Glu Tyr
1665                1670                1675                1680

Thr Phe Thr Leu Leu Glu Ala Leu Asp His Val Asp Gly Leu Asp Lys
            1685                1690                1695

Asn Asp Leu Ser Phe Asp Leu Pro Val Tyr Ala Val Asp Thr Asp Gly
            1700                1705                1710

Asp Asp Ser Leu Val Ser Gln Leu Asn Val Thr Ile Gly Asp Asp Val
            1715                1720                1725

Gln Ile Met Gln Asp Gly Thr Leu Asp Ile Ile Glu Pro Asn Leu Ala
            1730                1735                1740

Asp Gly Thr Ile Thr Thr Ser Thr Ile Asp Val Met Pro Asn Gln Ser
1745                1750                1755                1760

Ala Asp Gly Ala Thr Ile Thr Gln Phe Thr Tyr Asp Gly Gln Leu Arg
            1765                1770                1775

Thr Leu Asp Gln Asn Asp Thr Gly Glu Gln Gln Phe Ser Phe Thr Glu
            1780                1785                1790

Gly Glu Leu Phe Ile Thr Leu Glu Gly Glu Val Arg Phe Glu Pro Asn
            1795                1800                1805

Arg Asp Leu Asp His Thr Ala Ser Glu Asp Ile Val Lys Ser Ile Val
            1810                1815                1820

Val Thr Ser Ser Asp Phe Asp Asn Asp Ser Leu Thr Ser Thr Val Thr
1825                1830                1835                1840

Leu Thr Ile Thr Asp Gly Asp Asn Pro Thr Ile Asp Val Ile Pro Ser
            1845                1850                1855

Val Thr Leu Ser Glu Thr Asn Leu Ser Asp Gly Ser Ala Pro Ser Gly
            1860                1865                1870

Ser Ala Val Ser Ser Thr Gln Thr Ile Thr Phe Thr Asn Gln Ser Asp
            1875                1880                1885

Asp Val Val Arg Phe Arg Ile Glu Pro Thr Glu Phe Asn Thr Asn Asp
            1890                1895                1900

Asp Leu Lys Ser Asn Gly Leu Ala Val Glu Leu Arg Glu Asp Pro Ala
1905                1910                1915                1920
```

-continued

Gly Ser Gly Asp Tyr Ile Gly Phe Thr Thr Ser Ala Thr Asn Val Glu
            1925                1930                1935

Thr Thr Val Phe Thr Leu Ser Phe Ser Ser Thr Thr Leu Gly Glu Tyr
            1940                1945                1950

Thr Phe Thr Leu Leu Glu Ala Leu Asp His Gln Asp Ala Arg Gly Asn
            1955                1960                1965

Asn Asp Leu Ser Phe Glu Leu Pro Val Tyr Ala Val Asp Ser Asp Gly
            1970                1975                1980

Asp Asp Ser Leu Met Ser Pro Leu Asn Val Thr Ile Gly Asp Asp Val
1985                1990                1995                2000

Gln Ile Met Gln Asp Gly Thr Leu Asp Ile Val Glu Pro Thr Val Ala
            2005                2010                2015

Asp Leu Ala Ala Gly Ile Val Thr Thr Asn Thr Ile Asp Val Met Pro
            2020                2025                2030

Asn Gln Ser Ala Asp Gly Ala Thr Ile Thr Gln Phe Thr Tyr Asp Gly
            2035                2040                2045

Gln Leu Arg Thr Leu Asp Gln Asn Asp Asn Gly Glu Gln Gln Phe Ser
            2050                2055                2060

Phe Thr Glu Gly Glu Leu Phe Ile Thr Leu Glu Gly Glu Val Arg Phe
2065                2070                2075                2080

Glu Pro Asn Arg Asn Leu Asp His Thr Leu Asn Glu Asp Ile Val Lys
            2085                2090                2095

Ser Ile Val Val Thr Ser Ser Asp Ser Asp Asn Asp Val Leu Thr Ser
            2100                2105                2110

Thr Val Thr Leu Thr Ile Thr Asp Gly Asp Ile Pro Thr Ile Asp Asn
            2115                2120                2125

Val Pro Thr Val Ser Leu Ser Glu Thr Ser Leu Ser Asp Gly Ser Ser
            2130                2135                2140

Pro Ser Gly Ser Ala Val Ser Ser Thr Gln Thr Ile Thr Tyr Thr Thr
2145                2150                2155                2160

Gln Ser Asp Asp Val Thr Ser Phe Arg Ile Glu Pro Thr Glu Phe Asn
            2165                2170                2175

Val Gly Gly Ala Leu Lys Ser Asn Gly Leu Ala Val Glu Leu Lys Ala
            2180                2185                2190

Asp Pro Thr Thr Pro Gly Gly Tyr Ile Gly Phe Val Thr Asp Gly Ser
            2195                2200                2205

Asn Val Glu Thr Asn Val Phe Thr Ile Ser Phe Ser Asp Thr Asn Leu
            2210                2215                2220

Gly Gln Tyr Thr Phe Thr Leu Leu Glu Ala Leu Asp His Ala Asp Ser
2225                2230                2235                2240

Leu Ala Asn Asn Asp Leu Ser Phe Asp Leu Pro Val Tyr Ala Val Asp
            2245                2250                2255

Ser Asp Gly Asp Asp Ser Leu Val Ser Gln Leu Asn Val Thr Ile Gly
            2260                2265                2270

Asp Asp Val Gln Ile Met Gln Gly Gly Thr Leu Asp Ile Thr Glu Pro
            2275                2280                2285

Asn Leu Ala Asp Gly Thr Thr Thr Asn Thr Ile Asp Val Met Pro
            2290                2295                2300

Glu Gln Ser Ala Asp Gly Ala Thr Ile Thr Gln Phe Thr Tyr Asp Gly
2305                2310                2315                2320

Gln Val Arg Thr Leu Asp Gln Thr Asp Asn Gly Glu Gln Gln Phe Ser
            2325                2330                2335

Phe Thr Glu Gly Glu Leu Phe Ile Thr Leu Gln Gly Asp Val Arg Phe
            2340                2345                2350

```
Glu Pro Asn Arg Asn Leu Asp His Thr Ala Ser Glu Asp Ile Val Lys
        2355                2360                2365

Ser Ile Val Val Thr Ser Ser Asp Ser Asp Asn Asp Val Val Thr Ser
        2370                2375                2380

Thr Val Thr Leu Thr Ile Thr Asp Gly Asp Leu Pro Thr Ile Asp Ala
2385                2390                2395                2400

Val Pro Ser Val Thr Leu Ser Glu Thr Asn Leu Ser Asp Gly Ser Ala
        2405                2410                2415

Pro Ser Gly Ser Ala Val Ser Gln Thr Glu Thr Ile Thr Phe Thr Asn
        2420                2425                2430

Gln Ser Asp Asp Val Ala Ser Phe Arg Ile Glu Pro Thr Glu Phe Asn
        2435                2440                2445

Val Gly Gly Ala Leu Lys Ser Asn Gly Phe Ala Val Glu Ile Lys Glu
        2450                2455                2460

Asp Ser Ala Asn Pro Gly Thr Tyr Ile Gly Phe Ile Ala Asn Gly Ser
2465                2470                2475                2480

Ser Ala Glu Ile Pro Val Phe Thr Ile Ala Phe Ser Thr Ser Thr Leu
        2485                2490                2495

Gly Glu Tyr Thr Phe Thr Leu Leu Glu Ala Leu Asp His Ala Asp Gly
        2500                2505                2510

Leu Asp Lys Asn Asp Leu Ser Phe Glu Leu Pro Val Tyr Ala Val Asp
        2515                2520                2525

Thr Asp Gly Asp Asp Ser Leu Val Ser Gln Leu Asn Val Thr Ile Gly
        2530                2535                2540

Asp Asp Val Gln Ile Met Gln Asp Gly Thr Leu Asp Val Ile Glu Pro
2545                2550                2555                2560

Asn Leu Ala Asp Gly Thr Ile Thr Thr Asn Thr Ile Asp Val Met Pro
        2565                2570                2575

Glu Gln Ser Ala Asp Gly Ala Thr Ile Thr Gln Phe Thr Tyr Asp Gly
        2580                2585                2590

Gln Leu Arg Thr Leu Asp Gln Asn Asp Thr Gly Glu Gln Gln Phe Ser
        2595                2600                2605

Phe Thr Glu Gly Glu Leu Phe Ile Thr Leu Glu Gly Glu Val Arg Phe
        2610                2615                2620

Glu Pro Asn Arg Asp Leu Asp His Ser Val Ser Glu Asp Ile Val Lys
2625                2630                2635                2640

Ser Ile Val Val Thr Ser Ser Asp Phe Asp Asn Asp Pro Val Thr Ser
        2645                2650                2655

Ala Ile Thr Leu Thr Ile Thr Asp Gly Asp Asn Pro Thr Ile Asp Ser
        2660                2665                2670

Val Pro Ser Val Val Leu Glu Glu Ala Asp Leu Thr Asp Gly Ser Ser
        2675                2680                2685

Pro Ser Gly Ser Ala Val Ser Gln Thr Glu Thr Ile Thr Phe Thr Asn
        2690                2695                2700

Gln Ser Asp Asp Val Glu Lys Phe Arg Leu Glu Pro Ser Glu Phe Asn
2705                2710                2715                2720

Thr Asn Asn Ala Leu Lys Ser Asp Gly Leu Ile Ile Glu Ile Arg Glu
        2725                2730                2735

Glu Pro Thr Gly Ser Gly Asn Tyr Ile Gly Phe Thr Thr Asp Ile Ser
        2740                2745                2750

Asn Val Glu Thr Thr Val Phe Thr Leu Asp Phe Ser Ser Thr Thr Leu
        2755                2760                2765

Gly Glu Tyr Thr Phe Thr Leu Leu Glu Ala Ile Asp His Thr Pro Val
```

```
              2770            2775            2780
Gln Gly Asn Asn Asp Leu Thr Phe Asn Leu Pro Val Tyr Ala Val Asp
2785            2790            2795            2800

Ser Asp Gly Asp Asp Ser Leu Met Ser Leu Ser Val Thr Ile Thr
            2805            2810            2815

Asp Asp Val Gln Val Met Val Ser Gly Ser Leu Ser Ile Glu Glu Pro
            2820            2825            2830

Thr Val Ala Asp Leu Ala Ala Gly Thr Pro Thr Thr Ser Val Phe Asp
            2835            2840            2845

Val Leu Thr Ser Ala Ser Ala Asp Gly Ala Thr Ile Thr Gln Phe Thr
            2850            2855            2860

Tyr Asp Gly Gly Ala Val Leu Thr Leu Asp Gln Asn Asp Thr Gly Glu
2865            2870            2875            2880

Gln Lys Phe Val Val Ala Asp Gly Ala Leu Tyr Ile Thr Leu Gln Gly
                2885            2890            2895

Asp Ile Arg Phe Glu Pro Ser Arg Asn Leu Asp His Thr Gly Gly Asp
                2900            2905            2910

Ile Val Lys Ser Ile Val Val Thr Ser Ser Asp Ser Asp Leu
                2915            2920            2925

Val Ser Ser Thr Val Thr Leu Thr Ile Thr Asp Gly Asp Ile Pro Thr
                2930            2935            2940

Ile Asp Thr Val Pro Ser Val Thr Leu Ser Glu Thr Asn Leu Ser Asp
2945            2950            2955            2960

Gly Ser Ala Pro Asn Ala Ser Ala Val Ser Ser Thr Gln Thr Ile Thr
                2965            2970            2975

Phe Thr Asn Gln Ser Asp Asp Val Thr Ser Phe Arg Ile Glu Pro Thr
                2980            2985            2990

Asp Phe Asn Val Gly Gly Ala Leu Lys Ser Asn Gly Leu Ala Val Glu
                2995            3000            3005

Leu Lys Ala Asp Pro Thr Thr Pro Gly Gly Tyr Ile Gly Phe Val Thr
                3010            3015            3020

Asp Gly Ser Asn Val Glu Thr Asn Val Phe Thr Ile Ser Phe Ser Asp
3025            3030            3035            3040

Thr Asn Leu Gly Gln Tyr Thr Phe Thr Leu Leu Glu Ala Leu Asp His
                3045            3050            3055

Val Asp Gly Leu Val Lys Asn Asp Leu Thr Phe Asp Leu Pro Val Tyr
                3060            3065            3070

Ala Val Asp Ser Asp Gly Asp Asp Ser Leu Val Ser Gln Leu Asn Val
                3075            3080            3085

Thr Ile Gly Asp Asp Val Gln Val Met Gln Asn Gln Ala Leu Asn Ile
                3090            3095            3100

Ile Glu Pro Thr Val Ala Asp Leu Ala Ala Gly Thr Pro Thr Thr Ala
3105            3110            3115            3120

Thr Val Asp Val Met Pro Ser Gln Ser Ala Asp Gly Ala Thr Ile Thr
                3125            3130            3135

Gln Phe Thr Tyr Asp Gly Gly Ala Ala Ile Thr Leu Asp Gln Asn Asp
                3140            3145            3150

Thr Gly Glu Gln Lys Phe Val Phe Thr Glu Gly Ser Leu Phe Ile Thr
                3155            3160            3165

Leu Gln Gly Glu Val Arg Phe Glu Pro Asn Arg Asn Leu Asn His Thr
                3170            3175            3180

Ala Ser Glu Asp Ile Val Lys Ser Ile Val Val Thr Ser Ser Asp Leu
3185            3190            3195            3200
```

-continued

Asp Asn Asp Val Leu Thr Ser Thr Val Thr Leu Thr Ile Thr Asp Gly
            3205                3210                3215

Asp Ile Pro Thr Ile Asp Ala Val Pro Ser Val Thr Leu Ser Glu Thr
            3220                3225                3230

Asn Leu Ser Asp Gly Ser Ala Pro Ser Ser Ala Val Ser Gln Thr
        3235                3240                3245

Glu Thr Ile Thr Phe Ile Asn Gln Ser Asp Asp Val Ala Ser Phe Arg
            3250                3255                3260

Ile Glu Pro Thr Glu Phe Asn Val Gly Gly Ala Leu Lys Ser Asn Gly
3265                3270                3275                3280

Phe Ala Val Glu Ile Lys Glu Asp Ser Ala Asn Pro Gly Thr Tyr Ile
            3285                3290                3295

Gly Phe Ile Thr Asp Gly Ser Asn Thr Glu Val Pro Val Phe Thr Ile
            3300                3305                3310

Ala Phe Ser Thr Ser Thr Leu Gly Glu Tyr Thr Phe Thr Leu Leu Glu
            3315                3320                3325

Ala Leu Asp His Ala Asn Gly Leu Asp Lys Asn Asp Leu Ser Phe Asp
            3330                3335                3340

Leu Pro Val Tyr Ala Val Asp Ser Asp Gly Asp Asp Ser Leu Val Ser
3345                3350                3355                3360

Gln Leu Asn Val Thr Ile Gly Asp Asp Val Gln Ile Met Gln Asp Gly
            3365                3370                3375

Thr Leu Asp Ile Thr Glu Pro Asn Leu Ala Asp Gly Thr Ile Thr Thr
            3380                3385                3390

Asn Thr Ile Asp Val Met Pro Asn Gln Ser Ala Asp Gly Ala Thr Ile
            3395                3400                3405

Thr Glu Phe Ser Phe Gly Gly Ile Val Lys Thr Leu Asp Gln Ser Ile
            3410                3415                3420

Val Gly Glu Gln Gln Phe Ser Phe Thr Glu Gly Glu Leu Phe Ile Thr
3425                3430                3435                3440

Leu Gln Gly Gln Val Arg Phe Glu Pro Asn Arg Asp Leu Asp His Ser
            3445                3450                3455

Ala Ser Glu Asp Ile Val Lys Ser Ile Val Val Thr Ser Ser Asp Phe
            3460                3465                3470

Asp Asn Asp Pro Val Thr Ser Thr Val Thr Leu Thr Ile Thr Asp Gly
            3475                3480                3485

Asp Ile Pro Thr Ile Asp Ala Val Pro Ser Val Thr Leu Ser Glu Thr
            3490                3495                3500

Asn Leu Ala Asp Gly Ser Ala Pro Ser Gly Ala Val Ser Gln Thr
3505                3510                3515                3520

Glu Thr Ile Thr Phe Thr Asn Gln Ser Asp Asp Val Val Arg Phe Arg
            3525                3530                3535

Leu Glu Pro Thr Glu Phe Asn Thr Asn Asp Ala Leu Lys Ser Asn Gly
            3540                3545                3550

Leu Ala Val Glu Leu Arg Glu Pro Gln Gly Ser Gly Gln Tyr Ile
        3555                3560                3565

Gly Phe Thr Thr Ser Ser Ser Asn Val Glu Thr Thr Val Phe Thr Leu
            3570                3575                3580

Asp Phe Asn Ser Gly Thr Leu Gly Glu Tyr Thr Phe Thr Leu Ile Glu
3585                3590                3595                3600

Ala Leu Asp His Gln Asp Ala Arg Gly Asn Asn Asp Leu Ser Phe Asn
            3605                3610                3615

Leu Pro Val Tyr Ala Val Asp Ser Asp Gly Asp Asp Ser Leu Val Ser
            3620                3625                3630

```
Gln Leu Gly Val Thr Ile Gly Asp Asp Val Gln Leu Met Gln Asp Gly
            3635                3640                3645

Thr Ile Thr Ser Arg Glu Pro Ala Ala Ser Val Glu Thr Ser Asn Thr
        3650                3655                3660

Phe Asp Val Met Pro Asn Gln Ser Ala Asp Gly Ala Lys Val Thr Ser
3665                3670                3675                3680

Phe Val Phe Asp Gly Lys Thr Ala Glu Ser Leu Asp Leu Asn Val Asn
            3685                3690                3695

Gly Glu Gln Glu Phe Val Phe Thr Glu Gly Ser Val Phe Ile Thr Thr
        3700                3705                3710

Glu Gly Glu Ile Arg Phe Glu Pro Val Arg Asn Gln Asn His Ala Gly
    3715                3720                3725

Gly Asp Ile Thr Lys Ser Ile Glu Val Thr Ser Val Asp Leu Asp Gly
        3730                3735                3740

Asp Ile Val Thr Ser Thr Val Thr Leu Lys Ile Val Asp Gly Asp Leu
3745                3750                3755                3760

Pro Thr Ile Asp Leu Val Pro Gly Ile Thr Leu Ser Glu Val Asp Leu
            3765                3770                3775

Ala Asp Gly Ser Val Pro Thr Gly Asn Pro Val Thr Met Thr Gln Thr
        3780                3785                3790

Ile Thr Tyr Thr Ala Gly Ser Asp Asp Val Ser His Phe Arg Ile Asp
        3795                3800                3805

Pro Thr Gln Phe Asn Thr Ser Gly Val Leu Lys Ser Asn Gly Leu Asp
        3810                3815                3820

Val Glu Ile Lys Glu Gln Pro Ala Asn Ser Gly Asn Tyr Ile Gly Phe
3825                3830                3835                3840

Val Lys Asp Gly Ser Asn Val Glu Thr Asn Val Phe Thr Ile Ser Phe
            3845                3850                3855

Ser Thr Ser Asn Leu Gly Gln Tyr Thr Phe Thr Leu Leu Glu Ala Leu
        3860                3865                3870

Asp His Val Asp Gly Leu Gln Asn Asn Ile Leu Ser Phe Asp Val Pro
    3875                3880                3885

Val Leu Ala Val Asp Ala Asp Gly Asp Asp Ser Ala Met Ser Pro Met
    3890                3895                3900

Thr Val Ala Ile Thr Asp Asp Val Gln Gly Val Gln Asp Gly Thr Leu
3905                3910                3915                3920

Ser Ile Thr Glu Pro Ser Leu Ala Asp Leu Ala Ser Gly Thr Pro Pro
            3925                3930                3935

Thr Thr Ala Ile Ile Asp Val Met Pro Thr Gln Ser Ala Asp Gly Ala
        3940                3945                3950

Lys Val Thr Gln Phe Thr Tyr Asp Gly Gly Thr Ala Val Thr Leu Asp
        3955                3960                3965

Pro Ser Ile Ala Thr Glu Gln Val Phe Thr Val Thr Asp Gly Leu Leu
    3970                3975                3980

Tyr Ile Thr Ile Glu Gly Glu Val Arg Phe Glu Pro Ser Arg Asp Leu
3985                3990                3995                4000

Asp His Ser Ser Gly Asp Ile Val Arg Thr Ile Val Thr Thr Thr Ser
            4005                4010                4015

Asp Phe Asp Asn Asp Thr Asp Thr Ala Asp Val Thr Leu Thr Ile Lys
        4020                4025                4030

Asp Gly Ile Asn Pro Val Ile Asn Val Val Pro Asp Val Asn Leu Ser
        4035                4040                4045

Glu Val Asn Leu Ala Asp Gly Ser Thr Pro Ser Gly Ser Ala Val Ser
```

```
                4050                4055                4060
Ser Thr His Thr Ile Thr Tyr Thr Glu Gly Ser Asp Asp Phe Ser His
4065                4070                4075                4080

Phe Arg Ile Ala Thr Asn Glu Phe Asn Pro Gly Asp Leu Leu Lys Ser
                4085                4090                4095

Ser Gly Leu Val Val Gln Leu Lys Glu Asp Pro Ala Ser Ala Gly Asp
            4100                4105                4110

Tyr Ile Gly Tyr Thr Asp Asp Gly Met Gly Asn Val Thr Asp Val Phe
        4115                4120                4125

Thr Ile Ser Phe Asp Ser Ala Asn Lys Ala Gln Phe Thr Phe Thr Leu
    4130                4135                4140

Ile Glu Ala Leu Asp His Leu Asp Gly Val Leu Tyr Asn Asp Leu Thr
4145                4150                4155                4160

Phe Arg Leu Pro Ile Tyr Ala Val Asp Thr Asp Ser Glu Ser Thr
                4165                4170                4175

Lys Arg Asp Val Val Thr Ile Glu Asp Asp Ile Gln Gln Met Gln
            4180                4185                4190

Asp Gly Phe Leu Thr Ile Thr Glu Pro Asn Ser Gly Thr Pro Thr Thr
        4195                4200                4205

Thr Thr Val Asp Val Met Pro Ile Pro Ser Ala Asp Gly Ala Thr Ile
    4210                4215                4220

Thr Gln Phe Thr Tyr Asp Gly Gly Ser Pro Ile Thr Leu Asn Gln Ser
4225                4230                4235                4240

Ile Ser Gly Glu Gln Glu Phe Val Phe Thr Glu Gly Ser Leu Phe Val
                4245                4250                4255

Thr Leu Asp Gly Asp Val Arg Phe Glu Pro Asn Arg Asn Leu Asp His
            4260                4265                4270

Ser Ala Gly Asp Ile Val Lys Ser Ile Val Phe Thr Ser Ser Asp Phe
        4275                4280                4285

Asp Asn Asp Ile Phe Ser Ser Lys Val Thr Leu Thr Ile Val Asp Gly
    4290                4295                4300

Asp Gly Pro Thr Ile Asp Val Val Pro Gly Val Ala Leu Ser Glu Ser
4305                4310                4315                4320

Leu Leu Ala Asp Gly Ser Thr Pro Ser Val Asn Pro Val Ser Met Thr
                4325                4330                4335

Gln Thr Ile Thr Ser Leu Ala Ser Ser Asp Asp Ile Ala Glu Ile Val
            4340                4345                4350

Val Glu Val Gly Leu Phe Asn Thr Asn Gly Ala Leu Lys Ser Asp Gly
        4355                4360                4365

Leu Ser Leu Ser Leu Arg Glu Asp Pro Val Asn Ser Gly Asp Tyr Ile
    4370                4375                4380

Ala Phe Thr Thr Asn Gly Ser Gly Val Glu Lys Val Ile Phe Thr Leu
4385                4390                4395                4400

Asp Phe Asp Asp Thr Asn Pro Ser Gln Tyr Thr Phe Thr Leu Leu Glu
                4405                4410                4415

Arg Leu Asp His Val Asp Gly Leu Gly Asn Asn Asp Leu Ser Phe Asp
            4420                4425                4430

Leu Ser Val Tyr Ala Glu Asp Thr Asp Gly Asp Ile Ser Ala Ser Lys
        4435                4440                4445

Pro Leu Thr Val Thr Ile Thr Asp Asp Val Gln Leu Met Gln Ser Gly
    4450                4455                4460

Ala Leu Asn Ile Thr Glu Pro Thr Thr Gly Thr Pro Thr Thr Ala Val
4465                4470                4475                4480
```

```
Phe Asp Val Met Pro Ala Gln Ser Ala Asp Gly Ala Thr Ile Thr Lys
                4485                4490                4495

Phe Thr Tyr Gly Ser Gln Pro Glu Glu Ser Leu Val Gln Thr Val Thr
            4500                4505                4510

Gly Glu Gln Glu Phe Val Phe Thr Gly Ser Leu Phe Ile Asn Leu
        4515                4520                4525

Glu Gly Asp Val Arg Phe Glu Pro Asn Arg Asn Leu Asp His Ser Gly
    4530                4535                4540

Gly Asn Ile Val Lys Thr Ile Thr Val Thr Ser Glu Asp Lys Asp Gly
4545                4550                4555                4560

Asp Ile Val Thr Ser Thr Val Thr Leu Thr Ile Val Asp Gly Ala Pro
                4565                4570                4575

Pro Val Ile Asp Thr Val Pro Thr Val Ala Leu Glu Glu Ala Asn Leu
            4580                4585                4590

Val Asp Gly Ser Ser Pro Gly Leu Pro Val Ser Gln Thr Glu Ile Ile
        4595                4600                4605

Thr Phe Thr Ala Gly Ser Asp Asp Val Ser His Phe Arg Ile Asp Pro
    4610                4615                4620

Ala Gln Phe Asn Thr Ser Gly Asp Leu Lys Ala Asp Gly Leu Val Val
4625                4630                4635                4640

Gln Leu Lys Glu Asp Pro Leu Asn Ser Asp Asn Tyr Ile Gly Tyr Val
                4645                4650                4655

Glu Ser Gly Gly Val Gln Thr Asp Ile Phe Thr Ile Thr Phe Ser Ser
            4660                4665                4670

Val Val Leu Gly Glu Tyr Thr Phe Thr Leu Leu Glu Gly Leu Asp His
        4675                4680                4685

Leu Pro Val Gln Gly Asn Asn Asp Gln Ile Phe Thr Leu Pro Val Ile
    4690                4695                4700

Ala Val Asp Lys Asp Asn Thr Asp Ser Ala Val Lys Pro Leu Thr Val
4705                4710                4715                4720

Thr Ile Thr Asp Asp Val Pro Thr Ile Thr Asp Thr Thr Gly Ala Ser
                4725                4730                4735

Thr Phe Val Val Asp Glu Asp Asp Leu Gly Thr Leu Ala Gln Ala Thr
            4740                4745                4750

Gly Ser Phe Val Thr Thr Glu Gly Ala Asp Gln Val Glu Val Tyr Glu
        4755                4760                4765

Leu Arg Asn Ile Ser Thr Leu Glu Ala Thr Leu Ser Ser Gly Ser Glu
    4770                4775                4780

Gly Ile Lys Ile Thr Glu Ile Thr Gly Ala Ala Asn Thr Thr Thr Tyr
4785                4790                4795                4800

Gln Gly Ala Thr Asp Pro Ser Gly Thr Pro Ile Phe Thr Leu Val Leu
                4805                4810                4815

Thr Asp Asp Gly Ala Tyr Thr Phe Thr Leu Leu Gly Pro Leu Asn His
            4820                4825                4830

Ala Thr Thr Pro Ser Asn Leu Asp Thr Leu Thr Ile Pro Phe Asp Val
        4835                4840                4845

Val Ala Val Asp Gly Asp Gly Asp Asp Ser Asn Gln Tyr Val Leu Pro
    4850                4855                4860

Ile Glu Val Leu Asp Asp Val Pro Val Met Thr Ala Pro Thr Gly Glu
4865                4870                4875                4880

Thr Val Val Asp Glu Asp Asp Leu Thr Gly Ile Gly Ser Asp Gln Ser
                4885                4890                4895

Glu Asp Thr Ile Ile Asn Gly Leu Phe Thr Val Asp Glu Gly Ala Asp
            4900                4905                4910
```

Gly Val Val Leu Tyr Glu Leu Val Asp Glu Asp Leu Val Leu Thr Gly
              4915                4920                4925

Leu Thr Ser Asp Gly Glu Ser Leu Glu Trp Leu Ala Val Ser Gln Asn
              4930                4935                4940

Gly Thr Thr Phe Thr Tyr Val Ala Gln Thr Ala Thr Ser Asn Glu Ala
4945                4950                4955                4960

Val Phe Glu Ile Ile Phe Asp Thr Ser Asp Asn Ser Tyr Gln Phe Glu
              4965                4970                4975

Leu Phe Lys Pro Leu Lys His Pro Asp Gly Ala Asn Glu Asn Ala Ile
              4980                4985                4990

Asp Leu Asp Phe Ser Ile Val Ala Glu Asp Phe Asp Gln Asp Gln Ser
              4995                5000                5005

Asp Ala Ile Gly Leu Lys Ile Thr Val Thr Asp Val Pro Leu Val
              5010                5015                5020

Thr Thr Gln Ser Ile Thr Arg Leu Glu Gly Gln Gly Tyr Gly Asn Ser
5025                5030                5035                5040

Lys Val Asp Met Phe Ala Asn Ala Thr Asp Val Gly Ala Asp Gly Ala
              5045                5050                5055

Val Leu Ser Arg Ile Glu Gly Ile Ser Asn Asn Gly Ala Asp Ile Val
              5060                5065                5070

Phe Arg Ser Gly Asn Asn Gly Pro Tyr Ser Ser Gly Phe Asp Leu Asn
              5075                5080                5085

Ser Gly Ser Gln Gln Val Arg Val Tyr Glu Gln Thr Asn Gly Gly Ala
              5090                5095                5100

Asp Thr Arg Glu Leu Gly Arg Leu Arg Ile Asn Ser Asn Gly Glu Val
5105                5110                5115                5120

Glu Phe Arg Ala Asn Gly Tyr Leu Asp His Asp Gly Asp Thr Ile
              5125                5130                5135

Asp Phe Ser Ile Asn Val Ile Ala Thr Asp Gly Asp Leu Asp Thr Ser
              5140                5145                5150

Glu Thr Pro Leu Asp Ile Thr Ile Thr Asp Arg Asp Ser Thr Arg Ile
              5155                5160                5165

Ala Leu Lys Val Thr Thr Phe Glu Asp Ala Gly Arg Asp Ser Thr Ile
              5170                5175                5180

Pro Tyr Ala Thr Gly Asp Glu Pro Thr Leu Glu Asn Val Gln Asp Asn
5185                5190                5195                5200

Gln Asn Gly Leu Pro Asn Ala Pro Ala Gln Val Ala Leu Gln Val Ser
              5205                5210                5215

Leu Tyr Asp Gln Asp Asn Ala Glu Ser Ile Gly Gln Leu Thr Ile Lys
              5220                5225                5230

Ser Pro Asn Gly Gly Asp Ser His Gln Gly Thr Phe Tyr Tyr Phe Asp
              5235                5240                5245

Gly Ala Asp Tyr Ile Glu Leu Val Pro Glu Ser Asn Gly Ser Ile Ile
              5250                5255                5260

Phe Gly Ser Pro Glu Leu Glu Gln Ser Phe Ala Pro Asn Pro Ser Glu
5265                5270                5275                5280

Pro Arg Gln Thr Ile Ala Thr Ile Asp Asn Leu Phe Phe Val Pro Asp
              5285                5290                5295

Gln His Ala Ser Ser Asp Glu Thr Gly Gly Arg Val Arg Tyr Glu Leu
              5300                5305                5310

Glu Ile Glu Lys Asn Gly Ser Thr Asp His Thr Val Asn Ser Asn Phe
              5315                5320                5325

Arg Ile Glu Ile Glu Ala Val Ala Asp Ile Ala Thr Trp Asp Asp Ser

```
              5330           5335           5340
Asn Ser Thr Tyr Gln Tyr Gln Val Asn Glu Asp Glu Asp Asn Val Thr
5345           5350           5355           5360

Leu Gln Leu Asn Ala Glu Ser Gln Asp Asn Ser Asn Thr Glu Thr Ile
              5365           5370           5375

Thr Tyr Glu Leu Glu Ala Val Gln Gly Asp Gly Lys Phe Glu Leu Leu
              5380           5385           5390

Asp Gln Asn Gly Asn Val Leu Thr Pro Val Asn Gly Val Tyr Ile Ile
              5395           5400           5405

Ala Ser Ala Asp Ile Asn Ser Thr Val Val Asn Pro Ile Asp Asn Phe
              5410           5415           5420

Ser Gly Gln Ile Glu Phe Lys Ala Thr Ala Ile Thr Glu Glu Thr Leu
5425           5430           5435           5440

Asn Pro Tyr Asp Asp Ser Asp Asn Gly Gly Ala Asn Asp Lys Thr Thr
              5445           5450           5455

Ala Arg Ser Val Glu Gln Ser Ile Val Ile Asp Val Thr Ala Asp Ala
              5460           5465           5470

Asp Pro Gly Thr Phe Ser Val Ser Arg Ile Gln Ile Asn Glu Asp Asn
              5475           5480           5485

Ile Asp Asp Pro Asp Tyr Val Gly Pro Leu Asp Asn Lys Asp Ala Phe
              5490           5495           5500

Thr Leu Asp Glu Val Ile Thr Met Thr Gly Ser Val Ser Asp Ser
5505           5510           5515           5520

Ser Glu Glu Leu Phe Val Arg Ile Ser Asn Val Thr Glu Gly Ala Val
              5525           5530           5535

Leu Tyr Phe Leu Gly Thr Thr Thr Val Val Pro Thr Ile Thr Ile Asn
              5540           5545           5550

Gly Val Asp Tyr Gln Glu Ile Ala Tyr Ser Asp Leu Ala Asn Val Glu
              5555           5560           5565

Val Val Pro Thr Lys His Ser Asn Val Asp Phe Thr Phe Asp Val Thr
              5570           5575           5580

Gly Val Val Lys Asp Thr Ala Asn Leu Ser Thr Gly Ala Gln Ile Asp
5585           5590           5595           5600

Glu Glu Ile Leu Gly Thr Lys Thr Val Asn Val Glu Val Lys Gly Val
              5605           5610           5615

Ala Asp Thr Pro Tyr Gly Gly Thr Asn Gly Thr Ala Trp Ser Ala Ile
              5620           5625           5630

Thr Asp Gly Thr Thr Ser Gly Val Gln Thr Thr Ile Gln Glu Ser Gln
              5635           5640           5645

Asn Gly Asp Thr Phe Ala Glu Leu Asp Phe Thr Val Leu Ser Gly Glu
              5650           5655           5660

Arg Arg Pro Asp Thr Gly Thr Thr Pro Leu Ala Asp Asp Gly Ser Glu
5665           5670           5675           5680

Ser Ile Thr Val Ile Leu Ser Gly Ile Pro Asp Gly Val Val Leu Glu
              5685           5690           5695

Asp Gly Asp Gly Thr Val Ile Asp Leu Asn Phe Val Gly Tyr Glu Thr
              5700           5705           5710

Gly Pro Gly Gly Ser Pro Asp Leu Ser Lys Pro Ile Tyr Glu Ala Asn
              5715           5720           5725

Ile Thr Glu Ala Gly Lys Thr Ser Gly Ile Arg Ile Arg Pro Val Asp
              5730           5735           5740

Ser Ser Thr Glu Asn Ile His Ile Gln Gly Lys Val Ile Val Thr Glu
5745           5750           5755           5760
```

```
Asn Asp Gly His Thr Leu Thr Phe Asp Gln Glu Ile Arg Val Leu Val
            5765                5770                5775

Ile Pro Arg Ile Asp Thr Ser Ala Thr Tyr Val Asn Thr Thr Asn Gly
            5780                5785                5790

Asp Glu Asp Thr Ala Ile Asn Ile Asp Trp His Pro Glu Gly Thr Asp
            5795                5800                5805

Tyr Ile Asp Asp Asp Glu His Phe Thr Lys Ile Thr Ile Asn Gly Ile
            5810                5815                5820

Pro Leu Gly Val Thr Ala Val Val Asn Gly Asp Val Thr Val Asp Asp
5825                5830                5835                5840

Ser Thr Pro Gly Thr Leu Ile Ile Thr Pro Lys Asp Ala Ser Gln Thr
            5845                5850                5855

Pro Glu Gln Phe Thr Gln Ile Ala Leu Ala Asn Asn Phe Ile Gln Met
            5860                5865                5870

Thr Pro Pro Ala Asp Ser Ser Ala Asp Phe Thr Leu Thr Thr Glu Leu
            5875                5880                5885

Lys Met Glu Glu Arg Asp His Glu Tyr Thr Ser Ser Gly Leu Glu Asp
            5890                5895                5900

Glu Asp Gly Gly Tyr Val Glu Ala Asp Pro Asp Ile Thr Gly Ile Ile
5905                5910                5915                5920

Asn Val Gln Val Arg Pro Val Val Glu Pro Gly Asp Ala Asp Asn Lys
            5925                5930                5935

Ile Val Val Ser Asn Glu Asp Gly Ser Gly Asp Leu Thr Thr Ile Thr
            5940                5945                5950

Ala Asp Ala Asn Gly Val Ile Lys Phe Thr Thr Asn Ser Asp Asn Gln
            5955                5960                5965

Thr Thr Asp Thr Asn Gly Asp Glu Ile Trp Asp Gly Glu Tyr Val Val
            5970                5975                5980

Arg Tyr Gln Glu Thr Asp Leu Ser Thr Val Glu Glu Gln Val Asp Glu
5985                5990                5995                6000

Val Ile Val Gln Leu Thr Asn Thr Asp Gly Ser Ala Leu Ser Asp Asp
            6005                6010                6015

Ile Leu Gly Gln Leu Leu Val Thr Gly Ala Ser Tyr Glu Gly Gly Gly
            6020                6025                6030

Arg Trp Val Val Thr Asn Glu Asp Ala Phe Ser Val Ser Ala Pro Asn
            6035                6040                6045

Gly Leu Asp Phe Thr Pro Ala Asn Asp Ala Asp Val Ala Thr Asp
6050                6055                6060

Phe Asn Asp Ile Lys Met Thr Ile Phe Thr Leu Val Ser Asp Pro Gly
6065                6070                6075                6080

Asp Ala Asn Asn Glu Thr Ser Ala Gln Val Gln Arg Thr Gly Glu Val
            6085                6090                6095

Thr Leu Ser Tyr Pro Glu Val Leu Thr Ala Pro Asp Lys Val Ala Ala
            6100                6105                6110

Asp Ile Ala Ile Val Pro Asp Ser Val Ile Asp Ala Val Glu Asp Thr
            6115                6120                6125

Gln Leu Asp Leu Gly Ala Ala Leu Asn Gly Ile Leu Ser Leu Thr Gly
            6130                6135                6140

Arg Asp Asp Ser Thr Asp Gln Val Thr Val Ile Ile Asp Gly Thr Leu
6145                6150                6155                6160

Val Ile Asp Ala Thr Thr Ser Phe Pro Ile Ser Leu Ser Gly Thr Ser
            6165                6170                6175

Asp Val Asp Phe Val Asn Gly Lys Tyr Val Tyr Glu Thr Thr Val Glu
            6180                6185                6190
```

```
Gln Gly Val Ala Val Asp Ser Ser Gly Leu Leu Asn Leu Pro Pro
            6195                6200                6205
Asn Tyr Ser Gly Asp Phe Arg Leu Pro Met Thr Ile Val Thr Lys Asp
        6210                6215                6220
Leu Gln Ser Gly Asp Glu Lys Thr Leu Val Thr Glu Val Ile Ile Lys
6225                6230                6235                6240
Val Ala Pro Asp Ala Glu Thr Asp Pro Thr Ile Glu Val Asn Val Val
            6245                6250                6255
Gly Ser Leu Asp Asp Ala Phe Asn Pro Val Asp Thr Asp Gly Gln Ala
            6260                6265                6270
Gly Gln Asp Pro Val Gly Tyr Glu Asp Thr Tyr Ile Gln Leu Asp Phe
            6275                6280                6285
Asn Ser Thr Ile Ser Asp Gln Val Ser Gly Val Glu Gly Gly Gln Glu
            6290                6295                6300
Ala Phe Thr Ser Ile Thr Leu Thr Leu Asp Asp Pro Ser Ile Gly Ala
6305                6310                6315                6320
Phe Tyr Asp Asn Thr Gly Thr Ser Leu Gly Thr Ser Val Thr Phe Asn
            6325                6330                6335
Gln Ala Glu Ile Ala Ala Gly Ala Leu Asp Asn Val Leu Phe Arg Ala
            6340                6345                6350
Ile Glu Asn Tyr Pro Thr Gly Asn Asp Ile Asn Gln Val Gln Val Asn
            6355                6360                6365
Val Ser Gly Thr Val Thr Asp Thr Ala Thr Tyr Asn Asp Pro Ala Ser
            6370                6375                6380
Pro Ala Gly Thr Ala Thr Asp Ser Asp Thr Phe Ser Thr Ser Val Ser
6385                6390                6395                6400
Phe Glu Val Val Pro Val Asp Asp Val Ser Val Thr Gly Pro Gly
            6405                6410                6415
Ser Asp Pro Asp Val Ile Glu Ile Thr Gly Asn Glu Asp Gln Leu Ile
            6420                6425                6430
Ser Leu Ser Gly Thr Gly Pro Val Ser Ile Ala Leu Thr Asp Leu Asp
            6435                6440                6445
Gly Ser Glu Gln Phe Val Ser Ile Lys Phe Thr Asp Val Pro Asp Gly
            6450                6455                6460
Phe Gln Met Arg Ala Asp Ala Gly Ser Thr Tyr Thr Val Lys Asn Asn
6465                6470                6475                6480
Gly Asn Gly Glu Trp Ser Val Gln Leu Pro Gln Ala Ser Gly Leu Ser
            6485                6490                6495
Phe Asp Leu Ser Glu Ile Ser Ile Leu Pro Pro Lys Asn Phe Ser Gly
            6500                6505                6510
Thr Ala Glu Phe Gly Val Glu Val Phe Thr Gln Glu Ser Leu Leu Gly
            6515                6520                6525
Val Pro Thr Ala Ala Ala Asn Leu Pro Ser Phe Lys Leu His Val Val
            6530                6535                6540
Pro Val Gly Asp Asp Val Asp Thr Asn Pro Thr Asp Ser Val Thr Gly
6545                6550                6555                6560
Asn Glu Gly Gln Asn Ile Asp Ile Glu Ile Asn Ala Thr Ile Leu Asp
            6565                6570                6575
Lys Glu Leu Ser Ala Thr Gly Ser Gly Thr Tyr Thr Glu Asn Ala Pro
            6580                6585                6590
Glu Thr Leu Arg Val Glu Val Ala Gly Val Pro Gln Asp Ala Ser Ile
            6595                6600                6605
Phe Tyr Pro Asp Gly Thr Thr Leu Ala Ser Tyr Asp Pro Ala Thr Gln
```

-continued

```
            6610            6615            6620

Leu Trp Thr Leu Asp Val Pro Ala Gln Ser Leu Asp Lys Ile Val Phe
6625            6630            6635            6640

Asn Ser Gly Glu His Asn Ser Asp Thr Gly Asn Val Leu Gly Ile Asn
            6645            6650            6655

Gly Pro Leu Gln Ile Thr Val Arg Ser Val Asp Thr Asp Ala Asp Asn
            6660            6665            6670

Thr Glu Tyr Leu Gly Thr Pro Thr Ser Phe Asp Val Asp Leu Val Ile
            6675            6680            6685

Asp Pro Ile Asn Asp Gln Pro Ile Phe Val Asn Val Thr Asn Ile Glu
            6690            6695            6700

Thr Ser Glu Asp Ile Ser Val Ala Ile Asp Asn Phe Ser Ile Tyr Asp
6705            6710            6715            6720

Val Asp Ala Asn Phe Asp Asn Pro Asp Ala Pro Tyr Glu Leu Thr Leu
            6725            6730            6735

Lys Val Asp Gln Thr Leu Pro Gly Ala Gln Gly Val Phe Glu Phe Thr
            6740            6745            6750

Ser Ser Pro Asp Val Thr Phe Val Leu Gln Pro Asp Gly Ser Leu Val
            6755            6760            6765

Ile Thr Gly Lys Glu Ala Asp Ile Asn Thr Ala Leu Thr Asn Gly Ala
            6770            6775            6780

Val Thr Phe Lys Pro Asp Pro Asp Gln Asn Tyr Leu Asn Gln Thr Gly
6785            6790            6795            6800

Leu Val Thr Ile Asn Ala Thr Leu Asp Asp Gly Gly Asn Asn Gly Leu
            6805            6810            6815

Ile Asp Ala Val Asp Pro Asn Thr Ala Gln Thr Asn Gln Thr Thr Phe
            6820            6825            6830

Thr Ile Lys Val Thr Glu Val Asn Asp Ala Pro Val Ala Thr Asn Val
            6835            6840            6845

Asp Leu Gly Ser Ile Ala Glu Asp Ala Gln Ile Val Ile Val Glu Ser
            6850            6855            6860

Asp Leu Ile Ala Ala Ser Ser Asp Leu Glu Asn His Asn Leu Thr Val
6865            6870            6875            6880

Thr Gly Val Thr Leu Thr Gln Gly Gln Gly Gln Leu Thr Arg Tyr Glu
            6885            6890            6895

Asn Ala Gly Gly Ala Asp Asp Ala Ala Ile Thr Gly Pro Phe Trp Ile
            6900            6905            6910

Phe Ile Ala Asp Asn Asp Phe Asn Gly Asp Val Lys Phe Asn Tyr Ser
            6915            6920            6925

Ile Ile Asp Asp Gly Thr Thr Asn Gly Val Asp Phe Lys Thr Asp
            6930            6935            6940

Ser Ala Glu Ile Ser Leu Val Val Thr Glu Val Asn Asp Gln Pro Val
6945            6950            6955            6960

Ala Ser Asn Ile Asp Leu Gly Thr Met Leu Glu Glu Gly Gln Leu Val
            6965            6970            6975

Ile Lys Glu Glu Asp Leu Ile Ser Ala Thr Thr Asp Pro Glu Asn Asp
            6980            6985            6990

Thr Ile Thr Val Asn Ser Leu Val Leu Asp Gln Gly Gln Gly Gln Leu
            6995            7000            7005

Gln Arg Phe Glu Asn Val Gly Gly Ala Asp Asp Ala Thr Ile Thr Gly
            7010            7015            7020

Pro Tyr Trp Val Phe Thr Ala Ala Asn Glu Tyr Asn Gly Asp Val Lys
7025            7030            7035            7040
```

```
Phe Thr Tyr Thr Val Glu Asp Asp Gly Thr Thr Asn Gly Ala Asp Asp
            7045                7050                7055

Phe Leu Thr Asp Thr Gly Glu Ile Ser Val Val Thr Glu Val Asn
            7060                7065                7070

Asp Gln Pro Val Ala Thr Asp Ile Asp Leu Gly Asn Ile Leu Glu Glu
        7075                7080                7085

Gly Gln Leu Ile Ile Lys Glu Glu Asp Leu Ile Ala Ala Thr Ser Asp
        7090                7095                7100

Pro Glu Asn Asp Thr Ile Thr Val Thr Asn Leu Val Leu Asp Glu Gly
7105                7110                7115                7120

Gln Gly Gln Leu Gln Arg Phe Glu Asn Val Gly Gly Ala Asp Asp Ala
            7125                7130                7135

Met Ile Thr Gly Pro Tyr Trp Ile Phe Thr Ala Ala Asp Glu Tyr Asn
            7140                7145                7150

Gly Asn Val Lys Phe Thr Tyr Thr Val Glu Asp Gly Thr Thr Asn
            7155                7160                7165

Gly Ala Asn Asp Phe Leu Thr Asp Thr Ala Glu Ile Thr Ala Ile Val
            7170                7175                7180

Asp Gly Val Asn Asp Thr Pro Val Val Asn Gly Asp Ser Val Thr Thr
7185                7190                7195                7200

Ile Val Asp Glu Asp Ala Gly Gln Leu Leu Ser Gly Ile Asn Val Ser
            7205                7210                7215

Asp Pro Asp Tyr Val Asp Ala Phe Ser Asn Asp Leu Met Thr Val Thr
            7220                7225                7230

Leu Thr Val Asp Tyr Gly Thr Leu Asn Val Ser Leu Pro Ala Val Thr
            7235                7240                7245

Thr Val Met Val Asn Gly Asn Asn Thr Gly Ser Val Ile Leu Val Gly
            7250                7255                7260

Thr Leu Ser Asp Leu Asn Ala Leu Ile Asp Thr Pro Thr Ser Pro Asn
7265                7270                7275                7280

Gly Val Tyr Leu Asp Ala Ser Leu Ser Pro Thr Asn Ser Ile Gly Leu
            7285                7290                7295

Glu Val Ile Ala Lys Asp Ser Gly Asn Pro Ser Gly Ile Ala Ile Glu
            7300                7305                7310

Thr Ala Pro Val Val Tyr Asn Ile Ala Val Thr Pro Val Ala Asn Ala
            7315                7320                7325

Pro Thr Leu Ser Ile Asp Pro Ala Phe Asn Tyr Val Arg Asn Ile Thr
            7330                7335                7340

Thr Ser Ser Ser Val Val Ala Asn Ser Gly Val Ala Leu Val Gly Ile
7345                7350                7355                7360

Val Ala Ala Leu Thr Asp Ile Thr Glu Glu Leu Thr Leu Lys Ile Ser
            7365                7370                7375

Asp Val Pro Asp Gly Val Asp Val Thr Ser Asp Val Gly Thr Val Ser
            7380                7385                7390

Leu Val Gly Asp Thr Trp Ile Ala Thr Ala Asp Ala Ile Asp Ser Leu
            7395                7400                7405

Arg Leu Val Glu Gln Ser Ser Leu Gly Lys Pro Leu Thr Pro Gly Asn
            7410                7415                7420

Tyr Thr Leu Lys Val Glu Ala Leu Ser Glu Glu Thr Asp Asn Asn Asp
7425                7430                7435                7440

Ile Ala Ile Ser Gln Asn Ile Asp Leu Asn Leu Asn Ile Val Ala Asn
            7445                7450                7455

Pro Ile Asp Leu Asp Leu Ser Ser Glu Thr Asp Asp Val Gln Leu Leu
            7460                7465                7470
```

Ala Ser Asn Phe Asp Thr Asn Leu Thr Gly Gly Thr Gly Asn Asp Arg
          7475                7480                7485

Leu Val Gly Gly Ala Gly Asp Asp Thr Leu Val Gly Gly Asp Gly Asn
          7490                7495                7500

Asp Thr Leu Ile Gly Gly Gly Ser Asp Ile Leu Thr Gly Gly Asn
7505                7510                7515                7520

Gly Met Asp Ser Phe Val Trp Leu Asn Ile Glu Asp Gly Val Glu Asp
          7525                7530                7535

Thr Ile Thr Asp Phe Ser Leu Ser Glu Gly Asp Gln Ile Asp Leu Arg
          7540                7545                7550

Glu Val Leu Pro Glu Leu Lys Asn Thr Ser Pro Asp Met Ser Ala Leu
          7555                7560                7565

Leu Gln Gln Ile Asp Ala Lys Val Glu Gly Asp Ile Glu Leu Thr
          7570                7575                7580

Ile Lys Ser Asp Gly Leu Gly Thr Thr Glu Gln Val Ile Val Glu
7585                7590                7595                7600

Asp Leu Ala Pro Gln Leu Thr Leu Ser Gly Thr Met Pro Ser Asp Ile
          7605                7610                7615

Leu Asp Ala Leu Val Gln Gln Asn Val Ile Thr His Gly
          7620                7625

<210> SEQ ID NO 5
<211> LENGTH: 765
<212> TYPE: DNA
<213> ORGANISM: Vibrio splendidus

<400> SEQUENCE: 5
atgaaaaaaa catcactatt acttgcttcc attactctgg cactttctgg tgtagtacaa      60
gctgaccagc tagaagacat tcaaaaatca ggcacacttc gcgtcggcac acaggcgac     120
tacaaacctt tttcttactt cgacggcaaa acctactctg ttatgacat tgacgtagcc     180
aaacatgttg cagagcagtt gggcgttgaa ttacagattg ttcgtaccac atggaaagat    240
ctactgaccg atctagacag cgataaatac gacatcgcga tgggcggtat cacgcgtaaa    300
atgcagcgtc agttaaacgc agaacaaact caaggttaca tgacctttgg caagtgtttc    360
ttagttgcga aaggcaaagc agaacaatac aacagcattg agaaagtgaa cctctcttct    420
gtgcgtgttg gcgtcaatat cggtgggact aatgagatgt ttgcggatgc taacttgcaa    480
gacgcgagct ttacgcgtta cgagaacaac ctagacgttc gcaagccgt tgcggaaggt    540
aaagttgatg taatggtgac agaaactcct gaaggtctgt tctatcaagt gacggacgaa    600
cgtcttgaag cggcacgctg tgaaacaccg tttaccaaca gtcaattcgg ttacctgata    660
ccaaaaggtg aacaacgctt gttgaacaca gtgaacttca ttatggatga gatgaaattg    720
aaaggcgtcg aagaagagtt cctgatccac aactctctta agtaa                    765

<210> SEQ ID NO 6
<211> LENGTH: 254
<212> TYPE: PRT
<213> ORGANISM: Vibrio splendidus

<400> SEQUENCE: 6

Met Lys Lys Thr Ser Leu Leu Leu Ala Ser Ile Thr Leu Ala Leu Ser
1               5                   10                  15

Gly Val Val Gln Ala Asp Gln Leu Glu Asp Ile Gln Lys Ser Gly Thr
            20                  25                  30

Leu Arg Val Gly Thr Thr Gly Asp Tyr Lys Pro Phe Ser Tyr Phe Asp

```
                    35                  40                  45
Gly Lys Thr Tyr Ser Gly Tyr Asp Ile Asp Val Ala Lys His Val Ala
 50                  55                  60

Glu Gln Leu Gly Val Glu Leu Gln Ile Val Arg Thr Thr Trp Lys Asp
 65                  70                  75                  80

Leu Leu Thr Asp Leu Asp Ser Asp Lys Tyr Asp Ile Ala Met Gly Gly
                 85                  90                  95

Ile Thr Arg Lys Met Gln Arg Gln Leu Asn Ala Glu Gln Thr Gln Gly
            100                 105                 110

Tyr Met Thr Phe Gly Lys Cys Phe Leu Val Ala Lys Gly Lys Ala Glu
        115                 120                 125

Gln Tyr Asn Ser Ile Glu Lys Val Asn Leu Ser Ser Val Arg Val Gly
    130                 135                 140

Val Asn Ile Gly Gly Thr Asn Glu Met Phe Ala Asp Ala Asn Leu Gln
145                 150                 155                 160

Asp Ala Ser Phe Thr Arg Tyr Glu Asn Asn Leu Asp Val Pro Gln Ala
                165                 170                 175

Val Ala Glu Gly Lys Val Asp Val Met Val Thr Glu Thr Pro Glu Gly
            180                 185                 190

Leu Phe Tyr Gln Val Thr Asp Glu Arg Leu Glu Ala Ala Arg Cys Glu
        195                 200                 205

Thr Pro Phe Thr Asn Ser Gln Phe Gly Tyr Leu Ile Pro Lys Gly Glu
    210                 215                 220

Gln Arg Leu Leu Asn Thr Val Asn Phe Ile Met Asp Glu Met Lys Leu
225                 230                 235                 240

Lys Gly Val Glu Glu Glu Phe Leu Ile His Asn Ser Leu Lys
                245                 250

<210> SEQ ID NO 7
<211> LENGTH: 765
<212> TYPE: DNA
<213> ORGANISM: Vibrio splendidus

<400> SEQUENCE: 7
atgaaaaaaa catcactatt acttgcttcc attactctgg cactttctgg tgtagtacaa      60
gctgaccagc tagaagacat tcaaaaatca ggcacacttc gcgtcggcac acaggcgac     120 tacaaacctt tttcttactt cgacggcaaa acctactctg gttatgacat tgacgtagcc    180
aaacatgttg cagagcagtt gggcgttgaa ttacagattg ttcgtaccac atggaaagat    240
ctactgaccg atctagacag cgataaatac gacatcgcga tgggcggtat cacgcgtaaa    300
atgcagcgtc agttaaacgc agaacaaact caaggttaca tgacctttgg caagtgtttc    360
ttagttgcga aaggcaaagc agaacaatac aacagcattg agaaagtgaa cctctcttct    420
gtgcgtgttg gcgtcaatat cggtgggact aatgagatgt ttgcggatgc taacttgcaa    480
gacgcgagct ttacgcgtta cgagaacaac ctagacgttc cgcaagccgt tgcggaaggt    540
aaagttgatg taatggtgac agaaactcct gaaggtctgt tctatcaagt gacggacgaa    600
cgtcttgaag cggcacgctg tgaaacaccg tttaccaaca gtcaattcgg ttacctgata    660
ccaaaaggtg aacaacgctt gttgaacaca gtgaacttca ttatggatga gatgaaattg    720
aaaggcgtcg aagaagagtt cctgatccac aactctctta agtaa                    765

<210> SEQ ID NO 8
<211> LENGTH: 588
<212> TYPE: PRT
<213> ORGANISM: Vibrio splendidus
```

```
<400> SEQUENCE: 8

Met Thr Ile Asp Thr Phe Val Val Leu Ala Tyr Phe Phe Phe Leu Ile
1               5                   10                  15

Ala Ile Gly Trp Met Phe Arg Lys Phe Thr Thr Ser Thr Ser Asp Tyr
            20                  25                  30

Phe Arg Gly Gly Gly Lys Met Leu Trp Trp Met Val Gly Ala Thr Ala
        35                  40                  45

Phe Met Thr Gln Phe Ser Ala Trp Thr Phe Thr Gly Ala Ala Gly Arg
    50                  55                  60

Ala Phe Asn Asp Gly Phe Val Ile Val Ile Leu Phe Leu Ala Asn Ala
65                  70                  75                  80

Phe Gly Tyr Phe Met Asn Tyr Met Tyr Phe Ala Pro Lys Phe Arg Gln
                85                  90                  95

Leu Arg Val Val Thr Ala Ile Glu Ala Ile Arg Gln Arg Phe Gly Lys
            100                 105                 110

Thr Ser Glu Gln Phe Phe Thr Trp Ala Gly Met Pro Asp Ser Leu Ile
        115                 120                 125

Ser Ala Gly Ile Trp Leu Asn Gly Leu Ala Ile Phe Val Ala Ala Val
130                 135                 140

Phe Asn Ile Pro Met Glu Ala Thr Ile Val Thr Gly Met Val Leu
145                 150                 155                 160

Val Leu Met Ala Val Thr Gly Gly Ser Trp Ala Val Val Ala Ser Asp
                165                 170                 175

Phe Met Gln Met Leu Val Ile Met Ala Val Thr Ile Thr Cys Ala Val
            180                 185                 190

Ala Ala Tyr Phe His Gly Gly Gly Leu Thr Asn Ile Val Ala Asn Phe
        195                 200                 205

Asp Gly Asp Phe Met Leu Gly Asn Asn Leu Asn Tyr Met Ser Ile Phe
    210                 215                 220

Val Leu Trp Val Val Phe Ile Phe Val Lys Gln Phe Gly Val Met Asn
225                 230                 235                 240

Asn Ser Ile Asn Ala Tyr Arg Tyr Leu Cys Ala Lys Asp Ser Glu Asn
                245                 250                 255

Ala Arg Lys Ala Ala Gly Leu Ala Cys Ile Leu Met Val Val Gly Pro
            260                 265                 270

Leu Ile Trp Phe Leu Pro Pro Trp Tyr Val Ser Ala Phe Met Pro Asp
        275                 280                 285

Phe Ala Leu Glu Tyr Ala Ser Met Gly Asp Lys Ala Gly Asp Ala Ala
    290                 295                 300

Tyr Leu Ala Phe Val Gln Asn Val Met Pro Ala Gly Met Val Gly Leu
305                 310                 315                 320

Leu Met Ser Ala Met Phe Ala Ala Thr Met Ser Ser Met Asp Ser Gly
                325                 330                 335

Leu Asn Arg Asn Ala Gly Ile Phe Val Met Asn Phe Tyr Ser Pro Ile
            340                 345                 350

Leu Arg Gln Asn Ala Thr Gln Lys Glu Leu Val Ile Val Ser Lys Leu
        355                 360                 365

Thr Thr Ile Met Met Gly Ile Ile Ile Ala Ile Gly Leu Phe Ile
    370                 375                 380

Asn Ser Leu Arg His Leu Ser Leu Phe Asp Ile Val Met Asn Val Gly
385                 390                 395                 400

Ala Leu Ile Gly Phe Pro Met Leu Ile Pro Val Leu Leu Gly Met Trp
                405                 410                 415
```

Ile Arg Lys Thr Pro Asp Trp Ala Gly Trp Ser Thr Leu Ile Val Gly
            420                 425                 430

Gly Phe Val Ser Tyr Ile Phe Gly Ile Ser Leu Gln Ala Glu Asp Ile
        435                 440                 445

Glu His Leu Phe Gly Met Glu Thr Ala Leu Thr Gly Arg Glu Trp Ser
    450                 455                 460

Asp Leu Lys Val Gly Leu Ser Leu Ala Ala His Val Val Phe Thr Gly
465                 470                 475                 480

Gly Tyr Phe Ile Leu Thr Ser Arg Phe Tyr Lys Gly Leu Ser Pro Glu
                485                 490                 495

Arg Glu Lys Glu Val Asp Gln Leu Phe Thr Asn Trp Asn Thr Pro Leu
            500                 505                 510

Val Ala Glu Gly Glu Gln Gln Asn Leu Asp Thr Lys Gln Arg Ser
        515                 520                 525

Met Leu Gly Lys Leu Ile Ser Thr Ala Gly Phe Gly Ile Leu Ala Met
    530                 535                 540

Ala Leu Ile Pro Asn Glu Pro Thr Gly Arg Leu Leu Phe Leu Leu Cys
545                 550                 555                 560

Gly Ser Met Val Leu Thr Val Gly Ile Leu Leu Val Asn Ala Ser Lys
                565                 570                 575

Ala Pro Ala Lys Met Asn Asn Glu Ser Val Ala Lys
            580                 585

<210> SEQ ID NO 9
<211> LENGTH: 627
<212> TYPE: DNA
<213> ORGANISM: Vibrio splendidus

<400> SEQUENCE: 9
atgacgacat taaatgaaca actagcaaac ctaaaagtaa ttcctgtaat cgcgatcaac    60
cgtgctgaag acgctatccc tctaggtaaa gcgttggttg aaaatggcat gccatgtgca   120
gaaattacac tacgtacaga atgtgcaatc gaagcgattc gcatcatgcg taagaattc    180 ccagacatgc taatcggttc aggtactgta ctgactaacg agcaagttga cgcatctat   240 gaagctggtg ttgatttcat cgtaagccca ggttttaacc cacgtactgt tcaatactgt   300
atcgataaag gtattgcaat cgtaccgggt gttaacaacc aagcctagt tgagcaagca   360 atggaaatgg gtcttcgcac gttgaagttc tcccctgctg agccttcagg cggtactggc   420
atgcttaaag cactaacagc agtttaccct gttaaattca tgcctactgg tggcgtaagc   480
ttgaagaatg ttgatgaata cctatcgatc ccttctgttc ttgcgtgtgg cggtacttgg   540
atggttccaa ctaaccttat cgatgaaggt aagtgggacg aactaggcaa gcttgttcgt   600
gacgcagttg atcacgttaa cgcttaa                                        627

<210> SEQ ID NO 10
<211> LENGTH: 208
<212> TYPE: PRT
<213> ORGANISM: Vibrio splendidus

<400> SEQUENCE: 10

Met Thr Thr Leu Asn Glu Gln Leu Ala Asn Leu Lys Val Ile Pro Val
1               5                   10                  15

Ile Ala Ile Asn Arg Ala Glu Asp Ala Ile Pro Leu Gly Lys Ala Leu
            20                  25                  30

Val Glu Asn Gly Met Pro Cys Ala Glu Ile Thr Leu Arg Thr Glu Cys
        35                  40                  45

```
Ala Ile Glu Ala Ile Arg Ile Met Arg Lys Glu Phe Pro Asp Met Leu
        50                  55                  60

Ile Gly Ser Gly Thr Val Leu Thr Asn Glu Gln Val Asp Ala Ser Ile
 65                  70                  75                  80

Glu Ala Gly Val Asp Phe Ile Val Ser Pro Gly Phe Asn Pro Arg Thr
                 85                  90                  95

Val Gln Tyr Cys Ile Asp Lys Gly Ile Ala Ile Val Pro Gly Val Asn
            100                 105                 110

Asn Pro Ser Leu Val Glu Gln Ala Met Glu Met Gly Leu Arg Thr Leu
        115                 120                 125

Lys Phe Phe Pro Ala Glu Pro Ser Gly Gly Thr Gly Met Leu Lys Ala
    130                 135                 140

Leu Thr Ala Val Tyr Pro Val Lys Phe Met Pro Thr Gly Gly Val Ser
145                 150                 155                 160

Leu Lys Asn Val Asp Glu Tyr Leu Ser Ile Pro Ser Val Leu Ala Cys
                165                 170                 175

Gly Gly Thr Trp Met Val Pro Thr Asn Leu Ile Asp Glu Lys Trp
            180                 185                 190

Asp Glu Leu Gly Lys Leu Val Arg Asp Ala Val Asp His Val Asn Ala
        195                 200                 205
```

<210> SEQ ID NO 11
<211> LENGTH: 933
<212> TYPE: DNA
<213> ORGANISM: Vibrio splendidus

<400> SEQUENCE: 11

```
atgaaatcat taaacatcgc ggtcattggc gagtgcatgg ttgagctaca aaagaaacaa      60
gacgggctta agcaaagttt tggtggcgat acgctgaata ctgcacttta cttgtcacgc     120
ttaacaaaag agcaagatat caacacgagc tacgtaactg cactaggcac tgacccattc     180
agtaccgaca tgttaaaaaa ttggcaagcg gaaggtatcg acacgagctt aattgctcag     240
ctggaccaca acaaccagg gctttactac atcgagaccg atgaaactgg tgaacgcagt     300
ttccactact ggcgtagtga tgctgcagcg aagttcatgt ttgatcagga agacacgcct     360
gctcttcttg ataagctgtt ctcttttgac gcgatttact aagtggtat tacgctggca     420
atcttgacag aaaatggtcg cacgcagcta ttcaacttct tagacaaatt caaagctcaa     480
ggcggccaag tattcttcga caataactac cgacctaaac tttgggaaag ccaacaagaa     540
gcgatttctt ggtacttgaa atgcttaag tacacagata cggctctgct gacgtttgat     600
gatgagcaag agctatacgg cgacgaaagc attgaacaat gtattacacg tacgtcagag     660
tctggtgtga aagagatcgt cattaaacgt ggcgcgaaag actgcttagt ggttgaaagc     720
caaagcgctc aatacgttgc acccaaccct gtagacaaca tcgttgatac gactgccgct     780
ggcgactcgt tcagtgcagg cttcttggcc aagcgcttga gcggcggtag tgctcgtgat     840
gctgcatttg caggtcatat tgtggcagga accgtgattc agcatccagg tgctatcatt     900
cctctagaag cgacgcctga tctgtctcta taa                                  933
```

<210> SEQ ID NO 12
<211> LENGTH: 310
<212> TYPE: PRT
<213> ORGANISM: Vibrio splendidus

<400> SEQUENCE: 12

```
Met Lys Ser Leu Asn Ile Ala Val Ile Gly Glu Cys Met Val Glu Leu
```

```
              1               5                  10                 15
Gln Lys Lys Gln Asp Gly Leu Lys Gln Ser Phe Gly Gly Asp Thr Leu
                  20                  25                  30

Asn Thr Ala Leu Tyr Leu Ser Arg Leu Thr Lys Glu Gln Asp Ile Asn
                  35                  40                  45

Thr Ser Tyr Val Thr Ala Leu Gly Thr Asp Pro Phe Ser Thr Asp Met
             50                  55                  60

Leu Lys Asn Trp Gln Ala Glu Gly Ile Asp Thr Ser Leu Ile Ala Gln
65                  70                  75                  80

Leu Asp His Lys Gln Pro Gly Leu Tyr Tyr Ile Glu Thr Asp Glu Thr
                 85                  90                  95

Gly Glu Arg Ser Phe His Tyr Trp Arg Ser Asp Ala Ala Lys Phe
                100                 105                 110

Met Phe Asp Gln Glu Asp Thr Pro Ala Leu Leu Asp Lys Leu Phe Ser
                115                 120                 125

Phe Asp Ala Ile Tyr Leu Ser Gly Ile Thr Leu Ala Ile Leu Thr Glu
                130                 135                 140

Asn Gly Arg Thr Gln Leu Phe Asn Phe Leu Asp Lys Phe Lys Ala Gln
145                 150                 155                 160

Gly Gly Gln Val Phe Phe Asp Asn Asn Tyr Arg Pro Lys Leu Trp Glu
                165                 170                 175

Ser Gln Gln Glu Ala Ile Ser Trp Tyr Leu Lys Met Leu Lys Tyr Thr
                180                 185                 190

Asp Thr Ala Leu Leu Thr Phe Asp Asp Glu Gln Glu Leu Tyr Gly Asp
                195                 200                 205

Glu Ser Ile Glu Gln Cys Ile Thr Arg Thr Ser Glu Ser Gly Val Lys
                210                 215                 220

Glu Ile Val Ile Lys Arg Gly Ala Lys Asp Cys Leu Val Val Glu Ser
225                 230                 235                 240

Gln Ser Ala Gln Tyr Val Ala Pro Asn Pro Val Asp Asn Ile Val Asp
                245                 250                 255

Thr Thr Ala Ala Gly Asp Ser Phe Ser Ala Gly Phe Leu Ala Lys Arg
                260                 265                 270

Leu Ser Gly Gly Ser Ala Arg Asp Ala Ala Phe Ala Gly His Ile Val
                275                 280                 285

Ala Gly Thr Val Ile Gln His Pro Gly Ala Ile Ile Pro Leu Glu Ala
                290                 295                 300

Thr Pro Asp Leu Ser Leu
305                 310

<210> SEQ ID NO 13
<211> LENGTH: 336
<212> TYPE: DNA
<213> ORGANISM: Vibrio splendidus

<400> SEQUENCE: 13
atgaactctt tctttatcct agatgaaaat ccatgggaag aacttggtgg cggcattaag      60
cgtaaaatcg ttgcttacac tgacgatcta atggcagtac acctatgctt tgataagggc     120
gcgattggcc accctcatac tcacgaaatt cacgaccaaa tcggttatgt tgttcgtggt     180
agcttcgaag ctgaaatcga cggcgagaag aaagtgctta agaaggcga tgcttacttc      240 gctcgtaaac acatgatgca cggtgcagtt gctctagaac aagacagcat ccttcttgat     300
atcttcaatc ctgcgcgtga agatttccta aaataa                               336
```

<210> SEQ ID NO 14
<211> LENGTH: 111
<212> TYPE: PRT
<213> ORGANISM: Vibrio splendidus

<400> SEQUENCE: 14

Met Asn Ser Phe Phe Ile Leu Asp Glu Asn Pro Trp Glu Glu Leu Gly
1               5                   10                  15

Gly Gly Ile Lys Arg Lys Ile Val Ala Tyr Thr Asp Asp Leu Met Ala
            20                  25                  30

Val His Leu Cys Phe Asp Lys Gly Ala Ile Gly His Pro His Thr His
        35                  40                  45

Glu Ile His Asp Gln Ile Gly Tyr Val Val Arg Gly Ser Phe Glu Ala
    50                  55                  60

Glu Ile Asp Gly Glu Lys Lys Val Leu Lys Glu Gly Asp Ala Tyr Phe
65                  70                  75                  80

Ala Arg Lys His Met Met His Gly Ala Val Ala Leu Glu Gln Asp Ser
                85                  90                  95

Ile Leu Leu Asp Ile Phe Asn Pro Ala Arg Glu Asp Phe Leu Lys
            100                 105                 110

<210> SEQ ID NO 15
<211> LENGTH: 2208
<212> TYPE: DNA
<213> ORGANISM: Vibrio splendidus

<400> SEQUENCE: 15
atgacgacta aaccagtatt gttgactgaa gctgaaatcg aacagcttca tcttgaagtg      60
ggccgttcta gcttaatggg caaaaccatt gcagcgaacg cgaaagacct agaagcattc     120
atgcgtttac ctattgatgt ccaggtcac ggtgaagctg ggggttacga acataaccgc      180
cacaagcaaa attacacgta catgaaccta gctggtcgca tgttcttgat cactaaagag     240
caaaaatacg ctgactttgt tacagaatta ctagaagagt acgcagacaa atatctaacg     300
tttgattacc acgtacagaa aaacaccaac ccaacaggtc gtttgttcca ccaaatccta     360
aacgaacact gctggttaat gttctcaagc ttagcttatt cttgtgttgc ttcaacactg     420
acacaagatc agcgtgacaa tattgagtct cgcattttg aacccatgct agaaatgttc      480
acggttaaat acgcacacga cttcgaccgt attcacaatc acggtatttg ggcagtagcc     540
gctgtgggta tctgtggtct tgctttaggc aaacgtgaat acctagaaat gtcagtgtac     600
ggcatcgacc gtaatgatac tggcggttc ctagcgcaag tttctcagct atttgcacct      660
tctggctact acatggaagg tccttactac catcgttatg cgattcgccc aacgtgtgtg     720
ttcgctgaag tgattcaccg tcatatgcct gaagttgata tctacaacta caaaggcggc     780
gtgattggta acacagtaca agctatgctt gcgacagcgt acccgaacgg cgagttcccg     840
gctctgaatg atgcttctcg tactatgggt atcacagaca tgggtgttca ggttgcggtc     900
agtgtttaca gtaagcatta ctcttctgaa acggtgtag accaaaacat tctgggtatg     960
gcgaagattc aagacgcagt atggatgcat ccatgtggtc ttgagctatc taaagcatac    1020
gaagccgcat ctgcagagaa agaaatcggc atgcctttct ggccaagtgt tgaattgaat    1080
gaaggccctc aaggtcacaa cggcgcgcaa ggctttatcc gtatgcagga taagaaaggc    1140
gacgtttctc aacttgtgat gaactacggc caacacggca tgggtcacgg caactttgat    1200
acgctgggta tttctttctt taaccgcggt caagaagtgc tacgtgaata cggcttctgt    1260
cgttgggtta acgttgagcc aaaattcggc ggccgttacc tagacgaaaa caaatcttac    1320

-continued

```
gctcgtcaaa cgattgctca caatgcagtt acgattgatg aaaaatgtca gaacaacttt    1380
gacgttgaac gtgcagactc agtacatggt ttacctcact tctttaaagt agaagacgat    1440
caaatcaacg gtatgagtgc atttgctaac gatcattacc aaggctttga catgcaacgc    1500
agcgtgttca tgctaaatct tgaagaatta gaatctccgt tattgttaga cctataccgc    1560
ttagattcta caaaaggcgg cgaaggcgag caccaatacg actattcaca ccaatatgcg    1620
ggtcagattg ttcgcactaa cttcgaatac caagcgaaca aagagctaaa cactctaggt    1680
gacgatttcg gttaccaaca tctatggaac gtcgcaagcg gtgaagtgaa gggcacagca    1740
attgtaagtt ggctacaaaa caacacctac tacacatggc taggtgcaac gtctaacgat    1800
aatgctgaag taatatttac tcgcactggc gctaacgacc caagtttcaa tctacgttca    1860
gagcctgcgt tcattctacg cagcaaaggc gaaacaacac tgtttgcttc tgttgttgaa    1920
acgcacggtt atttcaacga agaattcgag caatctgtca atgcacgtgg tgttgtgaaa    1980
gacatcaaag tcgtggctca caccaatgtc ggttcggtag ttgagatcac cacagagaaa    2040
tcaaacgtga cagtgatgat cagcaaccaa cttggcgcga ctgacagcac tgaacacaaa    2100
gtagaactga acggcaaagt atacagctgg aaaggcttct actcagtaga gacaacttta    2160
caagaaacga attcagaaga acttagcact gcagggcagg ggaaataa                 2208
```

<210> SEQ ID NO 16
<211> LENGTH: 735
<212> TYPE: PRT
<213> ORGANISM: Vibrio splendidus

<400> SEQUENCE: 16

```
Met Thr Thr Lys Pro Val Leu Leu Thr Glu Ala Glu Ile Glu Gln Leu
1               5                   10                  15

His Leu Glu Val Gly Arg Ser Ser Leu Met Gly Lys Thr Ile Ala Ala
            20                  25                  30

Asn Ala Lys Asp Leu Glu Ala Phe Met Arg Leu Pro Ile Asp Val Pro
        35                  40                  45

Gly His Gly Glu Ala Gly Gly Tyr Glu His Asn Arg His Lys Gln Asn
    50                  55                  60

Tyr Thr Tyr Met Asn Leu Ala Gly Arg Met Phe Leu Ile Thr Lys Glu
65                  70                  75                  80

Gln Lys Tyr Ala Asp Phe Val Thr Glu Leu Glu Glu Tyr Ala Asp
            85                  90                  95

Lys Tyr Leu Thr Phe Asp Tyr His Val Gln Lys Asn Thr Asn Pro Thr
            100                 105                 110

Gly Arg Leu Phe His Gln Ile Leu Asn Glu His Cys Trp Leu Met Phe
        115                 120                 125

Ser Ser Leu Ala Tyr Ser Cys Val Ala Ser Thr Leu Thr Gln Asp Gln
130                 135                 140

Arg Asp Asn Ile Glu Ser Arg Ile Phe Glu Pro Met Leu Glu Met Phe
145                 150                 155                 160

Thr Val Lys Tyr Ala His Asp Phe Asp Arg Ile His Asn His Gly Ile
            165                 170                 175

Trp Ala Val Ala Ala Val Gly Ile Cys Gly Leu Ala Leu Gly Lys Arg
        180                 185                 190

Glu Tyr Leu Glu Met Ser Val Tyr Gly Ile Asp Arg Asn Asp Thr Gly
    195                 200                 205

Gly Phe Leu Ala Gln Val Ser Gln Leu Phe Ala Pro Ser Gly Tyr Tyr
    210                 215                 220
```

```
Met Glu Gly Pro Tyr Tyr His Arg Tyr Ala Ile Arg Pro Thr Cys Val
225                 230                 235                 240

Phe Ala Glu Val Ile His Arg His Met Pro Glu Val Asp Ile Tyr Asn
            245                 250                 255

Tyr Lys Gly Gly Val Ile Gly Asn Thr Val Gln Ala Met Leu Ala Thr
        260                 265                 270

Ala Tyr Pro Asn Gly Glu Phe Pro Ala Leu Asn Asp Ala Ser Arg Thr
    275                 280                 285

Met Gly Ile Thr Asp Met Gly Val Gln Val Ala Val Ser Val Tyr Ser
290                 295                 300

Lys His Tyr Ser Ser Glu Asn Gly Val Asp Gln Asn Ile Leu Gly Met
305                 310                 315                 320

Ala Lys Ile Gln Asp Ala Val Trp Met His Pro Cys Gly Leu Glu Leu
            325                 330                 335

Ser Lys Ala Tyr Glu Ala Ala Ser Ala Glu Lys Glu Ile Gly Met Pro
        340                 345                 350

Phe Trp Pro Ser Val Glu Leu Asn Glu Gly Pro Gln Gly His Asn Gly
    355                 360                 365

Ala Gln Gly Phe Ile Arg Met Gln Asp Lys Lys Gly Asp Val Ser Gln
370                 375                 380

Leu Val Met Asn Tyr Gly Gln His Gly Met Gly His Gly Asn Phe Asp
385                 390                 395                 400

Thr Leu Gly Ile Ser Phe Phe Asn Arg Gly Gln Val Leu Arg Glu
            405                 410                 415

Tyr Gly Phe Cys Arg Trp Val Asn Val Glu Pro Lys Phe Gly Gly Arg
        420                 425                 430

Tyr Leu Asp Glu Asn Lys Ser Tyr Ala Arg Gln Thr Ile Ala His Asn
    435                 440                 445

Ala Val Thr Ile Asp Glu Lys Cys Gln Asn Asn Phe Asp Val Glu Arg
450                 455                 460

Ala Asp Ser Val His Gly Leu Pro His Phe Phe Lys Val Glu Asp Asp
465                 470                 475                 480

Gln Ile Asn Gly Met Ser Ala Phe Ala Asn Asp His Tyr Gln Gly Phe
            485                 490                 495

Asp Met Gln Arg Ser Val Phe Met Leu Asn Leu Glu Glu Leu Glu Ser
        500                 505                 510

Pro Leu Leu Leu Asp Leu Tyr Arg Leu Asp Ser Thr Lys Gly Gly Glu
    515                 520                 525

Gly Glu His Gln Tyr Asp Tyr Ser His Gln Tyr Ala Gly Gln Ile Val
530                 535                 540

Arg Thr Asn Phe Glu Tyr Gln Ala Asn Lys Glu Leu Asn Thr Leu Gly
545                 550                 555                 560

Asp Asp Phe Gly Tyr Gln His Leu Trp Asn Val Ala Ser Gly Glu Val
            565                 570                 575

Lys Gly Thr Ala Ile Val Ser Trp Leu Gln Asn Asn Thr Tyr Tyr Thr
        580                 585                 590

Trp Leu Gly Ala Thr Ser Asn Asp Asn Ala Glu Val Ile Phe Thr Arg
    595                 600                 605

Thr Gly Ala Asn Asp Pro Ser Phe Asn Leu Arg Ser Glu Pro Ala Phe
610                 615                 620

Ile Leu Arg Ser Lys Gly Glu Thr Thr Leu Phe Ala Ser Val Val Glu
625                 630                 635                 640

Thr His Gly Tyr Phe Asn Glu Glu Phe Glu Gln Ser Val Asn Ala Arg
            645                 650                 655
```

```
Gly Val Val Lys Asp Ile Lys Val Ala His Thr Asn Val Gly Ser
            660                 665                 670

Val Val Glu Ile Thr Thr Glu Lys Ser Asn Val Thr Val Met Ile Ser
        675                 680                 685

Asn Gln Leu Gly Ala Thr Asp Ser Thr Glu His Lys Val Glu Leu Asn
            690                 695                 700

Gly Lys Val Tyr Ser Trp Lys Gly Phe Tyr Ser Val Glu Thr Thr Leu
705                 710                 715                 720

Gln Glu Thr Asn Ser Glu Glu Leu Ser Thr Ala Gly Gln Gly Lys
            725                 730                 735

<210> SEQ ID NO 17
<211> LENGTH: 2154
<212> TYPE: DNA
<213> ORGANISM: Vibrio splendidus

<400> SEQUENCE: 17
atgagctatc aaccactttt acttaacttt gatgaagcag ctgaacttcg taagaacttg      60
ggcaaggata gcctattagg taacgcactg actcgcgaca ttaaacaaac tgacgcttac     120
atggctgaag ttggcattga agtaccaggt cacggtgaag gcggcggtta cgagcacaac     180
cgtcataagc aaaactacat ccatatggat ctagcaggcc gttgttcct tatcactgag      240 gaaacaaaat accgagatta catcgttgat atgctaacag cgtacgcgac ggtatacccca    300 acacttgaaa gcaacgtaag ccgtgactct aaccctccgg gtaagctgtt ccaccaaacg     360
ttgaacgaga acatgtggat gctttacgct tcttgtgcgt acagctgcat ctaccacacg     420
atctctgaag agcaaaagcg tctgatcgaa gacgatcttc ttaagcaaat gatcgaaatg     480
ttcgttgtga cttacgcaca cgacttcgat atcgtacaca accacggctt atgggcagtg     540
gcagcagtag gtatctgtgg ttacgcaatc aacgatcaag agtctgtaga caaagcacta     600
tacggcctga aactagacaa agtcagcggc ggtttcttag cgcaactaga ccaactgttt     660
tcgccagacg gctactacat ggaaggtcct tactaccacc gtttctctct gcgtccaatc     720
tacctgttcg cagaagcgat tgaacgtcgt cagcctgaag ttggtatcta tgaattcaac     780
gattcagtga tcaagacaac gtcttactct gtattcaaaa cggcattccc agacggtaca     840
ttgcctgctc tgaacgattc atcgaagaca atctctatca cgatgaagg cgttatcatg      900 gcaacgtctg tgtgttacca ccgttacgag caaactgaaa ctctacttgg tatggctaac     960
caccagcaaa acgtttgggt tcatgcttca ggtaaaacac tgtctgacgc ggttgatgca    1020
gcagacgaca tcaaagcatt caactggggt agcctgtttg taaccgacgg ccctgaaggc    1080 gaaaaggcg gcgtaagcat ccttcgtcac cgtgacgaac aagatgacga cacgatggcg     1140
ttgatctggt ttggtcaaca cggttctgat caccagtacc actctgctct agaccacggt    1200
cactacgatg gcctgcacct aagcgtattt aaccgtggcc acgaagtgct gcacgatttc    1260
ggcttcggtc gctgggtaaa cgttgagcct aagtttggcg gtcgttacat cccagagaac    1320
aagtcttact gtaagcagac ggttgctcac aacacagtaa cggttgatca gaaaacgcag    1380
aacaacttca acacagcatt ggctgagtct aagtttggtc agaagcactt cttcgtagca    1440
gacgaccagt ctctacaagg catgagcggc acaatttctg agtactacac tggcgtagac    1500
atgcaacgca gcgtgattct tgctgaactt cctgagttcg agaagccact tgtaatcgac    1560
gtataccgca tcgaagctga cgctgaacac cagtacgacc tacccgttca ccactctggt    1620
cagatcatcc gtactgactt cgattacaac atggaaaaaa cgcttaagcc gctaggtgaa    1680
```

-continued

```
gacaacggtt accagcactt atggaacgtg gcttcaggca aagtgaacga agaaggttct    1740
ctagtaagct ggctacatga cagcagctac tacagcctag taaccagcgc gaatgcgggc    1800
agcgaagtga tttttgctcg cactggtgct aacgatccag acttcaacct taagagtgag    1860
cctgcgttca tcttcgtca gtctggtcaa aaccacgtgt ttgcttctgt actagaaacg    1920
catggttact ttaacgagtc tatcgaagcc tctgtaggcg ctcgtggtct agttaaatca    1980
gtatctgttg tgggccataa cagtgtcggg actgttgttc gcattcagac tacttctggc    2040
aacacttacc actacggtat ctcaaaccaa gctgaagaca cgcagcaagc aactcacact    2100
gttgagttcg cgggtgagac atactcgtgg gaaggatcat ttgctcaact gtaa          2154
```

<210> SEQ ID NO 18
<211> LENGTH: 717
<212> TYPE: PRT
<213> ORGANISM: Vibrio slpendidus

<400> SEQUENCE: 18

```
Met Ser Tyr Gln Pro Leu Leu Leu Asn Phe Asp Glu Ala Ala Glu Leu
1               5                   10                  15

Arg Lys Glu Leu Gly Lys Asp Ser Leu Leu Gly Asn Ala Leu Thr Arg
            20                  25                  30

Asp Ile Lys Gln Thr Asp Ala Tyr Met Ala Glu Val Gly Ile Glu Val
        35                  40                  45

Pro Gly His Gly Glu Gly Gly Tyr Glu His Asn Arg His Lys Gln
    50                  55                  60

Asn Tyr Ile His Met Asp Leu Ala Gly Arg Leu Phe Leu Ile Thr Glu
65                  70                  75                  80

Glu Thr Lys Tyr Arg Asp Tyr Ile Val Asp Met Leu Thr Ala Tyr Ala
                85                  90                  95

Thr Val Tyr Pro Thr Leu Glu Ser Asn Val Ser Arg Asp Ser Asn Pro
            100                 105                 110

Pro Gly Lys Leu Phe His Gln Thr Leu Asn Glu Asn Met Trp Met Leu
        115                 120                 125

Tyr Ala Ser Cys Ala Tyr Ser Cys Ile Tyr His Thr Ile Ser Glu Glu
    130                 135                 140

Gln Lys Arg Leu Ile Glu Asp Asp Leu Leu Lys Gln Met Ile Glu Met
145                 150                 155                 160

Phe Val Val Thr Tyr Ala His Asp Phe Asp Ile Val His Asn His Gly
                165                 170                 175

Leu Trp Ala Val Ala Ala Val Gly Ile Cys Gly Tyr Ala Ile Asn Asp
            180                 185                 190

Gln Glu Ser Val Asp Lys Ala Leu Tyr Gly Leu Lys Leu Asp Lys Val
        195                 200                 205

Ser Gly Gly Phe Leu Ala Gln Leu Asp Gln Leu Phe Ser Pro Asp Gly
    210                 215                 220

Tyr Tyr Met Glu Gly Pro Tyr Tyr His Arg Phe Ser Leu Arg Pro Ile
225                 230                 235                 240

Tyr Leu Phe Ala Glu Ala Ile Glu Arg Arg Gln Pro Glu Val Gly Ile
                245                 250                 255

Tyr Glu Phe Asn Asp Ser Val Ile Lys Thr Thr Ser Tyr Ser Val Phe
            260                 265                 270

Lys Thr Ala Phe Pro Asp Gly Thr Leu Pro Ala Leu Asn Asp Ser Ser
        275                 280                 285

Lys Thr Ile Ser Ile Asn Asp Glu Gly Val Ile Met Ala Thr Ser Val
    290                 295                 300
```

```
Cys Tyr His Arg Tyr Glu Gln Thr Glu Thr Leu Leu Gly Met Ala Asn
305                 310                 315                 320

His Gln Gln Asn Val Trp Val His Ala Ser Gly Lys Thr Leu Ser Asp
            325                 330                 335

Ala Val Asp Ala Ala Asp Ile Lys Ala Phe Asn Trp Gly Ser Leu
        340                 345                 350

Phe Val Thr Asp Gly Pro Glu Gly Lys Gly Gly Val Ser Ile Leu
        355                 360                 365

Arg His Arg Asp Glu Gln Asp Asp Thr Met Ala Leu Ile Trp Phe
        370                 375                 380

Gly Gln His Gly Ser Asp His Gln Tyr His Ser Ala Leu Asp His Gly
385                 390                 395                 400

His Tyr Asp Gly Leu His Leu Ser Val Phe Asn Arg Gly His Glu Val
                405                 410                 415

Leu His Asp Phe Gly Phe Gly Arg Trp Val Asn Val Glu Pro Lys Phe
                420                 425                 430

Gly Gly Arg Tyr Ile Pro Glu Asn Lys Ser Tyr Cys Lys Gln Thr Val
            435                 440                 445

Ala His Asn Thr Val Thr Val Asp Gln Lys Thr Gln Asn Asn Phe Asn
        450                 455                 460

Thr Ala Leu Ala Glu Ser Lys Phe Gly Gln Lys His Phe Phe Val Ala
465                 470                 475                 480

Asp Asp Gln Ser Leu Gln Gly Met Ser Gly Thr Ile Ser Glu Tyr Tyr
                485                 490                 495

Thr Gly Val Asp Met Gln Arg Ser Val Ile Leu Ala Glu Leu Pro Glu
                500                 505                 510

Phe Glu Lys Pro Leu Val Ile Asp Val Tyr Arg Ile Glu Ala Asp Ala
            515                 520                 525

Glu His Gln Tyr Asp Leu Pro Val His His Ser Gly Gln Ile Ile Arg
530                 535                 540

Thr Asp Phe Asp Tyr Asn Met Glu Lys Thr Leu Lys Pro Leu Gly Glu
545                 550                 555                 560

Asp Asn Gly Tyr Gln His Leu Trp Asn Val Ala Ser Gly Lys Val Asn
                565                 570                 575

Glu Glu Gly Ser Leu Val Ser Trp Leu His Asp Ser Ser Tyr Tyr Ser
            580                 585                 590

Leu Val Thr Ser Ala Asn Ala Gly Ser Glu Val Ile Phe Ala Arg Thr
        595                 600                 605

Gly Ala Asn Asp Pro Asp Phe Asn Leu Lys Ser Glu Pro Ala Phe Ile
610                 615                 620

Leu Arg Gln Ser Gly Gln Asn His Val Phe Ala Ser Val Leu Glu Thr
625                 630                 635                 640

His Gly Tyr Phe Asn Glu Ser Ile Glu Ala Ser Val Gly Ala Arg Gly
                645                 650                 655

Leu Val Lys Ser Val Ser Val Val Gly His Asn Ser Val Gly Thr Val
            660                 665                 670

Val Arg Ile Gln Thr Thr Ser Gly Asn Thr Tyr His Tyr Gly Ile Ser
        675                 680                 685

Asn Gln Ala Glu Asp Thr Gln Gln Ala Thr His Thr Val Glu Phe Ala
        690                 695                 700

Gly Glu Thr Tyr Ser Trp Glu Gly Ser Phe Ala Gln Leu
705                 710                 715
```

<210> SEQ ID NO 19
<211> LENGTH: 825
<212> TYPE: DNA
<213> ORGANISM: Vibrio splendidus

<400> SEQUENCE: 19

```
atgaagtggt tattggcaat agttgcgatg tctggtgtcg cattggcggc agaaaataag      60
aatgttgagg tgagcagtga gcatttcgtc cgttatcaat accaagacaa aatcagctat     120
ggaaagctag acaatgacgc agtgttaccg gtcagcggcg atctctttgg cgaatattcg     180
gtagcaaaaa attcgatccc gttagagtcg gttgaggtgt tactaccgac aaaaccagag     240
aaagtcttcg ccgtcgggat gaacttcgct agccacttag cctcacctgc cgatgcacca     300
ccgccgatgt ttcttaaact tccttcttct ttgattctca cgggcgaagt gattcaagtg     360
ccaccaaaag caagaaatgt tcattttgaa ggcgagctgg tggttgtgat ggtagagag     420 ctcagtcaag ccagtgaaga agaagccgaa caagcgatct ttggcgtcac ggtgggcaac     480
gatattactg aaagaagttg gcaaggcgcc gatttacaat ggctccgagc gaaagcttcc     540
gatggttttg gcccggttgg caacacaatt gtgcgcggca ttgattacaa caatattgag     600
ttaaccactc gtgttaacgg taaagtggtt caacaagaaa atacttcgtt catgatccac     660
aagccaagaa aagtcgtgag ctatttgagc tattatttta ccctcaaacc gggcgatcta     720
attttcatgg gcacgccagg tagaacttat gctctgtccg acaaagatca agtgagtgtc     780
acgattgaag gggtagggac tgtggtaaat gaagtgcggt tctga                    825
```

<210> SEQ ID NO 20
<211> LENGTH: 274
<212> TYPE: PRT
<213> ORGANISM: Vibrio splendidus

<400> SEQUENCE: 20

```
Met Lys Trp Leu Leu Ala Ile Val Ala Met Ser Gly Val Ala Leu Ala
1               5                   10                  15

Ala Glu Asn Lys Asn Val Glu Val Ser Ser Glu His Phe Val Arg Tyr
            20                  25                  30

Gln Tyr Gln Asp Lys Ile Ser Tyr Gly Lys Leu Asp Asn Asp Ala Val
        35                  40                  45

Leu Pro Val Ser Gly Asp Leu Phe Gly Glu Tyr Ser Val Ala Lys Asn
    50                  55                  60

Ser Ile Pro Leu Glu Ser Val Glu Val Leu Leu Pro Thr Lys Pro Glu
65                  70                  75                  80

Lys Val Phe Ala Val Gly Met Asn Phe Ala Ser His Leu Ala Ser Pro
                85                  90                  95

Ala Asp Ala Pro Pro Met Phe Leu Lys Leu Pro Ser Ser Leu Ile
            100                 105                 110

Leu Thr Gly Glu Val Ile Gln Val Pro Pro Lys Ala Arg Asn Val His
        115                 120                 125

Phe Glu Gly Glu Leu Val Val Val Ile Gly Arg Glu Leu Ser Gln Ala
    130                 135                 140

Ser Glu Glu Glu Ala Glu Gln Ala Ile Phe Gly Val Thr Val Gly Asn
145                 150                 155                 160

Asp Ile Thr Glu Arg Ser Trp Gln Gly Ala Asp Leu Gln Trp Leu Arg
                165                 170                 175

Ala Lys Ala Ser Asp Gly Phe Gly Pro Val Gly Asn Thr Ile Val Arg
            180                 185                 190

Gly Ile Asp Tyr Asn Asn Ile Glu Leu Thr Thr Arg Val Asn Gly Lys
```

```
                195                 200                 205
Val Val Gln Gln Glu Asn Thr Ser Phe Met Ile His Lys Pro Arg Lys
        210                 215                 220

Val Val Ser Tyr Leu Ser Tyr Tyr Phe Thr Leu Lys Pro Gly Asp Leu
225                 230                 235                 240

Ile Phe Met Gly Thr Pro Gly Arg Thr Tyr Ala Leu Ser Asp Lys Asp
                245                 250                 255

Gln Val Ser Val Thr Ile Glu Gly Val Gly Thr Val Val Asn Glu Val
        260                 265                 270

Arg Phe

<210> SEQ ID NO 21
<211> LENGTH: 717
<212> TYPE: DNA
<213> ORGANISM: Vibrio splendidus

<400> SEQUENCE: 21
atggctagca cttttaattc aatttcgggc tcgaagcgta gcctgcacgt gcaagtagca    60
cgcgaaatcg ctcgaggaat tttgtctggt gatctgccgc aaggttctat tattcctggt   120
gaaatggcgt tgtgtgaaca gtttggtatc agccgaacgg cacttcgtga agcagttaaa   180
ctactgacct ctaaaggtct gttagagtct cgccctaaaa ttggtactcg cgtagtcgac   240
cgcgcatact ggaacttcct tgatcctcaa ctgattgaat ggatggacgg actaaccgac   300
gtagaccaat tctgttctca gttttaggc cttcgccgtg cgatcgagcc tgaagcgtgt   360
gcactggcgg caaaatttgc gacagctgaa caacgtatcg agctttcaga gatcttccaa   420
aagatggtcg aagtggatga agctgaagtg tttgaccaag aacgttggac agacattgat   480
actcgtttcc atagcttgat cttcaatgcg accggtaacg acttctatct accgttcggt   540
aatattctga ctactatgtt cgttaacttc atagtgcatt cttctgaaga gggaagcaca   600
tgcatcaatg aacaccgcag aatctatgaa gctatcatgg ccggtgattg tgacaaggct   660
agaattgctt ctgctgttca cttgcaagat gccaaccacc gtttggcaac agcataa     717

<210> SEQ ID NO 22
<211> LENGTH: 238
<212> TYPE: PRT
<213> ORGANISM: Vibrio splendidus

<400> SEQUENCE: 22

Met Ala Ser Thr Phe Asn Ser Ile Ser Gly Ser Lys Arg Ser Leu His
1               5                   10                  15

Val Gln Val Ala Arg Glu Ile Ala Arg Gly Ile Leu Ser Gly Asp Leu
            20                  25                  30

Pro Gln Gly Ser Ile Ile Pro Gly Glu Met Ala Leu Cys Glu Gln Phe
        35                  40                  45

Gly Ile Ser Arg Thr Ala Leu Arg Glu Ala Val Lys Leu Leu Thr Ser
    50                  55                  60

Lys Gly Leu Leu Glu Ser Arg Pro Lys Ile Gly Thr Arg Val Val Asp
65                  70                  75                  80

Arg Ala Tyr Trp Asn Phe Leu Asp Pro Gln Leu Ile Glu Trp Met Asp
                85                  90                  95

Gly Leu Thr Asp Val Asp Gln Phe Cys Ser Gln Phe Gly Leu Arg
            100                 105                 110

Arg Ala Ile Glu Pro Glu Ala Cys Ala Leu Ala Ala Lys Phe Ala Thr
        115                 120                 125
```

Ala Glu Gln Arg Ile Glu Leu Ser Glu Ile Phe Gln Lys Met Val Glu
130                 135                 140

Val Asp Glu Ala Glu Val Phe Asp Gln Glu Arg Trp Thr Asp Ile Asp
145                 150                 155                 160

Thr Arg Phe His Ser Leu Ile Phe Asn Ala Thr Gly Asn Asp Phe Tyr
                165                 170                 175

Leu Pro Phe Gly Asn Ile Leu Thr Thr Met Phe Val Asn Phe Ile Val
                180                 185                 190

His Ser Ser Glu Glu Gly Ser Thr Cys Ile Asn Glu His Arg Arg Ile
                195                 200                 205

Tyr Glu Ala Ile Met Ala Gly Asp Cys Asp Lys Ala Arg Ile Ala Ser
        210                 215                 220

Ala Val His Leu Gln Asp Ala Asn His Arg Leu Ala Thr Ala
225                 230                 235

<210> SEQ ID NO 23
<211> LENGTH: 1779
<212> TYPE: DNA
<213> ORGANISM: Vibrio splendidus

<400> SEQUENCE: 23
atggaactca acacgattat tgtcggcatt tatttcctat tcttgattgc gataggttgg     60
atgtttagaa catttacaag tactactagt gactacttcc gcggggggcgg taacatgttg    120
tggtggatgg ttggtgcaac cgcctttatg acccagttta gtgcatggac attcaccggt    180
gcagcaggta aagcgtataa cgatggtttc gctgtagcgg tcatcttcgt agccaacgca    240
tttggttact tcatgaacta cgcgtacttc gcgccgaaat ccgtcaact tcgcgttgtt     300
acggtaatcg aagcgattcg tatgcgtttt ggtgcgacca cgaacaagt attcacttgg    360
tcttcaatgc caaactcagt ggtatctgcg ggtgtgtggt taaacgcatt ggcaatcatc    420
gcttcgggta tcttcggttt cgacatgaac atgactatct gggtgactgg cctagtggta    480
ttggcaatgt cggtaacagg tggttcatgg gcggtaatcg catctgactt catgcagatg    540
gttatcatca tggcggtaac ggtaacttgt gcggttgtag cggttgttca aggtggcggt    600
gttggtgaga ttgttaacaa cttcccagta caagatggtg gttcgttcct tggggcaac    660
aacatcaact acctaagcat ctttacgatt tgggcattct tcatcttcgt taagcagttc    720
tcaatcacga caacatgct taactcttac cgttacctag cggctaaaga ctcaaagaac    780
gctaagaaag ctgcactgct tgcttgtgtg ttgatgttgt gtggtgtgtt tatttggttc    840
atgccttctt ggttcattgc aggccaaggt gttgatttat cagcggctta cccgaatgca    900
ggtaaaaaag cgggtgactt tgcttaccta tacttcgtac aagagtacat gccagcaggt    960
atggttggtc tattagttgc cgcgatgttt gcagcgacaa tgtcttcaat ggactcaggt   1020
ctaaaccgta actcaggtat ttttgttaag aacttctacg aaacaatcgt tcgtaaaggt   1080
caagcatcag agaaagagct agtaaccgta tctaaaatta cttcagcggt atttggtttc   1140
gctattatcc taatcgcaca gttcatcaac tcattaaaag gcttaagcct gtttgatacg   1200
atgatgtacg taggtgcgtt aatcggcttc cctatgacga ttcctgcatt ccttggtttc   1260
ttcatcaaga agactccgga ctgggctggt tggggaacgc tagttgttgg tggtatcgta   1320
tcttatgtgg ttggttttgt tatcaacgcg gagatggtag cagcggcgtt tggtcttgat   1380
actctaacag gacgtgaatg gtctgatgtt aaagttgcga ttggtctgat tgctcacatc   1440
acgctaaccg gtggcttctt cgtactatct acgatgttct acaagcctct atcaaaagaa   1500
cgtcaagcgg atgttgataa gttctttggc aacttagata ccccattagt agctgaatcg   1560

```
gcagagcaaa aagtgttgga taacaaacaa cgtcaaatgc ttggtaaact gattgcggta    1620
gcgggtgttg gtattatgct gatggctctt ctgactaacc caatgtgggg gcgcctagtc    1680
ttcatcttat gtggtgtgat agtgggtggt gtcggtattc tacttgtgaa agcggtcgat    1740
gacggcggca agcaagcgaa agcagtaacc gaaagctaa                           1779
```

<210> SEQ ID NO 24
<211> LENGTH: 592
<212> TYPE: PRT
<213> ORGANISM: Vibrio splendidus

<400> SEQUENCE: 24

```
Met Glu Leu Asn Thr Ile Ile Val Gly Ile Tyr Phe Leu Phe Leu Ile
1               5                   10                  15

Ala Ile Gly Trp Met Phe Arg Thr Phe Thr Ser Thr Thr Ser Asp Tyr
            20                  25                  30

Phe Arg Gly Gly Gly Asn Met Leu Trp Trp Met Val Gly Ala Thr Ala
        35                  40                  45

Phe Met Thr Gln Phe Ser Ala Trp Thr Phe Thr Gly Ala Ala Gly Lys
    50                  55                  60

Ala Tyr Asn Asp Gly Phe Ala Val Ala Val Ile Phe Val Ala Asn Ala
65                  70                  75                  80

Phe Gly Tyr Phe Met Asn Tyr Ala Tyr Phe Ala Pro Lys Phe Arg Gln
                85                  90                  95

Leu Arg Val Val Thr Val Ile Glu Ala Ile Arg Met Arg Phe Gly Ala
            100                 105                 110

Thr Asn Glu Gln Val Phe Thr Trp Ser Ser Met Pro Asn Ser Val Val
        115                 120                 125

Ser Ala Gly Val Trp Leu Asn Ala Leu Ala Ile Ile Ala Ser Gly Ile
    130                 135                 140

Phe Gly Phe Asp Met Asn Met Thr Ile Trp Val Thr Gly Leu Val Val
145                 150                 155                 160

Leu Ala Met Ser Val Thr Gly Gly Ser Trp Ala Val Ile Ala Ser Asp
                165                 170                 175

Phe Met Gln Met Val Ile Ile Met Ala Val Thr Val Thr Cys Ala Val
            180                 185                 190

Val Ala Val Val Gln Gly Gly Val Gly Glu Ile Val Asn Asn Phe
        195                 200                 205

Pro Val Gln Asp Gly Gly Ser Phe Leu Trp Gly Asn Asn Ile Asn Tyr
    210                 215                 220

Leu Ser Ile Phe Thr Ile Trp Ala Phe Phe Ile Phe Val Lys Gln Phe
225                 230                 235                 240

Ser Ile Thr Asn Asn Met Leu Asn Ser Tyr Arg Tyr Leu Ala Ala Lys
                245                 250                 255

Asp Ser Lys Asn Ala Lys Lys Ala Ala Leu Leu Ala Cys Val Leu Met
            260                 265                 270

Leu Cys Gly Val Phe Ile Trp Phe Met Pro Ser Trp Phe Ile Ala Gly
        275                 280                 285

Gln Gly Val Asp Leu Ser Ala Ala Tyr Pro Asn Ala Gly Lys Lys Ala
    290                 295                 300

Gly Asp Phe Ala Tyr Leu Tyr Phe Val Gln Glu Tyr Met Pro Ala Gly
305                 310                 315                 320

Met Val Gly Leu Leu Val Ala Ala Met Phe Ala Ala Thr Met Ser Ser
                325                 330                 335
```

```
Met Asp Ser Gly Leu Asn Arg Asn Ser Gly Ile Phe Val Lys Asn Phe
            340                 345                 350

Tyr Glu Thr Ile Val Arg Lys Gly Gln Ala Ser Glu Lys Glu Leu Val
            355                 360                 365

Thr Val Ser Lys Ile Thr Ser Ala Val Phe Gly Phe Ala Ile Ile Leu
    370                 375                 380

Ile Ala Gln Phe Ile Asn Ser Leu Lys Gly Leu Ser Leu Phe Asp Thr
385                 390                 395                 400

Met Met Tyr Val Gly Ala Leu Ile Gly Phe Pro Met Thr Ile Pro Ala
                405                 410                 415

Phe Leu Gly Phe Ile Lys Lys Thr Pro Asp Trp Ala Gly Trp Gly
            420                 425                 430

Thr Leu Val Val Gly Gly Ile Val Ser Tyr Val Val Gly Phe Val Ile
            435                 440                 445

Asn Ala Glu Met Val Ala Ala Phe Gly Leu Asp Thr Leu Thr Gly
            450                 455                 460

Arg Glu Trp Ser Asp Val Lys Val Ala Ile Gly Leu Ile Ala His Ile
465                 470                 475                 480

Thr Leu Thr Gly Gly Phe Phe Val Leu Ser Thr Met Phe Tyr Lys Pro
                485                 490                 495

Leu Ser Lys Glu Arg Gln Ala Asp Val Asp Lys Phe Phe Gly Asn Leu
            500                 505                 510

Asp Thr Pro Leu Val Ala Glu Ser Ala Glu Gln Lys Val Leu Asp Asn
        515                 520                 525

Lys Gln Arg Gln Met Leu Gly Lys Leu Ile Ala Val Ala Gly Val Gly
530                 535                 540

Ile Met Leu Met Ala Leu Leu Thr Asn Pro Met Trp Gly Arg Leu Val
545                 550                 555                 560

Phe Ile Leu Cys Gly Val Ile Val Gly Gly Val Gly Ile Leu Leu Val
                565                 570                 575

Lys Ala Val Asp Asp Gly Gly Lys Gln Ala Lys Ala Val Thr Glu Ser
            580                 585                 590

<210> SEQ ID NO 25
<211> LENGTH: 2079
<212> TYPE: DNA
<213> ORGANISM: Vibrio splendidus

<400> SEQUENCE: 25
atgagcgacc aaaaatctct tgatgcaatc aggaagatga agctggaaaa cgatacttca        60
gcaggtaatc ttgtagacct actccctatc gaagttcaaa cacgtgactt cgacctatca       120
ttcctagaca ccttgagcga agcacgtccg cgtcttcttg ttcaagctga tcagctagaa       180
gaattcaaag caaaagtgaa agctgatcaa gctcactgta tgtttgatga tttctacaac       240
aactctaccg ttaagttcct tgagactgct cctttcgaag agcctcaagc gtacccagct       300
gagacggtag gtaaagcttc tctatggcgt ccttattggc gtcaaatgta cgttgattgc       360
caaatggcac tgaacgcgac acgtaaccta gcgattgctg tgttgtaaa agaagacgaa       420 gcgctcattg cgaaagcaaa agcttggact ctaaaactgt ctacgtacga tccagaaggc       480
gtgacttctc gtggctataa cgatgaagcg gctttccgtg ttatcgctgc tatggcttgg       540
ggttacgatt ggctacacgg ctacttcacc gatgaagaac gccagcaagt tcaagatgct       600
ttgattgagc gtctagacga aatcatgcac cacctgaaag tgacggttga tctattgaac       660
aacccactaa atagccacgg tgttcgttct atctcttctg ctatcatccc aacgtgtatc       720
```

```
gcgctttacc acgatcaccc gaaagcaggc gagtacattg catacgcgct agaatactac    780
gcagtacatt accccaccatg gggcggtgta cacggcggtt gggctgaagg tcctgattac    840
tggaacacgc aaactgcatt cctaggcgaa gcattcgacc tattgaaagc atactgtggt    900
gtagacatgt ttaacaaaac attctacgaa aacacaggtg atttcccgct ttactgcatg    960
ccagttcact ctaagcgcgc gagcttctgt gaccagtctt caatcggcga tttcccaggt   1020
ttaaaactgg cttacaacat caagcactac gcaggtgtta accagaagcc tgagtacgtt   1080
tggtactata accagcttaa aggccgtgat actgaagcac acaccaaatt ctacaacttc   1140
ggttggtggg acttcggtta tgacgatctt cgtttaact tcctttggga tgcacctgaa   1200
gagaaagccc catcgaacga tccactgttg aaagtattcc aatcacggg ttgggctgca    1260
ttccacaaca agatgactga gcgtgataac catattcaca tggtattcaa atgttctccg   1320
tttggctcaa tcagccactc tcacggtgac caaaacgcat ttacgcttca cgcatttggt   1380
gaaacgctag cgtcagtaac aggttactat ggtggtttcg gtgtagacat gcacacgaaa   1440
tggcgtcgtc aaacgttctc taaaaacctg ccactatttg gcggtaaagg tcagtacggc   1500
gagaacaaga acacaggcta cgaaaaccac caagatcgct tttgtatcga agcgggcggc   1560
actatctctg acttcgacac tgaatctgat gtgaagatgg ttgaaggtga tgcaacggca   1620
tcttacaagt acttcgttcc tgaaatcgaa tcttacaagc gtaaagtctg gttcgttcaa   1680
ggtaaagtct tcgtaatgca agacaaggca acgctttctg aagagaaaga catgacttgg   1740
ctaatgcaca caacttttcgc aaacgaagtg cagacaagt cttttcactat ccgtggcgaa   1800
gttgcgcacc tagacgtaaa cttcatcaac gagtctgctg ataacatcac gtcagttaag   1860
aacgttgaag ctttggcga agttgaccca tacgagttca aagatcttga gatccaccgt   1920
cacgtggaag tggaattcaa gccatcgaaa gagcacaaca tcctgacgct tcttgttcct   1980
aataagaatg aaggcgagca agttgaagtg tttcacaagc ttgaaggcaa cacgctactg   2040
ctaaatgttg acggcgaaac ggtttcaatc gaactgtaa                         2079

<210> SEQ ID NO 26
<211> LENGTH: 692
<212> TYPE: PRT
<213> ORGANISM: Vibrio splendidus

<400> SEQUENCE: 26

Met Ser Asp Gln Lys Ser Leu Asp Ala Ile Arg Lys Met Lys Leu Glu
1               5                  10                  15

Asn Asp Thr Ser Ala Gly Asn Leu Val Asp Leu Pro Ile Glu Val
        20                  25                  30

Gln Thr Arg Asp Phe Asp Leu Ser Phe Leu Asp Thr Leu Ser Glu Ala
        35                  40                  45

Arg Pro Arg Leu Leu Val Gln Ala Asp Gln Leu Glu Glu Phe Lys Ala
        50                  55                  60

Lys Val Lys Ala Asp Gln Ala His Cys Met Phe Asp Asp Phe Tyr Asn
65                  70                  75                  80

Asn Ser Thr Val Lys Phe Leu Glu Thr Ala Pro Phe Glu Glu Pro Gln
                85                  90                  95

Ala Tyr Pro Ala Glu Thr Val Gly Lys Ala Ser Leu Trp Arg Pro Tyr
                100                 105                 110

Trp Arg Gln Met Tyr Val Asp Cys Gln Met Ala Leu Asn Ala Thr Arg
        115                 120                 125

Asn Leu Ala Ile Ala Gly Val Val Lys Glu Asp Glu Ala Leu Ile Ala
        130                 135                 140
```

```
Lys Ala Lys Ala Trp Thr Leu Lys Leu Ser Thr Tyr Asp Pro Glu Gly
145                 150                 155                 160

Val Thr Ser Arg Gly Tyr Asn Asp Glu Ala Ala Phe Arg Val Ile Ala
                165                 170                 175

Ala Met Ala Trp Gly Tyr Asp Trp Leu His Gly Tyr Phe Thr Asp Glu
            180                 185                 190

Glu Arg Gln Gln Val Gln Asp Ala Leu Ile Glu Arg Leu Asp Glu Ile
        195                 200                 205

Met His His Leu Lys Val Thr Val Asp Leu Leu Asn Asn Pro Leu Asn
    210                 215                 220

Ser His Gly Val Arg Ser Ile Ser Ser Ala Ile Ile Pro Thr Cys Ile
225                 230                 235                 240

Ala Leu Tyr His Asp His Pro Lys Ala Gly Glu Tyr Ile Ala Tyr Ala
                245                 250                 255

Leu Glu Tyr Tyr Ala Val His Tyr Pro Pro Trp Gly Gly Val Asp Gly
            260                 265                 270

Gly Trp Ala Glu Gly Pro Asp Tyr Trp Asn Thr Gln Thr Ala Phe Leu
        275                 280                 285

Gly Glu Ala Phe Asp Leu Leu Lys Ala Tyr Cys Gly Val Asp Met Phe
    290                 295                 300

Asn Lys Thr Phe Tyr Glu Asn Thr Gly Asp Phe Pro Leu Tyr Cys Met
305                 310                 315                 320

Pro Val His Ser Lys Arg Ala Ser Phe Cys Asp Gln Ser Ser Ile Gly
                325                 330                 335

Asp Phe Pro Gly Leu Lys Leu Ala Tyr Asn Ile Lys His Tyr Ala Gly
            340                 345                 350

Val Asn Gln Lys Pro Glu Tyr Val Trp Tyr Asn Gln Leu Lys Gly
        355                 360                 365

Arg Asp Thr Glu Ala His Thr Lys Phe Tyr Asn Phe Gly Trp Trp Asp
    370                 375                 380

Phe Gly Tyr Asp Asp Leu Arg Phe Asn Phe Leu Trp Asp Ala Pro Glu
385                 390                 395                 400

Glu Lys Ala Pro Ser Asn Asp Pro Leu Leu Lys Val Phe Pro Ile Thr
                405                 410                 415

Gly Trp Ala Ala Phe His Asn Lys Met Thr Glu Arg Asp Asn His Ile
            420                 425                 430

His Met Val Phe Lys Cys Ser Pro Phe Gly Ser Ile Ser His Ser His
        435                 440                 445

Gly Asp Gln Asn Ala Phe Thr Leu His Ala Phe Gly Glu Thr Leu Ala
    450                 455                 460

Ser Val Thr Gly Tyr Tyr Gly Gly Phe Gly Val Asp Met His Thr Lys
465                 470                 475                 480

Trp Arg Arg Gln Thr Phe Ser Lys Asn Leu Pro Leu Phe Gly Gly Lys
                485                 490                 495

Gly Gln Tyr Gly Glu Asn Lys Asn Thr Gly Tyr Glu Asn His Gln Asp
            500                 505                 510

Arg Phe Cys Ile Glu Ala Gly Gly Thr Ile Ser Asp Phe Asp Thr Glu
        515                 520                 525

Ser Asp Val Lys Met Val Glu Gly Asp Ala Thr Ala Ser Tyr Lys Tyr
    530                 535                 540

Phe Val Pro Glu Ile Glu Ser Tyr Lys Arg Lys Val Trp Phe Val Gln
545                 550                 555                 560

Gly Lys Val Phe Val Met Gln Asp Lys Ala Thr Leu Ser Glu Glu Lys
```

```
                     565              570               575
Asp Met Thr Trp Leu Met His Thr Phe Ala Asn Glu Val Ala Asp
            580                 585                590

Lys Ser Phe Thr Ile Arg Gly Glu Val Ala His Leu Asp Val Asn Phe
        595                 600                 605

Ile Asn Glu Ser Ala Asp Asn Ile Thr Ser Val Lys Asn Val Glu Gly
610                 615                 620

Phe Gly Glu Val Asp Pro Tyr Glu Phe Lys Asp Leu Glu Ile His Arg
625                 630                 635                 640

His Val Glu Val Glu Phe Lys Pro Ser Lys Glu His Asn Ile Leu Thr
                645                 650                 655

Leu Leu Val Pro Asn Lys Asn Glu Gly Glu Gln Val Glu Val Phe His
            660                 665                 670

Lys Leu Glu Gly Asn Thr Leu Leu Leu Asn Val Asp Gly Glu Thr Val
        675                 680                 685

Ser Ile Glu Leu
    690

<210> SEQ ID NO 27
<211> LENGTH: 882
<212> TYPE: DNA
<213> ORGANISM: Vibrio splendidus

<400> SEQUENCE: 27
atgactaaac ctgtaatcgg tttcattggc ctaggtctta tgggcggcaa catggttgaa      60
aacctacaaa agcgcggcta ccacgtaaac gtaatggatc taagcgctga agctgttgct     120
cgcgtaacag atcgcggcaa cgcaactgca ttcacttctg ctaaagaact agctgctgca     180
agtgacatcg ttcagttttg tctgacaact tctgctgttg ttgaaaaaat cgtttacggc     240
gaagacggcg ttctagcggg catcaaagaa ggcgcagtac tagtagactt cggtacttct     300
atccctgctt ctactaagaa aatcggcgca gctcttgctg aaaaaggcgc gggcatgatc     360
gacgcacctc taggtcgtac tcctgcacac gctaaagatg gtcttctgaa catcatggct     420
gctggcgaca tggaaacttt caacaaagtt aaacctgttc ttgaagagca aggcgaaaac     480
gtattccacc taggggctct aggttctggt cacgtgacta agcttgtaaa caacttcatg     540
ggtatgacga ctgttgcgac tatgtctcaa gctttcgctg ttgctcaacg cgctggtgtt     600
gatggccaac aactgtttga catcatgtct gcaggtccat ctaactctcc gttcatgcaa     660
ttctgtaagt tctacgcggt agacggcgaa gagaagctag gtttctctgt tgctaacgca     720
aacaaagacc ttggttactt ccttgcactt tgtgaagagc taggtactga gtctctaatc     780
gctcaaggta ctgcaacaag cctacaagct gctgttgatg caggcatggg taacaacgac     840
gtaccagtaa tcttcgacta cttcgctaaa ctagagaagt aa                        882

<210> SEQ ID NO 28
<211> LENGTH: 293
<212> TYPE: PRT
<213> ORGANISM: Vibrio splendidus

<400> SEQUENCE: 28

Met Thr Lys Pro Val Ile Gly Phe Ile Gly Leu Gly Leu Met Gly Gly
1               5                   10                  15

Asn Met Val Glu Asn Leu Gln Lys Arg Gly Tyr His Val Asn Val Met
            20                  25                  30

Asp Leu Ser Ala Glu Ala Val Ala Arg Val Thr Asp Arg Gly Asn Ala
        35                  40                  45
```

```
Thr Ala Phe Thr Ser Ala Lys Glu Leu Ala Ala Ser Asp Ile Val
 50                  55                  60

Gln Phe Cys Leu Thr Thr Ser Ala Val Val Glu Lys Ile Val Tyr Gly
 65                  70                  75                  80

Glu Asp Gly Val Leu Ala Gly Ile Lys Glu Gly Ala Val Leu Val Asp
                 85                  90                  95

Phe Gly Thr Ser Ile Pro Ala Ser Thr Lys Lys Ile Gly Ala Ala Leu
            100                 105                 110

Ala Glu Lys Gly Ala Gly Met Ile Asp Ala Pro Leu Gly Arg Thr Pro
        115                 120                 125

Ala His Ala Lys Asp Gly Leu Leu Asn Ile Met Ala Ala Gly Asp Met
    130                 135                 140

Glu Thr Phe Asn Lys Val Lys Pro Val Leu Glu Glu Gln Gly Glu Asn
145                 150                 155                 160

Val Phe His Leu Gly Ala Leu Gly Ser Gly His Val Thr Lys Leu Val
                165                 170                 175

Asn Asn Phe Met Gly Met Thr Thr Val Ala Thr Met Ser Gln Ala Phe
            180                 185                 190

Ala Val Ala Gln Arg Ala Gly Val Asp Gly Gln Gln Leu Phe Asp Ile
        195                 200                 205

Met Ser Ala Gly Pro Ser Asn Ser Pro Phe Met Gln Phe Cys Lys Phe
    210                 215                 220

Tyr Ala Val Asp Gly Glu Glu Lys Leu Gly Phe Ser Val Ala Asn Ala
225                 230                 235                 240

Asn Lys Asp Leu Gly Tyr Phe Leu Ala Leu Cys Glu Glu Leu Gly Thr
                245                 250                 255

Glu Ser Leu Ile Ala Gln Gly Thr Ala Thr Ser Leu Gln Ala Ala Val
            260                 265                 270

Asp Ala Gly Met Gly Asn Asn Asp Val Pro Val Ile Phe Asp Tyr Phe
        275                 280                 285

Ala Lys Leu Glu Lys
        290

<210> SEQ ID NO 29
<211> LENGTH: 1872
<212> TYPE: DNA
<213> ORGANISM: Vibrio splendidus

<400> SEQUENCE: 29
atggtagcgg tcgtcagttc tagtgctttg catttacga actggtttac gcttaacttg      60
gccactgaac aggtaaacca aacgatttat aacgagattg atcactcgct tacgatagaa     120
atcaatcaaa tagaaagtac cgttcagcgc accatcgata ccgttaactc tgttgcacaa     180
gagttcatga atccccctta ccaagtgccg aatgaagcac tcatgcatta tgccgctaag     240
cttggtggca ttgacaagat tgtggtgggt tttgacgacg gccgttctta tacctctcgc     300
ccttcagagt ctttccctaa cggtgttgga ataaaagaaa atacaatcc aaccactcga     360 ccttggtatc aacaagcgaa attgaaatca ggcttatctt ttagtggtct gtttttcact     420
aagagtactc aagtgcctat gatcggtgtg acctactcat accagatcg tgtcatcatg     480 gccgatatac gctttgacga tttggaaacg cagcttgaac agctggacag catctacgaa     540
gccaaaggca ttatcatcga cgaaaagggg atggtggtcg cttcaacaat cgaaaacgtg     600
cttccgcaaa ccaatatatc ttctgcagac actcaaatga actcaacag tgccattgaa     660 cagcctgatc aattcattga gggtgtgatt gatggtaacc agagaatctt gatggccaag     720
```

```
aaagtggata ttggcagcca gaaagagtgg ttcatgatct ccagtattga ccctgaactc      780
gcgctcaatc agctgaatgg cgtgatgtcg agtgcgcgca tccttatcgt cgcttgtgta      840
cttggctcgg tgatattgat gattttactt ctgaatcgtt tctaccgccc aatcgtgtca      900
ctgcgcaaaa tcgtccacga tctatcacaa ggtaacggag acctcactca aaggcttgct      960
gagaagggga atgatgactt agggcatatc gccaaagaca tcaacttgtt cattatcggc     1020
ttacaagaga tggttaagga tgtgaaatac aagaactcgg atctcgatac caaggtactg     1080
agtattcgcg aaggttgtaa agaaaccagc gatgtactga agttcatact gatgaaacg      1140 gttcaagtgg tctctgcgat taacggcttg tctgaagcat caaacgaagt agagaagagt     1200
tctcagtcgg cggcagaagc agcaagagag gccgctgtgt tcagtgatga gacgaaacag     1260
attaacacgg tgacggaaac ctatatcagt gatcttgaga agcaagtctg caccacttct     1320
gatgacattc gctcaatggc caatgaaacg cagagcatcc agtctatcgt gtctgtgatt     1380
ggcggaattg cggaacaaac taatttgctg gcattgaatg cgtcaattga agcggcgagg     1440
gcgggtgaac atggtcgagg tttcgcggtg gttgctgatg aagtccgtgc gctagccaac     1500
cgaacgcaaa tcagtacctc tgaaattgat gaagcgttat ctggcttgca gtctaaatca     1560
gatggtttgg ttaaatctat tgagttgacc aaaagtaact gtgaactgac tcgcgctcaa     1620
gttgttcaag ctgtaaacat gttggcgaag ctaaccgagc agatggaaac agtaagtcgt     1680
tttaataatg acatttcggg ttcgtctgtt gagcaaaacg cccttattca gagcattgct     1740
aagaacatgc ataagattga agctttgtt gaggagctta ataaactaag ccaagatcag      1800
ttaactgaat cagcagaaat caaaacactt aacggtagcg ttagtgaatt gatgagcagc     1860
tttaaggttt aa                                                         1872

<210> SEQ ID NO 30
<211> LENGTH: 623
<212> TYPE: PRT
<213> ORGANISM: Vibrio splendidus

<400> SEQUENCE: 30

Met Val Ala Val Val Ser Ser Ser Ala Leu Ala Phe Thr Asn Trp Phe
1               5                   10                  15

Thr Leu Asn Leu Ala Thr Glu Gln Val Asn Gln Thr Ile Tyr Asn Glu
            20                  25                  30

Ile Asp His Ser Leu Thr Ile Glu Ile Asn Gln Ile Glu Ser Thr Val
        35                  40                  45

Gln Arg Thr Ile Asp Thr Val Asn Ser Val Ala Gln Glu Phe Met Lys
    50                  55                  60

Ser Pro Tyr Gln Val Pro Asn Glu Ala Leu Met His Tyr Ala Ala Lys
65                  70                  75                  80

Leu Gly Gly Ile Asp Lys Ile Val Val Gly Phe Asp Asp Gly Arg Ser
                85                  90                  95

Tyr Thr Ser Arg Pro Ser Glu Ser Phe Pro Asn Gly Val Gly Ile Lys
            100                 105                 110

Glu Lys Tyr Asn Pro Thr Thr Arg Pro Trp Tyr Gln Ala Lys Leu
        115                 120                 125

Lys Ser Gly Leu Ser Phe Ser Gly Leu Phe Phe Thr Lys Ser Thr Gln
    130                 135                 140

Val Pro Met Ile Gly Val Thr Tyr Ser Tyr Gln Asp Arg Val Ile Met
145                 150                 155                 160

Ala Asp Ile Arg Phe Asp Asp Leu Glu Thr Gln Leu Glu Gln Leu Asp
```

```
                165                 170                 175
Ser Ile Tyr Glu Ala Lys Gly Ile Ile Asp Glu Lys Gly Met Val
                180                 185                 190

Val Ala Ser Thr Ile Glu Asn Val Leu Pro Gln Thr Asn Ile Ser Ser
                195                 200                 205

Ala Asp Thr Gln Met Lys Leu Asn Ser Ala Ile Glu Gln Pro Asp Gln
        210                 215                 220

Phe Ile Glu Gly Val Ile Asp Gly Asn Gln Arg Ile Leu Met Ala Lys
225                 230                 235                 240

Lys Val Asp Ile Gly Ser Gln Lys Glu Trp Phe Met Ile Ser Ser Ile
                245                 250                 255

Asp Pro Glu Leu Ala Leu Asn Gln Leu Asn Gly Val Met Ser Ser Ala
                260                 265                 270

Arg Ile Leu Ile Val Ala Cys Val Leu Gly Ser Val Ile Leu Met Ile
        275                 280                 285

Leu Leu Leu Asn Arg Phe Tyr Arg Pro Ile Val Ser Leu Arg Lys Ile
        290                 295                 300

Val His Asp Leu Ser Gln Gly Asn Gly Asp Leu Thr Gln Arg Leu Ala
305                 310                 315                 320

Glu Lys Gly Asn Asp Asp Leu Gly His Ile Ala Lys Asp Ile Asn Leu
                325                 330                 335

Phe Ile Ile Gly Leu Gln Glu Met Val Lys Asp Val Lys Tyr Lys Asn
        340                 345                 350

Ser Asp Leu Asp Thr Lys Val Leu Ser Ile Arg Glu Gly Cys Lys Glu
        355                 360                 365

Thr Ser Asp Val Leu Lys Val His Thr Asp Glu Thr Val Gln Val Val
370                 375                 380

Ser Ala Ile Asn Gly Leu Ser Glu Ala Ser Asn Glu Val Glu Lys Ser
385                 390                 395                 400

Ser Gln Ser Ala Ala Glu Ala Ala Arg Glu Ala Ala Val Phe Ser Asp
                405                 410                 415

Glu Thr Lys Gln Ile Asn Thr Val Thr Glu Thr Tyr Ile Ser Asp Leu
                420                 425                 430

Glu Lys Gln Val Cys Thr Thr Ser Asp Asp Ile Arg Ser Met Ala Asn
        435                 440                 445

Glu Thr Gln Ser Ile Gln Ser Ile Val Ser Val Ile Gly Gly Ile Ala
        450                 455                 460

Glu Gln Thr Asn Leu Leu Ala Leu Asn Ala Ser Ile Glu Ala Ala Arg
465                 470                 475                 480

Ala Gly Glu His Gly Arg Gly Phe Ala Val Val Ala Asp Glu Val Arg
                485                 490                 495

Ala Leu Ala Asn Arg Thr Gln Ile Ser Thr Ser Glu Ile Asp Glu Ala
        500                 505                 510

Leu Ser Gly Leu Gln Ser Lys Ser Asp Gly Leu Val Lys Ser Ile Glu
        515                 520                 525

Leu Thr Lys Ser Asn Cys Glu Leu Thr Arg Ala Gln Val Val Gln Ala
        530                 535                 540

Val Asn Met Leu Ala Lys Leu Thr Glu Gln Met Glu Thr Val Ser Arg
545                 550                 555                 560

Phe Asn Asn Asp Ile Ser Gly Ser Ser Val Glu Gln Asn Ala Leu Ile
                565                 570                 575

Gln Ser Ile Ala Lys Asn Met His Lys Ile Glu Ser Phe Val Glu Glu
        580                 585                 590
```

Leu Asn Lys Leu Ser Gln Asp Gln Leu Thr Glu Ser Ala Glu Ile Lys
       595                 600                 605

Thr Leu Asn Gly Ser Val Ser Glu Leu Met Ser Ser Phe Lys Val
       610                 615                 620

<210> SEQ ID NO 31
<211> LENGTH: 1743
<212> TYPE: DNA
<213> ORGANISM: Vibrio splendidus

<400> SEQUENCE: 31

| | | | | | |
|---|---|---|---|---|---|
| gtgaataagc | caatctttgt | cgtcgtactc | gcttcgctta | cgtatggctg | cggtggaagc | 60 |
| agctccagtg | actctagtga | cccttctgat | accaataact | caggagcatc | ttatggtgtt | 120 |
| gttgctccct | atgatattgc | caagtatcaa | aacatccttt | ccagctcaga | tcttcaggtg | 180 |
| tctgatccta | tggagagga | gggcaataaa | acctctgaag | tcaaagatgg | taacttcgat | 240 |
| ggttatgtca | gtgattattt | ttatgctgac | gaagagacgg | aaaatctgat | cttcaaaatg | 300 |
| gcgaactaca | agatgcgctc | tgaagttcgt | gaaggagaaa | acttcgatat | caatgaagca | 360 |
| ggcgtaagac | gcagtctaca | tgcggaaata | agcctacctg | atattgagca | tgtaatggcg | 420 |
| agttctcccg | cagatcacga | tgaagtgacc | gtgctacaga | tccacaataa | aggtacagac | 480 |
| gagagtggca | cgggttatat | ccctcatccg | ctattgcgtg | tggtttggga | gcaagaacga | 540 |
| gatggcctca | caggtcacta | ctgggcagtc | atgaaaaata | atgccattga | ctgtagcagt | 600 |
| gccgctgact | cttcggattg | ttatgccact | tcatataatc | gctacgattt | gggagaggcg | 660 |
| gatctcgata | acttcaccaa | gtttgatctt | tctgtttatg | aaaatacccct | ttcgatcaaa | 720 |
| gtgaacgatg | aagttaaagt | cgacgaagac | atcaccctact | ggcagcatct | actgagttac | 780 |
| tttaaagcgg | gtatctacaa | tcaatttgaa | aatggtgaag | ccacggctca | ctttcaggca | 840 |
| ctgcgataca | ccaccacaca | ggtcaacggc | tcaaacgatt | gggatattaa | tgattggaag | 900 |
| ttgacgattc | ctgcgagtaa | agacacttgg | tatggaagtg | ggggtgacag | tgcggctgaa | 960 |
| ctagaacctg | agcgctgcga | atcgagcaaa | gaccttctcg | ccaacgacag | tgatgtctac | 1020 |
| gacagcgata | ttggtctttc | ttatttcaat | accgatgaag | ggagagtgca | ctttagagcg | 1080 |
| gatatgggat | atggcaccctc | taccgaaaat | tctagctata | ttcgctctga | gctcagggag | 1140 |
| ttgtatcaaa | gcagtgttca | accggattgt | agcaccagcg | atgaagatac | aagttggtat | 1200 |
| ttggacgaca | ctagaacgaa | cgctaccagt | cacgagttaa | ccgcaagctt | acgaattgaa | 1260 |
| gactacccga | acattaataa | ccaagacccg | aaagtggtgc | ttgggcaaat | acacggttgg | 1320 |
| aagatcaatc | aagcattggt | gaagttgtta | tgggaaggcg | agagtaagcc | agtaagagtg | 1380 |
| atactgaact | ctgattttga | gcgcaacaac | caagactgta | accattgtga | cccgttcagt | 1440 |
| gtcgagttag | gtacttattc | ggcaagtgaa | gagtggcgat | atacgattcg | agccaatcaa | 1500 |
| gacggtatct | acttagcgac | tcatgattta | gatggaacta | atacggtttc | tcatttaatc | 1560 |
| ccttggggac | aagattacac | agataaagat | ggggacacgg | tctcgttgac | gtcagattgg | 1620 |
| acatcgacag | acatcgcttt | ctatttcaaa | gcgggcatct | acccacaatt | taagcctgat | 1680 |
| agcgactatg | cgggtgaagt | gtttgatgtg | agctttagtt | ctctaagagc | agagcataac | 1740 |
| tga | | | | | | 1743 |

<210> SEQ ID NO 32
<211> LENGTH: 580
<212> TYPE: PRT
<213> ORGANISM: Vibrio splendidus

<400> SEQUENCE: 32

| | | | | | | | | | | | | | | |
|---|---|---|---|---|---|---|---|---|---|---|---|---|---|---|
|Met|Asn|Lys|Pro|Ile|Phe|Val|Val|Leu|Ala|Ser|Leu|Thr|Tyr|Gly|
|1| | | |5| | | | |10| | | | |15|
|Cys|Gly|Gly|Ser|Ser|Ser|Asp|Ser|Ser|Asp|Pro|Ser|Asp|Thr|Asn|
| | | |20| | | | |25| | | | |30| |
|Asn|Ser|Gly|Ala|Ser|Tyr|Gly|Val|Val|Ala|Pro|Tyr|Asp|Ile|Ala|Lys|
| | | |35| | | | |40| | | | |45| |
|Tyr|Gln|Asn|Ile|Leu|Ser|Ser|Asp|Leu|Gln|Val|Ser|Asp|Pro|Asn|
| |50| | | | |55| | | | |60| | | |
|Gly|Glu|Glu|Gly|Asn|Lys|Thr|Ser|Glu|Val|Lys|Asp|Gly|Asn|Phe|Asp|
|65| | | | |70| | | | |75| | | | |80|
|Gly|Tyr|Val|Ser|Asp|Tyr|Phe|Tyr|Ala|Asp|Glu|Glu|Thr|Glu|Asn|Leu|
| | | | |85| | | | |90| | | | |95| |
|Ile|Phe|Lys|Met|Ala|Asn|Tyr|Lys|Met|Arg|Ser|Glu|Val|Arg|Glu|Gly|
| | | |100| | | | |105| | | | |110| | |
|Glu|Asn|Phe|Asp|Ile|Asn|Glu|Ala|Gly|Val|Arg|Arg|Ser|Leu|His|Ala|
| | | |115| | | | |120| | | | |125| | |
|Glu|Ile|Ser|Leu|Pro|Asp|Ile|Glu|His|Val|Met|Ala|Ser|Ser|Pro|Ala|
| |130| | | | |135| | | | |140| | | | |
|Asp|His|Asp|Glu|Val|Thr|Val|Leu|Gln|Ile|His|Asn|Lys|Gly|Thr|Asp|
|145| | | | |150| | | | |155| | | | |160|
|Glu|Ser|Gly|Thr|Gly|Tyr|Ile|Pro|His|Pro|Leu|Leu|Arg|Val|Val|Trp|
| | | | |165| | | | |170| | | | |175| |
|Glu|Gln|Glu|Arg|Asp|Gly|Leu|Thr|Gly|His|Tyr|Trp|Ala|Val|Met|Lys|
| | | |180| | | | |185| | | | |190| | |
|Asn|Asn|Ala|Ile|Asp|Cys|Ser|Ser|Ala|Ala|Asp|Ser|Ser|Asp|Cys|Tyr|
| | | |195| | | | |200| | | | |205| | |
|Ala|Thr|Ser|Tyr|Asn|Arg|Tyr|Asp|Leu|Gly|Glu|Ala|Asp|Leu|Asp|Asn|
| |210| | | | |215| | | | |220| | | | |
|Phe|Thr|Lys|Phe|Asp|Leu|Ser|Val|Tyr|Glu|Asn|Thr|Leu|Ser|Ile|Lys|
|225| | | | |230| | | | |235| | | | |240|
|Val|Asn|Asp|Glu|Val|Lys|Val|Asp|Glu|Asp|Ile|Thr|Tyr|Trp|Gln|His|
| | | | |245| | | | |250| | | | |255| |
|Leu|Leu|Ser|Tyr|Phe|Lys|Ala|Gly|Ile|Tyr|Asn|Gln|Phe|Glu|Asn|Gly|
| | | |260| | | | |265| | | | |270| | |
|Glu|Ala|Thr|Ala|His|Phe|Gln|Ala|Leu|Arg|Tyr|Thr|Thr|Gln|Val|
| | |275| | | | |280| | | | |285| | |
|Asn|Gly|Ser|Asn|Asp|Trp|Asp|Ile|Asn|Asp|Trp|Lys|Leu|Thr|Ile|Pro|
| |290| | | | |295| | | | |300| | | | |
|Ala|Ser|Lys|Asp|Thr|Trp|Tyr|Gly|Ser|Gly|Asp|Ser|Ala|Ala|Glu|
|305| | | | |310| | | | |315| | | | |320|
|Leu|Glu|Pro|Glu|Arg|Cys|Glu|Ser|Ser|Lys|Asp|Leu|Leu|Ala|Asn|Asp|
| | | |325| | | | |330| | | | |335| | |
|Ser|Asp|Val|Tyr|Asp|Ser|Asp|Ile|Gly|Leu|Ser|Tyr|Phe|Asn|Thr|Asp|
| | |340| | | | |345| | | | |350| | |
|Glu|Gly|Arg|Val|His|Phe|Arg|Ala|Asp|Met|Gly|Tyr|Gly|Thr|Ser|Thr|
| | |355| | | | |360| | | | |365| | |
|Glu|Asn|Ser|Ser|Tyr|Ile|Arg|Ser|Glu|Leu|Arg|Glu|Leu|Tyr|Gln|Ser|
| |370| | | | |375| | | | |380| | | | |
|Ser|Val|Gln|Pro|Asp|Cys|Ser|Thr|Ser|Asp|Glu|Asp|Thr|Ser|Trp|Tyr|
|385| | | | |390| | | | |395| | | | |400|
|Leu|Asp|Asp|Thr|Arg|Thr|Asn|Ala|Thr|Ser|His|Glu|Leu|Thr|Ala|Ser|
| | | | |405| | | | |410| | | | |415| |

```
Leu Arg Ile Glu Asp Tyr Pro Asn Ile Asn Asn Gln Asp Pro Lys Val
            420                 425                 430
Val Leu Gly Gln Ile His Gly Trp Lys Ile Asn Gln Ala Leu Val Lys
        435                 440                 445
Leu Leu Trp Glu Gly Glu Ser Lys Pro Val Arg Val Ile Leu Asn Ser
450                 455                 460
Asp Phe Glu Arg Asn Asn Gln Asp Cys Asn His Cys Asp Pro Phe Ser
465                 470                 475                 480
Val Glu Leu Gly Thr Tyr Ser Ala Ser Glu Glu Trp Arg Tyr Thr Ile
                485                 490                 495
Arg Ala Asn Gln Asp Gly Ile Tyr Leu Ala Thr His Asp Leu Asp Gly
            500                 505                 510
Thr Asn Thr Val Ser His Leu Ile Pro Trp Gly Gln Asp Tyr Thr Asp
        515                 520                 525
Lys Asp Gly Asp Thr Val Ser Leu Thr Ser Asp Trp Thr Ser Thr Asp
530                 535                 540
Ile Ala Phe Tyr Phe Lys Ala Gly Ile Tyr Pro Gln Phe Lys Pro Asp
545                 550                 555                 560
Ser Asp Tyr Ala Gly Glu Val Phe Asp Val Ser Phe Ser Ser Leu Arg
                565                 570                 575
Ala Glu His Asn
            580

<210> SEQ ID NO 33
<211> LENGTH: 1569
<212> TYPE: DNA
<213> ORGANISM: Vibrio splendidus

<400> SEQUENCE: 33
atgaaacaaa ttactctaaa aactttactc gcttcttcta ttctacttgc ggttggttgt     60
gcgagcacga gcacgcctac tgctgatttt ccaaataaca aagaaactgg tgaagcgctt    120
ctgacgccag ttgctgtttc gctagtagc catgatggta acggacctga tcgtctcgtt     180
gaccaagacc taactacacg ttggtcatct gcgggtgacg gcgagtgggc aacgctagac    240
tatggttcag tacaggagtt tgacgcggtt caggcatctt tcagtaaagg taatcagcgc    300
caatctaaat tgatatcca agtgagtgtt gatggcgaaa gctggacaac ggtactagaa     360
aaccaactaa gctcaggtaa agcgatcggc ctagagcgtt tccaatttga gccagtagtg    420
caagcacgct acgtaagata cgttggtcac ggtaacacca aaaacggttg aacagtgtg     480 actggattag cggcggttaa ctgtagcatt aacgcatgtc ctgctagcca tatcatcact    540
tcagacgtgg ttgcagcaga agccgtgatt attgctgaaa tgaaagcggc agaaaaagca    600
cgtaaagatg cgcgcaaaga tctacgctct ggtaacttcg gtgtagcagc ggtttaccct    660
tgtgagacga ccgttgaatg tgacactcgc agtgcacttc cagttccgac aggcctgcca    720
gcgacaccag ttgcaggtaa ctcgccaagc gaaaactttg acatgacgca ttggtaccta    780
tctcaaccat tgaccatga caaaaatggc aaacctgatg atgtgtctga gtggaacctt    840
gcaaacggtt accaacaccc tgaaatcttc tacacagctg atgacggcgg cctagtattc    900
aaagcttacg tgaaaggtgt acgtacctct aaaaacacta gtacgcgcg tacagagctt    960 cgtgaaatga tgcgtcgtgg tgatcagtct attagcacta aaggtgttaa taagaataac   1020
tgggtattct caagcgctcc tgaatctgac ttagagtcgg cagcgggtat tgacggcgtt   1080
ctagaagcga cgttgaaaat cgaccatgca acaacgacgg gtaatgcgaa tgaagtaggg   1140
cgctttatca ttggtcagat tcacgatcaa aacgatgaac caattcgttt gtactaccgt   1200
```

-continued

```
aaactgccaa accaagaaac gggtgcggtt tacttcgcac atgaaagcca agacgcaact      1260
aaagaggact tctaccctct agtgggcgac atgacggctg aagtgggtga cgatggtatc      1320
gcgcttggcg aagtgttcag ctaccgtatt gacgttaaag caacacgat gactgtaacg       1380 ctaatacgtg aaggcaaaga cgatgttgta caagtggttg atatgagcaa cagcggctac      1440
gacgcaggcg gcaagtacat gtacttcaaa gccggtgttt acaaccaaaa catcagcggc      1500
gacctagacg attactcaca agcgactttc tatcagctag atgtatcgca cgatcaatac      1560
aaaaagtaa                                                              1569
```

<210> SEQ ID NO 34
<211> LENGTH: 522
<212> TYPE: PRT
<213> ORGANISM: Vibrio splendidus

<400> SEQUENCE: 34

```
Met Lys Gln Ile Thr Leu Lys Thr Leu Leu Ala Ser Ser Ile Leu Leu
 1               5                   10                  15

Ala Val Gly Cys Ala Ser Thr Ser Thr Pro Thr Ala Asp Phe Pro Asn
            20                  25                  30

Asn Lys Glu Thr Gly Glu Ala Leu Leu Thr Pro Val Ala Val Ser Ala
        35                  40                  45

Ser Ser His Asp Gly Asn Gly Pro Asp Arg Leu Val Asp Gln Asp Leu
    50                  55                  60

Thr Thr Arg Trp Ser Ser Ala Gly Asp Gly Glu Trp Ala Thr Leu Asp
65                  70                  75                  80

Tyr Gly Ser Val Gln Glu Phe Asp Ala Val Gln Ala Ser Phe Ser Lys
                85                  90                  95

Gly Asn Gln Arg Gln Ser Lys Phe Asp Ile Gln Val Ser Val Asp Gly
            100                 105                 110

Glu Ser Trp Thr Thr Val Leu Glu Asn Gln Leu Ser Ser Gly Lys Ala
        115                 120                 125

Ile Gly Leu Glu Arg Phe Gln Phe Glu Pro Val Val Gln Ala Arg Tyr
    130                 135                 140

Val Arg Tyr Val Gly His Gly Asn Thr Lys Asn Gly Trp Asn Ser Val
145                 150                 155                 160

Thr Gly Leu Ala Ala Val Asn Cys Ser Ile Asn Ala Cys Pro Ala Ser
                165                 170                 175

His Ile Ile Thr Ser Asp Val Val Ala Ala Glu Ala Val Ile Ile Ala
            180                 185                 190

Glu Met Lys Ala Ala Glu Lys Ala Arg Lys Asp Ala Arg Lys Asp Leu
        195                 200                 205

Arg Ser Gly Asn Phe Gly Val Ala Ala Val Tyr Pro Cys Glu Thr Thr
    210                 215                 220

Val Glu Cys Asp Thr Arg Ser Ala Leu Pro Val Pro Thr Gly Leu Pro
225                 230                 235                 240

Ala Thr Pro Val Ala Gly Asn Ser Pro Ser Glu Asn Phe Asp Met Thr
                245                 250                 255

His Trp Tyr Leu Ser Gln Pro Phe Asp His Asp Lys Asn Gly Lys Pro
            260                 265                 270

Asp Asp Val Ser Glu Trp Asn Leu Ala Asn Gly Tyr Gln His Pro Glu
        275                 280                 285

Ile Phe Tyr Thr Ala Asp Asp Gly Gly Leu Val Phe Lys Ala Tyr Val
    290                 295                 300
```

```
Lys Gly Val Arg Thr Ser Lys Asn Thr Lys Tyr Ala Arg Thr Glu Leu
305                 310                 315                 320

Arg Glu Met Met Arg Gly Asp Gln Ser Ile Ser Thr Lys Gly Val
            325                 330                 335

Asn Lys Asn Asn Trp Val Phe Ser Ser Ala Pro Glu Ser Asp Leu Glu
            340                 345                 350

Ser Ala Ala Gly Ile Asp Gly Val Leu Glu Ala Thr Leu Lys Ile Asp
            355                 360                 365

His Ala Thr Thr Thr Gly Asn Ala Asn Glu Val Gly Arg Phe Ile Ile
            370                 375                 380

Gly Gln Ile His Asp Gln Asn Asp Glu Pro Ile Arg Leu Tyr Tyr Arg
385                 390                 395                 400

Lys Leu Pro Asn Gln Glu Thr Gly Ala Val Tyr Phe Ala His Glu Ser
            405                 410                 415

Gln Asp Ala Thr Lys Glu Asp Phe Tyr Pro Leu Val Gly Asp Met Thr
            420                 425                 430

Ala Glu Val Gly Asp Asp Gly Ile Ala Leu Gly Glu Val Phe Ser Tyr
            435                 440                 445

Arg Ile Asp Val Lys Gly Asn Thr Met Thr Val Thr Leu Ile Arg Glu
450                 455                 460

Gly Lys Asp Asp Val Val Gln Val Val Asp Met Ser Asn Ser Gly Tyr
465                 470                 475                 480

Asp Ala Gly Gly Lys Tyr Met Tyr Phe Lys Ala Gly Val Tyr Asn Gln
            485                 490                 495

Asn Ile Ser Gly Asp Leu Asp Tyr Ser Gln Ala Thr Phe Tyr Gln
            500                 505                 510

Leu Asp Val Ser His Asp Gln Tyr Lys Lys
        515                 520

<210> SEQ ID NO 35
<211> LENGTH: 1230
<212> TYPE: DNA
<213> ORGANISM: Vibrio splendidus

<400> SEQUENCE: 35
atgcaaattt ctaaagtcgc tacagctgtc gctctttcga caggtttatt atttggttgt    60
aacagtgatg gtttacctat tccaacagat ccaggcggaa cagaccctgt tgaacctgtt   120
gaagtttact ctatagaaaa cgtctattgg gatctgacag gtggtgctgt tgctgcacag   180
tcactcagcg gaacttcacc atatcgcttt gataataatg aggaaggtac tcgtgctcta   240
agcatttaca gtggagacgt agctaatggc ttacttttg agagttcaat atatactgct   300
gaagaagaag gtgttgtttc ctttgaaggt aaggactgta cttacacagt gactgagcaa   360
cagctagata tgacctgtga aaagatgac gtagaaacag cttactcagc aacagagatt   420
acagatgaat ctgttataac tgcattagaa aatgccgatg atggaaaacc taaatcagtc   480
gatgatgtga acgctgcgat tgcatcagca gaagatggcg cgattattga tttatcatct   540
gaaggtacgt tgataccgg tgttattgag ctaaataaag ctgtcacaat tgatggtgct   600
ggtttagcaa ccattaccgg agatgcttgt attgatgtca ctgcacccgg tgcaggtatc   660
aaaaacatga cttttgctaa cgacaatttg gccgggtgtt ttggtaggga gtcagctggt   720
acttcagata tgaaactgg tgcgatcgtt attggtaaaa ttggtaaaga ttcagatcct   780
gtagcacttg aaaacctaaa gttcgatgca acggcatta ccgaagatga tctaggtact   840
aaaaaagcaa gttggttatt ctctcgaggt tactttacat tagacaatag cgaatttgtc   900
```

```
ggtttaagtg gcagtttcca aaataatgca attcgtatta actgtagtag tgacaacggg    960
cgatttggtt cacaaatcac aaataataca ttcactatta actctggtgg tagtgatgtg   1020
ggcggaatta agttggtga ttctagcagt gccgtcataa agaatagtga tgataacctt    1080
ggctgtaatg tcactattga aagcaatacg ttcaatggtt acaaaaccct actttcagct   1140
gacaacggta agatataag aaatacagcc atctacgcac aaccatctgc agtgaacact    1200
gcggcaggta agaaaatat cttgaactaa                                     1230

<210> SEQ ID NO 36
<211> LENGTH: 409
<212> TYPE: PRT
<213> ORGANISM: Vibrio splendidus

<400> SEQUENCE: 36

Met Gln Ile Ser Lys Val Ala Thr Ala Val Ala Leu Ser Thr Gly Leu
1               5                   10                  15

Leu Phe Gly Cys Asn Ser Asp Gly Leu Pro Ile Pro Thr Asp Pro Gly
            20                  25                  30

Gly Thr Asp Pro Val Glu Pro Val Glu Val Tyr Ser Ile Glu Asn Val
        35                  40                  45

Tyr Trp Asp Leu Thr Gly Gly Ala Val Ala Ala Gln Ser Leu Ser Gly
    50                  55                  60

Thr Ser Pro Tyr Arg Phe Asp Asn Asn Glu Glu Gly Thr Arg Ala Leu
65                  70                  75                  80

Ser Ile Tyr Ser Gly Asp Val Ala Asn Gly Phe Thr Phe Glu Ser Ser
                85                  90                  95

Ile Tyr Thr Ala Glu Glu Glu Gly Val Val Ser Phe Glu Gly Lys Asp
            100                 105                 110

Cys Thr Tyr Thr Val Thr Glu Gln Gln Leu Asp Met Thr Cys Glu Lys
        115                 120                 125

Asp Asp Val Glu Thr Ala Tyr Ser Ala Thr Glu Ile Thr Asp Glu Ser
    130                 135                 140

Val Ile Thr Ala Leu Glu Asn Ala Asp Asp Gly Lys Pro Lys Ser Val
145                 150                 155                 160

Asp Asp Val Asn Ala Ala Ile Ala Ser Ala Glu Asp Gly Ala Ile Ile
                165                 170                 175

Asp Leu Ser Ser Glu Gly Thr Phe Asp Thr Gly Val Ile Glu Leu Asn
            180                 185                 190

Lys Ala Val Thr Ile Asp Gly Ala Gly Leu Ala Thr Ile Thr Gly Asp
        195                 200                 205

Ala Cys Ile Asp Val Thr Ala Pro Gly Ala Gly Ile Lys Asn Met Thr
    210                 215                 220

Phe Ala Asn Asp Asn Leu Ala Gly Cys Phe Gly Arg Glu Ser Ala Gly
225                 230                 235                 240

Thr Ser Asp Asn Glu Thr Gly Ala Ile Val Ile Gly Lys Ile Gly Lys
                245                 250                 255

Asp Ser Asp Pro Val Ala Leu Glu Asn Leu Lys Phe Asp Ala Asn Gly
            260                 265                 270

Ile Thr Glu Asp Asp Leu Gly Thr Lys Lys Ala Ser Trp Leu Phe Ser
        275                 280                 285

Arg Gly Tyr Phe Thr Leu Asp Asn Ser Glu Phe Val Gly Leu Ser Gly
    290                 295                 300

Ser Phe Gln Asn Asn Ala Ile Arg Ile Asn Cys Ser Ser Asp Asn Gly
305                 310                 315                 320
```

Arg Phe Gly Ser Gln Ile Thr Asn Asn Thr Phe Thr Ile Asn Ser Gly
                325                 330                 335

Gly Ser Asp Val Gly Gly Ile Lys Val Gly Asp Ser Ser Ala Val
            340                 345                 350

Ile Lys Asn Ser Asp Asp Asn Leu Gly Cys Asn Val Thr Ile Glu Ser
            355                 360                 365

Asn Thr Phe Asn Gly Tyr Lys Thr Leu Leu Ser Ala Asp Asn Gly Lys
        370                 375                 380

Asp Ile Arg Asn Thr Ala Ile Tyr Ala Gln Pro Ser Ala Val Asn Thr
385                 390                 395                 400

Ala Ala Gly Lys Glu Asn Ile Leu Asn
            405

<210> SEQ ID NO 37
<211> LENGTH: 861
<212> TYPE: DNA
<213> ORGANISM: Vibrio splendidus

<400> SEQUENCE: 37

| | | | | | |
|---|---|---|---|---|---|
| atgaattctg | ttacaaaaat | tgctgcagct | gttgcatgta | ctcttttagc | gggcacagct | 60 |
| gctggtgcat | ctcttgatta | tcgttacgag | tatcgtgctg | cgacggatta | tacaaagact | 120 |
| aatggtgata | cggctcacgt | agacgctcgc | catcaacacc | gagttaagct | aggtgaaagc | 180 |
| tttaagctgt | cagacaagtg | gaagcactct | actggtctag | aacttaagtt | ccacggtgat | 240 |
| gactcttact | atgatgaaga | ttcaggttct | gttaaatcag | caaacagcca | gagttttttac | 300 |
| gatggcaatt | ggtacatcta | tggtatggag | atcgataaca | ctgcgacata | caaaatagac | 360 |
| aataattggt | atctacaaat | gggtatgcct | attgcttggg | attgggatga | gcctaatgct | 420 |
| aacgatggcg | actggaagat | gaaaaaggtt | acgtttaaac | tcagttccg | cgttggctat | 480 |
| aaagcagata | tgggtttaac | aactgctatt | cgttaccgtc | atgaatatgc | tgacttccgt | 540 |
| aaccacacac | aatttggcga | caaagattct | gaaactggcg | agcgtttaga | atcagctcaa | 600 |
| aagtctaaag | ttacactgac | gggctcttac | aaaattgaat | ctctacctaa | gcttggcctt | 660 |
| tcttacgaag | caaactatgt | aaaatctttg | gataacgtac | ttctttataa | tagtgatgac | 720 |
| tgggaatggg | atgctggctt | aaaggtaaac | tacaagttcg | gttcttggaa | accttttgct | 780 |
| gaaatctggt | cttctgatat | cagttcatct | tcaaagatc | gtgaagctaa | ataccgtgtt | 840 |
| ggtattgctt | actcattcta | a | | | | 861 |

<210> SEQ ID NO 38
<211> LENGTH: 286
<212> TYPE: PRT
<213> ORGANISM: Vibrio splendidus

<400> SEQUENCE: 38

Met Asn Ser Val Thr Lys Ile Ala Ala Ala Val Ala Cys Thr Leu Leu
1               5                   10                  15

Ala Gly Thr Ala Ala Gly Ala Ser Leu Asp Tyr Arg Tyr Glu Tyr Arg
            20                  25                  30

Ala Ala Thr Asp Tyr Thr Lys Thr Asn Gly Asp Thr Ala His Val Asp
        35                  40                  45

Ala Arg His Gln His Arg Val Lys Leu Gly Glu Ser Phe Lys Leu Ser
    50                  55                  60

Asp Lys Trp Lys His Ser Thr Gly Leu Glu Leu Lys Phe His Gly Asp
65                  70                  75                  80

Asp Ser Tyr Tyr Asp Glu Asp Ser Gly Ser Val Lys Ser Ala Asn Ser

```
                        85                  90                  95
Gln Ser Phe Tyr Asp Gly Asn Trp Tyr Ile Tyr Gly Met Glu Ile Asp
                100                 105                 110

Asn Thr Ala Thr Tyr Lys Ile Asp Asn Asn Trp Tyr Leu Gln Met Gly
            115                 120                 125

Met Pro Ile Ala Trp Asp Trp Asp Glu Pro Asn Ala Asn Asp Gly Asp
        130                 135                 140

Trp Lys Met Lys Lys Val Thr Phe Lys Pro Gln Phe Arg Val Gly Tyr
145                 150                 155                 160

Lys Ala Asp Met Gly Leu Thr Thr Ala Ile Arg Tyr Arg His Glu Tyr
                165                 170                 175

Ala Asp Phe Arg Asn His Thr Gln Phe Gly Asp Lys Asp Ser Glu Thr
            180                 185                 190

Gly Glu Arg Leu Glu Ser Ala Gln Lys Ser Lys Val Thr Leu Thr Gly
        195                 200                 205

Ser Tyr Lys Ile Glu Ser Leu Pro Lys Leu Gly Leu Ser Tyr Glu Ala
    210                 215                 220

Asn Tyr Val Lys Ser Leu Asp Asn Val Leu Leu Tyr Asn Ser Asp Asp
225                 230                 235                 240

Trp Glu Trp Asp Ala Gly Leu Lys Val Asn Tyr Lys Phe Gly Ser Trp
                245                 250                 255

Lys Pro Phe Ala Glu Ile Trp Ser Ser Asp Ile Ser Ser Ser Ser Lys
            260                 265                 270

Asp Arg Glu Ala Lys Tyr Arg Val Gly Ile Ala Tyr Ser Phe
        275                 280                 285

<210> SEQ ID NO 39
<211> LENGTH: 1038
<212> TYPE: DNA
<213> ORGANISM: Vibrio splendidus

<400> SEQUENCE: 39
atgtttaaga aaacatatt agcagtggcg ttattagcga ctgtgccaat ggttactttc     60
gcaaataacg gtgtttctta ccccgtacct gccgataaat cgatatgca taattggaaa    120
ataaccatac cttcagatat taatgaagat ggtcgcgttg atgaaataga aggggtcgct    180
atgatgagct actcacatag tgatttcttc catcttgata aagacggcaa ccttgtattt    240
gaagtgcaga accaagcgat tacgacgaaa aactcgaaga atgcgcgttc tgagttacgc    300
cagatgccaa gaggcgcaga tttctctatc gatacggctg ataaaggaaa ccagtgggca    360
ctgtcgagtc acccagcggc tagtgaatac agtgctgtgg gcggaacatt agaagcgaca    420
ttaaaagtga atcacgtctc agttaacgct aagttcccag aaaatacccc agctcattct    480
gttgtggttg gtcagattca tgctaaaaaa cacaacgagc taatcaaagc tggaaccggt    540
tatgggcatg gtaatgaacc actaaagatc ttctataaga gtttcctga ccaagaaatg     600
ggttcagtat tctggaacta tgaacgtaac ctagagaaaa aagatcctaa ccgtgccgat    660
atcgcttatc cagtgtgggg taacacgtgg gaaaaccctg cagagccggg tgaagccggt    720
attgctcttg gtgaagagtt tagctacaaa gtggaagtga aaggcaccat gatgtaccta    780
acgtttgaaa ccgagcgtca cgataccgtt aagtatgaaa tcgacctgag taagggcatc    840
gatgaacttg actcaccaac gggctatgct gaagatgatt tttactacaa agcgggcgca    900
tacggccaat gtagcgtgag cgattctcac cctgtatggg ggcctggttg tggcggtact    960
ggcgatttcg ctgtcgataa aaagaatggc gattacaaca gtgtgacttt ctctgcgctt   1020
```
aagttaaacg gtaaatag                                                  1038

<210> SEQ ID NO 40
<211> LENGTH: 345
<212> TYPE: PRT
<213> ORGANISM: Vibrio splendidus

<400> SEQUENCE: 40

Met Phe Lys Lys Asn Ile Leu Ala Val Ala Leu Leu Ala Thr Val Pro
1               5                   10                  15

Met Val Thr Phe Ala Asn Asn Gly Val Ser Tyr Pro Val Pro Ala Asp
            20                  25                  30

Lys Phe Asp Met His Asn Trp Lys Ile Thr Ile Pro Ser Asp Ile Asn
        35                  40                  45

Glu Asp Gly Arg Val Asp Glu Ile Glu Gly Val Ala Met Met Ser Tyr
    50                  55                  60

Ser His Ser Asp Phe Phe His Leu Asp Lys Asp Gly Asn Leu Val Phe
65                  70                  75                  80

Glu Val Gln Asn Gln Ala Ile Thr Thr Lys Asn Ser Lys Asn Ala Arg
                85                  90                  95

Ser Glu Leu Arg Gln Met Pro Arg Gly Ala Asp Phe Ser Ile Asp Thr
            100                 105                 110

Ala Asp Lys Gly Asn Gln Trp Ala Leu Ser Ser His Pro Ala Ala Ser
        115                 120                 125

Glu Tyr Ser Ala Val Gly Gly Thr Leu Glu Ala Thr Leu Lys Val Asn
    130                 135                 140

His Val Ser Val Asn Ala Lys Phe Pro Glu Lys Tyr Pro Ala His Ser
145                 150                 155                 160

Val Val Val Gly Gln Ile His Ala Lys Lys His Asn Glu Leu Ile Lys
                165                 170                 175

Ala Gly Thr Gly Tyr Gly His Gly Asn Glu Pro Leu Lys Ile Phe Tyr
            180                 185                 190

Lys Lys Phe Pro Asp Gln Glu Met Gly Ser Val Phe Trp Asn Tyr Glu
        195                 200                 205

Arg Asn Leu Glu Lys Lys Asp Pro Asn Arg Ala Asp Ile Ala Tyr Pro
    210                 215                 220

Val Trp Gly Asn Thr Trp Glu Asn Pro Ala Glu Pro Gly Glu Ala Gly
225                 230                 235                 240

Ile Ala Leu Gly Glu Glu Phe Ser Tyr Lys Val Glu Val Lys Gly Thr
                245                 250                 255

Met Met Tyr Leu Thr Phe Glu Thr Glu Arg His Asp Thr Val Lys Tyr
            260                 265                 270

Glu Ile Asp Leu Ser Lys Gly Ile Asp Glu Leu Asp Ser Pro Thr Gly
        275                 280                 285

Tyr Ala Glu Asp Asp Phe Tyr Tyr Lys Ala Gly Ala Tyr Gly Gln Cys
    290                 295                 300

Ser Val Ser Asp Ser His Pro Val Trp Gly Pro Gly Cys Gly Gly Thr
305                 310                 315                 320

Gly Asp Phe Ala Val Asp Lys Lys Asn Gly Asp Tyr Asn Ser Val Thr
                325                 330                 335

Phe Ser Ala Leu Lys Leu Asn Gly Lys
            340                 345

<210> SEQ ID NO 41
<211> LENGTH: 897
<212> TYPE: DNA

<213> ORGANISM: Vibrio splendidus

<400> SEQUENCE: 41

```
atggataact ctccggtgct gagccgattt ttagagaatg gattttact  ccagcagaaa    60
ctgagccttg ttctttgttg tgtgttgatc gcagcttctg catggatttt aggacagctt   120
gcatggttta ttgaacctgc tgagcaaacc gtcgtgccat ggacagcaac ggcttcctcg   180
tcttcaacgc ctcaatcgac tcttgatatc tcttctttgc agcagagcaa catgtttggt   240
gcttataacc caaccacgcc tgctgtggtt gagcagcaag ttatccaaga tgcgccaaag   300
acgcgactga acctcgtttt agtgggtgca gtagccagtt ctaatccaaa gctgagcttg   360
gctgtgattg ccaatcgcgg cacacaagca acctacggca ttaatgaaga gatcgaaggt   420
acgcgagcta agttaaaagc ggtattagtc gatcgcgtga ttattgataa ctcaggtcga   480
gacgaaacct tgatgcttga aggcattgag tacaagcgtt tgtctgtatc agcacctgcg   540
ccacctcgta cctcttcttc tgtgcgtggc aacaacccag cttctgcaga gagaagcta    600
gatgaaatta agcgaagat aatgaaagat ccgcaacaaa tcttccaata tgttcgactg    660
tctcaggtga aacgcgacga taaagtgatt ggttatcgtg tgagccctgg caaagattca   720
gaacttttta actctgttgg gctccaaaac ggagatattg ccactcagtt aaatggacaa   780
gacctgacag accctgctgc tatgggcaac atattccgtt ctatctcaga gctgacagag   840
ctaaacctcg tcgtcgagag agatggtcaa caacatgaag tgtttattga attttag      897
```

<210> SEQ ID NO 42
<211> LENGTH: 298
<212> TYPE: PRT
<213> ORGANISM: Vibrio splendidus

<400> SEQUENCE: 42

```
Met Asp Asn Ser Pro Val Leu Ser Arg Phe Leu Glu Asn Gly Phe Leu
1               5                   10                  15

Leu Gln Gln Lys Leu Ser Leu Val Leu Cys Cys Val Leu Ile Ala Ala
            20                  25                  30

Ser Ala Trp Ile Leu Gly Gln Leu Ala Trp Phe Ile Glu Pro Ala Glu
        35                  40                  45

Gln Thr Val Val Pro Trp Thr Ala Thr Ala Ser Ser Ser Thr Pro
    50                  55                  60

Gln Ser Thr Leu Asp Ile Ser Ser Leu Gln Gln Ser Asn Met Phe Gly
65                  70                  75                  80

Ala Tyr Asn Pro Thr Thr Pro Ala Val Val Glu Gln Gln Val Ile Gln
                85                  90                  95

Asp Ala Pro Lys Thr Arg Leu Asn Leu Val Leu Val Gly Ala Val Ala
            100                 105                 110

Ser Ser Asn Pro Lys Leu Ser Leu Ala Val Ile Ala Asn Arg Gly Thr
        115                 120                 125

Gln Ala Thr Tyr Gly Ile Asn Glu Glu Ile Glu Gly Thr Arg Ala Lys
    130                 135                 140

Leu Lys Ala Val Leu Val Asp Arg Val Ile Ile Asp Asn Ser Gly Arg
145                 150                 155                 160

Asp Glu Thr Leu Met Leu Glu Gly Ile Glu Tyr Lys Arg Leu Ser Val
                165                 170                 175

Ser Ala Pro Ala Pro Pro Arg Thr Ser Ser Ser Val Arg Gly Asn Asn
            180                 185                 190

Pro Ala Ser Ala Glu Glu Lys Leu Asp Glu Ile Lys Ala Lys Ile Met
        195                 200                 205
```

```
Lys Asp Pro Gln Gln Ile Phe Gln Tyr Val Arg Leu Ser Gln Val Lys
    210                 215                 220

Arg Asp Asp Lys Val Ile Gly Tyr Arg Val Ser Pro Gly Lys Asp Ser
225                 230                 235                 240

Glu Leu Phe Asn Ser Val Gly Leu Gln Asn Gly Asp Ile Ala Thr Gln
                245                 250                 255

Leu Asn Gly Gln Asp Leu Thr Asp Pro Ala Ala Met Gly Asn Ile Phe
            260                 265                 270

Arg Ser Ile Ser Glu Leu Thr Glu Leu Asn Leu Val Val Glu Arg Asp
        275                 280                 285

Gly Gln Gln His Glu Val Phe Ile Glu Phe
        290                 295

<210> SEQ ID NO 43
<211> LENGTH: 2025
<212> TYPE: DNA
<213> ORGANISM: Vibrio splendidus

<400> SEQUENCE: 43
gtgaagcatt ggtttaagaa aagtgcatgg ttattggcag gaagcttaat ctgcacaccc       60
gcagccatcg cgagtgattt tagtgccagc tttaaaggca ctgatattca agagtttatt      120
aatattgttg gtcgtaacct agagaagacg atcatcgttg acccttcggt gcgcggaaaa      180
atcgatgtac gcagctacga cgtactcaat gaagagcaat actacagctt cttcctaaac      240
gtattggaag tgtatggcta cgcggttgtc gaaatggact cgggtgttct taagatcatc      300
aaggccaaag attcgaaaac atcggcaatt ccagtcgttg agacagtga cacgatcaaa       360 ggcgacaatg tggtgacacg tgttgtgacg gttcgtaatg tctcggtgcg tgaacttttct     420 cctctgcttc gtcaactaaa cgacaatgca ggcgcgggta acgttgtgca ctacgaccca      480
gccaacatca tccttattac aggccgagcg gcggtagtaa accgtttagc tgaaatcatc      540
aagcgtgttg accaagcggg tgataaagag attgaagtcg ttgagctaaa gaatgcttct      600
gcggcagaaa tggtacgtat cgttgatgcg ttaagcaaaa ccactgatgc gaaaaacaca      660
cctgcatttc tacaacctaa attagttgcc gatgaacgta ccaatgcgat tcttatctca      720
ggcgacccta agtacgtag ccgttttaaga aggctgattg aacagcttga tgttgaaatg      780
gcaaccaagg gcaataacca agttatttac cttaaatatg caaaagccga agatctagtt      840
gatgtgctga aaggcgtgtc ggacaaccta caatcagaga agcagacatc aaccaaagga      900
agttcatcgc agcgtaacca agtgatgatc tcagctcaca gtgacaccaa ctctttagtg      960
attaccgcac agccggacat catgaatgcg cttcaagatg tgatcgcaca gctggatatt     1020
cgtcgtgctc aagtattgat tgaagcactg attgtcgaaa tggccgaagg tgacggcgtt     1080
aaccttggtg tgcagtgggg taaccttgaa acgggtgcca tgattcagta cagcaacact     1140
ggcgcttcca ttggcggtgt gatggttggt ttagaagaag cgaaagacag cgaaacgaca     1200
accgctgttt atgattcaga cggtaaattc ttacgtaatg aaaccacgac ggaagaaggt     1260
gactattcaa cattagcttc cgcactttct ggtgttaatg tgcggcaat gagtgtggta     1320 atgggtgact ggaccgcctt gatcagtgca gtagcgaccg attcaaattc aaatatccta     1380
tcttctccaa gtatcaccgt gatggataac ggcgaagcgt cattcattgt gggtgaagag     1440
gtgcctgttc taaccggttc tacagcaggc tcaagtaacg acaacccatt ccaaacagtt     1500
gaacgtaaag aagtggggtat caagcttaaa gtggtgccgc aaatcaatga aggtgattcg     1560
gttcaactgc aaatagaaca agaagtatcg aacgtattag cgccaatggg tgcggttgat     1620
```

```
gtgcgttttg ctaagcgaca gctaaataca tcagtgattg ttcaagacgg tcaaatgctg    1680
gtgttgggtg gcttgattga cgagcgagca ttggaaagtg aatctaaggt gccgttcttg    1740
ggagatattc ctgtgcttgg acacttgttc aaatcaacca gtactcaggt tgagaaaaag    1800
aacctaatgg tcttcatcaa accaaccatt attcgtgatg gtatgacagc cgatggtatc    1860
acgcagcgta atacaactt catccgtgct gagcagttgt acaaggctga gcaaggactg     1920
aagttaatgg cagacgataa catcccagta ttgcctaaat ttggtgccga catgaatcac    1980
ccggctgaaa ttcaagcctt catcgatcaa atggaacaag aataa                    2025
```

<210> SEQ ID NO 44
<211> LENGTH: 674
<212> TYPE: PRT
<213> ORGANISM: Vibrio splendidus

<400> SEQUENCE: 44

```
Met Lys His Trp Phe Lys Lys Ser Ala Trp Leu Leu Ala Gly Ser Leu
  1               5                  10                  15

Ile Cys Thr Pro Ala Ala Ile Ala Ser Asp Phe Ser Ala Ser Phe Lys
             20                  25                  30

Gly Thr Asp Ile Gln Glu Phe Ile Asn Ile Val Gly Arg Asn Leu Glu
         35                  40                  45

Lys Thr Ile Ile Val Asp Pro Ser Val Arg Gly Lys Ile Asp Val Arg
     50                  55                  60

Ser Tyr Asp Val Leu Asn Glu Glu Gln Tyr Tyr Ser Phe Phe Leu Asn
 65                  70                  75                  80

Val Leu Glu Val Tyr Gly Tyr Ala Val Val Glu Met Asp Ser Gly Val
                 85                  90                  95

Leu Lys Ile Ile Lys Ala Lys Asp Ser Lys Thr Ser Ala Ile Pro Val
            100                 105                 110

Val Gly Asp Ser Asp Thr Ile Lys Gly Asp Asn Val Val Thr Arg Val
        115                 120                 125

Val Thr Val Arg Asn Val Ser Val Arg Glu Leu Ser Pro Leu Leu Arg
    130                 135                 140

Gln Leu Asn Asp Asn Ala Gly Ala Gly Asn Val Val His Tyr Asp Pro
145                 150                 155                 160

Ala Asn Ile Ile Leu Ile Thr Gly Arg Ala Ala Val Val Asn Arg Leu
                165                 170                 175

Ala Glu Ile Ile Lys Arg Val Asp Gln Ala Gly Asp Lys Glu Ile Glu
            180                 185                 190

Val Val Glu Leu Lys Asn Ala Ser Ala Ala Glu Met Val Arg Ile Val
        195                 200                 205

Asp Ala Leu Ser Lys Thr Thr Asp Ala Lys Asn Thr Pro Ala Phe Leu
    210                 215                 220

Gln Pro Lys Leu Val Ala Asp Glu Arg Thr Asn Ala Ile Leu Ile Ser
225                 230                 235                 240

Gly Asp Pro Lys Val Arg Ser Arg Leu Arg Arg Leu Ile Glu Gln Leu
                245                 250                 255

Asp Val Glu Met Ala Thr Lys Gly Asn Asn Gln Val Ile Tyr Leu Lys
            260                 265                 270

Tyr Ala Lys Ala Glu Asp Leu Val Asp Val Leu Lys Gly Val Ser Asp
        275                 280                 285

Asn Leu Gln Ser Glu Lys Gln Thr Ser Thr Lys Gly Ser Ser Ser Gln
    290                 295                 300
```

Arg Asn Gln Val Met Ile Ser Ala His Ser Asp Thr Asn Ser Leu Val
305                 310                 315                 320

Ile Thr Ala Gln Pro Asp Ile Met Asn Ala Leu Gln Asp Val Ile Ala
            325                 330                 335

Gln Leu Asp Ile Arg Arg Ala Gln Val Leu Ile Glu Ala Leu Ile Val
            340                 345                 350

Glu Met Ala Glu Gly Asp Gly Val Asn Leu Gly Val Gln Trp Gly Asn
            355                 360                 365

Leu Glu Thr Gly Ala Met Ile Gln Tyr Ser Asn Thr Gly Ala Ser Ile
370                 375                 380

Gly Gly Val Met Val Gly Leu Glu Glu Ala Lys Asp Ser Glu Thr Thr
385                 390                 395                 400

Thr Ala Val Tyr Asp Ser Asp Gly Lys Phe Leu Arg Asn Glu Thr Thr
            405                 410                 415

Thr Glu Glu Gly Asp Tyr Ser Thr Leu Ala Ser Ala Leu Ser Gly Val
            420                 425                 430

Asn Gly Ala Ala Met Ser Val Val Met Gly Asp Trp Thr Ala Leu Ile
            435                 440                 445

Ser Ala Val Ala Thr Asp Ser Asn Ser Asn Ile Leu Ser Ser Pro Ser
450                 455                 460

Ile Thr Val Met Asp Asn Gly Glu Ala Ser Phe Ile Val Gly Glu Glu
465                 470                 475                 480

Val Pro Val Leu Thr Gly Ser Thr Ala Gly Ser Ser Asn Asp Asn Pro
            485                 490                 495

Phe Gln Thr Val Glu Arg Lys Glu Val Gly Ile Lys Leu Lys Val Val
            500                 505                 510

Pro Gln Ile Asn Glu Gly Asp Ser Val Gln Leu Gln Ile Glu Gln Glu
            515                 520                 525

Val Ser Asn Val Leu Gly Ala Asn Gly Ala Val Asp Val Arg Phe Ala
530                 535                 540

Lys Arg Gln Leu Asn Thr Ser Val Ile Val Gln Asp Gly Gln Met Leu
545                 550                 555                 560

Val Leu Gly Gly Leu Ile Asp Glu Arg Ala Leu Glu Ser Glu Ser Lys
            565                 570                 575

Val Pro Phe Leu Gly Asp Ile Pro Val Leu Gly His Leu Phe Lys Ser
            580                 585                 590

Thr Ser Thr Gln Val Glu Lys Lys Asn Leu Met Val Phe Ile Lys Pro
            595                 600                 605

Thr Ile Ile Arg Asp Gly Met Thr Ala Asp Gly Ile Thr Gln Arg Lys
            610                 615                 620

Tyr Asn Phe Ile Arg Ala Glu Gln Leu Tyr Lys Ala Glu Gln Gly Leu
625                 630                 635                 640

Lys Leu Met Ala Asp Asp Asn Ile Pro Val Leu Pro Lys Phe Gly Ala
            645                 650                 655

Asp Met Asn His Pro Ala Glu Ile Gln Ala Phe Ile Asp Gln Met Glu
            660                 665                 670

Gln Glu

<210> SEQ ID NO 45
<211> LENGTH: 1503
<212> TYPE: DNA
<213> ORGANISM: Vibrio splendidus

<400> SEQUENCE: 45
atggctgaat tggtaggggc ggcacgtact tatcagcgct tgccgtttag ctttgcgaat     60

```
cgctacaaga tggtgttgga ataccaacat ccagagcgcg caccgatact ttattatgtt      120
gagccactga aatcggcggc gatcattgaa gtgagtcgtg ttgtgaaaaa tggtttcacg      180
ccacaagcga ttactctcga tgagtttgat aaaaaactaa ccgatgctta tcagcgtgac      240
tcgtcagaag ctcgtcagct catggaagac attggtgctg atagtgatga tttcttctca      300
ctagcggaag aactgcctca agacgaagac ttacttgaat cagaagatga tgcaccaatc      360
atcaagttaa tcaatgcgat gctgggtgag gcgatcaaag agggtgcttc ggatatacac      420
atcgaaacct ttgaaaagtc actttgtatc cgtttccgag ttgatggtgt gctgcgtgat      480
gttctagcgc aagccgtaa actggctccg ctattggttt cacgtgtcaa ggttatggct      540
aaactggata ttgcggaaaa acgcgtgcca caagatggtc gtatttctct gcgtattggt      600
ggccgagcgg ttgatgttcg tgtttcaacc atgccttctt cgcatggtga gcgtgtggta      660
atgcgtctgt tggacaaaaa tgccactcgt ctagacttgc acagtttagg tatgacagcc      720
gaaaaccatg aaaacttccg taagctgatt cagcgcccac atggcattat cttggtgacc      780
ggcccgacag gttcaggtaa atcgacgacc ttgtacgcag gtctgcaaga actcaacagc      840
aatgaacgaa acatttttaac cgttgaagac ccaatcgaat tcgatatcga tggcattggt      900
caaacacaag tgaaccctaa ggttgatatg acctttgcgc gtggtttacg tgccattctt      960
cgtcaagatc ctgatgttgt tatgattggt gagatccgtg acttggagac cgcagagatt     1020
gctgtccagg cctctttgac aggtcactta gttatgtcga ctctgcatac caatactgcc     1080
gtcggtgcga ttacacgtct acgtgatatg ggcattgaac ctttcttgat ctcttcttcg     1140
ctgctgggtg ttttggctca gcgcttggtt cgtactttat gtaacgaatg taaagaacct     1200
tatgaagccg ataaagagca gaagaaactg tttgggttga agaagaaaga aagcttgacg     1260
ctttaccatg ccaaaggttg tgaagagtgt ggccataagg gttatcgagg tcgtacgggt     1320
attcatgagc tgttgatgat tgatgattca gtacaagagc tgattcacag tgaagcgggt     1380
gagcaggcga ttgataaagc aattcgtggc acaacaccaa gtattcgaga tgatggcttg     1440
agcaaagttc tgaagggggt aacgtcccta gaagaagtga tgcgcgtgac caaggaagtc     1500
tag                                                                   1503
```

<210> SEQ ID NO 46
<211> LENGTH: 500
<212> TYPE: PRT
<213> ORGANISM: Vibrio splendidus

<400> SEQUENCE: 46

Met Ala Glu Leu Val Gly Ala Ala Arg Thr Tyr Gln Arg Leu Pro Phe
1               5                   10                  15

Ser Phe Ala Asn Arg Tyr Lys Met Val Leu Glu Tyr Gln His Pro Glu
            20                  25                  30

Arg Ala Pro Ile Leu Tyr Tyr Val Glu Pro Leu Lys Ser Ala Ala Ile
        35                  40                  45

Ile Glu Val Ser Arg Val Val Lys Asn Gly Phe Thr Pro Gln Ala Ile
    50                  55                  60

Thr Leu Asp Glu Phe Asp Lys Lys Leu Thr Asp Ala Tyr Gln Arg Asp
65                  70                  75                  80

Ser Ser Glu Ala Arg Gln Leu Met Glu Asp Ile Gly Ala Asp Ser Asp
                85                  90                  95

Asp Phe Ser Leu Ala Glu Glu Leu Pro Gln Asp Glu Asp Leu Leu
            100                 105                 110

Glu Ser Glu Asp Ala Pro Ile Ile Lys Leu Ile Asn Ala Met Leu
        115                 120                 125

Gly Glu Ala Ile Lys Glu Gly Ala Ser Asp Ile His Ile Glu Thr Phe
    130                 135                 140

Glu Lys Ser Leu Cys Ile Arg Phe Arg Val Asp Gly Val Leu Arg Asp
145                 150                 155                 160

Val Leu Ala Pro Ser Arg Lys Leu Ala Pro Leu Leu Val Ser Arg Val
                165                 170                 175

Lys Val Met Ala Lys Leu Asp Ile Ala Glu Lys Arg Val Pro Gln Asp
            180                 185                 190

Gly Arg Ile Ser Leu Arg Ile Gly Gly Arg Ala Val Asp Val Arg Val
                195                 200                 205

Ser Thr Met Pro Ser Ser His Gly Glu Arg Val Val Met Arg Leu Leu
    210                 215                 220

Asp Lys Asn Ala Thr Arg Leu Asp Leu His Ser Leu Gly Met Thr Ala
225                 230                 235                 240

Glu Asn His Glu Asn Phe Arg Lys Leu Ile Gln Arg Pro His Gly Ile
                245                 250                 255

Ile Leu Val Thr Gly Pro Thr Gly Ser Gly Lys Ser Thr Thr Leu Tyr
            260                 265                 270

Ala Gly Leu Gln Glu Leu Asn Ser Asn Glu Arg Asn Ile Leu Thr Val
                275                 280                 285

Glu Asp Pro Ile Glu Phe Asp Ile Asp Gly Ile Gly Gln Thr Gln Val
    290                 295                 300

Asn Pro Lys Val Asp Met Thr Phe Ala Arg Gly Leu Arg Ala Ile Leu
305                 310                 315                 320

Arg Gln Asp Pro Asp Val Val Met Ile Gly Glu Ile Arg Asp Leu Glu
                325                 330                 335

Thr Ala Glu Ile Ala Val Gln Ala Ser Leu Thr Gly His Leu Val Met
            340                 345                 350

Ser Thr Leu His Thr Asn Thr Ala Val Gly Ala Ile Thr Arg Leu Arg
                355                 360                 365

Asp Met Gly Ile Glu Pro Phe Leu Ile Ser Ser Leu Leu Gly Val
    370                 375                 380

Leu Ala Gln Arg Leu Val Arg Thr Leu Cys Asn Glu Cys Lys Glu Pro
385                 390                 395                 400

Tyr Glu Ala Asp Lys Glu Gln Lys Lys Leu Phe Gly Leu Lys Lys Lys
                405                 410                 415

Glu Ser Leu Thr Leu Tyr His Ala Lys Gly Cys Glu Cys Gly His
            420                 425                 430

Lys Gly Tyr Arg Gly Arg Thr Gly Ile His Glu Leu Leu Met Ile Asp
            435                 440                 445

Asp Ser Val Gln Glu Leu Ile His Ser Glu Ala Gly Glu Gln Ala Ile
    450                 455                 460

Asp Lys Ala Ile Arg Gly Thr Thr Pro Ser Ile Arg Asp Asp Gly Leu
465                 470                 475                 480

Ser Lys Val Leu Lys Gly Val Thr Ser Leu Glu Val Met Arg Val
                485                 490                 495

Thr Lys Glu Val
            500

<210> SEQ ID NO 47
<211> LENGTH: 1221
<212> TYPE: DNA
<213> ORGANISM: Vibrio splendidus

<400> SEQUENCE: 47

```
atggcggcat ttgaatacaa agcactggat gccaaaggca aaagtaaaaa aggctcaatt      60
gaagcagata atgctcgtca ggctcgccaa agaataaaag agcttggctt gatgccggtt     120
gagatgaccg aggctaaagc aaaaacagca aaaggtgctc agccatcgac cagctttaaa     180
cgcggcatca gtacgcctga tcttgcgctt attactcgtc aaatatccac gctcgttcaa     240
tctggtatgc cgctagaaga gtgtttgaaa gccgttgccg aacagtctga gaaacctcgt     300
attcgcacca tgctactcgc ggtgagatct aaggtgactg aaggttattc gttagcagac     360
agcttgtctg attatcccca tatcttcgat gagctattca gagccatggt tgctgctggt     420
gagaagtcag gcatctaga tgcggtattg gaacgattgg ctgactacgc agaaaaccgt     480
cagaagatgc gttctaagtt gctgcaagcg atgatctacc ccatcgtgct ggtggtgttt     540
gcggtgacga ttgtgtcgtt cctactggca acggtagtgc cgaagatcgt tgagcctatt     600
atccaaatgg acaagagct ccctcagtcg acacaatttt tattagcatc gagtgaattt     660
atccagaatt ggggcatcca attactggtg ttgaccattg gtgtgattgt gttggttaag     720
actgcgctga aaaagccggg cgttcgcatg agctgggatc gcaaattatt gagcatcccg     780
ctgataggca agatagcgaa agggatcaac acctctcgtt ttgcacgaac actttctatc     840
tgtacctcta gtgcgattcc tatccttgaa gggatgaagg tcgcggtaga gtgatgtcg      900
aatcatcacg tgaaacaaca agtattacag gcatcagata gcgttagaga aggggcaagc     960
ctgcgtaaag cgcttgatca aaccaaactc tttcccccga tgatgctgca tatgatcgcc    1020
agtggtgagc agagtggcca attggaacag atgctgacaa gagcggcaga taatcaggat    1080
caaagctttg aatcgaccgt taatatcgcg ttaggcattt ttaccccagc gcttattgcg    1140
ttgatggctg gcttagtgct gtttatcgtg atggcgacgc tgatgccaat gcttgaaatg    1200
aacaatttaa tgagtggtta a                                             1221
```

<210> SEQ ID NO 48
<211> LENGTH: 406
<212> TYPE: PRT
<213> ORGANISM: Vibrio splendidus

<400> SEQUENCE: 48

```
Met Ala Ala Phe Glu Tyr Lys Ala Leu Asp Ala Lys Gly Lys Ser Lys
  1               5                  10                  15

Lys Gly Ser Ile Glu Ala Asp Asn Ala Arg Gln Ala Arg Gln Arg Ile
             20                  25                  30

Lys Glu Leu Gly Leu Met Pro Val Glu Met Thr Glu Ala Lys Ala Lys
         35                  40                  45

Thr Ala Lys Gly Ala Gln Pro Ser Thr Ser Phe Lys Arg Gly Ile Ser
     50                  55                  60

Thr Pro Asp Leu Ala Leu Ile Thr Arg Gln Ile Ser Thr Leu Val Gln
 65                  70                  75                  80

Ser Gly Met Pro Leu Glu Glu Cys Leu Lys Ala Val Ala Glu Gln Ser
                 85                  90                  95

Glu Lys Pro Arg Ile Arg Thr Met Leu Leu Ala Val Arg Ser Lys Val
            100                 105                 110

Thr Glu Gly Tyr Ser Leu Ala Asp Ser Leu Ser Asp Tyr Pro His Ile
        115                 120                 125

Phe Asp Glu Leu Phe Arg Ala Met Val Ala Ala Gly Glu Lys Ser Gly
    130                 135                 140
```

His Leu Asp Ala Val Leu Glu Arg Leu Ala Asp Tyr Ala Glu Asn Arg
145                 150                 155                 160

Gln Lys Met Arg Ser Lys Leu Leu Gln Ala Met Ile Tyr Pro Ile Val
            165                 170                 175

Leu Val Val Phe Ala Val Thr Ile Val Ser Phe Leu Leu Ala Thr Val
            180                 185                 190

Val Pro Lys Ile Val Glu Pro Ile Ile Gln Met Gly Gln Glu Leu Pro
            195                 200                 205

Gln Ser Thr Gln Phe Leu Leu Ala Ser Ser Glu Phe Ile Gln Asn Trp
210                 215                 220

Gly Ile Gln Leu Leu Val Leu Thr Ile Gly Val Ile Val Leu Val Lys
225                 230                 235                 240

Thr Ala Leu Lys Lys Pro Gly Val Arg Met Ser Trp Asp Arg Lys Leu
                245                 250                 255

Leu Ser Ile Pro Leu Ile Gly Lys Ile Ala Lys Gly Ile Asn Thr Ser
            260                 265                 270

Arg Phe Ala Arg Thr Leu Ser Ile Cys Thr Ser Ser Ala Ile Pro Ile
            275                 280                 285

Leu Glu Gly Met Lys Val Ala Val Asp Val Met Ser Asn His His Val
290                 295                 300

Lys Gln Gln Val Leu Gln Ala Ser Asp Ser Val Arg Glu Gly Ala Ser
305                 310                 315                 320

Leu Arg Lys Ala Leu Asp Gln Thr Lys Leu Phe Pro Pro Met Met Leu
                325                 330                 335

His Met Ile Ala Ser Gly Glu Gln Ser Gly Gln Leu Glu Gln Met Leu
            340                 345                 350

Thr Arg Ala Ala Asp Asn Gln Asp Gln Ser Phe Glu Ser Thr Val Asn
            355                 360                 365

Ile Ala Leu Gly Ile Phe Thr Pro Ala Leu Ile Ala Leu Met Ala Gly
370                 375                 380

Leu Val Leu Phe Ile Val Met Ala Thr Leu Met Pro Met Leu Glu Met
385                 390                 395                 400

Asn Asn Leu Met Ser Gly
                405

<210> SEQ ID NO 49
<211> LENGTH: 444
<212> TYPE: DNA
<213> ORGANISM: Vibrio splendidus

<400> SEQUENCE: 49
atgaaaaata aaatgaaaaa acaatcaggc tttaccctat tagaagtcat ggttgttgtc      60
gttatccttg gtgttctagc aagttttgtt gtacctaacc tgttgggcaa caaagagaag     120
gcggatcaac aaaaagccat cactgatatt gtggcgctag agaacgcgct cgacatgtac     180
aaactggata cagcgtttta cccaacaacg gatcaaggcc tggacgggtt ggtgacaaag     240
ccaagcagtc cagagcctcg taactaccga gacggcggtt acatcaagcg tctacctaac     300
gacccatggg gcaatgagta ccaataccta agtcctggtg ataacggcac aattgatatc     360
ttcactcttg gcgcagatgg tcaagaaggt ggtgaaggta ttgctgcaga tatcggcaac     420
tggaacatgc aggacttcca ataa                                            444

<210> SEQ ID NO 50
<211> LENGTH: 146
<212> TYPE: PRT
<213> ORGANISM: Vibrio splendidus

<400> SEQUENCE: 50

| Lys | Asn | Lys | Met | Lys | Lys | Gln | Ser | Gly | Phe | Thr | Leu | Leu | Glu | Val | Met |
|---|---|---|---|---|---|---|---|---|---|---|---|---|---|---|---|
| 1 | | | | 5 | | | | | 10 | | | | | 15 | |

| Val | Val | Val | Val | Ile | Leu | Gly | Val | Leu | Ala | Ser | Phe | Val | Pro | Asn |
|---|---|---|---|---|---|---|---|---|---|---|---|---|---|---|
| | | | 20 | | | | | 25 | | | | | 30 | |

| Leu | Leu | Gly | Asn | Lys | Glu | Lys | Ala | Asp | Gln | Gln | Lys | Ala | Ile | Thr | Asp |
|---|---|---|---|---|---|---|---|---|---|---|---|---|---|---|---|
| | | | 35 | | | | | 40 | | | | | 45 | | |

| Ile | Val | Ala | Leu | Glu | Asn | Ala | Leu | Asp | Met | Tyr | Lys | Leu | Asp | Asn | Ser |
|---|---|---|---|---|---|---|---|---|---|---|---|---|---|---|---|
| | 50 | | | | | 55 | | | | | 60 | | | | |

| Val | Tyr | Pro | Thr | Thr | Asp | Gln | Gly | Leu | Asp | Gly | Leu | Val | Thr | Lys | Pro |
|---|---|---|---|---|---|---|---|---|---|---|---|---|---|---|---|
| 65 | | | | | 70 | | | | | 75 | | | | | 80 |

| Ser | Ser | Pro | Glu | Pro | Arg | Asn | Tyr | Arg | Asp | Gly | Gly | Tyr | Ile | Lys | Arg |
|---|---|---|---|---|---|---|---|---|---|---|---|---|---|---|---|
| | | | | 85 | | | | | 90 | | | | | 95 | |

| Leu | Pro | Asn | Asp | Pro | Trp | Gly | Asn | Glu | Tyr | Gln | Tyr | Leu | Ser | Pro | Gly |
|---|---|---|---|---|---|---|---|---|---|---|---|---|---|---|---|
| | | | 100 | | | | | 105 | | | | | 110 | | |

| Asp | Asn | Gly | Thr | Ile | Asp | Ile | Phe | Thr | Leu | Gly | Ala | Asp | Gly | Gln | Glu |
|---|---|---|---|---|---|---|---|---|---|---|---|---|---|---|---|
| | | | 115 | | | | | 120 | | | | | 125 | | |

| Gly | Gly | Glu | Gly | Ile | Ala | Ala | Asp | Ile | Gly | Asn | Trp | Asn | Met | Gln | Asp |
|---|---|---|---|---|---|---|---|---|---|---|---|---|---|---|---|
| | 130 | | | | | 135 | | | | | 140 | | | | |

| Phe | Gln |
|---|---|
| 145 | |

<210> SEQ ID NO 51
<211> LENGTH: 594
<212> TYPE: DNA
<213> ORGANISM: Vibrio splendidus

<400> SEQUENCE: 51

```
gtgaaaacta agcaaacaca gccaggtttc accttgattg agattctttt ggtgttggta      60
ttactgtcag tatcggcggt cgcggtgatc tcgaccatcc ctaccaatag caaagatgtt     120
gctaaaaaat acgctcaaag cttttatcag cgaattcagc tactcaatga agaggctatt     180
ttgagtggct tagattttgg tgttcgtgtt gatgaaaaaa aatcgactta cgttctgatg     240
actttgaagt ctgatggctg gcaagaaacg gagttcgaaa agatcccttc ttcaactgaa     300
ttaccggaag aactggcact gtcgctgaca ttaggtggtg gcgcgtggga agacgatgat     360
cggttgttca atccaggaag cttatttgat gaagatatgt ttgctgatct tgaagaggaa     420
aagaagccga aaccaccaca gatctacatc ttgtcgagtg ctgaaatgac gccatttgta     480
ctgtcgtttt acccaaatac cggtgacaca atacaagatg tttggcgcat tcgagtattg     540
gataatggtg tgattcgatt actcgagccg ggagaagaag atgaagaaga ataa           594
```

<210> SEQ ID NO 52
<211> LENGTH: 197
<212> TYPE: PRT
<213> ORGANISM: Vibrio splendidus

<400> SEQUENCE: 52

| Met | Lys | Thr | Lys | Gln | Thr | Gln | Pro | Gly | Phe | Thr | Leu | Ile | Glu | Ile | Leu |
|---|---|---|---|---|---|---|---|---|---|---|---|---|---|---|---|
| 1 | | | | 5 | | | | | 10 | | | | | 15 | |

| Leu | Val | Leu | Val | Leu | Leu | Ser | Val | Ser | Ala | Val | Ala | Val | Ile | Ser | Thr |
|---|---|---|---|---|---|---|---|---|---|---|---|---|---|---|---|
| | | | 20 | | | | | 25 | | | | | 30 | | |

| Ile | Pro | Thr | Asn | Ser | Lys | Asp | Val | Ala | Lys | Lys | Tyr | Ala | Gln | Ser | Phe |
|---|---|---|---|---|---|---|---|---|---|---|---|---|---|---|---|
| | | | 35 | | | | | 40 | | | | | 45 | | |

| Tyr | Gln | Arg | Ile | Gln | Leu | Leu | Asn | Glu | Glu | Ala | Ile | Leu | Ser | Gly | Leu |
|---|---|---|---|---|---|---|---|---|---|---|---|---|---|---|---|
| | 50 | | | | | 55 | | | | | 60 | | | | |

```
Asp Phe Gly Val Arg Val Asp Glu Lys Lys Ser Thr Tyr Val Leu Met
65                  70                  75                  80

Thr Leu Lys Ser Asp Gly Trp Gln Glu Thr Glu Phe Glu Lys Ile Pro
            85                  90                  95

Ser Ser Thr Glu Leu Pro Glu Glu Leu Ala Leu Ser Leu Thr Leu Gly
        100                 105                 110

Gly Gly Ala Trp Glu Asp Asp Arg Leu Phe Asn Pro Gly Ser Leu
        115                 120                 125

Phe Asp Glu Asp Met Phe Ala Asp Leu Glu Glu Lys Lys Pro Lys
130                 135                 140

Pro Pro Gln Ile Tyr Ile Leu Ser Ser Ala Glu Met Thr Pro Phe Val
145                 150                 155                 160

Leu Ser Phe Tyr Pro Asn Thr Gly Asp Thr Ile Gln Asp Val Trp Arg
                165                 170                 175

Ile Arg Val Leu Asp Asn Gly Val Ile Arg Leu Leu Glu Pro Gly Glu
                180                 185                 190

Glu Asp Glu Glu Glu
            195
```

<210> SEQ ID NO 53
<211> LENGTH: 396
<212> TYPE: DNA
<213> ORGANISM: Vibrio splendidus

<400> SEQUENCE: 53

```
atgaagaaga ataaccgttc tccttatcgt tctcgcggta tgcctcttgg ttctcgagga      60
atgactctgc ttgaagtatt ggttgcgctg gctatcttcg ctacggcggc gatcagtgtg     120
attcgtgctg tcacccagca catcaatacg ctcagttatc tcgaagaaaa aaccttcgcg     180
gcgatggtcg ttgataatca aatggcccta gtcatgctac atcctgagat gcttaaaaaa     240
gcgcagggca cgcaagagtt agcgggaaga gaatggttct ggaaggtgac tcccatcgat     300
accagcgata atttattaaa ggcgtttgat gtgagtgcgg caaccagtaa gaaagcgtct     360
ccagtcgtta cggtgcgcag ttatgtggtt aattaa                              396
```

<210> SEQ ID NO 54
<211> LENGTH: 131
<212> TYPE: PRT
<213> ORGANISM: Vibrio splendidus

<400> SEQUENCE: 54

```
Met Lys Lys Asn Asn Arg Ser Pro Tyr Arg Ser Arg Gly Met Pro Leu
1               5                   10                  15

Gly Ser Arg Gly Met Thr Leu Leu Glu Val Leu Val Ala Leu Ala Ile
            20                  25                  30

Phe Ala Thr Ala Ala Ile Ser Val Ile Arg Ala Val Thr Gln His Ile
        35                  40                  45

Asn Thr Leu Ser Tyr Leu Glu Glu Lys Thr Phe Ala Ala Met Val Val
    50                  55                  60

Asp Asn Gln Met Ala Leu Val Met Leu His Pro Glu Met Leu Lys Lys
65                  70                  75                  80

Ala Gln Gly Thr Gln Glu Leu Ala Gly Arg Glu Trp Phe Trp Lys Val
                85                  90                  95

Thr Pro Ile Asp Thr Ser Asp Asn Leu Leu Lys Ala Phe Asp Val Ser
            100                 105                 110

Ala Ala Thr Ser Lys Lys Ala Ser Pro Val Val Thr Val Arg Ser Tyr
```

Val Val Asn
    130

<210> SEQ ID NO 55
<211> LENGTH: 804
<212> TYPE: DNA
<213> ORGANISM: Vibrio slpendidus

<400> SEQUENCE: 55

```
atgtggttaa ttaagagaat gtggtcaatt aagagcatgt tattaattaa gaacagctcg      60
ctaactaaga gcgtgtcgct aactaagagc atgtcggaaa ataagcgtac gccgcgtaaa     120
caaggtctac cttcaaaagg gagaggcttt accttaattg aagtcttggt ctcgattgct     180
atctttgcca cgctaagtat ggcggcttat caggtggtta atcaggtgca gcgaagcaac     240
gagatctcta ttgagcgcag tgctcgtttg aaccaactgc aacgcagttt agtcatttta     300
gataatgatt ttcgccagat ggcggtgcga aaatttcgta ccaacggtga agaagcatca     360
tctaagctga tcttaatgaa agagtattta ttggactccg acagtgtagg catcatgttt     420
actcgtctag gttggcacaa cccacaacag cagtttcctc gcggtgaagt cacgaaggtt     480
ggctaccgta ttaagaaga  aacacttgag cgtgtatggt ggcgttatcc cgatacacct     540
tcaggccaag aagtgtgat  taccc ctctg cttgatgatg ttgaaagctt ggaattcgag     600
ttttatgacg aagccgctg  ggggaaagag tggcaaaccg ataaatcact gccgaaagcg     660
gtgaggctta agctgacact gaaagactat ggtgagatag agcgtgttta tctcactccc     720
ggtggcaccc tagatcaggc cgatgattct tcaaacagtg actcttcagg cagtagtgag     780
gggaataatg actcatcgaa ctaa                                             804
```

<210> SEQ ID NO 56
<211> LENGTH: 267
<212> TYPE: PRT
<213> ORGANISM: Vibrio splendidus

<400> SEQUENCE: 56

Met Trp Leu Ile Lys Arg Met Trp Ser Ile Lys Ser Met Leu Leu Ile
1               5                   10                  15

Lys Asn Ser Ser Leu Thr Lys Ser Val Ser Leu Thr Lys Ser Met Ser
            20                  25                  30

Glu Asn Lys Arg Thr Pro Arg Lys Gln Gly Leu Pro Ser Lys Gly Arg
        35                  40                  45

Gly Phe Thr Leu Ile Glu Val Leu Val Ser Ile Ala Ile Phe Ala Thr
    50                  55                  60

Leu Ser Met Ala Ala Tyr Gln Val Val Asn Gln Val Gln Arg Ser Asn
65                  70                  75                  80

Glu Ile Ser Ile Glu Arg Ser Ala Arg Leu Asn Gln Leu Gln Arg Ser
                85                  90                  95

Leu Val Ile Leu Asp Asn Asp Phe Arg Gln Met Ala Val Arg Lys Phe
            100                 105                 110

Arg Thr Asn Gly Glu Glu Ala Ser Ser Lys Leu Ile Leu Met Lys Glu
        115                 120                 125

Tyr Leu Leu Asp Ser Asp Ser Val Gly Ile Met Phe Thr Arg Leu Gly
    130                 135                 140

Trp His Asn Pro Gln Gln Gln Phe Pro Arg Gly Glu Val Thr Lys Val
145                 150                 155                 160

Gly Tyr Arg Ile Lys Glu Glu Thr Leu Glu Arg Val Trp Trp Arg Tyr

```
                 165                 170                 175
Pro Asp Thr Pro Ser Gly Gln Glu Gly Val Ile Thr Pro Leu Leu Asp
        180                 185                 190

Asp Val Glu Ser Leu Glu Phe Glu Phe Tyr Asp Gly Ser Arg Trp Gly
            195                 200                 205

Lys Glu Trp Gln Thr Asp Lys Ser Leu Pro Lys Ala Val Arg Leu Lys
        210                 215                 220

Leu Thr Leu Lys Asp Tyr Gly Glu Ile Glu Arg Val Tyr Leu Thr Pro
225                 230                 235                 240

Gly Gly Thr Leu Asp Gln Ala Asp Asp Ser Ser Asn Ser Asp Ser Ser
                245                 250                 255

Gly Ser Ser Glu Gly Asn Asn Asp Ser Ser Asn
            260                 265

<210> SEQ ID NO 57
<211> LENGTH: 1050
<212> TYPE: DNA
<213> ORGANISM: Vibrio splendidus

<400> SEQUENCE: 57
atgactcatc gaactaataa gcgtttagcg acaaggtcag ccttgggacg taaacaacgt      60
ggtgtcgcgc tgatcattat tttgatgcta ttggcgatca tggcaaccat tgctggcagc     120
atgtccgagc gtttgtttac gcaattcaag cgcgttggta ccaactgaa  ttaccaacag     180 gcttactggt acagcattgg tgtggaagcg cttgtgcaaa acggtattag caaagttac     240 aaagacagtg ataccgtgaa cctaagccaa ccatgggcgt tagaagagca ggtataccca    300
ttggattatg ccaagttaa  gggccgcatt gttgatgctc aggcatgttt taatcttaat    360
gccttagccg gagtggcgac cacttcaagt aaccagactc cttatttaat cacggtttgg    420
caaaccttat tggaaaaacca agacgttgag ccttatcagg ctgaggttat cgcaaattca   480
acgtgggaat ttgttgatgc ggatacacga accacctctt cgtctggtgt agaagacagc    540
acgtatgaag cgatgaagcc ctcttatttg gcggcgaatg gcttaatggc cgatgaatcc    600
gagctacgag cggtttatca agtcactggt gaagtgatga ataaggttcg ccccttttgtt   660 tgcgctctgc caaccgatga tttccgcttg aatgtgaata ctctcacgga aaaacaagca    720
ccgttattgg aagcgatgtt tgcgccaggc ttaagtgaat cggatgccaa acagctgata    780
gataaacgcc catttgatgg ctgggatacg gtagatgctt tcatggctga acctgccatt    840
gttggtgtaa gtgccgaagt cagcaagaaa gcgaaagcat atttaactgt agatagcgcc    900
tattttgagc tagatgcaga ggtattagtt gagcagtcac gtgtacgtat acggacgctt    960
ttctatagta gtaatcgaga aacagtgacg gtagtacgcc gtcgttttgg aggaatcagt   1020
gagcgagttt ctgaccgttc gactgagtag                                     1050

<210> SEQ ID NO 58
<211> LENGTH: 349
<212> TYPE: PRT
<213> ORGANISM: Vibrio splendidus

<400> SEQUENCE: 58

Met Thr His Arg Thr Asn Lys Arg Leu Ala Thr Arg Ser Ala Leu Gly
1               5                   10                  15

Arg Lys Gln Arg Gly Val Ala Leu Ile Ile Ile Leu Met Leu Leu Ala
            20                  25                  30

Ile Met Ala Thr Ile Ala Gly Ser Met Ser Glu Arg Leu Phe Thr Gln
        35                  40                  45
```

Phe Lys Arg Val Gly Asn Gln Leu Asn Tyr Gln Ala Tyr Trp Tyr
 50                  55                  60

Ser Ile Gly Val Glu Ala Leu Val Gln Asn Gly Ile Arg Gln Ser Tyr
 65                  70                  75                  80

Lys Asp Ser Asp Thr Val Asn Leu Ser Gln Pro Trp Ala Leu Glu Glu
                 85                  90                  95

Gln Val Tyr Pro Leu Asp Tyr Gly Gln Val Lys Gly Arg Ile Val Asp
            100                 105                 110

Ala Gln Ala Cys Phe Asn Leu Asn Ala Leu Ala Gly Val Ala Thr Thr
        115                 120                 125

Ser Ser Asn Gln Thr Pro Tyr Leu Ile Thr Val Trp Gln Thr Leu Leu
130                 135                 140

Glu Asn Gln Asp Val Glu Pro Tyr Gln Ala Val Ile Ala Asn Ser
145                 150                 155                 160

Thr Trp Glu Phe Val Asp Ala Asp Thr Arg Thr Thr Ser Ser Ser Gly
                165                 170                 175

Val Glu Asp Ser Thr Tyr Glu Ala Met Lys Pro Ser Tyr Leu Ala Ala
            180                 185                 190

Asn Gly Leu Met Ala Asp Glu Ser Glu Leu Arg Ala Val Tyr Gln Val
        195                 200                 205

Thr Gly Glu Val Met Asn Lys Val Arg Pro Phe Val Cys Ala Leu Pro
210                 215                 220

Thr Asp Asp Phe Arg Leu Asn Val Asn Thr Leu Thr Glu Lys Gln Ala
225                 230                 235                 240

Pro Leu Leu Glu Ala Met Phe Ala Pro Gly Leu Ser Glu Ser Asp Ala
                245                 250                 255

Lys Gln Leu Ile Asp Lys Arg Pro Phe Asp Gly Trp Asp Thr Val Asp
            260                 265                 270

Ala Phe Met Ala Glu Pro Ala Ile Val Gly Val Ser Ala Glu Val Ser
        275                 280                 285

Lys Lys Ala Lys Ala Tyr Leu Thr Val Asp Ser Ala Tyr Phe Glu Leu
290                 295                 300

Asp Ala Glu Val Leu Val Glu Gln Ser Arg Val Arg Ile Arg Thr Leu
305                 310                 315                 320

Phe Tyr Ser Ser Asn Arg Glu Thr Val Thr Val Arg Arg Phe
                325                 330                 335

Gly Gly Ile Ser Glu Arg Val Ser Asp Arg Ser Thr Glu
            340                 345

<210> SEQ ID NO 59
<211> LENGTH: 1248
<212> TYPE: DNA
<213> ORGANISM: Vibrio splendidus

<400> SEQUENCE: 59
gtgagcgagt tctgaccgt tcgactgagt agcgaaccac aaagccctgt gcagtggtta      60
gtttggtcga caagccaaca agaagtgata gcaagcggtg aactgtctag ctgggaacag    120
cttgacgagt taacgcctta cgctgaaaag cgcagctgta tcgctttatt gccgggaagt    180
gaatgcttaa ttaagcgtgt tgagatcccg aaaggtgctg ctcgccagtt tgattctatg    240
ctgccgttct tattagaaga cgaagtcgca caagatatcg aagacttaca cctgactatt    300
ttagataaag atgccactca cgctaccgtg tgtggtgtgg atcgtgaatg gctaaaacaa    360
gctttagacc tgtttcgcga agccaatata atcttccgta aggtgctacc agatacacta    420

-continued

```
gccgtgcctt ttgaagaaca aggcatcagt gcgttgcaga tagatcagca ttggttattg      480
cgccaaggtc actctcaacg tcaaggtcac tatcaagccg tatcgatcag tgaagcatgg      540
ttaccgatgt ttttgcaaag tgattgggtt gtcgctggtg aggaagagca agcgacgact      600
atcttcagct ataccgcgat gccgagcgac gacgttcaac agcaaagcgg cctcgagtgg      660
caagcaaagc ctgcggaatt ggtgatgtct ttattgagtc agcaagcgat cacaagcggc      720
gtaaatttac tgactggcac ctttaaaacc aaatcttcat tcagtaaata ttggcgtgtt      780
tggcagaaag tggcgattgc tgcttgtttg ctggtggccg tgattgtgac tcagcaagtg      840
ttgaaggttc agcaatacga agcgcaagca caagcctacc gcatggagag tgagcgtatc      900
tttagagctg tgctgcctgg caaacaacgc attccgaccg tgagttacct caagcgtcag      960
atgaatgatg aagctaagaa atacggtggt tcaggcgaag tgattctttt acttggttgg     1020
ttagctttgc tgcctgaaac cttagggcaa gtgaagacga tcgaagttga aagcattcgc     1080
tacgatggca accgttctga ggttcgactg caggctaaaa gttctgactt ccaacacttt     1140
gagaccgcaa gggtgaagct cgaagagaag tttgtcgttg agcaagggcc attgaaccgt     1200
aatggcgatg ccgtatttgg cagttttact cttaaacccc atcaataa                  1248
```

<210> SEQ ID NO 60
<211> LENGTH: 415
<212> TYPE: PRT
<213> ORGANISM: Vibrio splendidus

<400> SEQUENCE: 60

```
Met Ser Glu Phe Leu Thr Val Arg Leu Ser Ser Glu Pro Gln Ser Pro
1               5                   10                  15

Val Gln Trp Leu Val Trp Ser Thr Ser Gln Gln Glu Val Ile Ala Ser
            20                  25                  30

Gly Glu Leu Ser Ser Trp Glu Gln Leu Asp Glu Leu Thr Pro Tyr Ala
        35                  40                  45

Glu Lys Arg Ser Cys Ile Ala Leu Leu Pro Gly Ser Glu Cys Leu Ile
    50                  55                  60

Lys Arg Val Glu Ile Pro Lys Gly Ala Ala Arg Gln Phe Asp Ser Met
65                  70                  75                  80

Leu Pro Phe Leu Leu Glu Asp Glu Val Ala Gln Asp Ile Glu Asp Leu
                85                  90                  95

His Leu Thr Ile Leu Asp Lys Asp Ala Thr His Ala Thr Val Cys Gly
            100                 105                 110

Val Asp Arg Glu Trp Leu Lys Gln Ala Leu Asp Leu Phe Arg Glu Ala
        115                 120                 125

Asn Ile Ile Phe Arg Lys Val Leu Pro Asp Thr Leu Ala Val Pro Phe
    130                 135                 140

Glu Glu Gln Gly Ile Ser Ala Leu Gln Ile Asp Gln His Trp Leu Leu
145                 150                 155                 160

Arg Gln Gly His Ser Gln Arg Gln Gly His Tyr Gln Ala Val Ser Ile
                165                 170                 175

Ser Glu Ala Trp Leu Pro Met Phe Leu Gln Ser Asp Trp Val Ala
            180                 185                 190

Gly Glu Glu Gln Ala Thr Thr Ile Phe Ser Tyr Thr Ala Met Pro
        195                 200                 205

Ser Asp Asp Val Gln Gln Gln Ser Gly Leu Glu Trp Gln Ala Lys Pro
    210                 215                 220

Ala Glu Leu Val Met Ser Leu Leu Ser Gln Gln Ala Ile Thr Ser Gly
225                 230                 235                 240
```

Val Asn Leu Leu Thr Gly Thr Phe Lys Thr Lys Ser Ser Phe Ser Lys
            245                 250                 255

Tyr Trp Arg Val Trp Gln Lys Val Ala Ile Ala Ala Cys Leu Leu Val
        260                 265                 270

Ala Val Ile Val Thr Gln Gln Val Leu Lys Val Gln Gln Tyr Glu Ala
            275                 280                 285

Gln Ala Gln Ala Tyr Arg Met Glu Ser Glu Arg Ile Phe Arg Ala Val
290                 295                 300

Leu Pro Gly Lys Gln Arg Ile Pro Thr Val Ser Tyr Leu Lys Arg Gln
305                 310                 315                 320

Met Asn Asp Glu Ala Lys Lys Tyr Gly Gly Ser Gly Glu Gly Asp Ser
                325                 330                 335

Leu Leu Gly Trp Leu Ala Leu Leu Pro Glu Thr Leu Gly Gln Val Lys
            340                 345                 350

Thr Ile Glu Val Glu Ser Ile Arg Tyr Asp Gly Asn Arg Ser Glu Val
        355                 360                 365

Arg Leu Gln Ala Lys Ser Ser Asp Phe Gln His Phe Glu Thr Ala Arg
    370                 375                 380

Val Lys Leu Glu Glu Lys Phe Val Val Glu Gln Gly Pro Leu Asn Arg
385                 390                 395                 400

Asn Gly Asp Ala Val Phe Gly Ser Phe Thr Leu Lys Pro His Gln
                405                 410                 415

<210> SEQ ID NO 61
<211> LENGTH: 489
<212> TYPE: DNA
<213> ORGANISM: Vibrio splendidus

<400> SEQUENCE: 61
atgagaaata tgattgaacc actccaagcg tggtgggctt caataagtca gcgggaacaa      60
cgattagtca ttggttgttc tattttattg atactgggcg ttgtctattg gggattaata     120
caaccactta gccaacgagc cgagcttgca caaagccgca ttcaaagtga agcaacttt      180 ctggcttggg taacggacaa agcgaatcaa gtggttgaac tacgaggcag tggtggcatc     240
agtgccagtc agcctttgaa ccaatctgtg cctgcttcta tgcgccgttt taacatcgag     300
ctgatacgcg tgcaaccacg cggtgagatg ctgcaagttt ggattaagcc tgtgccattt     360
aataagttcg ttgactggct gacatacctg aaagaaaagc agggtgttga ggttgagttt     420
atggatattg atcgctctga tagccctggg gttattgaga tcaaccgact acagtttaaa     480
cgaggttaa                                                              489

<210> SEQ ID NO 62
<211> LENGTH: 162
<212> TYPE: PRT
<213> ORGANISM: Vibrio splendidus

<400> SEQUENCE: 62

Met Arg Asn Met Ile Glu Pro Leu Gln Ala Trp Trp Ala Ser Ile Ser
1               5                   10                  15

Gln Arg Glu Gln Arg Leu Val Ile Gly Cys Ser Ile Leu Leu Ile Leu
            20                  25                  30

Gly Val Val Tyr Trp Gly Leu Ile Gln Pro Leu Ser Gln Arg Ala Glu
        35                  40                  45

Leu Ala Gln Ser Arg Ile Gln Ser Glu Lys Gln Leu Leu Ala Trp Val
    50                  55                  60

```
Thr Asp Lys Ala Asn Gln Val Val Glu Leu Arg Gly Ser Gly Gly Ile
 65                  70                  75                  80

Ser Ala Ser Gln Pro Leu Asn Gln Ser Val Pro Ala Ser Met Arg Arg
                 85                  90                  95

Phe Asn Ile Glu Leu Ile Arg Val Gln Pro Arg Gly Glu Met Leu Gln
            100                 105                 110

Val Trp Ile Lys Pro Val Pro Phe Asn Lys Phe Val Asp Trp Leu Thr
        115                 120                 125

Tyr Leu Lys Glu Lys Gln Gly Val Glu Val Glu Phe Met Asp Ile Asp
130                 135                 140

Arg Ser Asp Ser Pro Gly Val Ile Glu Ile Asn Arg Leu Gln Phe Lys
145                 150                 155                 160

Arg Gly

<210> SEQ ID NO 63
<211> LENGTH: 780
<212> TYPE: DNA
<213> ORGANISM: Vibrio splendidus

<400> SEQUENCE: 63
gtgaaacgcg gtttatcttt caaatacggc ctgttattca gcgtcatttt tatcgttttt      60
ttctcggtaa gcttgttgct gcatttgcct gccgcttttg ctctcaagca tgcacccgtc     120
gtgcgtggtt taagcattga aggcgttgag ggcaccgttt ggcaaggtcg cgctaacaat     180
atcgcgtggc agcgtgtcaa ttacggctca gtgcagtggg acttccagtt ctctaaacta     240
ttccaagcca aagcagaact tgcggttcgc tttggccgca acagcgacat gaacttatca     300
ggtaaaggac gtgtcggata tagcatgagt ggtgcttacg cggaaaactt agtggcatca     360
atgccagcca gcaacgtgat gaaatatgcg ccagctatcc cagtgcctgt gtctattgca     420
gggcaagttg aactgacgat caaacatgcg gttcatgctc aaccttggtg tcaatcaggt     480
gaaggtacgc ttgcttggtc tggtgcagca gtcgactcgc cagtgggttc gttagacctt     540
ggccctgtga ttgcggacat aacgtgtgaa gacagcacaa ttgcagccaa aggcactcag     600
aagagcgatc aggtagacag cgagttctca gcgagcgtaa cacctaacca acgctacacc     660
tcggcagcat ggtttaagcc aggcgctgaa ttcccgccag caatgcagag tcagcttaag     720
tggttgggca atcctgatag ccaaggtaaa taccaattta cttatcaagg ccgcttttag     780

<210> SEQ ID NO 64
<211> LENGTH: 259
<212> TYPE: PRT
<213> ORGANISM: Vibrio splendidus

<400> SEQUENCE: 64

Met Lys Arg Gly Leu Ser Phe Lys Tyr Gly Leu Leu Phe Ser Val Ile
 1               5                  10                  15

Phe Ile Val Phe Phe Ser Val Ser Leu Leu His Leu Pro Ala Ala
             20                  25                  30

Phe Ala Leu Lys His Ala Pro Val Val Arg Gly Leu Ser Ile Glu Gly
            35                  40                  45

Val Glu Gly Thr Val Trp Gln Gly Arg Ala Asn Asn Ile Ala Trp Gln
        50                  55                  60

Arg Val Asn Tyr Gly Ser Val Gln Trp Asp Phe Gln Phe Ser Lys Leu
 65                 70                  75                  80

Phe Gln Ala Lys Ala Glu Leu Ala Val Arg Phe Gly Arg Asn Ser Asp
                85                  90                  95
```

```
Met Asn Leu Ser Gly Lys Gly Arg Val Gly Tyr Ser Met Ser Gly Ala
            100                 105                 110

Tyr Ala Glu Asn Leu Val Ala Ser Met Pro Ala Ser Asn Val Met Lys
            115                 120                 125

Tyr Ala Pro Ala Ile Pro Val Pro Val Ser Ile Ala Gly Gln Val Glu
        130                 135                 140

Leu Thr Ile Lys His Ala Val His Ala Gln Pro Trp Cys Gln Ser Gly
145                 150                 155                 160

Glu Gly Thr Leu Ala Trp Ser Gly Ala Ala Val Asp Ser Pro Val Gly
                165                 170                 175

Ser Leu Asp Leu Gly Pro Val Ile Ala Asp Ile Thr Cys Glu Asp Ser
            180                 185                 190

Thr Ile Ala Ala Lys Gly Thr Gln Lys Ser Asp Gln Val Asp Ser Glu
            195                 200                 205

Phe Ser Ala Ser Val Thr Pro Asn Gln Arg Tyr Thr Ser Ala Ala Trp
        210                 215                 220

Phe Lys Pro Gly Ala Glu Phe Pro Pro Ala Met Gln Ser Gln Leu Lys
225                 230                 235                 240

Trp Leu Gly Asn Pro Asp Ser Gln Gly Lys Tyr Gln Phe Thr Tyr Gln
                245                 250                 255

Gly Arg Phe

<210> SEQ ID NO 65
<211> LENGTH: 10967
<212> TYPE: DNA
<213> ORGANISM: Erwinia carotovora subsp. Atroseptica SCRI1043

<400> SEQUENCE: 65
aagttgcagg atatgacgaa agcgtggccg acgactatac cggccacgct ttgaggaatt      60
acaggaaatc agctcgctta ggcgagaaag catcgatcag tacgctaccg tcttccagcg     120
aaaccacgcc gtgcatctcg tgtttcaccg ccagataggc gtcgcccgtt ttcagggtgc     180 gttttttcacc ttcgatcacg acttcaaagc tgccagcggc aacataagca atctggtcgt    240
gaatctcatg gaagtgcggc gtaccaatcg cacctttatc aaagtgcacg taaaccatca     300
tcagctcatc gctccatgtc atgatttac gtttaatgcc accgcccagc tcttcccatg      360
gcgtttcatc atcaataaag tatcttctca tcatctctct cctctaacgc tcttttttgcc   420 cataccttct attgcgtcaa caaaccgtgt acgacaacga atgcatggct atggattgcg     480 acatttttagc cacatcagta ccagaagaaa cataaaataa gcaaaaccat gacggccctc    540
aagaaataaa taaaacatta tttcattttt attgaattcg catctcatcc aaactatcat     600
cccgcataac aagaaagaac cgggcatgtt gaggaacagg tgacgttgtc actgccacgc     660
aacatcatct gtttcgcccg gcgctttcgc caggaacgat tcctcttctt ggaacggcgc     720
ctgatttttg tttttctctg aaagagaggc taagaaatgc aagttcgtca agcattcac      780 agcgatcacg cgaagcagct agatacagca ggcctgcgtc gtgaattcct gatcgaacag     840 atttttctg ccgatgccta cactatgacc tatagccaca tcgaccgaat catcgtcggt     900
ggcatcatgc ccgtacacag cgccgtaacg attggcggtg aagtgggtaa caactcggc      960 gttagctatt tccttgagcg tcgcgaactc ggagccatca acattggcgg cgcgggtacc    1020
gttactgtcg atggcgagcg ctatgacgtg gtaatgaag aagcaattta tgttggcatg     1080
ggcgtgaaag acgtgcagtt taccagcact gatgccacta cccggccaa gttctactac      1140 aacagcgcgc ctgcacatac gacatatcct acccgcaaga ttacccaagc tgacgcttca   1200
```

```
ccacaaaccg tgggagaaga tgcaagctgt aatcgtcgca caattaacaa atacattgtt    1260
cccgatgtat tgccaacctg ccagctcacc atgggattaa ccaagttagc tgaaggcagc    1320
ctgtggaaca ccatgccttg tcatacgcat gagcgccgga tggaagtcta tttctatttt    1380
gatatggatg aggaaacggc cgttttccac atgatgggc aaccgcagga aacccgtcac    1440
atagttatta aaaacgagca ggcggtgatt tcaccgagct ggtcgattca ttccggtgtt    1500
ggcaccagac gctacacctt tatctggggc atggttggcg agaatcaagt tttcggtgac    1560
atggatcacg tcaaggttag cgagttacgt taatcgcttt caaccggaat taccggtgtt    1620
ccctacagta acagctaacg actaagtatt gtcgcttata gagagattat tgatatgatt    1680
ttaaattctt ttgatttgca aggtaaagtt gctcttatca cggggttgtga tacgggttta    1740 ggtcagggta tggctatcgg tctggcacaa gctggctgtg atatcgttgg cgtcaacatc    1800
gttgaaccaa aagataccat cgaaaaagtt accgcactgg gacgccgttt cctcagcctg    1860
accgctgaca tgagcaacgt agcgggtcat gccgagctgg tagagaaagc cgttgctgaa    1920
tttggtcacg ttgacattct ggtcaacaac gccggtatca tccgtcgtga agatgctatc    1980
gagttcagcg agaaaaactg ggacgacgtc atgaatctga acattaagag cgttttcttt    2040
atgtctcagg ctgttgcacg ccagtttatc aaacaaggta aaggcggcaa gatcatcaac    2100
atcgcctcta tgctgtcctt ccaaggcggt atccgcgtgc cttcttacac tgcgtcaaaa    2160
agcgccgtta tgggtgtaac ccgtctgctg gctaacgagt gggcaaaaca cggcatcaac    2220
gttaacgcca ttgctccagg gtacatggca accaacaata ctcagcaact gcgcgccgat    2280
gaagaccgca gcaaagagat tctggaccgt atcccggctg gccgttgggg tttaccacag    2340
gatctgatgg gccatcgt cttcctggca tccagcgcat ctgattacat caatggctac    2400
acgattgccg ttgatggtgg ctggctggct cgctaagtgt aatttttctt agcggcattt    2460
cgctaatcca cgataaaaag cacaatttag gttgtgcttt ttatttattt ttcaagttgt    2520
tatttcgttt tttataattc tcttttctgc ctaaatcctt tcttaaaaaa aaatcaaaac    2580
aacgttccga ctttgatcac actttcgata ttgcgtgcat gacgacaagg ttaatagcgc    2640
aatataatca atcaaaacag tgtttctatt tataaggaac tgttcacgca gttccataag    2700
aaggtactcc atgagtattt ttgaaaactt atacaccagc aggaaatcgc agctcgacga    2760
atgggttgct gcacttgata gccacatatc ctgcgttcag gaaaaaggcc gcagccaaag    2820
ccaaccgacg ctattactgg ccgatggttt tgatgtggaa aattatgcgc ctgcggtatg    2880
gcaatttccg gatgggcaca gcgcgcctat ttctaatttt gccagccagc agaattggct    2940
aagaacgctg tgcgccatga gcgtcgttac gggtaatgat agttaccaac agcacgctat    3000
cgcacaaagc gaatatttcc tggatcattt cgttgatgat aatagcggcc tgttctactg    3060
gggcggccat cgctttatta atctggatac gctggaaggc gaagggccag aatccaaagc    3120
tcaggtgcat gaattaaagc accacctgcc ctattacgcg ctgttacatc gtgttaacgc    3180
ggaaaagacg ctgaacttct ttcaggggtt ctggaacgca cacgttgaag attggaattc    3240
actggatctg ggtcgtcatg gcgattacag caaaaaacgc gatcctgatg ttttcctgca    3300
taaccgtcat gatgtcgtcg atccggcaca gtggcccgtt ctgccattaa cgaaaggcct    3360
gacgtttgtt aatgccggca cggatctgat ttacgcgca ttcaaatatg cagaatatac    3420
gggcgatagc catgccgcgg catggggtaa acacctttat cgccaatacg ttctggctcg    3480
caacccagaa accggtatgc cggtgtatca attcagttca ccacagcagc gccagccagt    3540
gccggaagac gataaccaga cgcagtcctg gtttggcgat cgcgctcaac gccagtttgg    3600
```

```
cccagagttc ggtgaaatcg cacgtgaagc caatgtgctg ttccgcgata tgcgtccact    3660
gctgattgat aacccgctgg caatgctgga tatcctccgc acacagcctg atgcagaaat    3720
gctgaattgg gtaatctctg gattaaaaaa ttattaccag tacgcctacg atgtcaccag    3780
caatacgttg cgcccgatgt ggaacaacgg gcaggacatg acaggctacc gttttaaacg    3840
cgatggctat tacggcaaag cgggaacgga attaaaaccg ttcgcattag aaggtgatta    3900
tttattacct ctggttcgtg cttatcgtct gagcggtgat gaagacctgt acgcactggt    3960
taacaccatg ctgacacggc tgaataaaga agatattcag cacatcgcca gtccgctact    4020
tttgttgacc gttatcgaac tggccgatca caagcaatca gaatcctggg cacattacgc    4080
cgcacaactg gcgggcgtta tgtttgaaca acatttccat cgtggtttgt tgttcgctc     4140
tgcacagcat cgttatgttc gtctggatga tacctatccg ctggctttac tgactttcgt    4200
tgccgcctgt cgcaacaaat taaacgatat cccgccgtat ctgacacaag gtggatatgt    4260
tcacggcgat tttcacgtta acggggaaaa tagaattgtt tatgacgtgg aattaatttta   4320
tccagagtta ttaacagctt aatttatgt ttttttaat gattcacaat taatcaatag      4380
gtaagcatta tgaatgaaaa cagaatgctg gggttagcct atatctcccc ctatattata    4440
gggctgatag ttttaccgc tttcccctt atttcgtcat ttatcctcag ttttactgag      4500
tatgatttga tgagtccgcc tgagtttacg ggtcttgaga actatcaccg tatgttcatg    4560
gaggatgatc ttttttggaa atcaatgggc gtcacctttg cctatgtatt tctgaccatt    4620
ccattgaaat taatcttcgc actgttaatt gcgtttgtac ttaatttcaa attacgtggt    4680
atcggtttct tccgtactgc ttactatgtg ccttctattc tgggcagcag cgtggccatt    4740
gccgttctgt ggcgtgccct attcgccatc gatggcttgc tgaacagctt cctcggcgta    4800
tttggctttg atgccatcaa ctggctgggc gaaccttcgc tggcactgat gtcggtaacc    4860
ctgctgcgcg tatggcagtt tggttccgcc atggttatct ccttgctgc attgcagaac     4920
gtcccgcaat cacagtatga agcagccatg atcgacggtg catccaaatg gcaaatgttc    4980
ctgaaagtaa cggttccact gattacgccg gttattttct ttaactttat catgcagacc    5040
actcaggcat tccaggagtt tacggcacct tacgtcatca ctggcggcgg tccaacgcac    5100
tacacctatc tgttctcgct ctatatctat gataccgcgt tcaagtattt cgatatgggc    5160
tatggtgctg cgctggcatg ggtctgttc ctggttgttg cggtatttgc ggcaatctcc     5220
tttaagtcgt cgaaatactg ggtgttctac tccgctgata aaggaggaaa aaatggctga    5280
catgcattca aacctgacta cagcacaaga aattgctgct gcagaagtac gccgcacgct    5340
gcgtaaagag aaactcagtg cctccatccg ttacgtgata ctgctgttcg ttggcttact    5400
gatgctttac ccactagcgt ggatgttctc agcgtcgttc aaaccgaacc aagagatctt    5460
cacgacactg ggcctgtggc cggaacacgc cacatgggac ggtttcgtta acggttggaa    5520
aaccggtacg gaatacaatt tcggtcacta catgatcaat acgctcaagt tcgtgattcc    5580
gaaagtgcta ctgaccatta tctcttccac cattgtcgct tacggctttg cccgtttcga    5640
gattccatgg aagggcttct ggttcggac gctgatcacc accatgctgt taccaagcac    5700
cgtgttgctg attccgcagt acatcatgtt ccgtgaaatg gcatgctga acagctatct     5760
gccactgtac ttgccgatgg cgtttgcaac acaagggttc tttgtgttca tgctgatcca    5820
gttcctgcgt ggtgtaccac gtgatatgga agaagccgcc cagatcgatg gtgtaactc     5880
cttccaggtt ctgtggtatg tggtcgtgcc gatttttgaaa ccagccatca tctctgttgc   5940
gctgttccag ttcatgtggt caatgaacga cttcatcggt ccgctgattt atgtctatag    6000
```

```
cgtggataaa tatccgattg cgctggcgct gaaaatgtct atcgacgtta ctgaaggcgc    6060
tccgtggaat gaaatcctgg caatgtccag catctccatt ctgccatcca ttattgtttt    6120
cttcctggca cagcgttact tcgtacaagg cgtgaccagc agcggaatta aggttaata    6180 gaggatttat catggctgaa gttattttca ataaactgga aaaagtatac accaacggct    6240
tcaaagcggt tcacggcatc gacctgacca ttaaagacgg tgagttcatg gttatcgtcg    6300
gcccgtcagc ctgtgcgaaa tcaacgacgc tgcgtatgtt agcgggtctg gaaaccatca    6360
gcggcggtga agttcgcatc ggcgagcgcg ttgttaacaa tctggcaccg aaagagcgtg    6420
ggattgcaat ggtgttccag aactatgcgc tctaccctca tatgacggta aaagagaacc    6480
tggcgtttgg tctgaagctg agcaaaatgc ctaaagatca aattgaagcg caagtaacgg    6540
aagcagccaa aattctggag ctggaagacc tgatggatcg tctgccacgc cagctatctg    6600
gtggtcaggc gcagcgtgtg gccgtaggcc gtgccatcgt taaaaagccg gatgttttcc    6660
tgtttgatga accgttatct aacctggatg ccaaactgcg tgcttccatg cgtatccgta    6720
tttctgacct gcataagcag ttgaagaaaa gcggtaaagc ggcaacgacg gtatatgtta    6780
cccacgacca gactgaagcc atgaccatgg gcgaccgtat ctgcgttatg aagctgggtc    6840
acatcatgca ggtcgatacg ccggataacc tgtaccattt ccctgtcaac atgttcgttg    6900
ctggcttcat tggctcacca gaaatgaaca ttaagccgtg caaactggtc gagaaagacg    6960
gtcagattgg cgttgttgtg ggtaataacg cgctggtatt aaatactgaa aaacaagata    7020
aagtgcgcag ctacgtagga caagacgtat tcttcggcgt tcgcccagac tatgtttcct    7080
tgtcagatac gccatttgaa ggcagccact cacagggtga actggttcgc gtagaaaaca    7140
tgggtcacga attctttatg tacattaaag tcgatggctt tgaattaacc agccgcattc    7200
cttatgacga aggtcggctg attatcgaga agggactgca tcgtccggta tatttccagt    7260
tcgacatgga aaaatgccat atttttgatg caaaaacaga aaaaaatatc tctctttaac    7320
aggagtagta accgatgaaa aaagcgatcc tacacacgtt aatagcttca tctttggcat    7380
tagttgcaat gccatctctg gcagccgatc aggttgagtt gagaatgtcc tggtggggcg    7440
gcaacagccg tcaccaacag acgctcaagg cgattgaaga gttccataag cagcacccag    7500
acatcaccgt gaaagcggaa tacaccggat gggatggtca cctgtctcgt ctgacaacac    7560
agattgccgg taacactgag ccagatgtga tgcagactaa ctggaactgg ctgccgattt    7620
tctccaaaaa cggcgatggt tttatgatc tgaacaaagt gaaagattct ctggatctga    7680
cccagttcga agcaaaagaa ctgcaaaaca ccacggttaa cggcaagctg aacggtattc    7740
ctatttctgt taccgctcgc gtgttctatt tcaacaacga agctgggca aaagcgggac    7800 tggaataccc gaaaacgtgg gacgaactgc tgaacgccgg taaagtgttc aaagagaagc    7860
tgggcgacca atactaccct atcgtgttgg aacaccagga ttctctggca ctgctgaact    7920
cttacatggt tcaaaaatac aacattcctg ctattgatgt gaaaagtcag aaattcgcct    7980
ataccgatgc acaatgggtt gaattctttg gcatgtataa gaaactgatc gacagccatg    8040
tcatgcctga tgcgaaatac tatgcctctt tcggtaagag caacatgtat gagatgaagc    8100
catggatcaa tggcgagtgg tctggtactt acatgtggaa ctccactatc actaagtact    8160
ctgcaaactt gcaaccacca gcaaaactgg cgttaggtaa ctacccaatg ctgcctggtg    8220
caaaagatgc tggcttgttc ttcaaacctg cacaaatgct gtctatcggt aagtcaacca    8280
agcatcctaa agagtctgct cagttgatca acttcctgct gaacagcaaa gaaggtgctc    8340
aggctttggg tctggaacgt ggtgtaccgt tgagtaaagc ggctgtggct cagctgaccg    8400
```

```
ctgatggcat catcaaagat gatgctccag cagttgccgg gttgaagctg gcgctgtctc    8460
tgccgcatga agttgctgtt tctccttatt tcgacgaccc acaaatcgtt tctctgtttg    8520
gtgataccat ccaatctatc gattatggtc agaaatctgt ggaagacgca gcgaaatact    8580
tccagcgtca atctgagcgt gttctgaaac gcgcaatgaa ataatgtagc actcgattta    8640
ccctgtaatt catccctgcc gcaccgacgg cagggatttt tcatttaaat taaaacatcc    8700
tctatattca attcgatctc cctcacaatt tgaaaccctcta ttttactttt tgttactcaa    8760
aacgatctcg atcacagaac gtaatttaat aataaataga atagaacttg tcccaaaaaa    8820
cataatgcgc ctttcgaatt aaagtattaa gcacagtcct aaccaatggg gaatataaca    8880
atgaaattta aattattagc tctggctgtt acatcattaa ttagtgtgaa tgcaatggct    8940
gtaactatcg attaccgtca tgaaatgaaa gatacaccga aaaatgatca ccgcgatcgt    9000
ttgtcaatgt cacaccgttt tgccaatggc tttggtttat ccgttgaagc aaaatggcgt    9060
caatccagtg ctgacagcac accgaataaa ccatttaatg aaaccgtcag caacggtact    9120
gaagttgtcg ccagctatgt ttacaacttc aacaaaactt tttctctgga gccaggtttc    9180
tctttagatt caagctctac ctctaacaac tatcgccctt atctgcgcgg taaagtgaat    9240
atcactgacg atctttctac ctctttacgt tatcgtcctt actacaaacg taacagcggt    9300
gatgttccaa atgcatcaaa aaacaaccaa gagaatggtt ataacctaac cgccgttctc    9360
agctataaat tcctgaaaga tttccaagtt gattacgaac tggactacaa aaaagcaaat    9420
aaagccggtg cgtatcaata cgacaatgaa acatacaatt tcgaccatga tgtaaaattg    9480
tcttataaaa tggataaaaa ctggaagcct tatatggctg taggtaatgt tgcagattcc    9540
ggcaccaacg atcatcgtca aactcgttac cgtgttggtg tgcaatacag cttctaataa    9600
cggccttgtt atttaaataa gcgttattag gtagcagaag ggatgttatt gttaatcgat    9660
ttactcagat ctacttttat cattaacatc cctttattat ggtgtccgtt gtaggttaag    9720
caggttagtt acgtttcttt gttgtacatg atttagttat atgcgtttta gctgctgtaa    9780
ttgctgtgtc tgatttaccc tcttcgtgta tgaatgttat ttctttatta aaatttgcgg    9840
ttcagggtag tcattttttc tccgatgtga tggctaccct atttttttacc accgcccaac    9900 gattccccccc tcattccctt tgtcaggtga tctatcatga ttgttcgttc tctgcttgtc    9960
ggggccatta tgatgtctgt aaatggatta agttacgcac aacctgtttt ctctgtctgg    10020
ccacacggtg aagcaccggg tgcctcttct tcaacggcac agccgcaagt ggtcgaacgg    10080
agtaaagatc cttctcttcc cgatcgagcc gcaacgggta ttcgcagccc tgaaattacc    10140
gtttatccgg cagagaaacc caatggcatg gcattactca ttacgccggg cggttcttat    10200
cagcgcgtcg tgctagataa agaaggcagc gatctagccc ctttctttaa tcaacaaggc    10260
tacacccttt tcgtgatgac ctatcgtatg cccggtgaag gccataaaga aggcgctgac    10320
gctccgctag ccgatgccca acgagccatc agaacactga gagccaacgc cgaaaagtgg    10380
cacattaacc cgcagcgcat cggtattatg gggttctccg ccggtggtca cgttgccgcc    10440
agccttggaa cccgattcgc acagtccgtt taccccgcga tggacgccgt tgataacgta    10500
agcgcacgcc ctgacttcat ggtgttgatg taccccgtaa tttctatgca ggcagatatt    10560
gcgcacgccg gttcacgtaa acagttaatc ggcgagcaac cgatggaagt acaagcggta    10620
cgttattctc ctgagaaaca ggttactgat cagactcccc ccacgttttt ggtgcatgcg    10680
gttgacgatc cgtcagtgtc ggttgataac agcctggtga tgtttagcgc gctgcgggca    10740
aagcagattc cggtcgaaat gcatctcttt gagaaaggta aacacggctt cggtctccgc    10800
```

-continued

```
ggcaccaagg ggcttcctgc cgctgcctgg cctcaactgc tggacaactg gctacgcgct      10860
ttacctgcaa gcaacgaatt gccgaaagcc gcgccataag gtatagcaaa catcgtaacc      10920
gaaataaatc gttacgccgt caccgcttcc gcagacaggg ataatct                    10967
```

```
<210> SEQ ID NO 66
<211> LENGTH: 2582
<212> TYPE: DNA
<213> ORGANISM: Erwinia carotovora subsp. Atroseptica SCRI1043

<400> SEQUENCE: 66
```

```
ccaacggcgg gtgcgacata aacataagcg aatcgaagcg ctgcgctccg gtgagtatct        60
gaagtaattt acgatagttt cttttccaaag gcccattcgg gcctttgtta tttcagcgtt      120
tattgattca tcaaacctgc gctttctctg ctcgaatgtt ttcactagat ctgaaacagg       180
tggtgaaaac atgaagaatg ttttataaaa taaaaccacg atcacggaaa aatgaaacat       240
tgtttctata ataccgatat gacaggcgtc tcgcgtgaga tttgtggcct gattttgaa        300 caaccggtgt cggggtgacc gattcgtcgg acgttcagta atgtcaggtt atcgaagcgt       360
atgcgtgtgt ggcgtcaaat tcttcatgat aagttctaag gatttacgga tggccaaagg      420
taataagatc cccctaacgt ttcataccta ccaggatgca gcaaccggca ccgaagttgt      480
gcgtttaacc ccgcccgatg ttatctgcca ccggaattat ttctaccaga agtgtttctt      540
caatgacggt agcaagctgc tgtttggcgc tgcatttgat ggcccatgga actactatct       600
gctggattta aaagagcaga acgccacaca gttgacggaa ggcaaaggcg acaatacttt       660
tggtggtttc ctgtctccga atgacgatgc gctatattac gttaaaaata cccgtaattt      720
gatgcgtgtc gatctgacta cgctggaaga gaaaacgatt tatcaggtgc ctgacgattg       780
ggtcggctac ggtacttggg ttgccaactc cgattgcacc aaaatggtcg gtattgagat       840
caagaaagaa gactgaaagc cactgaccga ttggaaaaaa ttccaggagt tctacttcac       900
taatccttgc tgtcgtctga ttcgcgtcga tttggtaacg ggcgaagcgg agactatcct       960
tcaggaaaac cagtggctgg gtcacccaat ctaccgtcca ggtgatgaca acacggttgc      1020
tttctgtcac gaaggcccgc atgacctggt tgatgctcgt atgtggttca tcaacgaaga      1080
tgcaccaaac atgcgcaaag tgaaagagca tgcagaaggc gaaagctgca cccacgaatt      1140
ttgggtgccg gatggctccg cgatgattta tgtctcttat cttaaagacg ataccaaccg      1200
ttatattcgc agcatcgatc ccgttacgct ggaagatcgc caactgcgtg taatgccgcc      1260
gtgttctcac ctgatgagta actatgatgg cacactgttg gtcggtgatg gttccgatgc      1320
accggtcgac gtgcaggatg atggtggcta caaaattgag aacgatccgt tcctgtatgt      1380
tttcaacctg aaaactggca agaacatcg tattgcgcag cacaatacat cctgggaagt      1440
gttggaaggg gaccgtcagg tcactcaccc gcaccgtctt ttcacgccgg ataataaaca      1500
agttctgttt acttctgacg tagatggaaa acctgcgttg tatctggcga aggttcctga      1560
ttcagtctgg aactaataat actaataaat ccgcgtcacg tttcatggcg cggattattt      1620
taaaatattt acttacatat tattttatta agtctctgac gcggttattt ctcaaactta      1680
acttgattat cgttgttgct ccattgccat aatcaaagcg ttccctttat actaaaacca      1740
ttgttctatt tttttaaaa caaaaaacc tgagtagggt aaccacaaaa atggctagtg       1800
cagatttaga taaacaaccc gattccgtgt cgtccgtttt aaaggttttt ggtattttgc     1860
aggcattagg tgaagagaga gaaattggta ttaccgagct ttctcagcga gtcatgatgt     1920
ctaagagtac cgtttaccgt ttcttgcaga cgatgaaatc cctgggctat gtcgcgcagg    1980
```

| aaggtgaatc agagaagtat tcgctaacgc tcaagttgtt tgaacttggt gcaaaagcat | 2040 |
| tgcagaacgt agacttaatc cgcagtgcgg atatacagat gcgcgagttg tctgtgctga | 2100 |
| cgcgggaaac gattcacctt ggcgcgttgg atgaagacgg catcgtttat atccacaaga | 2160 |
| ttgattctat gtataacctg cgtatgtatt cgcgcatcgg tcgccgtaat ccactacaca | 2220 |
| gtaccgcaat tggtaaagtg ttgctggctt ggcgcgatcg cggtgaagtg aagaggttc | 2280 |
| tgtcgactgt cgaattcacg cgtagtacgc cacacacatt gtgtactgct gaagatcttc | 2340 |
| tcaatcaact ggatgtcgtg cgtgagcaag ctacgggga agataaagaa gagcaggaag | 2400 |
| aagggctgcg ttgtatcgct gtgccagtat tcgatcgttt tggtgtggtg attgccggcc | 2460 |
| tcagtatttc cttcccaacg attcgttttt cagaagaaaa caaacacgaa tatgtggcca | 2520 |
| tgctgcacac cgcagctaga aatatctctg agcaaatggg ctaccacaat ttccctttct | 2580 |
| ga | 2582 |

<210> SEQ ID NO 67
<211> LENGTH: 2331
<212> TYPE: DNA
<213> ORGANISM: Agrobacterium tumefaciens

<400> SEQUENCE: 67

| atgcgtccct ctgccccggc catctccaga cagacacttc tcgatgaacc ccgcccgggc | 60 |
| tcattgacca ttggctacga gccgagcgaa gaagcacaac cgacggagaa ccctccgcgc | 120 |
| ttttcatggc tacccgatat tgacgacggc gcgcgttacg tgctgcgcat ttcgaccgat | 180 |
| cccggtttta cagacaaaaa aacgctcgtc ttcgaggatc tcgcctggaa tttcttcacc | 240 |
| ccggatgaag cactgccgga cggccattat cactggtgtt atgcgctatg ggatcagaaa | 300 |
| tccgcaacag cgcattccaa ctggagcacc gtacgcagtt tcgagatcag tgaagcactg | 360 |
| ccgaaaacgc cgctgcccgg caggtctgcc cgccatgctg ccgcgcaaac cagccaccct | 420 |
| cggctgtggc tcaactccga gcaattgagt gccttcgccg atgccgttgc gaaggacccc | 480 |
| aaccattgtg gctgggccga gttttacgaa aaatcggtcg agccgtggct cgagcggccg | 540 |
| gtcatgccgg aaccgcagcc ctatcccaac aacacgcgtg tcgccacgct ctggcggcag | 600 |
| atgtatatag actgccagga agtgatctat gcgatccggc acctggccat tgccggccgc | 660 |
| gtgctcggac gcgacgacct tctcgatgca tcccgcaaat ggctgctggc cgtcgccgcc | 720 |
| tgggacacga aggtgcgac ctcacgcgcc tataatgacg aggcggggtt ccgcgtcgtc | 780 |
| gtcgcactcg cctggggtta tgactggctg tacgaccatc tgagcgaaga cgaacgcagg | 840 |
| accgtgcgat ccgttcttct cgaacggacg cgggaagttg ccgatcatgt catcgcacac | 900 |
| gcccgcattc acgtctttcc ctatgacagc catgcggtgc gctcgctttc ggctgtattg | 960 |
| acgccggcct gcatcgcact tcagggagaa agcgacgagg ctggcgaatg gctcgactat | 1020 |
| accgtcgaat tccttgccac gctctattct ccctgggcgg gaaccgatgg tggttgggcg | 1080 |
| gaaggtccgc attactggat gaccggcatg gcctatctca tcgaggccgc caatctgatc | 1140 |
| cgctcctata ttggttatga cctctatcaa cggccgtttt tccagaatac cggtcgcttc | 1200 |
| ccgctttaca ccaaggcgcc gggaacccgc cgcgccaact tcggcgacga ctccaccctt | 1260 |
| ggcgaccttc ccgcctgaa gctgggatac aacgtccggc aattcgccgg cgtcaccggc | 1320 |
| aatggccatt accagtggta tttcgatcac atcaaggccg atgcgacagg cacggaaatg | 1380 |
| gccttttaca attaccggctg gtgggacctc aacttgacg atctcgtcta tcgccacgat | 1440 |
| tacccgcagg tggaagccgt gtctcccgcc gacctgccgg cactcgccgt tttcgatgat | 1500 |

-continued

```
attggttggg cgaccatcca aaaagacatg gaagacccgg accggcacct gcagttcgtc   1560
ttcaaatcca gccgttacgg ttcgctcagc cacagtcacg gcgaccagaa tgcctttgtg   1620
ctttatgccc atggcgagga tctggcgatc cagtccggtt attacgtggc gttcaattcg   1680
cagatgcatc tgaattggcg gcgtcagaca cggtcgaaaa atgccgtgct gatcggcggc   1740
aaaggccaat atgcggaaaa ggacaaggcg cttgcacgcc gcgccgccgg ccgcatcgtc   1800
tcggtggagg aacagcccgg ccatgttcgt atcgtcggcg atgcaaccgc cgcctaccag   1860
gttgcgaacc cgctggttca aaaggtgctg cgcgaaaccc acttcgttaa tgacagctat   1920
ttcgtgattg tcgacgaagt cgaatgttcg gaacccagg aactgcaatg gctttgccat    1980
acactcggag cgccgcagac cggcaggtca agcttccgct acaatggccg gaaagccggt   2040
ttctacggac agttcgttta ctcttcgggc ggcacgccgc aaatcagcgc cgtggagggt   2100
tttcccgata tcgacccgaa agaattcgaa gggctcgaca tacaccacca tgtctgcgcc   2160
acggttccgg ccgccacccg gcatcgcctt gtcacccttc tggtgcctta cagcctgaag   2220
gagccgaagc gcatttttcag cttcatcgat gatcagggtt tttccaccga catctacttc   2280
agtgatgtcg atgacgagcg tttcaagctc tcccttccca agcagttcta a            2331
```

<210> SEQ ID NO 68
<211> LENGTH: 776
<212> TYPE: PRT
<213> ORGANISM: Agrobacterium tumefaciens

<400> SEQUENCE: 68

```
Met Arg Pro Ser Ala Pro Ala Ile Ser Arg Gln Thr Leu Leu Asp Glu
1               5                   10                  15

Pro Arg Pro Gly Ser Leu Thr Ile Gly Tyr Glu Pro Ser Glu Glu Ala
            20                  25                  30

Gln Pro Thr Glu Asn Pro Pro Arg Phe Ser Trp Leu Pro Asp Ile Asp
        35                  40                  45

Asp Gly Ala Arg Tyr Val Leu Arg Ile Ser Thr Asp Pro Gly Phe Thr
    50                  55                  60

Asp Lys Lys Thr Leu Val Phe Glu Asp Leu Ala Trp Asn Phe Phe Thr
65                  70                  75                  80

Pro Asp Glu Ala Leu Pro Asp Gly His Tyr His Trp Cys Tyr Ala Leu
                85                  90                  95

Trp Asp Gln Lys Ser Ala Thr Ala His Ser Asn Trp Ser Thr Val Arg
            100                 105                 110

Ser Phe Glu Ile Ser Glu Ala Leu Pro Lys Thr Pro Leu Pro Gly Arg
        115                 120                 125

Ser Ala Arg His Ala Ala Ala Gln Thr Ser His Pro Arg Leu Trp Leu
    130                 135                 140

Asn Ser Glu Gln Leu Ser Ala Phe Ala Asp Ala Val Ala Lys Asp Pro
145                 150                 155                 160

Asn His Cys Gly Trp Ala Glu Phe Tyr Glu Lys Ser Val Glu Pro Trp
                165                 170                 175

Leu Glu Arg Pro Val Met Pro Glu Pro Gln Pro Tyr Pro Asn Asn Thr
            180                 185                 190

Arg Val Ala Thr Leu Trp Arg Gln Met Tyr Ile Asp Cys Gln Glu Val
        195                 200                 205

Ile Tyr Ala Ile Arg His Leu Ala Ile Ala Gly Arg Val Leu Gly Arg
    210                 215                 220

Asp Asp Leu Leu Asp Ala Ser Arg Lys Trp Leu Leu Ala Val Ala Ala
225                 230                 235                 240
```

```
Trp Asp Thr Lys Gly Ala Thr Ser Arg Ala Tyr Asn Asp Glu Ala Gly
            245                 250                 255

Phe Arg Val Val Ala Leu Ala Trp Gly Tyr Asp Trp Leu Tyr Asp
            260                 265                 270

His Leu Ser Glu Asp Glu Arg Arg Thr Val Arg Ser Val Leu Leu Glu
            275                 280                 285

Arg Thr Arg Glu Val Ala Asp His Val Ile Ala His Ala Arg Ile His
            290                 295                 300

Val Phe Pro Tyr Asp Ser His Ala Val Arg Ser Leu Ser Ala Val Leu
305                 310                 315                 320

Thr Pro Ala Cys Ile Ala Leu Gln Gly Glu Ser Asp Glu Ala Gly Glu
                325                 330                 335

Trp Leu Asp Tyr Thr Val Glu Phe Leu Ala Thr Leu Tyr Ser Pro Trp
                340                 345                 350

Ala Gly Thr Asp Gly Gly Trp Ala Glu Gly Pro His Tyr Trp Met Thr
            355                 360                 365

Gly Met Ala Tyr Leu Ile Glu Ala Ala Asn Leu Ile Arg Ser Tyr Ile
    370                 375                 380

Gly Tyr Asp Leu Tyr Gln Arg Pro Phe Phe Gln Asn Thr Gly Arg Phe
385                 390                 395                 400

Pro Leu Tyr Thr Lys Ala Pro Gly Thr Arg Arg Ala Asn Phe Gly Asp
                405                 410                 415

Asp Ser Thr Leu Gly Asp Leu Pro Gly Leu Lys Leu Gly Tyr Asn Val
            420                 425                 430

Arg Gln Phe Ala Gly Val Thr Gly Asn Gly His Tyr Gln Trp Tyr Phe
    435                 440                 445

Asp His Ile Lys Ala Asp Ala Thr Gly Thr Glu Met Ala Phe Tyr Asn
    450                 455                 460

Tyr Gly Trp Trp Asp Leu Asn Phe Asp Asp Leu Val Tyr Arg His Asp
465                 470                 475                 480

Tyr Pro Gln Val Glu Ala Val Ser Pro Ala Asp Leu Pro Ala Leu Ala
                485                 490                 495

Val Phe Asp Asp Ile Gly Trp Ala Thr Ile Gln Lys Asp Met Glu Asp
                500                 505                 510

Pro Asp Arg His Leu Gln Phe Val Phe Lys Ser Ser Pro Tyr Gly Ser
            515                 520                 525

Leu Ser His Ser His Gly Asp Gln Asn Ala Phe Val Leu Tyr Ala His
    530                 535                 540

Gly Glu Asp Leu Ala Ile Gln Ser Gly Tyr Tyr Val Ala Phe Asn Ser
545                 550                 555                 560

Gln Met His Leu Asn Trp Arg Arg Gln Thr Arg Ser Lys Asn Ala Val
                565                 570                 575

Leu Ile Gly Gly Lys Gly Gln Tyr Ala Glu Lys Asp Lys Ala Leu Ala
            580                 585                 590

Arg Arg Ala Ala Gly Arg Ile Val Ser Val Glu Glu Gln Pro Gly His
    595                 600                 605

Val Arg Ile Val Gly Asp Ala Thr Ala Ala Tyr Gln Val Ala Asn Pro
    610                 615                 620

Leu Val Gln Lys Val Leu Arg Glu Thr His Phe Val Asn Asp Ser Tyr
625                 630                 635                 640

Phe Val Ile Val Asp Glu Val Glu Cys Ser Glu Pro Gln Glu Leu Gln
                645                 650                 655

Trp Leu Cys His Thr Leu Gly Ala Pro Gln Thr Gly Arg Ser Ser Phe
```

```
                   660              665                670
Arg Tyr Asn Gly Arg Lys Ala Gly Phe Tyr Gly Gln Phe Val Tyr Ser
            675                 680                685

Ser Gly Gly Thr Pro Gln Ile Ser Ala Val Glu Gly Phe Pro Asp Ile
        690                 695                700

Asp Pro Lys Glu Phe Glu Gly Leu Asp Ile His His His Val Cys Ala
705                 710                715                720

Thr Val Pro Ala Ala Thr Arg His Arg Leu Val Thr Leu Leu Val Pro
                725                 730                735

Tyr Ser Leu Lys Glu Pro Lys Arg Ile Phe Ser Phe Ile Asp Asp Gln
            740                 745                750

Gly Phe Ser Thr Asp Ile Tyr Phe Ser Asp Val Asp Asp Glu Arg Phe
        755                 760                765

Lys Leu Ser Leu Pro Lys Gln Phe
    770                 775

<210> SEQ ID NO 69
<211> LENGTH: 1068
<212> TYPE: DNA
<213> ORGANISM: Agrobacterium temefaciens C58

<400> SEQUENCE: 69
atgttcacaa cgtccgccta tgcctgcgat gacggctctt cgccgatgaa gctcgcgacc     60
atcaggcgcc gcgatcccgg tccgcgcgat gtcgaaatcg agatagaatt ctgtggcgtc    120
tgccactcgg acatccatac ggcccgcagc gaatggccgg gctccctcta cccttgcgtc    180
cccggccacg aaatcgtcgg ccgtgtcggt cgggtgggcg cgcaagtcac ccggttcaag    240
acgggtgacc gcgtcggtgt cggctgtatc gtcgatagct gccgcgaatg cgcaagctgc    300
gccgaagggc tggagcaata ttgcgaaaac ggcatgaccg gcacctataa ctcccctgac    360
aaggcgatgg gcgcggcgc gcatacgctt ggcggctatt ccgcccatgt ggtggtggat    420
gaccgctatg tgctcaatat tcccgaaggg ctcgatccgg cggcagcagc accgctactc    480
tgcgctggta tcaccaccta ctcgccgctg cgccactgga atgccggccc cggcaaacgc    540
gtcggcgtcg tcggtctggg cggcctcggc catatggccg tcaagctcgc caatgccatg    600
ggtgcgactg tcgtgatgat caccaccctcg cccggcaagg cggaggatgc caaaaaactc    660
ggcgcacacg aggtgatcat ctcccgcgat gcggagcaga tgaagaaggc tacctcgagc    720
ctcgatctca tcatcgatgc tgtcgccgcc gaccacgaca tcgacgccta tctggcgctg    780
ctgaaacgcg atggcgcgct ggtgcaggtg ggcgcgccgg aaaagccact ttcggtgatg    840
gccttcagcc tcatcccggg ccgcaagacc tttgccggct cgatgatcgg cggtattccc    900
gagactcagg aaatgctgga tttctgcgcc gaaaaaggca tcgccggcga aatcgagatg    960
atcgatatcg atcagatcaa tgacgcttat gaacgcatga taaaaagcga tgtgcgttat   1020
cgtttcgtca ttgatatgaa gagcctgccg cgccagaagg ccgcctga                1068

<210> SEQ ID NO 70
<211> LENGTH: 355
<212> TYPE: PRT
<213> ORGANISM: Agrobacterium tumefaciens C58

<400> SEQUENCE: 70

Met Phe Thr Thr Ser Ala Tyr Ala Cys Asp Asp Gly Ser Ser Pro Met
1               5                   10                  15

Lys Leu Ala Thr Ile Arg Arg Arg Asp Pro Gly Pro Arg Asp Val Glu
            20                  25                  30
```

Ile Glu Ile Glu Phe Cys Gly Val Cys His Ser Asp Ile His Thr Ala
            35                  40                  45

Arg Ser Glu Trp Pro Gly Ser Leu Tyr Pro Cys Val Pro Gly His Glu
    50                  55                  60

Ile Val Gly Arg Val Gly Arg Val Gly Ala Gln Val Thr Arg Phe Lys
65                  70                  75                  80

Thr Gly Asp Arg Val Gly Val Gly Cys Ile Val Asp Ser Cys Arg Glu
                85                  90                  95

Cys Ala Ser Cys Ala Glu Gly Leu Glu Gln Tyr Cys Glu Asn Gly Met
            100                 105                 110

Thr Gly Thr Tyr Asn Ser Pro Asp Lys Ala Met Gly Gly Ala His
            115                 120                 125

Thr Leu Gly Gly Tyr Ser Ala His Val Val Asp Asp Arg Tyr Val
    130                 135                 140

Leu Asn Ile Pro Glu Gly Leu Asp Pro Ala Ala Ala Pro Leu Leu
145                 150                 155                 160

Cys Ala Gly Ile Thr Thr Tyr Ser Pro Leu Arg His Trp Asn Ala Gly
                165                 170                 175

Pro Gly Lys Arg Val Gly Val Val Gly Leu Gly Gly Leu Gly His Met
            180                 185                 190

Ala Val Lys Leu Ala Asn Ala Met Gly Ala Thr Val Val Met Ile Thr
    195                 200                 205

Thr Ser Pro Gly Lys Ala Glu Asp Ala Lys Lys Leu Gly Ala His Glu
    210                 215                 220

Val Ile Ile Ser Arg Asp Ala Glu Gln Met Lys Lys Ala Thr Ser Ser
225                 230                 235                 240

Leu Asp Leu Ile Ile Asp Ala Val Ala Ala Asp His Asp Ile Asp Ala
                245                 250                 255

Tyr Leu Ala Leu Leu Lys Arg Asp Gly Ala Leu Val Gln Val Gly Ala
            260                 265                 270

Pro Glu Lys Pro Leu Ser Val Met Ala Phe Ser Leu Ile Pro Gly Arg
    275                 280                 285

Lys Thr Phe Ala Gly Ser Met Ile Gly Gly Ile Pro Glu Thr Gln Glu
    290                 295                 300

Met Leu Asp Phe Cys Ala Glu Lys Gly Ile Ala Gly Glu Ile Glu Met
305                 310                 315                 320

Ile Asp Ile Asp Gln Ile Asn Asp Ala Tyr Glu Arg Met Ile Lys Ser
                325                 330                 335

Asp Val Arg Tyr Arg Phe Val Ile Asp Met Lys Ser Leu Pro Arg Gln
            340                 345                 350

Lys Ala Ala
        355

<210> SEQ ID NO 71
<211> LENGTH: 1047
<212> TYPE: DNA
<213> ORGANISM: Agrobacterium tumefaciens C58

<400> SEQUENCE: 71
atggctattg caagaggtta tgctgcgacc gacgcgtcga agccgcttac cccgttcacc    60
ttcgaacgcc gcgagccgaa tgatgacgac gtcgtcatcg atatcaaata tgccggcatc   120
tgccactcgg acatccacac cgtccgcaac gaatggcaca atgccgttta cccgatcgtt   180
ccgggccacg aaatcgccgg tgtcgtgcgg gccgttggtt ccaaggtcac gcggttcaag   240

```
gtcggcgacc atgtcggcgt cggctgcttt gtcgattcct gcgttggctg cgccacccgc    300
gatgtcgaca atgagcagta tatgccgggt ctcgtgcaga cctacaattc gttgaacgg     360
gacggcaaga gcgcgaccca gggcggttat tccgaccata tcgtggtcag ggaagactac    420
gtcctgtcca tcccggacaa cctgccgctc gatgcctccg cgccgcttct ctgcgccggc    480
atcacgctct attcgccgct gcagcactgg aatgcaggcc ccggcaagaa agtggctatc    540
gtcggcatgg gtggccttgg ccacatgggc gtgaagatcg gctcggccat gggcgctgat    600
atcaccgttc tctcgcagac gctgtcgaag aaggaagacg gcctcaagct cggcgcgaag    660
gaatattacg ccaccagcga cgcctcgacc tttgagaaac tcgccggcac cttcgacctg    720
atcctgtgca cagtctcggc cgaaatcgac tggaacgcct acctcaacct gctcaaggtc    780
aacggcacga tggttctgct cggcgtgccg aacatgcga tcccggtgca cgcattctcg     840
gtcattcccg cccgccgttc gctcgccggt tcgatgatcg gctcgatcaa ggaaacccag    900
gaaatgctgg atttctgcgg caagcacgac atcgtttcgg aaatcgaaac gatcggcatc    960
aaggacgtca acgaagccta tgagcgcgtg ctgaagagcg acgtgcgtta ccgcttcgtc   1020
atcgacatgg cctcgctcga cgcttga                                       1047

<210> SEQ ID NO 72
<211> LENGTH: 348
<212> TYPE: PRT
<213> ORGANISM: Agrobacterium tumefaciens C58

<400> SEQUENCE: 72

Met Ala Ile Ala Arg Gly Tyr Ala Ala Thr Asp Ala Ser Lys Pro Leu
1               5                   10                  15

Thr Pro Phe Thr Phe Glu Arg Arg Glu Pro Asn Asp Asp Val Val
            20                  25                  30

Ile Asp Ile Lys Tyr Ala Gly Ile Cys His Ser Asp Ile His Thr Val
        35                  40                  45

Arg Asn Glu Trp His Asn Ala Val Tyr Pro Ile Val Pro Gly His Glu
    50                  55                  60

Ile Ala Gly Val Val Arg Ala Val Gly Ser Lys Val Thr Arg Phe Lys
65                  70                  75                  80

Val Gly Asp His Val Gly Val Gly Cys Phe Val Asp Ser Cys Val Gly
                85                  90                  95

Cys Ala Thr Arg Asp Val Asp Asn Glu Gln Tyr Met Pro Gly Leu Val
            100                 105                 110

Gln Thr Tyr Asn Ser Val Glu Arg Asp Gly Lys Ser Ala Thr Gln Gly
        115                 120                 125

Gly Tyr Ser Asp His Ile Val Val Arg Glu Asp Tyr Val Leu Ser Ile
    130                 135                 140

Pro Asp Asn Leu Pro Leu Asp Ala Ser Ala Pro Leu Leu Cys Ala Gly
145                 150                 155                 160

Ile Thr Leu Tyr Ser Pro Leu Gln His Trp Asn Ala Gly Pro Gly Lys
                165                 170                 175

Lys Val Ala Ile Val Gly Met Gly Gly Leu Gly His Met Gly Val Lys
            180                 185                 190

Ile Gly Ser Ala Met Gly Ala Asp Ile Thr Val Leu Ser Gln Thr Leu
        195                 200                 205

Ser Lys Lys Glu Asp Gly Leu Lys Leu Gly Ala Lys Glu Tyr Tyr Ala
    210                 215                 220

Thr Ser Asp Ala Ser Thr Phe Glu Lys Leu Ala Gly Thr Phe Asp Leu
225                 230                 235                 240
```

```
Ile Leu Cys Thr Val Ser Ala Glu Ile Asp Trp Asn Ala Tyr Leu Asn
                245                 250                 255

Leu Leu Lys Val Asn Gly Thr Met Val Leu Gly Val Pro Glu His
            260                 265                 270

Ala Ile Pro Val His Ala Phe Ser Val Ile Pro Ala Arg Arg Ser Leu
        275                 280                 285

Ala Gly Ser Met Ile Gly Ser Ile Lys Glu Thr Gln Glu Met Leu Asp
    290                 295                 300

Phe Cys Gly Lys His Asp Ile Val Ser Glu Ile Glu Thr Ile Gly Ile
305                 310                 315                 320

Lys Asp Val Asn Glu Ala Tyr Glu Arg Val Leu Lys Ser Asp Val Arg
                325                 330                 335

Tyr Arg Phe Val Ile Asp Met Ala Ser Leu Asp Ala
            340                 345

<210> SEQ ID NO 73
<211> LENGTH: 1029
<212> TYPE: DNA
<213> ORGANISM: Agrobacterium tumefaciens C58

<400> SEQUENCE: 73
atgactaaaa caatgaaggc ggcggttgtc cgcgcatttg gaaaaccgct gaccatcgag      60
gaagtggcaa taccggatcc cggccccggt gaaattctca tcaactacaa ggcgacgggc    120
gtttgccaca ccgacctgca cgccgcaacg ggggattggc cggtcaagcc caacccgccc    180
ttcattcccg acatgaaggt gcaggttac gtcgccaaga tcggcgctgg cgtcaccggc     240
atcaaggagg cgaccgcgc cggcacgccc tggctctaca ccgcctgcgg atgctgcatt    300
ccctgccgta ccggctggga aaccctgtgc ccgagccaga agaactcagg ttattccgtc    360
aacggcagct tgccgaata tggccttgcc gatccgaaat tcgtcggccg cctgcctgac    420
aatctcgatt tcggcccagc cgcacccgtg ctctgcgccg gcgttacagt ctataagggc    480
ctgaaggaaa ccgaagtcag gcccggtgaa tgggtggtca tttcaggcat tggcgggctt    540
ggccacatgg ccgtgcaata tgcgaaagcc atgggcatgc atgtggttgc cgccgatatt    600
ttcgacgaca agctggcgct tgccaaaaag ctcggagccg acgtcgtcgt caacggccgc    660
gcgcctgacg cggtggagca agtgcaaaag gcaaccggcg cgtccatgg cgcgctggtg    720 acggcggttt caccgaaggc catggagcag gcttatggct tcctgcgctc caagggcacg    780
atggcgcttg tcggtctgcc gccgggcttc atctccattc cggtgttcga cacggtgctg    840
aagcgcatca cggtgcgtgg ctccatcgtc ggcacgcggc aggatctgga ggaggcgttg    900
accttcgccg tgaaggcaa ggtggccgcc cacttctcgt gggacaagct cgaaaacatc    960
aatgatatct tccatcgcat ggaagagggc aagatcgacg ccgtatcgt cgtggatctc   1020 gccgcctga                                                           1029

<210> SEQ ID NO 74
<211> LENGTH: 342
<212> TYPE: PRT
<213> ORGANISM: Agrobacterium tumefaciens C58

<400> SEQUENCE: 74

Met Thr Lys Thr Met Lys Ala Ala Val Val Arg Ala Phe Gly Lys Pro
1               5                   10                  15

Leu Thr Ile Glu Glu Val Ala Ile Pro Asp Pro Gly Pro Gly Glu Ile
            20                  25                  30
```

```
Leu Ile Asn Tyr Lys Ala Thr Gly Val Cys His Thr Asp Leu His Ala
         35                  40                  45

Ala Thr Gly Asp Trp Pro Val Lys Pro Asn Pro Phe Ile Pro Gly
    50                  55                  60

His Glu Gly Ala Gly Tyr Val Ala Lys Ile Gly Ala Gly Val Thr Gly
 65                  70                  75                  80

Ile Lys Glu Gly Asp Arg Ala Gly Thr Pro Trp Leu Tyr Thr Ala Cys
                 85                  90                  95

Gly Cys Cys Ile Pro Cys Arg Thr Gly Trp Glu Thr Leu Cys Pro Ser
                100                 105                 110

Gln Lys Asn Ser Gly Tyr Ser Val Asn Gly Ser Phe Ala Glu Tyr Gly
                115                 120                 125

Leu Ala Asp Pro Lys Phe Val Gly Arg Leu Pro Asp Asn Leu Asp Phe
    130                 135                 140

Gly Pro Ala Ala Pro Val Leu Cys Ala Gly Val Thr Val Tyr Lys Gly
145                 150                 155                 160

Leu Lys Glu Thr Glu Val Arg Pro Gly Glu Trp Val Val Ile Ser Gly
                165                 170                 175

Ile Gly Gly Leu Gly His Met Ala Val Gln Tyr Ala Lys Ala Met Gly
                180                 185                 190

Met His Val Ala Ala Asp Ile Phe Asp Asp Lys Leu Ala Leu Ala
    195                 200                 205

Lys Lys Leu Gly Ala Asp Val Val Asn Gly Arg Ala Pro Asp Ala
210                 215                 220

Val Glu Gln Val Gln Lys Ala Thr Gly Val His Gly Ala Leu Val
225                 230                 235                 240

Thr Ala Val Ser Pro Lys Ala Met Glu Gln Ala Tyr Gly Phe Leu Arg
    245                 250                 255

Ser Lys Gly Thr Met Ala Leu Val Gly Leu Pro Pro Gly Phe Ile Ser
                260                 265                 270

Ile Pro Val Phe Asp Thr Val Leu Lys Arg Ile Thr Val Arg Gly Ser
    275                 280                 285

Ile Val Gly Thr Arg Gln Asp Leu Glu Glu Ala Leu Thr Phe Ala Gly
    290                 295                 300

Glu Gly Lys Val Ala Ala His Phe Ser Trp Asp Lys Leu Glu Asn Ile
305                 310                 315                 320

Asn Asp Ile Phe His Arg Met Glu Glu Gly Lys Ile Asp Gly Arg Ile
                325                 330                 335

Val Val Asp Leu Ala Ala
            340

<210> SEQ ID NO 75
<211> LENGTH: 1008
<212> TYPE: DNA
<213> ORGANISM: Agrobacterium tumefaciens C58

<400> SEQUENCE: 75
atgaccgggg cgaaccagcc ttgggaggtt caagaggttc ccgttccgaa ggcagagcca      60
ggacttgtcc ttgttaaaat ccacgcctcc ggcatgtgct acacggacgt gtgggcgacg     120
cagggtgccg gtggcgacat ctatccgcag acccccggcc atgaggttgt cggcgagatc     180
atcgaggtcg gcgcgggcgt tcatacgcgc aaggtgggag accgggtcgg caccacctgg     240
gtgcagtcct cttgtggacg atgctcctac tgccgccaga accgtccgtt gaccggccag     300
acagccatga actgcgattc acccaggaca acggggttcg cgacgcaagg cgggcacgca     360
```

```
gagtacatcg cgatctctgc tgaaggcaca gtgttattac ccgacgggct cgactacacg    420
gatgccgcac ccatgatgtg cgcaggctac acgacctgga gcggcttgcg cgacgccgag    480
cccaaacctg gtgacagaat tgcggtactt ggcatcggcg ggctggggca cgtcgccgtg    540
cagttctcca aagccttggg gtttgagacc atcgcgatca cgcattcacc cgacaagcac    600
aagttggcca ccgatcttgg tgcagacatc gtcgtcgccg atggcaaaga gttattggag    660
gccggcggtg cggacgttct tctggttacg accaacgact cgacaccgc cgaaaaagcg    720 atggcgggcg taaggcctga cgggcgcatc gttctttgcg cgctcgactt cagcaagccg    780
ttctcgatcc cgtccgacgg caagccgttc cacatgatgc cgaacgcgt ggttgggtcc    840 acgcatggcg gacagcacta tctcgccgaa atcctcgatc tcgccgccaa gggcaaggtc    900
aagccgattg tcgagacctt cgccctcgag caggcaaccg aggcatatga gcggctatcc    960
accgggaaga tgcgcttccg gggcgtgttc cttccgcacg gcgcttga              1008
```

<210> SEQ ID NO 76
<211> LENGTH: 335
<212> TYPE: PRT
<213> ORGANISM: Agrobacterium tumefaciens C58

<400> SEQUENCE: 76

Met Thr Gly Ala Asn Gln Pro Trp Glu Val Gln Glu Val Pro Val Pro
1               5                   10                  15

Lys Ala Glu Pro Gly Leu Val Leu Val Lys Ile His Ala Ser Gly Met
                20                  25                  30

Cys Tyr Thr Asp Val Trp Ala Thr Gln Gly Ala Gly Gly Asp Ile Tyr
            35                  40                  45

Pro Gln Thr Pro Gly His Glu Val Val Gly Glu Ile Ile Glu Val Gly
        50                  55                  60

Ala Gly Val His Thr Arg Lys Val Gly Asp Arg Val Gly Thr Thr Trp
65                  70                  75                  80

Val Gln Ser Ser Cys Gly Arg Cys Ser Tyr Cys Arg Gln Asn Arg Pro
                85                  90                  95

Leu Thr Gly Gln Thr Ala Met Asn Cys Asp Ser Pro Arg Thr Thr Gly
            100                 105                 110

Phe Ala Thr Gln Gly Gly His Ala Glu Tyr Ile Ala Ile Ser Ala Glu
        115                 120                 125

Gly Thr Val Leu Leu Pro Asp Gly Leu Asp Tyr Thr Asp Ala Ala Pro
    130                 135                 140

Met Met Cys Ala Gly Tyr Thr Thr Trp Ser Gly Leu Arg Asp Ala Glu
145                 150                 155                 160

Pro Lys Pro Gly Asp Arg Ile Ala Val Leu Gly Ile Gly Gly Leu Gly
                165                 170                 175

His Val Ala Val Gln Phe Ser Lys Ala Leu Gly Phe Glu Thr Ile Ala
            180                 185                 190

Ile Thr His Ser Pro Asp Lys His Lys Leu Ala Thr Asp Leu Gly Ala
        195                 200                 205

Asp Ile Val Val Ala Asp Gly Lys Glu Leu Leu Glu Ala Gly Gly Ala
    210                 215                 220

Asp Val Leu Leu Val Thr Thr Asn Asp Phe Asp Thr Ala Glu Lys Ala
225                 230                 235                 240

Met Ala Gly Val Arg Pro Asp Gly Arg Ile Val Leu Cys Ala Leu Asp
                245                 250                 255

Phe Ser Lys Pro Phe Ser Ile Pro Ser Asp Gly Lys Pro Phe His Met
            260                 265                 270

```
Met Arg Gln Arg Val Val Gly Ser Thr His Gly Gly Gln His Tyr Leu
            275                 280                 285

Ala Glu Ile Leu Asp Leu Ala Ala Lys Gly Lys Val Lys Pro Ile Val
            290                 295                 300

Glu Thr Phe Ala Leu Glu Gln Ala Thr Glu Ala Tyr Glu Arg Leu Ser
305                 310                 315                 320

Thr Gly Lys Met Arg Phe Arg Gly Val Phe Leu Pro His Gly Ala
                325                 330                 335
```

<210> SEQ ID NO 77
<211> LENGTH: 1017
<212> TYPE: DNA
<213> ORGANISM: Agrobacterium tumefaciens C58

<400> SEQUENCE: 77

```
atgaccatgc atgccattca attcgtcgag aagggacgcg ccgtgctggc ggaactcccc    60
gtcgccgatc tgccgccggg ccatgcgctc gtgcgggtca aggcttcggg ctttgccat   120
accgatatcg acgtgctgca tgcgcgttat ggcgacggtg cgttccccgt cattccgggg   180
catgaatatg ctggcgaagt cgcagccgtg cttccgatg tgacagtctt caaggctggc    240
gaccgggttg tcgtcgatcc caatctgccc tgtggcacct gcgccagctg caggaaaggg   300
ctgaccaacc tttgcagcac attgaaagct acgcgtttt cccacaatgg cggctttgcg    360
gagttcagtg tggtgcgtgc cgatcacctg cacggtatcg gttcgatgcc ctatcacgtc   420
gcggcgctgg ctgagccgct tgcctgtgtt gtcaatggca tgcagagtgc gggtattggc   480
gagagtggcg tggtgccgga gaatgcgctt gttttcggtg ctgggcccat cggcctgctg   540
cttgccctgt cgctgaaatc acgcggcatt gcgacggtga cgatggccga tatcaatgaa   600
agcaggctgg cctttgccca ggacctcggg cttcagacgg cggtatccgg ctcggaagcg   660
ctctcgcggc agcggaagga gttcgatttc gtggccgatg cgacgggtat tgccccggtc   720
gccgaggcga tgatcccgct ggttgcggat ggcggcacgg cgctattctt cggcgtctgc   780
gcgccggatg cccgtatttc ggtggcaccg tttgaaatct ccggcgcca gctgaaactt    840
gtcggctcgc attcgctgaa ccgcaacata ccgcaggcgc ttgccattct ggagacggat   900
ggcgaggtca tggcgcggct cgtttcgcac gcttgccgc tttcggagat gctgccgttc   960
tttacgaaaa aaccgtctga tccggcgacg atgaaagtgc aatttgcagc cgaatga     1017
```

<210> SEQ ID NO 78
<211> LENGTH: 338
<212> TYPE: PRT
<213> ORGANISM: Agrobacterium tumefaciens C58

<400> SEQUENCE: 78

```
Met Thr Met His Ala Ile Gln Phe Val Glu Lys Gly Arg Ala Val Leu
1               5                   10                  15

Ala Glu Leu Pro Val Ala Asp Leu Pro Pro Gly His Ala Leu Val Arg
                20                  25                  30

Val Lys Ala Ser Gly Leu Cys His Thr Asp Ile Asp Val Leu His Ala
            35                  40                  45

Arg Tyr Gly Asp Gly Ala Phe Pro Val Ile Pro Gly His Glu Tyr Ala
        50                  55                  60

Gly Glu Val Ala Ala Val Ala Ser Asp Val Thr Val Phe Lys Ala Gly
65                  70                  75                  80

Asp Arg Val Val Val Asp Pro Asn Leu Pro Cys Gly Thr Cys Ala Ser
                85                  90                  95
```

| | | | | | | | | | | | |
|---|---|---|---|---|---|---|---|---|---|---|---|
|Cys|Arg|Lys|Gly|Leu|Thr|Asn|Leu|Cys|Ser|Thr|Leu|Lys|Ala|Tyr|Gly|
| | |100| | | |105| | | |110| |

Cys Arg Lys Gly Leu Thr Asn Leu Cys Ser Thr Leu Lys Ala Tyr Gly
            100                 105                 110

Val Ser His Asn Gly Gly Phe Ala Glu Phe Ser Val Val Arg Ala Asp
            115                 120                 125

His Leu His Gly Ile Gly Ser Met Pro Tyr His Val Ala Ala Leu Ala
        130                 135                 140

Glu Pro Leu Ala Cys Val Val Asn Gly Met Gln Ser Ala Gly Ile Gly
145                 150                 155                 160

Glu Ser Gly Val Val Pro Glu Asn Ala Leu Val Phe Gly Ala Gly Pro
                165                 170                 175

Ile Gly Leu Leu Leu Ala Leu Ser Leu Lys Ser Arg Gly Ile Ala Thr
            180                 185                 190

Val Thr Met Ala Asp Ile Asn Glu Ser Arg Leu Ala Phe Ala Gln Asp
        195                 200                 205

Leu Gly Leu Gln Thr Ala Val Ser Gly Ser Glu Ala Leu Ser Arg Gln
    210                 215                 220

Arg Lys Glu Phe Asp Phe Val Ala Asp Ala Thr Gly Ile Ala Pro Val
225                 230                 235                 240

Ala Glu Ala Met Ile Pro Leu Val Ala Asp Gly Gly Thr Ala Leu Phe
                245                 250                 255

Phe Gly Val Cys Ala Pro Asp Ala Arg Ile Ser Val Ala Pro Phe Glu
            260                 265                 270

Ile Phe Arg Arg Gln Leu Lys Leu Val Gly Ser His Ser Leu Asn Arg
        275                 280                 285

Asn Ile Pro Gln Ala Leu Ala Ile Leu Glu Thr Asp Gly Glu Val Met
    290                 295                 300

Ala Arg Leu Val Ser His Arg Leu Pro Leu Ser Glu Met Leu Pro Phe
305                 310                 315                 320

Phe Thr Lys Lys Pro Ser Asp Pro Ala Thr Met Lys Val Gln Phe Ala
                325                 330                 335

Ala Glu

<210> SEQ ID NO 79
<211> LENGTH: 1044
<212> TYPE: DNA
<213> ORGANISM: Agrobacterium tumefaciens C58

<400> SEQUENCE: 79

```
atgcgcgcgc tttattacga acgattcggc gagacccctg tagtcgcgtc cctgcctgat      60
ccggcaccga gcgatggcgg cgtggtgatt gcggtgaagg caaccggcct ctgccgcagc     120
gactggcatg gctggatggg acatgacacg gatatccgtc tgccgcatgt gcccggccac     180
gagttcgccg gcgtcatctc cgcagtcggc agaaacgtca cccgcttcaa gacgggtgat     240
cgcgttaccg tgccttttcgt ctccggctgc ggccattgcc atgagtgccg ctccggcaat     300
cagcaggtct gcgaaacgca gttccagccc ggcttcaccc attggggttc cttcgccgaa     360
tatgtcgcca tcgactatgc cgatcagaac ctcgtgcacc tgccggaatc gatgagttac     420
gccaccgccg ccggcctcgg ttgccgtttc gccacctcct tccgggcggt gacggatcag     480
ggacgcctga agggcggcga atggctggct gtccatggct cggcggtgt cggtctctcc     540 gccatcatga tcggcgccgg cctcggcgca caggtcgtcg ccatcgatat tgccgaagac     600
aagctcgaac tcgcccggca actgggtgca accgcaacca tcaacagccg ctccgttgcc     660
gatgtcgccg aagcggtgcg cgacatcacc ggtggcggcg cgcatgtgtc ggtggatgcg     720
```

```
cttggccatc cgcagacctg ctgcaattcc atcagcaacc tgcgccggcg cggacgccat    780
gtgcaggtgg ggctgatgct ggcagaccat gccatgccgg ccattcccat ggcccgggtg    840
atcgctcatg agctggagat ctatggcagc cacggcatgc aggcatggcg ttacgaggac    900
atgctggcca tgatcgaaag cggcaggctt gcgccggaaa agctgattgg ccgccatatc    960
tcgctgaccg aagcggccgt cgccctgccc ggaatggata ggttccagga gagcggcatc   1020
agcatcatcg accggttcga atag                                          1044
```

<210> SEQ ID NO 80
<211> LENGTH: 357
<212> TYPE: PRT
<213> ORGANISM: Agrobacterium tumefaciens C58

<400> SEQUENCE: 80

```
Met Asn Leu Arg Thr Asn Asp Glu Ala Met Met Arg Ala Leu Tyr Tyr
1               5                   10                  15

Glu Arg Phe Gly Glu Thr Pro Val Val Ala Ser Leu Pro Asp Pro Ala
            20                  25                  30

Pro Ser Asp Gly Gly Val Val Ile Ala Val Lys Ala Thr Gly Leu Cys
        35                  40                  45

Arg Ser Asp Trp His Gly Trp Met Gly His Asp Thr Asp Ile Arg Leu
    50                  55                  60

Pro His Val Pro Gly His Glu Phe Ala Gly Val Ile Ser Ala Val Gly
65                  70                  75                  80

Arg Asn Val Thr Arg Phe Lys Thr Gly Asp Arg Val Thr Val Pro Phe
                85                  90                  95

Val Ser Gly Cys Gly His Cys His Glu Cys Arg Ser Gly Asn Gln Gln
            100                 105                 110

Val Cys Glu Thr Gln Phe Gln Pro Gly Phe Thr His Trp Gly Ser Phe
        115                 120                 125

Ala Glu Tyr Val Ala Ile Asp Tyr Ala Asp Gln Asn Leu Val His Leu
    130                 135                 140

Pro Glu Ser Met Ser Tyr Ala Thr Ala Ala Gly Leu Gly Cys Arg Phe
145                 150                 155                 160

Ala Thr Ser Phe Arg Ala Val Thr Asp Gln Gly Arg Leu Lys Gly Gly
                165                 170                 175

Glu Trp Leu Ala Val His Gly Cys Gly Gly Val Gly Leu Ser Ala Ile
            180                 185                 190

Met Ile Gly Ala Gly Leu Gly Ala Gln Val Val Ala Ile Asp Ile Ala
        195                 200                 205

Glu Asp Lys Leu Glu Leu Ala Arg Gln Leu Gly Ala Thr Ala Thr Ile
    210                 215                 220

Asn Ser Arg Ser Val Ala Asp Val Ala Glu Ala Val Arg Asp Ile Thr
225                 230                 235                 240

Gly Gly Gly Ala His Val Ser Val Asp Ala Leu Gly His Pro Gln Thr
                245                 250                 255

Cys Cys Asn Ser Ile Ser Asn Leu Arg Arg Arg Gly Arg His Val Gln
            260                 265                 270

Val Gly Leu Met Leu Ala Asp His Ala Met Pro Ala Ile Pro Met Ala
        275                 280                 285

Arg Val Ile Ala His Glu Leu Glu Ile Tyr Gly Ser His Gly Met Gln
    290                 295                 300

Ala Trp Arg Tyr Glu Asp Met Leu Ala Met Ile Glu Ser Gly Arg Leu
305                 310                 315                 320
```

Ala Pro Glu Lys Leu Ile Gly Arg His Ile Ser Leu Thr Glu Ala Ala
              325                 330                 335

Val Ala Leu Pro Gly Met Asp Arg Phe Gln Glu Ser Gly Ile Ser Ile
          340                 345                 350

Ile Asp Arg Phe Glu
        355

<210> SEQ ID NO 81
<211> LENGTH: 1011
<212> TYPE: DNA
<213> ORGANISM: Agrobacterium tumefaciens C58

<400> SEQUENCE: 81

```
atgctggcga ttttctgtga cactcccggt caattaaccg ccaaggatct gccgaacccc    60
gtgcgcggcg aaggtgaagt cctggtacgt attcgccgga ttggcgtttg cggcacggat   120
ctgcacatct ttaccggcaa ccagccctat ctttcctatc cgcggatcat gggtcacgaa   180
ctttccggca cggttgagga ggcacccgct ggcagccacc tttccgctgg cgatgtggtg   240
accataattc cctatatgtc ctgcgggaaa tgcaatgcct gcctgaaggg taagagcaat   300
tgctgccgca atatcggtgt gcttggcgtt catcgcgatg cggcatggt ggaatatctg    360
agcgtgccgc agcaattcgt gctgaaggcg aggggctga gcctcgacca ggcagccatg    420
acggaatttc tggcgatcgg tgcccatgcg gtgcgtcgcg gtgccgtcga aaagggcaa    480
aaggtcctga tcgtcggtgc cggcccgatc ggcatggcgg ttgctgtctt gcggttctc    540
gatggcacgg aagtgacgat gatcgacggt cgcaccgacc ggctggattt ctgcaaggac    600
cacctcggtg tcgctcatac agtcgccctc ggcgacggtg acaaagatcg tctgtccgac    660
attaccggtg gcaatttctt cgatgcggtg tttgatgcga ccggcaatcc gaaagccatg    720
gagcgcggtt tctccttcgt cggtcacggc ggctcctatg ttctggtgtc catcgtcgcc    780
agcgatatca gcttcaacga cccggaattt cacaagcgtg agacgacgct gctcggcagc    840
cgcaacgcga cggctgatga tttcgagcgg gtgcttcgcg ccttgcgcga agggaaagtg    900
ccggaggcac taatcaccca tcgcatgaca cttgccgatg ttccctcgaa gttcgccggc    960
ctgaccgatc cgaaagccgg agtcatcaag ggcatggtgg aggtcgcatg a           1011
```

<210> SEQ ID NO 82
<211> LENGTH: 336
<212> TYPE: PRT
<213> ORGANISM: Agrobacterium tumefaciens C58

<400> SEQUENCE: 82

Met Leu Ala Ile Phe Cys Asp Thr Pro Gly Gln Leu Thr Ala Lys Asp
1               5                  10                  15

Leu Pro Asn Pro Val Arg Gly Glu Gly Glu Val Leu Val Arg Ile Arg
            20                  25                  30

Arg Ile Gly Val Cys Gly Thr Asp Leu His Ile Phe Thr Gly Asn Gln
        35                  40                  45

Pro Tyr Leu Ser Tyr Pro Arg Ile Met Gly His Glu Leu Ser Gly Thr
    50                  55                  60

Val Glu Glu Ala Pro Ala Gly Ser His Leu Ser Ala Gly Asp Val Val
65                  70                  75                  80

Thr Ile Ile Pro Tyr Met Ser Cys Gly Lys Cys Asn Ala Cys Leu Lys
                85                  90                  95

Gly Lys Ser Asn Cys Cys Arg Asn Ile Gly Val Leu Gly Val His Arg
            100                 105                 110

```
Asp Gly Gly Met Val Glu Tyr Leu Ser Val Pro Gln Gln Phe Val Leu
            115                 120                 125
Lys Ala Glu Gly Leu Ser Leu Asp Gln Ala Ala Met Thr Glu Phe Leu
130                 135                 140
Ala Ile Gly Ala His Ala Val Arg Arg Gly Ala Val Glu Lys Gly Gln
145                 150                 155                 160
Lys Val Leu Ile Val Gly Ala Gly Pro Ile Gly Met Ala Val Ala Val
                165                 170                 175
Phe Ala Val Leu Asp Gly Thr Glu Val Thr Met Ile Asp Gly Arg Thr
            180                 185                 190
Asp Arg Leu Asp Phe Cys Lys Asp His Leu Gly Val Ala His Thr Val
        195                 200                 205
Ala Leu Gly Asp Gly Asp Lys Asp Arg Leu Ser Asp Ile Thr Gly Gly
    210                 215                 220
Asn Phe Phe Asp Ala Val Phe Asp Ala Thr Gly Asn Pro Lys Ala Met
225                 230                 235                 240
Glu Arg Gly Phe Ser Phe Val Gly His Gly Ser Tyr Val Leu Val
                245                 250                 255
Ser Ile Val Ala Ser Asp Ile Ser Phe Asn Asp Pro Glu Phe His Lys
            260                 265                 270
Arg Glu Thr Thr Leu Leu Gly Ser Arg Asn Ala Thr Ala Asp Asp Phe
        275                 280                 285
Glu Arg Val Leu Arg Ala Leu Arg Glu Gly Lys Val Pro Glu Ala Leu
    290                 295                 300
Ile Thr His Arg Met Thr Leu Ala Asp Val Pro Ser Lys Phe Ala Gly
305                 310                 315                 320
Leu Thr Asp Pro Lys Ala Gly Val Ile Lys Gly Met Val Glu Val Ala
                325                 330                 335

<210> SEQ ID NO 83
<211> LENGTH: 1005
<212> TYPE: DNA
<213> ORGANISM: Agrobacterium tumefaciens C58

<400> SEQUENCE: 83
gtgaaagcct tcgtcgtcga caagtacaag aagaagggcc cgctgcgtct ggccgacatg     60
cccaatccgg tcatcggcgc caatgatgtg ctggttcgca tccatgccac tgccatcaat    120
cttctcgact ccaaggtgcg cgacggggaa ttcaagctgt tcctgcccta cgtcctccc    180
ttcattctcg gtcatgatct ggccggaacg gtcatccgcg tcggcgcgaa tgtacggcag    240
ttcaagacag gcgacgaggt tttcgctcgc ccgcgtgatc accgggtcgg aaccttcgca    300
gaaatgattg cggtcgatgc cgcagacctt gcgctgaagc caacgagcct gtccatggag    360
caggcagcgt cgatcccgct cgtcggactg actgcctggc aggcgcttat cgaggttggc    420
aaggtcaagt ccgccagaa ggttttcatc caggccggtt ccggcggtgt cggcaccttc    480
gccatccagc ttgccaagca tctcggcgct accgtggcca cgaccaccag cgccgcgaat    540
gccgaactgg tcaaaagcct cggcgcagat gtggtgatcg actacaagac gcaggacttc    600
gaacaggtgc tgtccggcta cgatctcgtc ctgaacagcc aggatgccaa gacgctggaa    660
aagtcgttga acgtgctgag accgggcgga aagctcattt cgatctccgg tccgccggat    720
gttgcctttg ccagatcgtt gaaactgaat ccgctcctgc gttttgtcgt cagaatgctg    780
agccgtggtg tcctgaaaaa ggcaagcaga gcggtgtcg attactcttt cctgttcatg    840
cgcgccgaag gtcagcaatt gcatgagatc gccgaactga tcgatgccgg caccatccgt    900
```

```
ccggtcgtcg acaaggtgtt tcaatttgcg cagacgcccg acgccctggc ctatgtcgag    960
accggacggg caaggggcaa ggttgtggtt acatacgcat cctag                   1005
```

<210> SEQ ID NO 84
<211> LENGTH: 359
<212> TYPE: PRT
<213> ORGANISM: Agrobacterium tumefaciens C58

<400> SEQUENCE: 84

| | | | | | | | | | | | | | | |
|---|---|---|---|---|---|---|---|---|---|---|---|---|---|---|
| Met | Pro | Ser | Leu | Cys | Arg | Lys | Pro | Trp | Leu | Ser | Ser | Leu | Pro | Asp | Leu |
| 1 | | | | 5 | | | | | 10 | | | | | 15 | |
| Ile | Asn | Val | Ser | His | Trp | Arg | Lys | Pro | Val | Lys | Ala | Phe | Val | Val | Asp |
| | | | 20 | | | | | 25 | | | | | 30 | | |
| Lys | Tyr | Lys | Lys | Lys | Gly | Pro | Leu | Arg | Leu | Ala | Asp | Met | Pro | Asn | Pro |
| | 35 | | | | | 40 | | | | | 45 | | | | |
| Val | Ile | Gly | Ala | Asn | Asp | Val | Leu | Val | Arg | Ile | His | Ala | Thr | Ala | Ile |
| 50 | | | | | 55 | | | | | 60 | | | | | |
| Asn | Leu | Leu | Asp | Ser | Lys | Val | Arg | Asp | Gly | Glu | Phe | Lys | Leu | Phe | Leu |
| 65 | | | | | 70 | | | | | 75 | | | | | 80 |
| Pro | Tyr | Arg | Pro | Pro | Phe | Ile | Leu | Gly | His | Asp | Leu | Ala | Gly | Thr | Val |
| | | | | 85 | | | | | 90 | | | | | 95 | |
| Ile | Arg | Val | Gly | Ala | Asn | Val | Arg | Gln | Phe | Lys | Thr | Gly | Asp | Glu | Val |
| | | | 100 | | | | | 105 | | | | | 110 | | |
| Phe | Ala | Arg | Pro | Arg | Asp | His | Arg | Val | Gly | Thr | Phe | Ala | Glu | Met | Ile |
| | 115 | | | | | 120 | | | | | 125 | | | | |
| Ala | Val | Asp | Ala | Ala | Asp | Leu | Ala | Leu | Lys | Pro | Thr | Ser | Leu | Ser | Met |
| 130 | | | | | 135 | | | | | 140 | | | | | |
| Glu | Gln | Ala | Ala | Ser | Ile | Pro | Leu | Val | Gly | Leu | Thr | Ala | Trp | Gln | Ala |
| 145 | | | | | 150 | | | | | 155 | | | | | 160 |
| Leu | Ile | Glu | Val | Gly | Lys | Val | Lys | Ser | Gly | Gln | Lys | Val | Phe | Ile | Gln |
| | | | | 165 | | | | | 170 | | | | | 175 | |
| Ala | Gly | Ser | Gly | Gly | Val | Gly | Thr | Phe | Ala | Ile | Gln | Leu | Ala | Lys | His |
| | | | 180 | | | | | 185 | | | | | 190 | | |
| Leu | Gly | Ala | Thr | Val | Ala | Thr | Thr | Thr | Ser | Ala | Ala | Asn | Ala | Glu | Leu |
| | 195 | | | | | 200 | | | | | 205 | | | | |
| Val | Lys | Ser | Leu | Gly | Ala | Asp | Val | Val | Ile | Asp | Tyr | Lys | Thr | Gln | Asp |
| 210 | | | | | 215 | | | | | 220 | | | | | |
| Phe | Glu | Gln | Val | Leu | Ser | Gly | Tyr | Asp | Leu | Val | Leu | Asn | Ser | Gln | Asp |
| 225 | | | | | 230 | | | | | 235 | | | | | 240 |
| Ala | Lys | Thr | Leu | Glu | Lys | Ser | Leu | Asn | Val | Leu | Arg | Pro | Gly | Gly | Lys |
| | | | | 245 | | | | | 250 | | | | | 255 | |
| Leu | Ile | Ser | Ile | Ser | Gly | Pro | Pro | Asp | Val | Ala | Phe | Ala | Arg | Ser | Leu |
| | | | 260 | | | | | 265 | | | | | 270 | | |
| Lys | Leu | Asn | Pro | Leu | Leu | Arg | Phe | Val | Val | Arg | Met | Leu | Ser | Arg | Gly |
| | 275 | | | | | 280 | | | | | 285 | | | | |
| Val | Leu | Lys | Lys | Ala | Ser | Arg | Arg | Gly | Val | Asp | Tyr | Ser | Phe | Leu | Phe |
| 290 | | | | | 295 | | | | | 300 | | | | | |
| Met | Arg | Ala | Glu | Gly | Gln | Gln | Leu | His | Glu | Ile | Ala | Glu | Leu | Ile | Asp |
| 305 | | | | | 310 | | | | | 315 | | | | | 320 |
| Ala | Gly | Thr | Ile | Arg | Pro | Val | Val | Asp | Lys | Val | Phe | Gln | Phe | Ala | Gln |
| | | | | 325 | | | | | 330 | | | | | 335 | |
| Thr | Pro | Asp | Ala | Leu | Ala | Tyr | Val | Glu | Thr | Gly | Arg | Ala | Arg | Gly | Lys |
| | | | 340 | | | | | 345 | | | | | 350 | | |
| Val | Val | Val | Thr | Tyr | Ala | Ser | | | | | | | | | |
| | | | | 355 | | | | | | | | | | | |

<210> SEQ ID NO 85
<211> LENGTH: 1032
<212> TYPE: DNA
<213> ORGANISM: Agrobacterium tumefaciens C58

<400> SEQUENCE: 85

```
atgaaagcga ttgtcgccca cggggcaaag gatgtgcgca tcgaagaccg gccggaggaa      60
aagccgggtc cggggcgaggt gcggctccgt ctggcgaggg gcgggatctg cggcagtgat    120
ctgcattatt acaatcatgg cggtttcggc gccgtgcggc ttcgtgaacc catggtgctg    180
ggccatgagg tttccgccgt catcgaggaa ctgggcgaag cgttgaggg gctgaagatc      240
ggcggtctgg tggcggtttc gccgtcgcgc ccatgccgaa cctgccgctt ctgccaggag    300
ggtctgcaca atcagtgcct caacatgcgg ttttatggca cgccatgcc tttcccgcat      360
attcagggcg cgttccggga aattctggtg gcggacgccc tgcaatgcgt gccggccgat    420
ggtctcagcg ccggggaagc cgccatggcg gaaccgctgg cggtgacgct gcatgccaca    480
cgccgggccg gcgatttgct gggaaaacgt gtgctcgtca cggggttgcgg ccccatcggc    540
attctctcca ttctggctgc gcgccggggcg ggtgctgctg aaatcgtcgc caccgacctt    600
tccgatttca cgctcggcaa ggcgcgtgaa gcggggggcgg accgtgtcat caacagcaag    660
gatgagcccg atgcgctcgc cgcttatggt gcaaacaagg gaaccttcga cattctctat    720
gaatgctcgg gtgcggccgt ggcgcttgcc ggcggcatta cggcactgcg gccgcgcggc    780
atcatcgtcc agctcgggct cggcggcgat atgagcctgc cgatgatggc gatcacagcc    840
aaggaactcg acctgcgtgg ttcctttcgc ttccacgagg aattcgccac cggcgtcgag    900
ctgatgcgca agggcctgat cgacgtcaaa cccttcatca cccagaccgt cgatcttgcc    960
gacgccatct cggccttcga attcgcctcg gatcgcagcc gcgccatgaa ggtgcagatc    1020
gccttttcct aa                                                        1032
```

<210> SEQ ID NO 86
<211> LENGTH: 343
<212> TYPE: PRT
<213> ORGANISM: Agrobacterium tumefaciens C58

<400> SEQUENCE: 86

```
Met Lys Ala Ile Val Ala His Gly Ala Lys Asp Val Arg Ile Glu Asp
1               5                   10                  15

Arg Pro Glu Glu Lys Pro Gly Pro Gly Glu Val Arg Leu Arg Leu Ala
            20                  25                  30

Arg Gly Gly Ile Cys Gly Ser Asp Leu His Tyr Tyr Asn His Gly Gly
        35                  40                  45

Phe Gly Ala Val Arg Leu Arg Glu Pro Met Val Leu Gly His Glu Val
    50                  55                  60

Ser Ala Val Ile Glu Glu Leu Gly Glu Gly Val Glu Gly Leu Lys Ile
65                  70                  75                  80

Gly Gly Leu Val Ala Val Ser Pro Ser Arg Pro Cys Arg Thr Cys Arg
                85                  90                  95

Phe Cys Gln Glu Gly Leu His Asn Gln Cys Leu Asn Met Arg Phe Tyr
            100                 105                 110

Gly Ser Ala Met Pro Phe Pro His Ile Gln Gly Ala Phe Arg Glu Ile
        115                 120                 125

Leu Val Ala Asp Ala Leu Gln Cys Val Pro Ala Asp Gly Leu Ser Ala
    130                 135                 140
```

```
Gly Glu Ala Ala Met Ala Glu Pro Leu Ala Val Thr Leu His Ala Thr
145                 150                 155                 160

Arg Arg Ala Gly Asp Leu Leu Gly Lys Arg Val Leu Val Thr Gly Cys
            165                 170                 175

Gly Pro Ile Gly Ile Leu Ser Ile Leu Ala Ala Arg Arg Ala Gly Ala
        180                 185                 190

Ala Glu Ile Val Ala Thr Asp Leu Ser Asp Phe Thr Leu Gly Lys Ala
    195                 200                 205

Arg Glu Ala Gly Ala Asp Arg Val Ile Asn Ser Lys Asp Glu Pro Asp
210                 215                 220

Ala Leu Ala Ala Tyr Gly Ala Asn Lys Gly Thr Phe Asp Ile Leu Tyr
225                 230                 235                 240

Glu Cys Ser Gly Ala Ala Val Ala Leu Ala Gly Gly Ile Thr Ala Leu
                245                 250                 255

Arg Pro Arg Gly Ile Ile Val Gln Leu Gly Leu Gly Gly Asp Met Ser
            260                 265                 270

Leu Pro Met Met Ala Ile Thr Ala Lys Glu Leu Asp Leu Arg Gly Ser
        275                 280                 285

Phe Arg Phe His Glu Glu Phe Ala Thr Gly Val Glu Leu Met Arg Lys
    290                 295                 300

Gly Leu Ile Asp Val Lys Pro Phe Ile Thr Gln Thr Val Asp Leu Ala
305                 310                 315                 320

Asp Ala Ile Ser Ala Phe Glu Phe Ala Ser Asp Arg Ser Arg Ala Met
                325                 330                 335

Lys Val Gln Ile Ala Phe Ser
            340

<210> SEQ ID NO 87
<211> LENGTH: 939
<212> TYPE: DNA
<213> ORGANISM: Agrobacterium tumefaciens C58

<400> SEQUENCE: 87
atgccgatgg cgctcgggca cgaagcggcg ggcgtcgtcg aggcattggg cgaaggcgtg      60
cgcgatcttg agcccggcga tcatgtggtc atggtcttca tgcccagttg cggacattgc     120
ctgccctgtg cggaaggcag gcccgctctg tgcgagccgg cgccgccgc caatgcagca     180
ggcaggctgt tgggtggcgc caccgcctg aactatcatg gcgaggtcgt ccatcatcac     240
cttggtgtgt cggcctttgc cgaatatgcc gtggtgtcgc gcaattcgct ggtcaagatc     300
gaccgcgatc ttccatttgt cgaggcggca ctcttcggct gcgcggttct caccggcgtc     360
ggcgccgtcg tgaataccgg caagggtcagg accggctcga ctgcggtcgt catcggactt     420
ggcggtgtgg gccttgccgc ggttctcgga gcccgggcgg ccggtgccag caagatcgtc     480
gccgtcgacc tttcgcagga aaagcttgca ctcgccagcg aactgggcgc gaccgccatc     540
gtgaacggac gcgatgagga tgccgtcgag caggtccgcg agctcacttc cggcggtgcc     600
gattatgcct tcgagatggc agggtctatt cgcgccctcg aaaacgcctt caggatgacc     660
aaacgtggcg gcaccaccgt taccgccggt ctgccaccgc cgggtgcggc cctgccgctc     720
aacgtcgtgc agctcgtcgg cgaggagcgg acactcaagg gcagctatat cggcacctgt     780
gtgcctctcc gggatattcc gcgcttcatc gcccttatc gcgacggccg gttgccggtg     840
aaccgccttc tgagcggaag gctgaagcta gaagacatca tgaagggtt cgaccgcctg     900
cacgacggaa gcgccgttcg gcaagtcatc gaattctga                           939
```

<210> SEQ ID NO 88
<211> LENGTH: 312
<212> TYPE: PRT
<213> ORGANISM: Agrobacterium tumefaciens C58

<400> SEQUENCE: 88

Met Pro Met Ala Leu Gly His Glu Ala Ala Gly Val Val Glu Ala Leu
1               5                   10                  15

Gly Glu Gly Val Arg Asp Leu Glu Pro Gly Asp His Val Met Val
            20                  25                  30

Phe Met Pro Ser Cys Gly His Cys Leu Pro Cys Ala Glu Gly Arg Pro
        35                  40                  45

Ala Leu Cys Glu Pro Gly Ala Ala Asn Ala Ala Gly Arg Leu Leu
    50                  55                  60

Gly Gly Ala Thr Arg Leu Asn Tyr His Gly Glu Val Val His His His
65                  70                  75                  80

Leu Gly Val Ser Ala Phe Ala Glu Tyr Ala Val Val Ser Arg Asn Ser
                85                  90                  95

Leu Val Lys Ile Asp Arg Asp Leu Pro Phe Val Glu Ala Ala Leu Phe
            100                 105                 110

Gly Cys Ala Val Leu Thr Gly Val Gly Ala Val Val Asn Thr Ala Arg
        115                 120                 125

Val Arg Thr Gly Ser Thr Ala Val Val Ile Gly Leu Gly Gly Val Gly
    130                 135                 140

Leu Ala Ala Val Leu Gly Ala Arg Ala Ala Gly Ala Ser Lys Ile Val
145                 150                 155                 160

Ala Val Asp Leu Ser Gln Glu Lys Leu Ala Leu Ala Ser Glu Leu Gly
                165                 170                 175

Ala Thr Ala Ile Val Asn Gly Arg Asp Glu Asp Ala Val Glu Gln Val
            180                 185                 190

Arg Glu Leu Thr Ser Gly Gly Ala Asp Tyr Ala Phe Glu Met Ala Gly
        195                 200                 205

Ser Ile Arg Ala Leu Glu Asn Ala Phe Arg Met Thr Lys Arg Gly Gly
    210                 215                 220

Thr Thr Val Thr Ala Gly Leu Pro Pro Pro Gly Ala Ala Leu Pro Leu
225                 230                 235                 240

Asn Val Val Gln Leu Val Gly Glu Glu Arg Thr Leu Lys Gly Ser Tyr
                245                 250                 255

Ile Gly Thr Cys Val Pro Leu Arg Asp Ile Pro Arg Phe Ile Ala Leu
            260                 265                 270

Tyr Arg Asp Gly Arg Leu Pro Val Asn Arg Leu Leu Ser Gly Arg Leu
        275                 280                 285

Lys Leu Glu Asp Ile Asn Glu Gly Phe Asp Arg Leu His Asp Gly Ser
    290                 295                 300

Ala Val Arg Gln Val Ile Glu Phe
305                 310

<210> SEQ ID NO 89
<211> LENGTH: 1035
<212> TYPE: DNA
<213> ORGANISM: Agrobacterium tumefaciens C58

<400> SEQUENCE: 89
atgaaacatt ctcaggacaa accacgcctg ctgattgcga tgcgtagcga gcttccagaa    60
ggcttcttcg gtccgcgcga atgggcaagg ctgaatgccg tagcggacat tattccgggc   120
tttccccata cggatttcga cacggcgaac ggtgccgagg ctctcgccga agcggatatt   180

```
ctgctcgctg cctggggtac gccatccctg acacgcgaac gactttcacg cgcgccgcgg    240
ctgaaaatgc tggcctatgc ggcatcatcg gtgcggatgg ttgcgcccgc agaattctgg    300
gagacgtcgg atattctggt cacgacagca gcttccgcca tggccgtgcc ggttgccgaa    360
ttcacctatg cggcaatcat catgtgcggc aaggatgtgt ttcgattgcg ggatgaacat    420
agaacagagc gcggcaccgg cgttttggc agcaggcgcg gcagaagcct gccctatctt     480
ggcaatcatg cccgcaaggt tggcattgtc ggcgcctcgc gcatcgggcg gctggtgatg    540
gagatgctgg cgcgcggcac attcgagatt gccgtttacg atccctttct gtcggcggaa    600
gaggccgcat cccttggcgc gaagaaagcc gaactggacg agcttctcgc atggtccgat    660
gtggtctcgc tgcacgcgcc gatcctgccg gaaacgcacc atatgatcgg cgcccgcgaa    720
ctggcgctga tggcggacca tgccatcttc atcaacacgg cgcggggctg gctggtcgac    780
cacgatgcat tgctgactga agcgatttcc ggacggctgc gcattctgat tgacacgccc    840
gaacccgagc ccctgcccac ggacagcccg ttttacgatc tgcccaatgt cgttctaacc    900
ccccatatag ccggggcgct gggcaatgaa ttgcgcgcac tttccgatct ggccattacc    960
gaaattgaac gtttcgtggc gggacttgcg cccctccacc cggtccacaa gcaggatatg    1020
gaacgtatgg catga                                                     1035
```

<210> SEQ ID NO 90
<211> LENGTH: 331
<212> TYPE: PRT
<213> ORGANISM: Agrobacterium tumefaciens C58

<400> SEQUENCE: 90

```
Met Arg Ser Glu Leu Pro Glu Gly Phe Phe Gly Pro Arg Glu Trp Ala
1               5                   10                  15

Arg Leu Asn Ala Val Ala Asp Ile Ile Pro Gly Phe Pro His Thr Asp
            20                  25                  30

Phe Asp Thr Ala Asn Gly Ala Glu Ala Leu Ala Glu Ala Asp Ile Leu
        35                  40                  45

Leu Ala Ala Trp Gly Thr Pro Ser Leu Thr Arg Glu Arg Leu Ser Arg
    50                  55                  60

Ala Pro Arg Leu Lys Met Leu Ala Tyr Ala Ala Ser Ser Val Arg Met
65                  70                  75                  80

Val Ala Pro Ala Glu Phe Trp Glu Thr Ser Asp Ile Leu Val Thr Thr
                85                  90                  95

Ala Ala Ser Ala Met Ala Val Pro Val Ala Glu Phe Thr Tyr Ala Ala
            100                 105                 110

Ile Ile Met Cys Gly Lys Asp Val Phe Arg Leu Arg Asp Glu His Arg
        115                 120                 125

Thr Glu Arg Gly Thr Gly Val Phe Gly Ser Arg Arg Gly Arg Ser Leu
    130                 135                 140

Pro Tyr Leu Gly Asn His Ala Arg Lys Val Gly Ile Val Gly Ala Ser
145                 150                 155                 160

Arg Ile Gly Arg Leu Val Met Glu Met Leu Ala Arg Gly Thr Phe Glu
                165                 170                 175

Ile Ala Val Tyr Asp Pro Phe Leu Ser Ala Glu Glu Ala Ser Leu
            180                 185                 190

Gly Ala Lys Lys Ala Glu Leu Asp Glu Leu Leu Ala Trp Ser Asp Val
        195                 200                 205

Val Ser Leu His Ala Pro Ile Leu Pro Glu Thr His His Met Ile Gly
    210                 215                 220
```

```
Ala Arg Glu Leu Ala Leu Met Ala Asp His Ala Ile Phe Ile Asn Thr
225                 230                 235                 240

Ala Arg Gly Trp Leu Val Asp His Asp Ala Leu Leu Thr Glu Ala Ile
                245                 250                 255

Ser Gly Arg Leu Arg Ile Leu Ile Asp Thr Pro Glu Pro Glu Pro Leu
            260                 265                 270

Pro Thr Asp Ser Pro Phe Tyr Asp Leu Pro Asn Val Val Leu Thr Pro
        275                 280                 285

His Ile Ala Gly Ala Leu Gly Asn Glu Leu Arg Ala Leu Ser Asp Leu
    290                 295                 300

Ala Ile Thr Glu Ile Glu Arg Phe Val Ala Gly Leu Ala Pro Leu His
305                 310                 315                 320

Pro Val His Lys Gln Asp Met Glu Arg Met Ala
                325                 330

<210> SEQ ID NO 91
<211> LENGTH: 750
<212> TYPE: DNA
<213> ORGANISM: Agrobacterium tumefaciens C58

<400> SEQUENCE: 91
atgcagcgtt ttaccaacag aaccatcgtt gtcgccgggg ccggccggga tatcggccgg      60
gcatgcgcca tccgtttcgc acaggaaggc gccaatgtcg ttcttaccta taatggcgcg     120
gcagagggcg cggccacagc cgttgccgaa atcgaaaagc ttggtcgttc ggctctggcg     180
atcaaggcgg atctcacaaa cgccgccgaa gtcgaggctg ccatatctgc ggctgcggac     240
aagtttgggg agatccacgg cctcgtccat gttgccggcg gcctgatcgc cgcaagaca      300 atcgcagaaa tggatgaagc cttctggcat caggtcctcg acgtcaatct gacatcgctg     360
ttcctgacgg ccaagaccgc attgccgaag atggccaagg gcggcgcgat cgtcactttc     420
tcgtcgcagg ccggccgtga tggcggcggc ccgggcgctc ttgcctatgc cacttccaag     480
ggtgccgtga tgaccttcac ccgcggactt gccaagaag tcggccccaa atccgcgtc      540 aacgccgttt gccccggtat gatctccacc accttccacg ataccttcac caagccggag     600
gtgcgcgaac gggtggccgg cgcgacgtcg ctcaagcgcg aagggtcgag cgaagacgtc     660
gccggtctgg tggccttcct cgcgtctgac gatgccgctt atgtcaccgg cgcctgctac     720
gacatcaatg gcggcgtcct gttttcctga                                     750

<210> SEQ ID NO 92
<211> LENGTH: 249
<212> TYPE: PRT
<213> ORGANISM: Agrobacterium tumefaciens C58

<400> SEQUENCE: 92

Met Gln Arg Phe Thr Asn Arg Thr Ile Val Val Ala Gly Ala Gly Arg
1               5                   10                  15

Asp Ile Gly Arg Ala Cys Ala Ile Arg Phe Ala Gln Glu Gly Ala Asn
            20                  25                  30

Val Val Leu Thr Tyr Asn Gly Ala Ala Glu Gly Ala Ala Thr Ala Val
        35                  40                  45

Ala Glu Ile Glu Lys Leu Gly Arg Ser Ala Leu Ala Ile Lys Ala Asp
    50                  55                  60

Leu Thr Asn Ala Ala Glu Val Glu Ala Ala Ile Ser Ala Ala Ala Asp
65                  70                  75                  80

Lys Phe Gly Glu Ile His Gly Leu Val His Val Ala Gly Gly Leu Ile
```

```
                    85                  90                  95
Ala Arg Lys Thr Ile Ala Glu Met Asp Glu Ala Phe Trp His Gln Val
                100                 105                 110

Leu Asp Val Asn Leu Thr Ser Leu Phe Leu Thr Ala Lys Thr Ala Leu
            115                 120                 125

Pro Lys Met Ala Lys Gly Gly Ala Ile Val Thr Phe Ser Ser Gln Ala
        130                 135                 140

Gly Arg Asp Gly Gly Pro Gly Ala Leu Ala Tyr Ala Thr Ser Lys
145                 150                 155                 160

Gly Ala Val Met Thr Phe Thr Arg Gly Leu Ala Lys Glu Val Gly Pro
                165                 170                 175

Lys Ile Arg Val Asn Ala Val Cys Pro Gly Met Ile Ser Thr Thr Phe
            180                 185                 190

His Asp Thr Phe Thr Lys Pro Glu Val Arg Glu Arg Val Ala Gly Ala
        195                 200                 205

Thr Ser Leu Lys Arg Glu Gly Ser Ser Glu Asp Val Ala Gly Leu Val
    210                 215                 220

Ala Phe Leu Ala Ser Asp Asp Ala Ala Tyr Val Thr Gly Ala Cys Tyr
225                 230                 235                 240

Asp Ile Asn Gly Gly Val Leu Phe Ser
                245
```

```
<210> SEQ ID NO 93
<211> LENGTH: 930
<212> TYPE: DNA
<213> ORGANISM: Escherichia coli DH10B

<400> SEQUENCE: 93
atgtccaaaa agattgccgt gattggcgaa tgcatgattg agctttccga gaaaggcgcg      60
gacgttaagc gcggtttcgg cggcgatacc ctgaacactt ccgtctatat cgcccgtcag     120
gtcgatcctg cggcattaac cgttcattac gtaacggcgc tgggaacgga cagttttagc     180
cagcagatgc tggacgcctg cacggcgag aacgttgata cttccctgac caacggatg      240 gaaaaccgtc tgccgggcct ttactacatt gaaaccgaca gcaccggcga gcgtacgttc     300
tactactggc ggaacgaagc cgccgccaaa ttctggctgg agagtgagca gtctgcggcg     360
atttgcgaag agctggcgaa tttcgattat ctctacctga gcgggattag cctggcgatc     420
ttaagcccga ccagccgcga aaagctgctt tccctgctgc gcgaatgccg cgccaacggc     480
ggaaaagtga ttttcgacaa taactatcgt ccgcgcctgt gggccagcaa agaagagaca     540
cagcaggtgt accaacaaat gctggaatgc acggatatcg ccttcctgac gctggacgac     600
gaagacgcgc tgtggggtca acagccggtg gaagacgtca ttgcgcgcac ccataacgcg     660
ggcgtgaaag aagtggtggt gaaacgcggg gcggattctt gcctggtgtc cattgctggc     720
gaagggttag tggatgttcc ggcggtgaaa ctgccgaaag aaaaagtgat cgataccacc     780
gcagctggcg actctttcag tgccggttat ctggcggtac gtctgacagg cggcagcgcg     840
gaagacgcgg cgaaacgtgg gcacctgacc gcaagtaccg ttattcagta tcgcggcgcg     900
attatcccgc gtgaggcgat gccagcgtaa                                      930
```

```
<210> SEQ ID NO 94
<211> LENGTH: 309
<212> TYPE: PRT
<213> ORGANISM: Escherichia coli DH10B

<400> SEQUENCE: 94
```

```
Met Ser Lys Lys Ile Ala Val Ile Gly Glu Cys Met Ile Glu Leu Ser
1               5                   10                  15

Glu Lys Gly Ala Asp Val Lys Arg Gly Phe Gly Asp Thr Leu Asn
                20                  25                  30

Thr Ser Val Tyr Ile Ala Arg Gln Val Asp Pro Ala Ala Leu Thr Val
            35                  40                  45

His Tyr Val Thr Ala Leu Gly Thr Asp Ser Phe Ser Gln Gln Met Leu
    50                  55                  60

Asp Ala Trp His Gly Glu Asn Val Asp Thr Ser Leu Thr Gln Arg Met
65                  70                  75                  80

Glu Asn Arg Leu Pro Gly Leu Tyr Tyr Ile Glu Thr Ser Thr Gly
                85                  90                  95

Glu Arg Thr Phe Tyr Tyr Trp Arg Asn Glu Ala Ala Ala Lys Phe Trp
            100                 105                 110

Leu Glu Ser Glu Gln Ser Ala Ala Ile Cys Glu Glu Leu Ala Asn Phe
        115                 120                 125

Asp Tyr Leu Tyr Leu Ser Gly Ile Ser Leu Ala Ile Leu Ser Pro Thr
    130                 135                 140

Ser Arg Glu Lys Leu Leu Ser Leu Leu Arg Glu Cys Arg Ala Asn Gly
145                 150                 155                 160

Gly Lys Val Ile Phe Asp Asn Asn Tyr Arg Pro Arg Leu Trp Ala Ser
                165                 170                 175

Lys Glu Glu Thr Gln Gln Val Tyr Gln Gln Met Leu Glu Cys Thr Asp
            180                 185                 190

Ile Ala Phe Leu Thr Leu Asp Asp Glu Asp Ala Leu Trp Gly Gln Gln
        195                 200                 205

Pro Val Glu Asp Val Ile Ala Arg Thr His Asn Ala Gly Val Lys Glu
    210                 215                 220

Val Val Val Lys Arg Gly Ala Asp Ser Cys Leu Val Ser Ile Ala Gly
225                 230                 235                 240

Glu Gly Leu Val Asp Val Pro Ala Val Lys Leu Pro Lys Glu Lys Val
                245                 250                 255

Ile Asp Thr Thr Ala Ala Gly Asp Ser Phe Ser Ala Gly Tyr Leu Ala
            260                 265                 270

Val Arg Leu Thr Gly Gly Ser Ala Glu Asp Ala Ala Lys Arg Gly His
        275                 280                 285

Leu Thr Ala Ser Thr Val Ile Gln Tyr Arg Gly Ala Ile Ile Pro Arg
    290                 295                 300

Glu Ala Met Pro Ala
305

<210> SEQ ID NO 95
<211> LENGTH: 642
<212> TYPE: DNA
<213> ORGANISM: Escherichia coli DH10B

<400> SEQUENCE: 95
atgaaaaact ggaaaacaag tgcagaatca atcctgacca ccggcccggt tgtaccggtt      60
atcgtggtaa aaaaactgga acacgcggtg ccgatggcaa aagcgttggt tgctggtggg     120
gtgcgcgttc tggaagtgac tctgcgtacc gagtgtgcag ttgacgctat ccgtgctatc     180
gccaaagaag tgcctgaagc gattgtgggt gccggtacgg tgctgaatcc acagcagctg     240
gcagaagtca ctgaagcggg tgcacagttc gcaattagcc cgggtctgac cgagccgctg     300
ctgaaagctg ctaccgaagg gactattcct ctgattccgg ggatcagcac tgtttccgaa     360
```

-continued

```
ctgatgctgg gtatggacta cggtttgaaa gagttcaaat tcttcccggc tgaagctaac    420
ggcggcgtga aagccctgca ggcgatcgcg ggtccgttct cccaggtccg tttctgcccg    480
acgggtggta tttctccggc taactaccgt gactacctgg cgctgaaaag cgtgctgtgc    540
atcggtggtt cctggctggt tccggcagat gcgctggaag cgggcgatta cgaccgcatt    600
actaagctgg cgcgtgaagc tgtagaaggc gctaagctgt aa                      642
```

<210> SEQ ID NO 96
<211> LENGTH: 213
<212> TYPE: PRT
<213> ORGANISM: Escherichia coli DH10B

<400> SEQUENCE: 96

```
Met Lys Asn Trp Lys Thr Ser Ala Glu Ser Ile Leu Thr Thr Gly Pro
1               5                   10                  15

Val Val Pro Val Ile Val Val Lys Lys Leu Glu His Ala Val Pro Met
            20                  25                  30

Ala Lys Ala Leu Val Ala Gly Gly Val Arg Val Leu Glu Val Thr Leu
        35                  40                  45

Arg Thr Glu Cys Ala Val Asp Ala Ile Arg Ala Ile Ala Lys Glu Val
    50                  55                  60

Pro Glu Ala Ile Val Gly Ala Gly Thr Val Leu Asn Pro Gln Gln Leu
65                  70                  75                  80

Ala Glu Val Thr Glu Ala Gly Ala Gln Phe Ala Ile Ser Pro Gly Leu
                85                  90                  95

Thr Glu Pro Leu Leu Lys Ala Ala Thr Glu Gly Thr Ile Pro Leu Ile
            100                 105                 110

Pro Gly Ile Ser Thr Val Ser Glu Leu Met Leu Gly Met Asp Tyr Gly
        115                 120                 125

Leu Lys Glu Phe Lys Phe Phe Pro Ala Glu Ala Asn Gly Gly Val Lys
    130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Ala Asp Ala Leu
            180                 185                 190

Glu Ala Gly Asp Tyr Asp Arg Ile Thr Lys Leu Ala Arg Glu Ala Val
        195                 200                 205

Glu Gly Ala Lys Leu
    210
```

<210> SEQ ID NO 97
<211> LENGTH: 780
<212> TYPE: DNA
<213> ORGANISM: Lactobaccilus brevis ATCC 367

<400> SEQUENCE: 97

```
atggcatcaa atggaaaagt agcaatggtt accggtggcg acaaggaat tggtgaagcc    60 atctcgaaac ggttagctaa cgacggcttt gctgtggcaa ttgctgattt gaacttggac   120
aatgccaaca aggtcgtttc tgatattgaa gctgctggtg gcaaggccat gcgtggtcaag   180 accgatgtct ctgatcgtga tagcgtgttt gctgcggtta atgaagcggc cgacaagctg   240
ggcggctttg acgttatcgt taataacgcc ggccttggcc caaccacgcc aattgacacc   300
atcacccaag aacagtttga tacgcttaat gcggttatcg tttaacg tgggtggggt tctttggggc   360
```

```
attcaagcag cccatgcgaa gttcaaggaa ttgggtcatg gtgggaagat catttccgcg    420
acgtctcaag ccggggttgt tggtaacccg aacttagctc tgtacagtgg aactaagttt    480
gccattcgtg gtgtgaccca agttgcggcg cgtgacttag ccgctgaagg tatcacggtc    540
aatgcttatg cacccgggat tgttaagaca ccaatgatgt ttgacatcgc tcacaaggtt    600
ggtcaaaatg ctggtaaaga cgacgaatgg gggatgcaaa ccttctcaaa ggacatcgct    660
ttatgtcgat tgtcagaacc agaagatgtg gctaacgggg tggctttctt agccggtccc    720
gattctaact acattacggg tcaaacactt gaagttgatg gtgggatgca gttccactaa    780
```

<210> SEQ ID NO 98
<211> LENGTH: 259
<212> TYPE: PRT
<213> ORGANISM: Lactobaccilus brevis ATCC 367

<400> SEQUENCE: 98

Met Ala Ser Asn Gly Lys Val Ala Met Val Thr Gly Gly Gln Gly
1               5                   10                  15

Ile Gly Glu Ala Ile Ser Lys Arg Leu Ala Asn Asp Gly Phe Ala Val
            20                  25                  30

Ala Ile Ala Asp Leu Asn Leu Asp Asn Ala Asn Lys Val Ser Asp
        35                  40                  45

Ile Glu Ala Ala Gly Gly Lys Ala Ile Ala Val Lys Thr Asp Val Ser
    50                  55                  60

Asp Arg Asp Ser Val Phe Ala Ala Val Asn Glu Ala Ala Asp Lys Leu
65                  70                  75                  80

Gly Gly Phe Asp Val Ile Val Asn Asn Ala Gly Leu Gly Pro Thr Thr
                85                  90                  95

Pro Ile Asp Thr Ile Thr Gln Glu Gln Phe Asp Thr Val Tyr His Val
            100                 105                 110

Asn Val Gly Gly Val Leu Trp Gly Ile Gln Ala Ala His Ala Lys Phe
        115                 120                 125

Lys Glu Leu Gly His Gly Gly Lys Ile Ile Ser Ala Thr Ser Gln Ala
    130                 135                 140

Gly Val Val Gly Asn Pro Asn Leu Ala Leu Tyr Ser Gly Thr Lys Phe
145                 150                 155                 160

Ala Ile Arg Gly Val Thr Gln Val Ala Ala Arg Asp Leu Ala Ala Glu
                165                 170                 175

Gly Ile Thr Val Asn Ala Tyr Ala Pro Gly Ile Val Lys Thr Pro Met
            180                 185                 190

Met Phe Asp Ile Ala His Lys Val Gly Gln Asn Ala Gly Lys Asp Asp
        195                 200                 205

Glu Trp Gly Met Gln Thr Phe Ser Lys Asp Ile Ala Leu Cys Arg Leu
    210                 215                 220

Ser Glu Pro Glu Asp Val Ala Asn Gly Val Ala Phe Leu Ala Gly Pro
225                 230                 235                 240

Asp Ser Asn Tyr Ile Thr Gly Gln Thr Leu Glu Val Asp Gly Gly Met
                245                 250                 255

Gln Phe His

<210> SEQ ID NO 99
<211> LENGTH: 1089
<212> TYPE: DNA
<213> ORGANISM: Pseudomonas putida KT2440

<400> SEQUENCE: 99

```
atgaatgacc tgagccacac ccacatgcgc gcggccgtct ggcatggccg ccacgatatt    60
cgtgtcgaac aggtaccttt gccggccgac cctgcgccgg gctgggtgca gatcaaggtg   120
gactggtgcg gcatctgcgg ctccgacctg cacgaatatg ttgccggccc ggtgttcatc   180
ccggtagagg ccccgcaccc gctgaccggc attcagggcc agtgcatcct cggccacgaa   240
ttctgcggcc acatcgccaa gcttggcgaa ggcgtggaag ctatgccgt aggcgacccg    300
gtggcggcag acgcgtgcca gcattgtggt acctgctatt actgcaccca tggcctgtac   360
aacatctgcg aacgcctggc gttcaccggc ctgatgaaca cggtgccttt cgccgagctg   420
gtcaacgtgc cgccaaccct gctctaccgg ctgccgcagg gcttccctgc cgaagccggg   480
gcactgatcg agccgctggc ggtgggtatg cacgcggtga aaaaggccgg cagcctgctt   540
gggcaaaccg ttgtagtggt tggggccggc accatcggcc tgtgcaccat catgtgcgcc   600
aaggctgcag gtgcggcaca ggtcatcgcc cttgagatgt cctctgcgcg caaagccaag   660
gccaaggaag cgggcgccaa cgtggtgctg acccccagcc agtgcgatgc cctggcggaa   720
atccgcgcac tgactgctgg gctgggcgcc gatgtgagtt ttgagtgcat cggcaacaaa   780
catacggcca gctggccat cgacaccatc cgcaaagcag gcaagtgcgt gctggtgggt   840
attttcgaag agcccagcga gttcaacttc ttcgagctgg tgtccaccga aagcaagtg    900
ctgggggcgt tggcgtacaa cggcgagttt gctgacgtga ttgccttcat tgctgatggt   960
cggctggata ttcgcccgct ggtaaccggc cggatcggat tggagcagat tgtcgagctg  1020
ggcttcgagg aactggtgaa caacaaagag gagaacgtga agatcatcgt ttcaccaggt  1080
gtgcgctga                                                          1089
```

<210> SEQ ID NO 100
<211> LENGTH: 362
<212> TYPE: PRT
<213> ORGANISM: Pseudomonas putida KT2440

<400> SEQUENCE: 100

```
Met Asn Asp Leu Ser His Thr His Met Arg Ala Ala Val Trp His Gly
1               5                   10                  15

Arg His Asp Ile Arg Val Glu Gln Val Pro Leu Pro Ala Asp Pro Ala
            20                  25                  30

Pro Gly Trp Val Gln Ile Lys Val Asp Trp Cys Gly Ile Cys Gly Ser
        35                  40                  45

Asp Leu His Glu Tyr Val Ala Gly Pro Val Phe Ile Pro Val Glu Ala
    50                  55                  60

Pro His Pro Leu Thr Gly Ile Gln Gly Gln Cys Ile Leu Gly His Glu
65                  70                  75                  80

Phe Cys Gly His Ile Ala Lys Leu Gly Glu Gly Val Glu Gly Tyr Ala
                85                  90                  95

Val Gly Asp Pro Val Ala Ala Asp Ala Cys Gln His Cys Gly Thr Cys
            100                 105                 110

Tyr Tyr Cys Thr His Gly Leu Tyr Asn Ile Cys Glu Arg Leu Ala Phe
        115                 120                 125

Thr Gly Leu Met Asn Asn Gly Ala Phe Ala Glu Leu Val Asn Val Pro
    130                 135                 140

Ala Asn Leu Leu Tyr Arg Leu Pro Gln Gly Phe Pro Ala Glu Ala Gly
145                 150                 155                 160

Ala Leu Ile Glu Pro Leu Ala Val Gly Met His Ala Val Lys Lys Ala
                165                 170                 175

Gly Ser Leu Leu Gly Gln Thr Val Val Val Val Gly Ala Gly Thr Ile
```

```
                        180                 185                 190
Gly Leu Cys Thr Ile Met Cys Ala Lys Ala Ala Gly Ala Ala Gln Val
                195                 200                 205

Ile Ala Leu Glu Met Ser Ser Ala Arg Lys Ala Lys Ala Lys Glu Ala
            210                 215                 220

Gly Ala Asn Val Val Leu Asp Pro Ser Gln Cys Asp Ala Leu Ala Glu
225                 230                 235                 240

Ile Arg Ala Leu Thr Ala Gly Leu Gly Ala Asp Val Ser Phe Glu Cys
                245                 250                 255

Ile Gly Asn Lys His Thr Ala Lys Leu Ala Ile Asp Thr Ile Arg Lys
            260                 265                 270

Ala Gly Lys Cys Val Leu Val Gly Ile Phe Glu Glu Pro Ser Glu Phe
        275                 280                 285

Asn Phe Phe Glu Leu Val Ser Thr Glu Lys Gln Val Leu Gly Ala Leu
            290                 295                 300

Ala Tyr Asn Gly Glu Phe Ala Asp Val Ile Ala Phe Ile Ala Asp Gly
305                 310                 315                 320

Arg Leu Asp Ile Arg Pro Leu Val Thr Gly Arg Ile Gly Leu Glu Gln
                325                 330                 335

Ile Val Glu Leu Gly Phe Glu Glu Leu Val Asn Asn Lys Glu Glu Asn
            340                 345                 350

Val Lys Ile Ile Val Ser Pro Gly Val Arg
        355                 360

<210> SEQ ID NO 101
<211> LENGTH: 771
<212> TYPE: DNA
<213> ORGANISM: Klebsiella pneumoniae MGH78578

<400> SEQUENCE: 101
atgaaaaaag tcgcacttgt taccggcgcc ggccagggga ttggtaaagc tatcgccctt      60
cgtctggtga aggatggatt tgccgtggcc attgccgatt ataacgacgc caccgccaaa     120
gcggtcgcct cggaaatcaa ccaggccggc ggacacgccg tggcggtgaa agtggatgtc     180
tccgaccgcg atcaggtatt tgccgccgtt gaacaggcgc gcaaaacgct gggcggcttc     240
gacgtcatcg tcaataacgc cggtgtggca ccgtctacgc cgatcgagtc cattaccccg     300
gagattgtcg acaaagtcta caacatcaac gtcaaagggg tgatctgggg tattcaggcg     360
gcggtcgagg cctttaagaa agaggggcac ggcgggaaaa tcatcaacgc ctgttcccag     420
gccggccacg tcggcaaccc ggagctggcg gtgtatagct ccagtaaatt cgcggtacgc     480
ggcttaaccc agaccgccgc tcgcgacctc gcgccgctgg catcaccggt caacggctac     540
tgcccgggga ttgtcaaaac gccaatgtgg gccgaaattg accgccaggt gtccgaagcc     600
gccggtaaac cgctgggcta cggtaccgcc gagttcgcca aacgcatcac tctcggtcgt     660
ctgtccgagc cggaagatgt cgccgcctgc gtctcctatc ttgccagccc ggattctgat     720
tacatgaccg tcagtcgtt gctgatcgac ggcgggatgg tatttaacta a              771

<210> SEQ ID NO 102
<211> LENGTH: 256
<212> TYPE: PRT
<213> ORGANISM: Klebsiella pneumoniae MGH78578

<400> SEQUENCE: 102

Met Lys Lys Val Ala Leu Val Thr Gly Ala Gly Gln Gly Ile Gly Lys
1               5                   10                  15
```

```
Ala Ile Ala Leu Arg Leu Val Lys Asp Gly Phe Ala Val Ala Ile Ala
         20                  25                  30

Asp Tyr Asn Asp Ala Thr Ala Lys Ala Val Ala Ser Glu Ile Asn Gln
         35                  40                  45

Ala Gly Gly His Ala Val Ala Val Lys Val Asp Val Ser Asp Arg Asp
 50                  55                  60

Gln Val Phe Ala Ala Val Glu Gln Ala Arg Lys Thr Leu Gly Gly Phe
 65                  70                  75                  80

Asp Val Ile Val Asn Asn Ala Gly Val Ala Pro Ser Thr Pro Ile Glu
                 85                  90                  95

Ser Ile Thr Pro Glu Ile Val Asp Lys Val Tyr Asn Ile Asn Val Lys
             100                 105                 110

Gly Val Ile Trp Gly Ile Gln Ala Ala Val Glu Ala Phe Lys Lys Glu
             115                 120                 125

Gly His Gly Gly Lys Ile Ile Asn Ala Cys Ser Gln Ala Gly His Val
130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                 165                 170                 175

Val Asn Gly Tyr Cys Pro Gly Ile Val Lys Thr Pro Met Trp Ala Glu
             180                 185                 190

Ile Asp Arg Gln Val Ser Glu Ala Ala Gly Lys Pro Leu Gly Tyr Gly
             195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                 245                 250                 255
```

<210> SEQ ID NO 103
<211> LENGTH: 1665
<212> TYPE: DNA
<213> ORGANISM: Klebsiella pneumoniae MGH78578

<400> SEQUENCE: 103

```
atgagatcga aaagatttga agcactggcg aaacgccctg tgaatcagga tggtttcgtt      60
aaggagtgga ttgaagaggg ctttatcgcg atggaaagcc ctaacgatcc caaaccttct     120
atccgcatcg tcaacggcgc ggtgaccgaa ctcgacgata aaccggttga gcagttcgac     180
ctgattgacc actttatcgc gcgctacggc attaatctcg cccgggccga agaagtgatg     240
gccatggatt cggttaagct cgccaacatg ctctgcgacc cgaacgttaa acgcagcgac     300
atcgtgccgc tcactaccgc gatgaccccg gcgaaaatcg tggaagtggt gtcgcatatg     360
aacgtggtcg agatgatgat ggcgatgcaa aaaatgcgcg cccgccgcac gccgtcccag     420
caggcgcatg tcactaatat caaagataat ccggtacaga ttgccgccga cgccgctgaa     480
ggcgcatggc gcggctttga cgagcaggag accaccgtcg ccgtgcgcg  ctacgcgccg     540 ttcaacgcca tcgccctgct ggtcggttca caggttggcc gccccggcgt cctcacccag     600
tgttcgctgg aagaagccac cgagctgaaa ctgggcatgc tgggccacac ctgctatgcc     660
gaaaccattt cggtatacgg tacggaaccg gtgtttaccg atggcgatga caccccgtgg     720
tcgaaaggct tcctcgcctc ctcctacgcc tcgcgcggcc tgaaaatgcg ctttacctcc     780
ggttccggct cggaggtgca gatgggctat gccgaaggca atcgatgct  ttatctcgaa     840
```

-continued

```
gcgcgctgca tctacatcac caaagccgcc ggggtgcaag gcctgcagaa tggctccgtc    900
agctgtatcg gcgtgccgtc cgccgtgccg tccgggatcc gcgccgtact ggcggaaaac    960
ctgatctgct cagcgctgga tctggagtgc gcctccagca acgatcaaac ctttacccac   1020
tcggatatgc ggcgtaccgc gcgtctgctg atgcagttcc tgccaggtac cgactttatc   1080
tcctccggtt actcggcggt gccgaactac gacaacatgt tcgccggttc caacgaagat   1140
gccgaagact tcgatgacta caacgtgatc cagcgcgacc tgaaggtcga tggcggcctg   1200
cggccggtgc gtgaagagga cgtgatcgcc attcgcaaca agccgcccg cgcgctgcag    1260 gcggtatttg ccggcatggg tttgccgcct attacggatg aagaagtaga agccgccacc   1320
tacgcccacg gttcaaaaga tatgcctgag cgcaatatcg tcgaggacat caagtttgct   1380
caggagatca tcaacaagaa ccgcaacggc ctggaggtgg tgaaagccct ggcgaaaggc   1440
ggcttccccg atgtcgccca ggacatgctc aatattcaga agccaagct caccggcgac    1500 tacctgcata cctccgccat cattgttggc gagggccagg tgctctcggc cgtgaatgac   1560
gtgaacgatt atgccggtcc ggcaacaggc taccgcctgc aaggcgagcg ctgggaagag   1620
attaaaaata tcccgggcgc gctcgatccc aatgaacttg gctaa                   1665
```

<210> SEQ ID NO 104
<211> LENGTH: 554
<212> TYPE: PRT
<213> ORGANISM: Klebsiella pneumoniae MGH78578

<400> SEQUENCE: 104

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Arg Ile Val Asn Gly Ala Val
        35                  40                  45

Thr Glu Leu Asp Asp Lys Pro Val Glu Gln Phe Asp Leu Ile Asp His
    50                  55                  60

Phe Ile Ala Arg Tyr Gly Ile Asn Leu Ala Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Asp Ile Val Pro Leu Thr Thr Ala Met Thr Pro Ala Lys
            100                 105                 110

Ile Val Glu Val Val Ser His Met Asn Val Val Glu Met Met Met Ala
        115                 120                 125

Met Gln Lys Met Arg Ala Arg Thr Pro Ser Gln Gln Ala His Val
    130                 135                 140

Thr Asn Ile Lys Asp Asn Pro Val Gln Ile Ala Ala Asp Ala Ala Glu
145                 150                 155                 160

Gly Ala Trp Arg Gly Phe Asp Glu Gln Glu Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
```

```
                225                 230                 235                 240
Ser Lys Gly Phe Leu Ala Ser Ser Tyr Ala Ser Arg Gly Leu Lys Met
                    245                 250                 255

Arg Phe Thr Ser Gly Ser Gly Ser Glu Val Gln Met Gly Tyr Ala Glu
                260                 265                 270

Gly Lys Ser Met Leu Tyr Leu Glu Ala Arg Cys Ile Tyr Ile Thr Lys
            275                 280                 285

Ala Ala Gly Val Gln Gly Leu Gln Asn Gly Ser Val Ser Cys Ile Gly
        290                 295                 300

Val Pro Ser Ala Val Pro Ser Gly Ile Arg Ala Val Leu Ala Glu Asn
305                 310                 315                 320

Leu Ile Cys Ser Ala Leu Asp Leu Glu Cys Ala Ser Ser Asn Asp Gln
                325                 330                 335

Thr Phe Thr His Ser Asp Met Arg Arg Thr Ala Arg Leu Leu Met Gln
                340                 345                 350

Phe Leu Pro Gly Thr Asp Phe Ile Ser Ser Gly Tyr Ser Ala Val Pro
            355                 360                 365

Asn Tyr Asp Asn Met Phe Ala Gly Ser Asn Glu Asp Ala Glu Asp Phe
        370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Lys Gly
465                 470                 475                 480

Gly Phe Pro Asp Val Ala Gln Asp Met Leu Asn Ile Gln Lys Ala Lys
                485                 490                 495

Leu Thr Gly Asp Tyr Leu His Thr Ser Ala Ile Ile Val Gly Glu Gly
            500                 505                 510

Gln Val Leu Ser Ala Val Asn Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540

Pro Gly Ala Leu Asp Pro Asn Glu Leu Gly
545                 550

<210> SEQ ID NO 105
<211> LENGTH: 690
<212> TYPE: DNA
<213> ORGANISM: Klebsiella pneumoniae MGH78578

<400> SEQUENCE: 105
atggaaatta cgaaacgct gctgcgccag attatcgaag aggtgctgtc ggagatgaaa      60
tcaggcgcag ataagccggt ctcctttagc gcgcctgcgg cttctgtcgc ctctgccgcg     120
ccggtcgccg ttgcgcctgt gtccggcgac agcttcctga cggaaatcgg cgaagccaaa    180
cccggcacgc agcaggatga agtcattatt gccgtcgggc agcgtttggt ctggcgcaa    240 accgccaata tcgtcggcat tccgcataaa aatattctgc gcgaagtgat cgccggcatt    300
```

-continued

| | |
|---|---:|
| gaggaagaag gcatcaaagc ccgggtgatc cgctgcttta agtcttctga cgtcgccttc | 360 |
| gtggcagtgg aaggcaaccg cctgagcggc tccggcatct cgatcggtat tcagtcgaaa | 420 |
| ggcaccaccg tcatccacca gcgcggcctg ccgccgcttt ccaatctgga actcttcccg | 480 |
| caggcgccgc tgctgacgct ggaaacctac cgtcagattg gcaaaaacgc cgcgcgctac | 540 |
| gccaaacgcg agtcgccgca gccggtgccg acgcttaacg atcagatggc tcgtcccaaa | 600 |
| taccaggcga gtcggccat tttgcacatt aaagagacca aatacgtggt gacgggcaaa | 660 |
| aacccgcagg aactgcgcgt ggcgctttaa | 690 |

<210> SEQ ID NO 106
<211> LENGTH: 229
<212> TYPE: PRT
<213> ORGANISM: Klebsiella pneumoniae MGH78578

<400> SEQUENCE: 106

```
Met Glu Ile Asn Glu Thr Leu Leu Arg Gln Ile Ile Glu Glu Val Leu
1               5                   10                  15

Ser Glu Met Lys Ser Gly Ala Asp Lys Pro Val Ser Phe Ser Ala Pro
            20                  25                  30

Ala Ala Ser Val Ala Ser Ala Ala Pro Val Ala Val Ala Pro Val Ser
        35                  40                  45

Gly Asp Ser Phe Leu Thr Glu Ile Gly Glu Ala Lys Pro Gly Thr Gln
    50                  55                  60

Gln Asp Glu Val Ile Ile Ala Val Gly Pro Ala Phe Gly Leu Ala Gln
65                  70                  75                  80

Thr Ala Asn Ile Val Gly Ile Pro His Lys Asn Ile Leu Arg Glu Val
                85                  90                  95

Ile Ala Gly Ile Glu Glu Glu Gly Ile Lys Ala Arg Val Ile Arg Cys
            100                 105                 110

Phe Lys Ser Ser Asp Val Ala Phe Val Ala Val Glu Gly Asn Arg Leu
        115                 120                 125

Ser Gly Ser Gly Ile Ser Ile Gly Ile Gln Ser Lys Gly Thr Thr Val
    130                 135                 140

Ile His Gln Arg Gly Leu Pro Pro Leu Ser Asn Leu Glu Leu Phe Pro
145                 150                 155                 160

Gln Ala Pro Leu Leu Thr Leu Glu Thr Tyr Arg Gln Ile Gly Lys Asn
                165                 170                 175

Ala Ala Arg Tyr Ala Lys Arg Glu Ser Pro Gln Pro Val Pro Thr Leu
            180                 185                 190

Asn Asp Gln Met Ala Arg Pro Lys Tyr Gln Ala Lys Ser Ala Ile Leu
        195                 200                 205

His Ile Lys Glu Thr Lys Tyr Val Val Thr Gly Lys Asn Pro Gln Glu
    210                 215                 220

Leu Arg Val Ala Leu
225
```

<210> SEQ ID NO 107
<211> LENGTH: 525
<212> TYPE: DNA
<213> ORGANISM: Klebsiella pneumoniae MGH78578

<400> SEQUENCE: 107

| | |
|---|---:|
| atgaataccg acgcaattga atccatggta cgcgacgtgc tgagccggat gaacagccta | 60 |
| caggacggga taacgcccgc gccagccgcg ccgacaaacg acaccgttcg ccagccaaaa | 120 |
| gttagcgact acccgttagc gacccgccat ccggagtggg tcaaaaccgc taccaataaa | 180 |

```
acgctcgatg acctgacgct ggagaacgta ttaagcgatc gcgttacggc gcaggacatg    240
cgcatcactc cggaaacgct gcgtatgcag gcggcgatcg cccaggatgc cggacgcgat    300
cggctggcga tgaactttga gcgggccgca gagctcaccg cggttcccga cgaccgaatc    360
cttgagatct acaacgccct gcgcccatac cgttccaccc aggcggagct actggcgatc    420
gctgatgacc tcgagcatcg ctaccaggca cgactctgtg ccgcctttgt tcgggaagcg    480
gccgggctgt acatcgagcg taagaagctg aaaggcgacg attaa                    525
```

<210> SEQ ID NO 108
<211> LENGTH: 174
<212> TYPE: PRT
<213> ORGANISM: Klebsiella pneumoniae MGH78578

<400> SEQUENCE: 108

```
Met Asn Thr Asp Ala Ile Glu Ser Met Val Arg Asp Val Leu Ser Arg
1               5                   10                  15

Met Asn Ser Leu Gln Asp Gly Ile Thr Pro Ala Pro Ala Pro Thr
            20                  25                  30

Asn Asp Thr Val Arg Gln Pro Lys Val Ser Asp Tyr Pro Leu Ala Thr
        35                  40                  45

Arg His Pro Glu Trp Val Lys Thr Ala Thr Asn Lys Thr Leu Asp Asp
    50                  55                  60

Leu Thr Leu Glu Asn Val Leu Ser Asp Arg Val Thr Ala Gln Asp Met
65                  70                  75                  80

Arg Ile Thr Pro Glu Thr Leu Arg Met Gln Ala Ile Ala Gln Asp
                85                  90                  95

Ala Gly Arg Asp Arg Leu Ala Met Asn Phe Glu Arg Ala Ala Glu Leu
            100                 105                 110

Thr Ala Val Pro Asp Asp Arg Ile Leu Glu Ile Tyr Asn Ala Leu Arg
        115                 120                 125

Pro Tyr Arg Ser Thr Gln Ala Glu Leu Leu Ala Ile Ala Asp Asp Leu
    130                 135                 140

Glu His Arg Tyr Gln Ala Arg Leu Cys Ala Ala Phe Val Arg Glu Ala
145                 150                 155                 160

Ala Gly Leu Tyr Ile Glu Arg Lys Lys Leu Lys Gly Asp Asp
                165                 170
```

<210> SEQ ID NO 109
<211> LENGTH: 789
<212> TYPE: DNA
<213> ORGANISM: Pseudomonas putida KT2440

<400> SEQUENCE: 109

```
atgacagtca attatgattt tccggaaaaa gtcgtgctgg ttaccggcgc tggctctggt    60
attggccgtg ccactgcgct tgccttcgcg cagtcgggcg catccgttgc ggtcgcagac    120
atctcgactg accacggttt gaaaaccgta gagttggtca agccgaagg aggcgaggcg    180 accttcttcc atgtcgatgt aggctctgaa cccagcgtcc agtcgatgct ggctggtgtc    240
gtggcgcatt acggcggcct ggacattgcg cacaacaacg ccggcattga ggccaatatc    300
gtgccgctgg ccgagctgga ctccgacaac tggcgtcgtg tcatcgatgt gaacctttcc    360
tcggtgttct attgcctgaa aggtgaaatc cctctgatgc tgaaaggggg cggcggcgcc    420
attgtgaata ccgcatcggc ctccgggctg attggcggct atcgcctttc cgggtatacc    480
gccacgaagc acgcgtagt ggggctgact aaggctgctg ctatcgatta tgcaaaccag    540
```

```
aatatccgga ttaatgccgt gtgccctggt ccagttgact ccccattcct ggctgacatg    600
ccgcaaccca tgcgcgatcg acttctcttt ggcactccaa ttggacgatt ggccaccgca    660
gaggagatcg cgcgttcggt tctgtggctg tgttctgacg atgcaaaata cgtggtgggc    720
cattcgatgt cagtcgacgg tggcgtggca gtgactgcgg ttggtactcg aatggatgat    780
ctcttttaa                                                            789
```

```
<210> SEQ ID NO 110
<211> LENGTH: 262
<212> TYPE: PRT
<213> ORGANISM: Pseudomonas putida KT2440

<400> SEQUENCE: 110

Met Thr Val Asn Tyr Asp Phe Ser Gly Lys Val Val Leu Val Thr Gly
1               5                   10                  15

Ala Gly Ser Gly Ile Gly Arg Ala Thr Ala Leu Ala Phe Ala Gln Ser
            20                  25                  30

Gly Ala Ser Val Ala Val Ala Asp Ile Ser Thr Asp His Gly Leu Lys
        35                  40                  45

Thr Val Glu Leu Val Lys Ala Glu Gly Gly Ala Thr Phe Phe His
    50                  55                  60

Val Asp Val Gly Ser Glu Pro Ser Val Gln Ser Met Leu Ala Gly Val
65                  70                  75                  80

Val Ala His Tyr Gly Gly Leu Asp Ile Ala His Asn Asn Ala Gly Ile
                85                  90                  95

Glu Ala Asn Ile Val Pro Leu Ala Glu Leu Asp Ser Asp Asn Trp Arg
            100                 105                 110

Arg Val Ile Asp Val Asn Leu Ser Ser Val Phe Tyr Cys Leu Lys Gly
        115                 120                 125

Glu Ile Pro Leu Met Leu Lys Arg Gly Gly Gly Ala Ile Val Asn Thr
    130                 135                 140

Ala Ser Ala Ser Gly Leu Ile Gly Gly Tyr Arg Leu Ser Gly Tyr Thr
145                 150                 155                 160

Ala Thr Lys His Gly Val Val Gly Leu Thr Lys Ala Ala Ala Ile Asp
                165                 170                 175

Tyr Ala Asn Gln Asn Ile Arg Ile Asn Ala Val Cys Pro Gly Pro Val
            180                 185                 190

Asp Ser Pro Phe Leu Ala Asp Met Pro Gln Pro Met Arg Asp Arg Leu
        195                 200                 205

Leu Phe Gly Thr Pro Ile Gly Arg Leu Ala Thr Ala Glu Glu Ile Ala
    210                 215                 220

Arg Ser Val Leu Trp Leu Cys Ser Asp Asp Ala Lys Tyr Val Val Gly
225                 230                 235                 240

His Ser Met Ser Val Asp Gly Gly Val Ala Val Thr Ala Val Gly Thr
                245                 250                 255

Arg Met Asp Asp Leu Phe
            260
```

```
<210> SEQ ID NO 111
<211> LENGTH: 762
<212> TYPE: DNA
<213> ORGANISM: Pseudomonas putida KT2440

<400> SEQUENCE: 111
atgagcatga cctttctgg ccaggtagcc ctggtgaccg gcgcgggtgc cggcatcggc    60
cgggcaaccg ccctggcgtt cgcccacgag ggcatgaaag tggtggtggc ggacctcgac   120
```

-continued

```
ccggtcggcg gcgaggccac cgtggcgcag atccacgcgg caggcggcga agcgctgttc      180
attgcctgcg acgtgacccg cgacgccgag gtgcgccagt tgcatgagcg cctgatggcc      240
gcctacggcc ggctggacta cgccttcaac aacgccggga tcgagatcga gcaacaccgc      300
ctggccgaag gcagcgaagc ggagttcgat gccatcatgg gcgtgaacgt gaagggcgtg      360
tggttgtgca tgaagtatca gttgcccttg ttgctggccc aaggcggtgg ggccatcgtc      420
aataccgcgt cggtggcggg gctaggggcg cgccaaaga tgagcatcta cagcgccagc      480
aagcatgcgg tcatcggtct gaccaagtcg gcggccatcg agtacgccaa gaagggcatc      540
cgcgtgaacg ccgtgtgccc ggccgtgatc gacaccgaca tgttccgccg cgcttaccag      600
gccgacccgc gcaaggccga gttcgccgca gccatgcacc cggtagggcg cattggcaag      660
gtcgaggaaa tcgccagcgc cgtgctgtat ctgtgcagtg acggcgcggc gtttaccacc      720
gggcattgcc tgacggtgga tggtggggct acggcgatct ga                         762
```

<210> SEQ ID NO 112
<211> LENGTH: 253
<212> TYPE: PRT
<213> ORGANISM: Pseudomonas putida KT2440

<400> SEQUENCE: 112

```
Met Ser Met Thr Phe Ser Gly Gln Val Ala Leu Val Thr Gly Ala Gly
1               5                   10                  15

Ala Gly Ile Gly Arg Ala Thr Ala Leu Ala Phe Ala His Glu Gly Met
            20                  25                  30

Lys Val Val Ala Asp Leu Asp Pro Val Gly Gly Glu Ala Thr Val
        35                  40                  45

Ala Gln Ile His Ala Ala Gly Gly Glu Ala Leu Phe Ile Ala Cys Asp
    50                  55                  60

Val Thr Arg Asp Ala Glu Val Arg Gln Leu His Glu Arg Leu Met Ala
65                  70                  75                  80

Ala Tyr Gly Arg Leu Asp Tyr Ala Phe Asn Asn Ala Gly Ile Glu Ile
                85                  90                  95

Glu Gln His Arg Leu Ala Glu Gly Ser Glu Ala Glu Phe Asp Ala Ile
            100                 105                 110

Met Gly Val Asn Val Lys Gly Val Trp Leu Cys Met Lys Tyr Gln Leu
        115                 120                 125

Pro Leu Leu Leu Ala Gln Gly Gly Ala Ile Val Asn Thr Ala Ser
    130                 135                 140

Val Ala Gly Leu Gly Ala Ala Pro Lys Met Ser Ile Tyr Ser Ala Ser
145                 150                 155                 160

Lys His Ala Val Ile Gly Leu Thr Lys Ser Ala Ala Ile Glu Tyr Ala
                165                 170                 175

Lys Lys Gly Ile Arg Val Asn Ala Val Cys Pro Ala Val Ile Asp Thr
            180                 185                 190

Asp Met Phe Arg Arg Ala Tyr Gln Ala Asp Pro Arg Lys Ala Glu Phe
        195                 200                 205

Ala Ala Ala Met His Pro Val Gly Arg Ile Gly Lys Val Glu Glu Ile
    210                 215                 220

Ala Ser Ala Val Leu Tyr Leu Cys Ser Asp Gly Ala Ala Phe Thr Thr
225                 230                 235                 240

Gly His Cys Leu Thr Val Asp Gly Gly Ala Thr Ala Ile
                245                 250
```

<210> SEQ ID NO 113
<211> LENGTH: 810
<212> TYPE: DNA
<213> ORGANISM: Pseudomonas putida KT2440

<400> SEQUENCE: 113

```
atgtcttttc aaaacaaaat cgttgtgctc acaggcgcag cttctggcat cggcaaagcg      60
acagcacagc tgctagtgga gcagggcgcc catgtggttg ccatggatct taaaagcgac     120
ttgcttcaac aagcattcgg cagtgaggag cacgttctgt gcatccctac cgacgtcagc     180
gatagcgaag ccgtgcgagc cgccttccag gcagtggacg cgaaatttgg ccgtgtcgac     240
gtgattatta cgccgcgggg catcaacgca cctacgcgag aagccaacca gaaaatggtt     300
gatgccaacg tcgctgccct cgatgccatg aagagcgggc gggcgcccac tttcgacttc     360
ctggccgata cctcggatca ggatttccgg cgcgtaatgg aagtcaattt gttcagccag     420
ttttactgca ttcgagaggg tgttccgctg atgcgccgag cgggtggcgg cagcatcgtc     480
aacatctcca gcgtggcagc gctcctgggc gtggcaatgc cactttacta ccccgcctcc     540
aaggcggcgg tgctgggcct cacccgtgca gcggcagctg agttggcacc ttacaacatt     600
cgtgtgaatg ccatcgctcc aggctctgtc gacacaccat tgatgcatga gcaaccaccg     660
gaagtcgttc agttcctggt cagcatgcaa cccatcaagc ggctggccca acccgaggag     720
cttgcccaaa gcatcctgtt ccttgccggt gagcattcgt ccttcatcac cggacagacg     780
ctttctccca acggcgggat gcacatgtaa                                      810
```

<210> SEQ ID NO 114
<211> LENGTH: 269
<212> TYPE: PRT
<213> ORGANISM: Pseudomonas putida KT2440

<400> SEQUENCE: 114

```
Met Ser Phe Gln Asn Lys Ile Val Val Leu Thr Gly Ala Ala Ser Gly
 1               5                  10                  15

Ile Gly Lys Ala Thr Ala Gln Leu Leu Val Glu Gln Gly Ala His Val
             20                  25                  30

Val Ala Met Asp Leu Lys Ser Asp Leu Leu Gln Gln Ala Phe Gly Ser
         35                  40                  45

Glu Glu His Val Leu Cys Ile Pro Thr Asp Val Ser Asp Ser Glu Ala
     50                  55                  60

Val Arg Ala Ala Phe Gln Ala Val Asp Ala Lys Phe Gly Arg Val Asp
 65                  70                  75                  80

Val Ile Ile Asn Ala Ala Gly Ile Asn Ala Pro Thr Arg Glu Ala Asn
                 85                  90                  95

Gln Lys Met Val Asp Ala Asn Val Ala Ala Leu Asp Ala Met Lys Ser
            100                 105                 110

Gly Arg Ala Pro Thr Phe Asp Phe Leu Ala Asp Thr Ser Asp Gln Asp
        115                 120                 125

Phe Arg Arg Val Met Glu Val Asn Leu Phe Ser Gln Phe Tyr Cys Ile
    130                 135                 140

Arg Glu Gly Val Pro Leu Met Arg Arg Ala Gly Gly Gly Ser Ile Val
145                 150                 155                 160

Asn Ile Ser Ser Val Ala Ala Leu Leu Gly Val Ala Met Pro Leu Tyr
                165                 170                 175

Tyr Pro Ala Ser Lys Ala Ala Val Leu Gly Leu Thr Arg Ala Ala Ala
            180                 185                 190

Ala Glu Leu Ala Pro Tyr Asn Ile Arg Val Asn Ala Ile Ala Pro Gly
```

```
                    195                 200                 205
Ser Val Asp Thr Pro Leu Met His Glu Gln Pro Glu Val Val Gln
        210                 215                 220

Phe Leu Val Ser Met Gln Pro Ile Lys Arg Leu Ala Gln Pro Glu Glu
225                 230                 235                 240

Leu Ala Gln Ser Ile Leu Phe Leu Ala Gly Glu His Ser Ser Phe Ile
                245                 250                 255

Thr Gly Gln Thr Leu Ser Pro Asn Gly Gly Met His Met
            260                 265

<210> SEQ ID NO 115
<211> LENGTH: 771
<212> TYPE: DNA
<213> ORGANISM: Pseudomonas putida KT2440

<400> SEQUENCE: 115
atgacccttg aaggcaaaac tgcactcgtc accggttcca ccagcggcat tggcctgggc      60
atcgcccagg tattggcccg ggctggcgcc aacatcgtgc tcaacggctt tggtgacccg     120
ggccccgcca tggcggaaat tgcccggcac ggggtgaagg ttgtgcacca cccgccgac     180 ctgtcggatg tggtccagat cgaggctttg ttcaacctgg ccgaacgcga gttcggcggc     240
gtcgacatcc tggtcaacaa cgccggtatc cagcatgtgg caccggttga gcagttcccg     300
ccagaaagct gggacaagat catcgccctg aacctgtcgg ccgtattcca tggcacgcgc     360
ctggcgctgc cgggcatgcg cacgcgcaac tggggcgca tcatcaatat cgcttcggtg     420
catggcctgg tcggctcgat tggcaaggca gcctacgtgg cagccaagca tggcgtgatc     480
ggcctgacca aggtggtcgg cctggaaacc gccaccagtc atgtcacctg caatgccata     540
tgcccgggct gggtgctgac accgctggtg caaaagcaga tcgacgatcg tgcggccaag     600
ggtggcgatc ggctgcaagc gcagcacgat ctgctggcag aaaagcaacc gtcgctggct     660
tcgtcacccc cgaacacct cggtgagctg gtactctttc tgtgcagcga ggccggtagc     720
caggttcgcg cgccgccctg gaacgtcgat ggtggctggt tggcccagtg a              771

<210> SEQ ID NO 116
<211> LENGTH: 256
<212> TYPE: PRT
<213> ORGANISM: Pseudomonas putida KT2440

<400> SEQUENCE: 116

Met Thr Leu Glu Gly Lys Thr Ala Leu Val Thr Gly Ser Thr Ser Gly
1               5                   10                  15

Ile Gly Leu Gly Ile Ala Gln Val Leu Ala Arg Ala Gly Ala Asn Ile
                20                  25                  30

Val Leu Asn Gly Phe Gly Asp Pro Gly Pro Ala Met Ala Glu Ile Ala
            35                  40                  45

Arg His Gly Val Lys Val Val His His Pro Ala Asp Leu Ser Asp Val
        50                  55                  60

Val Gln Ile Glu Ala Leu Phe Asn Leu Ala Glu Arg Glu Phe Gly Gly
65                  70                  75                  80

Val Asp Ile Leu Val Asn Asn Ala Gly Ile Gln His Val Ala Pro Val
                85                  90                  95

Glu Gln Phe Pro Pro Glu Ser Trp Asp Lys Ile Ile Ala Leu Asn Leu
                100                 105                 110

Ser Ala Val Phe His Gly Thr Arg Leu Ala Leu Pro Gly Met Arg Thr
            115                 120                 125
```

```
Arg Asn Trp Gly Arg Ile Ile Asn Ile Ala Ser Val His Gly Leu Val
            130                 135                 140

Gly Ser Ile Gly Lys Ala Ala Tyr Val Ala Lys His Gly Val Ile
145                 150                 155                 160

Gly Leu Thr Lys Val Val Gly Leu Glu Thr Ala Thr Ser His Val Thr
                165                 170                 175

Cys Asn Ala Ile Cys Pro Gly Trp Val Leu Thr Pro Leu Val Gln Lys
                180                 185                 190

Gln Ile Asp Asp Arg Ala Ala Lys Gly Gly Asp Arg Leu Gln Ala Gln
            195                 200                 205

His Asp Leu Leu Ala Glu Lys Gln Pro Ser Leu Ala Phe Val Thr Pro
        210                 215                 220

Glu His Leu Gly Glu Leu Val Leu Phe Leu Cys Ser Glu Ala Gly Ser
225                 230                 235                 240

Gln Val Arg Gly Ala Ala Trp Asn Val Asp Gly Gly Trp Leu Ala Gln
                245                 250                 255

<210> SEQ ID NO 117
<211> LENGTH: 750
<212> TYPE: DNA
<213> ORGANISM: Pseudomonas putida KT2440

<400> SEQUENCE: 117
atgtccaagc aacttacact cgaaggcaaa gtggccctgg ttcagggcgg ttcccgaggc      60
attggcgcag ctatcgtaag gcgcctggcc cgcgaaggcg cgcaagtggc cttcacctat     120
gtcagctctg ccggcccggc tgaagaactg gctcgggaaa ttaccgagaa cggcggcaaa     180
gccttggccc tgcgggctga cagcgctgat gccgcggccg tgcagctggc ggttgatgac     240
accgagaaag ccttgggccg gctggatatc ctggtcaaca acgccggtgt gctggcagtg     300
gccccagtga cagagttcga cctggccgac ttcgatcata tgctggccgt gaacgtacgc     360
agcgtgttcg tcgccagcca ggccgcggca cgctatatgg ccagggcgg tcgtatcatc     420 aacattggca gcaccaacgc cgagcgcatg ccgtttgccg gtggtgcacc gtacgccatg     480
agcaagtcgg cactggttgg tctgacccgc ggcatggcac gcgacctcgg ccgcagggc      540 attaccgtga caacgtgca gcccggcccg gtggacaccg acatgaaccc ggccagtggc     600
gagtttgccg agagcctgat tccgctgatg gccattgggc gatatggcga gccggaggag     660
attgccagct tcgtggctta cctggcaggg cctgaagccg gtatatcac cggggccagc     720 ctgactgtag atggtgggtt tgcagcctga                                     750

<210> SEQ ID NO 118
<211> LENGTH: 249
<212> TYPE: PRT
<213> ORGANISM: Pseudomonas putida KT2440

<400> SEQUENCE: 118

Met Ser Lys Gln Leu Thr Leu Glu Gly Lys Val Ala Leu Val Gln Gly
1               5                   10                  15

Gly Ser Arg Gly Ile Gly Ala Ala Ile Val Arg Arg Leu Ala Arg Glu
            20                  25                  30

Gly Ala Gln Val Ala Phe Thr Tyr Val Ser Ser Ala Gly Pro Ala Glu
        35                  40                  45

Glu Leu Ala Arg Glu Ile Thr Glu Asn Gly Gly Lys Ala Leu Ala Leu
    50                  55                  60

Arg Ala Asp Ser Ala Asp Ala Ala Ala Val Gln Leu Ala Val Asp Asp
65                  70                  75                  80
```

```
Thr Glu Lys Ala Leu Gly Arg Leu Asp Ile Leu Val Asn Asn Ala Gly
                85                  90                  95
Val Leu Ala Val Ala Pro Val Thr Glu Phe Asp Leu Ala Asp Phe Asp
            100                 105                 110
His Met Leu Ala Val Asn Val Arg Ser Val Phe Val Ala Ser Gln Ala
        115                 120                 125
Ala Ala Arg Tyr Met Gly Gln Gly Arg Ile Ile Asn Ile Gly Ser
    130                 135                 140
Thr Asn Ala Glu Arg Met Pro Phe Ala Gly Gly Ala Pro Tyr Ala Met
145                 150                 155                 160
Ser Lys Ser Ala Leu Val Gly Leu Thr Arg Gly Met Ala Arg Asp Leu
                165                 170                 175
Gly Pro Gln Gly Ile Thr Val Asn Asn Val Gln Pro Gly Pro Val Asp
            180                 185                 190
Thr Asp Met Asn Pro Ala Ser Gly Glu Phe Ala Glu Ser Leu Ile Pro
        195                 200                 205
Leu Met Ala Ile Gly Arg Tyr Gly Glu Pro Glu Glu Ile Ala Ser Phe
    210                 215                 220
Val Ala Tyr Leu Ala Gly Pro Glu Ala Gly Tyr Ile Thr Gly Ala Ser
225                 230                 235                 240
Leu Thr Val Asp Gly Gly Phe Ala Ala
                245

<210> SEQ ID NO 119
<211> LENGTH: 858
<212> TYPE: DNA
<213> ORGANISM: Pseudomonas putida KT2440

<400> SEQUENCE: 119
atgagcgact accctacccc tccattccca tcccaaccgc aaagcgttcc cggttcccag    60
cgcaagatgg atccgtatcc ggactgcggt gagcagagct acaccggcaa caatcgcctc   120
gcaggcaaga tcgccttgat aaccggtgct gacagcggca tcgggcgtgc ggtggcgatt   180
gcctatgccc gagaaggcgc tgacgttgcc attgcctatc tgaatgaaca cgacgatgcg   240
caggaaaccg cgcgctgggt caaagcggct ggccgccagt gcctgctgct gcccggcgac   300
ctggcacaga acagcactg ccacgacatc gtcgacaaga ccgtggcgca gtttggtcgc   360
atcgatatcc tggtcaacaa cgccgcgttc cagatggccc atgaaagcct ggacgacatt   420
gatgacgatg aatgggtgaa gaccttcgat accaacatca ccgccatttt ccgcatttgc   480
cagcgcgctt tgccctcgat gccaaagggc ggttcgatca tcaacaccag ttcggtcaac   540
tctgacgacc cgtcacccag cctgttggcc tatgccgcga ccaaagggc tattgccaat   600 ttcactgcag gccttgcgca actgctgggc aagcagggca ttcgcgtcaa cagcgtcgca   660
cccggcccga tctggacccc gctgatcccg gccaccatgc tgatgaggc ggtgagaaac   720 ttcggttccg gttacccgat gggacggccg ggtcaacctg tggaggtggc gccaatctat   780
gtcttgctgg gtccgatga agccagctac atctcgggtt cgcgttacgc cgtgacggga   840
ggcaaaccta ttctgtga                                                 858

<210> SEQ ID NO 120
<211> LENGTH: 285
<212> TYPE: PRT
<213> ORGANISM: Pseudomonas putida KT2440

<400> SEQUENCE: 120
```

```
Met Ser Asp Tyr Pro Thr Pro Pro Phe Pro Ser Gln Pro Gln Ser Val
1               5                   10                  15

Pro Gly Ser Gln Arg Lys Met Asp Pro Tyr Pro Asp Cys Gly Glu Gln
            20                  25                  30

Ser Tyr Thr Gly Asn Asn Arg Leu Ala Gly Lys Ile Ala Leu Ile Thr
        35                  40                  45

Gly Ala Asp Ser Gly Ile Gly Arg Ala Val Ala Ile Ala Tyr Ala Arg
50                  55                  60

Glu Gly Ala Asp Val Ala Ile Ala Tyr Leu Asn Glu His Asp Asp Ala
65              70                  75                  80

Gln Glu Thr Ala Arg Trp Val Lys Ala Ala Gly Arg Gln Cys Leu Leu
                85                  90                  95

Leu Pro Gly Asp Leu Ala Gln Lys Gln His Cys His Asp Ile Val Asp
            100                 105                 110

Lys Thr Val Ala Gln Phe Gly Arg Ile Asp Ile Leu Val Asn Asn Ala
        115                 120                 125

Ala Phe Gln Met Ala His Glu Ser Leu Asp Asp Ile Asp Asp Asp Glu
    130                 135                 140

Trp Val Lys Thr Phe Asp Thr Asn Ile Thr Ala Ile Phe Arg Ile Cys
145                 150                 155                 160

Gln Arg Ala Leu Pro Ser Met Pro Lys Gly Gly Ser Ile Ile Asn Thr
                165                 170                 175

Ser Ser Val Asn Ser Asp Asp Pro Ser Pro Ser Leu Leu Ala Tyr Ala
            180                 185                 190

Ala Thr Lys Gly Ala Ile Ala Asn Phe Thr Ala Gly Leu Ala Gln Leu
        195                 200                 205

Leu Gly Lys Gln Gly Ile Arg Val Asn Ser Val Ala Pro Gly Pro Ile
210                 215                 220

Trp Thr Pro Leu Ile Pro Ala Thr Met Pro Asp Glu Ala Val Arg Asn
225                 230                 235                 240

Phe Gly Ser Gly Tyr Pro Met Gly Arg Pro Gly Gln Pro Val Glu Val
                245                 250                 255

Ala Pro Ile Tyr Val Leu Leu Gly Ser Asp Glu Ala Ser Tyr Ile Ser
            260                 265                 270

Gly Ser Arg Tyr Ala Val Thr Gly Gly Lys Pro Ile Leu
        275                 280                 285
```

<210> SEQ ID NO 121
<211> LENGTH: 774
<212> TYPE: DNA
<213> ORGANISM: Pseudomonas putida KT2440

<400> SEQUENCE: 121

```
atgatcgaaa tcagcggcag caccccgggc acaatggcc gggtagcctt ggtcacgggc      60
gccgcccgcg catcggtct gggcattgcc gcatggctga tctgcgaagg ctggcaagtg     120
gtgctgagtg atctggaccg ccagcgtggt accaaagtgg ccaaggcgtt gggcgacaac    180
gcctggttca tcaccatgga cgttgccgac gaggcccagg tcagtgccgg cgtgtccgaa    240
gtgctcgggc agttcggccg gctggacgcg ctggtgtgca atgcggccat tgccaacccg    300
cacaaccaga cgctggaaag cctgagcctg gcacaatgga accgggtgct ggggtcaac    360
ctcagcggcc ccatgctgct ggccaagcat tgtgcgccgt acctgcgtgc gcacaatggg    420
gcgatcgtca acctgacctc taccgtgct cggcagtccg aacccgacac cgaggcttac    480
gcggcaagca agggcggcct ggtggctttg acccatgccc tggccatgag cctgggcccg    540
```

```
gagattcgcg tcaatgcggt gagcccgggc tggatcgatg cccgtgatcc gtcgcagcgc    600
cgtgccgagc cgttgagcga agctgaccat gcccagcatc aacgggcag ggtagggacc    660 gtggaagatg tcgcggccat ggttgcctgg ttgctgtcac gccaggcggc atttgtcacc    720
ggccaggagt ttgtggtcga tggcggcatg acccgcaaga tgatctatac ctga         774
```

<210> SEQ ID NO 122
<211> LENGTH: 257
<212> TYPE: PRT
<213> ORGANISM: Pseudomonas putida KT2440

<400> SEQUENCE: 122

```
Met Ile Glu Ile Ser Gly Ser Thr Pro Gly His Asn Gly Arg Val Ala
1               5                   10                  15

Leu Val Thr Gly Ala Ala Arg Gly Ile Gly Leu Gly Ile Ala Ala Trp
            20                  25                  30

Leu Ile Cys Glu Gly Trp Gln Val Val Leu Ser Asp Leu Asp Arg Gln
        35                  40                  45

Arg Gly Thr Lys Val Ala Lys Ala Leu Gly Asp Asn Ala Trp Phe Ile
    50                  55                  60

Thr Met Asp Val Ala Asp Glu Ala Gln Val Ser Ala Gly Val Ser Glu
65                  70                  75                  80

Val Leu Gly Gln Phe Gly Arg Leu Asp Ala Leu Val Cys Asn Ala Ala
                85                  90                  95

Ile Ala Asn Pro His Asn Gln Thr Leu Glu Ser Leu Ser Leu Ala Gln
            100                 105                 110

Trp Asn Arg Val Leu Gly Val Asn Leu Ser Gly Pro Met Leu Leu Ala
        115                 120                 125

Lys His Cys Ala Pro Tyr Leu Arg Ala His Asn Gly Ala Ile Val Asn
    130                 135                 140

Leu Thr Ser Thr Arg Ala Arg Gln Ser Glu Pro Asp Thr Glu Ala Tyr
145                 150                 155                 160

Ala Ala Ser Lys Gly Gly Leu Val Ala Leu Thr His Ala Leu Ala Met
                165                 170                 175

Ser Leu Gly Pro Glu Ile Arg Val Asn Ala Val Ser Pro Gly Trp Ile
            180                 185                 190

Asp Ala Arg Asp Pro Ser Gln Arg Arg Ala Glu Pro Leu Ser Glu Ala
        195                 200                 205

Asp His Ala Gln His Pro Thr Gly Arg Val Gly Thr Val Glu Asp Val
    210                 215                 220

Ala Ala Met Val Ala Trp Leu Leu Ser Arg Gln Ala Ala Phe Val Thr
225                 230                 235                 240

Gly Gln Glu Phe Val Val Asp Gly Gly Met Thr Arg Lys Met Ile Tyr
                245                 250                 255

Thr
```

<210> SEQ ID NO 123
<211> LENGTH: 741
<212> TYPE: DNA
<213> ORGANISM: Pseudomonas putida KT2440

<400> SEQUENCE: 123

```
atgagcctgc aaggtaaagt tgcactggtt accggcgcca gccgtggcat tggccaggcc    60
atcgccctcg agctgggccg ccagggcgcg accgtgatcg taccgccac gtcggcgtcc    120 ggtgccgagc gcatcgctgc caccctgaaa gaacacggca ttaccggcac tggcatggag    180
```

```
ctgaacgtga ccagcgccga atcggttgaa gccgtactgg ccgccattgg cgagcagttc    240
ggcgcgccgg ccatcttggt caacaatgcc ggtatcaccc gcgacaacct catgctgcgc    300
atgaaagacg acgagtggtt tgatgtcatc gacaccaacc tgaacagcct ctaccgtctg    360
tccaagggcg tgctgcgtgg catgaccaag gcgcgttggg gtcgtatcat cagcatcggc    420
tcggtcgttg gtgccatggg taacgcaggt caggccaact acgcggctgc caaggccggt    480
ctggaaggtt tcagccgcgc cctggcgcgt gaagtgggtt cgcgtggtat caccgtcaac    540
tcggtgaccc caggcttcat cgataccgac atgacccgcg agctgccaga agctcagcgc    600
gaagccctgc agacccagat ccgctgggcc gcctgggcc aggctgacga aattgccaag    660
gtggtttcgt tcctggcatc cgacggcgcc gcctacgtga ccggcgctac cgtgccggtc    720
aacggcggga tgtacatgta a                                              741

<210> SEQ ID NO 124
<211> LENGTH: 246
<212> TYPE: PRT
<213> ORGANISM: Pseudomonas putida KT2440

<400> SEQUENCE: 124

Met Ser Leu Gln Gly Lys Val Ala Leu Val Thr Gly Ala Ser Arg Gly
1               5                   10                  15

Ile Gly Gln Ala Ile Ala Leu Glu Leu Gly Arg Gln Gly Ala Thr Val
            20                  25                  30

Ile Gly Thr Ala Thr Ser Ala Ser Gly Ala Glu Arg Ile Ala Ala Thr
        35                  40                  45

Leu Lys Glu His Gly Ile Thr Gly Thr Gly Met Glu Leu Asn Val Thr
    50                  55                  60

Ser Ala Glu Ser Val Glu Ala Val Leu Ala Ala Ile Gly Glu Gln Phe
65                  70                  75                  80

Gly Ala Pro Ala Ile Leu Val Asn Asn Ala Gly Ile Thr Arg Asp Asn
                85                  90                  95

Leu Met Leu Arg Met Lys Asp Asp Glu Trp Phe Asp Val Ile Asp Thr
            100                 105                 110

Asn Leu Asn Ser Leu Tyr Arg Leu Ser Lys Gly Val Leu Arg Gly Met
        115                 120                 125

Thr Lys Ala Arg Trp Gly Arg Ile Ile Ser Ile Gly Ser Val Val Gly
    130                 135                 140

Ala Met Gly Asn Ala Gly Gln Ala Asn Tyr Ala Ala Ala Lys Ala Gly
145                 150                 155                 160

Leu Glu Gly Phe Ser Arg Ala Leu Ala Arg Glu Val Gly Ser Arg Gly
                165                 170                 175

Ile Thr Val Asn Ser Val Thr Pro Gly Phe Ile Asp Thr Asp Met Thr
            180                 185                 190

Arg Glu Leu Pro Glu Ala Gln Arg Glu Ala Leu Gln Thr Gln Ile Pro
        195                 200                 205

Leu Gly Arg Leu Gly Gln Ala Asp Glu Ile Ala Lys Val Val Ser Phe
    210                 215                 220

Leu Ala Ser Asp Gly Ala Ala Tyr Val Thr Gly Ala Thr Val Pro Val
225                 230                 235                 240

Asn Gly Gly Met Tyr Met
                245

<210> SEQ ID NO 125
<211> LENGTH: 738
<212> TYPE: DNA
```

<213> ORGANISM: Pseudomonas putida KT2440

<400> SEQUENCE: 125

```
atgactcaga aaatagctgt cgtgaccggc ggcagtcgcg gcattggcaa gtccatcgtg      60
ctggccctgg ccggcgcggg ttatcaggtt gccttcagtt atgtccgtga cgaggcgtca     120
gccgctgcct tgcaggcgca ggtcgaaggg ctcggccggg actgcctggc cgtgcagtgt     180
gatgtcaagg aagcgccgag cattcaggcg ttttttgaac gggtcgagca acgtttcgag     240
cgtatcgact tgttggtcaa caacgccggt attacccgtg acggtttgct cgccacgcaa     300
tcgttgaacg acatcaccga ggtcatccag accaacctgg tcggcacgtt gttgtgctgt     360
cagcaggtgc tgccctgcat gatgcgccaa cgcagcgggt gcatcgtcaa cctcagttcg     420
gtggccgcgc aaaagcccgg caagggccag agcaactacg ccgccgccaa aggcggtgta     480
gaagcattga cacgcgcact ggcggtggag ttggcgccgc gcaacatccg ggtcaacgcg     540
gtggcgcccg catcgtcag caccgacatg agccaagccc tggtcggcgc ccatgagcag      600
gaaatccagt cgcggctgtt gatcaaacgg ttcgcccggc ctgaagaaat tgccgacgcg     660
gtgctgtatc tggccgagcg cggcctgtac atcacgggcg aagtcctgtc cgtcaacggc     720
ggattgaaaa tgccatga                                                  738
```

<210> SEQ ID NO 126
<211> LENGTH: 245
<212> TYPE: PRT
<213> ORGANISM: Pseudomonas putida KT2440

<400> SEQUENCE: 126

```
Met Thr Gln Lys Ile Ala Val Val Thr Gly Gly Ser Arg Gly Ile Gly
 1               5                  10                  15

Lys Ser Ile Val Leu Ala Leu Ala Gly Ala Gly Tyr Gln Val Ala Phe
             20                  25                  30

Ser Tyr Val Arg Asp Glu Ala Ser Ala Ala Leu Gln Ala Gln Val
         35                  40                  45

Glu Gly Leu Gly Arg Asp Cys Leu Ala Val Gln Cys Asp Val Lys Glu
     50                  55                  60

Ala Pro Ser Ile Gln Ala Phe Phe Glu Arg Val Glu Gln Arg Phe Glu
 65                  70                  75                  80

Arg Ile Asp Leu Leu Val Asn Asn Ala Gly Ile Thr Arg Asp Gly Leu
                 85                  90                  95

Leu Ala Thr Gln Ser Leu Asn Asp Ile Thr Glu Val Ile Gln Thr Asn
            100                 105                 110

Leu Val Gly Thr Leu Leu Cys Cys Gln Gln Val Leu Pro Cys Met Met
        115                 120                 125

Arg Gln Arg Ser Gly Cys Ile Val Asn Leu Ser Ser Val Ala Ala Gln
    130                 135                 140

Lys Pro Gly Lys Gly Gln Ser Asn Tyr Ala Ala Ala Lys Gly Gly Val
145                 150                 155                 160

Glu Ala Leu Thr Arg Ala Leu Ala Val Glu Leu Ala Pro Arg Asn Ile
                165                 170                 175

Arg Val Asn Ala Val Ala Pro Gly Ile Val Ser Thr Asp Met Ser Gln
            180                 185                 190

Ala Leu Val Gly Ala His Glu Gln Glu Ile Gln Ser Arg Leu Leu Ile
        195                 200                 205

Lys Arg Phe Ala Arg Pro Glu Glu Ile Ala Asp Ala Val Leu Tyr Leu
    210                 215                 220
```

-continued

Ala Glu Arg Gly Leu Tyr Ile Thr Gly Glu Val Leu Ser Val Asn Gly
225                 230                 235                 240

Gly Leu Lys Met Pro
            245

<210> SEQ ID NO 127
<211> LENGTH: 768
<212> TYPE: DNA
<213> ORGANISM: Pseudomonas putida KT2440

<400> SEQUENCE: 127

```
atgtccaaga cccacctgtt cgacctcgac ggcaagattg cctttgtttc cggcgccagc    60
cgtggcatcg gcgaggccat cgcccacttg ctcgcgcagc aaggggccca tgtgatcgtt   120
tccagccgca agcttgacgg gtgccagcag gtggccgacg ccatcattgc cgccggcggc   180
aaggccacgg ctgtggcctg ccacattggt gagctggaac agattcagca ggtgttcgcc   240
ggcattcgcg aacagttcgg gcgactggac gtgctggtca acaatgcagc caccaacccg   300
caattctgca atgtgctgga caccgaccca ggggcgttcc agaagaccgt ggacgtgaac   360
atccgtggtt acttcttcat gtcggtggag gctggcaagc tgatgcgcga aacggcggc    420
ggcagcatca tcaacgtggc gtcgatcaac ggtgtttcac ccgggctgtt ccaaggcatc   480
tactcggtga ccaaggcggc ggtcatcaac atgaccaagg tgttcgccaa agagtgtgca   540
cccttcggta ttcgctgcaa cgcgctactg ccggggctga ccgataccaa gttcgcttcg   600
gcattggtga gaacgaagc catcctcaac gccgccttgc agcagatccc cctcaaacgc   660
gtggccgacc ccaaggaaat ggcgggtgcg gtgctgtacc tggccagcga tgcctccagc   720
tacaccaccg gcaccacgct caatgtcgac ggtggcttcc tgtcctga              768
```

<210> SEQ ID NO 128
<211> LENGTH: 255
<212> TYPE: PRT
<213> ORGANISM: Pseudomonas putida KT2440

<400> SEQUENCE: 128

Met Ser Lys Thr His Leu Phe Asp Leu Asp Gly Lys Ile Ala Phe Val
1               5                   10                  15

Ser Gly Ala Ser Arg Gly Ile Gly Glu Ala Ile Ala His Leu Leu Ala
            20                  25                  30

Gln Gln Gly Ala His Val Ile Val Ser Ser Arg Lys Leu Asp Gly Cys
        35                  40                  45

Gln Gln Val Ala Asp Ala Ile Ala Ala Gly Gly Lys Ala Thr Ala
    50                  55                  60

Val Ala Cys His Ile Gly Glu Leu Glu Gln Ile Gln Gln Val Phe Ala
65                  70                  75                  80

Gly Ile Arg Glu Gln Phe Gly Arg Leu Asp Val Leu Val Asn Asn Ala
                85                  90                  95

Ala Thr Asn Pro Gln Phe Cys Asn Val Leu Asp Thr Asp Pro Gly Ala
            100                 105                 110

Phe Gln Lys Thr Val Asp Val Asn Ile Arg Gly Tyr Phe Phe Met Ser
        115                 120                 125

Val Glu Ala Gly Lys Leu Met Arg Glu Asn Gly Gly Ser Ile Ile
    130                 135                 140

Asn Val Ala Ser Ile Asn Gly Val Ser Pro Gly Leu Phe Gln Gly Ile
145                 150                 155                 160

Tyr Ser Val Thr Lys Ala Ala Val Ile Asn Met Thr Lys Val Phe Ala
                165                 170                 175

Lys Glu Cys Ala Pro Phe Gly Ile Arg Cys Asn Ala Leu Leu Pro Gly
            180                 185                 190

Leu Thr Asp Thr Lys Phe Ala Ser Ala Leu Val Lys Asn Glu Ala Ile
            195                 200                 205

Leu Asn Ala Ala Leu Gln Gln Ile Pro Leu Lys Arg Val Ala Asp Pro
            210                 215                 220

Lys Glu Met Ala Gly Ala Val Leu Tyr Leu Ala Ser Asp Ala Ser Ser
225                 230                 235                 240

Tyr Thr Thr Gly Thr Thr Leu Asn Val Asp Gly Gly Phe Leu Ser
            245                 250                 255

<210> SEQ ID NO 129
<211> LENGTH: 762
<212> TYPE: DNA
<213> ORGANISM: Pseudomonas fluorescens Pf-5

<400> SEQUENCE: 129
atgagcatga cgttttccgg ccaggtggcc ctagtgaccg gcgcagccaa tggtatcggc      60
cgcgccaccg cccaggcatt tgccgcacaa ggcttgaagg tggtggtggc ggacctggac     120
acggcggggg gcgagggcac cgtggcgctg atccgcgagg ccgtggcgga gcattgttc     180
gtgccgtgca acgttaccct ggaggcggat gtgcaaagcc tcatggcccg caccatcgaa     240
gcctatgggc gcctggatta cgccttcaac aatgccggta tcgagatcga aaagggccgc     300
cttgcgaggg ctccatgga tgagttcgac gccatcatgg gggtcaacgt caaaggggtc     360
tggctgtgca tgaagtacca gttgccgctg ctgctggccc agggcggtgg ggcgatcgtc     420
aacaccgcct cggtggcggg cctgggcgcg gcgccgaaga tgagcatcta tgcggcctcc     480
aagcatgcgg tgatcggcct gaccaagtcg gcggccatcg aatatgcgaa gaagaaaatc     540
cgcgtgaacg cggtatgccc ggcggtgatc gacaccgaca tgttccgccg tgcctacgag     600
gcggacccga agaaggccga gttcgccgcg gccatgcacc cggtggggcg catcggcaag     660
gtcgaggaga tcgccagtgc ggtgctctac ctgtgcagcg atggcgcggc ctttaccacc     720
ggccatgcac tggcggtcga cggcggggcc accgcgatct ga                      762

<210> SEQ ID NO 130
<211> LENGTH: 253
<212> TYPE: PRT
<213> ORGANISM: Pseudomonas fluorscens Pf-5

<400> SEQUENCE: 130

Met Ser Met Thr Phe Ser Gly Gln Val Ala Leu Val Thr Gly Ala Ala
1               5                   10                  15

Asn Gly Ile Gly Arg Ala Thr Ala Gln Ala Phe Ala Ala Gln Gly Leu
            20                  25                  30

Lys Val Val Val Ala Asp Leu Asp Thr Ala Gly Gly Glu Gly Thr Val
            35                  40                  45

Ala Leu Ile Arg Glu Ala Gly Gly Glu Ala Leu Phe Val Pro Cys Asn
            50                  55                  60

Val Thr Leu Glu Ala Asp Val Gln Ser Leu Met Ala Arg Thr Ile Glu
65                  70                  75                  80

Ala Tyr Gly Arg Leu Asp Tyr Ala Phe Asn Asn Ala Gly Ile Glu Ile
            85                  90                  95

Glu Lys Gly Arg Leu Ala Glu Gly Ser Met Asp Glu Phe Asp Ala Ile
            100                 105                 110

Met Gly Val Asn Val Lys Gly Val Trp Leu Cys Met Lys Tyr Gln Leu

```
                115                 120                 125
Pro Leu Leu Leu Ala Gln Gly Gly Ala Ile Val Asn Thr Ala Ser
            130                 135                 140

Val Ala Gly Leu Gly Ala Ala Pro Lys Met Ser Ile Tyr Ala Ala Ser
145                 150                 155                 160

Lys His Ala Val Ile Gly Leu Thr Lys Ser Ala Ala Ile Glu Tyr Ala
                165                 170                 175

Lys Lys Lys Ile Arg Val Asn Ala Val Cys Pro Ala Val Ile Asp Thr
            180                 185                 190

Asp Met Phe Arg Arg Ala Tyr Glu Ala Asp Pro Lys Lys Ala Glu Phe
                195                 200                 205

Ala Ala Ala Met His Pro Val Gly Arg Ile Gly Lys Val Glu Glu Ile
            210                 215                 220

Ala Ser Ala Val Leu Tyr Leu Cys Ser Asp Gly Ala Ala Phe Thr Thr
225                 230                 235                 240

Gly His Ala Leu Ala Val Asp Gly Gly Ala Thr Ala Ile
                245                 250

<210> SEQ ID NO 131
<211> LENGTH: 735
<212> TYPE: DNA
<213> ORGANISM: Klebsiella pneumoniae subsp. pneumoniae MGH78578

<400> SEQUENCE: 131
atgaaacttg ccagtaaaac cgccattgtc accggcgccg cacgcggtat cggctttggc      60
attgcccagg tgcttgcgcg ggaaggcgcg cgagtgatta tcgccgatcg tgatgcacac     120
ggcgaagccg ccgccgcttc cctgcgcgaa tcgggcgcac aggcgctgtt tatcagctgc     180
aatatcgctg aaaaaacgca ggtcgaagcc ctgtattccc aggccgaaga ggcgtttggc     240
ccggtagaca ttctggtgaa taacgccgga atcaaccgcg acgccatgct gcacaaatta     300
acggaagcgg actgggacac ggttatcgac gttaacctga aaggcacttt cctctgtatg     360
cagcaggccg ctatccgcat gcgcgagcgc ggtgcgggcc gcattatcaa tatcgcttcc     420
gccagttggc ttggcaacgt cgggcaaacc aactattcgg cgtcaaaagc cggcgtggtg     480
ggaatgacca aaaccgcctg ccgcgaactg gcgaaaaaag tgtcacggt gaatgccatc     540 tgcccgggct ttatcgatac cgacatgacg cgcggcgtac cggaaaacgt ctggcaaatc     600
atggtcagca aaattcccgc gggttacgcc ggcgaggcga agacgtcgg cgagtgtgtg     660 gcgtttctgg cgtccgatgg cgcgcgctat atcaatggtg aagtgattaa cgtcggcggc     720
ggcatggtgc tgtaa                                                     735

<210> SEQ ID NO 132
<211> LENGTH: 253
<212> TYPE: PRT
<213> ORGANISM: Klebsiella pneumoniae subsp. pneumoniae MGH78578

<400> SEQUENCE: 132

Met Ser Met Thr Phe Ser Gly Gln Val Ala Leu Val Thr Gly Ala Ala
1               5                   10                  15

Asn Gly Ile Gly Arg Ala Thr Ala Gln Ala Phe Ala Ala Gln Gly Leu
            20                  25                  30

Lys Val Val Val Ala Asp Leu Asp Thr Ala Gly Gly Glu Gly Thr Val
        35                  40                  45

Ala Leu Ile Arg Glu Ala Gly Gly Glu Ala Leu Phe Val Pro Cys Asn
    50                  55                  60
```

Val Thr Leu Glu Ala Asp Val Gln Ser Leu Met Ala Arg Thr Ile Glu
65                  70                  75                  80

Ala Tyr Gly Arg Leu Asp Tyr Ala Phe Asn Asn Ala Gly Ile Glu Ile
                85                  90                  95

Glu Lys Gly Arg Leu Ala Glu Gly Ser Met Asp Glu Phe Asp Ala Ile
            100                 105                 110

Met Gly Val Asn Val Lys Gly Val Trp Leu Cys Met Lys Tyr Gln Leu
        115                 120                 125

Pro Leu Leu Ala Gln Gly Gly Ala Ile Val Asn Thr Ala Ser
    130                 135                 140

Val Ala Gly Leu Gly Ala Ala Pro Lys Met Ser Ile Tyr Ala Ala Ser
145                 150                 155                 160

Lys His Ala Val Ile Gly Leu Thr Lys Ser Ala Ala Ile Glu Tyr Ala
                165                 170                 175

Lys Lys Lys Ile Arg Val Asn Ala Val Cys Pro Ala Val Ile Asp Thr
            180                 185                 190

Asp Met Phe Arg Arg Ala Tyr Glu Ala Asp Pro Lys Lys Ala Glu Phe
        195                 200                 205

Ala Ala Ala Met His Pro Val Gly Arg Ile Gly Lys Val Glu Glu Ile
    210                 215                 220

Ala Ser Ala Val Leu Tyr Leu Cys Ser Asp Gly Ala Ala Phe Thr Thr
225                 230                 235                 240

Gly His Ala Leu Ala Val Asp Gly Gly Ala Thr Ala Ile
                245                 250

<210> SEQ ID NO 133
<211> LENGTH: 750
<212> TYPE: DNA
<213> ORGANISM: Klebsiella pneumoniae subsp. pneumoniae MGH78578

<400> SEQUENCE: 133
atgttattga aagataaagt cgccattatt actggcgcgg cctccgcacg cggtttgggc      60
ttcgcgactg cgaaattatt cgccgaaaac ggcgcgaaag tggtcattat cgacctcaat     120
ggcgaagcca gtaaaaccgc cgcggcggca ttaggcgaag accatctcgg cctggcggcc     180
aacgtcgctg atgaagtgca ggtgcaggcg ccatcgaac agatcctggc gaaatacggt      240
cgggttgatg tactggtcaa taacgccggg attacccagc cgctgaagct gatggatatc     300
aagcgcgcca actatgacgc ggtgcttgat gttagcctgc gcggcacgct gctgatgtcg     360
caggcggtta tccccaccat gcgggcgcaa aaatccggca gcatcgtctg catctcgtcc     420
gtctccgccc agcgcggcgg cggtatttc ggcggaccgc actacagcgc ggcaaaagcc      480
ggggtgctgg gtctggcgcg ggcgatggcg cgcgagcttg gccgggataa cgtccgcgtt     540
aactgcatca ccccggggct gattcagacc gacattaccg ccggcaagct gactgatgac     600
atgacggcca acattcttgc cggcattccg atgaaccgcc ttggcgacgc gatagacatc     660
gcgcgcgccg cgctgttcct cggcagcgat ctttcctcct actccaccgg catcaccctg     720
gacgttaacg gcggcatgtt aattcactaa                                      750

<210> SEQ ID NO 134
<211> LENGTH: 249
<212> TYPE: PRT
<213> ORGANISM: Klebsiella pneumoniae subsp. pneumoniae MGH78578

<400> SEQUENCE: 134

Met Leu Leu Lys Asp Lys Val Ala Ile Ile Thr Gly Ala Ala Ser Ala
1               5                   10                  15

Arg Gly Leu Gly Phe Ala Thr Ala Lys Leu Phe Ala Glu Asn Gly Ala
            20                  25                  30

Lys Val Ile Ile Asp Leu Asn Gly Glu Ala Ser Lys Thr Ala Ala
        35                  40                  45

Ala Ala Leu Gly Glu Asp His Leu Gly Leu Ala Ala Asn Val Ala Asp
50                  55                  60

Glu Val Gln Val Gln Ala Ala Ile Glu Gln Ile Leu Ala Lys Tyr Gly
65                  70                  75                  80

Arg Val Asp Val Leu Val Asn Asn Ala Gly Ile Thr Gln Pro Leu Lys
                85                  90                  95

Leu Met Asp Ile Lys Arg Ala Asn Tyr Asp Ala Val Leu Asp Val Ser
            100                 105                 110

Leu Arg Gly Thr Leu Leu Met Ser Gln Ala Val Ile Pro Thr Met Arg
        115                 120                 125

Ala Gln Lys Ser Gly Ser Ile Val Cys Ile Ser Ser Val Ser Ala Gln
130                 135                 140

Arg Gly Gly Gly Ile Phe Gly Gly Pro His Tyr Ser Ala Ala Lys Ala
145                 150                 155                 160

Gly Val Leu Gly Leu Ala Arg Ala Met Ala Arg Glu Leu Gly Pro Asp
                165                 170                 175

Asn Val Arg Val Asn Cys Ile Thr Pro Gly Leu Ile Gln Thr Asp Ile
            180                 185                 190

Thr Ala Gly Lys Leu Thr Asp Asp Met Thr Ala Asn Ile Leu Ala Gly
        195                 200                 205

Ile Pro Met Asn Arg Leu Gly Asp Ala Ile Asp Ile Ala Arg Ala Ala
210                 215                 220

Leu Phe Leu Gly Ser Asp Leu Ser Ser Tyr Ser Thr Gly Ile Thr Leu
225                 230                 235                 240

Asp Val Asn Gly Gly Met Leu Ile His
                245

<210> SEQ ID NO 135
<211> LENGTH: 750
<212> TYPE: DNA
<213> ORGANISM: Klebsiella pneumoniae subsp. pneumoniae MGH78578

<400> SEQUENCE: 135
atgttattga agataaagt cgccattatt actggcgcgg cctccgcacg cggtttgggc      60
ttcgcgactg cgaaattatt cgccgaaaac ggcgcgaaag tggtcattat cgacctcaat     120
ggcgaagcca gtaaaaccgc cgcggcggca ttaggcgaag accatctcgg cctggcggcc     180
aacgtcgctg atgaagtgca ggtgcaggcg gccatcgaac agatcctggc gaaatacggt     240
cgggttgatg tactggtcaa taacgccggg attacccagc cgctgaagct gatggatatc     300
aagcgcgcca actatgacgc ggtgcttgat gttagcctgc gcggcacgct gctgatgtcg     360
caggcggtta tccccaccat gcgggcgcaa aaatccggca gcatcgtctg catctcgtcc     420
gtctccgccc agcgcggcgg cggtattttc ggcggaccgc actacagcgc ggcaaaagcc     480
ggggtgctgg gtctggcgcg gcgatggcg cgcgagcttg gcccggataa cgtccgcgtt     540
aactgcatca ccccggggct gattcagacc gacattaccg ccggcaagct gactgatgac     600
atgacggcca acattcttgc cggcattccg atgaaccgcc ttggcgacgc gatagacatc     660
gcgcgcgccg cgctgttcct cggcagcgat ctttcctcct actccaccgg catcaccctg     720
gacgttaacg gcggcatgtt aattcactaa                                     750

<210> SEQ ID NO 136
<211> LENGTH: 249
<212> TYPE: PRT
<213> ORGANISM: Klebsiella pneumoniae subsp. pneumoniae MGH78578

<400> SEQUENCE: 136

```
Met Leu Leu Lys Asp Lys Val Ala Ile Ile Thr Gly Ala Ala Ser Ala
1               5                   10                  15

Arg Gly Leu Gly Phe Ala Thr Ala Lys Leu Phe Ala Glu Asn Gly Ala
            20                  25                  30

Lys Val Val Ile Ile Asp Leu Asn Gly Glu Ala Ser Lys Thr Ala Ala
        35                  40                  45

Ala Ala Leu Gly Glu Asp His Leu Gly Leu Ala Ala Asn Val Ala Asp
    50                  55                  60

Glu Val Gln Val Gln Ala Ala Ile Glu Gln Ile Leu Ala Lys Tyr Gly
65                  70                  75                  80

Arg Val Asp Val Leu Val Asn Asn Ala Gly Ile Thr Gln Pro Leu Lys
                85                  90                  95

Leu Met Asp Ile Lys Arg Ala Asn Tyr Asp Ala Val Leu Asp Val Ser
            100                 105                 110

Leu Arg Gly Thr Leu Leu Met Ser Gln Ala Val Ile Pro Thr Met Arg
        115                 120                 125

Ala Gln Lys Ser Gly Ser Ile Val Cys Ile Ser Ser Val Ser Ala Gln
    130                 135                 140

Arg Gly Gly Gly Ile Phe Gly Gly Pro His Tyr Ser Ala Ala Lys Ala
145                 150                 155                 160

Gly Val Leu Gly Leu Ala Arg Ala Met Ala Arg Glu Leu Gly Pro Asp
                165                 170                 175

Asn Val Arg Val Asn Cys Ile Thr Pro Gly Leu Ile Gln Thr Asp Ile
            180                 185                 190

Thr Ala Gly Lys Leu Thr Asp Asp Met Thr Ala Asn Ile Leu Ala Gly
        195                 200                 205

Ile Pro Met Asn Arg Leu Gly Asp Ala Ile Asp Ile Ala Arg Ala Ala
    210                 215                 220

Leu Phe Leu Gly Ser Asp Leu Ser Ser Tyr Ser Thr Gly Ile Thr Leu
225                 230                 235                 240

Asp Val Asn Gly Gly Met Leu Ile His
                245
```

<210> SEQ ID NO 137
<211> LENGTH: 714
<212> TYPE: DNA
<213> ORGANISM: Klebsiella pneumoniae subsp. pneumoniae MGH78578

<400> SEQUENCE: 137

```
atgacagcgt tcacaacaa  atcagtgctg gttttaggcg ggagtcgggg aattggcgcg    60
gcgatcgtca ggcgttttgt cgccgatggc cgtcggtgg  tgtttagcta ttccggttcg   120
ccggaagcgg ccgagcggct ggcggcagag accggcagca cggcggtgca ggcggacagc   180
gccgatcgcg atgcggtgat aagcctggtc cgcgacagcg gcccgctgga cgtgttagtg   240
gtcaatgccg ggatcgcgct tttcggtgac gctctcgagc aggacagcga tgcaatcgat   300
cgcctgttcc acatcaatat tcacgccccc taccatgcct ccgtcgaagc ggcgcgccgc   360
atgccggaag cgggcgcat  tattgtcatc ggctcagtca atggcgatcg catgccgttg   420
ccgggaatgg cggcctatgc gctcagcaaa tcggccctgc aggggctggc gcgcggcctg   480
```

-continued

```
gcgcgggatt ttggcccgcg cggcatcacg gtcaacgtcg tccagcccgg cccaattgat    540
accgacgcca acccggagaa cggcccgatg aaagagctga tgcacagctt tatggccatt    600
aagcgccatg gccgtccgga agaggtggcg ggaatggtgg cgtggctggc cggtccggag    660
gcgtcgtttg tcactggcgc catgcacacc atcgacggag cgtttggcgc ctga          714
```

<210> SEQ ID NO 138
<211> LENGTH: 237
<212> TYPE: PRT
<213> ORGANISM: Klebsiella pneumoniae subsp. pneumoniae MGH78578

<400> SEQUENCE: 138

```
Met Thr Ala Phe His Asn Lys Ser Val Leu Val Gly Gly Ser Arg
1               5                   10                  15

Gly Ile Gly Ala Ala Ile Val Arg Arg Phe Val Ala Asp Gly Ala Ser
            20                  25                  30

Val Val Phe Ser Tyr Ser Gly Ser Pro Glu Ala Ala Glu Arg Leu Ala
        35                  40                  45

Ala Glu Thr Gly Ser Thr Ala Val Gln Ala Asp Ser Ala Asp Arg Asp
    50                  55                  60

Ala Val Ile Ser Leu Val Arg Asp Ser Gly Pro Leu Asp Val Leu Val
65                  70                  75                  80

Val Asn Ala Gly Ile Ala Leu Phe Gly Asp Ala Leu Glu Gln Asp Ser
                85                  90                  95

Asp Ala Ile Asp Arg Leu Phe His Ile Asn Ile His Ala Pro Tyr His
            100                 105                 110

Ala Ser Val Glu Ala Ala Arg Arg Met Pro Glu Gly Gly Arg Ile Ile
        115                 120                 125

Val Ile Gly Ser Val Asn Gly Asp Arg Met Pro Leu Pro Gly Met Ala
    130                 135                 140

Ala Tyr Ala Leu Ser Lys Ser Ala Leu Gln Gly Leu Ala Arg Gly Leu
145                 150                 155                 160

Ala Arg Asp Phe Gly Pro Arg Gly Ile Thr Val Asn Val Val Gln Pro
                165                 170                 175

Gly Pro Ile Asp Thr Asp Ala Asn Pro Glu Asn Gly Pro Met Lys Glu
            180                 185                 190

Leu Met His Ser Phe Met Ala Ile Lys Arg His Gly Arg Pro Glu Glu
        195                 200                 205

Val Ala Gly Met Val Ala Trp Leu Ala Gly Pro Glu Ala Ser Phe Val
    210                 215                 220

Thr Gly Ala Met His Thr Ile Asp Gly Ala Phe Gly Ala
225                 230                 235
```

<210> SEQ ID NO 139
<211> LENGTH: 750
<212> TYPE: DNA
<213> ORGANISM: Klebsiella pneumoniae subp. pneumoniae MGH78578

<400> SEQUENCE: 139

```
atgaacggcc tgctaaacgg taaacgtatt gtcgtcaccg gtgcggcgcg cggtctcggg    60
taccactttg ccgaagcctg cgccgctcag ggcgcgacgg tggtgatgtg cgacatcctg   120
cagggagagc tggcggaaag cgctcatcgc ctgcagcaga agggctatca ggtcgaatct   180
cacgccatcg atcttgccag tcaagcatcg atcgagcagg tcttcagcgc catcggcgcg   240 cagggggtcta tcgatggctt agtcaataac gcagcgatgg ccaccggcgt cggcggaaaa   300
aatatgatcg attacgatcc ggatctgtgg gatcgggtaa tgacggtcaa cgttaaaggc   360
```

```
acctggttgg tgacccgcgc ggcggtaccg ctgctgcgcg aaggggcggc gatcgtcaac      420
gtcgcttcgg ataccgcgct gtggggcgcg ccgcggctga tggcctatgt cgccagtaag      480
ggcgcggtga ttgcgatgac ccgctccatg gcccgcgagc tgggtgaaaa gcggatccgt      540
atcaacgcca tcgcgccggg actgacccgc gttgaggcca cggaatacgt tcccgccgag      600
cgtcatcagc tgtatgagaa cggccgcgcg ctcagcggcg cgcagcagcc ggaagatgtc      660
accggcagcg tggtctggct gctgagcgat ctttcgcgct ttatcaccgg ccaactgatc      720
ccggtcaacg gcggttttgt ctttaactaa                                       750
```

<210> SEQ ID NO 140
<211> LENGTH: 249
<212> TYPE: PRT
<213> ORGANISM: Klebsiella pneumoniae subsp. pneumoinae MGH78578

<400> SEQUENCE: 140

```
Met Asn Gly Leu Leu Asn Gly Lys Arg Ile Val Val Thr Gly Ala Ala
1               5                  10                  15

Arg Gly Leu Gly Tyr His Phe Ala Glu Ala Cys Ala Ala Gln Gly Ala
            20                  25                  30

Thr Val Val Met Cys Asp Ile Leu Gln Gly Glu Leu Ala Glu Ser Ala
        35                  40                  45

His Arg Leu Gln Gln Lys Gly Tyr Gln Val Glu Ser His Ala Ile Asp
    50                  55                  60

Leu Ala Ser Gln Ala Ser Ile Glu Gln Val Phe Ser Ala Ile Gly Ala
65                  70                  75                  80

Gln Gly Ser Ile Asp Gly Leu Val Asn Asn Ala Ala Met Ala Thr Gly
                85                  90                  95

Val Gly Gly Lys Asn Met Ile Asp Tyr Asp Pro Asp Leu Trp Asp Arg
            100                 105                 110

Val Met Thr Val Asn Val Lys Gly Thr Trp Leu Val Thr Arg Ala Ala
        115                 120                 125

Val Pro Leu Leu Arg Glu Gly Ala Ala Ile Val Asn Val Ala Ser Asp
    130                 135                 140

Thr Ala Leu Trp Gly Ala Pro Arg Leu Met Ala Tyr Val Ala Ser Lys
145                 150                 155                 160

Gly Ala Val Ile Ala Met Thr Arg Ser Met Ala Arg Glu Leu Gly Glu
                165                 170                 175

Lys Arg Ile Arg Ile Asn Ala Ile Ala Pro Gly Leu Thr Arg Val Glu
            180                 185                 190

Ala Thr Glu Tyr Val Pro Ala Glu Arg His Gln Leu Tyr Glu Asn Gly
        195                 200                 205

Arg Ala Leu Ser Gly Ala Gln Gln Pro Glu Asp Val Thr Gly Ser Val
    210                 215                 220

Val Trp Leu Leu Ser Asp Leu Ser Arg Phe Ile Thr Gly Gln Leu Ile
225                 230                 235                 240

Pro Val Asn Gly Gly Phe Val Phe Asn
                245
```

<210> SEQ ID NO 141
<211> LENGTH: 795
<212> TYPE: DNA
<213> ORGANISM: Klebsiella pneumoniae subsp. pneumoinae MGH78578

<400> SEQUENCE: 141

```
atgaatgcac aaattgaagg gcgcgtcgcg gtagtcaccg gcggttcgtc aggaatcggc       60
```

```
tttgaaacgc tgcgcctgct gctgggcgaa ggggcgaaag tcgccttttg cggccgcaac      120
ccggatcggc ttgccagcgc ccatgcggcg ttgcaaaacg aatatccaga aggtgaggtg      180
ttctcctggc gctgtgacgt actgaacgaa gctgaagttg aggcgttcgc cgccgcggtc      240
gccgcgcgtt tcggcggcgt cgatatgctg attaataacg ccggccaggg ctatgtcgcc      300
cacttcgccg atacgccacg tgaggcctgg ctgcacgaag ccgaactgaa actgttcggc      360
gtgattaacc cggtaaaggc ctttcagtcc ctgctagagg cgtcggatat cgcctcgatt      420
acctgtgtga actcgctgct ggcgttacag ccggaagagc acatgatcgc cacctctgcc      480
gcccgcgccg cgctgctcaa tatgacgctg actctgtcga agagctggt ggataaaggt       540 attcgtgtga attccattct gctggggatg gtggagtccg gcagtggca gcgccgtttt       600 gagagccgaa gcgataagag ccagagttgg cagcagtgga ccgccgatat cgcccgtaag      660
cgggggatcc cgatggcgcg tctcggtaag ccgcaggagc cagcgcaagc gctgctattc      720
ctcgcttcgc cgctggcctc ctttaccacc ggcgcggcgc tggacgtttc cggcggtttc      780
tgtcgccatc tgtaa                                                       795

<210> SEQ ID NO 142
<211> LENGTH: 264
<212> TYPE: PRT
<213> ORGANISM: Klebsiella pneumoniae subsp. pneumoniae MGH78578

<400> SEQUENCE: 142

Met Asn Ala Gln Ile Glu Gly Arg Val Ala Val Thr Gly Gly Ser
1               5                   10                  15

Ser Gly Ile Gly Phe Glu Thr Leu Arg Leu Leu Leu Gly Glu Gly Ala
                20                  25                  30

Lys Val Ala Phe Cys Gly Arg Asn Pro Asp Arg Leu Ala Ser Ala His
            35                  40                  45

Ala Ala Leu Gln Asn Glu Tyr Pro Glu Gly Glu Val Phe Ser Trp Arg
        50                  55                  60

Cys Asp Val Leu Asn Glu Ala Glu Val Glu Ala Phe Ala Ala Ala Val
65                  70                  75                  80

Ala Ala Arg Phe Gly Gly Val Asp Met Leu Ile Asn Asn Ala Gly Gln
                85                  90                  95

Gly Tyr Val Ala His Phe Ala Asp Thr Pro Arg Glu Ala Trp Leu His
            100                 105                 110

Glu Ala Glu Leu Lys Leu Phe Gly Val Ile Asn Pro Val Lys Ala Phe
        115                 120                 125

Gln Ser Leu Leu Glu Ala Ser Asp Ile Ala Ser Ile Thr Cys Val Asn
    130                 135                 140

Ser Leu Leu Ala Leu Gln Pro Glu Glu His Met Ile Ala Thr Ser Ala
145                 150                 155                 160

Ala Arg Ala Ala Leu Leu Asn Met Thr Leu Thr Leu Ser Lys Glu Leu
                165                 170                 175

Val Asp Lys Gly Ile Arg Val Asn Ser Ile Leu Leu Gly Met Val Glu
            180                 185                 190

Ser Gly Gln Trp Gln Arg Arg Phe Glu Ser Arg Ser Asp Lys Ser Gln
        195                 200                 205

Ser Trp Gln Gln Trp Thr Ala Asp Ile Ala Arg Lys Arg Gly Ile Pro
    210                 215                 220

Met Ala Arg Leu Gly Lys Pro Gln Glu Pro Ala Gln Ala Leu Leu Phe
225                 230                 235                 240
```

Leu Ala Ser Pro Leu Ala Ser Phe Thr Thr Gly Ala Ala Leu Asp Val
                245                 250                 255

Ser Gly Gly Phe Cys Arg His Leu
            260

<210> SEQ ID NO 143
<211> LENGTH: 1795
<212> TYPE: DNA
<213> ORGANISM: Pseudomonas fluorescens

<400> SEQUENCE: 143

| | | | | | |
|---|---|---|---|---|---|
| cgccaagcaa | tcgggctttg | ggcagaatt | gggtcgcgaa | gggcttgagg | agtttgccca | 60 |
| gtccaagatc | atcaacgccg | cgctataaat | taaaggatcc | cccatggcga | tgattacagg | 120 |
| cggcgaactg | gttgttcgca | ccctaataaa | ggctggggtc | gaacatctgt | tcggcctgca | 180 |
| cggcgcgcat | atcgatacga | tttttcaagc | ctgtctcgat | catgatgtgc | cgatcatcga | 240 |
| cacccgccat | gaggccgccg | cagggcatgc | ggccgagggc | tatgcccgcg | ctggcgccaa | 300 |
| gctgggcgtg | gctggtcacg | gcgggcgggg | gatttaccaa | tgcggtcacg | cccattgcca | 360 |
| acgcttggct | ggatcgcaag | gccggtgtat | tcctcacccg | gatcgggcg | cgctgcgtga | 420 |
| tgatgaaacc | aacacgttgc | aggcggggat | tgatcaggtc | gccatggcgg | cgcccattac | 480 |
| caaatgggcg | catcgggtga | tgcaaccga | gcatatccca | cggctggtga | tgcaggcgat | 540 |
| ccgcgccgcg | ttgagcgcgc | cacgcgggcc | ggtgttgctg | atctgccgt | gggatattct | 600 |
| gatgaaccag | attgatgagg | atagcgtcat | tatccccgat | ctggtcttgt | ccgcgcatgg | 660 |
| ggccagaccc | gaccctgccg | atctggatca | ggctctcgcg | cttttgcgca | aggcggagcg | 720 |
| gccggtcatc | gtgctcggct | cagaagcctc | gcggacagcg | cgcaagacgg | cgcttagcgc | 780 |
| cttcgtggcg | gcgactggcg | tgccggtgtt | tgccgattat | gaagggctaa | gcatgctctc | 840 |
| ggggctgccc | gatgctatgc | ggggcgggct | ggtgcaaaac | ctctattctt | ttgccaaagc | 900 |
| cgatgccgcg | ccagatctcg | tgctgatgct | ggggcgcgc | tttggcctta | acaccgggca | 960 |
| tggatctggg | cagttgatcc | cccatagcgc | gcaggtcatt | caggtcgacc | ctgatgcctg | 1020 |
| cgagctggga | cgcctgcagg | gcatcgctct | gggcattgtg | ccgatgtgg | gtgggaccat | 1080 |
| cgaggctttg | gcgcaggcca | ccgcgcaaga | tgcggcttgg | ccggatcgcg | gcgactggtg | 1140 |
| cgccaaagtg | acggatctgg | cgcaagagcg | ctatgccagc | atcgctgcga | atcgagcag | 1200 |
| cgagcatgcg | ctccaccct | ttcacgcctc | gcaggtcatt | gccaaacacg | tcgatgcagg | 1260 |
| ggtgacggtg | gtagcggatg | gtgcgctgac | ctatctctgg | ctgtccgaag | tgatgagccg | 1320 |
| cgtgaaaccc | ggcggttttc | tctgccacgg | ctatctaggc | tcgatgggcg | tgggcttcgg | 1380 |
| cacgcgcctg | ggcgcgcaag | tggccgatct | tgaagcaggc | cgccgcacga | tccttgtgac | 1440 |
| cggcgatggc | tcggtgggct | atagcatcgg | tgaatttgat | acgctggtgc | gcaaacaatt | 1500 |
| gccgctgatc | gtcatcatca | tgaacaacca | aagctggggg | gcgacattgc | atttccagca | 1560 |
| attggccgtc | ggccccaatc | gcgtgacggg | cacccgtttg | gaaaatggct | cctatcacgg | 1620 |
| ggtgccgcc | gcctttggcg | cggatggcta | tcatgtcgac | agtgtggaga | gcttttctgc | 1680 |
| ggctctggcc | caagcgctcg | cccataatcg | ccccgcctgc | atcaatgtcg | cggtcgcgct | 1740 |
| cgatccgatc | ccgcccgaag | aactcattct | gatcggcatg | gacccctccg | catga | 1795 |

<210> SEQ ID NO 144
<211> LENGTH: 563
<212> TYPE: PRT
<213> ORGANISM: Pseudomonas fluorescens -continued

```
<400> SEQUENCE: 144

Met Ala Met Ile Thr Gly Gly Glu Leu Val Arg Thr Leu Ile Lys
1               5                   10                  15

Ala Gly Val Glu His Leu Phe Gly Leu His Gly Ala His Ile Asp Thr
            20                  25                  30

Ile Phe Gln Ala Cys Leu Asp His Asp Val Pro Ile Ile Asp Thr Arg
                35                  40                  45

His Glu Ala Ala Ala Gly His Ala Ala Glu Gly Tyr Ala Arg Ala Gly
        50                  55                  60

Ala Lys Leu Gly Val Ala Gly His Gly Arg Gly Ile Tyr Gln Cys
65                  70                  75                  80

Gly His Ala His Cys Gln Arg Leu Ala Gly Ser Gln Gly Arg Cys Ile
                85                  90                  95

Pro His Pro Gly Ser Gly Ala Leu Arg Asp Asp Glu Thr Asn Thr Leu
            100                 105                 110

Gln Ala Gly Ile Asp Gln Val Ala Met Ala Ala Pro Ile Thr Lys Trp
            115                 120                 125

Ala His Arg Val Met Ala Thr Glu His Ile Pro Arg Leu Val Met Gln
130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                165                 170                 175

Ile Pro Asp Leu Val Leu Ser Ala His Gly Ala Arg Pro Asp Pro Ala
            180                 185                 190

Asp Leu Asp Gln Ala Leu Ala Leu Leu Arg Lys Ala Glu Arg Pro Val
        195                 200                 205

Ile Val Leu Gly Ser Glu Ala Ser Arg Thr Ala Arg Lys Thr Ala Leu
210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
                245                 250                 255

Val Gln Asn Leu Tyr Ser Phe Ala Lys Ala Asp Ala Ala Pro Asp Leu
            260                 265                 270

Val Leu Met Leu Gly Ala Arg Phe Gly Leu Asn Thr Gly His Gly Ser
        275                 280                 285

Gly Gln Leu Ile Pro His Ser Ala Gln Val Ile Gln Val Asp Pro Asp
290                 295                 300

Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
                325                 330                 335

Ala Ala Trp Pro Asp Arg Gly Asp Trp Cys Ala Lys Val Thr Asp Leu
            340                 345                 350

Ala Gln Glu Arg Tyr Ala Ser Ile Ala Ala Lys Ser Ser Glu His
        355                 360                 365

Ala Leu His Pro Phe His Ala Ser Gln Val Ile Ala Lys His Val Asp
370                 375                 380

Ala Gly Val Thr Val Ala Asp Gly Ala Leu Thr Tyr Leu Trp Leu
385                 390                 395                 400

Ser Glu Val Met Ser Arg Val Lys Pro Gly Gly Phe Leu Cys His Gly
                405                 410                 415
```

```
Tyr Leu Gly Ser Met Gly Val Gly Phe Gly Thr Ala Leu Gly Ala Gln
            420                 425                 430

Val Ala Asp Leu Glu Ala Gly Arg Arg Thr Ile Leu Val Thr Gly Asp
        435                 440                 445

Gly Ser Val Gly Tyr Ser Ile Gly Glu Phe Asp Thr Leu Val Arg Lys
        450                 455                 460

Gln Leu Pro Leu Ile Val Ile Met Asn Asn Gln Ser Trp Gly Ala
465                 470                 475                 480

Thr Leu His Phe Gln Gln Leu Ala Val Gly Pro Asn Arg Val Thr Gly
                485                 490                 495

Thr Arg Leu Glu Asn Gly Ser Tyr His Gly Val Ala Ala Ala Phe Gly
            500                 505                 510

Ala Asp Gly Tyr His Val Asp Ser Val Glu Ser Phe Ser Ala Ala Leu
        515                 520                 525

Ala Gln Ala Leu Ala His Asn Arg Pro Ala Cys Ile Asn Val Ala Val
        530                 535                 540

Ala Leu Asp Pro Ile Pro Pro Glu Glu Leu Ile Leu Ile Gly Met Asp
545                 550                 555                 560

Pro Phe Ala

<210> SEQ ID NO 145
<211> LENGTH: 9
<212> TYPE: PRT
<213> ORGANISM: Artificial Sequence
<220> FEATURE:
<223> OTHER INFORMATION: A polypeptide that is similar to an
      autotransporter adhesion or type I secretion
      target repeat.
<220> FEATURE:
<221> NAME/KEY: VARIANT
<222> LOCATION: 3, 5, 7, 8, 9
<223> OTHER INFORMATION: Xaa = Any Amino Acid

<400> SEQUENCE: 145

Gly Gly Xaa Gly Xaa Asp Xaa Xaa Xaa
1               5

<210> SEQ ID NO 146
<211> LENGTH: 50
<212> TYPE: DNA
<213> ORGANISM: Artificial Sequence
<220> FEATURE:
<223> OTHER INFORMATION: Primer

<400> SEQUENCE: 146
gtctttattc atatatatat cctccttaat tcaaccgttc aatcaccatc         50

<210> SEQ ID NO 147
<211> LENGTH: 30
<212> TYPE: DNA
<213> ORGANISM: Artificial Sequence
<220> FEATURE:
<223> OTHER INFORMATION: Primer

<400> SEQUENCE: 147
gggcggccgc aagggggttcg cgttggccga                              30

<210> SEQ ID NO 148
<211> LENGTH: 22
<212> TYPE: DNA
<213> ORGANISM: Artificial Sequence
<220> FEATURE:
<223> OTHER INFORMATION: Primer
```

```
<400> SEQUENCE: 148
ggagaaaata ccgcatcagg cg                                           22

<210> SEQ ID NO 149
<211> LENGTH: 32
<212> TYPE: DNA
<213> ORGANISM: Artificial Sequence
<220> FEATURE:
<223> OTHER INFORMATION: Primer

<400> SEQUENCE: 149
cgggatccaa gttgcaggat atgacgaaag cg                                32

<210> SEQ ID NO 150
<211> LENGTH: 33
<212> TYPE: DNA
<213> ORGANISM: Artificial Sequence
<220> FEATURE:
<223> OTHER INFORMATION: Primer

<400> SEQUENCE: 150
gctctagaag attatccctg tctgcggaag cgg                               33

<210> SEQ ID NO 151
<211> LENGTH: 32
<212> TYPE: DNA
<213> ORGANISM: Artificial Sequence
<220> FEATURE:
<223> OTHER INFORMATION: Primer

<400> SEQUENCE: 151
gctctagagg ggtgcctaat gagtgagcta ac                                32

<210> SEQ ID NO 152
<211> LENGTH: 33
<212> TYPE: DNA
<213> ORGANISM: Artificial Sequence
<220> FEATURE:
<223> OTHER INFORMATION: Primer

<400> SEQUENCE: 152
cgggatccgc gttaatattt tgttaaaatt cgc                               33

<210> SEQ ID NO 153
<211> LENGTH: 31
<212> TYPE: DNA
<213> ORGANISM: Artificial Sequence
<220> FEATURE:
<223> OTHER INFORMATION: Primer

<400> SEQUENCE: 153
gctctagagt ttatgtcgca cccgccgttg g                                 31

<210> SEQ ID NO 154
<211> LENGTH: 32
<212> TYPE: DNA
<213> ORGANISM: Artificial Sequence
<220> FEATURE:
<223> OTHER INFORMATION: Primer

<400> SEQUENCE: 154
cccaagctta gaaagggaaa ttgtggtagc cc                                32

<210> SEQ ID NO 155
<211> LENGTH: 31
<212> TYPE: DNA
```

```
<213> ORGANISM: Artificial Sequence
<220> FEATURE:
<223> OTHER INFORMATION: Primer

<400> SEQUENCE: 155
ggaattccat atgcgtccct ctgccccggc c                                31

<210> SEQ ID NO 156
<211> LENGTH: 30
<212> TYPE: DNA
<213> ORGANISM: Artificial Sequence
<220> FEATURE:
<223> OTHER INFORMATION: Primer

<400> SEQUENCE: 156
cgggatcctt agaactgctt gggaagggag                                  30

<210> SEQ ID NO 157
<211> LENGTH: 50
<212> TYPE: DNA
<213> ORGANISM: Artificial Sequence
<220> FEATURE:
<223> OTHER INFORMATION: Primer

<400> SEQUENCE: 157
aggtacggtg aaataaagga ggatatacat atgtccaaaa agattgccgt            50

<210> SEQ ID NO 158
<211> LENGTH: 37
<212> TYPE: DNA
<213> ORGANISM: Artificial Sequence
<220> FEATURE:
<223> OTHER INFORMATION: Primer

<400> SEQUENCE: 158
ttttcctttt gcggccgccc cgctggcatc gcctcac                          37

<210> SEQ ID NO 159
<211> LENGTH: 50
<212> TYPE: DNA
<213> ORGANISM: Artificial Sequence
<220> FEATURE:
<223> OTHER INFORMATION: Primer

<400> SEQUENCE: 159
ggcgatgcca gcgtaaagga ggatatacat atgaaaaact ggaaaacaag            50

<210> SEQ ID NO 160
<211> LENGTH: 37
<212> TYPE: DNA
<213> ORGANISM: Artificial Sequence
<220> FEATURE:
<223> OTHER INFORMATION: Primer

<400> SEQUENCE: 160
ttttcctttt gcggccgccc cagcttagcg ccttcta                          37

<210> SEQ ID NO 161
<211> LENGTH: 31
<212> TYPE: DNA
<213> ORGANISM: Artificial Sequence
<220> FEATURE:
<223> OTHER INFORMATION: Primer

<400> SEQUENCE: 161
cccgagctct taggaggatt agtcatggaa c                                31
```

<210> SEQ ID NO 162
<211> LENGTH: 32
<212> TYPE: DNA
<213> ORGANISM: Artificial Sequence
<220> FEATURE:
<223> OTHER INFORMATION: Primer

<400> SEQUENCE: 162
gctctagatt attttgaata atcgtagaaa cc              32

<210> SEQ ID NO 163
<211> LENGTH: 42
<212> TYPE: DNA
<213> ORGANISM: Artificial sequence
<220> FEATURE:
<223> OTHER INFORMATION: Primer

<400> SEQUENCE: 163
gctctagagg aggatatata tatgaaaaat tgtgtcatcg tc    42

<210> SEQ ID NO 164
<211> LENGTH: 30
<212> TYPE: DNA
<213> ORGANISM: Artificial Sequence
<220> FEATURE:
<223> OTHER INFORMATION: Primer

<400> SEQUENCE: 164
aactgcagtt aattcaaccg ttcaatcacc                 30

<210> SEQ ID NO 165
<211> LENGTH: 46
<212> TYPE: DNA
<213> ORGANISM: Artificial Sequence
<220> FEATURE:
<223> OTHER INFORMATION: Primer

<400> SEQUENCE: 165
cgagctcagg aggatatata tatgaaaaat tgtgtcatcg tcagtg    46

<210> SEQ ID NO 166
<211> LENGTH: 50
<212> TYPE: DNA
<213> ORGANISM: Artificial Sequence
<220> FEATURE:
<223> OTHER INFORMATION: Primer

<400> SEQUENCE: 166
ggttgaatta aggaggatat atatatgaat aaagacacac taatacctac    50

<210> SEQ ID NO 167
<211> LENGTH: 30
<212> TYPE: DNA
<213> ORGANISM: Artificial Sequence
<220> FEATURE:
<223> OTHER INFORMATION: Primer

<400> SEQUENCE: 167
cccaagctta gccggcaagt acacatcttc                 30

<210> SEQ ID NO 168
<211> LENGTH: 46
<212> TYPE: DNA
<213> ORGANISM: Artificial Sequence
<220> FEATURE:
<223> OTHER INFORMATION: Primer

<400> SEQUENCE: 168
cgagctcagg aggatatata tatgaaaaat tgtgtcatcg tcagtg          46

<210> SEQ ID NO 169
<211> LENGTH: 30
<212> TYPE: DNA
<213> ORGANISM: Artificial Sequence
<220> FEATURE:
<223> OTHER INFORMATION: Primer

<400> SEQUENCE: 169
cccaagctta gccggcaagt acacatcttc          30

<210> SEQ ID NO 170
<211> LENGTH: 40
<212> TYPE: DNA
<213> ORGANISM: Artificial Sequence
<220> FEATURE:
<223> OTHER INFORMATION: Primer

<400> SEQUENCE: 170
aaggaaaaaa gcggccgccc ctgaaccgac gaccgggtcg          40

<210> SEQ ID NO 171
<211> LENGTH: 35
<212> TYPE: DNA
<213> ORGANISM: Artificial Sequence
<220> FEATURE:
<223> OTHER INFORMATION: Primer

<400> SEQUENCE: 171
cggggtaccg cggatacata tttgaatgta tttag          35

<210> SEQ ID NO 172
<211> LENGTH: 44
<212> TYPE: DNA
<213> ORGANISM: Artificial Sequence
<220> FEATURE:
<223> OTHER INFORMATION: Primer

<400> SEQUENCE: 172
aaggaaaaaa gcggccgcgc ggatacatat ttgaatgtat ttag          44

<210> SEQ ID NO 173
<211> LENGTH: 43
<212> TYPE: DNA
<213> ORGANISM: Artificial Sequence
<220> FEATURE:
<223> OTHER INFORMATION: Primer

<400> SEQUENCE: 173
gctctagagg aggatatata tatggctaac tacttcaata cac          43

<210> SEQ ID NO 174
<211> LENGTH: 50
<212> TYPE: DNA
<213> ORGANISM: Artificial Sequence
<220> FEATURE:
<223> OTHER INFORMATION: Primer

<400> SEQUENCE: 174
tgctgttgcg ggttaaggag gatatatata tgcctaagta ccgttccgcc          50

<210> SEQ ID NO 175
<211> LENGTH: 50
<212> TYPE: DNA

<210> SEQ ID NO 175
<211> LENGTH: 50
<212> TYPE: DNA
<213> ORGANISM: Artificial Sequence
<220> FEATURE:
<223> OTHER INFORMATION: Primer

<400> SEQUENCE: 175
aacggtactt aggcatatat atatcctcct taacccgcaa cagcaatacg          50

<210> SEQ ID NO 176
<211> LENGTH: 30
<212> TYPE: DNA
<213> ORGANISM: Artificial Sequence
<220> FEATURE:
<223> OTHER INFORMATION: Primer

<400> SEQUENCE: 176
acatgcatgc ttaaccccccc agtttcgatt          30

<210> SEQ ID NO 177
<211> LENGTH: 43
<212> TYPE: DNA
<213> ORGANISM: Artificial Sequence
<220> FEATURE:
<223> OTHER INFORMATION: Primer

<400> SEQUENCE: 177
gctctagagg aggatatata tatggctaac tacttcaata cac          43

<210> SEQ ID NO 178
<211> LENGTH: 30
<212> TYPE: DNA
<213> ORGANISM: Artificial Sequence
<220> FEATURE:
<223> OTHER INFORMATION: Primer

<400> SEQUENCE: 178
acatgcatgc ttaaccccccc agtttcgatt          30

<210> SEQ ID NO 179
<211> LENGTH: 43
<212> TYPE: DNA
<213> ORGANISM: Artificial Sequence
<220> FEATURE:
<223> OTHER INFORMATION: Primer

<400> SEQUENCE: 179
cccgagctca ggaggatata tatggata acagtatcc ggt          43

<210> SEQ ID NO 180
<211> LENGTH: 28
<212> TYPE: DNA
<213> ORGANISM: Artificial Sequence
<220> FEATURE:
<223> OTHER INFORMATION: Primer

<400> SEQUENCE: 180
gctctagatt acagaatttg actcaggt          28

<210> SEQ ID NO 181
<211> LENGTH: 45
<212> TYPE: DNA
<213> ORGANISM: Artificial Sequence
<220> FEATURE:
<223> OTHER INFORMATION: Primer

<400> SEQUENCE: 181
cccgagctca ggaggatata tatgttga caaaagcaac aaaag          45

```
<210> SEQ ID NO 182
<211> LENGTH: 25
<212> TYPE: DNA
<213> ORGANISM: Artificial Sequence
<220> FEATURE:
<223> OTHER INFORMATION: Primer

<400> SEQUENCE: 182
ctctaaatct ctggaaaggg taccg                                         25

<210> SEQ ID NO 183
<211> LENGTH: 30
<212> TYPE: DNA
<213> ORGANISM: Artificial Sequence
<220> FEATURE:
<223> OTHER INFORMATION: Primer

<400> SEQUENCE: 183
gctctagatt agagagcttt cgttttcatg                                    30

<210> SEQ ID NO 184
<211> LENGTH: 45
<212> TYPE: DNA
<213> ORGANISM: Artificial Sequence
<220> FEATURE:
<223> OTHER INFORMATION: Primer

<400> SEQUENCE: 184
cccgagctca ggaggatata tatatgttga caaaagcaac aaaag                   45

<210> SEQ ID NO 185
<211> LENGTH: 30
<212> TYPE: DNA
<213> ORGANISM: Artificial Sequence
<220> FEATURE:
<223> OTHER INFORMATION: Primer

<400> SEQUENCE: 185
gctctagatt agagagcttt cgttttcatg                                    30

<210> SEQ ID NO 186
<211> LENGTH: 46
<212> TYPE: DNA
<213> ORGANISM: Artificial Sequence
<220> FEATURE:
<223> OTHER INFORMATION: Primer

<400> SEQUENCE: 186
cgagctcagg aggatatata tatgagccag caagtcatta ttttcg                  46

<210> SEQ ID NO 187
<211> LENGTH: 35
<212> TYPE: DNA
<213> ORGANISM: Artificial Sequence
<220> FEATURE:
<223> OTHER INFORMATION: Primer

<400> SEQUENCE: 187
aaaactgcag cgtttgatga cgtggacgat agcgg                              35

<210> SEQ ID NO 188
<211> LENGTH: 46
<212> TYPE: DNA
<213> ORGANISM: Artificial Sequence
<220> FEATURE:
<223> OTHER INFORMATION: Primer
```

<400> SEQUENCE: 188
cgagctcagg aggatatata tatgagccag caagtcatta ttttcg        46

<210> SEQ ID NO 189
<211> LENGTH: 50
<212> TYPE: DNA
<213> ORGANISM: Artificial Sequence
<220> FEATURE:
<223> OTHER INFORMATION: Primer

<400> SEQUENCE: 189
aggggtgtaa ggaggatata tatatggcta agacgttata cgaaaaattg        50

<210> SEQ ID NO 190
<211> LENGTH: 50
<212> TYPE: DNA
<213> ORGANISM: Artificial Sequence
<220> FEATURE:
<223> OTHER INFORMATION: Primer

<400> SEQUENCE: 190
cgtcttagcc atatatatat cctccttaca ccccttctgc tacatagcgg        50

<210> SEQ ID NO 191
<211> LENGTH: 35
<212> TYPE: DNA
<213> ORGANISM: Artificial Sequence
<220> FEATURE:
<223> OTHER INFORMATION: Primer

<400> SEQUENCE: 191
aaaactgcag cgtttgatga cgtggacgat agcgg        35

<210> SEQ ID NO 192
<211> LENGTH: 46
<212> TYPE: DNA
<213> ORGANISM: Artificial Sequence
<220> FEATURE:
<223> OTHER INFORMATION: Primer

<400> SEQUENCE: 192
cgagctcagg aggatatata tatgagccag caagtcatta ttttcg        46

<210> SEQ ID NO 193
<211> LENGTH: 35
<212> TYPE: DNA
<213> ORGANISM: Artificial Sequence
<220> FEATURE:
<223> OTHER INFORMATION: Primer

<400> SEQUENCE: 193
aaaactgcag cgtttgatga cgtggacgat agcgg        35

<210> SEQ ID NO 194
<211> LENGTH: 46
<212> TYPE: DNA
<213> ORGANISM: Artificial Sequence
<220> FEATURE:
<223> OTHER INFORMATION: Primer

<400> SEQUENCE: 194
cgagctcagg aggatatata tatgagccag caagtcatta ttttcg        46

<210> SEQ ID NO 195
<211> LENGTH: 50
<212> TYPE: DNA

```
<213> ORGANISM: Artificial Sequence
<220> FEATURE:
<223> OTHER INFORMATION: Primer

<400> SEQUENCE: 195
gaaaccgtgt gaggaggata tatatatgtc gaagaattac catattgccg              50

<210> SEQ ID NO 196
<211> LENGTH: 50
<212> TYPE: DNA
<213> ORGANISM: Artificial Sequence
<220> FEATURE:
<223> OTHER INFORMATION: Primer

<400> SEQUENCE: 196
aggggtgtaa ggaggatata tatatggcta agacgttata cgaaaaattg              50

<210> SEQ ID NO 197
<211> LENGTH: 50
<212> TYPE: DNA
<213> ORGANISM: Artificial Sequence
<220> FEATURE:
<223> OTHER INFORMATION: Primer

<400> SEQUENCE: 197
acattaaata aggaggatat atatatggca gagaaattta tcaaacacac              50

<210> SEQ ID NO 198
<211> LENGTH: 50
<212> TYPE: DNA
<213> ORGANISM: Artificial Sequence
<220> FEATURE:
<223> OTHER INFORMATION: Primer

<400> SEQUENCE: 198
attcttcgac atatatatat cctcctcaca cggtttcctt gttgttttcg              50

<210> SEQ ID NO 199
<211> LENGTH: 50
<212> TYPE: DNA
<213> ORGANISM: Artificial Sequence
<220> FEATURE:
<223> OTHER INFORMATION: Primer

<400> SEQUENCE: 199
cgtcttagcc atatatatat cctccttaca ccccttctgc tacatagcgg              50

<210> SEQ ID NO 200
<211> LENGTH: 50
<212> TYPE: DNA
<213> ORGANISM: Artificial Sequence
<220> FEATURE:
<223> OTHER INFORMATION: Primer

<400> SEQUENCE: 200
tttctctgcc atatatatat cctccttatt aatgttgcg aatgtcggcg               50

<210> SEQ ID NO 201
<211> LENGTH: 35
<212> TYPE: DNA
<213> ORGANISM: Artificial Sequence
<220> FEATURE:
<223> OTHER INFORMATION: Primer

<400> SEQUENCE: 201
aaaactgcag cgtttgatga cgtggacgat agcgg                              35
```

```
<210> SEQ ID NO 202
<211> LENGTH: 46
<212> TYPE: DNA
<213> ORGANISM: Artificial Sequence
<220> FEATURE:
<223> OTHER INFORMATION: Primer

<400> SEQUENCE: 202
cgagctcagg aggatatata tatgagccag caagtcatta ttttcg            46

<210> SEQ ID NO 203
<211> LENGTH: 35
<212> TYPE: DNA
<213> ORGANISM: Artificial Sequence
<220> FEATURE:
<223> OTHER INFORMATION: Primer

<400> SEQUENCE: 203
aaaactgcag cgtttgatga cgtggacgat agcgg                         35

<210> SEQ ID NO 204
<211> LENGTH: 40
<212> TYPE: DNA
<213> ORGANISM: Artificial Sequence
<220> FEATURE:
<223> OTHER INFORMATION: Primer

<400> SEQUENCE: 204
aaggaaaaaa gcggccgccc ctgaaccgac gaccgggtcg                    40

<210> SEQ ID NO 205
<211> LENGTH: 35
<212> TYPE: DNA
<213> ORGANISM: Artificial Sequence
<220> FEATURE:
<223> OTHER INFORMATION: Primer

<400> SEQUENCE: 205
cggggtaccg cggatacata tttgaatgta tttag                         35

<210> SEQ ID NO 206
<211> LENGTH: 42
<212> TYPE: DNA
<213> ORGANISM: Artificial Sequence
<220> FEATURE:
<223> OTHER INFORMATION: Primer

<400> SEQUENCE: 206
aaggaaaaaa gcggccgcac ttttcatact cccgccattc ag                 42

<210> SEQ ID NO 207
<211> LENGTH: 31
<212> TYPE: DNA
<213> ORGANISM: Artificial Sequence
<220> FEATURE:
<223> OTHER INFORMATION: Primer

<400> SEQUENCE: 207
caaaggccgt ctgcacgcgc cgaaaggcaa a                             31

<210> SEQ ID NO 208
<211> LENGTH: 31
<212> TYPE: DNA
<213> ORGANISM: Artificial Sequence
<220> FEATURE:
<223> OTHER INFORMATION: Primer
```

-continued

<400> SEQUENCE: 208
tttgcctttc ggcgcgtgca gacggccttt g                          31

<210> SEQ ID NO 209
<211> LENGTH: 35
<212> TYPE: DNA
<213> ORGANISM: Artificial Sequence
<220> FEATURE:
<223> OTHER INFORMATION: Primer

<400> SEQUENCE: 209
acatgcatgc cgtttgatga cgtggacgat agcgg                      35

<210> SEQ ID NO 210
<211> LENGTH: 42
<212> TYPE: DNA
<213> ORGANISM: Artificial Sequence
<220> FEATURE:
<223> OTHER INFORMATION: Primer

<400> SEQUENCE: 210
aaggaaaaaa gcggccgcac ttttcatact cccgccattc ag              42

<210> SEQ ID NO 211
<211> LENGTH: 35
<212> TYPE: DNA
<213> ORGANISM: Artificial Sequence
<220> FEATURE:
<223> OTHER INFORMATION: Primer

<400> SEQUENCE: 211
acatgcatgc cgtttgatga cgtggacgat agcgg                      35

<210> SEQ ID NO 212
<211> LENGTH: 48
<212> TYPE: DNA
<213> ORGANISM: Artificial Sequence
<220> FEATURE:
<223> OTHER INFORMATION: Primer

<400> SEQUENCE: 212
cccgagctca ggaggatata tatatgaatt atcagaacga cgatttac        48

<210> SEQ ID NO 213
<211> LENGTH: 50
<212> TYPE: DNA
<213> ORGANISM: Artificial Sequence
<220> FEATURE:
<223> OTHER INFORMATION: Primer

<400> SEQUENCE: 213
gcgtcgcggg taaggaggaa aattttatgt cctcacgtaa agagcttgcc      50

<210> SEQ ID NO 214
<211> LENGTH: 50
<212> TYPE: DNA
<213> ORGANISM: Artificial Sequence
<220> FEATURE:
<223> OTHER INFORMATION: Primer

<400> SEQUENCE: 214
gaactgctgt aaggaggtta aaattatgga gaggattgtc gttactctcg      50

<210> SEQ ID NO 215
<211> LENGTH: 50
<212> TYPE: DNA

```
<213> ORGANISM: Artificial Sequence
<220> FEATURE:
<223> OTHER INFORMATION: Primer

<400> SEQUENCE: 215
caatcagcgt aaggaggtat atataatgaa aaccgtaact gtaaaagatc        50

<210> SEQ ID NO 216
<211> LENGTH: 50
<212> TYPE: DNA
<213> ORGANISM: Artificial Sequence
<220> FEATURE:
<223> OTHER INFORMATION: Primer

<400> SEQUENCE: 216
tacaccaggc ataaggagga attaattatg gaaacctatg ctgttttggg        50

<210> SEQ ID NO 217
<211> LENGTH: 50
<212> TYPE: DNA
<213> ORGANISM: Artificial Sequence
<220> FEATURE:
<223> OTHER INFORMATION: Primer

<400> SEQUENCE: 217
tacgtgagga cataaaattt tcctccttac ccgcgacgcg cttttactgc        50

<210> SEQ ID NO 218
<211> LENGTH: 50
<212> TYPE: DNA
<213> ORGANISM: Artificial Sequence
<220> FEATURE:
<223> OTHER INFORMATION: Primer

<400> SEQUENCE: 218
caatcctctc cataatttta acctccttac agcagttctt ttgctttcgc        50

<210> SEQ ID NO 219
<211> LENGTH: 50
<212> TYPE: DNA
<213> ORGANISM: Artificial Sequence
<220> FEATURE:
<223> OTHER INFORMATION: Primer

<400> SEQUENCE: 219
caatcagcgt aaggaggtat atataatgaa aaccgtaact gtaaaagatc        50

<210> SEQ ID NO 220
<211> LENGTH: 50
<212> TYPE: DNA
<213> ORGANISM: Artificial Sequence
<220> FEATURE:
<223> OTHER INFORMATION: Primer

<400> SEQUENCE: 220
tacggttttc attatatata cctccttacg ctgattgaca atcggcaatg        50

<210> SEQ ID NO 221
<211> LENGTH: 34
<212> TYPE: DNA
<213> ORGANISM: Artificial Sequence
<220> FEATURE:
<223> OTHER INFORMATION: Primer

<400> SEQUENCE: 221
acatgcatgc ttacgcggac aattcctcct gcaa        34
```

```
<210> SEQ ID NO 222
<211> LENGTH: 48
<212> TYPE: DNA
<213> ORGANISM: Artificial Sequence
<220> FEATURE:
<223> OTHER INFORMATION: Primer

<400> SEQUENCE: 222
cccgagctca ggaggatata tatgaatt atcagaacga cgatttac                    48

<210> SEQ ID NO 223
<211> LENGTH: 34
<212> TYPE: DNA
<213> ORGANISM: Artificial Sequence
<220> FEATURE:
<223> OTHER INFORMATION: Primer

<400> SEQUENCE: 223
acatgcatgc ttacgcggac aattcctcct gcaa                                 34

<210> SEQ ID NO 224
<211> LENGTH: 48
<212> TYPE: DNA
<213> ORGANISM: Artificial Sequence
<220> FEATURE:
<223> OTHER INFORMATION: Primer

<400> SEQUENCE: 224
cccgagctca ggaggatata tatgacat cggaaaaccc gttactgg                    48

<210> SEQ ID NO 225
<211> LENGTH: 50
<212> TYPE: DNA
<213> ORGANISM: Artificial Sequence
<220> FEATURE:
<223> OTHER INFORMATION: Primer

<400> SEQUENCE: 225
gatccaacct aaggaggaaa attttatgac acaacctctt tttctgatcg                50

<210> SEQ ID NO 226
<211> LENGTH: 50
<212> TYPE: DNA
<213> ORGANISM: Artificial Sequence
<220> FEATURE:
<223> OTHER INFORMATION: Primer

<400> SEQUENCE: 226
gatcaattgt taaggaggta tatataatgg aatccctgac gttacaaccc                50

<210> SEQ ID NO 227
<211> LENGTH: 50
<212> TYPE: DNA
<213> ORGANISM: Artificial Sequence
<220> FEATURE:
<223> OTHER INFORMATION: Primer

<400> SEQUENCE: 227
caggcagcct aaggaggaat taattatggc tggaaacaca attggacaac                50

<210> SEQ ID NO 228
<211> LENGTH: 50
<212> TYPE: DNA
<213> ORGANISM: Artificial Sequence
<220> FEATURE:
<223> OTHER INFORMATION: Primer
```

```
<400> SEQUENCE: 228
aggttgtgtc ataaaatttt cctccttagg ttggatcaac aggcactacg            50

<210> SEQ ID NO 229
<211> LENGTH: 50
<212> TYPE: DNA
<213> ORGANISM: Artificial Sequence
<220> FEATURE:
<223> OTHER INFORMATION: Primer

<400> SEQUENCE: 229
cagggattcc attatatata cctccttaac aattgatcgt ctgtgccagg            50

<210> SEQ ID NO 230
<211> LENGTH: 50
<212> TYPE: DNA
<213> ORGANISM: Artificial Sequence
<220> FEATURE:
<223> OTHER INFORMATION: Primer

<400> SEQUENCE: 230
gtttccagcc ataattaatt cctccttagg ctgcctggct aatccgcgcc            50

<210> SEQ ID NO 231
<211> LENGTH: 35
<212> TYPE: DNA
<213> ORGANISM: Artificial Sequence
<220> FEATURE:
<223> OTHER INFORMATION: Primer

<400> SEQUENCE: 231
acatgcatgc ttaccagcgt ggaatatcag tcttc                            35

<210> SEQ ID NO 232
<211> LENGTH: 48
<212> TYPE: DNA
<213> ORGANISM: Artificial Sequence
<220> FEATURE:
<223> OTHER INFORMATION: Primer

<400> SEQUENCE: 232
cccgagctca ggaggatata tatatgacat cggaaaaccc gttactgg              48

<210> SEQ ID NO 233
<211> LENGTH: 35
<212> TYPE: DNA
<213> ORGANISM: Artificial Sequence
<220> FEATURE:
<223> OTHER INFORMATION: Primer

<400> SEQUENCE: 233
acatgcatgc ttaccagcgt ggaatatcag tcttc                            35

<210> SEQ ID NO 234
<211> LENGTH: 48
<212> TYPE: DNA
<213> ORGANISM: Artificial Sequence
<220> FEATURE:
<223> OTHER INFORMATION: Primer

<400> SEQUENCE: 234
cccgagctca ggaggatata tatatggttg ctgaattgac cgcattac              48

<210> SEQ ID NO 235
<211> LENGTH: 50
<212> TYPE: DNA
```

```
<213> ORGANISM: Artificial Sequence
<220> FEATURE:
<223> OTHER INFORMATION: Primer

<400> SEQUENCE: 235
aatcgccagt aaggaggaaa attttatgac acaacctctt tttctgatcg            50

<210> SEQ ID NO 236
<211> LENGTH: 50
<212> TYPE: DNA
<213> ORGANISM: Artificial Sequence
<220> FEATURE:
<223> OTHER INFORMATION: Primer

<400> SEQUENCE: 236
gatcaattgt taaggaggta tatataatgg aatccctgac gttacaaccc            50

<210> SEQ ID NO 237
<211> LENGTH: 50
<212> TYPE: DNA
<213> ORGANISM: Artificial Sequence
<220> FEATURE:
<223> OTHER INFORMATION: Primer

<400> SEQUENCE: 237
caggcagcct aaggaggaat taattatggc tggaaacaca attggacaac            50

<210> SEQ ID NO 238
<211> LENGTH: 50
<212> TYPE: DNA
<213> ORGANISM: Artificial Sequence
<220> FEATURE:
<223> OTHER INFORMATION: Primer

<400> SEQUENCE: 238
gaggttgtgt cataaaattt cctccttac tggcgattgt cattcgcctg             50

<210> SEQ ID NO 239
<211> LENGTH: 50
<212> TYPE: DNA
<213> ORGANISM: Artificial Sequence
<220> FEATURE:
<223> OTHER INFORMATION: Primer

<400> SEQUENCE: 239
cagggattcc attatatata cctccttaac aattgatcgt ctgtgccagg            50

<210> SEQ ID NO 240
<211> LENGTH: 50
<212> TYPE: DNA
<213> ORGANISM: Artificial Sequence
<220> FEATURE:
<223> OTHER INFORMATION: Primer

<400> SEQUENCE: 240
gtttccagcc ataattaatt cctccttagg ctgcctggct aatccgcgcc            50

<210> SEQ ID NO 241
<211> LENGTH: 35
<212> TYPE: DNA
<213> ORGANISM: Artificial Sequence
<220> FEATURE:
<223> OTHER INFORMATION: Primer

<400> SEQUENCE: 241
acatgcatgc ttaccagcgt ggaatatcag tcttc                            35
```

<210> SEQ ID NO 242
<211> LENGTH: 48
<212> TYPE: DNA
<213> ORGANISM: Artificial Sequence
<220> FEATURE:
<223> OTHER INFORMATION: Primer

<400> SEQUENCE: 242
cccgagctca ggaggatata tatatggttg ctgaattgac cgcattac          48

<210> SEQ ID NO 243
<211> LENGTH: 35
<212> TYPE: DNA
<213> ORGANISM: Artificial Sequence
<220> FEATURE:
<223> OTHER INFORMATION: Primer

<400> SEQUENCE: 243
acatgcatgc ttaccagcgt ggaatatcag tcttc                        35

<210> SEQ ID NO 244
<211> LENGTH: 40
<212> TYPE: DNA
<213> ORGANISM: Artificial Sequence
<220> FEATURE:
<223> OTHER INFORMATION: Primer

<400> SEQUENCE: 244
aaggaaaaaa gcggccgccc ctgaaccgac gaccgggtcg                   40

<210> SEQ ID NO 245
<211> LENGTH: 32
<212> TYPE: DNA
<213> ORGANISM: Artificial Sequence
<220> FEATURE:
<223> OTHER INFORMATION: Primer

<400> SEQUENCE: 245
gctctagaac ttttcatact cccgccattc ag                           32

<210> SEQ ID NO 246
<211> LENGTH: 34
<212> TYPE: DNA
<213> ORGANISM: Artificial Sequence
<220> FEATURE:
<223> OTHER INFORMATION: Primer

<400> SEQUENCE: 246
gctctagagc ggatacatat ttgaatgtat ttag                         34

<210> SEQ ID NO 247
<211> LENGTH: 44
<212> TYPE: DNA
<213> ORGANISM: Artificial Sequence
<220> FEATURE:
<223> OTHER INFORMATION: Primer

<400> SEQUENCE: 247
aaggaaaaaa gcggccgcgc ggatacatat ttgaatgtat ttag              44

<210> SEQ ID NO 248
<211> LENGTH: 26
<212> TYPE: DNA
<213> ORGANISM: Artificial Sequence
<220> FEATURE:
<223> OTHER INFORMATION: Primer

```
<400> SEQUENCE: 248
catgccatgg ctatgattac tggtgg                                         26

<210> SEQ ID NO 249
<211> LENGTH: 33
<212> TYPE: DNA
<213> ORGANISM: Artificial Sequence
<220> FEATURE:
<223> OTHER INFORMATION: Primer

<400> SEQUENCE: 249
ccccgagctc ttacgcgccg gattggaaat aca                                 33

<210> SEQ ID NO 250
<211> LENGTH: 31
<212> TYPE: DNA
<213> ORGANISM: Artificial Sequence
<220> FEATURE:
<223> OTHER INFORMATION: Primer

<400> SEQUENCE: 250
catgccatgg ccaaagttac aaatcaaaaa g                                   31

<210> SEQ ID NO 251
<211> LENGTH: 32
<212> TYPE: DNA
<213> ORGANISM: Artificial Sequence
<220> FEATURE:
<223> OTHER INFORMATION: Primer

<400> SEQUENCE: 251
cgagctctta aaatgatttt atatagatat cc                                  32

<210> SEQ ID NO 252
<211> LENGTH: 31
<212> TYPE: DNA
<213> ORGANISM: Artificial Sequence
<220> FEATURE:
<223> OTHER INFORMATION: Primer

<400> SEQUENCE: 252
catgccatgg gtattccaga aactcaaaaa g                                   31

<210> SEQ ID NO 253
<211> LENGTH: 31
<212> TYPE: DNA
<213> ORGANISM: Artificial Sequence
<220> FEATURE:
<223> OTHER INFORMATION: Primer

<400> SEQUENCE: 253
cccgagctct tatttagaag tgtcaacaac g                                   31

<210> SEQ ID NO 254
<211> LENGTH: 47
<212> TYPE: DNA
<213> ORGANISM: Artificial Sequence
<220> FEATURE:
<223> OTHER INFORMATION: Primer

<400> SEQUENCE: 254
ccccgagctc aggaggatat acatatgaat aaagacacac taatacc                  47

<210> SEQ ID NO 255
<211> LENGTH: 30
<212> TYPE: DNA
```

```
<213> ORGANISM: Artificial Sequence
<220> FEATURE:
<223> OTHER INFORMATION: Primer

<400> SEQUENCE: 255
cccaagctta gccggcaagt acacatcttc                                30

<210> SEQ ID NO 256
<211> LENGTH: 45
<212> TYPE: DNA
<213> ORGANISM: Artificial Sequence
<220> FEATURE:
<223> OTHER INFORMATION: Primer

<400> SEQUENCE: 256
cccgagctca ggaggatata tatatgtata cagtaggaga ttacc               45

<210> SEQ ID NO 257
<211> LENGTH: 33
<212> TYPE: DNA
<213> ORGANISM: Artificial Sequence
<220> FEATURE:
<223> OTHER INFORMATION: Primer

<400> SEQUENCE: 257
gctctagatt atgatttatt ttgttcagca aat                            33

<210> SEQ ID NO 258
<211> LENGTH: 45
<212> TYPE: DNA
<213> ORGANISM: Artificial Sequence
<220> FEATURE:
<223> OTHER INFORMATION: Primer

<400> SEQUENCE: 258
cccgagctca ggaggatata tatatgtata cagtaggaga ttacc               45

<210> SEQ ID NO 259
<211> LENGTH: 33
<212> TYPE: DNA
<213> ORGANISM: Artificial Sequence
<220> FEATURE:
<223> OTHER INFORMATION: Primer

<400> SEQUENCE: 259
gctctagatt atgatttatt ttgttcagca aat                            33

<210> SEQ ID NO 260
<211> LENGTH: 46
<212> TYPE: DNA
<213> ORGANISM: Artificial Sequence
<220> FEATURE:
<223> OTHER INFORMATION: Primer

<400> SEQUENCE: 260
cgagctcagg aggatatata tatgaaaaaa gtcgcacttg ttaccg              46

<210> SEQ ID NO 261
<211> LENGTH: 31
<212> TYPE: DNA
<213> ORGANISM: Artificial Sequence
<220> FEATURE:
<223> OTHER INFORMATION: Primer

<400> SEQUENCE: 261
ggccggcggc cgcgcgatgg cggtgaaagt g                              31
```

<210> SEQ ID NO 262
<211> LENGTH: 50
<212> TYPE: DNA
<213> ORGANISM: Artificial Sequence
<220> FEATURE:
<223> OTHER INFORMATION: Primer

<400> SEQUENCE: 262
aactaatcta gaggaggata tatatatgag catgacgttt tccggccagg        50

<210> SEQ ID NO 263
<211> LENGTH: 31
<212> TYPE: DNA
<213> ORGANISM: Artificial Sequence
<220> FEATURE:
<223> OTHER INFORMATION: Primer

<400> SEQUENCE: 263
ccttgcggag ggctcgatgg atgagttcga c                            31

<210> SEQ ID NO 264
<211> LENGTH: 31
<212> TYPE: DNA
<213> ORGANISM: Artificial Sequence
<220> FEATURE:
<223> OTHER INFORMATION: Primer

<400> SEQUENCE: 264
cactttcacc gccatcgcgc ggccgccggc c                            31

<210> SEQ ID NO 265
<211> LENGTH: 50
<212> TYPE: DNA
<213> ORGANISM: Artificial Sequence
<220> FEATURE:
<223> OTHER INFORMATION: Primer

<400> SEQUENCE: 265
gctcatatat atatcctcct ctagattagt taaacaccat cccgccgtcg        50

<210> SEQ ID NO 266
<211> LENGTH: 31
<212> TYPE: DNA
<213> ORGANISM: Artificial Sequence
<220> FEATURE:
<223> OTHER INFORMATION: Primer

<400> SEQUENCE: 266
gtcgaactca tccatcgagc cctccgcaag g                            31

<210> SEQ ID NO 267
<211> LENGTH: 32
<212> TYPE: DNA
<213> ORGANISM: Artificial Sequence
<220> FEATURE:
<223> OTHER INFORMATION: Primer

<400> SEQUENCE: 267
cccaagctta gatcgcggtg gccccgccgt cg                           32

<210> SEQ ID NO 268
<211> LENGTH: 46
<212> TYPE: DNA
<213> ORGANISM: Artificial Sequence
<220> FEATURE:
<223> OTHER INFORMATION: Primer

<400> SEQUENCE: 268
cgagctcagg aggatatata tatgaaaaaa gtcgcacttg ttaccg    46

<210> SEQ ID NO 269
<211> LENGTH: 32
<212> TYPE: DNA
<213> ORGANISM: Artificial Sequence
<220> FEATURE:
<223> OTHER INFORMATION: Primer

<400> SEQUENCE: 269
cccaagctta gatcgcggtg gccccgccgt cg    32

<210> SEQ ID NO 270
<211> LENGTH: 43
<212> TYPE: DNA
<213> ORGANISM: Artificial Sequence
<220> FEATURE:
<223> OTHER INFORMATION: Primer

<400> SEQUENCE: 270
gctctagagg aggatttaaa aatggaaatt aacgaaacgc tgc    43

<210> SEQ ID NO 271
<211> LENGTH: 45
<212> TYPE: DNA
<213> ORGANISM: Artificial Sequence
<220> FEATURE:
<223> OTHER INFORMATION: Primer

<400> SEQUENCE: 271
tccccgcggt taagcatggc gatcccgaaa tggaatccct tgac    45

<210> SEQ ID NO 272
<211> LENGTH: 44
<212> TYPE: DNA
<213> ORGANISM: Artificial Sequence
<220> FEATURE:
<223> OTHER INFORMATION: Primer

<400> SEQUENCE: 272
ccgctcgagg aggatatata tatgagatcg aaaagatttg aagc    44

<210> SEQ ID NO 273
<211> LENGTH: 30
<212> TYPE: DNA
<213> ORGANISM: Artificial Sequence
<220> FEATURE:
<223> OTHER INFORMATION: Primer

<400> SEQUENCE: 273
gctctagatt agccaagttc attgggatcg    30

<210> SEQ ID NO 274
<211> LENGTH: 33
<212> TYPE: DNA
<213> ORGANISM: Artificial Sequence
<220> FEATURE:
<223> OTHER INFORMATION: Primer

<400> SEQUENCE: 274
cggggtacca cttttcatac tcccgccatt cag    33

<210> SEQ ID NO 275
<211> LENGTH: 25
<212> TYPE: DNA

```
<213> ORGANISM: Artificial Sequence
<220> FEATURE:
<223> OTHER INFORMATION: Primer

<400> SEQUENCE: 275
cggtaccctt tccagagatt tagag                                    25

<210> SEQ ID NO 276
<211> LENGTH: 30
<212> TYPE: DNA
<213> ORGANISM: Artificial Sequence
<220> FEATURE:
<223> OTHER INFORMATION: Primer

<400> SEQUENCE: 276
ggaattccat atgttcacaa cgtccgccta                               30

<210> SEQ ID NO 277
<211> LENGTH: 27
<212> TYPE: DNA
<213> ORGANISM: Artificial Sequence
<220> FEATURE:
<223> OTHER INFORMATION: Primer

<400> SEQUENCE: 277
gcttgacggc catgtggccg aggccgc                                  27

<210> SEQ ID NO 278
<211> LENGTH: 27
<212> TYPE: DNA
<213> ORGANISM: Artificial Sequence
<220> FEATURE:
<223> OTHER INFORMATION: Primer

<400> SEQUENCE: 278
gcggcctcgg ccacatggcc gtcaagc                                  27

<210> SEQ ID NO 279
<211> LENGTH: 28
<212> TYPE: DNA
<213> ORGANISM: Artificial Sequence
<220> FEATURE:
<223> OTHER INFORMATION: Primer

<400> SEQUENCE: 279
cgggatcctt aggcggcctt ctggcgcg                                 28

<210> SEQ ID NO 280
<211> LENGTH: 30
<212> TYPE: DNA
<213> ORGANISM: Artificial Sequence
<220> FEATURE:
<223> OTHER INFORMATION: Primer

<400> SEQUENCE: 280
ggaattccat atggctattg caagaggtta                               30

<210> SEQ ID NO 281
<211> LENGTH: 28
<212> TYPE: DNA
<213> ORGANISM: Artificial Sequence
<220> FEATURE:
<223> OTHER INFORMATION: Primer

<400> SEQUENCE: 281
cgggatcctt aagcgtcgag cgaggcca                                 28
```

```
<210> SEQ ID NO 282
<211> LENGTH: 30
<212> TYPE: DNA
<213> ORGANISM: Artificial Sequence
<220> FEATURE:
<223> OTHER INFORMATION: Primer

<400> SEQUENCE: 282
ggaattccat atgactaaaa caatgaaggc                                    30

<210> SEQ ID NO 283
<211> LENGTH: 27
<212> TYPE: DNA
<213> ORGANISM: Artificial Sequence
<220> FEATURE:
<223> OTHER INFORMATION: Primer

<400> SEQUENCE: 283
caccggggcc ggggtccggt attgcca                                       27

<210> SEQ ID NO 284
<211> LENGTH: 27
<212> TYPE: DNA
<213> ORGANISM: Artificial Sequence
<220> FEATURE:
<223> OTHER INFORMATION: Primer

<400> SEQUENCE: 284
tggcaatacc ggaccccggc cccggtg                                       27

<210> SEQ ID NO 285
<211> LENGTH: 28
<212> TYPE: DNA
<213> ORGANISM: Artificial Sequence
<220> FEATURE:
<223> OTHER INFORMATION: Primer

<400> SEQUENCE: 285
cgggatcctt aggcggcgag atccacga                                      28

<210> SEQ ID NO 286
<211> LENGTH: 30
<212> TYPE: DNA
<213> ORGANISM: Artificial Sequence
<220> FEATURE:
<223> OTHER INFORMATION: Primer

<400> SEQUENCE: 286
ggaattccat atgaccgggg cgaaccagcc                                    30

<210> SEQ ID NO 287
<211> LENGTH: 27
<212> TYPE: DNA
<213> ORGANISM: Artificial Sequence
<220> FEATURE:
<223> OTHER INFORMATION: Primer

<400> SEQUENCE: 287
atagccgctc atacgcctcg gttgcct                                       27

<210> SEQ ID NO 288
<211> LENGTH: 27
<212> TYPE: DNA
<213> ORGANISM: Artificial Sequence
<220> FEATURE:
<223> OTHER INFORMATION: Primer
```

```
<400> SEQUENCE: 288
aggcaaccga ggcgtatgag cggctat                                          27

<210> SEQ ID NO 289
<211> LENGTH: 28
<212> TYPE: DNA
<213> ORGANISM: Artificial Sequence
<220> FEATURE:
<223> OTHER INFORMATION: Primer

<400> SEQUENCE: 289
cgggatcctt aagcgccgtg cggaagga                                         28

<210> SEQ ID NO 290
<211> LENGTH: 30
<212> TYPE: DNA
<213> ORGANISM: Artificial Sequence
<220> FEATURE:
<223> OTHER INFORMATION: Primer

<400> SEQUENCE: 290
ggaattccat atgaccatgc atgccattca                                       30

<210> SEQ ID NO 291
<211> LENGTH: 28
<212> TYPE: DNA
<213> ORGANISM: Artificial Sequence
<220> FEATURE:
<223> OTHER INFORMATION: Primer

<400> SEQUENCE: 291
cgggatcctt attcggctgc aaattgca                                         28

<210> SEQ ID NO 292
<211> LENGTH: 30
<212> TYPE: DNA
<213> ORGANISM: Artificial Sequence
<220> FEATURE:
<223> OTHER INFORMATION: Primer

<400> SEQUENCE: 292
ggaattccat atgcgcgcgc tttattacga                                       30

<210> SEQ ID NO 293
<211> LENGTH: 28
<212> TYPE: DNA
<213> ORGANISM: Artificial Sequence
<220> FEATURE:
<223> OTHER INFORMATION: Primer

<400> SEQUENCE: 293
cgggatcctt attcgaaccg gtcgatga                                         28

<210> SEQ ID NO 294
<211> LENGTH: 30
<212> TYPE: DNA
<213> ORGANISM: Artificial Sequence
<220> FEATURE:
<223> OTHER INFORMATION: Primer

<400> SEQUENCE: 294
ggaattccat atgctggcga ttttctgtga                                       30

<210> SEQ ID NO 295
<211> LENGTH: 28
<212> TYPE: DNA
```

<213> ORGANISM: Artificial Sequence
<220> FEATURE:
<223> OTHER INFORMATION: Primer

<400> SEQUENCE: 295
cgggatcctt atgcgacctc caccatgc        28

<210> SEQ ID NO 296
<211> LENGTH: 30
<212> TYPE: DNA
<213> ORGANISM: Artificial Sequence
<220> FEATURE:
<223> OTHER INFORMATION: Primer

<400> SEQUENCE: 296
ggaattccat atgaaagcct tcgtcgtcga        30

<210> SEQ ID NO 297
<211> LENGTH: 28
<212> TYPE: DNA
<213> ORGANISM: Artificial Sequence
<220> FEATURE:
<223> OTHER INFORMATION: Primer

<400> SEQUENCE: 297
cgggatcctt aggatgcgta tgtaacca        28

<210> SEQ ID NO 298
<211> LENGTH: 30
<212> TYPE: DNA
<213> ORGANISM: Artificial Sequence
<220> FEATURE:
<223> OTHER INFORMATION: Primer

<400> SEQUENCE: 298
ggaattccat atgaaagcga ttgtcgccca        30

<210> SEQ ID NO 299
<211> LENGTH: 28
<212> TYPE: DNA
<213> ORGANISM: Artificial Sequence
<220> FEATURE:
<223> OTHER INFORMATION: Primer

<400> SEQUENCE: 299
cgggatcctt aggaaaaggc gatctgca        28

<210> SEQ ID NO 300
<211> LENGTH: 30
<212> TYPE: DNA
<213> ORGANISM: Artificial Sequence
<220> FEATURE:
<223> OTHER INFORMATION: Primer

<400> SEQUENCE: 300
ggaattccat atgccgatgg cgctcgggca        30

<210> SEQ ID NO 301
<211> LENGTH: 28
<212> TYPE: DNA
<213> ORGANISM: Artificial Sequence
<220> FEATURE:
<223> OTHER INFORMATION: Primer

<400> SEQUENCE: 301
cgggatcctt agaattcgat gacttgcc        28

```
<210> SEQ ID NO 302
<211> LENGTH: 30
<212> TYPE: DNA
<213> ORGANISM: Artificial Sequence
<220> FEATURE:
<223> OTHER INFORMATION: Primer

<400> SEQUENCE: 302
ggaattccat atgaaacatt ctcaggacaa                                    30

<210> SEQ ID NO 303
<211> LENGTH: 27
<212> TYPE: DNA
<213> ORGANISM: Artificial Sequence
<220> FEATURE:
<223> OTHER INFORMATION: Primer

<400> SEQUENCE: 303
gggcgccgat catgtggtgc gtttccg                                       27

<210> SEQ ID NO 304
<211> LENGTH: 27
<212> TYPE: DNA
<213> ORGANISM: Artificial Sequence
<220> FEATURE:
<223> OTHER INFORMATION: Primer

<400> SEQUENCE: 304
cggaaacgca ccacatgatc ggcgccc                                       27

<210> SEQ ID NO 305
<211> LENGTH: 28
<212> TYPE: DNA
<213> ORGANISM: Artificial Sequence
<220> FEATURE:
<223> OTHER INFORMATION: Primer

<400> SEQUENCE: 305
cgggatcctt atgccatacg ttccatat                                      28

<210> SEQ ID NO 306
<211> LENGTH: 30
<212> TYPE: DNA
<213> ORGANISM: Artificial Sequence
<220> FEATURE:
<223> OTHER INFORMATION: Primer

<400> SEQUENCE: 306
ggaattccat atgcagcgtt ttaccaacag                                    30

<210> SEQ ID NO 307
<211> LENGTH: 28
<212> TYPE: DNA
<213> ORGANISM: Artificial Sequence
<220> FEATURE:
<223> OTHER INFORMATION: Primer

<400> SEQUENCE: 307
cgggatcctt aggaaaacag gacgccgc                                      28

<210> SEQ ID NO 308
<211> LENGTH: 610
<212> TYPE: PRT
<213> ORGANISM: Klebsiella pneumoniae subsp. pneumoniae MGH 78578

<400> SEQUENCE: 308
```

```
Met Arg Tyr Ile Ala Gly Ile Asp Ile Gly Asn Ser Ser Thr Glu Val
1               5                   10                  15

Ala Leu Ala Thr Val Asp Asp Ala Gly Val Leu Asn Ile Arg His Ser
            20                  25                  30

Ala Leu Ala Glu Thr Thr Gly Ile Lys Gly Thr Leu Arg Asn Val Phe
            35                  40                  45

Gly Ile Gln Glu Ala Leu Thr Gln Ala Lys Ala Ala Gly Ile Gln
50                  55                  60

Leu Ser Asp Ile Ser Leu Ile Arg Ile Asn Glu Ala Thr Pro Val Ile
65                  70                  75                  80

Gly Asp Val Ala Met Glu Thr Ile Thr Glu Thr Ile Ile Thr Glu Ser
                85                  90                  95

Thr Met Ile Gly His Asn Pro Lys Thr Pro Gly Gly Val Gly Leu Gly
                100                 105                 110

Val Gly Ile Thr Ile Thr Pro Glu Ala Leu Leu Ser Cys Ser Ala Asp
            115                 120                 125

Thr Pro Tyr Ile Leu Val Val Ser Ser Ala Phe Asp Phe Ala Asp Val
        130                 135                 140

Ala Ala Met Val Asn Ala Ala Thr Ala Ala Gly Tyr Gln Ile Thr Gly
145                 150                 155                 160

Ile Ile Leu Gln Gln Asp Asp Gly Val Leu Val Asn Asn Arg Leu Gln
                165                 170                 175

Gln Pro Leu Pro Val Ile Asp Glu Val Gln His Ile Asp Arg Ile Pro
                180                 185                 190

Leu Gly Met Leu Ala Ala Val Glu Val Ala Leu Pro Gly Lys Ile Ile
            195                 200                 205

Glu Thr Leu Ser Asn Pro Tyr Gly Ile Ala Thr Val Phe Asp Leu Asn
210                 215                 220

Ala Glu Glu Thr Lys Asn Ile Val Pro Met Ala Arg Ala Leu Ile Gly
225                 230                 235                 240

Asn Arg Ser Ala Val Val Lys Thr Pro Ser Gly Asp Val Lys Ala
                245                 250                 255

Arg Ala Ile Pro Ala Gly Asn Leu Leu Leu Ile Ala Gln Gly Arg Ser
                260                 265                 270

Val Gln Val Asp Val Ala Ala Gly Ala Glu Ala Ile Met Lys Ala Val
            275                 280                 285

Asp Gly Cys Gly Lys Leu Asp Asn Val Ala Gly Glu Ala Gly Thr Asn
            290                 295                 300

Ile Gly Gly Met Leu Glu His Val Arg Gln Thr Met Ala Glu Leu Thr
305                 310                 315                 320

Asn Lys Pro Ala Gln Glu Ile Arg Ile Gln Asp Leu Leu Ala Val Asp
                325                 330                 335

Thr Ala Val Pro Val Ser Val Thr Gly Gly Leu Ala Gly Glu Phe Ser
                340                 345                 350

Leu Glu Gln Ala Val Gly Ile Ala Ser Met Val Lys Ser Asp Arg Leu
            355                 360                 365

Gln Met Ala Leu Ile Ala Arg Glu Ile Glu His Lys Leu Gln Ile Ala
    370                 375                 380

Val Gln Val Gly Gly Ala Glu Ala Glu Ala Ile Leu Gly Ala Leu
385                 390                 395                 400

Thr Thr Pro Gly Thr Thr Arg Pro Leu Ala Ile Leu Asp Leu Gly Ala
                405                 410                 415

Gly Ser Thr Asp Ala Ser Ile Ile Asn Ala Gln Gly Glu Ile Ser Ala
                420                 425                 430
```

```
Thr His Leu Ala Gly Ala Gly Asp Met Val Thr Met Ile Ile Ala Arg
            435                 440                 445
Glu Leu Gly Leu Glu Asp Arg Tyr Leu Ala Glu Glu Ile Lys Lys Tyr
        450                 455                 460
Pro Leu Ala Lys Val Glu Ser Leu Phe His Leu Arg His Glu Asp Gly
465                 470                 475                 480
Ser Val Gln Phe Phe Pro Ser Ala Leu Pro Pro Ala Val Phe Ala Arg
                485                 490                 495
Val Cys Val Val Lys Pro Asp Glu Leu Val Pro Leu Pro Gly Asp Leu
                500                 505                 510
Pro Leu Glu Lys Val Arg Ala Ile Arg Arg Ser Ala Lys Ser Arg Val
        515                 520                 525
Phe Val Thr Asn Ala Leu Arg Ala Leu Arg Gln Val Ser Pro Thr Gly
        530                 535                 540
Asn Ile Arg Asp Ile Pro Phe Val Val Leu Val Gly Gly Ser Ser Leu
545                 550                 555                 560
Asp Phe Glu Ile Pro Gln Leu Val Thr Asp Ala Leu Ala His Tyr Arg
                565                 570                 575
Leu Val Ala Gly Arg Gly Asn Ile Arg Gly Cys Glu Gly Pro Arg Asn
                580                 585                 590
Ala Val Ala Ser Gly Leu Leu Leu Ser Trp Gln Lys Gly Gly Thr His
        595                 600                 605
Gly Glu
    610

<210> SEQ ID NO 309
<211> LENGTH: 116
<212> TYPE: PRT
<213> ORGANISM: Klebsiella pneumoniae subsp. pneumoniae MGH78578

<400> SEQUENCE: 309

Met Glu Ser Ser Val Val Ala Pro Ala Ile Val Ile Ala Val Thr Asp
1               5                   10                  15
Glu Cys Ser Glu Gln Trp Arg Asp Val Leu Leu Gly Ile Glu Glu Glu
            20                  25                  30
Gly Ile Pro Phe Val Leu Gln Pro Gln Thr Gly Gly Asp Leu Ile His
        35                  40                  45
His Ala Trp Gln Ala Ala Gln Arg Ser Pro Leu Gln Val Gly Ile Ala
    50                  55                  60
Cys Asp Arg Glu Arg Leu Ile Val His Tyr Lys Asn Leu Pro Ala Ser
65                  70                  75                  80
Thr Pro Leu Phe Ser Leu Met Tyr His Gln Asn Arg Leu Ala Arg Arg
                85                  90                  95
Asn Thr Gly Asn Asn Ala Ala Arg Leu Val Lys Gly Ile Pro Phe Arg
            100                 105                 110
Asp Arg His Ala
        115

<210> SEQ ID NO 310
<211> LENGTH: 787
<212> TYPE: PRT
<213> ORGANISM: Clostridium butyricum

<400> SEQUENCE: 310

Met Ile Ser Lys Gly Phe Ser Thr Gln Thr Glu Arg Ile Asn Ile Leu
1               5                   10                  15
```

-continued

```
Lys Ala Gln Ile Leu Asn Ala Lys Pro Cys Val Glu Ser Glu Arg Ala
             20                  25                  30

Ile Leu Ile Thr Glu Ser Phe Lys Gln Thr Glu Gly Gln Pro Ala Ile
             35                  40                  45

Leu Arg Arg Ala Leu Ala Leu Lys His Ile Leu Glu Asn Ile Pro Ile
 50                  55                  60

Thr Ile Arg Asp Gln Glu Leu Ile Val Gly Ser Leu Thr Lys Glu Pro
 65                  70                  75                  80

Arg Ser Ser Gln Val Phe Pro Glu Phe Ser Asn Lys Trp Leu Gln Asp
                 85                  90                  95

Glu Leu Asp Arg Leu Asn Lys Arg Thr Gly Asp Ala Phe Gln Ile Ser
             100                 105                 110

Glu Glu Ser Lys Glu Lys Leu Lys Asp Val Phe Glu Tyr Trp Asn Gly
             115                 120                 125

Lys Thr Thr Ser Glu Leu Ala Thr Ser Tyr Met Thr Glu Glu Thr Arg
 130                 135                 140

Glu Ala Val Asn Cys Asp Val Phe Thr Val Gly Asn Tyr Tyr Tyr Asn
145                 150                 155                 160

Gly Val Gly His Val Ser Val Asp Tyr Gly Lys Val Leu Arg Val Gly
                 165                 170                 175

Phe Asn Gly Ile Ile Asn Glu Ala Lys Glu Gln Leu Glu Lys Asn Arg
             180                 185                 190

Ser Ile Asp Pro Asp Phe Ile Lys Lys Glu Lys Phe Leu Asn Ser Val
             195                 200                 205

Ile Ile Ser Cys Glu Ala Ala Ile Thr Tyr Val Asn Arg Tyr Ala Lys
210                 215                 220

Lys Ala Lys Glu Ile Ala Asp Asn Thr Ser Asp Ala Lys Arg Lys Ala
225                 230                 235                 240

Glu Leu Asn Glu Ile Ala Lys Ile Cys Ser Lys Val Ser Gly Glu Gly
                 245                 250                 255

Ala Lys Ser Phe Tyr Glu Ala Cys Gln Leu Phe Trp Phe Ile His Ala
             260                 265                 270

Ile Ile Asn Ile Glu Ser Asn Gly His Ser Ile Ser Pro Ala Arg Phe
             275                 280                 285

Asp Gln Tyr Met Tyr Pro Tyr Tyr Glu Asn Asp Lys Asn Ile Thr Asp
 290                 295                 300

Lys Phe Ala Gln Glu Leu Ile Asp Cys Ile Trp Ile Lys Leu Asn Asp
305                 310                 315                 320

Ile Asn Lys Val Arg Asp Glu Ile Ser Thr Lys His Phe Gly Gly Tyr
                 325                 330                 335

Pro Met Tyr Gln Asn Leu Ile Val Gly Gly Gln Asn Ser Glu Gly Lys
             340                 345                 350

Asp Ala Thr Asn Lys Val Ser Tyr Met Ala Leu Glu Ala Val His
             355                 360                 365

Val Lys Leu Pro Gln Pro Ser Leu Ser Val Arg Ile Trp Asn Lys Thr
 370                 375                 380

Pro Asp Glu Phe Leu Leu Arg Ala Ala Glu Leu Thr Arg Glu Gly Leu
385                 390                 395                 400

Gly Leu Pro Ala Tyr Tyr Asn Asp Glu Val Ile Ile Pro Ala Leu Val
                 405                 410                 415

Ser Arg Gly Leu Thr Leu Glu Asp Ala Arg Asp Tyr Gly Ile Ile Gly
             420                 425                 430

Cys Val Glu Pro Gln Lys Pro Gly Lys Thr Glu Gly Trp His Asp Ser
             435                 440                 445
```

```
Ala Phe Phe Asn Leu Ala Arg Ile Val Glu Leu Thr Ile Asn Ser Gly
    450                 455                 460

Phe Asp Lys Asn Lys Gln Ile Gly Pro Lys Thr Gln Asn Phe Glu Glu
465                 470                 475                 480

Met Lys Ser Phe Asp Glu Phe Met Lys Ala Tyr Lys Ala Gln Met Glu
                485                 490                 495

Tyr Phe Val Lys His Met Cys Cys Ala Asp Asn Cys Ile Asp Ile Ala
            500                 505                 510

His Ala Glu Arg Ala Pro Leu Pro Phe Leu Ser Ser Met Val Asp Asn
        515                 520                 525

Cys Ile Gly Lys Gly Lys Ser Leu Gln Asp Gly Ala Glu Tyr Asn
    530                 535                 540

Phe Ser Gly Pro Gln Gly Val Gly Val Ala Asn Ile Gly Asp Ser Leu
545                 550                 555                 560

Val Ala Val Lys Lys Ile Val Phe Asp Glu Asn Lys Ile Thr Pro Ser
                565                 570                 575

Glu Leu Lys Lys Thr Leu Asn Asn Asp Phe Lys Asn Ser Glu Glu Ile
                580                 585                 590

Gln Ala Leu Leu Lys Asn Ala Pro Lys Phe Gly Asn Asp Ile Asp Glu
            595                 600                 605

Val Asp Asn Leu Ala Arg Glu Gly Ala Leu Val Tyr Cys Arg Glu Val
610                 615                 620

Asn Lys Tyr Thr Asn Pro Arg Gly Gly Asn Phe Gln Pro Gly Leu Tyr
625                 630                 635                 640

Pro Ser Ser Ile Asn Val Tyr Phe Gly Ser Leu Thr Gly Ala Thr Pro
                645                 650                 655

Asp Gly Arg Lys Ser Gly Gln Pro Leu Ala Asp Gly Val Ser Pro Ser
            660                 665                 670

Arg Gly Cys Asp Val Ser Gly Pro Thr Ala Ala Cys Asn Ser Val Ser
        675                 680                 685

Lys Leu Asp His Phe Ile Ala Ser Asn Gly Thr Leu Phe Asn Gln Lys
    690                 695                 700

Phe His Pro Ser Ala Leu Lys Gly Asp Asn Gly Leu Met Asn Leu Ser
705                 710                 715                 720

Ser Leu Ile Arg Ser Tyr Phe Asp Gln Lys Gly Phe His Val Gln Phe
                725                 730                 735

Asn Val Ile Asp Lys Lys Ile Leu Leu Ala Ala Gln Lys Asn Pro Glu
            740                 745                 750

Lys Tyr Gln Asp Leu Ile Val Arg Val Ala Gly Tyr Ser Ala Gln Phe
        755                 760                 765

Ile Ser Leu Asp Lys Ser Ile Gln Asn Asp Ile Ile Ala Arg Thr Glu
    770                 775                 780

His Val Met
785

<210> SEQ ID NO 311
<211> LENGTH: 304
<212> TYPE: PRT
<213> ORGANISM: Clostridium buyricum

<400> SEQUENCE: 311

Met Ser Lys Glu Ile Lys Gly Val Leu Phe Asn Ile Gln Lys Phe Ser
1               5                   10                  15

Leu His Asp Gly Pro Gly Ile Arg Thr Ile Val Phe Phe Lys Gly Cys
            20                  25                  30
```

Ser Met Ser Cys Leu Trp Cys Ser Asn Pro Glu Ser Gln Asp Ile Lys
        35                  40                  45

Pro Gln Val Met Phe Asn Lys Asn Leu Cys Thr Lys Cys Gly Arg Cys
 50                  55                  60

Lys Ser Gln Cys Lys Ser Ala Ala Ile Asp Met Asn Ser Glu Tyr Arg
 65                  70                  75                  80

Ile Asp Lys Ser Lys Cys Thr Glu Cys Thr Lys Cys Val Asp Asn Cys
                 85                  90                  95

Leu Ser Gly Ala Leu Val Ile Glu Gly Arg Asn Tyr Ser Val Glu Asp
            100                 105                 110

Val Ile Lys Glu Leu Lys Lys Asp Ser Val Gln Tyr Arg Arg Ser Asn
        115                 120                 125

Gly Gly Ile Thr Leu Ser Gly Gly Glu Val Leu Gln Pro Asp Phe
    130                 135                 140

Ala Val Glu Leu Leu Lys Glu Cys Lys Ser Tyr Gly Trp His Thr Ala
145                 150                 155                 160

Ile Glu Thr Ala Met Tyr Val Asn Ser Glu Ser Val Lys Lys Val Ile
                165                 170                 175

Pro Tyr Ile Asp Leu Ala Met Ile Ile Lys Ser Met Asn Asp Glu
            180                 185                 190

Ile His Arg Lys Phe Thr Gly Val Ser Asn Glu Ile Ile Leu Gln Asn
        195                 200                 205

Ile Lys Leu Ser Asp Glu Leu Ala Lys Glu Ile Ile Arg Ile Pro
    210                 215                 220

Val Ile Glu Gly Phe Asn Ala Asp Leu Gln Ser Ile Gly Ala Ile Ala
225                 230                 235                 240

Gln Phe Ser Lys Ser Leu Thr Asn Leu Lys Arg Ile Asp Leu Leu Pro
                245                 250                 255

Tyr His Asn Tyr Gly Glu Asn Lys Tyr Gln Ala Ile Gly Arg Glu Tyr
            260                 265                 270

Ser Leu Lys Glu Leu Lys Ser Pro Ser Lys Asp Lys Met Glu Arg Leu
        275                 280                 285

Lys Ala Leu Val Glu Ile Met Gly Ile Pro Cys Thr Ile Gly Ala Glu
    290                 295                 300

<210> SEQ ID NO 312
<211> LENGTH: 545
<212> TYPE: PRT
<213> ORGANISM: Azospirillum brasilense

<400> SEQUENCE: 312

Met Lys Leu Ala Glu Ala Leu Leu Arg Ala Leu Lys Asp Arg Gly Ala
1               5                   10                  15

Gln Ala Met Phe Gly Ile Pro Gly Asp Phe Ala Leu Pro Phe Phe Lys
            20                  25                  30

Val Ala Glu Glu Thr Gln Ile Leu Pro Leu His Thr Leu Ser His Glu
        35                  40                  45

Pro Ala Val Gly Phe Ala Ala Asp Ala Ala Ala Arg Tyr Ser Ser Thr
    50                  55                  60

Leu Gly Val Ala Ala Val Thr Tyr Gly Ala Gly Ala Phe Asn Met Val
65                  70                  75                  80

Asn Ala Val Ala Gly Ala Tyr Ala Glu Lys Ser Pro Val Val Val Ile
                85                  90                  95

Ser Gly Ala Pro Gly Thr Thr Glu Gly Asn Ala Gly Leu Leu Leu His
            100                 105                 110

```
His Gln Gly Arg Thr Leu Asp Thr Gln Phe Gln Val Phe Lys Glu Ile
        115                 120                 125

Thr Val Ala Gln Ala Arg Leu Asp Asp Pro Ala Lys Ala Pro Ala Glu
        130                 135                 140

Ile Ala Arg Val Leu Gly Ala Ala Arg Ala Gln Ser Arg Pro Val Tyr
145                 150                 155                 160

Leu Glu Ile Pro Arg Asn Met Val Asn Ala Glu Val Glu Pro Val Gly
                    165                 170                 175

Asp Asp Pro Ala Trp Pro Val Asp Arg Asp Ala Leu Ala Ala Cys Ala
                180                 185                 190

Asp Glu Val Leu Ala Ala Met Arg Ser Ala Thr Ser Pro Val Leu Met
            195                 200                 205

Val Cys Val Glu Val Arg Arg Tyr Gly Leu Glu Ala Lys Val Ala Glu
        210                 215                 220

Leu Ala Gln Arg Leu Gly Val Pro Val Val Thr Thr Phe Met Gly Arg
225                 230                 235                 240

Gly Leu Leu Ala Asp Ala Pro Thr Pro Pro Leu Gly Thr Tyr Ile Gly
                    245                 250                 255

Val Ala Gly Asp Ala Glu Ile Thr Arg Leu Val Glu Glu Ser Asp Gly
                260                 265                 270

Leu Phe Leu Leu Gly Ala Ile Leu Ser Asp Thr Asn Phe Ala Val Ser
            275                 280                 285

Gln Arg Lys Ile Asp Leu Arg Lys Thr Ile His Ala Phe Asp Arg Ala
        290                 295                 300

Val Thr Leu Gly Tyr His Thr Tyr Ala Asp Ile Pro Leu Ala Gly Leu
305                 310                 315                 320

Val Asp Ala Leu Leu Glu Arg Leu Pro Pro Ser Asp Arg Thr Thr Arg
                    325                 330                 335

Gly Lys Glu Pro His Ala Tyr Pro Thr Gly Leu Gln Ala Asp Gly Glu
                340                 345                 350

Pro Ile Ala Pro Met Asp Ile Ala Arg Ala Val Asn Asp Arg Val Arg
            355                 360                 365

Ala Gly Gln Glu Pro Leu Leu Ile Ala Ala Asp Met Gly Asp Cys Leu
        370                 375                 380

Phe Thr Ala Met Asp Met Ile Asp Ala Gly Leu Met Ala Pro Gly Tyr
385                 390                 395                 400

Tyr Ala Gly Met Gly Phe Gly Val Pro Ala Gly Ile Gly Ala Gln Cys
                    405                 410                 415

Val Ser Gly Gly Lys Arg Ile Leu Thr Val Val Gly Asp Gly Ala Phe
                420                 425                 430

Gln Met Thr Gly Trp Glu Leu Gly Asn Cys Arg Arg Leu Gly Ile Asp
            435                 440                 445

Pro Ile Val Ile Leu Phe Asn Asn Ala Ser Trp Glu Met Leu Arg Thr
        450                 455                 460

Phe Gln Pro Glu Ser Ala Phe Asn Asp Leu Asp Asp Trp Arg Phe Ala
465                 470                 475                 480

Asp Met Ala Ala Gly Met Gly Asp Gly Val Arg Val Arg Thr Arg
                    485                 490                 495

Ala Glu Leu Lys Ala Ala Leu Asp Lys Ala Phe Ala Thr Arg Gly Arg
                500                 505                 510

Phe Gln Leu Ile Glu Ala Met Ile Pro Arg Gly Val Leu Ser Asp Thr
            515                 520                 525

Leu Ala Arg Phe Val Gln Gly Gln Lys Arg Leu His Ala Ala Pro Arg
```

Glu
545

<210> SEQ ID NO 313
<211> LENGTH: 348
<212> TYPE: PRT
<213> ORGANISM: Rhodococcus sp. ST-10

<400> SEQUENCE: 313

Met Lys Ala Ile Gln Tyr Thr Arg Ile Gly Ala Glu Pro Glu Leu Thr
1               5                   10                  15
Glu Ile Pro Lys Pro Glu Pro Gly Pro Gly Glu Val Leu Leu Glu Val
                20                  25                  30
Thr Ala Ala Gly Val Cys His Ser Asp Asp Phe Ile Met Ser Leu Pro
            35                  40                  45
Glu Glu Gln Tyr Thr Tyr Gly Leu Pro Leu Thr Leu Gly His Glu Gly
        50                  55                  60
Ala Gly Lys Val Ala Ala Val Gly Glu Gly Val Glu Gly Leu Asp Ile
65                  70                  75                  80
Gly Thr Asn Val Val Val Tyr Gly Pro Trp Gly Cys Gly Asn Cys Trp
                85                  90                  95
His Cys Ser Gln Gly Leu Glu Asn Tyr Cys Ser Arg Ala Gln Glu Leu
            100                 105                 110
Gly Ile Asn Pro Pro Gly Leu Gly Ala Pro Gly Ala Leu Ala Glu Phe
        115                 120                 125
Met Ile Val Asp Ser Pro Arg His Leu Val Pro Ile Gly Asp Leu Asp
130                 135                 140
Pro Val Lys Thr Val Pro Leu Thr Asp Ala Gly Leu Thr Pro Tyr His
145                 150                 155                 160
Ala Ile Lys Arg Ser Leu Pro Lys Leu Arg Gly Gly Ser Tyr Ala Val
                165                 170                 175
Val Ile Gly Thr Gly Gly Leu Gly His Val Ala Ile Gln Leu Leu Arg
            180                 185                 190
His Leu Ser Ala Ala Thr Val Ile Ala Leu Asp Val Ser Ala Asp Lys
        195                 200                 205
Leu Glu Leu Ala Thr Lys Val Gly Ala His Glu Val Val Leu Ser Asp
    210                 215                 220
Lys Asp Ala Ala Glu Asn Val Arg Lys Ile Thr Gly Ser Gln Gly Ala
225                 230                 235                 240
Ala Leu Val Leu Asp Phe Val Gly Tyr Gln Pro Thr Ile Asp Thr Ala
                245                 250                 255
Met Ala Val Ala Gly Val Gly Ser Asp Val Thr Ile Val Gly Ile Gly
            260                 265                 270
Asp Gly Gln Ala His Ala Lys Val Gly Phe Phe Gln Ser Pro Tyr Glu
        275                 280                 285
Ala Ser Val Thr Val Pro Tyr Trp Gly Ala Arg Asn Glu Leu Ile Glu
    290                 295                 300
Leu Ile Asp Leu Ala His Ala Gly Ile Phe Asp Ile Ser Val Glu Thr
305                 310                 315                 320
Phe Ser Leu Asp Asn Gly Ala Glu Ala Tyr Arg Arg Leu Ala Ala Gly
                325                 330                 335
Thr Leu Ser Gly Arg Ala Val Val Val Pro Gly Leu
            340                 345

<210> SEQ ID NO 314
<211> LENGTH: 31
<212> TYPE: DNA
<213> ORGANISM: Artificial Sequence
<220> FEATURE:
<223> OTHER INFORMATION: Primer

<400> SEQUENCE: 314
catgccatgg gactggctga ggcactgctg c          31

<210> SEQ ID NO 315
<211> LENGTH: 47
<212> TYPE: DNA
<213> ORGANISM: Artificial Sequence
<220> FEATURE:
<223> OTHER INFORMATION: Primer

<400> SEQUENCE: 315
cgagctcagg aggatatata tatgaaagct atccagtaca cccgtat          47

<210> SEQ ID NO 316
<211> LENGTH: 32
<212> TYPE: DNA
<213> ORGANISM: Artificial Sequence
<220> FEATURE:
<223> OTHER INFORMATION: Primer

<400> SEQUENCE: 316
cgagctctta ttcgcgcggt gccgcgtgca gg          32

<210> SEQ ID NO 317
<211> LENGTH: 34
<212> TYPE: DNA
<213> ORGANISM: Artificial Sequence
<220> FEATURE:
<223> OTHER INFORMATION: Primer

<400> SEQUENCE: 317
gctctagatt acaggcccgg aaccacaacg gcgc          34

<210> SEQ ID NO 318
<211> LENGTH: 46
<212> TYPE: DNA
<213> ORGANISM: Artificial Sequence
<220> FEATURE:
<223> OTHER INFORMATION: Primer

<400> SEQUENCE: 318
ccgctcgagg aggatatata tatgatttct aaaggcttta gcaccc          46

<210> SEQ ID NO 319
<211> LENGTH: 50
<212> TYPE: DNA
<213> ORGANISM: Artificial Sequence
<220> FEATURE:
<223> OTHER INFORMATION: Primer

<400> SEQUENCE: 319
acgtgatgta atctagagga ggatatatat atgagcaaag aaattaaagg          50

<210> SEQ ID NO 320
<211> LENGTH: 50
<212> TYPE: DNA
<213> ORGANISM: Artificial Sequence
<220> FEATURE:
<223> OTHER INFORMATION: Primer

<400> SEQUENCE: 320
tctttgctca tatatatatc ctcctctaga ttacatcacg tgttcagtac  50

<210> SEQ ID NO 321
<211> LENGTH: 32
<212> TYPE: DNA
<213> ORGANISM: Artificial Sequence
<220> FEATURE:
<223> OTHER INFORMATION: Primer

<400> SEQUENCE: 321
cgagctctta ttcggcgcca atggtgcacg gg  32

<210> SEQ ID NO 322
<211> LENGTH: 46
<212> TYPE: DNA
<213> ORGANISM: Artificial Sequence
<220> FEATURE:
<223> OTHER INFORMATION: Primer

<400> SEQUENCE: 322
ccgctcgagg aggatatata tatgatttct aaaggcttta gcaccc  46

<210> SEQ ID NO 323
<211> LENGTH: 32
<212> TYPE: DNA
<213> ORGANISM: Artificial Sequence
<220> FEATURE:
<223> OTHER INFORMATION: Primer

<400> SEQUENCE: 323
cgagctctta ttcggcgcca atggtgcacg gg  32

<210> SEQ ID NO 324
<211> LENGTH: 26
<212> TYPE: DNA
<213> ORGANISM: Artificial Sequence
<220> FEATURE:
<223> OTHER INFORMATION: Primer

<400> SEQUENCE: 324
cacccaagcg atagtttata tagcgt  26

<210> SEQ ID NO 325
<211> LENGTH: 20
<212> TYPE: DNA
<213> ORGANISM: Artificial Sequence
<220> FEATURE:
<223> OTHER INFORMATION: Primer

<400> SEQUENCE: 325
gaaatgaacg gatattacgt  20

<210> SEQ ID NO 326
<211> LENGTH: 19
<212> TYPE: DNA
<213> ORGANISM: Artificial Sequence
<220> FEATURE:
<223> OTHER INFORMATION: Primer

<400> SEQUENCE: 326
cggaacaggt gattgtggt  19

<210> SEQ ID NO 327
<211> LENGTH: 26
<212> TYPE: DNA
<213> ORGANISM: Artificial Sequence
<220> FEATURE:
<223> OTHER INFORMATION: Primer

<400> SEQUENCE: 327
caccgcccac ttcaagatga agctgt        26

<210> SEQ ID NO 328
<211> LENGTH: 26
<212> TYPE: DNA
<213> ORGANISM: Artificial Sequence
<220> FEATURE:
<223> OTHER INFORMATION: Primer

<400> SEQUENCE: 328
cacccaagcg atagtttata tagcgt        26

<210> SEQ ID NO 329
<211> LENGTH: 20
<212> TYPE: DNA
<213> ORGANISM: Artificial Sequence
<220> FEATURE:
<223> OTHER INFORMATION: Primer

<400> SEQUENCE: 329
gtggctaagt acatgccggt        20

<210> SEQ ID NO 330
<211> LENGTH: 35
<212> TYPE: DNA
<213> ORGANISM: Artificial Sequence
<220> FEATURE:
<223> OTHER INFORMATION: Primer

<400> SEQUENCE: 330
ggaattccat atgacaaaga atatgacgac taaac        35

<210> SEQ ID NO 331
<211> LENGTH: 32
<212> TYPE: DNA
<213> ORGANISM: Artificial Sequence
<220> FEATURE:
<223> OTHER INFORMATION: Primer

<400> SEQUENCE: 331
cgggatcctt attatttccc ctgccctgca gt        32

<210> SEQ ID NO 332
<211> LENGTH: 32
<212> TYPE: DNA
<213> ORGANISM: Artificial Sequence
<220> FEATURE:
<223> OTHER INFORMATION: Primer

<400> SEQUENCE: 332
ggaattccat atgagctatc aaccactttt ac        32

<210> SEQ ID NO 333
<211> LENGTH: 29
<212> TYPE: DNA
<213> ORGANISM: Artificial Sequence
<220> FEATURE:
<223> OTHER INFORMATION: Primer

<400> SEQUENCE: 333
cgggatcctt acagttgagc aaatgatcc        29

BIOFUEL PRODUCTION

CROSS-REFERENCE TO RELATED APPLICATION

This application is a continuation of copending U.S. patent application Ser. No. 12/245,537, with a filing date of Oct. 3, 2008, which claims the benefit under 35 U.S.C. §119(e) of U.S. Provisional Patent Application No. 60/977,628 filed Oct. 4, 2007, all of which are incorporated herein by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 690212000604SeqList.txt, date recorded: Mar. 23, 2011, size: 519 KB).

TECHNICAL FIELD

The present application relates generally to the use of microbial and chemical systems to convert biomass to commodity chemicals, such as biofuels/biopetrols.

BACKGROUND

Petroleum is facing declining global reserves and contributes to more than 30% of greenhouse gas emissions driving global warming. Annually 800 billion barrels of transportation fuel are consumed globally. Diesel and jet fuels account for greater than 50% of global transportation fuels.

Significant legislation has been passed, requiring fuel producers to cap or reduce the carbon emissions from the production and use of transportation fuels. Fuel producers are seeking substantially similar, low carbon fuels that can be blended and distributed through existing infrastructure (e.g., refineries, pipelines, tankers).

Due to increasing petroleum costs and reliance on petrochemical feedstocks, the chemicals industry is also looking for ways to improve margin and price stability, while reducing its environmental footprint. The chemicals industry is striving to develop greener products that are more energy, water, and $CO_2$ efficient than current products. Fuels produced from biological sources, such as biomass, represent one aspect of process.

Presents method for converting biomass into biofuels focus on the use of lignocellulolic biomass, and there are many problems associated with using this process. Large-scale cultivation of lignocellulolic biomass requires substantial amount of cultivated land, which can be only achieved by replacing food crop production with energy crop production, deforestation, and by recultivating currently uncultivated land. Other problems include a decrease in water availability and quality and an increase in the use of pesticides and fertilizers.

The degradation of lignocellulolic biomass using biological systems is a very difficult challenge due to its substantial mechanistic strength and the complex chemical components. Approximately thirty different enzymes are required to fully convert lignocellulose to monosaccharides. The only available alternate to this complex approach requires a substantial amount of heat, pressure, and strong acids. The art therefore needs an economic and technically simple process for converting biomass into hydrocarbons for use as biofuels or biopetrols.

BRIEF DESCRIPTION OF THE DRAWINGS

FIG. 5 shows the growth of recombinant strain of *E. coli* on galacturonates and pectin.

FIG. 6 shows the degradation of alginate to form pyruvate.

FIG. 7 shows the biological activity of various alcohol dehydrogenases isolated from *Agrobacterium tumefaciens* C58.

FIG. 12 shows the biological activity of diol dehydratases.

FIG. 13 summarizes the results of kinetic studies for various substrates in the oxidation reactions catalyzed by the DDH polypeptides. These reactions were NAD+ dependent.

FIG. 14 shows the nucleotide sequence (FIG. 14A) (SEQ ID NO:97) and polypeptide sequence (FIG. 14B) (SEQ ID NO:98) of diol dehydrogenase DDH1 isolated from *Lactobaccilus brevis* ATCC 367.

FIG. 15 shows the nucleotide sequence (FIG. 15A) (SEQ ID NO:99) and polypeptide sequence (FIG. 15B) (SEQ ID NO:100) of diol dehydrogenase DDH2 isolated from *Pseudomonas putida* KT2440.

FIG. 16 shows the nucleotide sequence (FIG. 16A) (SEQ ID NO:101) and polypeptide sequence (FIG. 16B) (SEQ ID NO:102) of diol dehydrogenase DDH3 isolated from *Kiebsiella pneumoniae* MGH78578.

FIG. 17 shows the sequential in vivo biological activity of a benzaldehyde lyase (bal) gene isolated from *Pseudomonas fluorescens* (codon usage was optimized for *E. coli* protein expression) and a ddh gene isolated from *Klebsiella pneumoniae* subsp. *pneumoniae* MGH 78578 (DDH3). This reaction illustrates the sequential conversion of butanal into 5-hydroxy-4-octanone and then 4,5-octanonediol.

FIG. 18 shows the sequential in vivo biological activity of a benzaldehyde lyase (bal) gene isolated from *Pseudomonas fluorescens* (codon usage was optimized for *E. coli* protein expression) and a ddh gene isolated from *Klebsiella pneumoniae* subsp. *pneumoniae* MGH 78578 (DDH3). This Figure illustrates the sequential conversion of n-pentanal into 6-hydroxy-5-decanone and then 5,6-decanediol.

FIG. 19 shows the sequential in vivo biological activity of a benzaldehyde lyase (bal) gene isolated from *Pseudomonas fluorescens* (codon usage was optimized for *E. coli* protein expression) and a ddh gene isolated from *Klebsiella pneumoniae* subsp. *pneumoniae* MGH 78578 (DDH3). This Figure illustrates the sequential conversion of 3-methylbutanal into 2,7-dimethyl-5-hydroxy-4-octanone and then 2,7-dimethyl-4,5-octanediol.

FIG. 20 shows the sequential in vivo biological activity of a benzaldehyde lyase (bal) gene isolated from *Pseudomonas fluorescens* (codon usage was optimized for *E. coli* protein expression) and a ddh gene isolated from *Klebsiella pneumoniae* subsp. *pneumoniae* MGH 78578 (DDH3). This Figure illustrates the sequential conversion of n-hexanal into 7-hydroxy-6-dodecanone and then 6,7-dodecanediol.

FIG. 21 shows the sequential in vivo biological activity of a benzaldehyde lyase (bal) gene isolated from *Pseudomonas fluorescens* (codon usage was optimized for *E. coli* protein expression) and a ddh gene isolated from *Klebsiella pneumoniae* subsp. *pneumoniae* MGH 78578 (DDH3). This Figure illustrates the sequential conversion of 4-methylpentanal into 2,9-dimethyl-6-hydroxy-5-decanone and then 2,9-dimethyl-5,6-decanediol. FIG. 21A shows the detection of isohexanoin (2,9-Dimethyl-6-hydroxy-5-decanone) at 9.45 minutes.

FIG. 23 shows the in vivo biological activity of a benzaldehyde lyase (bal) gene isolated from *Pseudomonas fluorescens* (codon usage was optimized for *E. coli* protein expression) and a ddh gene isolated from *Klebsiella pneumoniae* subsp. *pneumoniae* MGH 78578 (DDH3). This Figure illustrates the conversion of acetaldehyde into 3-hydroxy-2-butanone by showing the detection of acetoin (3-hydroxy-2-butanone) at rt=0.91 minutes.

FIG. 24 shows the sequential in vivo biological activity of a benzaldehyde lyase (bal) gene isolated from *Pseudomonas fluorescens* (codon usage was optimized for *E. coli* protein expression) and a ddh gene isolated from *Klebsiella pneumoniae* subsp. *pneumoniae* MGH 78578 (DDH3). This Figure illustrates the sequential conversion of n-propanal into 4-hydroxy-3-hexanone and then 3,4-hexanediol.

FIG. 26 shows the sequential biological activity of a diol dehydrogenase ddh from *Kiebsiella pneumoniae* MGH 78578 (DDH3) and a diol dehydratase pduCDE from *Kiebsiella pneumoniae* MGH 78578. FIG. 26A shows GC-MS data which confirms the presence of 4,5-octanediol in the sample extraction, which is the expected product resulting from the reduction of butyroin by ddh3.

FIG. 27 shows the sequential biological activity of a diol dehydrogenase ddh from *Kiebsiella pneumoniae* MGH 78578 (DDH3) and a diol dehydratase pduCDE from *Kiebsiella pneumoniae* MGH 78578.

FIG. 28 shows the nucleotide sequence (FIG. 28A) (SEQ ID NO:103) and polypeptide sequence (FIG. 28B) (SEQ ID NO:104) of a diol dehydratase large subunit (pduC) isolated from *Klebsiella pneumoniae* MGH78578.

FIG. 29 shows the nucleotide sequence (FIG. 29A) (SEQ ID NO:105) and polypeptide sequence (FIG. 29B) (SEQ ID NO:106) of a diol dehydratase medium subunit isolated from *Klebsiella pneumoniae* MGH78578 (pduD), in addition to the nucleotide sequence (FIG. 29C) (SEQ ID NO:107) and polypeptide sequence (FIG. 29D) (SEQ ID NO:108) of a diol dehydratase small subunit isolated from *Klebsiella pneumoniae* MGH78578 (pduE).

FIG. 33 shows the oxidation and reduction activity of 2ADH11 and 2ADH16.

FIG. 34 shows the oxidation and reduction of cyclopentanol by secondary alcohol dehydrogenases.

FIG. 35 shows the calculated rate constants for the illustrated reduction reactions for each substrate catalyzed by secondary alcohol dehydrogenase ADH-16 (SEQ ID NO:138).

FIG. 36 shows the calculated rate constants for the illustrated oxidation reactions for each substrate catalyzed by secondary alcohol dehydrogenase ADH-16 (SEQ ID NO:138).

FIGS. 37A-B show a list of alginate lyases genes/proteins that may be utilized according to the methods and recombinant microorganisms described herein.

FIGS. 38A-E show a list of pectate lyase genes/proteins that may be utilized according to the methods and recombinant microorganisms described herein.

FIG. 39A shows a list of rhamnogalacturonan lyase genes/proteins that may be utilized according to the methods and recombinant microorganisms described herein. FIG. 39B shows a list of rhamnogalacturonate hydrolase genes/proteins that may be utilized according to the methods and recombinant microorganisms described herein.

FIGS. 40A-B show a list of pectin methyl esterase genes/proteins that may be utilized according to the methods and recombinant microorganisms described herein.

FIG. 41 shows a list of pectin acetyl esterase genes/proteins that may be utilized according to the methods and recombinant microorganisms described herein.

FIG. 51 shows the in vivo biological activity of a C—C ligase isolated from *Pseudomonas fluorescens* and cloned into *E. coli*. The GC-MS chromatogram results show that codon-optimized BAL catalyzed the in vivo production of 6-methyl-3-hydroxy-2-heptanone from ligation reaction between acetaldehyde and 4-methylhexanal (FIG. 51A), and catalyzed the in vivo production of 7-methyl-4-hydroxy-3-octanone from a ligation reaction between 4-methylhexanal and propionaldehyde (FIG. 51B).

FIG. 52 shows the in vivo biological activity of a C—C ligase isolated from *Pseudomonas fluorescens* and cloned into *E. coli*. The GC-MS chromatogram results show that codon-optimized BAL catalyzed the in vivo production of 8-methyl-5-hydroxy-4-nonanone from ligation reaction between 4-methylhexanal and butyraldehyde (FIG. 52A), and catalyzed the in vivo production of 3-hydroxy-2-decanone from a ligation reaction between acetaldehyde and octanal (FIG. 52B).

FIG. 53 shows the in vivo biological activity of a C—C ligase isolated from *Pseudomonas fluorescens* and cloned into *E. coli*. The GC-MS chromatogram results show that codon-optimized BAL catalyzed the in vivo production of 4-hydroxy-3-undecanone from ligation reaction between octanal and propionaldehyde (FIG. 53A), and catalyzed the in vivo production of 5-hydroxy-4-dodecanone from a ligation reaction between octanal and butyraldehyde (FIG. 53B).

FIG. 55 shows the in vivo biological activity of a C—C ligase isolated from *Pseudomonas fluorescens* and cloned into E. coli. The GC-MS chromatogram results show that codon-optimized BAL catalyzed the in vivo production of 2-methyl-6-hydroxy-5-tridecanone from a ligation reaction between octanal and 4-methylpentanal.

BRIEF SUMMARY

Figure 1:
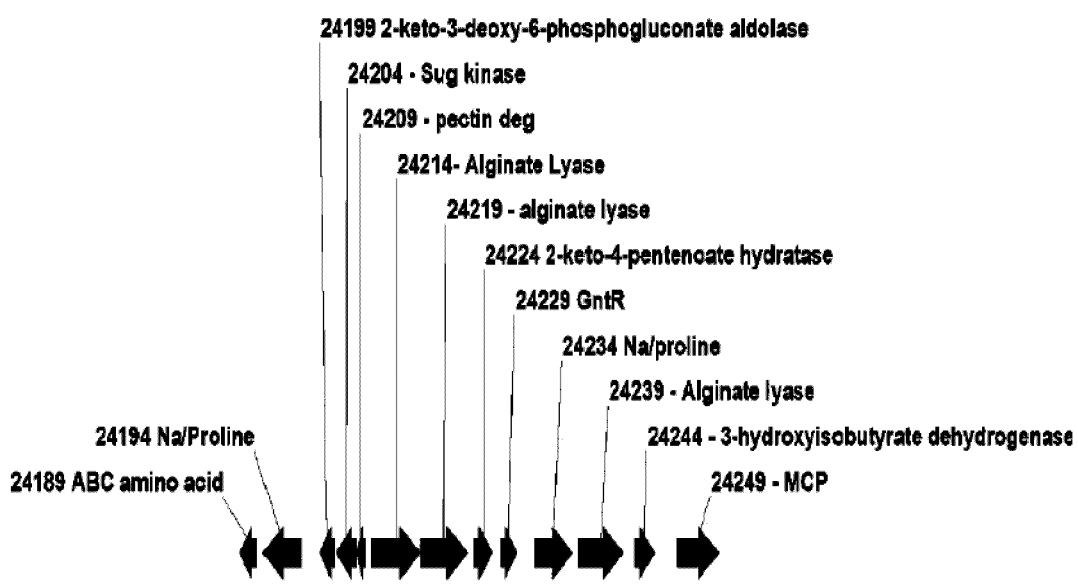
FIG. 1 shows the *Vibrio splendidus* genomic region of the fosmid clone described in Example 1. Genes are indicated with orange arrows. Labels show the numerical gene indices and the predicted function of the proteins.

Embodiments of the present invention include methods for converting a polysaccharide to a commodity chemical, comprising (a) contacting the polysaccharide, wherein the polysaccharide is optionally derived from biomass, with a polysaccharide degrading or depolymerizing metabolic system, wherein the metabolic system is selected from; (i) enzymatic or chemical catalysis, and (ii) a microbial system, wherein the microbial system comprises a recombinant microorganism, wherein the recombinant microorganism comprises one or exogenous genes that allow it to grow on the polysaccharide as a sole source of carbon, thereby converting the polysaccharide to a suitable monosaccharide or oligosaccharide; and (b) contacting the suitable monosaccharide or oligosaccharide with commodity chemical biosynthesis pathway, wherein the commodity chemical biosynthesis pathway comprises an aldehyde or ketone biosynthesis pathway, thereby converting the polysaccharide to the commodity chemical.

In certain aspects, the biomass is selected from marine biomass and vegetable/fruit/plant biomass. In certain aspects, the marine biomass is selected from kelp, giant kelp, sargasso, seaweed, algae, marine microflora, microalgae, and sea grass. In certain aspects, the vegetable/fruit/plant biomass comprises plant peel or pomace. In certain aspects, the vegetable/fruit/plant biomass is selected from citrus, potato, tomato, grape, gooseberry, carrot, mango, sugar-beet, apple, switchgrass, wood, and stover.

In certain aspects, the polysaccharide is selected from alginate, agar, carrageenan, fucoidan, pectin, polygalacturonate, cellulose, hemicellulose, xylan, arabinan, and mannan. In certain aspects, the suitable monosaccharide or oligosaccharide is selected from 2-keto-3-deoxy D-gluconate (KDG), D-mannitol, guluronate, mannuronate, mannitol, lyxose, glycerol, xylitol, glucose, mannose, galactose, xylose, arabinose, glucuronate, galacturonates, and rhamnose.

In certain aspects, the commodity chemical is selected from methane, methanol, ethane, ethene, ethanol, n-propane, 1-propene, 1-propanol, propanal, acetone, propionate, n-butane, 1-butene, 1-butanol, butanal, butanoate, isobutanal, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl)butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-)ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl)pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl)pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4-hydroxyphenyl)-3-pentanol, 4-methyl-1-(4-hydroxyphenyl)-2-pentanol, 4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl- 1-(4-hydroxyphenyl)-2,3-pentanedione, 4-methyl-1-(4-hydroxyphenyl)-3-hydroxy-2-pentanone, 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3-pentanone, 1-(indole-3)-3-hydroxy-2-pentanone, 1-(indole-3)-2,3-pentanedione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3-hexene, 5-methyl-1-hexene, 5-methyl-2-hexene, 4-methyl-1-hexene, 4-methyl-2-hexene, 3-methyl-2-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3-hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hexene, 4-methyl-1-phenyl-2-hexene, 4-methyl-1-phenyl-3-hexene, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl)hexane, 5-methyl-1-(4-hydroxyphenyl)-1-hexene, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4-hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-)hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethylheptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-4-octanol, 3-methyl-4-octanol, 6-methyl-4-octanol, 2-methyl-4-octanone, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3-octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4- hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone, n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethylnonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl-4,5-nonanedione, 3,8-dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal. undecanoate, n-dodecane, 1-dodecene, 1-dodecanol, dodecanal, dodecanoate, n-dodecane, 1-decadecene, 1-dodecanol, ddodecanal, dodecanoate, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, 1-octadecene, 1-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydrxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanene, 1,2-cyclopentanediol, cyclopentanone, cyclopentanol, (S)-2-acetolactate, (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5,6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-2-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-2-butanone, 4-hydroxyphenylacetoaldehyde, 1,4-di(4-hydroxyphenyl)butane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-)butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl-4-(indole-3)-3-hydroxy-2-butanone, indole-3-acetoaldehyde, 1,4-di(indole-3-)butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3-butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1,8-dicarboxylic acid, fucoidan, iodine, chlorophyll, carotenoid, calcium, magnesium, iron, sodium, potassium, and phosphate.

Certain embodiments of the present invention include methods for converting a polysaccharide to a suitable monosaccharide or oligosaccharide, comprising: (a) contacting the polysaccharide, wherein the polysaccharide is optionally obtained from biomass, with a microbial system for a time sufficient to convert the polysaccharide to a suitable monosaccharide or oligosaccharide, wherein the microbial system comprises, (i) at least one gene encoding and expressing an enzyme selected from a lyase and a hydrolase, wherein the lyase and/or hydrolase optionally comprises at least one signal peptide or at least one autotransporter domain; (ii) at least one gene encoding and expressing an enzyme selected from a monosaccharide transporter, a disaccharide transporter, a trisaccharide transporter, an oligosaccharide transporter, a polysaccharide transporter, and a superchannel; and (iii) at least one gene encoding and expressing an enzyme selected from a monosaccharide dehydrogenase, an isomerase, a dehydratase, a kinase, and an aldolase, thereby converting the polysaccharide to a suitable monosaccharide or oligosaccharide.

Certain embodiments of the present invention include methods for converting a polysaccharide to a suitable monosaccharide or oligosaccharide, comprising: (a) contacting the polysaccharide, wherein the polysaccharide is optionally obtained from biomass, with a chemical or enzymatic catalysis pathway for a time sufficient to convert the polysaccharide to a first monosaccharide or oligosaccharide; and (b) contacting the first monosaccharide or oligosaccharide with a microbial system for a time sufficient to convert the first monosaccharide or oligosaccharide to the suitable monosaccharide or oligosaccharide, wherein the microbial system comprises, (i) at least one gene encoding and expressing an enzyme selected from a lyase and a hydrolase, (ii) at least one gene encoding and expressing an enzyme selected from a monosaccharide transporter, a disaccharide transporter, a trisaccharide transporter, an oligosaccharide transporter, a polysaccharide transporter, and a superchannel; and (ii) at least one gene encoding and expressing an enzyme selected from a monosaccharide dehydrogenase, an isomerase, a dehydratase, a kinase, and an aldolase, thereby converting the polysaccharide to the suitable monosaccharide or oligosaccharide.

In certain aspects, the lyase is selected from an alginate lyase, a pectate lyase, a polymannuronate lyase, a polygluronate lyase, a polygalacturonate lyase and a rhamnogalacturonate lyase. In certain aspects, the hydrolase is selected from an alginate hydrolase, a rhamnogalacturonate hydrolase, a polymannuronate hydrolase, a pectin hydrolase, and a polygalacturonate hydrolase. In certain aspects, the transporter is selected from an ABC transporter, a symporter, and an outer membrane porin. In certain aspects, the ABC transporter is selected from Atu3021, Atu3022, Atu3023, Atu3024, algM1, algM2, AlgQ1, AlgQ2, AlgS, OG2516_05558, OG2516_05563, OG2516_05568, OG2516_05573, TogM, TogN, TogA, TogB, and functional variants thereof. In certain aspects, the symporter is selected from V12B01_24239 (SEQ ID NO:26), V12B01_24194 (SEQ ID NO:8), and TogT, and functional variants thereof. In certain aspects, the outermembrane porin comprises a porin selected from V12B01_24269, KdgM, and KdgN, and functional variants thereof.

Certain embodiments include a recombinant microorganism that is capable of growing on a polysaccharide as a sole source of carbon, wherein the polysaccharide is selected from alginate, pectin, tri-galacturonate, di-galacturonate, cellulose, and hemi-cellulose. In certain aspects, the polysaccharide is alginate. In certain aspects, the polysaccharide is pectin. In certain aspects, the polysaccharide is tri-galacturonate.

Certain embodiments include a recombinant microorganism, comprising (i) at least one gene encoding and expressing an enzyme selected from a lyase and a hydrolase, wherein the lyase or hydrolase optionally comprises at least one signal peptide or at least one autotransporter domain; (ii) at least one gene encoding and expressing an enzyme selected from a monosaccharide transporter, a disaccharide transporter, a trisaccharide transporter, an oligosaccharide transporter, a polysaccharide transporter, and a superchannel; and (iii) at least one gene encoding and expressing an enzyme selected from a monosaccharide dehydrogenase, an isomerase, a dehydratase, a kinase, and an aldolase. In certain aspects, the microorganism is capable of growing on a polysaccharide as a sole source of carbon. In certain aspects, the polysaccharide is selected from alginate, pectin, and tri-galacturonate.

Certain embodiments include methods for converting a suitable monosaccharide or oligosaccharide to a first commodity chemical comprising, (a) contacting the suitable monosaccharide or oligosaccharide with a microbial system for a time sufficient to convert to the suitable monosaccharide or oligosaccharide to the commodity chemical, wherein the microbial system comprises a recombinant microorganism, wherein the microorganism comprises a commodity chemical biosynthesis pathway, thereby converting the suitable monosaccharide or oligosaccharide to the first commodity chemical. In certain aspects, the commodity chemical pathway comprises one or more genes encoding an aldehyde or ketone biosynthesis pathway.

In certain aspects, the aldehyde or ketone biosynthesis pathway is selected from one or more of an acetoaldehyde, a propionaldehyde, a butyraldehyde, an isobutyraldehyde, a 2-methyl-butyraldehyde, a 3-methyl-butyraldehyde, a 2-phenyl acetoaldehyde, a 2-(4-hydroxyphenyl)acetaldehyde, a 2-Indole-3-acetoaldehyde, a glutaraldehyde, a 5-amino-pentaldehyde, a succinate semialdehyde, and a succinate 4-hydroxyphenyl acetaldehyde biosynthesis pathway. In certain aspects, the aldehyde or ketone biosynthesis pathway comprises an acetoaldehyde biosynthesis pathway and a biosynthesis pathway selected from a propionaldehyde, butyraldehyde, isobutyraldehyde, 2-methyl-butyraldehyde, 3-methyl-butyraldehyde, a 2-phenyl acetoaldehyde, a 2-(4-hydroxyphenyl)acetaldehyde, and a 2-Indole-3-acetoaldehyde biosynthesis pathway.

In certain aspects, the aldehyde or ketone biosynthesis pathway comprises a propionaldehyde biosynthesis pathway and a biosynthesis pathway selected from a butyraldehyde, isobutyraldehyde, 2-methyl-butyraldehyde, 3-methyl-butyraldehyde, and phenylacetoaldehyde biosynthesis pathway. In certain aspects, the aldehyde or ketone biosynthesis pathway comprises a butyraldehyde biosynthesis pathway and a biosynthesis pathway selected from an isobutyraldehyde, 2-methyl-butyraldehyde, 3-methyl-butyraldehyde, a 2-phenyl acetoaldehyde, a 2-(4-hydroxyphenyl)acetaldehyde, and a 2-Indole-3-acetoaldehyde biosynthesis pathway. In certain aspects, the aldehyde or ketone biosynthesis pathway comprises an isobutyraldehyde biosynthesis pathway and a biosynthesis pathway selected from a 2-methyl-butyraldehyde, 3-methyl-butyraldehyde, a 2-phenyl acetoaldehyde, a 2-(4-hydroxyphenyl)acetaldehyde, and a 2-Indole-3-acetoaldehyde biosynthesis pathway.

In certain aspects, the aldehyde or ketone biosynthesis pathway comprises a 2-methyl-butyraldehyde biosynthesis pathway and a biosynthesis pathway selected from a 3-methyl-butyraldehyde, a 2-phenyl acetoaldehyde, a 2-(4-hydroxyphenyl)acetaldehyde, and a 2-Indole-3-acetoaldehyde biosynthesis pathway. In certain aspects, the aldehyde or ketone biosynthesis pathway comprises a 3-methyl-butyraldehyde biosynthesis pathway and a biosynthesis pathway selected from a 2-phenyl acetoaldehyde, a 2-(4-hydroxyphenyl)acetaldehyde, and a 2-Indole-3-acetoaldehyde biosynthesis pathway. In certain aspects, the aldehyde or ketone biosynthesis pathway comprises a 2-phenyl acetoaldehyde biosynthesis pathway and a biosynthesis pathway selected from a 2-(4-hydroxyphenyl)acetaldehyde and a 2-Indole-3-acetoaldehyde biosynthesis pathway.

In certain aspects, the aldehyde or ketone biosynthesis pathway comprises a 2-(4-hydroxyphenyl)acetaldehyde biosynthesis pathway and a 2-Indole-3-acetoaldehyde biosynthesis pathway. In certain aspects, the first commodity chemical is further enzymatically and/or chemically reduced and dehydrated to a second commodity chemical.

Certain embodiments include methods for converting a suitable monosaccharide or oligosaccharide to a commodity chemical comprising, (a) contacting the suitable monosaccharide or oligosaccharide with a microbial system for a time sufficient to convert to the suitable monosaccharide or oligosaccharide to the commodity chemical, wherein the microbial system comprises; (i) one or more genes encoding and expressing an aldehyde biosynthesis pathway, wherein the aldehyde biosynthesis pathway comprises one or more genes encoding and expressing a decarboxylase enzyme; and (ii) one or more genes encoding and expressing an aldehyde reductase, thereby converting the suitable monosaccharide or oligosaccharide to the commodity chemical. In certain aspects, the decarboxylase enzyme is an indole-3-pyruvate decarboxylase (IPDC). In certain aspects, the IPDC comprises an amino acid sequence that is at least 80%, 90%, 95%, 98%, or 99% identical to the amino acid sequence set forth in SEQ ID NO: 312. In certain aspects, the aldehyde reductase enzyme is a phenylacetaldehyde reductase (PAR). In certain aspects, the PAR comprises an amino acid sequence that is at least 80%, 90%, 95%, 98%, or 99% identical to the amino acid sequence set forth in SEQ ID NO: 313. In certain aspects, the commodity chemical is selected from 2-phenylethanol, 2-(4-hydroxyphenyl)ethanol, and indole-3-ethanol.

Certain embodiments include a recombinant microorganism, comprising (i) one or more genes encoding and expressing an aldehyde biosynthesis pathway, wherein the aldehyde biosynthesis pathway comprises one or more genes encoding and expressing a decarboxylase enzyme; and (ii) one or more genes encoding and expressing an aldehyde reductase. In certain aspects, the aldehyde biosynthesis pathway further comprises one or more genes encoding and expressing an enzyme selected from a CoA-linked aldehyde dehydrogenase, an aldehyde dehydrogenase, and an alcohol dehydrogenase. In certain aspects, the decarboxylase enzyme is an indole-3-pyruvate decarboxylase (IPDC). In certain aspects, the aldehyde reductase enzyme is a phenylacetoaldehyde reductase (PAR). In certain aspects, the microorganism is capable of converting a suitable monosaccharide or oligosaccharide to a commodity chemical. In certain aspects, the commodity chemical is selected from 2-phenylethanol, 2-(4-hydroxyphenyl)ethanol, and indole-3-ethanol.

Certain embodiments include a recombinant microorganism, wherein the microorganism comprises reduced ethanol production capability compared to a wild-type microorganism. In certain aspects, the microorganism comprises a reduction or inhibition in the conversion of acetyl-coA to ethanol. In certain aspects, the recombinant microorganism comprises a reduction of an ethanol dehydrogenase, thereby providing a reduced ethanol production capability. In certain aspects, the ethanol dehydrogenase is an adhE, homolog or variant thereof. In certain aspects, the microorganism comprises a deletion or knockout of an adhE, homolog or variant thereof. In certain aspects, the recombinant microorganism comprises one or more deletions or knockouts in a gene encoding an enzyme selected from an enzyme that catalyzes the conversion of acetyl-coA to ethanol, an enzyme that catalyzes the conversion of pyruvate to lactate, an enzyme that catalyzes the conversion of fumarate to succinate, an enzyme that catalyzes the conversion of acetyl-coA and phosphate to coA and acetyl phosphate, an enzyme that catalyzes the conversion of acetyl-coA and formate to coA and pyruvate, and an enzyme that catalyzes the conversion of alpha-keto acid to branched chain amino acids.

Certain embodiments include wherein the microbial systems or recombinant microorganisms described herein comprise a microorganism selected from *Acetobacter aceti, Achromobacter, Acidiphilium, Acinetobacter, Actinomadura, Actinoplanes, Aeropyrum pernix, Agrobacterium, Alcaligenes, Ananas comosus* (M), *Arthrobacter, Aspargillus niger, Aspargillus oryze, Aspergillus melleus, Aspergillus pulverulentus, Aspergillus saitoi, Aspergillus sojea, Aspergillus usamii, Bacillus alcalophilus, Bacillus amyloliquefaciens, Bacillus brevis, Bacillus circulans, Bacillus clausii, Bacillus lentus, Bacillus licheniformis, Bacillus macerans, Bacillus stearothermophilus, Bacillus subtilis, Bifidobacterium, Brevibacillus brevis, Burkholderia cepacia, Candida cylindracea, Candida rugosa, Carica papaya* (L), *Cellulosimicrobium, Cephalosporium, Chaetomium erraticum, Chaetomium gracile, Clostridium, Clostridium butyricum, Clostridium acetobutylicum, Clostridium thermocellum, Corynebacterium* (glutamicum), *Corynebacterium efficiens, Escherichia coli, Enterococcus, Erwina chrysanthemi, Gliconobacter, Gluconacetobacter, Haloarcula, Humicola insolens, Humicola nsolens, Kitasatospora setae, Klebsiella, Klebsiella oxytoca, Kluyveromyces, Kluyveromyces fragilis, Kluyveromyces lactis, Kocuria, Lactlactis, Lactobacillus, Lactobacillus fermentum, Lactobacillus sake, Lactococcus, Lactococcus lactis, Leuconostoc, Methylocystis, Methanolobus siciliae, Methanogenium organophilum, Methanobacterium bryantii, Microbacterium imperiale, Micrococcus lysodeikticus, Microlunatus, Mucor javanicus, Mycobacterium, Myrothecium, Nitrobacter, Nitrosomonas, Nocardia, Papaya carica, Pediococcus, Pediococcus halophilus, Penicillium, Penicillium camemberti, Penicillium citrinum, Penicillium emersonii, Penicillium roqueforti, Penicillum lilactinum, Penicillum multicolor, Paracoccus pantotrophus, Propionibacterium, Pseudomonas, Pseudomonas fluorescens, Pseudomonas denitrificans, Pyrococcus, Pyrococcus furiosus, Pyrococcus horikoshii, Rhizobium, Rhizomucor miehei, Rhizomucor pusillus Lindt, Rhizopus, Rhizopus delemar, Rhizopus japonicus, Rhizopus niveus, Rhizopus oryzae, Rhizopus oligosporus, Rhodococcus, Sccharomyces cerevisiae, Sclerotina libertina, Sphingobacterium multivorum, Sphingobium, Sphingomonas, Streptococcus, Streptococcus thermophilus Y-1, Streptomyces, Streptomyces griseus, Streptomyces lividans, Streptomyces murinus, Streptomyces rubiginosus, Streptomyces violaceoruber, Streptoverticillium mobaraense, Tetragenococcus, Thermus, Thiosphaera pantotropha, Trametes, Trichoderma, Trichoderma longibrachiatum, Trichoderma reesei, Trichoderma viride, Trichosporon penicillatum, Vibrio alginolyticus, Xanthomonas,* yeast, *Zygosaccharomyces rouxii, Zymomonas,* and *Zymomonus mobilis.*

Certain embodiments include a commodity chemical produced by the methods described herein. Certain aspects include a blended commodity chemical comprising a commodity chemical produced by the methods provided herein and a refinery-produced petroleum product. In certain aspects, the commodity chemical is selected from a C10-C12 hydrocarbon, 2-phenylethanol, 2-(4-hydroxyphenyl)ethanol, and indole-3-ethanol. In certain aspects, the C10-C12 hydrocarbon is selected from 2,7-dimethyloctane and 2,9-dimethyldecane. In certain aspects, the refinery-produced petroleum product is selected from jet fuel and diesel fuel.

Certain embodiments include methods of producing a commodity chemical enriched refinery-produced petroleum product, comprising (a) blending the refinery-produced petroleum product with the commodity chemical produced by the methods described herein, thereby producing the commodity chemical enriched refinery-produced petroleum product.

DETAILED DESCRIPTION

Embodiments of the present invention relate to the unexpected discovery that microorganisms which are otherwise incapable of growing on certain polysaccharides derived from biomass as a sole source of carbon, can be engineered to grow on these polysaccharides as a sole source of carbon. Such microorganisms can include both prokaryotic and eukaryotic microorganisms, such as bacteria and yeast. In some aspects, certain laboratory and/or wild-type strains of *E. coli* can be engineered to grow on biomass derived from either alginate or pectin as a sole source of carbon to produce suitable monosaccharides or other molecules. Among other uses apparent to a person skilled in the art, the monosaccharides and other molecules produced by the growth of these engineered or recombinant microorganisms on alginate or pectin may be utilized as feedstock in the production of various commodity chemicals, such as biofuels.

Alginate and pectin provide advantages over other biomass sources in the production of biofuel feedstocks. For example, large-scale aquatic-farming can generate a significant amount of biomass without replacing food crop production with energy crop production, deforestation, and recultivating currently uncultivated land, as most of hydrosphere including oceans, rivers, and lakes remains untapped. As one particular example, the Pacific coast of North America is abundant in minerals necessary for large-scale aqua-farming. Giant kelp, which lives in the area, grows as fast as 1 m/day, the fastest among plants on earth, and grows up to 50 m. Additionally, aqua-farming has other benefits including the prevention of a red tide outbreak and the creation of a fish-friendly environment.

As an additional advantage, and in contrast to lignocellulolic biomass, biomass derived from aquatic, fruit, plant and/or vegetable sources is easy to degrade. Such biomass typically lacks lignin and is significantly more fragile than lignocellulolic biomass and can thus be easily degraded using either enzymes or chemical catalysts (e.g., formate). As one example, aquatic biomass such as seaweed may be easily converted to monosaccharides using either enzymes or chemical catalysis, as seaweed has significantly simpler major sugar components (Alginate: 30%, Mannitol: 15%) as compared to lignocellulose (Glucose: 24.1-39%, Mannose: 0.2-4.6%, Galactose: 0.5-2.4%, Xylose: 0.4-22.1%, Arabinose 1.5-2.8%, and Uronic acids: 1.2-20.7%, and total sugar contents are corresponding to 36.5-70% of dried weight).

As an additional example, biomass from plants such as fruit and/or vegetable contains pectin, a heteropolysaccharide derived from the plant cell wall. The characteristic structure of pectin is a linear chain of $\alpha$-(1-4)-linked D-galacturonic acid that forms the pectin-backbone, a homogalacturonan. Pectin can be easily converted to oligosaccharides or suitable monosaccharides using either enzymes, chemical catalysis, and/or microbial systems designed to utilize pectin as a source of carbon, as described herein. Saccharification and fermentation using aquatic, fruit, and/or vegetable biomass is much easier than using lignocellulose.

In this regard, embodiments of the present invention also relate to the surprising discovery that certain microorganisms can be engineered to produce various commodity chemicals, such as biofuels. In certain aspects, these biofuels may include alkanes, such as medium to long chain alkanes, which provide advantages over ethanol based biofuels. In certain aspects, the monosaccharides (e.g., 2-keto-3-deoxy D-gluconate; KDG) and other molecules produced by the growth of various engineered or recombinant microorganisms (e.g., recombinant microorganisms growing on pectin or alginate as a source of carbon) may be useful in the production of commodity chemicals, such as biofuels. As one example, suitable monosaccharides such as KDG may be utilized by recombinant microorganisms to produce alkanes, such as medium to long chain alkanes, among other chemicals. In certain aspects, such recombinant microorganisms may be utilized to produce such commodity chemical as 2,7 dimethyl octane and 2,9 dimethyl decane, among others provided herein and known in the art.

Such processes produce biofuels with significant advantages over other biofuels. In particular, medium to long chain alkanes provide a number of important advantages over the existing common biofuels such as ethanol and butanol, and are attractive long-term replacements of petroleum-based fuels such as gasoline, diesels, kerosene, and heavy oils in the future. As one example, medium to long chain alkanes and alcohols are major components in all petroleum products and jet fuel in particular, and hence alkanes we produce can be utilized directly by existing engines. By way of further example, medium to long chain alcohols are far better fuels than ethanol, and have a nearly comparable energy density to gasoline.

As another example, n-alkanes are major components of all oil products including gasoline, diesels, kerosene, and heavy oils. Microbial systems or recombinant microorganisms may be used to produce n-alkanes with different carbon lengths ranging, for example, from C7 to over C20: C7 for gasoline (e.g., motor vehicles), C10-C15 for diesels (e.g., motor vehicles, trains, and ships), and C8-C16 for kerosene (e.g., aviations and ships), and for all heavy oils.

As one aspect of the invention, the commodity chemicals produced by the methods and recombinant microorganisms described herein may be utilized by existing petroleum refineries for the purposes of blending with petroleum products produced by traditional refinery methods. To this end, as noted above, fuel producers are seeking substantially similar, low carbon fuels that can be blended and distributed through existing infrastructure (refineries, pipelines, tankers). As hydrocarbons, the commodity chemicals produced according to the methods herein are substantially similar to petroleum derived fuels, reduce green house gas emissions by more than 80% from petroleum derived fuels, and are compatible with existing infrastructure in the oil and gas industry. For instance, certain of the commodity chemicals produced herein, including, for example, various C10-C12 hydrocarbons such as 2,7 dimethyloctane, 2,7 dimethyldecanone, among others, are blendable directly into refinery-produced petroleum products, such as jet and diesel fuels. By using such biologically produced commodity chemicals as a blendstock for jet and diesel fuels, refineries may reduce Green House Gas emissions by more than 80%.

Accordingly, certain embodiments of the present invention relate generally to methods for converting biomass to a commodity chemical, comprising obtaining a polysaccharide from biomass; contacting the polysaccharide with a polysaccharide degrading or depolymerizing pathway, thereby converting the polysaccharide to a suitable monosaccharide. The suitable monosaccharide obtained from such as process may be used for any desired purpose. For instance, in certain aspects, the suitable monosaccharide may then be converted to a commodity chemical (e.g., biofuel) by contacting the suitable monosaccharide with a biofuel biosynthesis pathway, whether as part of a recombinant microorganism, an in vitro enzymatic or chemical pathway, or a combination thereof, thereby converting the monosaccharide to a commodity chemical.

In other aspects, in producing a commodity chemical such as a biofuel, a suitable monosaccharide may be obtained directly from any available source and converted to a commodity chemical by contacting the suitable monosaccharide with a biofuel biosynthesis pathway, as described herein. Among other uses apparent to a person skilled in the art, such biofuels may then be blended directly with refinery produced petroleum products, such as jet and diesel fuels, to produce commodity chemical enriched, refinery-produced petroleum products.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below. All references referred to herein are incorporated by reference in their entirety.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

The term "biologically active fragment", as applied to fragments of a reference polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity of a reference sequence.

The term "reference sequence" refers generally to a nucleic acid coding sequence, or amino acid sequence, of any enzyme having a biological activity described herein (e.g., saccharide dehydrogenase, alcohol dehydrogenase, dehydratase, lyase, transporter, decarboxylase, hydrolase, etc.), such as a "wild-type" sequence, including those reference sequences exemplified by SEQ ID NOS:1-144, and 308-313. A reference sequence may also include naturally-occurring, functional variants (i.e., orthologs or homologs) of the sequences described herein.

Included within the scope of the present invention are biologically active fragments of at least about 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, 500, 600 or more contiguous nucleotides or amino acid residues in length, including all integers in between, which comprise or encode a polypeptide having an enzymatic activity of a reference polynucleotide or polypeptide. Representative biologically active fragments generally participate in an interaction, e.g., an intra-molecular or an inter-molecular interaction. An inter-molecular interaction can be a specific binding interaction or an enzymatic interaction. Examples of enzymatic interactions or activities include saccharide dehydrogenase activities, alcohol dehydrogenase activities, dehydratases activities, lyase activities, transporter activities, isomerase activities, kinase activities, among others described herein. Biologically active fragments typically comprise one or more active sites or enzymatic/binding motifs, as described herein and known in the art.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "consisting of," is meant including, and limited to, whatever follows the phrase "consisting of" Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

By "enzyme reactive conditions" it is meant that any necessary conditions are available in an environment (i.e., such factors as temperature, pH, lack of inhibiting substances) which will permit the enzyme to function. Enzyme reactive conditions can be either in vitro, such as in a test tube, or in vivo, such as within a cell.

As used herein, the terms "function" and "functional" and the like refer to a biological or enzymatic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395) which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected, transformed, or infected in vivo or in vitro with a recombinant vector or a polynucleotide of the invention. A host cell which comprises a recombinant vector of the invention is a recombinant host cell, recombinant cell, or recombinant microrganism.

By "isolated" is meant material that is substantially or essentially free from components that normally accompany it in its native state. For example, an "isolated polynucleotide", as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell, i.e., it is not associated with in vivo substances.

By "increased" or "increasing" is meant the ability of one or more recombinant microorganisms to produce a greater amount of a given product or molecule (e.g., commodity chemical, biofuel, or intermediate product thereof) as compared to a control microorganism, such as an unmodified microorganism or a differently modified microorganism. An "increased" amount is typically a "statistically significant" amount, and may include an increase that is 1, 2, 3, 4, 5, 6, 7, 8, 9, 10, 15, 20, 30 or more times (including all integers and decimal points in between, e.g., 1.5, 1.6, 1.7. 1.8, etc.) the amount produced by an unmodified microorganism or a differently modified microorganism.

By "obtained from" is meant that a sample such as, for example, a polynucleotide extract or polypeptide extract is isolated from, or derived from, a particular source, such as a desired organism, typically a microorganism. "Obtained from" can also refer to the situation in which a polynucleotide or polypeptide sequence is isolated from, or derived from, a particular organism or microorganism. For example, a polynucleotide sequence encoding a benzaldehyde lyase enzyme may be isolated from a variety of prokaryotic or eukaryotic microorganisms, such as *Pseudomonas*.

The term "operably linked" as used herein means placing a gene under the regulatory control of a promoter, which then controls the transcription and optionally the translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived. "Constitutive promoters" are typically active, i.e., promote transcription, under most conditions. "Inducible promoters" are typically active only under certain conditions, such as in the presence of a given molecule factor (e.g., IPTG) or a given environmental condition (e.g., $CO_2$ concentration, nutrient levels, light, heat). In the absence of that condition, inducible promoters typically do not allow significant or measurable levels of transcriptional activity.

The recitation "polynucleotide" or "nucleic acid" as used herein designates mRNA, RNA, cRNA, rRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence) or may comprise a variant, or a biological functional equivalent of such a sequence. Polynucleotide variants may contain one or more substitutions, additions, deletions and/or insertions, as further described below, preferably such that the enzymatic activity of the encoded polypeptide is not substantially diminished relative to the unmodified polypeptide, and preferably such that the enzymatic activity of the encoded polypeptide is improved (e.g., optimized) relative to the unmodified polypeptide. The effect on the enzymatic activity of the encoded polypeptide may generally be assessed as described herein.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

The terms "polynucleotide variant" and "variant" and the like refer to polynucleotides that display substantial sequence identity with any of the reference polynucleotide sequences or genes described herein, and to polynucleotides that hybridize with any polynucleotide reference sequence described herein, or any polynucleotide coding sequence of any gene or protein referred to herein, under low stringency, medium stringency, high stringency, or very high stringency conditions that are defined hereinafter and known in the art. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide, or has increased activity in relation to the reference polynucleotide (i.e., optimized). Polynucleotide variants include, for example, polynucleotides having at least 50% (and at least 51% to at least 99% and all integer percentages in between) sequence identity with a reference polynucleotide described herein.

The terms "polynucleotide variant" and "variant" also include naturally-occurring allelic variants that encode these enzymes. Examples of naturally-occurring variants include allelic variants (same locus), homologs (different locus), and orthologs (different organism). Naturally occurring variants such as these can be identified and isolated using well-known molecular biology techniques including, for example, various polymerase chain reaction (PCR) and hybridization-based techniques as known in the art. Naturally occurring variants can be isolated from any organism that encodes one or more genes having a suitable enzymatic activity described herein (e.g., C—C ligase, diol dehyodrogenase, pectate lyase, alginate lyase, diol dehydratase, transporter, etc.).

Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. In certain aspects, non-naturally occurring variants may have been optimized for use in a given microorganism (e.g., *E.* coli), such as by engineering and screening the enzymes for increased activity, stability, or any other desirable feature. The variations can produce both conservative and non-conservative amino acid substitutions (as compared to the originally encoded product). For nucleotide sequences, conservative variants include those sequences that, because of the degeneracy of the genetic code, encode the amino acid sequence of a reference polypeptide. Variant nucleotide sequences also include synthetically derived nucleotide sequences, such as those generated, for example, by using site-directed mutagenesis but which still encode a biologically active polypeptide. Generally, variants of a particular reference nucleotide sequence will have at least about 30%, 40% 50%, 55%, 60%, 65%, 70%, generally at least about 75%, 80%, 85%, 90% to 95% or more, and even about 97% or 98% or more sequence identity to that particular nucleotide sequence as determined by sequence alignment programs described elsewhere herein using default parameters.

As used herein, the term "hybridizes under low stringency, medium stringency, high stringency, or very high stringency conditions" describes conditions for hybridization and washing. Guidance for performing hybridization reactions can be found in Ausubel et al., "Current Protocols in Molecular Biology", John Wiley & Sons Inc, 1994-1998, Sections 6.3.1-6.3.6. Aqueous and non-aqueous methods are described in that reference and either can be used.

Reference herein to "low stringency" conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

"Medium stringency" conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C.

"High stringency" conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

One embodiment of "very high stringency" conditions includes hybridizing in 0.5 M sodium phosphate, 7% SDS at 65° C., followed by one or more washes in 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al., Current Protocols in Molecular Biology (1989), at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m=81.5+16.6$ (log$_{10}$ M)+0.41 (% G+C)−0.63 (% formamide)−(600/length) wherein: M is the concentration of Na$^+$, preferably in the range of 0.01 molar to 0.4 molar; % G+C is the sum of guano sine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m-15°$ C. for high stringency, or $T_m-30°$ C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionizer formamide, 5×SSC, 5× Reinhardt's solution (0.1% fecal, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2× SSC and 0.1% SDS solution for 12 min at 65-68° C.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a selected enzyme in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such nucleotides are typically referred to as "codon-optimized." Any of the nucleotide sequences described herein may be utilized in such a "codon-optimized" form. For example, the nucleotide coding sequence of the benzaldehyde lyase from *Pseudomonas fluorescens* may be codon-optimized for expression in *E. coli*.

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector that contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The recitation polypeptide "variant" refers to polypeptides that are distinguished from a reference polypeptide sequence by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The present invention contemplates the use in the methods described herein of variants of full-length polypeptides having any of the enzymatic activities described herein, truncated fragments of these full-length polypeptides, variants of truncated fragments, as well as their related biologically active fragments. Typically, biologically active fragments of a polypeptide may participate in an interaction, for example, an intra-molecular or an inter-molecular interaction. An intermolecular interaction can be a specific binding interaction or an enzymatic interaction (e.g., the interaction can be transient and a covalent bond is formed or broken). Biologically active fragments of a polypeptide/enzyme an enzymatic activity described herein include peptides comprising amino acid sequences sufficiently similar to, or derived from, the amino acid sequences of a (putative) full-length reference polypeptide sequence. Typically, biologically active fragments comprise a domain or motif with at least one enzymatic activity, and may include one or more (and in some cases all) of the various active domains. A biologically active fragment of a an enzyme can be a polypeptide fragment which is, for example, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 220, 240, 260, 280, 300, 320, 340, 360, 380, 400, 450, 500, 600 or more contiguous amino acids, including all integers in between, of a reference polypeptide sequence. In certain embodiments, a biologically active fragment comprises a conserved enzymatic sequence, domain, or motif, as described elsewhere herein and known in the art. Suitably, the biologically-active fragment has no less than about 1%, 10%, 25%, 50% of an activity of the wild-type polypeptide from which it is derived.

The term "exogenous" refers generally to a polynucleotide sequence or polypeptide that does not naturally occur in a wild-type cell or organism, but is typically introduced into the cell by molecular biological techniques, i.e., engineering to produce a recombinant microorganism. Examples of "exogenous" polynucleotides include vectors, plasmids, and/or man-made nucleic acid constructs encoding a desired protein or enzyme. The term "endogenous" refers generally to naturally occurring polynucleotide sequences or polypeptides that may be found in a given wild-type cell or organism. For example, certain naturally-occurring bacterial or yeast species do not typically contain a benzaldehyde lyase gene, and, therefore, do not comprise an "endogenous" polynucleotide sequence that encodes a benzaldehyde lyase. In this regard, it is also noted that even though an organism may comprise an endogenous copy of a given polynucleotide sequence or gene, the introduction of a plasmid or vector encoding that sequence, such as to over-express or otherwise regulate the expression of the encoded protein, represents an "exogenous" copy of that gene or polynucleotide sequence. Any of the of pathways, genes, or enzymes described herein may utilize or rely on an "endogenous" sequence, or may be provided as one or more "exogenous" polynucleotide sequences, and/or may be utilized according to the endogenous sequences already contained within a given microorganism.

A "recombinant" microorganism typically comprises one or more exogenous nucleotide sequences, such as in a plasmid or vector.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

"Transformation" refers generally to the permanent, heritable alteration in a cell resulting from the uptake and incorporation of foreign DNA into the host-cell genome; also, the transfer of an exogenous gene from one organism into the genome of another organism.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. Such a vector may comprise specific sequences that allow recombination into a particular, desired site of the host chromosome. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a bacterial cell, such as a cyanobacterial cell. The vector can include a reporter gene, such as a green fluorescent protein (GFP), which can be either fused in frame to one or more of the encoded polypeptides, or expressed separately. The vector can also include a selection marker such as an antibiotic resistance gene that can be used for selection of suitable transformants.

The terms "wild-type" and "naturally occurring" are used interchangeably to refer to a gene or gene product that has the characteristics of that gene or gene product when isolated from a naturally occurring source. A wild type gene or gene product (e.g., a polypeptide) is that which is most frequently observed in a population and is thus arbitrarily designed the "normal" or "wild-type" form of the gene.

Examples of "biomass" include aquatic or marine biomass, fruit-based biomass such as fruit waste, and vegetable-based biomass such as vegetable waste, among others. Examples of aquatic or marine biomass include, but are not limited to, kelp, giant kelp, seaweed, algae, and marine microflora, microalgae, sea grass, and the like. In certain aspects, biomass does not include fossilized sources of carbon, such as hydrocarbons that are typically found within the top layer of the Earth's crust (e.g., natural gas, nonvolatile materials composed of almost pure carbon, like anthracite coal, etc).

Examples of fruit and/or vegetable biomass include, but are not limited to, any source of pectin such as plant peel and pomace including citrus, orange, grapefruit, potato, tomato, grape, mango, gooseberry, carrot, sugar-beet, and apple, among others.

Examples of polysaccharides, oligosaccharides, monosaccharides or other sugar components of biomass include, but are not limited to, alginate, agar, carrageenan, fucoidan, pectin, gluronate, mannuronate, mannitol, lyxose, cellulose, hemicellulose, glycerol, xylitol, glucose, mannose, galactose, xylose, xylan, mannan, arabinan, arabinose, glucuronate, galacturonate (including di- and tri-galacturonates), rhamnose, and the like.

Certain examples of alginate-derived polysaccharides include saturated polysaccharides, such as β-D-mannuronate, α-L-gluronate, dialginate, trialginate, pentalginate, hexylginate, heptalginate, octalginate, nonalginate, decalginate, undecalginate, dodecalginate and polyalginate, as well as unsaturated polysaccharides such as 4-deoxy-L-erythro-5-hexoseulose uronic acid, 4-(4-deoxy-beta-D-mann-4-enuronosyl)-D-mannuronate or L-guluronate, 4-(4-deoxy-beta-D-mann-4-enuronosyl)-dialginate, 4-(4-deoxy-beta-D-mann-4-enuronosyl)-trialginate, 4-(4-deoxy-beta-D-mann-4-enuronosyl)-tetralginate, 4-(4-deoxy-beta-D-mann-4-enuronosyl)-pentalginate, 4-(4-deoxy-beta-D-mann-4-enuronosyl)-hexylginate, 4-(4-deoxy-beta-D-mann-4-enuronosyl)-heptalginate, 4-(4-deoxy-beta-D-mann-4-enuronosyl)-octalginate, 4-(4-deoxy-beta-D-mann-4-enuronosyl)-nonalginate, 4-(4-deoxy-beta-D-mann-4-enuronosyl)-undecalginate, and 4-(4-deoxy-beta-D-mann-4-enuronosyl)-dodecalginate.

Certain examples of pectin-derived polysaccharides include saturated polysaccharides, such as galacturonate, digalacturonate, trigalacturonate, tetragalacturonate, pentagalacturonate, hexagalacturonate, heptagalacturonate, octagalacturonate, nonagalacturonate, decagalacturonate, dodecagalacturonate, polygalacturonate, and rhamnopolygalacturonate, as well as saturated polysaccharides such as 4-deoxy-L-threo-5-hexosulose uronate, 4-(4-Deoxy-alpha-D-gluc-4-enuronosyl)-D-galacturonate, 4-(4-Deoxy-alpha-D-gluc-4-enuronosyl)-D-digalacturonate, 4-(4-Deoxy-alpha-D-gluc-4-enuronosyl)-D-trigalacturonate, 4-(4-Deoxy-alpha-D-gluc-4-enuronosyl)-D-tetragalacturonate, 4-(4-Deoxy-alpha-D-gluc-4-enuronosyl)-D-pentagalacturonate, 4-(4-Deoxy-alpha-D-gluc-4-enuronosyl)-D-hexagalacturonate, 4-(4-Deoxy-alpha-D-gluc-4-enuronosyl)-D-heptagalacturonate, 4-(4-Deoxy-alpha-D-gluc-4-enuronosyl)-D-octagalacturonate, 4-(4-Deoxy-alpha-D-gluc-4-enuronosyl)-D-nonagalacturonate, 4-(4-Deoxy-alpha-D-gluc-4-enuronosyl)-D-decagalacturonate, and 4-(4-Deoxy-alpha-D-gluc-4-enuronosyl)-D-dodecagalacturonate.

These polysaccharide or oligosaccharide components may be converted into "suitable monosaccharides" or other "suitable saccharides," such as "suitable oligosaccharides," by the microorganisms described herein which are capable of growing on such polysaccharides or other sugar components as a source of carbon (e.g., a sole source of carbon).

A "suitable monosaccharide" or "suitable saccharide" refers generally to any saccharide that may be produced by a recombinant microorganism growing on pectin, alginate, or other saccharide (e.g., galacturonate, cellulose, hemi-cellulose etc.) as a source or sole source of carbon, and also refers generally to any saccharide that may be utilized in a biofuel biosynthesis pathway of the present invention to produce hydrocarbons such as biofuels or biopetrols. Examples of suitable monosaccharides or oligosaccharides include, but are not limited to, 2-keto-3-deoxy D-gluconate (KDG), D-mannitol, gluronate, mannuronate, mannitol, lyxose, glycerol, xylitol, glucose, mannose, galactose, xylose, arabinose, glucuronate, galacturonates, and rhamnose, and the like. As noted herein, a "suitable monosaccharide" or "suitable saccharide" as used herein may be produced by an engineered or recombinant microorganism of the present invention, or may be obtained from commercially available sources.

The recitation "commodity chemical" as used herein includes any saleable or marketable chemical that can be produced either directly or as a by-product of the methods provided herein, including biofuels and/or biopetrols. General examples of "commodity chemicals" include, but are not limited to, biofuels, minerals, polymer precursors, fatty alcohols, surfactants, plasticizers, and solvents. The recitation "biofuels" as used herein includes solid, liquid, or gas fuels derived, at least in part, from a biological source, such as a recombinant microorganism.

Examples of commodity chemicals include, but are not limited to, methane, methanol, ethane, ethene, ethanol, n-propane, 1-propene, 1-propanol, propanal, acetone, propionate, n-butane, 1-butene, 1-butanol, butanal, butanoate, isobutanal, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl)butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-)ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl)pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl)pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4-hydroxyphenyl)-3-pentanol, 4-methyl-1-(4-hydroxyphenyl)-2-pentanol, 4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl-1-(4-hydroxyphenyl)-2,3-pentanedione, 4-methyl-1-(4-hydroxyphenyl)-3-hydroxy-2-pentanone, 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3-pentanone, 1-(indole-3)-3-hydroxy-2-pentanone, 1-(indole-3)-2,3-pentanedione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3-hexene, 5-methyl-1-hexene, 5-methyl-2-hexene, 4-methyl-1-hexene, 4-methyl-2-hexene, 3-methyl-3-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3- hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hexene, 4-methyl-1-phenyl-2-hexene, 4-methyl-1-phenyl-3-hexene, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl)hexane, 5-methyl-1-(4-hydroxyphenyl)-1-hexene, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4-hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-)hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethylheptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-4-octanol, 3-methyl-4-octanol, 6-methyl-4-octanol, 2-methyl-4-octanone, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3-octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4-hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone, n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethylnonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl-4,5-nonanedione, 3,8-dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal. undecanoate, n-dodecane, 1-dodecene, 1-dodecanol, dodecanal, dodecanoate, n-dodecane, 1-decadecene, 1-dodecanol, ddodecanal, dodecanoate, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, 1-octadecene, 1-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydrxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanone, 1,2-cyclopentanediol, cyclopentanone, cyclopentanol, (S)-2-acetolactate, (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5,6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-2-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-2-butanone, 4-hydroxyphenylacetoaldehyde, 1,4-di(4-hydroxyphenyl)butane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-)butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl-4-(indole-3)-3-hydroxy-2-butanone, indole-3-acetoaldehyde, 1,4-di(indole-3-)butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3-butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1,8-dicarboxylic acid, fucoidan, iodine, chlorophyll, carotenoid, calcium, magnesium, iron, sodium, potassium, phosphate, and the like.

The recitation "optimized" as used herein refers to a pathway, gene, polypeptide, enzyme, or other molecule having an altered biological activity, such as by the genetic alteration of a polypeptide's amino acid sequence or by the alteration/modification of the polypeptide's surrounding cellular environment, to improve its functional characteristics in relation to the original molecule or original cellular environment (e.g., a wild-type sequence of a given polypeptide or a wild-type microorganism). Any of the polypeptides or enzymes described herein may be optionally "optimized," and any of the genes or nucleotide sequences described herein may optionally encode an optimized polypeptide or enzyme. Any of the pathways described herein may optionally contain one or more "optimized" enzymes, or one or more nucleotide sequences encoding for an optimized enzyme or polypeptide.

Typically, the improved functional characteristics of the polypeptide, enzyme, or other molecule relate to the suitability of the polypeptide or other molecule for use in a biological pathway (e.g., a biosynthesis pathway, a C—C ligation pathway) to convert a monosaccharide or oligosaccharide into a biofuel. Certain embodiments, therefore, contemplate the use of "optimized" biological pathways. An exemplary "optimized" polypeptide may contain one or more alterations or mutations in its amino acid coding sequence (e.g., point mutations, deletions, addition of heterologous sequences) that facilitate improved expression and/or stability in a given microbial system or microorganism, allow regulation of polypeptide activity in relation to a desired substrate (e.g., inducible or repressible activity), modulate the localization of the polypeptide within a cell (e.g., intracellular localization, extracellular secretion), and/or effect the polypeptide's overall level of activity in relation to a desired substrate (e.g., reduce or increase enzymatic activity). A polypeptide or other molecule may also be "optimized" for use with a given microbial system or microorganism by altering one or more pathways within that system or organism, such as by altering a pathway that regulates the expression (e.g., up-regulation), localization, and/or activity of the "optimized" polypeptide or other molecule, or by altering a pathway that minimizes the production of undesirable by-products, among other alterations. In this manner, a polypeptide or other molecule may be "optimized" with or without altering its wild-type amino acid sequence or original chemical structure. Optimized polypeptides or biological pathways may be obtained, for example, by direct mutagenesis or by natural selection for a desired phenotype, according to techniques known in the art.

In certain aspects, "optimized" genes or polypeptides may comprise a nucleotide coding sequence or amino acid sequence that is 50% to 99% identical (including all integeres in between) to the nucleotide or amino acid sequence of a reference (e.g., wild-type) gene or polypeptide. In certain aspects, an "optimized" polypeptide or enzyme may have about 1, 2, 3, 4, 5, 6, 7, 8, 9, 10, 20, 30, 40, 50, 100 (including all integers and decimal points in between e.g., 1.2, 1.3, 1.4, 1.5, 5.5, 5.6, 5.7, 60, 70, etc.), or more times the biological activity of a reference polypeptide.

Certain aspects of the invention also include a commodity chemical, such as a biofuel, that is produced according to the methods and recombinant microorganisms described herein. Such a biofuel (e.g., medium to long chain alkane) may be distinguished from other fuels, such as those fuels produced by traditional refinery from crude carbon sources, by radiocarbon dating techniques. For instance, carbon has two stable, nonradioactive isotopes: carbon-12 ($^{12}C$), and carbon-13 ($^{13}C$). In addition, there are trace amounts of the unstable isotope carbon-14 ($^{14}C$) on Earth. Carbon-14 has a half-life of 5730 years, and would have long ago vanished from Earth were it not for the unremitting impact of cosmic rays on nitrogen in the Earth's atmosphere, which create more of this isotope. The neutrons resulting from the cosmic ray interactions participate in the following nuclear reaction on the atoms of nitrogen molecules ($N_2$) in the atmospheric air:

$$n + {}^{14}_{7}N \rightarrow {}^{14}_{6}C + p$$

Plants and other photosynthetic organisms take up atmospheric carbon dioxide by photosynthesis. Since many plants are ingested by animals, every living organism on Earth is constantly exchanging carbon-14 with its environment for the duration of its existence. Once an organism dies, however, this exchange stops, and the amount of carbon-14 gradually decreases over time through radioactive beta decay.

Most hydrocarbon-based fuels, such as crude oil and natural gas derived from mining operations, are the result of compression and heating of ancient organic materials (i.e., kerogen) over geological time. Formation of petroleum typically occurs from hydrocarbon pyrolysis, in a variety of mostly endothermic reactions at high temperature and/or pressure. Today's oil formed from the preserved remains of prehistoric zooplankton and algae, which had settled to a sea or lake bottom in large quantities under anoxic conditions (the remains of prehistoric terrestrial plants, on the other hand, tended to form coal). Over geological time the organic matter mixed with mud, and was buried under heavy layers of sediment resulting in high levels of heat and pressure (known as diagenesis). This process caused the organic matter to chemically change, first into a waxy material known as kerogen which is found in various oil shales around the world, and then with more heat into liquid and gaseous hydrocarbons in a process known as catagenesis. Most hydrocarbon based fuels derived from crude oil have been undergoing a process of carbon-14 decay over geological time, and, thus, will have little to no detectable carbon-14. In contrast, certain biofuels produced by the living microorganisms of the present invention will comprise carbon-14 at a level comparable to all other presently living things (i.e., an equilibrium level). In this manner, by measuring the carbon-12 to carbon-14 ratio of a hydrocarbon-based biofuel of the present invention, and comparing that ratio to a hydrocarbon based fuel derived from crude oil, the biofuels produced by the methods provided herein can be structurally distinguished from typical sources of hydrocarbon based fuels.

Embodiments of the present invention include methods for converting a polysaccharide to a suitable monosaccharide comprising, (a) obtaining the polysaccharide; and (b) contacting the polysaccharide with a recombinant microorganism or microbial system comprising such a microorganism for a time sufficient to convert the polysaccharide to a suitable monosaccharide, wherein the microbial system comprises, (i) at least one gene encoding and expressing an enzyme selected from a lyase and a hydrolase, wherein the lyase and/or hydrolase optionally comprises at least one signal peptide or at least one autotransporter domain; (ii) at least one gene encoding and expressing an enzyme selected from a monosaccharide transporter, a disaccharide transporter, a trisaccharide transporter, an oligosaccharide transporter, and a polysaccharide transporter; and (iii) at least one gene encoding and expressing an enzyme selected from a monosaccharide dehydrogenase, an isomerase, a dehydratase, a kinase, and an aldolase, thereby converting the polysaccharide to a suitable monosaccharide.

Alternatively, certain aspects may include methods for converting a polysaccharide to a suitable monosaccharide comprising, (a) obtaining the polysaccharide; and (b) contacting the polysaccharide with a microbial system for a time sufficient to convert the polysaccharide to a suitable monosaccharide, wherein the microbial system comprises, (i) at least one gene encoding and expressing an enzyme selected from a lyase and a hydrolase; (ii) at least one gene encoding and expressing a superchannel; and (iii) at least one gene encoding and expressing an enzyme selected from a monosaccharide dehydrogenase, an isomerase, a dehydratase, a kinase, and an aldolase, thereby converting the polysaccharide to a suitable monosaccharide.

In certain embodiments, a microbial system or isolated microorganism is capable of growing using a polysaccharide (e.g., alginate, pectin, etc.) as a sole source of carbon and/or energy. A "sole source of carbon" refers generally to the ability to grow on a given carbon source as the only carbon source in a given growth medium.

With regard to alginate, approximately 50 percent of seaweed dry-weight comprises various sugar components, among which alginate and mannitol are major components corresponding to 30 and 15 percent of seaweed dry-weight, respectively. With regard to pectin, although microorganisms such as $E.\ coli$ are generally considered as a host organisms in synthetic biology, and although such microorganism are able to metabolize mannitol, they completely lack the ability to degrade and metabolize alginate. In this regard, many laboratory or wild-type microorganisms, such as $E.\ coli$, are unable to grow on alginate as a sole source of carbon. Similarly, many organisms such as $E.\ coli$ are unable to degrade and metabolize pectin, a polysaccharide found in many food waste products, and, thus are unable to grown on pectin as a sole source of carbon. Accordingly, embodiments of the present application include engineered microorganisms, such as $E.\ coli$, or microbial systems containing such engineered microorganisms, that are capable of using polysaccharides, such as alginate and pectin, as a sole source of carbon and/or energy.

Alginate is a block co-polymer of β-D-mannuronate (M) and α-D-gluronate (G) (M and G are epimeric about the C5-carboxyl group). Each alginate polymer comprises regions of all M (polyM), all G (polyG), and/or the mixture of M and G (polyMG). To utilize alginate to produce one or more suitable monosaccharides, certain aspects of the present invention provide an engineered or recombinant microorganism or microbial system that is able to degrade or de-polymerize alginate and to use it as a source of carbon and/or energy. As one means of accomplishing this purpose, such recombinant microorganisms may incorporate a set of polysaccharide degrading or depolymerizing enzymes such as alginate lyases (ALs) to the microbial system.

ALs are mainly classified into two distinctive subfamilies depending on their acts of catalysis: endo-(EC 4.2.2.3) and exo-acting (EC 4.2.2.-) ALs. Endo-acting ALs are further classified based on their catalytic specificity; M specific and G specific ALs. The endo-acting ALs randomly cleave alginate via a β-elimination mechanism and mainly depolymerize alginate to di-, tri- and tetrasaccharides. The uronate at the non-reducing terminus of each oligosaccharide are converted to unsaturated sugar uronate, 4-deoxy-α-L-erythro-hex-4-ene pyranosyl uronates. The exo-acting ALs catalyze further depolymerization of these oligosaccharides and release unsaturated monosaccharides, which may be non-enzymatically converted to monosaccharides, including α-keto acid, 4-deoxy-α-L-erythro-hexoselulose uronate (DEHU). Certain embodiments of an engineered microbial system or isolated, engineered microorganism may include endoM-, endoG- and exo-acting ALs to degrade or depolymerize aquatic or marine-biomass polysaccharides such as alginate to a monosaccharide such as DEHU.

Embodiments of the present invention may also include lyases such as alginate lyases isolated from various sources, including, but not limited to, marine algae, mollusks, and wide varieties of microbes such as genus $Pseudomonas$, $Vibrio$, and $Sphingomonas$. Many alginate lyases are endo-acting M specific, several are G specific, and few are exo-acting. For example, ALs isolated from $Sphingomonas$ sp. strain A1 include five endo-acting ALs, Al-I, Al-II, Al-II', Al-III, and Al-IV' and an exo-acting AL, Al-IV.

Typically, Al-I, Al-II, and Al-III have molecular weights of 66 kDa, 25 kDa, and 40 kDa, respectively. AI-II and AI-III are self-splicing products of Al-1. AI-II may be more specific to G and Al-III may be specific to M. Al-I may have high activity for both M and G. Al-IV has molecular weight of about 85 kDa and catalyzes exo-lytic depolymerization of oligoalginate. Although both Al-II' and Al-IV' are functional homologues of Al-II and Al-IV. Al-II' has endo-lytic activity and may have no preference to M or G. Al-IV has primarily endo-lytic activity. In addition to these ALs, exo-lytic AL Atu3025 derived from *Agrobacterium tumefaciens* has high activity for depolymerization of oligoalginate, and may be used in certain embodiments of the present invention. Certain embodiments may incorporate into the microbial system or isolated microorganism the genes encoding Al-I, Al-II', Al-IV, and Atu3025, and may include optimal codon usage for the suitable host organisms, such as *E. coli*.

Certain examples of alginate lyases or oligoalginate lyases that may be utilized herein include enzymes or polypeptides sharing at least 60%, 70%, 80%, 90%, 95%, 98%, or more sequence identity (including all integers in between) to SEQ ID NOS:67-68, which show the nucleotide (SEQ ID NO:67) and polypeptide (SEQ ID NO:68) sequences of oligoalginate lyase Atu3025 isolated from *Agrobacterium tumefaciens*. Certain examples of alginate lyases that may be utilized herein include enzymes or polypeptides sharing at least 60%, 70%, 80%, 90%, 95%, 98%, or more sequence identity (including all integers in between) to the alginate lyase enzymes described in FIG. 37, as well as the secreted alginate lyase encoded by Vs24254 from *Vibrio splendidus*.

In certain embodiments, a microbial system or recombinant microorganism may be engineered to secrete or display the lyases or alginate lyases (ALs) to the culture media, such as by incorporating a signal peptide or autotransporter domain into the lyase. In this regard, it is typically understood that bacteria have at least four different types of protein secretion machinery (type I, II, III and IV). For example, in *E. coli*, the type II secretion machinery is used for the secretion of recombinant proteins. The type II secretion machinery may comprise a two-step process: the translocation of premature proteins tagged with signal peptides to the periplasm fraction and processing to the mature proteins followed by secretion to media.

The first process may proceed by any of three different pathways: secB-dependent pathway, signal recognition particle (SRP) pathway, or twin-arginine translocation (TAT) pathway. Recombinant proteins may be secreted into periplasm fraction. The fates of the mature proteins vary dependent on the type of proteins. For example, some proteins are secreted spontaneously by diffusion or passively by a secretion apparatus named secretion that consists of 12-16 proteins, and others stay in periplasm fraction and are eventually degraded.

Some proteins may also be secreted by an autotransporter apparatus, such as by utilizing an autotransporter domain. The proteins secreted by autotransporter domains typically comprise an N-terminal signal peptide that plays a role in translocation to the periplasm, which may be mediated by secB or SRP pathways, passenger domain, and/or C-terminal translocation unit (UT) having a characteristic β-barrel structure. The β-barrel portion of the UT builds an aqueous pore channel across the outer membrane and helps the transportation of passenger domain to media. Autodisplayed passenger proteins are often cleaved by the autotransporter and set free to media.

The type I secretion machinery may also be used for the secretion of recombinant proteins in *E. coli*. The type I secretion machinery may be used for the secretion of high-molecular-weight toxins and exoenzymes. The type I secretion machinery consist of two inner membrane proteins (HlyB and HlyD) that are the member of the ATP binding cassette (ABC) transporter family, and an endogenous outer membrane protein (TolC). The secretion of recombinant proteins based on type I secretion machinery may utilize the C-terminal region of α-haemolysin (HlyA) as a signal sequence. The recombinant proteins may readily pass through the inner membrane, periplasm, and outer membrane through the type I secretion machinery.

Depending on the types of linker and signal peptides utilized by various embodiments of the present application, both autotransporter and type I secretion machinery can be altered to the cell surface display machinery. Alternatively, a system specific to cell surface display may be used. For example, in this system, target proteins may be fused to PgsA protein (a poly-γ-glutamate synthetase complex) that is natively displayed on the surface of *Bacillus subtilis*.

Certain embodiments may include lyases such as alginate lyases fused with various signal peptides and/or autotransporter domains found in proteins secreted by both type I and type II secretion machinery. Other embodiments may include lyases such as alginate lyases fused with any combination of signal peptides and or autotransporter domains found in proteins secreted transport machinery as described herein or known to a person skilled in the art. Embodiments may also include signal peptides or autotransporter domains that are experimentally redesigned to maximize the secretion of lyases such as alginate lyases to the culture media, and may also include the use of many different linker sequences that fuse signal peptides, lyases, and autotransporters that improve the efficiency of secretion or the cell surface presentation of lyases.

Certain embodiments may include a microbial system or isolated microorganism that comprise saccharide transporters, which are able to transport monosaccharides (e.g., DEHU) and oligosaccharides from the media to the cytosol to efficiently utilize these monosaccharides as a source of carbon and/or energy. For instance, genes encoding monosaccharide permeases (i.e., monosaccharide transporters) such as DEHU permeases may be isolated from bacteria that grow on polysaccharides such as alginate as a source of carbon and/or energy, and may be incorporated into embodiments of the present microbial system or isolated microorganism. As an additional example, embodiments may also include redesigned native permeases or transporters with altered specificity for monosaccharide (e.g., DEHU) transportation.

In this regard, *E. coli* contains several permeases able to transport monosaccharides, which include, but are not limited to, KdgT for 2-keto-3-deoxy-D-gluconate (KDG) transporter, ExuT for aldohexuronates such as D-galacturonate and D-glucuronate transporter, GntT, GntU, GntP, and GntT for gluconate transporter, and KgtP for proton-driven α-ketoglutarate transporter. Microbial systems or recombinant microorganisms described herein may comprise any of these permeases, in addition to those permeases known to a person of skill in the art and not mentioned herein, and may also include permease enzymes redesigned to transport other monosaccharides, such as DEHU.

A microbial system or recombinant microorganism according to the present invention may also comprise permeases/transporters/superchannels/porins that catalyze the transport of monosaccharides (e.g., D-mannuronate and D-lyxose) from media to the periplasm or cytosol of a microorganism. For example, genes encoding the permeases of D-mannuronate in soil *Aeromonas* may be incorporated into a microbial system as described herein.

As one alternative example, a microbial system or microorganism may comprise native permeases/transporters that are redesigned to alter their specificity for efficient monosaccharide transportation, such as for D-mannuronate and D-lyxose transportation. For instance, E. coli contains several permeases that are able to transport monosaccharides or sugars such as D-mannonate and D-lyxose, including KdgT for 2-keto-3-deoxy-D-gluconate (KDG) transporter, ExuT for aldohexuronates such as D-galacturonate and D-glucuronate transporter, GntPTU for gluconate/fructuronate transporter, uidB for glucuronide transporter, fucP for L-fucose transporter, galP for galactose transporter, yghK for glycolate transporter, dgoT for D-galactonate transporter, uhpT for hexose phosphate transporter, dctA for orotate/citrate transporter, gntUT for gluconate transporter, malEGF for maltose transporter: alsABC for D-allose transporter, idnT for L-idonate/D-gluconate transporter, KgtP for proton-driven α-ketoglutarate transporter, lacY for lactose/galactose transporter, xylEFGH for D-xylose transporter, araEFGH for L-arabinose transporter, and rbsABC for D-ribose transporter. In certain embodiments, a microbial system or recombinant microorganism may comprise permeases or transporters as described above, including those that are re-designed or optimized for improved transport of certain monosaccharides, such as D-mannuronate, DEHU, and D-lyxose.

Certain aspects may employ a recombinant microorganism that comprises a "superchannel," by which aquatic or marine-biomass polysaccharides such as alginate polymers, or fruit or vegetable biomass such as pectin polymers, may be directly incorporated into the cytosol and degraded inside the microbial system. For instance, a group of bacteria characterized as Sphingomonads have a wide range in capability of degrading environmentally hazardous compounds such as polychlorinated polycyclic aromatics (dioxin). These bacteria contain characteristic large pleat-like molecules on their cell surfaces. In this regard, certain Sphingomonads have structures characterized as "superchannels" that enable the bacteria to directly take up macromolecules.

As one particular example of a microorganism comprising a superchannel, *Sphingomonas* sp. strain A1 directly incorporates polysaccharides such as alginate through a superchannel. Such superchannels may consist of a pit on the outer membrane (e.g., AlgR), alginate-binding proteins in the periplasm (e.g., AlgQ1 and Alg Q2), and an ATP-binding cassette (ABC) transporter (e.g., AlgM1, AlgM2, and AlgS). Incorporated polysaccharides such as alginate may be readily depolymerized by lyases such as alginate lyases produced in the cytosol. Thus, certain embodiments may incorporate genes encoding a superchannel (e.g., ccpA, algS, algM1, algM2, algQ1, algQ2) to introduce this ability to the microbial system or recombinant microorganism. Other embodiments may include microorganisms such as *Sphingomonas subarctica* IFO 16058$^T$, which harbor the plasmid containing genes that encode a superchannel, and which have significantly improved ability to utilize marine or aquatic biomass polysaccharides such as alginate as a source of carbon and/or energy. Certain recombinant microorganisms may employ these superchannel encoding plasmid sequences contained within *Sphingomonas subarctica* IFO 16058$^T$.

Certain examples of alginate ABC transporters that may be utilized herein, include ABC transporters Atu3021, Atu3022, Atu3023, Atu3024, algM1, algM2, AlgQ1, AlgQ2, AlgS, OG2516_05558, OG2516_05563, OG2516_05568, and OG2516_05573, including functional variants thereof. Certain examples of alginate symporters that may be utilized herein include symporters V12B01_24239 and V12B01_24194, among others, including functional variants thereof. One additional example of an alginate porin includes V12B01_24269, and variants thereof.

As noted above, certain embodiments may include recombinant microorganisms that comprise one or more monosaccharide dehydrogenases, isomerases, dehydratases, kinases, and aldolases. With regard to monosaccharide dehydrogenases, certain microbial systems or recombinant microorganism may incorporate enzymes that reduce various monosaccharides (e.g., DEHU, mannuronate) to a monosaccharide that is suitable for biofuel biosynthesis, such as 2-keto-3-deoxy-D-gluconate (KDG) or D-mannitol. Such exemplary enzymes, include, for example, DEHU hydrogenases and mannuronate hydrogenases, in addition to various alcohol dehydrogenases having DEHU hydrogenase and/or mannuronate dehydrogenase activity, such as the novel ADH1 through ADH12 enzymes isolated from *Agrobacterium tumefaciens* C58 (see, e.g., SEQ ID NOS:69-92).

For more detail on the ADH1 through ADH12 enzymes, SEQ ID NO:69 shows the nucleotide and SEQ ID NO:70 shows the polypeptide sequence of ADH1 Atu1557 isolated from *Agrobacterium tumefaciens* C58. SEQ ID NO:71 shows the nucleotide and SEQ ID NO:72 shows the polypeptide sequence of ADH2 Atu2022 isolated from *Agrobacterium tumefaciens* C58. SEQ ID NO:73 shows the nucleotide and SEQ ID NO:74 shows the polypeptide sequence of ADH3 Atu0626 isolated from *Agrobacterium tumefaciens* C58.

SEQ ID NO:75 shows the nucleotide and SEQ ID NO:76 shows the polypeptide sequence of ADH4 Atu5240 isolated from *Agrobacterium tumefaciens* C58. SEQ ID NO:77 shows the nucleotide and SEQ ID NO:78 shows the polypeptide sequence of ADH5 Atu3163 isolated from *Agrobacterium tumefaciens* C58. SEQ ID NO:79 shows the nucleotide and SEQ ID NO:80 shows the polypeptide sequence of ADH6 Atu2151 isolated from *Agrobacterium tumefaciens* C58.

SEQ ID NO:81 shows the nucleotide and SEQ ID NO:82 shows the polypeptide sequence of ADH7 Atu2814 isolated from *Agrobacterium tumefaciens* C58. SEQ ID NO:83 shows the nucleotide and SEQ ID NO:84 shows the polypeptide sequence of ADH8 Atu5447 isolated from *Agrobacterium tumefaciens* C58. SEQ ID NO:85 shows the nucleotide and SEQ ID NO:86 shows the polypeptide sequence of ADH9 Atu4087 isolated from *Agrobacterium tumefaciens* C58.

SEQ ID NO:87 shows the nucleotide and SEQ ID NO:88 shows the polypeptide sequence of ADH10 Atu4289 isolated from *Agrobacterium tumefaciens* C58.

SEQ ID NO:89 shows the nucleotide and SEQ ID NO:90 shows the polypeptide sequence of ADH11 Atu3027 isolated from *Agrobacterium tumefaciens* C58. SEQ ID NO:91 shows the nucleotide and SEQ ID NO:92 shows the polypeptide sequence of ADH12 Atu3026 isolated from *Agrobacterium tumefaciens* C58.

Further examples of enzymes having dehydrogenase activity include Atu3026, Atu3027, OG2516_05543, OG2516_05538 and V12B01_24244. The microorganisms and methods of the present invention may also utilize biologically active fragments and variants of these hydrogenase enzymes, including optimized variants thereof.

As a further example, *Pseudomonas* grown using alginate as a sole source of carbon and energy comprises a DEHU hydrogenase enzyme that uses NADPH as a co-factor, is more stable when NADP$^+$ is present in the solution, and is active at ambient pH. Thus, certain embodiments of a microbial system or a recombinant microorganism as described herein may incorporate genes encoding hydrogenases such as DEHU or mannuronate hydrogenase derived or obtained from various microbes, in which these microbes may be capable of growing on polysaccharides such as alginate or pectin as a source of carbon and/or energy.

Certain embodiments may incorporate components of a microbial system or isolated microorganism that is capable of efficiently growing on monosaccharides such as D-mannuronate or D-lyxose as a source of carbon and energy. For instance, both *Aeromonas* and *Aerobacter aerogenes* PRL-R3 comprise genes encoding monosaccharide dehydrogenases such as D-mannuronate hydrogenase and D-lyxose isomerase. Thus, certain microbial systems or recombinant microorganisms may comprise monosaccharide dehydrogenases such as D-mannuronate hydrogenase and D-lyxose isomerase from *Aeromonas, Aerobacter aerogenes* PRL-R3, or various other suitable microorganisms, including those microorganisms capable of growing on D-mannuronate or D-lyxose as a source of carbon and energy.

Certain embodiments may include a microbial system or isolated microorganism with enhanced efficiency for converting monosaccharides such as D-mannonate and D-xylulose into monosaccharides suitable for a biofuel biosynthesis pathway such as KDG. Merely by way of explanation, D-mannonate and D-xylulose are metabolites in microbes such as *E. coli*. D-mannonate is converted by a D-mannonate dehydratase to KDG. D-xylulose enters the pentose phosphate pathway. Thus, to increase conversion of D-mannonate to KDG, an exogenous or endogenous D-mannonate dehydratase (e.g., uxuA) gene may be over-expressed an a recombinant microorganism of the invention. Similarly, in other embodiments, suitable endogenous or exogenous genes such as kinases (e.g., kdgK), nad, as well as KDG aldolases (e.g., kdgA and eda) may be either incorporated or overexpressed in a given recombinant microorganism (see SEQ ID NOS:93-96), including biologically active variants or fragments thereof, such as optimized variants of these genes. SEQ ID NO:93 shows the nucleotide sequence and SEQ ID NO:94 shows the polypeptide sequence of a 2-keto-deoxy gluconate kinase (KdgK) from *Escherichia coli* DH10B. SEQ ID NO:95 shows the nucleotide sequence and SEQ ID NO:96 shows the polypeptide sequence of a 2-keto-deoxy gluconate-6-phosphate aldorase (KdgA) from *Escherichia coli* DH10B.

In certain aspects, as noted above, a recombinant microorganism that is capable of growing on alginate or pectin as a sole source of carbon may utilize a naturally-occurring or endogenous copy of a dehyradratase, kinase, and/or aldolase. For instance, *E. coli* contains endogenous dehydratases, kinases, and aldolases that are capable of catalyzing the appropriate steps in the conversion of polysaccharides to a suitable monosaccharide. In these and other related aspects, the naturally-occurring dehydratase or kinase may also be over-expressed, such as by providing an exogenous copy of the naturally-occurring dehydratase, kinase or aldolase operable linked to a highly constitutive or inducible promoter.

As one exemplary source of enzymes for engineering a recombinant microorganism to grow on alginate as a sole source of carbon, *Vibrio splendidus* is known to be able to metabolize alginate to support growth. For example, SEQ ID NO:1 shows a secretome region carrying certain *Vibrio splendidus* genes (V12B01_02425 to V12B01_02480), which encodes a type II secretion apparatus. SEQ ID NO:2 shows the nucleotide sequence of an entire genomic region between V12B01_24189 to V12B01_24249, which was derived from *Vibrio splendidus*, and which when transformed into *E. coli* as a fosmid clone was sufficient to confer the ability to grow on alginate as a sole source of carbon. SEQ ID NOS:3-64 show the individual putative genes contained within SEQ ID NO:2. Thus, in certain aspects, a recombinant microorganism (e.g., *E. coli*) that is able to grow on alginate as a sole source of carbon and/or energy may comprise one or more nucleotide or polypeptide reference sequences described in SEQ ID NOS:1-64, including biologically active fragments or variants thereof, such as optimized variants.

In certain aspects, a recombinant microorganism that is able to grow on alginate as a sole source of carbon may contain certain coding nucleotide or polypeptide sequences contained within SEQ ID NO:2, such as the sequences in SEQ ID NOS:3-64, or biologically active fragments or variants thereof, including optimized variants. These sequences are described in further detail below.

SEQ ID NO:3 shows the nucleotide coding sequence of the putative protein V12B01_24184. This putative coding sequence is contained within the polynucleotide sequence of SEQ ID NO:2, and encodes a polypeptide that is similar to an autotransporter adhesion or type I secretion target ggxgxdxxx (SEQ ID NO:145) repeat. SEQ ID NO:4 shows the polypeptide sequence of putative protein V12B01_24184, encoded by the polynucleotide of SEQ ID NO:3. This putative polypeptide is similar to autotransporter adhesion or type I secretion target ggxgxdxxx (SEQ ID NO:145) repeat.

SEQ ID NO:5 shows the nucleotide sequence that encodes the putative protein V12B01_24189. SEQ ID NO:6 shows the polypeptide sequence of the putative protein V12B01_24189, which is similar to cyclohexadienyl dehydratase.

SEQ ID NO:7 shows the nucleotide sequence that encodes the putative protein V12B01_24194. SEQ ID NO:8 shows the polypeptide sequence of the putative protein V12B01_24194, which is similar to a Na/proline transporter.

SEQ ID NO:9 shows the nucleotide sequence that encodes the putative protein V12B01_24199. SEQ ID NO:10 shows the polypeptide sequence of the putative protein V12B01_24199, which is similar to a keto-deoxy-phosphogluconate aldolase.

SEQ ID NO:11 shows the nucleotide sequence that encodes the putative protein V12B01_24204. SEQ ID NO:12 shows the polypeptide sequence of the putative protein V12B01_24204, which is similar to 2-dehydro-3-deoxy-gluconokinase.

SEQ ID NO:13 shows the nucleotide sequence that encodes the putative protein V12B01_241209. SEQ ID NO:14 shows the polypeptide sequence of the putative protein V12B01_241209.

SEQ ID NO:15 shows the nucleotide sequence that encodes the putative protein V12B01_24214. SEQ ID NO:16 shows the polypeptide sequence of the putative protein V12B01_24214, which is similar to a chondroitin AC/alginate lyase.

SEQ ID NO:17 shows the nucleotide sequence that encodes the putative protein V12B01_24219. SEQ ID NO:18 shows the polypeptide sequence of the putative protein V12B01_24219, which is similar to a chondroitin AC/alginate lyase.

SEQ ID NO:19 shows the nucleotide sequence that encodes the putative protein V12B01_24224. SEQ ID NO:20 shows the polypeptide sequence of the putative protein V12B01_24224, which is similar to a 2-keto-4-pentenoate hydratase/2-oxohepta-3-ene-1,7-dioic acid hydratase.

SEQ ID NO:21 shows the nucleotide sequence that encodes the putative protein V12B01_24229. SEQ ID NO:22 shows the polypeptide sequence of the putative protein V12B01_24229, which is similar to a GntR-family transcriptional regulator.

SEQ ID NO:23 shows the nucleotide sequence that encodes the putative protein V12B01_24234. SEQ ID NO:24 shows the polypeptide sequence of the putative protein V12B01_24234, which is similar to a Na$^+$/proline symporter.

SEQ ID NO:25 shows the nucleotide sequence that encodes the putative protein V12B01_24239. SEQ ID NO:26 shows the polypeptide sequence of the putative protein V12B01_24239, which is similar to an oligoalginate lyase.

SEQ ID NO:27 shows the nucleotide sequence that encodes the putative protein V12B01_24244. SEQ ID NO:28 shows the polypeptide sequence of putative protein V12B01_24244, which is similar to a 3-hydroxyisobutyrate dehydrogenase.

SEQ ID NO:29 shows the nucleotide sequence that encodes the putative protein V12B01_24249. SEQ ID NO:30 shows the polypeptide sequence of the putative protein V12B01_24249, which is similar to a methyl-accepting chemotaxis protein.

SEQ ID NO:31 shows the nucleotide sequence that encodes the putative protein V12B01_24254. SEQ ID NO:32 shows the polypeptide sequence of putative protein V12B01_24254, which is similar to an alginate lyase.

SEQ ID NO:33 shows the nucleotide sequence that encodes the putative protein V12B01_24259. SEQ ID NO:34 shows the polypeptide sequence of putative protein V12B01_24259, which is similar to an alginate lyase.

SEQ ID NO:35 shows the nucleotide sequence that encodes the putative protein V12B01_24264. SEQ ID NO:36 shows the polypeptide sequence of putative protein V12B01_24264.

SEQ ID NO:37 shows the nucleotide sequence that encodes the putative protein V12B01_24269. SEQ ID NO:38 shows the polypeptide sequence of putative protein V12B01_24269, which is similar to a putative oligogalacturonate specific porin.

SEQ ID NO:39 shows the nucleotide sequence that encodes the putative protein V12B01_24274. SEQ ID NO:40 shows the polypeptide sequence of putative protein V12B01_24274, which is similar to an alginate lyase.

Figure 32A:
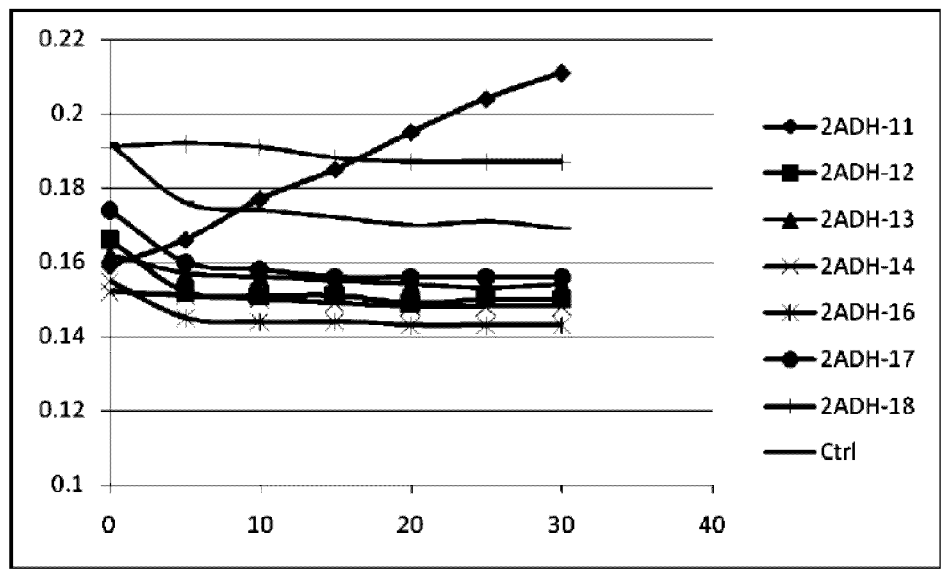
FIG. 32 shows the oxidation of 2,7-dimethyl octanol by secondary alcohol dehydrogenases as monitored by NADH production (FIG. 32A) and NADPH production (FIG. 32B).
Figure 32B:
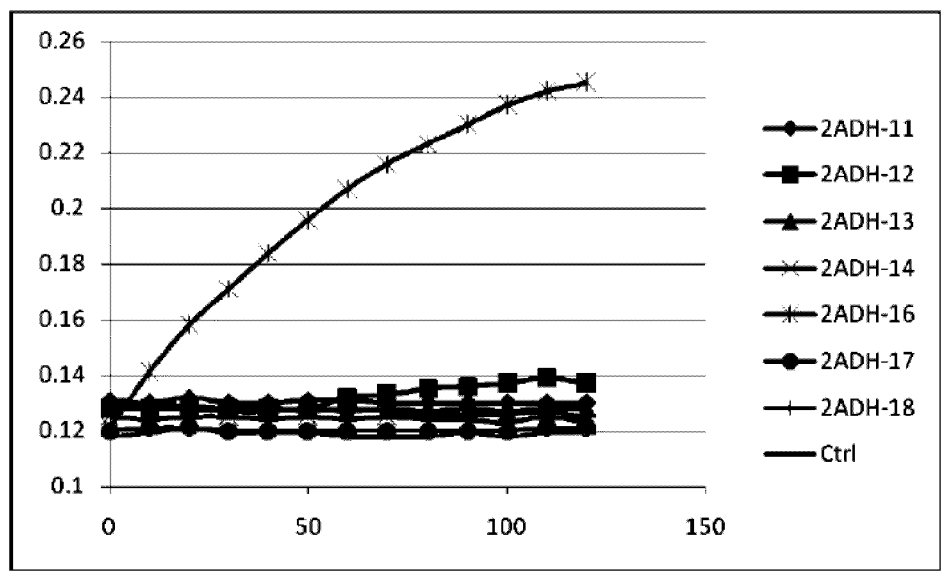

FIG. 32 shows the nucleotide coding sequence and polypeptide sequence of putative protein V12B01_02425. FIG. 32A shows the nucleotide sequence that encodes the putative protein V12B01_02425 (SEQ ID NO:41). FIG. 32B shows the polypeptide sequence of putative protein V12B01_02425 (SEQ ID NO:42), which is similar to a type II secretory pathway component EpsC.

SEQ ID NO:43 shows the nucleotide sequence that encodes the putative protein V12B01_02430. SEQ ID NO:44 shows the polypeptide sequence of putative protein V12B01_02430, which is similar to a type II secretory pathway component EpsD.

SEQ ID NO:45 shows the nucleotide sequence that encodes the putative protein V12B01_02435. SEQ ID NO:46 shows the polypeptide sequence of putative protein V12B01_02435, which is similar to a type II secretory pathway component EpsE.

SEQ ID NO:47 shows the nucleotide sequence that encodes the putative protein V12B01_02440. SEQ ID NO:48 shows the polypeptide sequence of putative protein V12B01_02440, which is similar to a type II secretory pathway component EpsF.

SEQ ID NO:49 shows the nucleotide sequence that encodes the putative protein V12B01_02445. SEQ ID NO:50 shows the polypeptide sequence of putative protein V12B01_02445, which is similar to a type II secretory pathway component EpsG.

SEQ ID NO:51 shows the nucleotide sequence that encodes the putative protein V12B01_02450. SEQ ID NO:52 shows the polypeptide sequence of putative protein V12B01_02450, which is similar to a type II secretory pathway component EpsH.

SEQ ID NO:53 shows the nucleotide sequence that encodes the putative protein V12B01_02455. SEQ ID NO:54 shows the polypeptide sequence of putative protein V12B01_02455, which is similar to a type II secretory pathway component EpsI.

SEQ ID NO:55 shows the nucleotide sequence that encodes the putative protein V12B01_02460. SEQ ID NO:56 shows the polypeptide sequence of putative protein V12B01_02460, which is similar to a type II secretory pathway component EpsJ.

SEQ ID NO:57 shows the nucleotide sequence that encodes the putative protein V12B01_02465. SEQ ID NO:58 shows the polypeptide sequence of putative protein V12B01_02465, which is similar to a type II secretory pathway component EpsK.

SEQ ID NO:59 shows the nucleotide sequence that encodes the putative protein V12B01_02470. SEQ ID NO:60 shows the polypeptide sequence of putative protein V12B01_02470, which is similar to a type II secretory pathway component EpsL.

SEQ ID NO:61 shows the nucleotide sequence that encodes the putative protein V12B01_02475. SEQ ID NO:62 shows the polypeptide sequence of putative protein V12B01_02475, which is similar to a type II secretory pathway component EpsM.

SEQ ID NO:63 shows the nucleotide sequence that encodes the putative protein V12B01_02480. SEQ ID NO:64 shows the nucleotide sequence that encodes the putative protein V12B01_02480, which is similar to a type II secretory pathway component EpsC.

As a further exemplary source of enzymes for engineering a microorganism to grow on alginate, *Agrobacterium tumefaciens* C58 is able to metabolize relatively small sizes of alginate molecules (~1000 mers) as a sole source of carbon and energy. Since *A. tumefaciens* C58 has long been used for plant biotechnology, the genetics of this organism has been relatively well studied, and many genetic tools are available and compatible with other gram-negative bacteria such as *E. coli*. Thus, certain aspects may employ this microbe, or the genes therein, for the production of suitable monosaccharides. For instance, as noted above, the present disclosure provides a series of novel ADH genes having both DEHU and mannuronate hydrogenase activity that were obtained from *Agrobacterium tumefaciens* C58 (see SEQ ID NOS: 67-92).

Figure 3:
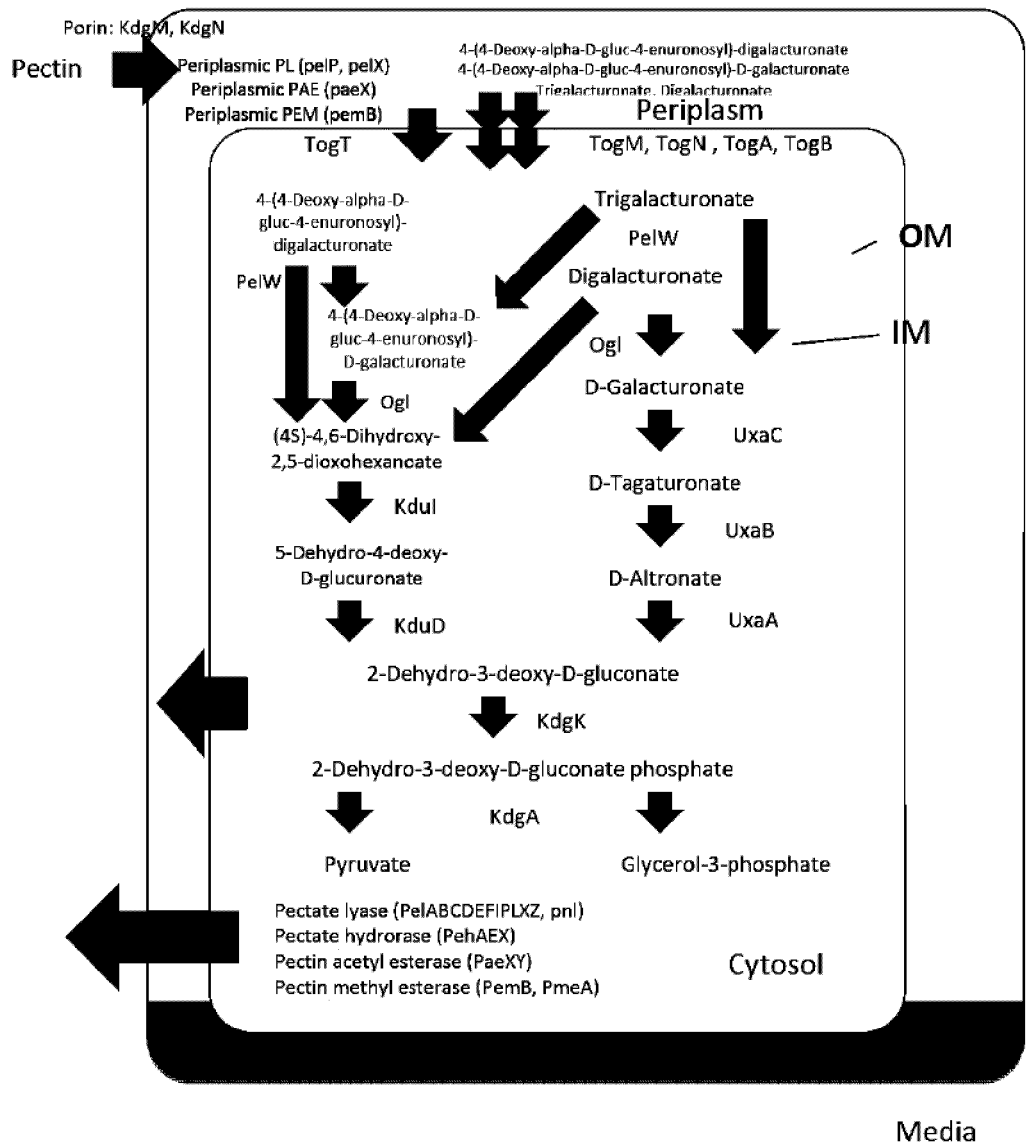
FIG. 3 illustrates the pathways involved in certain embodiment in which *E. coli* may be engineered to grow on pectin as a sole source of carbon.

As noted above, certain aspects may include a recombinant microorganism or microbial system that is capable of growing on pectin as a sole source of carbon and/or energy. Pectin is a linear chain of α-(1-4)-linked D-galacturonic acid that forms the pectin-backbone, a homogalacturonan. Into this backbone, there are regions where galacturonic acid is replaced by (1-2)-linked L-rhamnose. From rhamnose, side chains of various neutral sugars typically branch off. This type of pectin is called rhamnogalacturonan I. Over all, about up to every 25th galacturonic acid in the main chain is exchanged with rhamnose. Some stretches consisting of alternating galacturonic acid and rhamnose—"hairy regions", others with lower density of rhamnose—"smooth regions." The neutral sugars mainly comprise D-galactose, L-arabinose and D-xylose; the types and proportions of neutral sugars vary with the origin of pectin. In nature, around 80% of carboxyl groups of galacturonic acid are esterified with methanol. Some plants, like sugar-beet, potatoes and pears, contain pectins with acetylated galacturonic acid in addition to methyl esters. Acetylation prevents gel-formation but increases the stabilising and emulsifying effects of pectin. Certain pectin degradation and metabolic pathways are exemplified in FIG. 3.

In addition to the genes, enzymes, and biological pathways described above, certain recombinant microorganisms may incorporate features that are useful for growth on pectin as a sole source of carbon. For instance, to degrade and metabolize pectin as a sole source of carbon, pectin methyl and acetyl esterases first catalyze the hydrolysis of methyl and acetyl esters on pectin. Examples of pectin methyl esterases include, but are not limited to, pemA and pmeB. Examples of pectin acetyl esterases include, but are not limited to, PaeX and PaeY. Further examples of pectin methyl esterases that may be utilized herein include enzymes or polypeptides sharing at least 60%, 70%, 80%, 90%, 95%, 98%, or more sequence identity (including all integers in between) to the pectate methyl esterases in FIG. 40. Further examples of pectate acetyl esterases that may be utilized herein include enzymes or polypeptides sharing at least 60%, 70%, 80%, 90%, 95%, 98%, or more sequence identity (including all integers in between) to the pectate acetyl esterases described in FIG. 41.

Further to this end, pectate lyases and hydrolases may catalyze the endolytic cleavage of pectate via β-elimination and hydrolysis, respectively, to produce oligopectates. Other enzymes that may be utilized to metabolize pectin include Examples of pectate lyases include, but are not limited to, PelA, PelB, PelC, PelD, PelE, Pelf, PelI, PelL, and PelZ. Examples of pectate hydrolases include, but are not limited to, PehA, PehN, PehV, PehW, and PehX. Further examples of pectate lyases include polypeptides or enzymes sharing at least 60%, 70%, 80%, 90%, 95%, 98%, or more sequence identity (including all integers in between) to the pectate lyases described in FIG. 38.

Polygalacturonases, rhamnogalacturonan lyases, and rhamnogalacturonan hydrolyases may also be utilized herein to degrade and metabolize pectin. Examples of rhamnogalacturonan lyases include polypeptides or enzymes sharing at least 60%, 70%, 80%, 90%, 95%, 98%, or more sequence identity (including all integers in between) to the rhamnogalacturonan lyases (i.e., rhamnogalacturonases) described in FIG. 39A. Examples of rhamnogalacturonate hydrolyases include polypeptides or enzymes sharing at least 60%, 70%, 80%, 90%, 95%, 98%, or more sequence identity (including all integers in between) to the rhamnogalacturonate hydrolases described in FIG. 39B.

Thus, to degrade and metabolize pectin, certain of the recombinant microorganisms and methods of the present invention may incorporate one or more of the above noted methy and acetyl esterases, lyases, and/or hydrolases, among others known in the art. These may enzymes may be encoded and expressed by endogenous or exogenous genes, and may also include biologically active fragments or variants thereof, such as homologs, orthologs, and/or optimized variants of these enzymes.

To further metabolize the degradation products of pectin, oligopectates may be transported into the periplasm fraction of gram-negative bacteria by outer membrane porins, where they are further degraded into such components as di- and tri-galactonurates. Examples of outer membrane porins include that can transport oligopectates into the periplasm include, but are not limited to, kdgN and kdgM. Certain recombinant microorganism may incorporate these or similar genes.

Di- and tri-galactonurates may then be transported into the cytosol for further degradation. Bacteria contain at least two different transporter systems responsible for di- and tri-galacturonate transportation, including symporter and ABC transporter (e.g., TogT and TogMNAB, respectively). Thus, certain of the recombinant microorganisms provided herein may comprise one or more a di- or tri-galacturonate transoporter systems, such as TogT and/or TogMNAB.

Once di- and trigalacturonate are incorporated into the cytosol, short pectate or galacturonate lyases, break them down to D-galacturonate and (4S)-4,6-dihydroxy-2,5-dioxohexuronate. Examples of short pectate or galacturonate lyases include, but are not limited to, PelW and Ogl, which genes may be either endogenously or exogenously incorporated into certain recombinant microorganisms provided herein. D-galacturonate and (4S)-4,6-dihydroxy-2,5-dioxohexuronate are then converted to 5-dehydro-4-deoxy-D-glucuronate and further to KDG, which steps may be catalyzed by KduI and KduD, respectively. The KduI enzyme has an isomerase activity, and the KduD enzyme has a dehydrogenase activity, such as a 2-deoxy-D-gluconate 3-dehydrogenase activity. Accordingly, certain recombinant microorganisms provided herein may comprise one or more short pectate or galacturonate lyases, such as PelW and/or Ogl, and may optionally comprise one or more isomerases, such as KduI, as well as one or more dehydrogenases, such as KduD, to convert di- and trigalacturonates into a suitable monosaccharide, such as KDG.

In certain aspects, a recombinant microorganism, such as E. coli, that is able to grown on pectin or tri-galacturonate as a sole source of carbon and/or energy may comprise one or more of the gene sequences contained within SEQ ID NOS: 65 and 66, including biologically active fragments or variants thereof, such as optimized variants. SEQ ID NO:65 shows the nucleotide sequence of the kdgF-PaeX region from Erwinia carotovora subsp. Atroseptica SCRI1043. SEQ ID NO:66 shows the nucleotide sequence of ogl-kdgR from Erwinia carotovora subsp. Atroseptica SCRI1043.

In certain aspects, a recombinant microorganism, such as E. coli, that is able to grown on pectin or tri-galacturonate as a sole source of carbon and/or energy may comprise one or more genomic regions of Erwinia chrysanthemi, comprising several genes (kdgF, kduI, kduD, pelW, togM, togN, togA, togB, kdgM, paeX, ogl, and kdgR) encoding enzymes (kduI, kduD, ogl, pelW, and paeX), transporters (togM, togN, togA, togB, and kdgM), and regulatory proteins (kdgR) responsible for degradation of di- and trigalacturonate, as well as several genes (pelA, pelE, paeY, and pem) encoding pectate lyases (pelA and pelE), pectin acetylesterases (paeY), and pectin methylesterase (pem) (see Example 2).

Additional examples of isomerases that may be utilized herein include glucoronate isomerases, such as those in the family uxaC, as well as 4-deoxy-L-threo-5-hexylose uronate isomerases, such as those in the family KduI. Additional examples of reductases that may be utilized herein include tagaturonate reductases, such as those in the family uxaB. Additional examples of dehyadratases that may be utilized herein include altronate dehydratases, such as those in the family uxaA. Additional examples of dehydrogenases that may be utilized herein include 2-deoxy-D-gluconate 3-dehydrogenases, such as those in the family kduD.

Certain aspects my also utilize recombinant microorganisms engineered to enhance the efficiency of the KDG degradation pathway. For instance, in bacteria, KDG is a common metabolic intermediate in the degradation of hexuronates such as D-glucuronate and D-galacturonate and enters into Entner Doudoroff pathway where it is converted to pyruvate and glyceraldehyde-3-phosphate (G3P). In this pathway, KDG is first phosphorylated by KDG kinase (KdgK) followed by its cleavage into pyruvate and glyceraldehyde-3-phosphate (G3P) using 2-keto-3-deoxy-D-6- posphate-gluconate (KDPG) aldolase (KdgA). The expression of these enzymes concurrently with KDG permease (e.g., KdgT) is negatively regulated by KdgR and is almost none at basal level. The expression is dramatically (3-5-fold) induced upon the addition of hexuronates, and a similar result has been reported in *Pseudomonas* grown on alginate. Hence, to increase the conversion of KDG to pyruvate and G3P, the negative regulator KdgR may be removed. To further improve the pathway efficiency, exogenous copies of KdgK and KdgA may also be incorporated into a given recombinant microorganism.

In certain aspects, a recombinant microorganism that is able to grow on a polysaccharide (e.g., alginate, pectin, etc) as a sole source of carbon may be capable of producing an increased amount of a given commodity chemical (e.g., ethanol) while growing on that polysaccharide. For example, *E. coli* engineered to grown on alginate may be engineered to produced an increased amount of ethanol from alginate as compared to *E. coli* that is not engineered to grown on alginate (see Example 11). Thus, certain aspects include a recombinant microorganism that is capable of growing on alginate or pectin as a sole source carbon, and that is capable of producing an increased amount of ethanol, such as by comprising one or more genes encoding and expressing a pyruvate decarboxylase (pdc) and/or an alcohol dehydrogenase, including functional variants thereof. In certain aspects, such a recombinant microorganism may comprise a pyruvate decarboxylase (pdc) and two alcohol dehydrogenases (adhA and adhB) obtained from *Zymomonas mobilis*.

Embodiments of the present invention also include methods for converting polysaccharide to a suitable monosaccharide comprising, (a) obtaining a polysaccharide; (b) contacting the polysaccharide with a chemical catalysis or enzymatic pathway, thereby converting the polysaccharide to a first monosaccharide or oligosaccharide; and (c) contacting the first monosaccharide with a microbial system for a time sufficient to convert the first monosaccharide or oligosaccharide to the suitable monosaccharide, wherein the microbial system comprises, (i) at least one gene encoding and expressing an enzyme selected from a monosaccharide transporter, a disaccharide transporter, a trisaccharide transporter, an oligosaccharide transporter, and a polysaccharide transporter; and (ii) at least one gene encoding and expressing an enzyme selected from a monosaccharide dehydrogenase, an isomerase, a dehydratase, a kinase, and an aldolase, thereby converting the polysaccharide to a suitable monosaccharide.

In certain aspects of the present invention, aquatic or marine-biomass polysaccharides such as alginate may be chemically degraded using chemical catalysts such as acids. Similarly, biomass-derived pectin may be chemically degraded. For instance, the reaction catalyzed by chemical catalysts is typically through hydrolysis, as opposed to the β-elimination type of reactions catalyzed by enzymatic catalysts. Thus, certain embodiments may include boiling alginate or pectin with strong mineral acids to liberate carbon dioxide from D-mannuronate, thereby forming D-lyxose, a common sugar metabolite utilized by many microorganisms. Such embodiments may use, for example, formate, hydrochloric acid, sulfuric acid, in addition to other suitable acids known in the art as chemical catalysts.

An enzymatic pathway may utilized one or more enzymes described herein that are capable of catalyzing the degradation of polysaccharides, such as alginate or pectin.

Other embodiments may use variations of chemical catalysis similar to those described herein or known to a person skilled in the art, including improved or redesigned methods of chemical catalysis suitable for use with biomass related polysaccharides. Certain embodiments include those wherein the resulting monosaccharide uronate is D-mannuronate.

As noted above, the suitable monosaccharides or suitable oligosaccharides produced by the recombinant microorganisms and microbial systems of the present invention may be utilized as a feedstock in the production of commodity chemicals, such as biofuels, as well as commodity chemical intermediates. Thus, certain embodiments of the present invention relate generally to methods for converting a suitable monosaccharide or oligosaccharide to a commodity chemical, such as a biofuel, comprising, (a) obtaining a suitable monosaccharide or oligosaccharide; (b) contacting the suitable monosaccharide or oligosaccharide with a microbial system for a time sufficient to convert to the suitable monosaccharide to the biofuel, thereby converting the suitable monosaccharide to the biofuel.

Certain aspects include methods for converting a suitable monosaccharide to a first commodity chemical such as a biofuel, comprising, (a) obtaining a suitable monosaccharide; (b) contacting the suitable monosaccharide with a microbial system for a time sufficient to convert to the suitable monosaccharide to the first commodity chemical, wherein the microbial system comprises one or more genes encoding a aldehyde or ketone biosynthesis pathway, thereby converting the suitable monosaccharide to the first commodity chemical.

In these and other related aspects, depending on the particular ketone or aldehyde biosynthesis pathway employed, the first commodity chemical may be further enzymatically and/or chemically reduced and dehydrated to a second commodity chemical. Examples of such second commodity chemicals include, but are not limited to, butene or butane; 1-phenylbutene or 1-phenylbutane; pentene or pentane; 2-methylpentene or 2-methylpentane; 1-phenylpentene or 1-phenylpentane; 1-phenyl-4-methylpentene or 1-phenyl-4-methylpentane; hexene or hexane; 2-methylhexene or 2-methylhexane; 3-methylhexene or 3-methylhexane; 2,5-dimethylhexene or 2,5-dimethylhexane; 1-phenylhexene or 1-phenylhexane; 1-phenyl-4-methylhexene or 1-phenyl-4-methylhexane; 1-phenyl-5-methylhexene or 1-phenyl-5-methylhexane; heptene or heptane; 2-methylheptene or 2-methylheptane; 3-methylheptene or 3-methylheptane; 2,6-dimethylheptene or 2,6-dimethylheptane; 3,6-dimethylheptene or 3,6-dimethylheptane; 3-methyloctene or 3-methyloctane; 2-methyloctene or 2-methyloctane; 2,6-dimethyloctene or 2,6-dimethyloctane; 2,7-dimethyloctene or 2,7-dimethyloctane; 3,6-dimethyloctene or 3,6-dimethyloctane; and cyclopentane or cyclopentene.

Certain embodiments of the present invention may also include methods for converting a suitable monosaccharide or oligosaccharide to a commodity chemical comprising (a) obtaining a suitable monosaccharide or oligosaccharide; (b) contacting the suitable monosaccharide or oligosaccharide with a microbial system for a time sufficient to convert to the suitable monosaccharide or oligosaccharide to the commodity chemical, wherein the microbial system comprises; (i) one or more genes encoding a biosynthesis pathway; (ii) one or more genes encoding and expressing a C—C ligation pathway; and (iii) one or more genes encoding and expressing a reduction and dehydration pathway, comprising a diol dehydrogenase, a diol dehydratase, and a secondary alcohol dehydrogenase, thereby converting the suitable monosaccharide or oligosaccharide to the commodity chemical.

Certain aspects also include recombinant microorganism that comprise (i) one or more genes encoding a biosynthesis pathway; (ii) one or more genes encoding and expressing a C—C ligation pathway; and (iii) one or more genes encoding and expressing a reduction and dehydration pathway, comprising a diol dehydrogenase, a diol dehydratase, and a secondary alcohol dehydrogenase. Certain aspects also include recombinant microorganisms that comprise the above pathways individually or in certain combinations, such as recombinant microorganism that comprises one or more genes encoding a biosynthesis pathway, as described herein. Certain aspects may also include recombinant microorganisms that comprise one or more genes encoding and expressing a C—C ligation pathway, as described herein. Certain aspects may also include recombinant microorganisms that comprise one or more genes encoding and expressing a reduction and dehydration pathway, comprising a diol dehydrogenase, a diol dehydratase, and a secondary alcohol dehydrogenase, as described herein.

As for recombinant microorganisms that comprise combinations of the above-noted pathways, certain aspects may include recombinant microorganisms that comprise (i) one or more genes encoding a biosynthesis pathway; and (ii) one or more genes encoding and expressing a C—C ligation pathway. Certain aspects may also include recombinant microorganisms that comprise (i) one or more genes encoding and expressing a C—C ligation pathway; and (ii) one or more genes encoding and expressing a reduction and dehydration pathway, comprising a diol dehydrogenase, a diol dehydratase, and a secondary alcohol dehydrogenase.

Certain aspects may also include recombinant microorganisms that comprise one or more individual components of a dehydration and reduction pathway, such as a recombinant microorganism that comprises a diol dehydrogenase, a diol dehydratase, or a secondary alcohol dehydrogenase. These and other microorganisms may be utilized, for example, to convert a suitable polysaccharide to a first commodity chemical, or an intermediate thereof, or to convert a first commodity chemical, or an intermediate thereof, to a second commodity chemical.

Merely by way of illustration, a recombinant microorganism comprising a C—C ligation pathway may be utilized to convert butanal into a first commodity chemical, or an intermediate thereof, such as 5-hydroxy-4-octanone, which can then be converted into a second commodity chemical, or intermediate thereof, by any suitable pathway. As a further example, a recombinant microorganism comprising a C—C ligation pathway and a diol hydrogenase may be utilized for the sequential conversion of butanal into 5-hydroxy-4-octanone and then 4,5-octanonediol. Examples of recombinant microorganisms that comprise these and other various combinations of the individual pathways described herein, as well as various combinations of the individual components of those pathways, will be apparent to those skilled in the art, and may also be found in the Examples.

Also included are methods of converting a polysaccharide to a first commodity chemical, or an intermediate thereof, such as by utilizing a recombinant microorganism that comprises an aldehyde or ketone biosynthesis pathway. Also included are methods of converting a first commodity chemical, or intermediate thereof, to a second commodity chemical, such as by utilizing a recombinant microorganism that optionally comprises a biosynthesis pathway, optionally comprises C—C ligation pathway and/or optionally comprises one or more of the individual components of a dehydration and reduction pathway. Merely by way of illustration, a recombinant microorganism comprising an exogenous C—C ligase (e.g., benzaldehyde lyase from *Pseudomonas fluorescens*) could be utilized in a method to convert a first commodity chemical such as 3-methylbutanal to a second commodity chemical such as 2,7-dimethyl-5-hydroxy-4-octanone. Along this line of illustration, the same or different recombinant microorganism comprising a diol dehydrogenase could be utilized in a method to convert 2,7-dimethyl-5-hydroxy-4-octanone to another commodity chemical such as 2,7-dimethyl-4,5-octanediol (see Table 2 for other examples). As an additional illustrative example, a recombinant microorganism comprising an exogenous secondary alcohol dehydrogenase could be utilized in a method to convert a first commodity chemical such as 2,7-dimethyl-4-octanone to a second commodity chemical such as 2,7-dimethyloctanol.

Embodiments of a microbial system or isolated microorganism of the present application may include a naturally-occurring biosynthesis pathway, and/or an engineered, reconstructed, or re-designed biosynthesis pathway that has been optimized for improved functionality.

Embodiments of a microbial system or recombinant microorganism of the present invention may include a natural or reconstructed biosynthesis pathway, such as a butyraldehyde biosynthesis pathway, as found in such microorganisms as *Clostridium acetobutylicum* and *Streptomyces coelicolor*. In explanation, butyrate and butanol are the common fermentation products of certain bacterial species such as *Clostridia*, in which the production of butyrate and butanol is mediated by a synthetic thiolase dependent pathway characteristically similar to fatty acid degradation pathway. Such pathways may be initiated with the condensation of two molecules of acetyl-CoA to acetoacetyl-CoA, which is catalyzed by thiolase. Acetoacetyl-CoA is then reduced to β-hydroxy butyryl-CoA, which is catalyzed by NAD(P)H dependent β-hydroxy butyryl-CoA dehydrogenase (HBDH). Crotonase catalyzes dehydration from β-hydroxy butyryl-CoA to form crotonyl-CoA. Further reduction catalyzed by NADH-dependent butyryl-CoA dehydrogenase (BCDH) saturates the double bond at C2 of crotonyl-CoA to form butyryl-CoA.

In certain embodiments, thiolase, the first enzyme in this pathway, may be overexpressed to maximize production. In certain embodiments, thiolase may over-expressed in *E. coli*. In this regard, all three enzymes (e.g., HBDH, crotonase, and BCDH) catalyzing the following reaction steps are found in *Clostridium acetobutylicum* ATCC824. In certain embodiments, BDH, crotonase, and BCDH may be expressed or over-expressed in a suitable microorganism such as *E. coli*. Alternatively, a short-chain aliphatic acyl-CoA dehydrogenase derived from *Pseudomonas putida* KT2440 may be utilized in other embodiments of a microbial system or isolated microorganism of the present application.

Further to this end, butyryl-CoA in *Clostridia* may be readily converted to butanol and/or butyrate by at least a few different pathways. In one pathway, butyryl-CoA is directly reduced to butyraldehyde catalyzed by NADH dependent CoA-acylating aldehyde dehydrogenase (ALDH). Butyraldehyde may be further reduced to butanol by NADH-dependent butanol dehydrogenase. Although CoA-acylating ALDH catalyzes the one step reduction of butyryl-CoA to butyraldehyde, the incorporation of CoA-acylating ALDH to the microbial system may result in acetoaldehyde formation because of its promiscuous acetyl-CoA deacylating activity. In certain embodiments, the formation of acetoaldehyde may be minimized by functionally redesigning the relevant enzyme(s).

Butyryl-CoA in other biosynthesis pathways is deacylated to form butyryl phosphate catalyzed by phosphotransbutyrylase. Butyryl phosphate is then hydrolyzed by reversible butyryl phosphate kinase to form butyrate. This reaction is coupled with ATP generation from ADP. The butyrate formation through these enzymes is known to be significantly more specific. Certain embodiments may comprise phosphotransbutyrylase and butyryl phosphate kinase to the microbial system. In other embodiments, butyrate may be directly formed from butyryl-CoA by short chain acyl-CoA thioesterase.

Butyrate in *Clostridia* may also be sequentially reduced to butanol, which is catalyzed by a single alcohol/aldehyde dehydrogenase. Certain embodiments may comprise short chain aldehyde dehydrogenase from other bacteria such as *Pseudomonas putida* to complement the production of butyraldehyde in the microbial system. One potential concern in using short chain aldehyde dehydrogenase involves the possible formation of acetoaldehyde from acetate. Certain embodiments may be directed to minimizing the acetate formation in the microbial system, for example, by deleting several genes encoding enzymes involved in the acetate production.

Moreover, there are multiple routes in *E. coli* to form acetate, one of which is mediated by pyruvate oxygenase (POXB) from pyruvate, whereas another is mediated by phosphotransacetylase (PTA) and acetyl phosphate kinase (ACKA) from acetyl-CoA. The acetate production from *E. coli* mutant strains with poxB$^-$, pta$^-$, and acka$^-$ are significantly diminished. In addition, incorporation of acetyl-CoA synthase (ACS) which catalyses the acetyl-CoA formation from acetate is also known to significantly reduce the accumulation of acetate. Certain embodiments may comprise a microbial system or isolated microorganism with deleted POXB, PTA, and/or ACKA genes, and other embodiments may also comprise, separately or together with the deleted genes, one or more genes encoding and expressing ACS.

A microbial system or recombinant microorganism provided herein may also comprise a glutaraldehyde biosynthesis pathway. As one example, *Saccharomyces cerevisiae* has a lysine biosynthetic pathway in which acetyl-CoA is initially condensed to α-ketoglutarate, a common metabolite in citric acid cycle, to form homocitorate. This reaction is catalyzed by homocitrate synthase derived from Yeast, *Thermus thermophilus*, or *Deinococcus radiodurans*. Homoaconitase derived from Yeast, *Thermus thermophilus*, or *Deinococcus radiodurans* catalyzes the conversion between homocitrate and homoisocitrate. Homoisocitrate is then oxidatively decarboxylated to form 2-ketoadipate, which is catalyzed by homoisocitrate dehydrogenase derived from Yeast, *Thermus thermophilus*, or *Deinococcus radiodurans*. Homoisocitrate is also oxidatively decarboxylated to form glutaryl-CoA, which may be catalyzed by homoisocitrate dehydrogenase. Thus, certain embodiments may comprise a homocitrate synthase, a homoaconitase, and/or a homoisocitrate dehydrogenase.

Further to this end, in synthesizing 2-keto-adipicsemialdehyde, 2-ketoadipate is reduced to 2-keto-adipicsemialdehyde. This reaction can be catalyzed by dialdehyde dehydrogenase, which, for example, may be isolated from *Agrobacterium tumefaciens* C58. Thus, certain embodiments may incorporate dialdehyde dehydrogenases into a microbial system or recombinant microorganism.

In synthesizing glutaraldehyde, Acyl-CoA thioesterases (ACOT) may also catalyze the hydrolysis of glutaryl-CoA. The genes encoding (β-carboxylic acyl-CoA specific peroxisomal ACOTs are found in many mammalian species; both ACOT4 and ACOT8 derived from mice have been previously expressed in *E. coli* and shown that both enzymes are highly active on the hydrolysis of glutaryl-CoA to form glutarate. Certain embodiments may comprise one or more Acyl-CoA thioesterases.

Glutarate is sequentially reduced to glutaraldehyde. This reaction can be catalyzed by glutaraldehyde dehydrogenase (CpnE), which, for example, may be isolated from *Comomonas* sp. Strain NCIMB 9872. Certain embodiments may incorporate glutaraldehyde dehydrogenases such as CpnE into a microbial system or isolated microorganism. Other embodiments may comprise both ACOT and CpnE enzymes. Other embodiments may comprise CpnE enzymes redesigned to catalyze the reduction of 1-hydroxy propanoate and succinate to 1-hydroxy propanal and succinicaldehyde.

In certain aspects, the biosynthesis pathway may include an aldehyde biosynthesis pathway, a ketone biosynthesis pathway, or both. In certain aspects, the biosynthesis pathway may be include one or more of an acetoaldehyde, propionaldehyde, butyraldehyde, isobutyraldehyde, 2-methyl-butyraldehyde, 3-methyl-butyraldehyde, 4-methylpentaldehyde, phenylacetoaldehyde, 2-phenyl acetoaldehyde, 2-(4-hydroxyphenyl)acetaldehyde, 2-Indole-3-acetoaldehyde, glutaraldehyde, 5-amino-pentaldehyde, succinate semialdehyde, and/or succinate 4-hydroxyphenyl acetaldehyde biosynthesis pathway, including various combinations thereof.

With regard to combinations of biosynthesis pathways, a biosynthesis pathway may comprise an acetoaldehyde biosynthesis pathway in combination with at least one of a propionaldehyde, butyraldehyde, isobutyraldehyde, 2-methyl-butyraldehyde, 3-methyl-butyraldehyde, or phenylacetoaldehyde biosynthesis pathway. In certain aspects, a biosynthesis pathway may comprise a propionaldehyde biosynthesis pathway in combination with at least one of a butyraldehyde, isobutyraldehyde, 2-methyl-butyraldehyde, 3-methyl-butyraldehyde, or phenylacetoaldehyde biosynthesis pathway. In certain aspects, a biosynthesis pathway may comprise a butyraldehyde biosynthesis pathway in combination with at least one of an isobutyraldehyde, 2-methyl-butyraldehyde, 3-methyl-butyraldehyde, or phenylacetoaldehyde biosynthesis pathway. In certain aspects, a biosynthesis pathway may comprise an isobutyraldehyde biosynthesis pathway in combination with at least one of a 2-methyl-butyraldehyde, 3-methyl-butyraldehyde, or phenylacetoaldehyde biosynthesis pathway. In certain aspects, a biosynthesis pathway may comprise a 2-methyl-butyraldehyde biosynthesis pathway in combination with at least one of a 3-methyl-butyraldehyde or a phenylacetoaldehyde biosynthesis pathway. In certain aspects, a biosynthesis pathway may comprise a 3-methyl-butyraldehyde biosynthesis pathway in combination with a phenylacetoaldehyde biosynthesis pathway.

In certain aspects, a propionaldehyde biosynthesis pathway may comprise a threonine deaminase (ilvA) gene from an organism such as *Escherichia coli* and a keto-isovalerate decarboxylase (kivd) gene from an organism such as *Lactococcus lactis*, and/or functional variants of these enzymes, including homologs or orthologs thereof, as well as optimized variants. These enzymes may be utilized generally to convert L-threonine to propionaldehyde.

In certain aspects, a butyraldehyde biosyntheis pathway may comprise at least one of a thiolase (atoB) gene from an organism such as *E. coli*, a β-hydroxy butyryl-CoA dehydrogenase (hbd) gene, a crotonase (crt) gene, a butyryl-CoA dehydrogenase (bcd) gene, an electron transfer flavoprotein A (etfA) gene, and/or an electron transfer flavoprotein B (etfB) gene from an organism such as *Clostridium acetobutyricum* (e.g., ATCC 824), as well as a coenzyme A-linked butyraldehyde dehydrogenase (ald) gene from an organism such as *Clostridium beijerinckii acetobutyricum* ATCC 824. In certain aspects, a coenzyme A-linked alcohol dehydrogenase (adhE2) gene from an organism such as *Clostridium acetobutyricum* ATCC 824 may be used as an alternative to an ald gene.

In certain aspects, an isobutyraldehyde biosynthetic pathway may comprise an acetolactate synthase (alsS) from an organism such as *Bacillus subtilis* or an als gene from an organism such as *Klebsiella pneumoniae* subsp. *pneumoniae* MGH 78578 (codon usage may be optimized for *E. coli* protein expression). Such a pathway may also comprise acetolactate reductoisomerase (ilvC) and/or 2,3-dihydroxyisovalerate dehydratase (ilvD) genes from an organism such as *E. coli*, as well as a keto-isovalerate decarboxylase (kivd) gene from an organism such as *Lactococcus* lactis.

In certain aspects, a 3-methylbutyraldehyde and 2-methylbutyraldehyde biosynthesis pathway may comprise an acetolactate synthase (alsS) gene from an organism such as *Bacillus subtilis* or an (als) gene from an organism such as *Klebsiella pneumoniae* subsp. *pneumoniae* MGH 78578 (codon usage may be optimized for *E. coli* protein expression). Certain aspects of such a pathway may also comprise acetolactate reductoisomerase (ilvC), 2,3-dihydroxyisovalerate dehydratase (ilvD), isopropylmalate synthase (LeuA), isopropylmalate isomerase (LeuC and LeuD), and 3-isopropylmalate dehydrogenase (LeuB) genes from an organism such as *E. coli*, as well as a keto-isovalerate decarboxylase (kivd) from an organism such as *Lactococcus lactis*.

In certain aspects, a phenylacetoaldehyde and 4-hydroxyphenylacetoaldehyde biosynthesis pathway may comprise one or more of 3-deoxy-7-phosphoheptulonate synthase (aroF, aroG, and aroH), 3-dehydroquinate synthase (aroB), a 3-dehydroquinate dehydratase (aroD), dehydroshikimate reductase (aroE), shikimate kinase II (aroL), shikimate kinase I (aroK), 5-enolpyruvylshikimate-3-phosphate synthetase (aroA), chorismate synthase (aroC), fused chorismate mutase P/prephenate dehydratase (pheA), and/or fused chorismate mutase T/prephenate dehydrogenase (tyrA) genes from an organism such as *E. coli*, as well as a keto-isovalerate decarboxylase (kivd) from an organism such as *Lactococcus lactis*.

In certain aspects, such as for the ultimate production of 1,10-diamino-5-decanol and 1,10-dicarboxylic-5-decanol, a biosynthesis pathway may comprise one or more homocitrate synthase, homoaconitate hydratase, homoisocitrate dehydrogenase, and/or homoisocitrate dehydrogenase genes from an organism such as *Deinococcus radiodurans* and/or *Thermus thermophilus*, as well as a keto-adipate decarboxylase gene, a 2-aminoadipate transaminase gene, and a L-2-Aminoadipate-6-semialdehyde: NAD+6-oxidoreductase gene. Such a biosynthesis pathway would be able to convert α-ketoglutarate to 5-aminopentaldehyde.

In certain aspects, such as for one step in cyclopentanol production, a α-ketoadipate semialdehyde biosynthesis pathway may comprise homocitrate synthase (hcs), homoaconitate hydratase, and homoisocitrate dehydrogenase genes from an organism such as *Deinococcus radiodurans* and/or *Thermus thermophilus*, and an α-ketoadipate semialdehyde dehydrogenase gene. Such a biosynthesis pathway would be able to convert acetyl-CoA and α-ketoglutarate to α-ketoadipate semialdehyde.

For the production of certain commodity chemicals, such as 2-phenylethanol, 2-(4-hydroxyphenyl)ethanol, and indole-3-ethanol, among other similar chemicals, a biosynthesis pathway (e.g., aldehyde biosynthesis pathway) may optionally or further comprise one or more genes encoding a carboxylase enzyme, such as an indole-3-pyruvate decarboxylase (IPDC). An IPDC may be obtained, for example, from such microorganisms as *Azospirillum brasilense* and *Paenibacillus polymyxa* E681. In this regard, an IPDC may be utilized to more efficiently catalyze the dexarboxylation of various carboxylic acids to form the corresponding aldehyde, which can be further converted to a commodity chemical by a reductase or dehydrogenase, as detailed herein.

In certain aspects, a 2-phenylethanol, 2-(4-hydroxyphenyl) ethanol, and 2-(indole-3-)ethanol biosynthesis pathway may comprise a transketolase (tktA), a 3-deoxy-7-phosphoheptulonate synthase (aroF, aroG, and aroH), 3-dehydroquinate synthase (aroB), a 3-dehydroquinate dehydratase (aroD), a dehydroshikimate reductase (aroE), a shikimate kinase II (aroL), a shikimate kinase I (aroK), a 5-enolpyruvylshikimate-3-phosphate synthetase (aroA), a chorismate synthase (aroC, a fused chorismate mutase P/prephenate dehydratase (pheA), and a fused chorismate mutase T/prephenate dehydrogenase (tyrA) genes from *E. coli*, keto-isovalerate decarboxylase (kivd) from *Lactococcus* lactis, alcohol dehydrogenase (adh2) from *Saccharomyces cerevisiae*, Indole-3-pyruvate decarboxylase (ipdc) from *Azospirillum brasilense*, phenylethanol reductase (par) from *Rhodococcus* sp. ST-10, and abenzaldehyde lyase (bal) from *Pseudomonas fluorescence*.

As for all other pathways described herein, the components for each of the biosynthesis pathways described herein may be present in a recombinant microorganism either endogenously or exogenously. To improve the efficiency of a given biosynthesis pathway, endogenous genes, for example, may be up-regulated or over-expressed, such as by introducing an additional (i.e., exogenous) copy of that endogenous gene into the recombinant microorganism. Such pathways may also be optimized by altering via mutagenesis the endogenous version of a gene to improve functionality, followed by introduction of the altered gene into the microorganism. The expression of endogenous genes may be up or down-regulated, or even eliminated, according to known techniques in the art and described herein. Similarly, the expression levels of exogenously provided genes may be regulated as desired, such as by using various constitutive or inducible promoters. Such genes may also be "codon-optimized," as described herein and known in the art. Also included are functional naturally-occurring variants of the genes and enzymes described herein, including homologs or orthologs thereof.

Certain embodiments of a microbial system or isolated microorganism may comprise a CC-ligation pathway. In certain aspects, a CC-ligation pathway may comprise a ThDP-dependent enzyme, such as a C—C ligase, or an optimized C—C ligase. For example, eight-carbon unit molecules (butyroins) may be made from condensing together two four-carbon unit molecules (butyraldehydes). ThDP-dependent enzymes are a group of enzymes known to catalyze both breaking and formation of C—C bonds and have been utilized as catalysts in chemoenzymatic syntheses. The spectrum of chemical reactions that these enzymes catalyze ranges from decarboxylation of α-keto acids, oxidative decarboxylation, carboligation, and to the cleavage of C—C bonds.

To provide a few examples, benzaldehyde lyase (BAL) from *Pseudomonas fluorescens*, benzoylformate decarboxylase (BFD) from *Pseudomonas putida*, and pyruvate decarboxylase (PDC) from *Zymomonas mobilis* may catalyze a carboligation reaction between two aldehydes. BAL accepts the broadest spectrum of aldehydes as substrates among these three enzymes ranging from substituted benzaldehyde to acetoaldehyde, among others, as shown herein. BAL catalyzes stereospecific carboligation reaction between two aldehydes and forms α-hydroxy ketone swith over 99% ee for R-configuration. The benzoin formation from two benzaldehyde molecules is a favored reaction catalyzed by BAL and proceeds as fast as 320 μmol (benzoin) mg (protein)$^{-1}$ min$^{-1}$. The formation of α-hydroxy ketone may be carried out using many different aldehydes, including butyraldehyde.

BFD and PCD may also catalyze the carboligation reactions between two aldehyde molecules. BFD and PCD accept relatively larger and smaller aldehyde molecules, respectively. With the presence of benzaldehyde and acetoaldehyde, BFD catalyzes the formation of benzoin and (S)-α-hydroxy phenylpropanone (2S-HPP), whereas PCD catalyzes the formation of (R)-α-hydroxy phenylpropanone (2R-HPP) and (R)-α-hydroxy 2-butanone (acetoin). As detailed below, certain microbial systems or isolated microorganisms of the present application may comprise natural or optimized C—C ligases (ThDP-dependent enzymes) selected from benzaldehyde lyase (BAL) from *Pseudomonas fluorescens* benzoylformate decarboxylase (BFD) from *Pseudomonas putida*, and pyruvate decarboxylase (PDC) from *Zymomonas mobilis*. Other embodiments may comprise a benzaldehyde lyase (BAL) from *Pseudomonas fluorescens* (see SEQ ID NOS: 143-144, showing the nucleotide and polypeptide sequences, respectively) including biologically active variants thereof, such as optimized variants.

A C—C ligation pathway of the present invention typically comprises one or more C—C ligases, such as a lyase enzyme. Exemplary lyases include, but are not limited to, acetoaldehyde lyases, propionaldehyde lyases, butyraldehyde lyases, isobutyraldehyde lyases, 2-methyl-butyraldehyde lyases, 3-methyl-butyraldehyde lyases (isoveraldehyde), phenylacetaldehyde lyases, α-keto adipate carboxylyases, pentaldehyde lyases, 4-methyl-pentaldehyde lyases, hexyldehyde lyases, heptaldehyde lyases, octaldehyde lyases, 4-hydroxyphenylacetaldehyde lyases, indoleacetaldehyde lyases, indolephenylacetaldehyde lyases. In certain aspects, a selected CC-ligase or lyase enzyme may have one or more of the above exemplified lyase activities, such as acetoaldehyde lyase activity, a propionaldehyde lyase activity, a butyraldehyde lyase activity, and/or an isobutyraldehyde lyase activity, among others.

As noted above, a C—C ligase may comprise a benzaldehyde lyase, such as a benzaldehyde lyase isolated from *Pseudomonas fluorescens* (SEQ ID NOS: 143-144), as well as biologically active fragments or variants of this reference sequence, such as optimized variants of a benzaldehyde lyase. In this regard, certain aspects may comprise nucleotide sequences or polypeptide sequences having 80%, 85%, 90%, 95%, 97%, 98%, 99% sequence identity to SEQ ID NOS:143-144, and which are capable of catalyzing a carboligation reaction, or which possess C—C lyase activity, as described herein. In certain aspects, a BAL enzyme will comprise one or more conserved amino acid residues, including G27, E50, A57, G155, P162, P234, D271, G277, G422, G447, D448, and/or G512.

*Pseudomonas fluorescens* is able to grow on R-benzoin as the sole carbon and energy source because it harbours the enzyme benzaldehyde lyase that cleaves the acyloin linkage using thiamine diphosphate (ThDP) as a cofactor. In the reverse reaction, as utilized herein, benzaldehyde lyase catalyses the carboligation of two aldehydes with high substrate and stereospecificity. Structure-based comparisons with other proteins show that benzaldehyde lyase belongs to a group of closely related ThDP-dependent enzymes. The ThDP cofactors of these enzymes are fixed at their two ends in separate domains, suspending a comparatively mobile thiazolium ring between them. While the residues binding the two ends of ThDP are well conserved, the lining of the active centre pocket around the thiazolium moiety varies greatly within the group. The active sites for BAL have been described, for example, in Kneen et al (*Biochimica et Biophysica Acta* 1753:263-271, 2005) and Brandt et al. (*Biochemistry* 47:7734-43, 2008). Benzaldehyde lyase derived from *Pseudomonas fluorescens* has been demonstrated herein to at least have an acetoaldehyde lyase activity, a propionaldehyde lyase activity, a butyraldehyde lyase activity, a 3-methyl-butyraldehyde lyase activity, a pentaldehyde lyase activity, a 4-methylpentaldehyde lyase activity, a hexyldehyde lyase activity, a phenylacetoaldehyde lyase activity, and an octaldehyde lyase activity (see Table 2), among other in vivo lyase activities (see FIGS. 48-55).

In certain aspects, a C—C ligase, such as BAL derived from *Pseudomonas fluorescens*, BFD derived from *Pseudomonas putida*, or PDC derived from *Zymomonas mobilis* may comprise a lyase with a combination of lyase activities, such as a lyase having both a propionaldehyde lyase activity and a 3-methyl-butyraldehyde lyase activity, among other combinations and activities, such as those exemplary combinations detailed herein. Merely by way of illustration, a lyase having a combination of lyase activities may be referred to herein as a propionaldehyde/3-methyl-butyraldehyde lyase.

A dehydration and reduction pathway, comprising a diol dehydrogenase, a diol dehydratase, and a secondary alcohol dehydrogenase, may be utilized to further convert an aldehyde, ketone, or corresponding alcohol, to a commodity chemical, such as a biofuel.

To this end, a dehydration and reduction pathway may comprise one or more diol dehydrogenases. A "diol dehydrogenase" refers generally to an enzyme that catalyzes the reversible reduction and oxidation of a α-hydroxy ketone and/or its corresponding diol. Certain embodiments of a microbial system or isolated microorganism may comprise genes encoding a diol dehydrogenase that specifically catalyzes the reduction of α-hydroxy-ketones, including, for example, a 4, 5, octanediol dehydrogenase. Diol dehydrogenases, such as 4, 5, octanediol dehydrogenase, may be isolated from a variety of organisms and incorporated into a microbial system or isolated microorganism. A particular group of alcohol dehydrogenases has a characteristic ability to oxidize various α-hydroxy alcohols and reduce various α-hydroxy ketones and α-keto ketones. As such, the recitation "diol dehydrogenase" may also encompass such alcohol dehydrogenases.

By way of example regarding diol dehydrogenases from exemplary organisms, glycerol dehydrogenase isolated from *Hansenula ofunaensis* has broad substrate specificity and is capable of catalyzing the oxidation of various α-hydroxy alcohols, including 1,2-octane, as well as the reduction of various α-hydroxy ketones and α-keto ketones, including 3-hydroxy-2-butanone and 3,4-hexanedione, with the activity comparable to its native substrates, glycerol and dihydroxyaceton, respectively (40-200%). As one further example, glycerol dehydrogenase discovered in *Hansenula polumorpha* DI-1 works similarly. In certain embodiments, a microbial system or recombinant microorganism may comprise a glycerol dehydrogenase gene isolated from *Hansenula ofunaensis*, a glycerol dehydrogenase isolated from *Hansenula polumorpha* DI-1 and/or a meso-2,3-butane diol dehydrogenase from *Klebsiella pneumoniae*. In other embodiments, a microbial system or isolated microorganism may comprise a 4, 5, octanediol dehydrogenase, among others detailed herein. Diol dehyodregnases may also be obtained from *Lactobaccilus brevis* ATCC 367, *Pseudomanas putida* KT2440, and *Klebsiella pneumoniae* MGH78578), as described herein (see Example 5).

Exemplary diol dehydrogenases include, but are not limited to, 2,3-butanediol dehydrogenase, 3,4-hexanediol dehydrogenase, 4,5-octanediol dehydrogenase, 5,6-decanediol dehydrogenase, 6,7-dodecanediol dehydrogenase, 7,8-tetradecanediol dehydrogenase, 8,9-hexadecanediol dehydrogenase, 2,5-dimethyl-3,4-hexanediol dehydrogenase, 3,6-dimethyl-4,5-octanediol dehydrogenase, 2,7-dimethyl-4,5-octanediol dehydrogenase, 2,9-dimethyl-5,6-decanediol dehydrogenase, 1,4-diphenyl-2,3-butanediol dehydrogenase, bis-1,4-(4-hydroxyphenyl)-2,3-butanediol dehydrogenase, 1,4-diindole-2,3-butanediol dehydrogenase, 1,2-cyclopentanediol dehydrogenase, 2,3-pentanediol dehydrogenase, 2,3-hexanediol dehydrogenase, 2,3-heptanediol dehydrogenase, 2,3-octanediol dehydrogenase, 2,3-nonanediol dehydrogenase, 4-methyl-2,3-pentanediol dehydrogenase, 4-methyl-2,3-hexanediol dehydrogenase, 5-methyl-2,3-hexanediol dehydrogenase, 6-methyl-2,3-heptanediol dehydrogenase, 1-phenyl-2,3-butanediol dehydrogenase, 1-(4-hydroxyphenyl)-2,3-butanediol dehydrogenase, 1-indole-2,3-butanediol dehydrogenase, 3,4-heptanediol dehydrogenase, 3,4-octanediol dehydrogenase, 3,4-nonanediol dehydrogenase, 3,4-decanediol dehydrogenase, 3,4-undecanediol dehydrogenase, 2-methyl-3,4-hexanediol dehydrogenase, 5-methyl-3,4-heptanediol dehydrogenase, 6-methyl-3,4-heptanediol dehydrogenase, 7-methyl-3,4-octanediol dehydrogenase, 1-phenyl-2,3-pentanediol dehydrogenase, 1-(4-hydroxyphenyl)-2,3-pentanediol dehydrogenase, 1-indole-2,3-pentanediol dehydrogenase, 4,5-nonanediol dehydrogenase, 4,5-decanediol dehydrogenase, 4,5-undecanediol dehydrogenase, 4,5-dodecanediol dehydrogenase, 2-methyl-3,4-heptanediol dehydrogenase, 3-methyl-4,5-octanediol dehydrogenase, 2-methyl-4,5-octanediol dehydrogenase, 8-methyl-4,5-nonanediol dehydrogenase, 1-phenyl-2,3-hexanediol dehydrogenase, 1-(4-hydroxyphenyl)-2,3-hexanediol dehydrogenase, 1-indole-2,3-hexanediol dehydrogenase, 5,6-undecanediol dehydrogenase, 5,6-undecanediol dehydrogenase, 5,6-tridecanediol dehydrogenase, 2-methyl-3,4-octanediol dehydrogenase, 3-methyl-4,5-nonanediol dehydrogenase, 2-methyl-4,5-nonanediol dehydrogenase, 2-methyl-5,6-decanediol dehydrogenase, 1-phenyl-2,3-heptanediol dehydrogenase, 1-(4-hydroxyphenyl)-2,3-heptanediol dehydrogenase, 1-indole-2,3-heptanediol dehydrogenase, 6,7-tridecanediol dehydrogenase, 6,7-tetradecanediol dehydrogenase, 2-methyl-3,4-nonanediol dehydrogenase, 3-methyl-4,5-decanediol dehydrogenase, 2-methyl-4,5-decanediol dehydrogenase, 2-methyl-5,6-undecanediol dehydrogenase, 1-phenyl-2,3-octanediol dehydrogenase, 1-(4-hydroxyphenyl)-2,3-octanediol dehydrogenase, 1-indole-2,3-octanediol dehydrogenase, 7,8-pentadecanediol dehydrogenase, 2-methyl-3,4-decanediol dehydrogenase, 3-methyl-4,5-undecanediol dehydrogenase, 2-methyl-4,5-undecanediol dehydrogenase, 2-methyl-5,6-dodecanediol dehydrogenase, 1-phenyl-2,3-nonanediol dehydrogenase, 1-(4-hydroxyphenyl)-2,3-nonanediol dehydrogenase, 1-indole-2,3-nonanediol dehydrogenase, 2-methyl-3,4-undecanediol dehydrogenase, 3-methyl-4,5-dodecanediol dehydrogenase, 2-methyl-4,5-dodecanediol dehydrogenase, 2-methyl-5,6-tridecanediol dehydrogenase, 1-phenyl-2,3-decanediol dehydrogenase, 1-(4-hydroxyphenyl)-2,3-decanediol dehydrogenase, 1-indole-2,3-decanediol dehydrogenase, 2,5-dimethyl-3,4-heptanediol dehydrogenase, 2,6-dimethyl-3,4-heptanediol dehydrogenase, 2,7-dimethyl-3,4-octanediol dehydrogenase, 1-phenyl-4-methyl-2,3-pentanediol dehydrogenase, 1-(4-hydroxyphenyl)-4-methyl-2,3-pentanediol dehydrogenase, 1-indole-4-methyl-2,3-pentanediol dehydrogenase, 2,6-dimethyl-4,5-octanediol dehydrogenase, 3,8-dimethyl-4,5-nonanediol dehydrogenase, 1-phenyl-4-methyl-2,3-hexanediol dehydrogenase, 1-(4-hydroxyphenyl)-4-methyl-2,3-hexanediol dehydrogenase, 1-indole-4-methyl-2,3-hexanediol dehydrogenase, 2,8-dimethyl-4,5-nonanediol dehydrogenase, 1-phenyl-5-methyl-2,3-hexanediol dehydrogenase, 1-(4-hydroxyphenyl)-5-methyl-2,3-hexanediol dehydrogenase, 1-indole-5-methyl-2,3-hexanediol dehydrogenase, 1-phenyl-6-methyl-2,3-heptanediol dehydrogenase, 1-(4-hydroxyphenyl)-6-methyl-2,3-heptanediol dehydrogenase, 1-indole-6-methyl-2,3-heptanediol dehydrogenase, 1-(4-hydroxyphenyl)-4-phenyl-2,3-butanediol dehydrogenase, 1-indole-4-phenyl-2,3-butanediol dehydrogenase, 1-indole-4-(4-hydroxyphenyl)-2,3-butanediol dehydrogenase, 1,10-diamino-5,6-decanediol dehydrogenase, 1,4-di(4-hydroxyphenyl)-2,3-butanediol, 2,3-hexanediol-1,6-dicarboxylic acid dehydrogenase, and the like.

In certain aspects, a selected diol dehydrogenase enzyme may have one or more of the above exemplified diol dehydrogenase activities, such as a 2,3-butanediol dehydrogenase activity, a 3,4-hexanediol dehydrogenase activity, and/or a 4,5-octanediol dehydrogenase activity, among others.

In certain aspects, a recombinant microorganism may comprise a diol dehydrogenase encoded by a nucleotide reference sequence selected from SEQ ID NO:97, 99, and 101, or an enzyme having a polyeptide sequence selected from SEQ ID NO:98, 100, and 102, including biologically active fragments or variants thereof, such as optimized variants. Certain aspects may also comprises nucleotide sequences or polypeptide sequences having 80%, 85%, 90%, 95%, 97%, 98%, 99% sequence identity to SEQ ID NOS:97-102.

Other embodiments may comprise re-designed diol dehydrogenases for reduction of 1-hydroxy propanal, succinicaldehyde, and glutaraldehyde to 1,3-propanediol, 1,4-butanediol, and 1,5 pentanediol, respectively, among others.

A dehydration and reduction pathway, as described herein, may comprise one or more diol dehydratases. A "diol dehydratase" refers generally to an enzyme that catalyzes the irreversible dehydration of diols. For instance, this enzyme may serve to dehydrate octanediol to form 4-octane. It has been recognized that there are at least two different types of diol dehydratases: a group dependent on and independent of coenzyme B12 for its catalysis. Coenzyme B12 dependent diol dehydratases are known to catalyze a radical mediated dehydration reaction from α-hydroxy alcohol to aldehydes or ketones. For example, a diol dehydratase from *Klebsiella pneumoniae* catalyzes the dehydration of glycerol to form β-hydroxypropyl aldehyde, accepts 2,3-butanediol as a substrate, and catalyzes the dehydration reaction to form 2-butanone.

As a further example, *Clostridium butylicum* contains coenzyme B12 independent diol dehydratases. FIG. 46 shows the in vivo biological activity of coenzyme B12 independent diol dehydratase (dhaB1) and activator (dhaB2) isolated from *Clostridium butylicum* (see Example 9). 46A shows the in vivo production of 1-propanol from 1,2-propanediol, FIG. 46B shows the in vivo production of 2-butanol from meso-2,3 butanediol, and FIG. 46C shows the in vivo production of cyclopentanone from trans-1,2-cyclopentanediol.

Thus, certain embodiments of the present invention may comprise optimized or redesigned diol dehydratases that accommodate various substrates, such as 4,5-octanediol as a substrate, and may include diol dehydratases isolated and/or optimized from *Klebsiella pneumoniae* and *Clostridium* butylicum, among other organisms described herein and known in the art.

Exemplary diol dehydratases include, but are not limited to, 2,3-butanediol dehydratase, 3,4-hexanediol dehydratase, 4,5-octanediol dehydratase, 5,6-decanediol dehydratase, 6,7-dodecanediol dehydratase, 7,8-tetradecanediol dehydratase, 8,9-hexadecanediol dehydratase, 2,5-dimethyl-3,4-hexanediol dehydratase, 3,6-dimethyl-4,5-octanediol dehydratase, 2,7-dimethyl-4,5-octanediol dehydratase, 2,9-dimethyl-5,6-decanediol dehydratase, 1,4-diphenyl-2,3-butanediol dehydratase, bis-1,4-(4-hydroxyphenyl)-2,3-butanediol dehydratase, 1,4-diindole-2,3-butanediol dehydratase, 1,2-cyclopentanediol dehydratase, 2,3-pentanediol dehydratase, 2,3-hexanediol dehydratase, 2,3-heptanediol dehydratase, 2,3-octanediol dehydratase, 2,3-nonanediol dehydratase, 4-methyl-2,3-pentanediol dehydratase, 4-methyl-2,3-hexanediol dehydratase, 5-methyl-2,3-hexanediol dehydratase, 6-methyl-2,3-heptanediol dehydratase, 1-phenyl-2,3-butanediol dehydratase, 1-(4-hydroxyphenyl)-2,3-butanediol dehydratase, 1-indole-2,3-butanediol dehydratase, 3,4-heptanediol dehydratase, 3,4-octanediol dehydratase, 3,4-nonanediol dehydratase, 3,4-decanediol dehydratase, 3,4-undecanediol dehydratase, 2-methyl-3,4-hexanediol dehydratase, 5-methyl-3,4-heptanediol dehydratase, 6-methyl-3,4-heptanediol dehydratase, 7-methyl-3,4-octanediol dehydratase, 1-phenyl-2,3-pentanediol dehydratase, 1-(4-hydroxyphenyl)-2,3-pentanediol dehydratase, 1-indole-2,3-pentanediol dehydratase, 4,5-nonanediol dehydratase, 4,5-decanediol dehydratase, 4,5-undecanediol dehydratase, 4,5-dodecanediol dehydratase, 2-methyl-3,4-heptanediol dehydratase, 3-methyl-4,5-octanediol dehydratase, 2-methyl-4,5-octanediol dehydratase, 8-methyl-4,5-nonanediol dehydratase, 1-phenyl-2,3-hexanediol dehydratase, 1-(4-hydroxyphenyl)-2,3-hexanediol dehydratase, 1-indole-2,3-hexanediol dehydratase, 5,6-undecanediol dehydratase, 5,6-undecanediol dehydratase, 5,6-tridecanediol dehydratase, 2-methyl-3,4-octanediol dehydratase, 3-methyl-4,5-nonanediol dehydratase, 2-methyl-4,5-nonanediol dehydratase, 2-methyl-5,6-decanediol dehydratase, 1-phenyl-2,3-heptanediol dehydratase, 1-(4-hydroxyphenyl)-2,3-heptanediol dehydratase, 1-indole-2,3-heptanediol dehydratase, 6,7-tridecanediol dehydratase, 6,7-tetradecanediol dehydratase, 2-methyl-3,4-nonanediol dehydratase, 3-methyl-4,5-decanediol dehydratase, 2-methyl-4,5-decanediol dehydratase, 2-methyl-5,6-undecanediol dehydratase, 1-phenyl-2,3-octanediol dehydratase, 1-(4-hydroxyphenyl)-2,3-octanediol dehydratase, 1-indole-2,3-octanediol dehydratase, 7,8-pentadecanediol dehydratase, 2-methyl-3,4-decanediol dehydratase, 3-methyl-4,5-undecanediol dehydratase, 2-methyl-4,5-undecanediol dehydratase, 2-methyl-5,6-dodecanediol dehydratase, 1-phenyl-2,3-nonanediol dehydratase, 1-(4-hydroxyphenyl)-2,3-nonanediol dehydratase, 1-indole-2,3-nonanediol dehydratase, 2-methyl-3,4-undecanediol dehydratase, 3-methyl-4,5-dodecanediol dehydratase, 2-methyl-4,5-dodecanediol dehydratase, 2-methyl-5,6-tridecanediol dehydratase, 1-phenyl-2,3-decanediol dehydratase, 1-(4-hydroxyphenyl)-2,3-decanediol dehydratase, 1-indole-2,3-decanediol dehydratase, 2,5-dimethyl-3,4-heptanediol dehydratase, 2,6-dimethyl-3,4-heptanediol dehydratase, 2,7-dimethyl-3,4-octanediol dehydratase, 1-phenyl-4-methyl-2,3-pentanediol dehydratase, 1-(4-hydroxyphenyl)-4-methyl-2,3-pentanediol dehydratase, 1-indole-4-methyl-2,3-pentanediol dehydratase, 2,6-dimethyl-4,5-octanediol dehydratase, 3,8-dimethyl-4,5-nonanediol dehydratase, 1-phenyl-4-methyl-2,3-hexanediol dehydratase, 1-(4-hydroxyphenyl)-4-methyl-2,3-hexanediol dehydratase, 1-indole-4-methyl-2,3-hexanediol dehydratase, 2,8-dimethyl-4,5-nonanediol dehydratase, 1-phenyl-5-methyl-2,3-hexanediol dehydratase, 1-(4-hydroxyphenyl)-5-methyl-2,3-hexanediol dehydratase, 1-indole-5-methyl-2,3-hexanediol dehydratase, 1-phenyl-6-methyl-2,3-heptanediol dehydratase, 1-(4-hydroxyphenyl)-6-methyl-2,3-heptanediol dehydratase, 1-indole-6-methyl-2,3-heptanediol dehydratase, 1-(4-hydroxyphenyl)-4-phenyl-2,3-butanediol dehydratase, 1-indole-4-phenyl-2,3-butanediol dehydratase, 1-indole-4-(4-hydroxyphenyl)-2,3-butanediol dehydratase, 1,10-diamino-5,6-decanediol dehydratase, 1,4-di(4-hydroxyphenyl)-2,3-butanediol, 2,3-hexanediol-1,6-dicarboxylic acid dehydratase, and the like.

In certain aspects, a selected diol dehydratase enzyme may have one or more of the above exemplified diol dehydratase activities, such as a 2,3-butanediol dehydratase activity, a 3,4-hexanediol dehydratase activity, and/or a 4,5-octanediol dehydratase activity, among others.

In certain aspects, diol dehydratases may be obtained from *Klebsiella pneumoniae* MGH 78578, including from the pduCDE gene of this and other microorganisms. In certain aspects, a recombinant microorganism may comprise one or more diol dehydratases encoded by a nucleotide reference sequence selected from SEQ ID NO:103, 105, and 107, or an enzyme having a polypeptide sequence selected from SEQ ID NO:104, 106, and 108, including biologically active fragments or variants thereof, such as optimized variants. Certain aspects may also comprises nucleotide sequences or polypeptide sequences having 80%, 85%, 90%, 95%, 97%, 98%, 99% sequence identity to SEQ ID NOS:103-108. In certain aspects, polypeptides of SEQ ID NO:104 may comprise certain conserved amino acid residues, including those chosen from D149, P151, A155, A159, G165, E168, E170, A183, G189, G196, Q200, E208, G215, Y219, E221, T222, S224, Y226, G227, T228, F232, G235, D236, D237, T238, P239, S241, L245, Y249, S251, R252, G253, K255, R257, S260, E265, M268, G269, S275, Y278, L279, E280, C283, G291, Q293, G294, Q296, N297, G298, G312, E329, S341, R344, G356, D371, N372, F374, S377, R392, D393, R412, L477, A486, G499, D500, S516, N522, D523, Y524, G526, and G530.

In certain aspects, a diol dehydratase may include a polypeptide that comprises an amino acid sequence having 0%, 85%, 90%, 95%, 97%, 98%, 99% sequence identity to SEQ ID NOS:308-311. SEQ ID NO:308 shows the polypeptide sequence of PduG, a diol dehydratase reactivation large subunit derived from *Klebsiella pneumoniae* subsp. *pneumoniae* MGH 78578. SEQ ID NO:309 shows the polypeptide sequence of PduH, diol dehydratase reactivation small subunit derived from *Klebsiella pneumoniae* subsp. *pneumoniae* MGH 78578. SEQ ID NO:310 shows the polypeptide sequence of a B12-independent glycerol dehydratase from *Clostridium Butyricum*. SEQ ID NO:311 shows the polypeptide sequence of a glycerol dehydratase activator from *Clostridium Butyricum*. In certain aspects, a B12-independent glycerol dehydratase may comprise conserved amino acid residues, such as T36, G74, P87, E88, E97, W126, R221, A263, Q265, R287, D289, E309, R317, G335, G345, G346, N356, P374, R379, G399, G401, P403, D408, G432, C433, N452, C529, G533, G539, G540, S559, G603, N604, A654, G658, R659, D676, N702, Q735, N737, A747, P751, R760, V761, A762, G763, Q776, I780, and/or R782. In certain aspects, a B12-independent glycerol dehydratase activator may comprise certain conserved amino acid residues, including D19, G20, G22, R24, F28, G31, C32, C36, W38, C39, N41, P42, C58, C64, C96, G129, T132, G135, G136, D185, R187, N208, R222, and/or R264.

A dehydration and reduction pathway, as described herein, may comprise one or more alcohol dehydrogenases or secondary alcohol dehydrogenases. An "alcohol dehydrogenase" or "secondary alcohol dehydrogenase" that is part of a dehydration and reduction pathway refers generally to an enzyme that catalyzes the conversion of aldehyde or ketone substituents to alcohols. For instance, 4-octanone may be reduced to 4-octanol by a secondary alcohol dehydrogenase one enzymatic step for the conversion of butyroin to a biofuel. Pseudomonads express at least one secondary alcohol dehydrogenase that oxidizes 4-octanol to 4-octanone using NAD+ as a co-factor. As another example, *Rhodococcus erythropolis* ATCC4277 catalyzes oxidation of medium to long chain secondary fatty alcohols using NADH as a co-factor, using an enzyme that also catalyzes the oxidation of 3-decanol and 4-decanol. In addition, *Norcadia fusca* AKU2123 contains an (S)-specific secondary alcohol dehydrogenase.

Genes encoding secondary alcohol dehydrogenases may be isolated from these and other organisms according to known techniques in the art and incorporated into the microbial systems recombinant organisms as described herein. In certain embodiments, a microbial system or isolated microorganism may comprise natural or optimized secondary alcohol dehydrogenases from Pseudomonads, *Rhodococcus erythropolis* ATCC4277, *Norcadia fusca* AKU2123, or other suitable organisms.

Examples of secondary alcohol dehydrogenases include, but are not limited to, 2-butanol dehydrogenase, 3-hexanol dehydrogenase, 4-octanol dehydrogenase, 5-decanol dehydrogenase, 6-dodecanol dehydrogenase, 7-tetradecanol dehydrogenase, 8-hexadecanol dehydrogenase, 2,5-dimethyl-3-hexanol dehydrogenase, 3,6-dimethyl-4-hexanol dehydrogenase, 2,7-dimethyl-4-octanol dehydrogenase, 2,9-dimethyl-4-decanol dehydrogenase, 1,4-diphenyl-2-butanol dehydrogenase, bis-1,4-(4-hydroxyphenyl)-2-butanol dehydrogenase, 1,4-diindole-2-butanol dehydrogenase, cyclopentanol dehydrogenase, 2(or 3)-pentanol dehydrogenase, 2(or 3)-hexanol dehydrogenase, 2(or 3)-heptanol dehydrogenase, 2(or 3)-octanol dehydrogenase, 2(or 3)-nonanol dehydrogenase, 4-methyl-2(or 3)-pentanol dehydrogenase, 4-methyl-2(or 3)-hexanol dehydrogenase, 5-methyl-2(or 3)-hexanol dehydrogenase, 6-methyl-2(or 3)-heptanol dehydrogenase, 1-phenyl-2(or 3)-butanol dehydrogenase, 1-(4-hydroxyphenyl)-2(or 3)-butanol dehydrogenase, 1-indole-2(or 3)-butanol dehydrogenase, 3(or 4)-heptanol dehydrogenase, 3(or 4)-octanol dehydrogenase, 3(or 4)-nonanol dehydrogenase, 3(or 4)-decanol dehydrogenase, 3(or 4)-undecanol dehydrogenase, 2-methyl-3(or 4)-hexanol dehydrogenase, 5-methyl-3 (or 4)-heptanol dehydrogenase, 6-methyl-3 (or 4)-heptanol dehydrogenase, 7-methyl-3(or 4)-octanol dehydrogenase, 1-phenyl-2(or 3)-pentanol dehydrogenase, 1-(4-hydroxyphenyl)-2(or 3)-pentanol dehydrogenase, 1-indole-2(or 3)-pentanol dehydrogenase, 4(or 5)-nonanol dehydrogenase, 4(or 5)-decanol dehydrogenase, 4(or 5)-undecanol dehydrogenase, 4(or 5)-dodecanol dehydrogenase, 2-methyl-3(or 4)-heptanol dehydrogenase, 3-methyl-4(or 5)-octanol dehydrogenase, 2-methyl-4(or 5)-octanol dehydrogenase, 8-methyl-4(or 5)-nonanol dehydrogenase, 1-phenyl-2(or 3)-hexanol dehydrogenase, 1-(4-hydroxyphenyl)-2 (or 3)-hexanol dehydrogenase, 1-indole-2(or 3)-hexanol dehydrogenase, 4(or 5)-undecanol dehydrogenase, 5(or 6)-undecanol dehydrogenase, 5(or 6)-tridecanol dehydrogenase, 2-methyl-3(or 4)-octanol dehydrogenase, 3-methyl-4 (or 5)-nonanol dehydrogenase, 2-methyl-4(or 5)-nonanol dehydrogenase, 2-methyl-5(or 6)-decanol dehydrogenase, 1-phenyl-2(or 3)-heptanol dehydrogenase, 1-(4-hydroxyphenyl)-2(or 3)-heptanol dehydrogenase, 1-indole-2(or 3)-heptanol dehydrogenase, 6(or 7)-tridecanol dehydrogenase, 6(or 7)-tetradecanol dehydrogenase, 2-methyl-3(or 4)-nonanol dehydrogenase, 3-methyl-4(or 5)-decanol dehydrogenase, 2-methyl-4(or 5)-decanol dehydrogenase, 2-methyl-5(or 6)-undecanol dehydrogenase, 1-phenyl-2(or 3)-octanol dehydrogenase, 1-(4-hydroxyphenyl)-2(or 3)-octanol dehydrogenase, 1-indole-2(or 3)-octanol dehydrogenase, 7(or 8)-pentadecanol dehydrogenase, 2-methyl-3(or 4)-decanol dehydrogenase, 3-methyl-4(or 5)-undecanol dehydrogenase, 2-methyl-4(or 5)-undecanol dehydrogenase, 2-methyl-5 (or 6)-dodecanol dehydrogenase, 1-phenyl-2(or 3)-nonanol dehydrogenase, 1-(4-hydroxyphenyl)-2 (or 3)-nonanol dehydrogenase, 1-indole-2(or 3)-nonanol dehydrogenase, 2-methyl-3(or 4)-undecanol dehydrogenase, 3-methyl-4(or 5)-dodecanol dehydrogenase, 2-methyl-4(or 5)-dodecanol dehydrogenase, 2-methyl-5(or 6)-tridecanol dehydrogenase, 1-phenyl-2(or 3)-decanol dehydrogenase, 1-(4-hydroxyphenyl)-2 (or 3)-decanol dehydrogenase, 1-indole-2(or 3)-decanol dehydrogenase, 2,5-dimethyl-3(or 4)-heptanol dehydrogenase, 2,6-dimethyl-3(or 4)-heptanol dehydrogenase, 2,7-dimethyl-3(or 4)-octanol dehydrogenase, 1-phenyl-4-methyl-2(or 3)-pentanol dehydrogenase, 1-(4-hydroxyphenyl)-4-methyl-2(or 3)-pentanol dehydrogenase, 1-indole-4-methyl-2(or 3)-pentanol dehydrogenase, 2,6-dimethyl-4(or 5)-octanol dehydrogenase, 3,8-dimethyl-4(or 5)-nonanol dehydrogenase, 1-phenyl-4-methyl-2(or 3)-hexanol dehydrogenase, 1-(4-hydroxyphenyl)-4-methyl-2 (or 3)-hexanol dehydrogenase, 1-indole-4-methyl-2(or 3)-hexanol dehydrogenase, 2,8-dimethyl-4(or 5)-nonanol dehydrogenase, 1-phenyl-5-methyl-2(or 3)-hexanol dehydrogenase, 1-(4-hydroxyphenyl)-5-methyl-2(or 3)-hexanol dehydrogenase, 1-indole-5-methyl-2(or 3)-hexanol dehydrogenase, 1-phenyl-6-methyl-2(or 3)-heptanol dehydrogenase, 1-(4-hydroxyphenyl)-6-methyl-2(or 3)-heptanol dehydrogenase, 1-indole-6-methyl-2(or 3)-heptanol dehydrogenase, 1-(4-hydroxyphenyl)-4-phenyl-2(or 3)-butanol dehydrogenase, 1-indole-4-phenyl-2(or 3)-butanol dehydrogenase, 1-indole-4-(4-hydroxyphenyl)-2(or 3)-butanol dehydrogenase, 1,10-diamino-5-decanol dehydrogenase, 1,4-di(4-hydroxyphenyl)-2-butanol dehydrogenase, 2-hexanol-1,6-dicarboxylic acid dehydrogenase, phenylethanol dehydrogenase, 4-hydroxyphenylethanol dehydrogenase, Indole-3-ethanol dehydrogenase, and the like.

In certain aspects, a selected alcohol dehydrogenase or secondary alcohol dehydrogenase may have one or more of the above exemplified alcohol dehydrogenase activities, such as a 2-butanol dehydrogenase activity, 3-hexanol dehydrogenase activity, and/or a 4-octanol dehydrogenase activity, among others.

In certain aspects, a recombinant microorganism may comprise one or more secondary alcohol dehydrogenases encoded by a nucleotide reference sequence selected from SEQ ID NO:109, 111, 113, 115, 117, 119, 121, 123, 125, 127, 129, 131, 133, 135, 137, 139, and 141, or an enzyme having a polypeptide sequence selected from SEQ ID NO:110, 112, 114, 116, 118, 120, 122, 124, 126, 128, 130, 132, 134, 136, 138, 140, and 142, including biologically active fragments or variants thereof, such as optimized variants. Certain aspects may also comprises nucleotide sequences or polypeptide sequences having 80%, 85%, 90%, 95%, 97%, 98%, 99% sequence identity to SEQ ID NOS:109-142.

For the secondary alcohol dehydrogenase sequences referred to above, SEQ ID NO:109 is the nucleotide sequence and SEQ ID NO:110 is the polypeptide sequence of a secondary alcohol dehydrogenase (2adh-1: PP_1946) isolated from *Pseudomonas putida* KT2440. SEQ ID NO:111 is the nucleotide sequence and SEQ ID NO:112 is the polypeptide sequence of a secondary alcohol dehydrogenase (2adh-2: PP_1817) isolated from *Pseudomonas putida* KT2440.

SEQ ID NO:113 is the nucleotide sequence and SEQ ID NO:114 is the polypeptide sequence of a secondary alcohol dehydrogenase (2adh-3: PP_1953) isolated from *Pseudomonas putida* KT2440. SEQ ID NO:115 is the nucleotide sequence and SEQ ID NO:116 is the polypeptide sequence of a secondary alcohol dehydrogenase (2adh-4: PP_3037) isolated from *Pseudomonas putida* KT2440.

SEQ ID NO:117 is the nucleotide sequence and SEQ ID NO:118 is the polypeptide sequence of a secondary alcohol dehydrogenase (2adh-5: PP_1852) isolated from *Pseudomonas putida* KT2440. SEQ ID NO:119 is the nucleotide sequence and SEQ ID NO:120 is the polypeptide sequence of a secondary alcohol dehydrogenase (2adh-6: PP_2723) isolated from *Pseudomonas putida* KT2440.

SEQ ID NO:121 is the nucleotide sequence and SEQ ID NO:122 is the polypeptide sequence of a secondary alcohol dehydrogenase (2adh-7: PP_2002) isolated from *Pseudomonas putida* KT2440. SEQ ID NO:123 is the nucleotide sequence and SEQ ID NO:124 is the polypeptide sequence of a secondary alcohol dehydrogenase (2adh-8: PP_1914) isolated from *Pseudomonas putida* KT2440.

SEQ ID NO:125 is the nucleotide sequence and SEQ ID NO:126 is the polypeptide sequence of a secondary alcohol dehydrogenase (2adh-9: PP_1914) isolated from *Pseudomonas putida* KT2440. SEQ ID NO:127 is the nucleotide sequence and SEQ ID NO:128 is the polypeptide sequence of a secondary alcohol dehydrogenase (2adh-10: PP_3926) isolated from *Pseudomonas putida* KT2440.

SEQ ID NO:129 is the nucleotide sequence and SEQ ID NO:130 is the polypeptide sequence of a secondary alcohol dehydrogenase (2adh-11: PFL_1756) isolated from *Pseudomonas fluorescens* Pf-5. SEQ ID NO:131 is the nucleotide sequence and SEQ ID NO:132 is the polypeptide sequence of a secondary alcohol dehydrogenase (2adh-12: KPN_01694) isolated from *Klebsiella pneumoniae* subsp. *pneumoniae* MGH 78578.

SEQ ID NO:133 is the nucleotide sequence and SEQ ID NO:134 is the polypeptide sequence of a secondary alcohol dehydrogenase (2adh-13: KPN_02061) isolated from *Klebsiella pneumoniae* subsp. *pneumoniae* MGH 78578. SEQ ID NO:135 is the nucleotide sequence and SEQ ID NO:136 is the polypeptide sequence of a secondary alcohol dehydrogenase (2adh-14: KPN_00827) isolated from *Klebsiella pneumoniae* subsp. *pneumoniae* MGH 78578.

SEQ ID NO:137 is the nucleotide sequence and SEQ ID NO:138 is the polypeptide sequence of a secondary alcohol dehydrogenase (2adh-16: KPN_01350) isolated from *Klebsiella pneumoniae* subsp. *pneumoniae* MGH 78578. SEQ ID NO:139 is the nucleotide sequence and SEQ ID NO:140 is the polypeptide sequence of a secondary alcohol dehydrogenase (2adh-17: KPN_03369) isolated from *Klebsiella pneumoniae* subsp. *pneumoniae* MGH 78578. SEQ ID NO:141 is the nucleotide sequence and SEQ ID NO:142 is the polypeptide sequence of a secondary alcohol dehydrogenase (2adh-18: KPN_03363) isolated from *Klebsiella pneumoniae* subsp. *pneumoniae* MGH 78578.

In certain aspects, an alcohol dehydrogenase (e.g., DEHU hydrogenase), a secondary alcohol dehydrogenase (2ADH), a fragment, variant, or derivative thereof, or any other enzyme that utilizes such an active site, may comprise at least one of a nicotinamide adenine dinucleotide (NAD+), NADH, nicotinamide adenine dinucleotide phosphate (NADP+), or NADPH binding motif. In certain embodiments, the NAD+, NADH, NADP+, or NADPH binding motif may be selected from the group consisting of Y-X-G-G-X-Y, Y-X-X-G-G-X-Y, Y-X-X-X-G-G-X-Y, Y-X-G-G-X-X-Y, Y-X-X-G-G-X-X-Y, Y-X-X-X-G-X-X-Y, Y-X-G-X-Y, Y-X-X-G-X-Y, Y-X-X-X-G-X-Y, and Y-X-X-X-X-G-X-Y; wherein Y is independently selected from alanine, glycine, and serine, wherein G is glycine, and wherein X is independently selected from a genetically encoded amino acid.

As one example of a step in a reduction and dehydration pathway, α-hydroxy cyclopentanone may be reduced to 1,2-cyclopentanediol. For example, the glycerol dehydrogenase isolated from *Hansenula ofunaensis* favors the reduction of α-hydroxy ketones and α-keto ketones, and has very broad substrate specificity. The similar alcohol dehydrogenase derived from *Hansenula polumorpha* and meso-2,3-butanediol dehydrogenase has similar properties. Certain embodiments may incorporate a 1,2-cyclopentanediol dehydrogenase to the microbial system or isolated microorganism. Other embodiments may incorporate a glycerol dehydrogenase from *Hansenula ofunaensis, Hansenula polumorpha, Klebsiella pneumonia*, or any other suitable organism.

By way of example, a chemical or hydrocarbon such as 1,2-cyclopentanediol may be dehydrated to form cyclopentanone as one enzymatic step in a reduction and dehydration pathway. There are at least two different types of diol dehydratases that may catalyze dehydration of chemicals such as 1,2-cyclopentanediol. Certain embodiments of microbial system comprising a reduction and dehydration pathway will comprise diol dehydratases such as 1,2-cyclopentanediol dehydratase.

In the last enzymatic step for a reduction and dehydration pathway, the conversion of such exemplary chemicals as α-hydroxy cyclopentanone to cyclopentanol may include the reduction of cyclopentanone to cyclopentanol. This step may be catalyzed by cyclopentanol dehydrogenase, which is found in *Comomonas* sp. strain NCIMB 9872 and its gene (cpnA) has been isolated. Certain embodiments of a microbial system or isolated microorganism may comprise a cyclopentanol dehydrogenase, such as that expressed by cpnA in *Comomonas* sp. strain NCIMB 9872, among others described herein.

As detailed below, in certain embodiments, selected C—C ligation pathways may be utilized in combination with selected components or enzymes of a reduction and dehydration pathway to produce a commodity chemical, or intermediate thereof.

For example, certain embodiments include a method wherein the C—C ligation pathway may comprise an acetoaldehyde lyase and wherein the reduction and dehydration pathway may comprise at least one of a 2,3-butanediol dehydrogenase, a 2,3-butanediol dehydratase, and a 2-butanol dehydrogenase. Additional embodiments include a method wherein the C—C ligation pathway may comprise a propionaldehyde lyase and wherein the reduction and dehydration pathway may comprise at least one of a 3,4-hexanediol dehydrogenase, a 3,4-hexanediol dehydratase, and a 3-hexanol dehydrogenase.

Additional embodiments include a method wherein the C—C ligation pathway may comprise a butyraldehyde lyase and wherein the reduction and dehydration pathway may comprise at least one of a 4,5-octanediol dehydrogenase, a 4,5-octanediol dehydratase, and a 4-octanol dehydrogenase. Additional embodiments include a method wherein the C—C ligation pathway may comprise a butyraldehyde lyase and wherein the reduction and dehydration pathway may comprise at least one of a 5,6-decanediol dehydrogenase, a 5,6-decanediol dehydratase, and a 5-decanol dehydrogenase.

Additional embodiments include a method wherein the C—C ligation pathway may comprise a butyraldehyde lyase and wherein the reduction and dehydration pathway may comprise at least one of a 6,7-dodecanediol dehydrogenase, a 6,7-dodecanediol dehydratase, and a 6-dodecanol dehydrogenase. Additional embodiments include a method wherein the C—C ligation pathway may comprise a butyraldehyde lyase and wherein the reduction and dehydration pathway may comprise at least one of a 7,8-tetradecanediol dehydrogenase, a 7,8-tetradecanediol dehydratase, and a 7-tetradecanol dehydrogenase.

Additional embodiments include a method wherein the C—C ligation pathway may comprise a butyraldehyde lyase and wherein the reduction and dehydration pathway may comprise at least one of a 8,9-hexadecanediol dehydrogenase, a 8,9-hexadecanediol dehydratase, and a 8-hexadecanol dehydrogenase. Additional embodiments include a method wherein the C—C ligation pathway may comprise an isobutyraldehyde lyase and wherein the reduction and dehydration pathway may comprise at least one of a 2,5-dimethyl-3,4-hexanediol dehydrogenase, a 2,5-dimethyl-3,4-hexanediol dehydratase, and a 2,5-dimethyl-3-hexanol dehydrogenase.

Additional embodiments include a method wherein the C—C ligation pathway may comprise a 2-methyl-butyraldehyde lyase and wherein the reduction and dehydration pathway may comprise at least one of a 3,6-dimethyl-4,5-octanediol dehydrogenase, a 3,6-dimethyl-4,5-octanediol dehydratase, and a 3,6-dimethyl-4-octanol dehydrogenase. Additional embodiments include a method wherein the C—C ligation pathway may comprise a 3-methyl-butyraldehyde lyase and wherein the reduction and dehydration pathway may comprise at least one of a 2,7-dimethyl-4,5-octanediol dehydrogenase, a 2,7-dimethyl-4,5-octanediol dehydratase, and a 2,7-dimethyl-4-octanol dehydrogenase.

Additional embodiments include a method wherein the C—C ligation pathway may comprise a 3-methyl-butyraldehyde lyase and wherein the reduction and dehydration pathway may comprise at least one of a 2,9-dimethyl-5,6-decanediol dehydrogenase, a 2,9-dimethyl-4,5-decanediol dehydratase, and a 2,9-dimethyl-4-decanol dehydrogenase. Additional embodiments include a method wherein the C—C ligation pathway may comprise a phenylacetaldehyde lyase and wherein the reduction and dehydration pathway may comprise at least one of a 1,4-diphenyl-2,3-butanediol dehydrogenase, a 1,4-diphenyl-2,3-butanediol dehydratase, and a 1,4-diphenyl-2-butanol dehydrogenase.

Additional embodiments include a method wherein the C—C ligation pathway may comprise a phenylacetaldehyde lyase and wherein the reduction and dehydration pathway may comprise at least one of a bis-1,4-(4-hydroxyphenyl)-2,3-butanediol dehydrogenase, a bis-1,4-(4-hydroxyphenyl)-2,3-butanediol dehydratase, and a bis-1,4-(4-hydroxyphenyl)-2-butanol dehydrogenase. Additional embodiments include a method wherein the C—C ligation pathway may comprise a phenylacetaldehyde lyase and wherein the reduction and dehydration pathway may comprise at least one of a 1,4-diindole-2,3-butanediol dehydrogenase, a 1,4-diindole-2,3-butanediol dehydratase, and a 1,4-diindole-2-butanol dehydrogenase.

Additional embodiments include a method wherein the C—C ligation pathway may comprise an α-keto adipate carboxylyase, and wherein the reduction and dehydration pathway may comprise at least one of a 1,2-cyclopentanediol dehydrogenase, a 1,2-cyclopentanediol dehydratase, and a cyclopentanol dehydrogenase. Additional embodiments include a method wherein the C—C ligation pathway may comprise at least one of an acetoaldehyde/propiondehyde lyase and wherein the reduction and dehydration pathway may comprise at least one of a 2,3-pentanediol dehydrogenase, a 2,3-pentanediol dehydratase, and a 2(or 3)-pentanol dehydrogenase.

Additional embodiments include a method wherein the C—C ligation pathway may comprise at least one of an acetoaldehyde/butyraldehyde lyase and wherein the reduction and dehydration pathway may comprise at least one of a 2,3-hexanediol dehydrogenase, a 2,3-hexanediol dehydratase, and a 2(or 3)-hexanol dehydrogenase. Additional embodiments include a method wherein the C—C ligation pathway may comprise at least one of an acetoaldehyde/pentaldehyde lyase and wherein the reduction and dehydration pathway may comprise at least one of a 2,3-heptanediol dehydrogenase, a 2,3-heptanediol dehydratase, and a 2(or 3)-heptanol dehydrogenase.

Additional embodiments include a method wherein the C—C ligation pathway may comprise at least one of an acetoaldehyde/hexyldehyde lyase and wherein the reduction and dehydration pathway may comprise at least one of a 2,3-octanediol dehydrogenase, a 2,3-octanediol dehydratase, and a 2(or 3)-octanol dehydrogenase. Additional embodiments include a method wherein the C—C ligation pathway may comprise at least one of an acetoaldehyde/octaldehyde lyase and wherein the reduction and dehydration pathway may comprise at least one of a 2,3-nonanediol dehydrogenase, a 2,3-nonanediol dehydratase, and a 2(or 3)-nonanol dehydrogenase.

Additional embodiments include a method wherein the C—C ligation pathway may comprise at least one of an acetoaldehyde/isobutyraldehyde lyase and wherein the reduction and dehydration pathway may comprise at least one of a 4-methyl-2,3-pentanediol dehydrogenase, a 4-methyl-2,3-pentanediol dehydratase, and a 4-methyl-2(or 3)-pentanol dehydrogenase. Additional embodiments include a method wherein the C—C ligation pathway may comprise at least one of an acetoaldehyde/2-methyl-butyraldehyde lyase and wherein the reduction and dehydration pathway may comprise at least one of a 4-methyl-2,3-hexanediol dehydrogenase, a 4-methyl-2,3-hexanediol dehydratase, and a 4-methyl-2(or 3)-hexanol dehydrogenase.

Additional embodiments include a method wherein the C—C ligation pathway may comprise at least one of an acetoaldehyde/3-methyl-butyraldehyde lyase and wherein the reduction and dehydration pathway may comprise at least one of a 5-methyl-2,3-hexanediol dehydrogenase, a 5-methyl-2,3-hexanediol dehydratase, and a 5-methyl-2(or 3)-hexanol dehydrogenase. Additional embodiments include a method wherein the C—C ligation pathway may comprise at least one of an acetoaldehyde/4-methyl-pentaldehyde lyase and wherein the reduction and dehydration pathway may comprise at least one of a 6-methyl-2,3-heptanediol dehydrogenase, a 6-methyl-2,3-heptanediol dehydrogenase, and a 6-methyl-2(or 3)-heptanol dehydrogenase.

Additional embodiments include a method wherein the C—C ligation pathway may comprise at least one of an acetoaldehyde/phenylacetaldehyde lyase and wherein the reduction and dehydration pathway may comprise at least one of a 1-phenyl-2,3-butanediol dehydrogenase, a 1-phenyl-2,3-butanediol dehydratase, and a 1-phenyl-2(or 3)-butanol dehydrogenase. Additional embodiments include a method wherein the C—C ligation pathway may comprise at least one of an acetoaldehyde/4-hydroxyphenylacetaldehyde lyase and wherein the reduction and dehydration pathway may comprise at least one of a 1-(4-hydroxyphenyl)-2,3-butanediol dehydrogenase, a 1-(4-hydroxyphenyl)-2,3-butanediol dehydratase, and a 1-(4-hydroxyphenyl)-2(or 3)-butanol dehydrogenase.

Additional embodiments include a method wherein the C—C ligation pathway may comprise at least one of an acetoaldehyde/indoleacetaldehyde lyase and wherein the reduction and dehydration pathway may comprise at least one of a 1-indole-2,3-butanediol dehydrogenase, a 1-indole-2,3-butanediol dehydratase, and a 1-indole-2(or 3)-butanol dehydrogenase. Additional embodiments include a method wherein the C—C ligation pathway may comprise at least one of a propionaldehyde/butyraldehyde lyase and wherein the reduction and dehydration pathway may comprise at least one of a 3,4-heptanediol dehydrogenase, a 3,4-heptanediol dehydratase, and a 3(or 4)-heptanol dehydrogenase.

Additional embodiments include a method wherein the C—C ligation pathway may comprise at least one of a propionaldehyde/pentaldehyde lyase and wherein the reduction and dehydration pathway may comprise at least one of a 3,4-octanediol dehydrogenase, a 3,4-octanediol dehydratase, and a 3(or 4)-octanol dehydrogenase. Additional embodiments include a method wherein the C—C ligation pathway may comprise at least one of a propionaldehyde/hexyldehyde lyase and wherein the reduction and dehydration pathway may comprise at least one of a 3,4-nonanediol dehydrogenase, a 3,4-nonanediol dehydratase, and a 3(or 4)-nonanol dehydrogenase.

Additional embodiments include a method wherein the C—C ligation pathway may comprise at least one of a propionaldehyde/heptaldehyde lyase and wherein the reduction and dehydration pathway may comprise at least one of a 3,4-decanediol dehydrogenase, a 3,4-decanediol dehydratase, and a 3(or 4)-decanol dehydrogenase. Additional embodiments include a method wherein the C—C ligation pathway may comprise at least one of a propionaldehyde/octaldehyde lyase and wherein the reduction and dehydration pathway may comprise at least one of a 3,4-undecanediol dehydrogenase, a 3,4-undecanediol dehydratase, and a 3(or 4)-undecanol dehydrogenase.

Additional embodiments include a method wherein the C—C ligation pathway may comprise at least one of a propionaldehyde/isobutyraldehyde lyase and wherein the reduction and dehydration pathway may comprise at least one of a 2-methyl-3,4-hexanediol dehydrogenase, a 2-methyl-3,4-hexanediol dehydratase, and a 2-methyl-3(or 4)-hexanol dehydrogenase. Additional embodiments include a method wherein the C—C ligation pathway may comprise at least one of a propionaldehyde/2-methyl-butyraldehyde lyase and wherein the reduction and dehydration pathway may comprise at least one of a 5-methyl-3,4-heptanediol dehydrogenase, a 5-methyl-3,4-heptanediol dehydratase, and a 5-methyl-3 (or 4)-heptanol dehydrogenase.

Additional embodiments include a method wherein the C—C ligation pathway may comprise at least one of a propionaldehyde/3-methyl-butyraldehyde lyase and wherein the reduction and dehydration pathway may comprise at least one of a 6-methyl-3,4-heptanediol dehydrogenase, a 6-methyl-3,4-heptanediol dehydratase, and a 6-methyl-3(or 4)-heptanol dehydrogenase. Additional embodiments include a method wherein the C—C ligation pathway may comprise at least one of a propionaldehyde/4-methyl-pentaldehyde lyase and wherein the reduction and dehydration pathway may comprise at least one of a 7-methyl-3,4-octanediol dehydrogenase, a 7-methyl-3,4-octanediol dehydratase, and a 7-methyl-3(or 4)-octanol dehydrogenase.

Additional embodiments include a method wherein the C—C ligation pathway may comprise at least one of a propionaldehyde and a phenylacetaldehyde lyase and wherein the reduction and dehydration pathway may comprise at least one of a 1-phenyl-2,3-pentanediol dehydrogenase, a 1-phenyl-2,3-pentanediol dehydratase, and a 1-phenyl-2(or 3)-pentanol dehydrogenase. Additional embodiments include a method wherein the C—C ligation pathway may comprise at least one of a propionaldehyde/4-hydroxyphenylacetaldehyde lyase and wherein the reduction and dehydration pathway may comprise at least one of a 1-(4-hydroxyphenyl)-2,3-pentanediol dehydrogenase, a 1-(4-hydroxyphenyl)-2,3-pentanediol dehydratase, and a 1-(4-hydroxyphenyl)-2(or 3)-pentanol dehydrogenase.

Additional embodiments include a method wherein the C—C ligation pathway may comprise at least one of a propionaldehyde/indoleacetoaldehyde lyase and wherein the reduction and dehydration pathway may comprise at least one of a 1-indole-2,3-pentanediol dehydrogenase, a 1-indole-2,3-pentanediol dehydratase, and a 1-indole-2(or 3)-pentanol dehydrogenase. Additional embodiments include a method wherein the C—C ligation pathway may comprise at least one of a butyraldehyde/pentaldehyde lyase and wherein the reduction and dehydration pathway may comprise at least one of a 4,5-nonanediol dehydrogenase, a 4,5-nonanediol dehydratase, and a 4(or 5)-nonanol dehydrogenase.

Additional embodiments include a method wherein the C—C ligation pathway may comprise at least one of a butyraldehyde/hexyldehyde lyase and wherein the reduction and dehydration pathway may comprise at least one of a 4,5-decanediol dehydrogenase, a 4,5-decanediol dehydratase, and a 4(or 5)-decanol dehydrogenase. Additional embodiments include a method wherein the C—C ligation pathway may comprise at least one of a butyraldehyde/heptaldehyde lyase and wherein the reduction and dehydration pathway may comprise at least one of a 4,5-undecanediol dehydrogenase, a 4,5-undecanediol dehydratase, and a 4(or 5)-undecanol dehydrogenase.

Additional embodiments include a method wherein the C—C ligation pathway may comprise at least one of a butyraldehyde/octaldehyde lyase and wherein the reduction and dehydration pathway may comprise at least one of a 4,5-dodecanediol dehydrogenase, a 4,5-dodecanediol dehydratase, and a 4(or 5)-dodecanol dehydrogenase. Additional embodiments include a method wherein the C—C ligation pathway may comprise at least one of a butyraldehyde/isobutyraldehyde lyase and wherein the reduction and dehydration pathway may comprise at least one of a 2-methyl-3,4-heptanediol dehydrogenase, a 2-methyl-3,4-heptanediol dehydratase, and a 2-methyl-3(or 4)-heptanol dehydrogenase.

Additional embodiments include a method wherein the C—C ligation pathway may comprise at least one of a butyraldehyde/2-methyl-butyraldehyde lyase and wherein the reduction and dehydration pathway may comprise at least one of a 3-methyl-4,5-octanediol dehydrogenase, a 3-methyl-4,5-octanediol dehydratase, and a 3-methyl-4(or 5)-octanol dehydrogenase. Additional embodiments include a method wherein the C—C ligation pathway may comprise at least one of a butyraldehyde/3-methyl-butyraldehyde lyase and wherein the reduction and dehydration pathway may comprise at least one of a 2-methyl-4,5-octanediol dehydrogenase, a 2-methyl-4,5-octanediol dehydratase, and a 2-methyl-4(or 5)-octanol dehydrogenase.

Additional embodiments include a method wherein the C—C ligation pathway may comprise at least one of a butyraldehyde/4-methyl-pentaldehyde lyase and wherein the reduction and dehydration pathway may comprise at least one of an 8-methyl-4,5-nonanediol dehydrogenase, an 8-methyl-4,5-nonanediol dehydratase, and an 8-methyl-4(or 5)-nonanol dehydrogenase. Additional embodiments include a method wherein the C—C ligation pathway may comprise at least one of a butyraldehyde/phenylacetaldehyde lyase and wherein the reduction and dehydration pathway may comprise at least one of a 1-phenyl-2,3-hexanediol dehydrogenase, a 1-phenyl-2,3-hexanediol dehydratase, and a 1-phenyl-2(or 3)-hexanol dehydrogenase.

Additional embodiments include a method wherein the C—C ligation pathway may comprise at least one of a butyraldehyde/4-hydroxyphenylacetaldehyde lyase and wherein the reduction and dehydration pathway may comprise at least one of a 1-(4-hydroxyphenyl)-2,3-hexanediol dehydrogenase, a 1-(4-hydroxyphenyl)-2,3-hexanediol dehydratase, and a 1-(4-hydroxyphenyl)-2(or 3)-hexanol dehydrogenase. Additional embodiments include a method wherein the C—C ligation pathway may comprise at least one of a butyraldehyde/indoleacetaldehyde lyase and wherein the reduction and dehydration pathway may comprise at least one of a 1-indole-2,3-hexanediol dehydrogenase, a 1-indole-2,3-hexanediol dehydratase, and a 1-indole-2(or 3)-hexanol dehydrogenase.

Additional embodiments include a method wherein the C—C ligation pathway may comprise at least one of a pentaldehyde/hexyldehyde lyase and wherein the reduction and dehydration pathway may comprise at least one of a 5,6-undecanediol dehydrogenase, a 4,5-undecanediol dehydratase, and a 4(or 5)-undecanol dehydrogenase. Additional embodiments include a method wherein the C—C ligation pathway may comprise at least one of a pentaldehyde/heptaldehyde lyase and wherein the reduction and dehydration pathway may comprise at least one of a 5,6-undecanediol dehydrogenase, a 5,6-undecanediol dehydratase, and a 5(or 6)-undecanol dehydrogenase.

Additional embodiments include a method wherein the C—C ligation pathway may comprise at least one of a pentaldehyde/octaldehyde lyase and wherein the reduction and dehydration pathway may comprise at least one of a 5,6-tridecanediol dehydrogenase, a 5,6-tridecanediol dehydratase, and a 5(or 6)-tridecanol dehydrogenase. Additional embodiments include a method wherein the C—C ligation pathway may comprise at least one of a pentaldehyde/isobutyraldehyde lyase and wherein the reduction and dehydration pathway may comprise at least one of a 2-methyl-3,4-octanediol dehydrogenase, a 2-methyl-3,4-octanediol dehydratase, and a 2-methyl-3(or 4)-octanol dehydrogenase.

Additional embodiments include a method wherein the C—C ligation pathway may comprise at least one of a pentaldehyde/2-methyl-butyraldehyde lyase and wherein the reduction and dehydration pathway may comprise at least one of a 3-methyl-4,5-nonanediol dehydrogenase, a 3-methyl-4,5-nonanediol dehydratase, and a 3-methyl-4(or 5)-nonanol dehydrogenase. Additional embodiments include a method wherein the C—C ligation pathway may comprise at least one of a pentaldehyde/3-methyl-butyraldehyde lyase and wherein the reduction and dehydration pathway may comprise at least one of a 2-methyl-4,5-nonanediol dehydrogenase, a 2-methyl-4,5-nonanediol dehydratase, and a 2-methyl-4(or 5)-nonanol dehydrogenase.

Additional embodiments include a method wherein the C—C ligation pathway may comprise at least one of a pentaldehyde/4-methyl-pentaldehyde lyase and wherein the reduction and dehydration pathway may comprise at least one of a 2-methyl-5,6-decanediol dehydrogenase, a 2-methyl-5,6-decanediol dehydratase, and a 2-methyl-5(or 6)-decanol dehydrogenase. Additional embodiments include a method wherein the C—C ligation pathway may comprise at least one of a pentaldehyde/phenylacetaldehyde lyase and wherein the reduction and dehydration pathway may comprise at least one of a 1-phenyl-2,3-heptanediol dehydrogenase, a 1-phenyl-2,3-heptanediol dehydratase, and a 1-phenyl-2(or 3)-heptanol dehydrogenase.

Additional embodiments include a method wherein the C—C ligation pathway may comprise at least one of a pentaldehyde/4-hydroxyphenylacetaldehyde lyase and wherein the reduction and dehydration pathway may comprise at least one of a 1-(4-hydroxyphenyl)-2,3-heptanediol dehydrogenase, a 1-(4-hydroxyphenyl)-2,3-heptanediol dehydratase, and a 1-(4-hydroxyphenyl)-2(or 3)-heptanol dehydrogenase. Additional embodiments include a method wherein the C—C ligation pathway may comprise at least one of a pentaldehyde/indoleacetaldehyde lyase and wherein the reduction and dehydration pathway may comprise at least one of a 1-indole-2,3-heptanediol dehydrogenase, a 1-indole-2,3-heptanediol dehydratase, and a 1-indole-2(or 3)-heptanol dehydrogenase.

Additional embodiments include a method wherein the C—C ligation pathway may comprise at least one of a hexyldehyde/heptaldehyde lyase and wherein the reduction and dehydration pathway may comprise at least one of a 6,7-tridecanediol dehydrogenase, a 6,7-tridecanediol dehydratase, and a 6(or 7)-tridecanol dehydrogenase. Additional embodiments include a method wherein the C—C ligation pathway may comprise at least one of a hexyldehyde/octaldehyde lyase and wherein the reduction and dehydration pathway may comprise at least one of a 6,7-tetradecanediol dehydrogenase, a 6,7-tetradecanediol dehydratase, and a 6(or 7)-tetradecanol dehydrogenase.

Additional embodiments include a method wherein the C—C ligation pathway may comprise at least one of a hexyldehyde/isobutyraldehyde lyase and wherein the reduction and dehydration pathway may comprise at least one of a 2-methyl-3,4-nonanediol dehydrogenase, a 2-methyl-3,4-nonanediol dehydratase, and a 2-methyl-3(or 4)-nonanol dehydrogenase. Additional embodiments include a method wherein the C—C ligation pathway may comprise at least one of a hexyldehyde/2-methyl-butyraldehyde lyase and wherein the reduction and dehydration pathway may comprise at least one of a 3-methyl-4,5-decanediol dehydrogenase, a 3-methyl-4,5-decanediol dehydratase, and a 3-methyl-4(or 5)-decanol dehydrogenase.

Additional embodiments include a method wherein the C—C ligation pathway may comprise at least one of a hexyldehyde/3-methyl-butyraldehyde lyase and wherein the reduction and dehydration pathway may comprise at least one of a 2-methyl-4,5-decanediol dehydrogenase, a 2-methyl-4,5-decanediol dehydratase, and a 2-methyl-4(or 5)-decanol dehydrogenase. Additional embodiments include a method wherein the C—C ligation pathway may comprise at least one of a hexyldehyde/4-methyl-pentaldehyde lyase and wherein the reduction and dehydration pathway may comprise at least one of a 2-methyl-5,6-undecanediol dehydrogenase, a 2-methyl-5,6-undecanediol dehydratase, and a 2-methyl-5(or 6)-undecanol dehydrogenase.

Additional embodiments include a method wherein the C—C ligation pathway may comprise at least one of a hexyldehyde/phenylacetaldehyde lyase and wherein the reduction and dehydration pathway may comprise at least one of a 1-phenyl-2,3-octanediol dehydrogenase, a 1-phenyl-2,3-octanediol dehydratase, and a 1-phenyl-2(or 3)-octanol dehydrogenase. Additional embodiments include a method wherein the C—C ligation pathway may comprise at least one of a hexyldehyde/4-hydroxyphenylacetaldehyde lyase and wherein the reduction and dehydration pathway may comprise at least one of a 1-(4-hydroxyphenyl)-2,3-octanediol dehydrogenase, a 1-(4-hydroxyphenyl)-2,3-octanediol dehydratase, and a 1-(4-hydroxyphenyl)-2(or 3)-octanol dehydrogenase.

Additional embodiments include a method wherein the C—C ligation pathway may comprise at least one of a hexyldehyde/indoleacetaldehyde lyase and wherein the reduction and dehydration pathway may comprise at least one of a 1-indole-2,3-octanediol dehydrogenase, a 1-indole-2,3-octanediol dehydratase, and a 1-indole-2(or 3)-octanol dehydrogenase. Additional embodiments include a method wherein the C—C ligation pathway may comprise at least one of a heptaldehyde/octaldehyde lyase and wherein the reduction and dehydration pathway may comprise at least one of a 7,8-pentadecanediol dehydrogenase, a 7,8-pentadecanediol dehydratase, and a 7(or 8)-pentadecanol dehydrogenase.

Additional embodiments include a method wherein the C—C ligation pathway may comprise at least one of a heptaldehyde/isobutyraldehyde lyase and wherein the reduction and dehydration pathway may comprise at least one of a 2-methyl-3,4-decanediol dehydrogenase, a 2-methyl-3,4-decanediol dehydratase, and a 2-methyl-3(or 4)-decanol dehydrogenase. Additional embodiments include a method wherein the C—C ligation pathway may comprise at least one of a heptaldehyde/2-methyl-butyraldehyde lyase and wherein the reduction and dehydration pathway may comprise at least one of a 3-methyl-4,5-undecanediol dehydrogenase, a 3-methyl-4,5-undecanediol dehydratase, and a 3-methyl-4(or 5)-undecanol dehydrogenase.

Additional embodiments include a method wherein the C—C ligation pathway may comprise at least one of a heptaldehyde/3-methyl-butyraldehyde lyase and wherein the reduction and dehydration pathway may comprise at least one of a 2-methyl-4,5-undecanediol dehydrogenase, a 2-methyl-4,5-undecanediol dehydratase, and a 2-methyl-4(or 5)-undecanol dehydrogenase. Additional embodiments include a method wherein the C—C ligation pathway may comprise at least one of a heptaldehyde/4-methyl-pentaldehyde lyase and wherein the reduction and dehydration pathway may comprise at least one of a 2-methyl-5,6-dodecanediol dehydrogenase, a 2-methyl-5,6-dodecanediol dehydratase, and a 2-methyl-5(or 6)-dodecanol dehydrogenase.

Additional embodiments include a method wherein the C—C ligation pathway may comprise at least one of a heptaldehyde/phenylacetaldehyde lyase and wherein the reduction and dehydration pathway may comprise at least one of a 1-phenyl-2,3-nonanediol dehydrogenase, a 1-phenyl-2,3-nonanediol dehydratase, and a 1-phenyl-2(or 3)-nonanol dehydrogenase. Additional embodiments include a method wherein the C—C ligation pathway may comprise at least one of a heptaldehyde/4-hydroxyphenylacetaldehyde lyase and wherein the reduction and dehydration pathway may comprise at least one of a 1-(4-hydroxyphenyl)-2,3-nonanediol dehydrogenase, a 1-(4-hydroxyphenyl)-2,3-nonanediol dehydratase, and a 1-(4-hydroxyphenyl)-2 (or 3)-nonanol dehydrogenase.

Additional embodiments include a method wherein the C—C ligation pathway may comprise at least one of a heptaldehyde/indoleacetaldehyde lyase and wherein the reduction and dehydration pathway may comprise at least one of a 1-indole-2,3-nonanediol dehydrogenase, a 1-indole-2,3-nonanediol dehydratase, and a 1-indole-2(or 3)-nonanol dehydrogenase. Additional embodiments include a method wherein the C—C ligation pathway may comprise at least one of an octaldehyde/isobutyraldehyde lyase and wherein the reduction and dehydration pathway may comprise at least one of a 2-methyl-3,4-undecanediol dehydrogenase, a 2-methyl-3,4-undecanediol dehydratase, and a 2-methyl-3(or 4)-undecanol dehydrogenase.

Additional embodiments include a method wherein the C—C ligation pathway may comprise at least one of an octaldehyde/2-methyl-butyraldehyde lyase and wherein the reduction and dehydration pathway may comprise at least one of a 3-methyl-4,5-dodecanediol dehydrogenase, a 3-methyl-4,5-dodecanediol dehydratase, and a 3-methyl-4(or 5)-dodecanol dehydrogenase. Additional embodiments include a method wherein the C—C ligation pathway may comprise at least one of an octaldehyde/3-methyl-butyraldehyde lyase and wherein the reduction and dehydration pathway may comprise at least one of a 2-methyl-4,5-dodecanediol dehydrogenase, a 2-methyl-4,5-dodecanediol dehydratase, and a 2-methyl-4(or 5)-dodecanol dehydrogenase.

Additional embodiments include a method wherein the C—C ligation pathway may comprise at least one of an octaldehyde/4-methyl-pentaldehyde lyase and wherein the reduction and dehydration pathway may comprise at least one of a 2-methyl-5,6-tridecanediol dehydrogenase, a 2-methyl-5,6-tridecanediol dehydratase, and a 2-methyl-5(or 6)-tridecanol dehydrogenase. Additional embodiments include a method wherein the C—C ligation pathway may comprise at least one of an octaldehyde/phenylacetaldehyde lyase and wherein the reduction and dehydration pathway may comprise at least one of a 1-phenyl-2,3-decanediol dehydrogenase, a 1-phenyl-2,3-decanediol dehydratase, and a 1-phenyl-2(or 3)-decanol dehydrogenase.

Additional embodiments include a method wherein the C—C ligation pathway may comprise at least one of an octaldehyde/4-hydroxyphenylacetaldehyde lyase and wherein the reduction and dehydration pathway may comprise at least one of a 1-(4-hydroxyphenyl)-2,3-decanediol dehydrogenase, a 1-(4-hydroxyphenyl)-2,3-decanediol dehydratase, and a 1-(4-hydroxyphenyl)-2 (or 3)-decanol dehydrogenase. Additional embodiments include a method wherein the C—C ligation pathway may comprise at least one of an octaldehyde/indoleacetaldehyde lyase and wherein the reduction and dehydration pathway may comprise at least one of a 1-indole-2,3-decanediol dehydrogenase, a 1-indole-2,3-decanediol dehydratase, and a 1-indole-2(or 3)-decanol dehydrogenase.

Additional embodiments include a method wherein the C—C ligation pathway may comprise at least one of an isobutyraldehyde/2-methyl-butyraldehyde lyase and wherein the reduction and dehydration pathway may comprise at least one of a 2,5-dimethyl-3,4-heptanediol dehydrogenase, a 2,5-dimethyl-3,4-heptanediol dehydratase, and a 2,5-dimethyl-3(or 4)-heptanol dehydrogenase. Additional embodiments include a method wherein the C—C ligation pathway may comprise at least one of an isobutyraldehyde/3-methyl-butyraldehyde lyase and wherein the reduction and dehydration pathway may comprise at least one of a 2,6-dimethyl-3,4-heptanediol dehydrogenase, a 2,6-dimethyl-3,4-heptanediol dehydratase, and a 2,6-dimethyl-3(or 4)-heptanol dehydrogenase.

Additional embodiments include a method wherein the C—C ligation pathway may comprise at least one of an isobutyraldehyde/4-methyl-pentaldehyde lyase and wherein the reduction and dehydration pathway may comprise at least one of a 2,7-dimethyl-3,4-octanediol dehydrogenase, a 2,7-dimethyl-3,4-octanediol dehydratase, and a 2,7-dimethyl-3(or 4)-octanol dehydrogenase. Additional embodiments include a method wherein the C—C ligation pathway may comprise at least one of an isobutyraldehyde/phenylacetaldehyde lyase and wherein the reduction and dehydration pathway may comprise at least one of a 1-phenyl-4-methyl-2,3-pentanediol dehydrogenase, a 1-phenyl-4-methyl-2,3-pentanediol dehydratase, and a 1-phenyl-4-methyl-2(or 3)-pentanol dehydrogenase.

Additional embodiments include a method wherein the C—C ligation pathway may comprise at least one of an isobutyraldehyde/4-hydroxyphenylacetaldehyde lyase and wherein the reduction and dehydration pathway may comprise at least one of a 1-(4-hydroxyphenyl)-4-methyl-2,3-pentanediol dehydrogenase, a 1-(4-hydroxyphenyl)-4-methyl-2,3-pentanediol dehydratase, and a 1-(4-hydroxyphenyl)-4-methyl-2(or 3)-pentanol dehydrogenase. Additional embodiments include a method wherein the C—C ligation pathway may comprise at least one of an isobutyraldehyde/indoleacetaldehyde lyase and wherein the reduction and dehydration pathway may comprise at least one of a 1-indole-4-methyl-2,3-pentanediol dehydrogenase, a 1-indole-4-methyl-2,3-pentanediol dehydratase, and a 1-indole-4-methyl-2(or 3)-pentanol dehydrogenase.

Additional embodiments include a method wherein the C—C ligation pathway may comprise at least one of a 2-methyl-butyraldehyde/3-methyl-butyraldehyde lyase and wherein the reduction and dehydration pathway may comprise at least one of a 2,6-dimethyl-4,5-octanediol dehydrogenase, a 2,6-dimethyl-4,5-octanediol dehydratase, and a 2,6-dimethyl-4(or 5)-octanol dehydrogenase. Additional embodiments include a method wherein the C—C ligation pathway may comprise at least one of a 2-methyl-butyraldehyde/4-methyl-pentaldehyde lyase and wherein the reduction and dehydration pathway may comprise at least one of a 3,8-dimethyl-4,5-nonanediol dehydrogenase, a 3,8-dimethyl-4,5-nonanediol dehydratase, and a 3,8-dimethyl-4(or 5)-nonanol dehydrogenase.

Additional embodiments include a method wherein the C—C ligation pathway may comprise at least one of a 2-methyl-butyraldehyde/phenylacetaldehyde lyase and wherein the reduction and dehydration pathway may comprise at least one of a 1-phenyl-4-methyl-2,3-hexanediol dehydrogenase, a 1-phenyl-4-methyl-2,3-hexanediol dehydratase, and a 1-phenyl-4-methyl-2(or 3)-hexanol dehydrogenase. Additional embodiments include a method wherein the C—C ligation pathway may comprise at least one of a 2-methyl-butyraldehyde/4-hydroxyphenylacetaldehyde lyase and wherein the reduction and dehydration pathway may comprise at least one of a 1-(4-hydroxyphenyl)-4-methyl-2,3-hexanediol dehydrogenase, a 1-(4-hydroxyphenyl)-4-methyl-2,3-hexanediol dehydratase, and a 1-(4-hydroxyphenyl)-4-methyl-2 (or 3)-hexanol dehydrogenase.

Additional embodiments include a method wherein the C—C ligation pathway may comprise at least one of a 2-methyl-butyraldehyde/indoleacetaldehyde lyase and wherein the reduction and dehydration pathway may comprise at least one of a 1-indole-4-methyl-2,3-hexanediol dehydrogenase, a 1-indole-4-methyl-2,3-hexanediol dehydratase, and a 1-indole-4-methyl-2(or 3)-hexanol dehydrogenase. Additional embodiments include a method wherein the C—C ligation pathway may comprise at least one of a 3-methyl-butyraldehyde/4-methyl-pentaldehyde lyase and wherein the reduction and dehydration pathway may comprise at least one of a 2,8-dimethyl-4,5-nonanediol dehydrogenase, a 2,8-dimethyl-4,5-nonanediol dehydratase, and a 2,8-dimethyl-4(or 5)-nonanol dehydrogenase.

Additional embodiments include a method wherein the C—C ligation pathway may comprise at least one of a 3-methyl-butyraldehyde/phenylacetaldehyde lyase and wherein the reduction and dehydration pathway may comprise at least one of a 1-phenyl-5-methyl-2,3-hexanediol dehydrogenase, a 1-phenyl-5-methyl-2,3-hexanediol dehydratase, and a 1-phenyl-5-methyl-2(or 3)-hexanol dehydrogenase. Additional embodiments include a method wherein the C—C ligation pathway may comprise at least one of a 3-methyl-butyraldehyde/4-hydroxyphenylacetaldehyde lyase and wherein the reduction and dehydration pathway may comprise at least one of a 1-(4-hydroxyphenyl)-5-methyl-2,3-hexanediol dehydrogenase, a 1-(4-hydroxyphenyl)-5-methyl-2,3-hexanediol dehydratase, and a 1-(4-hydroxyphenyl)-5-methyl-2(or 3)-hexanol dehydrogenase.

Additional embodiments include a method wherein the C—C ligation pathway may comprise at least one of a 3-methyl-butyraldehyde/indoleacetaldehyde lyase and wherein the reduction and dehydration pathway may comprise at least one of a 1-indole-5-methyl-2,3-hexanediol dehydrogenase, a 1-indole-5-methyl-2,3-hexanediol dehydratase, and a 1-indole-5-methyl-2(or 3)-hexanol dehydrogenase. Additional embodiments include a method wherein the C—C ligation pathway may comprise at least one of a 4-methyl-pentaldehyde/phenylacetaldehyde lyase and wherein the reduction and dehydration pathway may comprise at least one of a 1-phenyl-6-methyl-2,3-heptanediol dehydrogenase, a 1-phenyl-6-methyl-2,3-heptanediol dehydratase, and a 1-phenyl-6-methyl-2(or 3)-heptanol dehydrogenase.

Additional embodiments include a method wherein the C—C ligation pathway may comprise at least one of a 4-methyl-pentaldehyde/4-hydroxyphenylacetaldehyde lyase and wherein the reduction and dehydration pathway may comprise at least one of a 1-(4-hydroxyphenyl)-6-methyl-2,3-heptanediol dehydrogenase, a 1-(4-hydroxyphenyl)-6-methyl-2,3-heptanediol dehydratase, and a 1-(4-hydroxyphenyl)-6-methyl-2(or 3)-heptanol dehydrogenase. Additional embodiments include a method wherein the C—C ligation pathway may comprise at least one of a 4-methyl-pentaldehyde/Indoleacetaldehyde lyase and wherein the reduction and dehydration pathway may comprise at least one of a 1-indole-6-methyl-2,3-heptanediol dehydrogenase, a 1-indole-6-methyl-2,3-heptanediol dehydratase, and a 1-indole-6-methyl-2(or 3)-heptanol dehydrogenase.

Additional embodiments include a method wherein the C—C ligation pathway may comprise at least one of a phenylacetaldehyde/4-hydroxyphenylacetaldehyde lyase and wherein the reduction and dehydration pathway may comprise at least one of a 1-(4-hydroxyphenyl)-4-phenyl-2,3-butanediol dehydrogenase, a 1-(4-hydroxyphenyl)-4-phenyl-2,3-butanediol dehydratase, and a 1-(4-hydroxyphenyl)-4-phenyl-2(or 3)-butanol dehydrogenase. Additional embodiments include a method wherein the C—C ligation pathway may comprise at least one of a phenylacetaldehyde/indolephenylacetaldehyde lyase and wherein the reduction and dehydration pathway may comprise at least one of a 1-indole-4-phenyl-2,3-butanediol dehydrogenase, a 1-indole-4-phenyl-2,3-butanediol dehydratase, and a 1-indole-4-phenyl-2(or 3)-butanol dehydrogenase.

Additional embodiments include a method wherein the C—C ligation pathway may comprise at least one of a 4-hydroxyphenylacetaldehyde/indolephenylacetaldehyde lyase and wherein the reduction and dehydration pathway may comprise at least one of a 1-indole-4-(4-hydroxyphenyl)-2,3-butanediol dehydrogenase, a 1-indole-4-(4-hydroxyphenyl)-2,3-butanediol dehydratase, and a 1-indole-4-(4-hydroxyphenyl)-2(or 3)-butanol dehydrogenase. Additional embodiments include a method wherein the C—C ligation pathway may comprise a 5-amino-pantaldehyde lyase, and wherein the reduction and dehydration pathway may comprise at least one of a 1,10-diamino-5,6-decanediol dehydrogenase, a 1,10-diamino-5,6-decanediol dehydratase, and a 1,10-diamino-5-decanol dehydrogenase.

Additional embodiments include a method wherein the C—C ligation pathway may comprise a 4-hydroxyphenyl acetaldehyde lyase, and wherein the reduction and dehydration pathway may comprise at least one of a 1,4-di(4-hydroxyphenyl)-2,3-butanediol, a 1,4-di(4-hydroxyphenyl)-2,3-butanediol dehydratase, and a 1,4-di(4-hydroxyphenyl)-2-butanol dehydrogenase. Additional embodiments include a method wherein the C—C ligation pathway may comprise a succinate semialdehyde lyase, and wherein the reduction and dehydration pathway may comprise at least one of a 2,3-hexanediol-1,6-dicarboxylic acid dehydrogenase, a 2,3-hexanediol-1,6-dicarboxylic acid dehydratase, and a 2-hexanol-1,6-dicarboxylic dehydrogenase.

Certain embodiments of a microbial system or recombinant microorganism may comprise genes encoding enzymes that are able to catalyze (e.g., reduction and dehydration) the conversion of 4-octanol to octene or octane. Other embodiments may comprise redesigned or de novo designed enzymes for this reduction and dehydration pathway. For example, three redesigned enzymes could convert 4-octanone to either 3- and 4-octene. The first step could be catalyzed by redesigned isocitrate dehydrogenase. This enzyme could catalyze the formation of 4-hydroxy-3(or 5)-carboxylic octane. The 4-hydroxy group could be phosphorylated by redesigned kinase. Finally, redesigned mevalonate diphosphate decarboxylase catalyzes the formation of 3(or 4)-octene.

In other embodiments, several redesigned enzymes could convert 4-octanone to octane. For example, the 4-hydroxy-3 (or 5)-carboxylic octane is sequentially reduced and dehydrated to form 3(or 5)-carboxylic octane. Redesigned enzymes involved in fatty acid metabolism can catalyze these reactions. The 3(or 5)-carboxylic octane can be reduced to corresponding aldehyde by aldehyde dehydrogenase and the product may be decarbonylated to form octane catalyzed by a redesigned decarbonylase.

As noted above, for the production of certain commodity chemicals, such as 2-phenylethanol, 2-(4-hydroxyphenyl) ethanol, and indole-3-ethanol, among other similar chemicals, a biosynthesis pathway (e.g., aldehyde biosynthesis pathway) may optionally or further comprise one or more genes encoding a decarboxylase enzyme, such as an indole-3-pyruvate decarboxylase (IPDC), to produce an aldehyde. In certain aspects, an IPDC may comprise an amino acid sequence that is at least 80%, 90%, 95%, 98%, or 99% identical to the amino acid sequence set forth in SEQ ID NO:312. An IDPC enzyme may comprise certain conserved amino acid residues, such as G24, D25, E48, A55, R60, G75, E89, H113, G252, G405, G413, G428, G430, and/or N456.

In these and other embodiments, a recombinant microorganism may comprise an aldehyde reductase, such as a phenylacetoaldehyde reductase (PAR), to convert an aldehyde to a commodity chemical. In certain aspects, a PAR may comprise an amino acid sequence that is at least 80%, 90%, 95%, 98%, or 99% identical to the amino acid sequence set forth in SEQ ID NO:313, which shows the sequence of a PAR enzymed derived from *Rhodococcus* sp. ST-10. In certain aspects, a PAR enzyme may comprise at least one of a nicotinamide adenine dinucleotide (NAD+), NADH, nicotinamide adenine dinucleotide phosphate (NADP+), or NADPH binding motif. In certain embodiments, the NAD+, NADH, NADP+, or NADPH binding motif may be selected from the group consisting of Y-X-G-G-X-Y, Y-X-X-G-G-X-Y, Y-X-X-X-G-G-X-Y, Y-X-G-X-X-Y, Y-X-X-G-G-X-X-Y, Y-X-X-X-G-X-X-Y, Y-X-G-X-Y, Y-X-X-G-X-Y, Y-X-X-X-G-X-Y, and Y-X-X-X-X-G-X-Y; wherein Y is independently selected from alanine, glycine, and serine, wherein G is glycine, and wherein X is independently selected from a genetically encoded amino acid.

In certain embodiments, such a recombinant microorganism may also or alternatively comprise a secondary alcohol dehydrogenase having an activity selected from at least one of a phenylethanol dehydrogenase activity, a 4-hydroxyphenylethanol dehydrogenase activity, and an Indole-3-ethanol dehydrogenase activity, to reduce the aldehyde to its corresponding alcohol (e.g. 2-phenylethanol, 2-(4-hydroxyphenyl)ethanol, and indole-3-ethanol).

Embodiments of the present invention also include methods for converting a suitable monosaccharide to a commodity chemical comprising, (a) obtaining a suitable monosaccharide; (b) contacting the suitable monosaccharide with a microbial system for a time sufficient to convert to the suitable monosaccharide to the biofuel, wherein the microbial system comprises, (i) one or more genes encoding and expressing a fatty acid biosynthesis pathway, an amino acid biosynthetic pathway, and/or a short chain alcohol biosynthetic pathway; (ii) one or more genes encoding and expressing a keto-acid decarboxylase, aldehyde dehydrogenase, and/or alcohol dehydrogenase; and (iii) an enzymatic reduction pathway selected from (1) an enzymatic long chain alcohol reduction pathway, (2) an enzymatic decarbonylation pathway, (3) an enzymatic decarboxylation pathway, and (4) an enzymatic reduction pathway comprising (1), (2), and/or (3), thereby converting the suitable monosaccharide to the commodity chemical.

Embodiments of the present invention may comprise one or more genes encoding and expressing enzymes in a fatty acid synthesis pathway, which may be used, as one example, to produce biofuels in the form of alkanes, such as medium to long chain alkanes. In certain embodiments, the specificity of the fatty acid biosynthesis pathway in the microbial system may be recalibrated or redesigned. Merely by way of example, microorganisms generally produce a mixture of long chain fatty acids (e.g., *E. coli* naturally produce large quantities of long chain fatty acids (C16-C19: <95% in whole cells) and small quantity of medium chain fatty acids (C12: 2% and C14: 5% in whole cells)).

In certain embodiments, the recalibration or re-engineering may be directed to increasing production of medium chain alkanes, including, but not limited to, caprylate (C8), caprate (C10), laurate (C12), myristate (C14), and palmitate (C16), as alkanes produced from these fatty acids are major components of gasoline, diesels, and kerosene. In addition to these fatty acids, other embodiments may be directed to increased production of long chain fatty acids, including, but not limited to, stearate (C18), arachidonate (C20), behenate (C22) and longer fatty acids, as n-alkanes produced from these fatty acids are one of major components in heavy oils.

For example, *Cuphea* mainly accumulate medium chain fatty acids as major components in their seed oils, and these compositions alter depending on species. In particular, *Cuphea pulcherrima* accumulates caprylate (C8:0) 96%, *Cuphea koehneana* accumulates caprate (C10:0) 95.3%, and *Cuphea polymorpha* accumulates laurate (C12:0) 80.1%. Embodiments of the microbial systems or isolated microorganisms according to the present application may incorporate genes from various *Cuphea* species encoding enzymes involved in a fatty acid biosynthesis pathway, and these microorganisms may be directed in part to the production of middle chain fatty acids.

In other embodiments, acyl-acyl carrier protein (ACP) thioesterases (TEs) derived from various species including *Cuphea hookeriana, Cuphea palustris, Umbellularia californica*, and *Cinnamomum camphorum* may be over-expressed in such microorganisms as *E. coli*, wherein the specific activity for the formation of each medium chain fatty acids, caprylate (C8), caprate (C10), laurate (C12), myristate (C14), and palmitate (C16) is improved over the wild type. Certain embodiments may include other enzyme components involved in fatty acid biosynthesis as known to a person skilled in the arts, including, but not limited to, ACP and β-ketoacyl ACP synthase (KAS) IV.

Microbial systems and isolated microorganisms of the present application may also incorporate fatty aldehyde dehydrogenases to reduce fatty acids to fatty aldehydes. Merely by way of explanation, the conversion of fatty acids to fatty aldehydes may be catalyzed by medium and/or long chain fatty aldehyde dehydrogenases isolated from various suitable organisms. Certain embodiments may incorporate, for example, a fatty aldehyde dehydrogenase derived from *Vibrio harveyi*.

Microbial systems and isolated microorganisms of the present application may also incorporate one or more enzymes that catalyze the conversion of fatty aldehydes to biofuels such as n-alkanes, including, for example, enzymes comprising an enzymatic long chain alcohol reduction pathway. Certain embodiments may incorporate genes from various other sources that encode enzymes capable of catalyzing the reduction and dehydration of fatty acids to biofuels, such as alkanes. For example, bacterial strain HD-1 is able to produce biofuels, such as n-alkanes, with various chain lengths, and also produces both odd and even numbered alkanes. Certain embodiments of the microbial systems and recombinant microorganisms provided herein may incorporate the HD-1 genes encoding the enzymes involved in this pathway.

Other embodiments may incorporate redesigned or de novo designed enzymes for this reduction pathway. For example, embodiments of the present invention may include a redesigned isocitrate dehydrogenase, which may catalyze the formation of 2-carboxy-1-alcohols. In certain embodiments, the 2-carboxy-1-alcohols may be sequentially reduced and dehydrated to form 2-carboxy-alkanes, which may be catalyzed by redesigned enzymes involved in fatty acid metabolism. The 2-carboxy-alkanes can be reduced to corresponding aldehyde by aldehyde dehydrogenase and then decarbonylated to form n-alkanes catalyzed by the redesigned decarbonylase as discussed below. Certain embodiments of these microbial systems may produce either even numbered n-alkanes, odd numbered n-alkanes, or both.

Certain embodiments of the present application may incorporate the genes encoding enzymes catalyzing decarbonylation, or an enzymatic decarbonylation pathway. Merely by way of example, green colonial alga *Botyrococcus braunii*, race A, produces linear odd-numbered C27, C29, and C31 hydrocarbons that total up to 32% of the alga's dry weight. Microsomal preparations of this organism have decarbonylation activity. This decarbonylase from *B. braunii* culture is a cobalt-protoporphyrin IX containing enzyme. Certain microbial systems of isolated microorganisms may incorporate the gene encoding fatty aldehyde decarbonylase from *Botyrococcus braunii*.

Other embodiments may include redesigned decarbonylase enzymes, for example, wherein the N-terminal membrane sequence is substituted. By way of explanation, the functional activity of a similar enzyme, cytochrome P450 containing Fe-protopolphyrin IX (heme), is improved by substituting N-terminal membrane associated sequence, and the functional activity of decarbonylases of the present microbial systems may comprise similar substitutions or improvements.

Other embodiments may incorporate the genes encoding a Co-porphyrin synthase. In explanation, decarbonylase enzymes may use Co-protoporphyrin IX as a co-factor, and *Clostridium tetranomorphum* is able to incorporate cobalt into incubated protopolphyrin IX. Certain embodiments may incorporate the Co-porphyrin synthase from *Clostridium tetranomorphum*, or from other suitable microorganisms. Other embodiments may incorporate de novo designed decarbonylation enzymes using inorganic metals such as $Co^{2+}$, $Fe^{2+}$, and $Ni^{2+}$ as catalysts.

Certain embodiments may comprise genes encoding the enzymes responsible for the formation of alkenes, or an enzymatic decarboxylation pathway. These genes may be derived or isolated from various sources, such as higher plants and insects. For example, higher plants such as germinating safflower (*Carthamus tinctorius* L.) produce a number of odd numbered 1-alkenes, including 1-pentadecene, 1-heptadecene, 1,8-heptadecadiene and 1,8,11-heptadecatriene besides about 80-90% 1,8,11,14-heptadecatetraene by decarboxylation from their corresponding fatty acids. Certain embodiments may incorporate the genes from higher plants such as *Carthamus tinctorius*.

Other embodiments may incorporate the genes encoding the enzymes responsible for the formation of alkenes (e.g., an enzymatic decarboxylation pathway) from microorganisms, including, but not limited to, such as bacterial strain DH-1. By way of explanation, bacterial strain DH-1 produces n-alkenes in addition to n-alkanes.

Other embodiments may incorporate the genes from de novo designed enzymes for an enzymatic decarboxylation pathway. For example, these redesigned enzymes convert β-hydroxy fatty acids to n-alkenes. The first step is catalyzed by a redesigned kinase, which catalyzes the phosphorylation of a β-hydroxy group. A redesigned mevalonate diphosphate decarboxylase then catalyzes the formation of n-alkenes, such as n-1-alkene.

Any microorganism may be utilized according to the present invention. In certain aspects, a microorganism is a eukaryotic or prokaryotic microorganism. In certain aspects, a microrganism is a yeast, such as *S. cerevisiae*. In certain aspects, a microorganism is a bacteria, such as a gram-positive bacteria or a gram-negative bacteria. Given its rapid growth rate, well-understood genetics, the variety of available genetic tools, and its capability in producing heterologous proteins, genetically modified *E. coli* may be used in certain embodiments of a microbial system as described herein, whether for the degradation and metabolism of a polysaccharide, such as alginate or pectin, or the formation or biosynthesis of commodity chemicals, such as biofuels.

Other microorganisms may be used according to the present invention, based in part on the compatibility of enzymes and metabolites to host organisms. For example, other organisms such as *Acetobacter aceti, Achromobacter, Acidiphilium, Acinetobacter, Actinomadura, Actinoplanes, Aeropyrum pernix, Agrobacterium, Alcaligenes, Ananas comosus* (M), *Arthrobacter, Aspargillus niger, Aspargillus oryze, Aspergillus melleus, Aspergillus pulverulentus, Aspergillus saitoi, Aspergillus sojea, Aspergillus usamii, Bacillus alcalophilus, Bacillus amyloliquefaciens, Bacillus brevis, Bacillus circulans, Bacillus clausii, Bacillus lentus, Bacillus licheniformis, Bacillus macerans, Bacillus stearothermophilus, Bacillus subtilis, Bifidobacterium, Brevibacillus brevis, Burkholderia cepacia, Candida cylindracea, Candida rugosa, Carica papaya* (L), *Cellulosimicrobium, Cephalosporium, Chaetomium erraticum, Chaetomium gracile, Clostridium, Clostridium butyricum, Clostridium acetobutylicum, Clostridium thermocellum, Corynebacterium* (glutamicum), *Corynebacterium efficiens, Escherichia coli, Enterococcus, Erwina chrysanthemi, Gliconobacter, Gluconacetobacter, Haloarcula, Humicola insolens, Humicola nsolens, Kitasatospora setae, Klebsiella, Klebsiella oxytoca, Kluyveromyces, Kluyveromyces fragilis, Kluyveromyces lactis, Kocuria, Lactlactis, Lactobacillus, Lactobacillus fermentum, Lactobacillus sake, Lactococcus, Lactococcus lactis, Leuconostoc, Methylocystis, Methanolobus siciliae, Methanogenium organophilum, Methanobacterium bryantii, Microbacterium imperiale, Micrococcus lysodeikticus,*

*Microlunatus, Mucor javanicus, Mycobacterium, Myrothecium, Nitrobacter, Nitrosomonas, Nocardia, Papaya carica, Pediococcus, Pediococcus halophilus, Penicillium, Penicillium camemberti, Penicillium citrinum, Penicillium emersonii, Penicillium roqueforti, Penicillum lilactinum, Penicillium multicolor, Paracoccus pantotrophus, Propionibacterium, Pseudomonas, Pseudomonas fluorescens, Pseudomonas denitrificans, Pyrococcus, Pyrococcus furiosus, Pyrococcus horikoshii, Rhizobium, Rhizomucor miehei, Rhizomucor pusillus Lindt, Rhizopus, Rhizopus delemar, Rhizopus japonicus, Rhizopus niveus, Rhizopus oryzae, Rhizopus oligosporus, Rhodococcus, Sccharomyces cerevisiae, Sclerotina libertina, Sphingobacterium multivorum, Sphingobium, Sphingomonas, Streptococcus, Streptococcus thermophilus Y-1, Streptomyces, Streptomyces griseus, Streptomyces lividans, Streptomyces murinus, Streptomyces rubiginosus, Streptomyces violaceoruber, Streptoverticillium mobaraense, Tetragenococcus, Thermus, Thiosphaera pantotropha, Trametes, Trichoderma, Trichoderma longibrachiatum, Trichoderma reesei, Trichoderma viride, Trichosporon penicillatum, Vibrio alginolyticus, Xanthomonas,* yeast, *Zygosaccharomyces rouxii, Zymomonas,* and *Zymomonus mobilis,* may be utilized as recombinant microorganisms provided herein, and, thus, may be utilized according to the various methods of the present invention.

The following Examples are offered by way of illustration, not limitation.

EXAMPLES

Example 1

Engineering E. Coli to Grow on Alginate as a Sole Source of Carbon

Wild type *E. coli* cannot use alginate polymer or degraded alginate as its sole carbon source (see FIG. 4). *Vibrio splendidus*, however, is known to be able to metabolize alginate to support growth. To generate recombinant *E. coli* that use degraded alginate as its sole carbon source, a *Vibrio splendidus* fosmid library was constructed and cloned into *E. coli*.

To prepare the *Vibrio splendidus* fosmid library, genomic DNA was isolated from *Vibrio Splendidus* B01 (gift from Dr. Martin Polz, MIT) using the DNeasy Blood and Tissue Kit (Qiagen, Valencia, Calif.). A fosmid library was then constructed using Copy Control Fosmid Library Production Kit (Epicentre, Madison, Wis.). This library consisted of random genomic fragments of approximately 40 kb inserted into the vector pCC1FOS (Epicentre, Madison, Wis.).

The fosmid library was packaged into phage, and *E. coli* DH10B cells harboring a pDONR221 plasmid (Invitrogen, Carlsbad, Calif.) carrying certain *Vibrio splendidus* genes (V12B01_02425 to V12B01_02480; encoding a type II secretion apparatus; see SEQ ID NO:1) were transfected with the phage library. This secretome region encodes a type II secretion apparatus derived from *Vibrio splendidus*, which was cloned into a pDONR221 plasmid and introduced into *E. coli* strain DH10B (see Example 1).

Transformants were selected for chloroamphenicol resistance and then screened for their ability to grow on degraded alginate. The resultant transformants were screened for growth on degraded alginate media. Degraded alginate media was prepared by incubating 2% Alginate (Sigma-Aldrich, St. Louis, Mo.) 10 mM Na-Phosphate buffer, 50 mM KCl, 400 mM NaCl with alginate lyase from *Flavobacterium* sp. (Sigma-Aldrich, St. Louis, Mo.) at room temperature for at least one week. This degraded alginate was diluted to a concentration of 0.8% to make growth media that had a final concentration of 1×M9 salts, 2 mM MgSO$_4$, 100 µM CaCl2, 0.007% Leucine, 0.01% casamino acids, 1.5% NaCl (this includes all sources of sodium: M9, diluted alginate and added NaCl).

One fosmid-containing *E. coli* clone was isolated that grew well on this media. The fosmid DNA from this clone was isolated and prepared using FosmidMAX DNA Purification Kit (Epicentre, Madison, Wis.). This isolated fosmid was transferred back into DH10B cells, and these cells were tested for the ability to grown on alginate.

Figure 4:
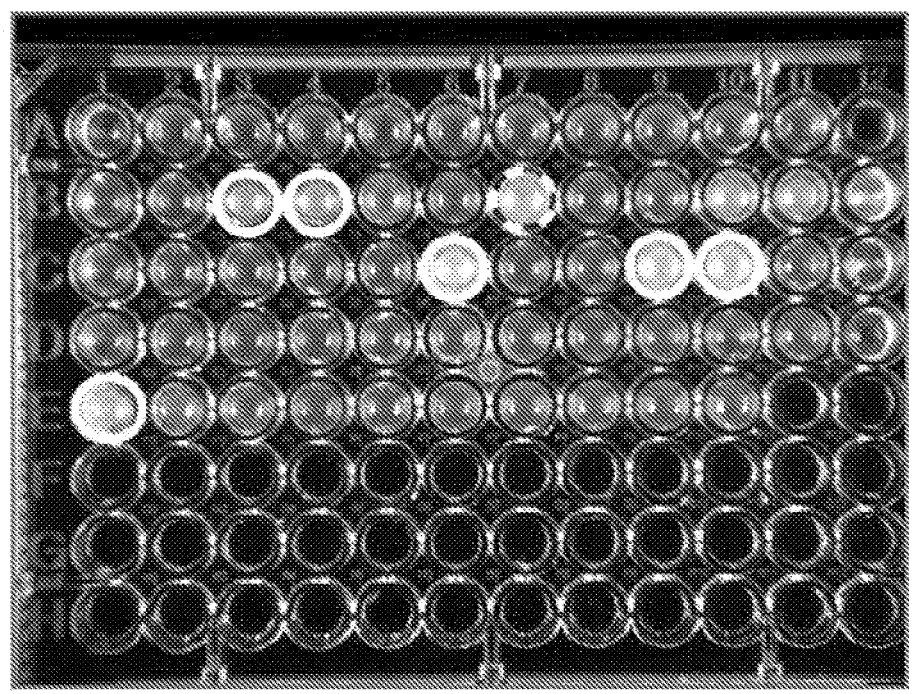
FIG. 4 shows the results of engineered or recombinant *E. coli* growing on alginate as a sole source of carbon (see solid circles). *Agrobacterium tumefaciens* cells provide a positive control (see hatched circles). The well to the immediate left of the of the *A. tumefaciens* positive control contains DH10B *E. coli* cells, which provide a negative control.

The results are illustrated in FIG. 4, which shows that certain fosmid-containing *E. coli* clones are capable of growing on alginate as a sole source of carbon. *Agrobacterium tumefaciens* provides a positive control (see hatched circles). As a negative control, *E. coli* DH10B cells are not capable of growing on alginate (see immediate left of positive control).

These results also demonstrate that the sequences contained within this *Vibrio splendidus* derived fosmid clone are sufficient to confer on *E. coli* the ability to grow on degraded alginate as a sole source of carbon. Accordingly, the type II secretion machinery sequences contained within the pDONR221 vector (i.e., SEQ ID NO:1), which was harbored by the original DH10B cells, were not necessary for growth on degraded alginate.

The isolated fosmid sufficient to confer growth alginate as a sole source of carbon was sequenced by Elim Biopharmaceuticals (Hayward, Calif.) using the following primers: Uni R3—GGGCGGCCGCAAGGGGTTCGCGTTGGCCGA (SEQ ID NO:147) and PCC1FOS_uni_F— GGAGAAAATACCGCATCAGGCG (SEQ ID NO:148). Sequencing showed that the vector contained a genomic DNA section that contained the full length genes V12B01_24189 to V12B01_24249 (see SEQ ID NOS:2-64). SEQ ID NO:2 shows the nucleotide sequence of entire region between V12B01_24189 to V12B01_24249. SEQ ID NOS:3-64 show the individual putative genes contained within SEQ ID NO:2. In this sequence, there is a large gene before V12B01_24189 that is truncated in the fosmid clone. The large gene V12B01_24184 is a putative protein with similarity to autotransporters and belongs to COG3210, which is a cluster of orthologous proteins that include large exoproteins involved in heme utilization or adhesion. In the fosmid clone, V12B01_24184 is N-terminally truncated such that the first 5893 bp are missing from the predicted open reading frame (which is predicted to contain 22889 bp in total).

Example 2

Engineering E. Coli to Grow on Pectin as a Sole Source of Carbon

Wild type *E. coli* is not capable of growing on pectin, di-, or tri-galacturonates as a sole source of carbon. To identify the minimal components to confer on *E. coli* the capability of growing on pectin, di- and/or tri-galacturonates as a sole source of carbon, an *E. coli* strain BL21(DE3) harboring both the pBBRGal3P plasmid and the pTrcogl-kdgR plasmid was engineered and tested for the ability to grown on these polysaccharides.

The pBBRGal3P plasmid was engineered to contain certain genomic region of *Erwinia carotovora* subsp. *Atroseptica* SCRI 1043, comprising several genes (kdgF, kduI, kduD, pelW, togM, togN, toga, togB, kdgM, and paeX) encoding certain enzymes (kduI, kduD, ogl, pelW and paeX), transporters (togM, togN, togA, togB, and kdgM), and regulatory proteins (kdgR) responsible for the degradation of di- and trigalacturonate. SEQ ID NO:65 shows the nucleotide sequence of the kdgF-PaeX region from *Erwinia carotovora* subsp. *Atroseptica* SCRI1043.

To construct this plasmid, the DNA sequence encoding kduI, kduD, pelW, togM, togN, togA, togB, kdgM, paeX, ogl, and kdgR of *Erwinia carotovora* subsp. *Atroseptica* SCRI 1043 was amplified by polymerase chain reaction (PCR): 98° C. for 10 sec, 60° C. for 15 sec, and 72° C. for 6 min, repeated 30 times. The reaction mixture contained 1× Phusion buffer (NEB), 2 mM dNTP, 0.5 µM forward (5'-CG GGATCC AAGTTGCAGGATATGACGAAAGCG-3') (SEQ ID NO:149) and reverse (5'-GCTCTAGA AGATTATC-CCTGTCTGCGGAAGCGG-3') (SEQ ID NO:150) primers, 1 U Phusion High Fidelity DNA polymerase (NEB), and 50 ng *Erwinia carotovora* subsp. *Atroseptica* SCRI 1043 genome (ATCC) in 50 µl.

The vector pBBR1MCS-2 was then amplified by polymerase chain reaction (PCR): 98° C. for 10 sec, 60° C. for 15 sec, and 72° C. for 2.5 min, repeated 30 times. The reaction mixture contained 1× Phusion buffer (NEB), 2 mM dNTP, 0.5 µM forward (5'-GCTCTAGA GGGGTGCCTAATGAGT-GAGCTAAC-3') (SEQ ID NO:151) and reverse (5'-CGG-GATCC GCGTTAATATTTTGTTAAAATTCGC-3') (SEQ ID NO:152) primers, 1 U Phusion High Fidelity DNA polymerase (NEB), and 50 ng pBBR1MCS-2 in 50 µl. Both amplified DNA fragments were digested with BamHI and XbaI and ligated.

The pTrcogl-kdgR plasmid was engineered to contain certain genomic regions of *Erwinia carotovora* subsp. *Atroseptica* SCRI 1043, comprising two genes (ogl and kdgR) encoding an enzyme (ogl) and a regulatory protein (kdgR) responsible for degradation of di- and trigalacturonate. SEQ ID NO:66 shows the nucleotide sequence of ogl-kdgR from *Erwinia carotovora* subsp. *Atroseptica* SCRI1043.

To prepare this construct, the DNA sequence encoding ogl and kdgR of *Erwinia carotovora* subsp. *Atroseptica* SCRI 1043 was amplified by polymerase chain reaction (PCR): 98° C. for 10 sec, 60° C. for 15 sec, and 72° C. for 4 min, repeated 30 times. The reaction mixture contained 1× Phusion buffer (NEB), 2 mM dNTP, 0.5 µM forward (5'-GCTCTAGA GTT-TATGTCGCACCCGCCGTTGG-3') (SEQ ID NO:153) and reverse (5'-CCCAAGC TTAGAAAGGGAAATTGTGG-TAGCCC-3') (SEQ ID NO:154) primers, 1 U Phusion High Fidelity DNA polymerase (NEB), and 50 ng *Erwinia carotovora* subsp. *Atroseptica* SCRI 1043 genome (ATCC) in 50 µl. The amplified DNA fragment was digested with XbaI and HindIII and ligated into pTrc99A pre-digested with the same restriction enzymes.

The plasmids pBBRGal3P and pTrcogl-kdgR were co-transformed into *E. coli* strain BL21(DE3). A single colony was inoculated into LB media containing 50 ug/ml kanamycin and 100 ug/ml ampicillin, and the culture was grown in incubation shaker with 200 rpm at 37 C. When culture reached OD 600 nm of 0.6, 500 ul of culture was transferred to eppendorf tube and centrifuged to pellet the cells. The cells were resuspended into 50 ul of M9 media containing 2 mM $MgSO_4$, 100 uM $CaCl_2$, 0.4% di- or trigalacturonate, and 5 ul of this solution was inoculated into 500 ul of fresh M9 media containing 2 mM $MgSO_4$, 100 uM $CaCl_2$, 0.4% di- or trigalacturonate. The culture was grown in incubation shaker with 200 rpm at 37 C.

Figure 5A:
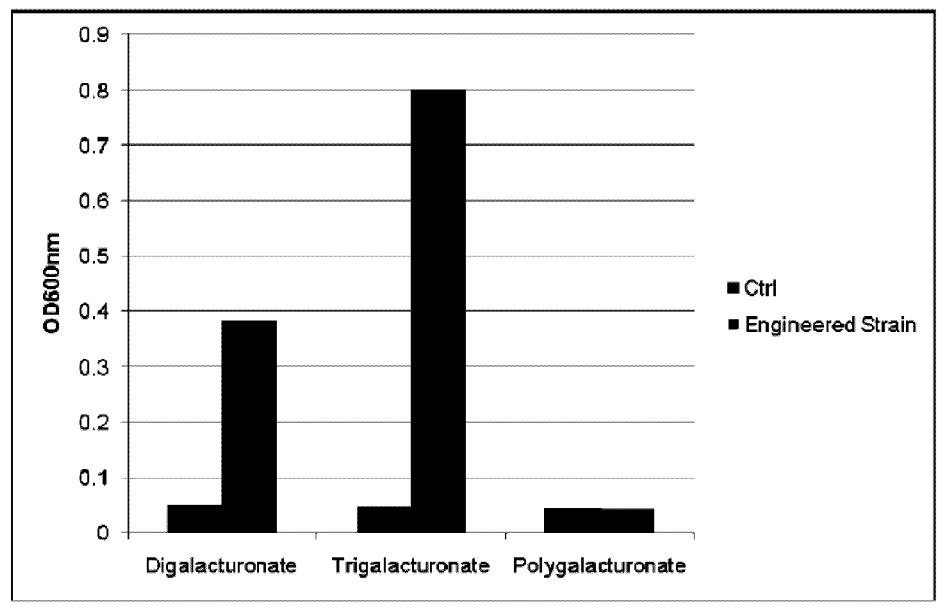
FIG. 5A shows the growth of *E. coli* on various lengths of galacturonate after 24 hr. The recombinant strain in FIG. 5A is the *E. coli* BL21(DE3) strain harboring pTrlogl-kdgR+pBBRGal3P, and the control strain is the BL21(DE3) strain harboring pTrc99A+pBBR1MCS-2, as described in Example 2.

The results in FIG. 5A show that these two plasmids were sufficient to provide *E. coli* ability to grow on di- and trigalacturonate as sole source of carbon, but not pectin. In particular, these results show that the regions kdgF-paeX and ogl-kdgR were sufficient to confer this ability on *E. coli*.

Based on the information obtained from the above experiments, it was considered whether the introduction of pectate lyase, pectate acetylesterase, and methylesterase might confer *E. coli* capability of growing on pectin. To test this hypothesis, *E. coli* strain DH5α bacterial cells were engineered to contain both the pROU2 plasmid and the pPEL74 plasmid.

The pROU2 plasmid contains certain genomic regions of *Erwinia chrysanthemi*, comprising several genes (kdgF, kduI, kduD, pelW, togM, togN, togA, togB, kdgM, paeX, ogl, and kdgR) encoding enzymes (kduI, kduD, ogl, pelW, and paeX), transporters (togM, togN, togA, togB, and kdgM), and regulatory proteins (kdgR) responsible for degradation of di- and trigalacturonate.

The pPEL74 plasmid contains certain genomic regions of *Erwinia chrysanthemi*, comprising several genes (pelA, pelE, paeY, and pem) encoding pectate lyases (pelA and pelE), pectin acetylesterases (paeY), and pectin methylesterase (pem).

Figure 5B:
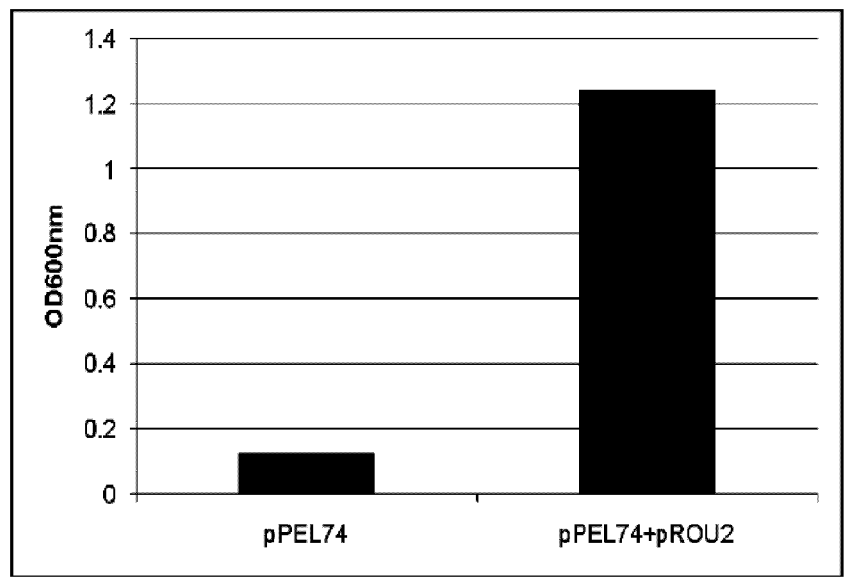
FIG. 5B shows the growth of recombinant *E. coli* on pectin after 3-4 days. The recombinant strain in FIG. 5B is *E. coli* DH5a strain containing pPEL74 (Ctrl) and pPEL74 and pROU2, as described in Example 2.

As shown in FIG. 5B, *E. coli* DH5a engineered with pROU2 and pPEL74 was able to grow on pectin as a sole source of carbon, showing that the genes contained within these plasmids are sufficient to confer this property on an organism that is otherwise incapable of growing on pectin as a sole source of carbon.

Example 3

In Vitro Conversion of Alginate to Pyruvate and Glyceraldehyde-3-Phosphate

The ability of an enzyme mixture containing all required enzymes for alginate degradation and metabolism was investigated for its ability to produce pyruvate from alginate. In addition, various novel alcohol dehydrogenases (ADHs), such as ADH1-12 (see SEQ ID NOS:69-92), isolated from *Agrobacterium tumefaciens*, were tested for their ability to catalyze either DEHU or mannuronate hydrogenation.

Figure 2:
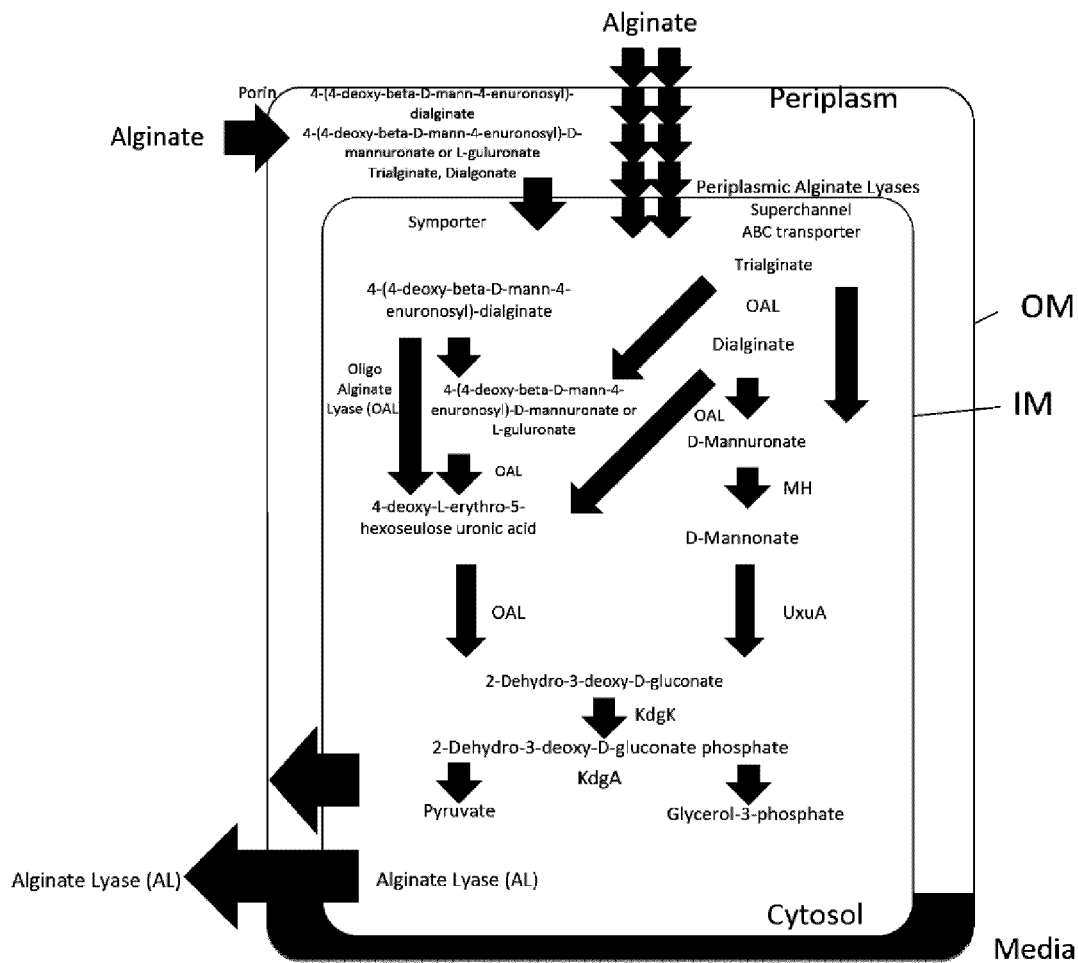
FIG. 2 illustrates the pathways involved in certain embodiment in which *E. coli* may be engineered to grow on alginate as a sole source of carbon.

A simplified metabolic pathway for alginate degradation and metabolism is shown in FIG. 2. Alginate can be degraded by at least two different methodologies: enzymatic and chemical methodologies.

In enzymatic degradation, the degradation of alginate is catalyzed by a family of enzymes called alginate lyases. For this experiment, Atu3025 was used. Atu3025 is an exolytically acting enzyme and yields DEHU from alginate polymer. DEHU is converted to the common hexuronate metabolite, KDG. This reaction is catalyzed by alcohol dehydrogenases (e.g., DEHU hydrogenases).

Chemical degradation catalyzed by acid solution, such as formate, yields a monosaccharide mannuronate. Mannuronate is then converted to mannonate, which is catalyzed by enzymes with mannonate dehydrogenase (mannuronate reductase) activity. In bacteria, mannonate dehydratase (UxuA) catalyzes dehydration from mannonate to form KDG.

KDG is readily metabolized to form of pyruvate and glyceraldehydes-3-phosphate (G3P). KDG is first phosphorylated to KDG-6-phosphate (KDGP), which is catalyzed by KDG kinase, and then broken down to pyruvate and G3P, which is catalyzed by KDGP aldolase.

Preparation of oligoalginate lyase Atu3025 derived from *Agrobacterium tumefaciens* C58. pETAtu3025 was constructed based on pET29 plasmid backbone (Novagen). The oligoalginate lyase Atu3025 was amplified by PCR: 98° C. for 10 sec, 55° C. for 15 sec, and 72° C. for 60 sec, repeated for 30 times. The reaction mixture contained 1× Phusion buffer, 2 mM dNTP, 0.5 µM forward (5'-GGAATTCCATAT- GCGTCCCTCTGCCCCGGCC-3') (SEQ ID NO:155) and reverse (5'-CGGGATCCTTAGAACTGCTTGGGAAGG-GAG-3') (SEQ ID NO:156) primers, 2.5 U Phusion DNA polymerase (Finezyme), and an aliquot of *Agrobacterium tumefaciens* C58 (gift from Professor Eugene Nester, University of Washington) cells as a template in total volume of 100 μl. The amplified fragment was digested with NdeI and BamHI and ligated into pET29 pre-digested with the same enzymes using T4 DNA ligase to form pETAtu3025. The constructed plasmid was sequenced (Elim Biopharmaceuticals) and the DNA sequence of the insert was confirmed. The nucleotide sequence of the Atu3025 insert is provided in SEQ ID NO:67. The polypeptide sequence encoded by the Atu3025 insert is provided in SEQ ID NO:68.

The pETAtu3025 was transformed into *Escherichia coli* strain BL21(DE3). A colony of BL21(DE3) containing pETAtu3025 was inoculated into 50 ml of LB media containing 50 μg/ml kanamycin ($Km^{50}$). This strain was grown in an orbital shaker with 200 rpm at 37° C. The 0.2 mM IPTG was added to the culture when the $OD_{600\ nm}$ reached 0.6, and the induced culture was grown in an orbital shaker with 200 rpm at 20° C. 24 hours after the induction, the cells were harvested by centrifugation at 4,000 rpm×g for 10 min and the pellet was resuspended into 2 ml of Bugbuster (Novagen) containing 10 μl of Lysonase™ Bioprocessing Reagent (Novagen). The solution was again centrifuged at 4,000 rpm×g for 10 min and the supernatant was obtained.

Construction of pETADH1 through pETADH12. DNA sequences of ADH1-12 of *Agrobacterium tumefaciens* C58 were amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 μM forward (Table 1) and reverse (Table 1) primers, 1 U Phusion High Fidelity DNA polymerase (NEB), and 50 ng *Agrobacterium tumefaciens* C58 genome in 50 μl. Amplified DNA fragment was digested with NdeI and BamHI and ligated into pET28 pre-digested with the same restriction enzymes. For DNA sequences with internal NdeI or BamHI site, front and bottom half sequences of each ADH were first amplified using described method. The resulting two DNA fragments were gel purified and spliced by overlapping PCR.

TABLE 1

Primers used to amplify ADH1-12 from *Agrobacterium tumefaciens* C58.

| Name | A. tumefaciens C58 | Forward Primer | Reverse Primer |
|---|---|---|---|
| ADH1 | Atu1557 | GGAATTCCATATGTTCACAACGTCCGCCTA (SEQ ID NO: 276) | GCTTGACGGCCATGTGGCCGAGGCCGC (SEQ ID NO: 277) |
|  |  | GCGGCCTCGGCCACATGGCCGTCAAGC (SEQ ID NO: 278) | CGGGATCCTTAGGCGGCCTTCTGGCGCG (SEQ ID NO: 279) |
| ADH2 | Atu2022 | GGAATTCCATATGGCTATTGCAAGAGGTTA (SEQ ID NO: 280) | CGGGATCCTTAAGCGTCGAGCGAGGCCA (SEQ ID NO: 281) |
| ADH3 | Atu0626 | GGAATTCCATATGACTAAAACAATGAAGGC (SEQ ID NO: 282) | CACCGGGGCCGGGGTCCGGTATTGCCA (SEQ ID NO: 283) |
|  |  | TGGCAATACCGGACCCCGGCCCCGGTG (SEQ ID NO: 284) | CGGGATCCTTAGGCGGCGAGATCCACGA (SEQ ID NO: 285) |
| ADH4 | Atu5240 | GGAATTCCATATGACCGGGGCGAACCAGCC (SEQ ID NO: 286) | ATAGCCGCTCATACGCCTCGGTTGCCT (SEQ ID NO: 287) |
|  |  | AGGCAACCGAGGCGTATGAGCGGCTAT (SEQ ID NO: 288) | CGGGATCCTTAAGCGCCGTGCGGAAGGA (SEQ ID NO: 289) |
| ADH5 | Atu3163 | GGAATTCCATATGACCATGCATGCCATTCA (SEQ ID NO: 290) | CGGGATCCTTATTCGGCTGCAAATTGCA (SEQ ID NO: 291) |
| ADH6 | Atu2151 | GGAATTCCATATGCGCGCGCTTTATTACGA (SEQ ID NO: 292) | CGGGATCCTTATTCGAACCGGTCGATGA (SEQ ID NO: 293) |
| ADH7 | Atu2814 | GGAATTCCATATGCTGGCGATTTTCTGTGA (SEQ ID NO: 294) | CGGGATCCTTATGCGACCTCCACCATGC (SEQ ID NO: 295) |
| ADH8 | Atu5447 | GGAATTCCATATGAAAGCCTTCGTCGTCGA (SEQ ID NO: 296) | CGGGATCCTTAGGATGCGTATGTAACCA (SEQ ID NO: 297) |
| ADH9 | Atu4087 | GGAATTCCATATGAAAGCGATTGTCGCCCA (SEQ ID NO: 298) | CGGGATCCTTAGGAAAAGGCGATCTGCA (SEQ ID NO: 299) |
| ADH10 | Atu4289 | GGAATTCCATATGCCGATGGCGCTCGGGCA (SEQ ID NO: 300) | CGGGATCCTTAGAATTCGATGACTTGCC (SEQ ID NO: 301) |
| ADH11 | Atu3027 | GGAATTCCATATGAAACATTCTCAGGACAA (SEQ ID NO: 302) | GGGCGCCGATCATGTGGTGCGTTTCCG (SEQ ID NO: 303) |
|  |  | CGGAAACGCACCACATGATCGGCGCCC (SEQ ID NO: 304) | CGGGATCCTTATGCCATACGTTCCATAT (SEQ ID NO: 305) |
| ADH12 | Atu3026 | GGAATTCCATATGCAGCGTTTTACCAACAG (SEQ ID NO: 306) | CGGGATCCTTAGGAAAACAGGACGCCGC (SEQ ID NO: 307) |

Expression and Purification of ADH 1-10.

All plasmids were transformed into *Escherichia coli* strain BL21(DE3). The single colonies of BL21(DE3) containing respective alcohol dehydrogenase (ADH) genes were inoculated into 50 ml of LB media containing 50 µg/ml kanamycin ($Km^{50}$). These strains were grown in an orbital shaker with 200 rpm at 37° C. The 0.2 mM IPTG was added to each culture when the $OD_{600\ nm}$ reached 0.6, and the induced culture was grown in an orbital shaker with 200 rpm at 20° C. 24 hours after the induction, the cells were harvested by centrifugation at 4,000 rpm×g for 10 min and the pellet was resuspended into 2 ml of Bugbuster (Novagen) containing 10 µl of Lysonase™ Bioprocessing Reagent (Novagen). The solution was again centrifuged at 4,000 rpm×g for 10 min and the supernatant was obtained.

Preparation of ~2% DEHU Solution by Enzymatic Degradation.

DEHU solution was enzymatically prepared. A 2% alginate solution was prepared by adding 10 g of low viscosity alginate into the 500 ml of 20 mM Tris-HCl (pH7.5) solution. An approximately 10 mg of alginate lyase derived from *Flavobacterium* sp. (purchased from Sigma-aldrich) was added to the alginate solution. 250 ml of this solution was then transferred to another bottle and the *E. coli* cell lysate containing Atu3025 prepared above section was added. The alginate degradation was carried out at room temperature over night. The resulting products were analyzed by thin layer chromatography, and DEHU formation was confirmed.

Preparation of D-Mannuronate Solution by Chemical Degradation.

D-mannuronate solution was chemically prepared based on the protocol previously described by Spoehr (*Archive of Biochemistry*, 14: pp 153-155). Fifty milligram of alginate was dissolved into 800 µL of ninety percent formate. This solution was incubated at 100° C. for over night. Formate was then evaporated and the residual substances were washed with absolute ethanol twice. The residual substance was again dissolved into absolute ethanol and filtrated. Ethanol was evaporated and residual substances were resuspended into 20 mL of 20 mM Tris-HCl (pH 8.0) and the solution was filtrated to make a D-mannuronate solution. This D-mannuronate solution was diluted 5-fold and used for assay.

Assay for DEHU Hydrogenase.

To identify DEHU hydrogenase, a NADPH dependent DEHU hydrogenation assay was performed. 20 µl of prepared cell lysate containing each ADH was added to 160 µl of 20-fold diluted DEHU solution prepared in the above section. 20 µl of 2.5 mg/ml of NADPH solution (20 mM Tris-HCl, pH 8.0) was added to initiate the hydrogenation reaction, as a preliminary study using cell lysate of *A. tumefaciens* C58 have shown that DEHU hydrogenation requires NADPH as a co-factor. The consumption of NADPH was monitored an absorbance at 340 nm for 30 min using the kinetic mode of ThermoMAX 96 well plate reader (Molecular Devises). *E. coli* cell lysate containing alcohol dehydrogenase (ADH) 10 lacking a portion of N-terminal domain was used in a control reaction mixture.

Assay for D-Mannuronate Hydrogenase.

To identify D-mannuronate hydrogenase, a NADPH dependent D-mannuronate hydrogenation assay was performed. 20 µl of prepared cell lysate containing each ADH was added to 160 µl of D-mannuronate solution prepared in the above section. 20 µl of 2.5 mg/ml of NADPH solution (20 mM Tris-HCl, pH 8.0) was added to initiate the hydrogenation reaction. The consumption of NADPH was monitored an absorbance at 340 nm for 30 min using the kinetic mode of ThermoMAX 96 well plate reader (Molecular Devises). *E. coli* cell lysate containing alcohol dehydrogenase (ADH) 10 lacking a portion of N-terminal domain was used in a control reaction mixture.

Construction of pETkdgK.

DNA sequence of kdgK of *Escherichia coli* encoding 2-keto-deoxy gluconate kinase was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-AGGTACGGTGAAATAA AGGAGG ATATA CATATGTCCAAAAAGATTGCCGT-3') (SEQ ID NO:157) and reverse (5'-TTTTCCTTTT GCGGCCGCCCCGCTGGCATCGCCTCAC-3') (SEQ ID NO:158) primers, 1 U Phusion High Fidelity DNA polymerase (NEB), and 50 ng *Escherichia coli* DH10B genome in 50 µl. Amplified DNA fragment was digested with NdeI and NotI and ligated into pET29 pre-digested with the same restriction enzymes.

Construction of pETkd2A.

DNA sequence of kdgA *Escherichi coli* encoding 2-keto-deoxy gluconate-6-phosphate aldolase was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-GGCGATGCCAGCGTAA AGGAGG ATATACATATGAAAAACTGGAAAACAAG-3') (SEQ ID NO:159) and reverse (5'-TTTTCCTTTT GCGGCCGCCCCAGCTTAGCGCCTTCTA-3') (SEQ ID NO:160) primers, 1 U Phusion High Fidelity DNA polymerase (NEB), and 50 ng *Escherichia coli* DH10B genome in 50 µl. Amplified DNA fragment was digested with NdeI and NotI and ligated into pET29 pre-digested with the same restriction enzymes.

Protein Expression and Purification.

All plasmids (pETAtu3025, pETADH11, pETADH12, pETkdgA, pETkdgK, and pETuxuA) were transformed into *Escherichia coli* strain BL21(DE3). The single colonies of BL21(DE3) containing respective plasmids were inoculated into 50 ml of LB media containing 50 µg/ml kanamycin ($KM^{50}$). These strains were grown in an orbital shaker with 200 rpm at 37° C. The 0.2 mM IPTG was added to each culture when the $OD_{600\ nm}$ reached 0.6, and the induced culture was grown in an orbital shaker with 200 rpm at 20° C. 24 hours after the induction, the cells were harvested by centrifugation at 4,000 rpm×g for 10 min and the pellet was resuspended into 2 ml of Bugbuster (Novagen) containing 10 µl of Lysonase™ Bioprocessing Reagent (Novagen) and suggested amount of protease inhibitor cocktail (SIGMA). The solution was again centrifuged at 4,000 rpm×g for 10 min and the supernatant was obtained. The supernatant was applied to Nickel-NTA spin column (Qiagen) to purify His-tagged proteins.

Figure 7A:
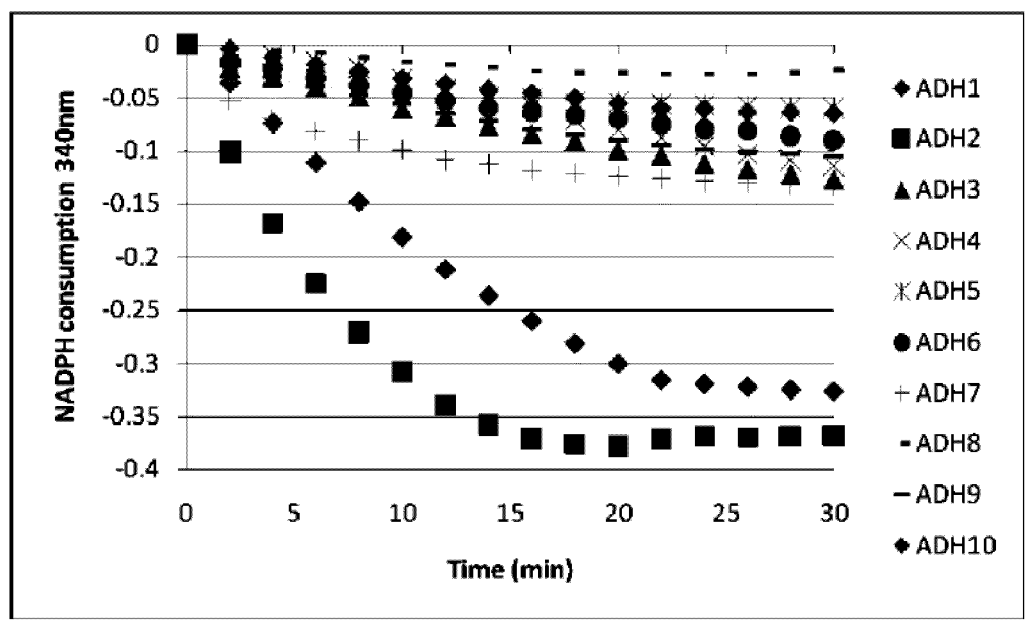
FIG. 7A shows DEHU hydrogenase activity as monitored by NADPH consumption.
Figure 7B:
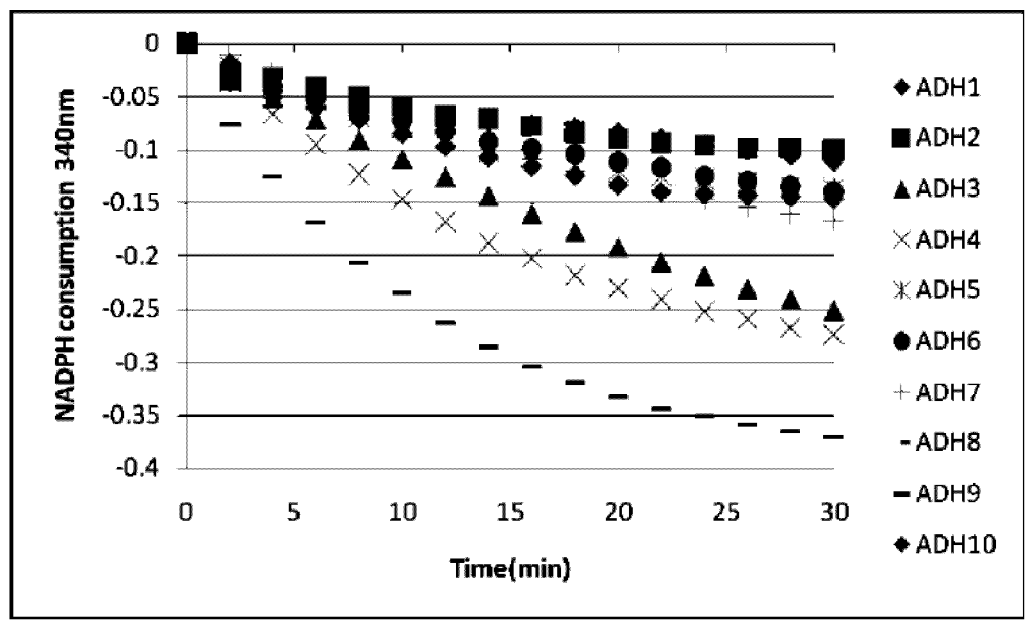
FIG. 7B shows mannuronate hydrogenase activity as monitored by NADPH consumption.

The results of the assays for DEHU hydrogenase activity and D-mannuronate hydrogenase activity of ADH1-10 are shown in FIGS. 7A and 7B. These results demonstrate that the novel enzymes ADH1 and ADH2 showed significant DEHU hydrogenase activity (FIG. 7A), and that the novel enzymes ADH3, ADH4, and ADH9 showed significant mannuronate hydrogenase activity (FIG. 7B).

In Vitro Pyruvate Formation.

The reaction mixture contained 1% alginate or ~0.5% mannuronate, ~5 ug of purified Atu3026 (ADH12) or Atu3027 (ADH11), and ~5 ug of purified oligoalginate lyase (Atu3025), UxuA, KdgK, and KdgA, 2 mM of ATP, and 0.6 mM of NADPH in 20 mM Tris-HCl pH7.0. The reaction was carried out over night and the pyruvate formation was monitored by the pyruvate assay kit (BioVision, Inc).

Figure 6A:
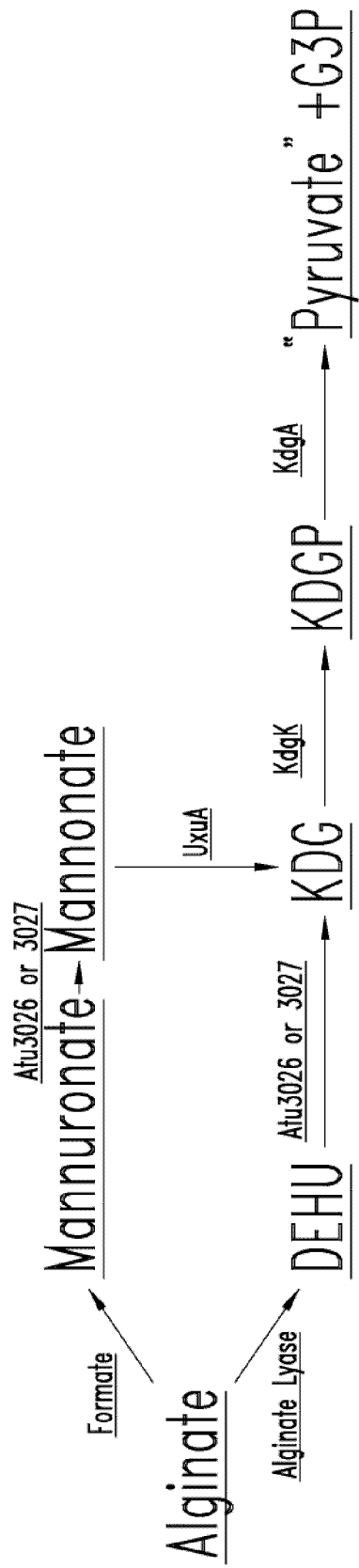
FIG. 6A illustrates a simplified metabolic pathway for alginate degradation and metabolism.
Figure 6B:
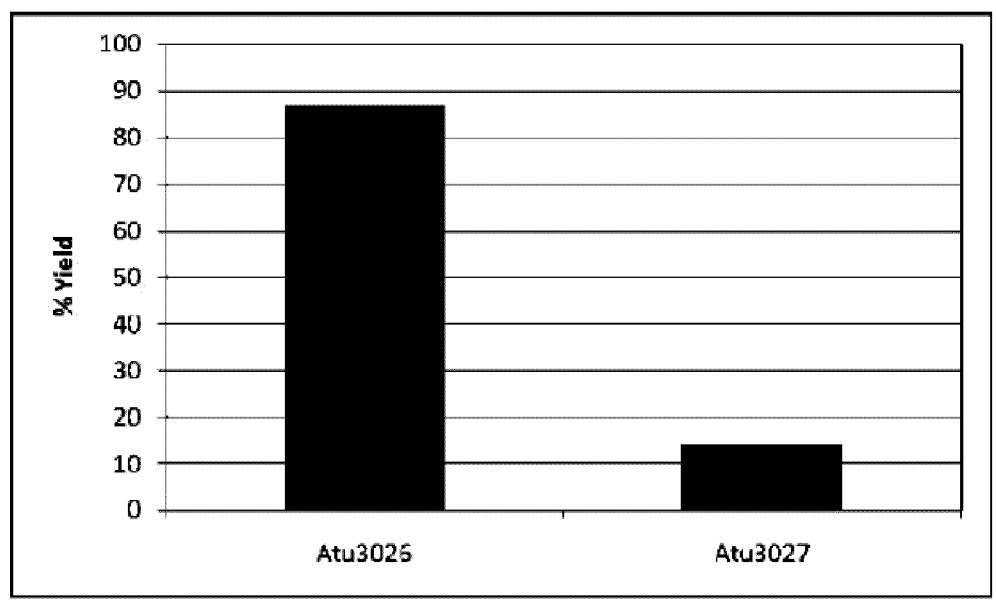
FIG. 6B shows the results of in vitro degradation of alginate to form pyruvate by an enzymatic degradation route.
Figure 6C:
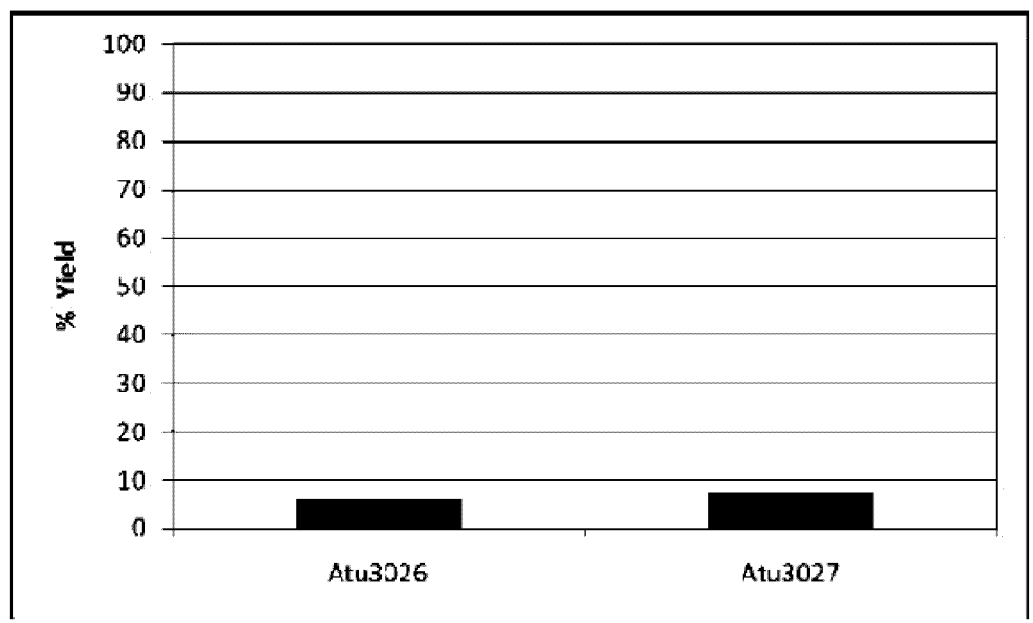
FIG. 6C shows the results of in vitro degradation of alginate to form pyruvate by a chemical degradation route.

The results of in vitro pyruvate formation from alginate mediated by enzymatic and chemical degradation are shown in FIG. 6B and FIG. 6C, respectively. As can be seen in these figures, alginate was converted to pyruvate via the isolated enzymes. These results also show that each of Atu3026 (ADH12) and Atu3027 (ADH11) are capable of catalyzing both DEHU hydrogenase and mannuronate hydrogenase reactions.

Example 4

Construction and Biological Activity of Biosynthesis Pathways

Construction of Pathways:

A propionaldehyde biosynthetic pathway comprising a threonine deaminase (ilvA) gene from *Escherichia coli* and keto-isovalerate decarboxylase (kivd) from *Lactococcus lactis* is constructed and tested for the ability to convert L-threonine to propionaldehyde.

A butyraldehyde biosynthetic pathway comprising a thiolase (atoB) gene from *E. coli*, β-hydroxy butyryl-CoA dehydrogenase (hbd), crotonase (crt), butyryl-CoA dehydrogenase (bcd), electron transfer flavoprotein A (etfA), and electron transfer flavoprotein B (etfB) genes from *Clostridium acetobutyricum* ATCC 824, and a coenzyme A-linked butyraldehyde dehydrogenase (ald) gene from *Clostridium beijerinckii acetobutyricum* ATCC 824 was constructed in *E. coli* and tested for the ability to produce butyraldehyde. Also, a coenzyme A-linked alcohol dehydrogenase (adhE2) gene from *Clostridium acetobutyricum* ATCC 824 was used as an alternative to ald and tested for the ability to produce butanol.

An isobutyraldehyde biosynthetic pathway comprising an acetolactate synthase (alsS) from *Bacillus subtilis* or (als) from *Klebsiella pneumoniae* subsp. *pneumoniae* MGH 78578 (codon usage was optimized for *E. coli* protein expression) and acetolactate reductoisomerase (ilvC) and 2,3-dihydroxyisovalerate dehydratase (ilvD), genes from *E. coli* and keto-isovalerate decarboxylase (kivd) from *Lactococcus lactis* was constructed and tested for the ability to produce isobutyraldehyde, as measured by isobutanal production.

3-methylbutyraldehyde and 2-methylbutyraldehyde biosynthesis pathways comprising an acetolactate synthase (alsS) from *Bacillus subtilis* or (als) from *Klebsiella pneumoniae* subsp. *pneumoniae* MGH 78578 (codon usage was optimized for *E. coli* protein expression), acetolactate reductoisomerase (ilvC), 2,3-dihydroxyisovalerate dehydratase (ilvD), isopropylmalate synthase (LeuA), isopropylmalate isomerase (LeuC and LeuD), and 3-isopropylmalate dehydrogenase (LeuB) genes from *E. coli* and keto-isovalerate decarboxylase (kivd) from *Lactococcus lactis* were constructed and tested for the ability to produce 3-isovaleraldehyde and 2-isovaleraldehyde.

Phenylacetoaldehyde and 4-hydroxyphenylacetoaldehyde biosynthesis pathways comprising a transketolase (tktA), a 3-deoxy-7-phosphoheptulonate synthase (aroF, aroG, and aroH), 3-dehydroquinate synthase (aroB), a 3-dehydroquinate dehydratase (aroD), a dehydroshikimate reductase (aroE), a shikimate kinase II (aroL), a shikimate kinase I (aroK), a 5-enolpyruvylshikimate-3-phosphate synthetase (aroA), a chorismate synthase (aroC), a fused chorismate mutase P/prephenate dehydratase (pheA), and a fused chorismate mutase T/prephenate dehydrogenase (tyrA) genes from *E. coli*, keto-isovalerate decarboxylase (kivd) from *Lactococcus lactis* were constructed and tested for the ability to produce phenylacetoaldehyde and/or 4-hydroxyphenylacetoaldehyde.

A 2-phenylethanol, 2-(4-hydroxyphenyl)ethanol, and 2-(indole-3-)ethanol biosynthesis pathway comprising a transketolase (tktA), a 3-deoxy-7-phosphoheptulonate synthase (aroF, aroG, and aroH), 3-dehydroquinate synthase (aroB), a 3-dehydroquinate dehydratase (aroD), a dehydroshikimate reductase (aroE), a shikimate kinase II (aroL), a shikimate kinase I (aroK), a 5-enolpyruvylshikimate-3-phosphate synthetase (aroA), a chorismate synthase (aroC), a fused chorismate mutase P/prephenate dehydratase (pheA), and a fused chorismate mutase T/prephenate dehydrogenase (tyrA) genes from *E. coli*, keto-isovalerate decarboxylase (kivd) from *Lactococcus lactis*, alcohol dehydrogenase (adh2) from *Saccharomyces cerevisiae*, Indole-3-pyruvate decarboxylase (ipdc) from *Azospirillum brasilense*, phenylethanol reductase (par) from *Rhodococcus* sp. ST-10, and benzaldehyde lyase (bal) from *Pseudomonas fluorescence* was constructed and tested for the ability to produce 2-phenylethanol, 2-(4-hydroxyphenyl)ethanol and/or 2-(indole-3)ethanol.

Construction of pBADButP.

The DNA sequence encoding hbd, crt, bcd, etfA, and etfB of *Clostridium acetobutyricum* ATCC 824 was amplified by polymerase chain reaction (PCR): 98° C. for 10 sec, 60° C. for 15 sec, and 72° C. for 3 min, repeated 30 times. The reaction mixture contained 1× Phusion buffer (NEB), 2 mM dNTP, 0.5 µM forward (5'-CCC GAGCTCTTAGGAGGATTAGTCATGGAAC-3') (SEQ ID NO:161) and reverse (5'-GCTCTAGA TTATTTTGAATAATCGTAGAAACC-3') (SEQ ID NO:162) primers, 1 U Phusion High Fidelity DNA polymerase (NEB), and 50 ng *Clostridium acetobutyricum* ATCC 824 genome (ATCC) in 50 µl. Amplified DNA fragment was digested with BamHI and XbaI and ligated into pBAD33 pre-digested with the same restriction enzymes.

Construction of pBADButP-atoB.

The DNA sequence encoding atoB of *Escherichia coli* DH10B was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-GC TCTAGAGGAGGATATATATATGAAAAATTGTGTCAT-CGTC-3') (SEQ ID NO:163) and reverse (5'-AA CTGCAGTTAATTCAACCGTTCAATCACC-3') (SEQ ID NO:164) primers, 1 U Phusion High Fidelity DNA polymerase (NEB), and 50 ng *Escherichia coli* DH10B genome in 50 µl. Amplified DNA fragment was digested with XbaI and PstI and ligated into pBADButP pre-digested with the same restriction enzymes.

Construction of pBADatoB-ald.

The DNA sequence encoding atoB of *Escherichia coli* DH10B and ald from *Clostridium beijerinckii* were amplified separately by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CGAGCTC AGGAG-GATATATATATGAAAAATTGTGTCATCGTCAGTG-3') (SEQ ID NO:165) for atoB and 5'-GGTTGAATTAAGGAG-GATATATATATGAATAAAGACACACTAATACCTAC-3' for ald) (SEQ ID NO:166) and reverse (5'-GTCTTTAT-TCATATATATATCCTCCTTAATTCAAC-CGTTCAATCACCATC-3' (SEQ ID NO:146) for atoB and 5'-CCCAAGCTTAGCCGGCAAGTACACATCTTC-3' for ald) (SEQ ID NO:167) primers, 1 U Phusion High Fidelity DNA polymerase (NEB), and 50 ng *Escherichia coli* DH10B and *Clostridium beijerinckii* genome (ATCC) in 501, respectively. The amplified DNA fragments were gel purified and eluted into 30 ul of EB buffer (Qiagen). 5 ul from each DNA solution was combined and each DNA fragment was spliced by another round of PCR: 98° C. for 10 sec, 60° C. for 15 sec, and 72° C. for 2 min, repeated 30 times. The reaction mixture contained 1× Phusion buffer (NEB), 2 mM dNTP, 0.5 µM forward (5'-CGAGCTC AGGGAGGATATATATAT-GAAAAATTGTGTCATCGTCAGTG-3') (SEQ ID NO:168) and reverse (5'-CCCAAGCTTAGCCGGCAAG-TACACATCTTC-3') (SEQ ID NO:169) primers, 1 U Phusion High Fidelity DNA polymerase (NEB). The spliced fragment was digested with SacI and HindIII and ligated into pBAD-ButP pre-digested with the same restriction enzymes.

Construction of pBADButP-atoB-ALD.

The DNA fragment 1 encoding chloramphenicol acetyltransferase (CAT), P15 origin of replication, araBAD promoter, atoB of *Escherichia coli* DH10B and ald of *Clostridium beijerinckii* and the DNA fragment 2 encoding araBAD promoter, hbd, crt, bcd, etfA, and etfB of *Clostridium acetobutyricum* ATCC 824 were amplified separately by polymerase chain reaction (PCR): 98° C. for 10 sec, 60° C. for 15 sec, and 72° C. for 4 min, repeated 30 times. The reaction mixture contained 1× Phusion buffer (NEB), 2 mM dNTP, 0.5 µM forward (5'-AAGGAAAAAA GCGGCCGCCCCTGAACCGACGACCGGGTCG-3') (SEQ ID NO:170) for fragment 1 and 5'-CGG GGTACCACTTTTCATACTCCCGCCATTCAG-3' (SEQ ID NO:274) for fragment 2, and reverse (5'-CGG GGTACCGCGGATACATATTTGAATGTATTTAG-3') (SEQ ID NO:171) for fragment 1 and (5'-AAGGAAAAAA GCGGCCGCGCGGATACATATTTGAATGTATTTAG-3') (SEQ ID NO:172) for fragment 2) primers, 1 U Phusion High Fidelity DNA polymerase (NEB), and 50 ng pBADatoB-ald and pBADButP in 50 µl, respectively. Amplified DNA fragments were digested with NotI and KpnI and ligated each other.

Construction of pBADilvCD.

The DNA fragments encoding ilvC and ilvD of *Escherichia coli* DH10B were amplified separately by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-GCTCTAGAGGAGGATATATATATGGC TAACTA-CTTCAATACAC-3') (SEQ ID NO:173) for ilvC and 5'-TGCTGTTGCGGGTTAAGGAG-GATATATATATGCCTAAGTACCGTTCCGCC-3' for ilvD) (SEQ ID NO:174) and reverse (5'-AACGGTACTTAG-GCATATATATATCCTCCTTAACCCGCAA-CAGCAATACG-3') (SEQ ID NO:175) for ilvC and 5'-AC ATGCATGCTTAACCCCCCAGTTTCGATT-3') (SEQ ID NO:176) for ilvD) primers, 1 U Phusion High Fidelity DNA polymerase (NEB), and 50 ng *Escherichia coli* DH10B genome (ATCC) in 50 µl. The amplified DNA fragments were gel purified and eluted into 30 ul of EB buffer (Qiagen). 5 ul from each DNA solution was combined and each DNA fragment was spliced by another round of PCR: 98° C. for 10 sec, 60° C. for 15 sec, and 72° C. for 2 min, repeated 30 times. The reaction mixture contained 1× Phusion buffer (NEB), 2 mM dNTP, 0.5 µM forward (5'-GCTCTAGAG GAGGATATATATATGGCTAACTACTTCAATACAC-3') (SEQ ID NO:177) and reverse (5'-AC ATGCATGCTTAACCCCCCAGTTTCGATT-3') (SEQ ID NO:178) primers, 1 U Phusion High Fidelity DNA polymerase (NEB). The spliced fragment was digested with XbaI and SphI and ligated into pBAD33 pre-digested with the same restriction enzymes.

Construction of pBADals-ilvCD.

The DNA fragment encoding als of *Klebsiella pneumoniae* subsp. *pneumoniae* MGH 78578 of its codon usage optimized for over-expression in *E. coli* was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CCCGAGCTCAGGAGGATATATATATGGAT AAACAGTATCCGGT-3') (SEQ ID NO:179) and reverse (5'-GCTCTAGATTACAGAATTTGACTCAGGT-3') (SEQ ID NO:180) primers, 1 U Phusion High Fidelity DNA polymerase (NEB), and 50 ng pETals in 50 µl. The amplified DNA fragment was digested with SacI and XbaI and ligated into pBADilvCD pre-digested with the same restriction enzymes.

Construction of pBADalsS-ilvCD.

The DNA fragments encoding front and bottom halves of alsS of *Bacillus subtilis* B26 were amplified by polymerase chain reaction (PCR): 98° C. for 10 sec, 60° C. for 15 sec, and 72° C. for 0.5 min, repeated 30 times. The reaction mixture contained 1× Phusion buffer (NEB), 2 mM dNTP, 0.5 µM forward (5'-CCCGAGCTCAGGAGGATATATATA TGTTGACAAAAGCAACAAAAG-3') (SEQ ID NO:181) for front and 5'-CGGTACCCTTTCCAGAGATTTAGAG-3' (SEQ ID NO:275) for back halves, and reverse (5'-CTCTAAATCTCTGGAAAGGGTACCG-3') (SEQ ID NO:182) for front and (5'-GC TCTAGATTAGAGAGCTTTCGTTTTCATG-3' for back halves) (SEQ ID NO:183) primers, 1 U Phusion High Fidelity DNA polymerase (NEB), and 50 ng *Bacillus subtilis* B26 genome (ATCC) in 50 µl. The amplified DNA fragments were gel purified and eluted into 30 ul of EB buffer (Qiagen). 5 ul from each DNA solution was combined and each DNA fragment was spliced by another round of PCR: 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CCCGAGCTCA GGAGGATATATATATGTTGACAAAAGCAACAAAAG-3') (SEQ ID NO:184) and reverse (5'-GC TCTAGATTAGAGAGCTTTCGTTTTCATG-3') (SEQ ID NO:185) primers, 1 U Phusion High Fidelity DNA polymerase (NEB). The spliced fragment was internal XbaI site free and thus was digested with SacI and XbaI and ligated into pBADilvCD pre-digested with the same restriction enzymes.

Construction of pBADLeuABCD.

The DNA fragment encoding leuA, leuB, leuC, and leuD of *Escherichia coli* BL21(DE3) was amplified by polymerase chain reaction (PCR): 98° C. for 10 sec, 60° C. for 15 sec, and 72° C. for 3 min, repeated 30 times. The reaction mixture contained 1× Phusion buffer (NEB), 2 mM dNTP, 0.5 µM forward (5'-CGAGCTCAGGAGGATATATATATGAGC CAGCAAGTCATTATTTTCG-3') (SEQ ID NO:186) and reverse (5'-AAAA CTGCAGCGTTTGATGACGTGGACGATAGCGG-3') (SEQ ID NO:187) primers, 1 U Phusion High Fidelity DNA polymerase (NEB), and 50 ng *Escherichia coli* BL21(DE3) genome in 50 µl. The amplified DNA fragment was digested with SacI and XbaI and ligated into pBAD33 pre-digested with the same restriction enzymes.

Construction of pBADLeuABCD2.

The DNA fragment 1 encoding leuA and leuB and the DNA fragment 2 encoding leuC and leuD of *Escherichia coli* BL21 (DE3) were amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CG AGCTCAGGAGGATATATATATGAGCCAGCAAGTCAT TATTTTCG-3') (SEQ ID NO:188) for fragment 1 and (5'-AGGGGTGTAAGGAGGATATATATATG-GCTAAGACGTTATACGAAAAATTG-3') (SEQ ID NO:189) for fragment 2 and reverse (5'-CGTCTTAGC-CATATATATATCCTCCTTA- CACCCCTTCTGCTACATAGCGG-3') (SEQ ID NO:190) for fragment 1 and (5'-AAAACTGCAGCGTTTGATGACGTGGACGATAGCGG-3') (SEQ ID NO:191) for fragment 2 primers, 1 U Phusion High Fidelity DNA polymerase (NEB), and 50 ng *Escherichia coli* BL21(DE3) genome in 50 µl, respectively. The amplified DNA fragments were gel purified and eluted into 30 ul of EB buffer (Qiagen). 5 ul from each DNA solution was combined and each DNA fragment was spliced by another round of PCR: 98° C. for 10 sec, 60° C. for 15 sec, and 72° C. for 3 min, repeated 30 times. The reaction mixture contained 1× Phusion buffer (NEB), 2 mM dNTP, 0.5 µM forward (5'-CGAGCTCAGGAGGATATATATATGAGCCAGCAAGTCATTATTTTCG-3') (SEQ ID NO:192) and reverse (5'-AAAACTGCAGCGTTTGATGACGTGGACGATAGCGG-3') (SEQ ID NO:193) primers, 1 U Phusion High Fidelity DNA polymerase (NEB). The spliced fragment was digested with SacI and XbaI and ligated into pBAD33 pre-digested with the same restriction enzymes.

Construction of pBADLeuABCD4.

The DNA fragments encoding leuA, leuB, leuC and leuD of *Escherichia coli* BL21(DE3) were amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CGAGCTCAGGAGGATATATATATGAGCCAGCAAGTCATTATTTTCG-3') (SEQ ID NO:194) for leuA, (5'-GAAACCGTGTGAGGAGGATATATATATGTCGAAGAATTACCATATTGCCG-3') (SEQ ID NO:195) for leuB, (5'-AGGGGTGTAAGGAGGATATATATATGGCTAAGACGTTATACGAAAAATTG-3') (SEQ ID NO:196) for leuC, and (5'-ACATTAAATAAGGAGGATATATATATGCAGAGAAATTTATCAAACACAC-3') (SEQ ID NO:197) for leuD and reverse (5'-ATTCTTCGACATATATATATCCTCCTCACACGGTTTCCTTGTTGTTTTCG-3') (SEQ ID NO:198) for leuA, (5'-CGTCTTAGCCATATATATATCCTCCTTACACCCCTTCTGCTACATAGCGG-3') (SEQ ID NO:199) for leuB, (5'-TTTCTCTGCCATATATATATCCTCCTTATTTAATGTTGCGAATGTCGGCG-3') (SEQ ID NO:200) for leuC, and (5'-AAAACTGCAGCGTTTGATGACGTGGACGATAGCGG-3') (SEQ ID NO:201) for leuD primers, 1 U Phusion High Fidelity DNA polymerase (NEB), and 50 ng *Escherichia coli* BL21(DE3) genome in 50 µl, respectively. The amplified DNA fragments were gel purified and eluted into 30 ul of EB buffer (Qiagen). 5 ul from each DNA solution was combined and each DNA fragment was spliced by another round of PCR: 98° C. for 10 sec, 60° C. for 15 sec, and 72° C. for 3 min, repeated 30 times. The reaction mixture contained 1× Phusion buffer (NEB), 2 mM dNTP, 0.5 µM forward (5'-CGAGCTCAGGAGGATATATATATGAGCCAGCAAGTCATTATTTTCG-3') (SEQ ID NO:202) and reverse (5'-AAAACTGCAGCGTTTGATGACGTGGACGATAGCGG-3') (SEQ ID NO:203) primers, 1 U Phusion High Fidelity DNA polymerase (NEB). The spliced fragment was digested with SacI and XbaI and ligated into pBAD33 pre-digested with the same restriction enzymes.

Construction of pBADals-ilvCD-leuABCD, pBADals-ilvCD-leuABCD2, pBADals-ilvCD-leuABCD4 pBADalsS-ilvCD-leuABCD, pBADalsS-ilvCD-leuABCD2 pBADalsS-ilvCD-leuABCD4.

The DNA fragments 1 (for als) and 2 (for alsS) encoding chloramphenicol acetyltransferase (CAT), P15 origin of replication, araBAD promoter, als of *Klebsiella pneumoniae* subsp. *pneumoniae* MGH 78578 of its codon usage optimized for over-expression in *E. coli* or alsS of *Bacillus subtilis* B26 and ilvC and ilvD of *E. coli* DH 10B were amplified separately by polymerase chain reaction (PCR): 98° C. for 10 sec, 60° C. for 15 sec, and 72° C. for 4 min, repeated 30 times. The reaction mixture contained 1× Phusion buffer (NEB), 2 mM dNTP, 0.5 µM forward (5'-AAGGAAAAAAGCGGCCGCCCCTGAACCGACGACCGGGTCG-3') (SEQ ID NO:204) and reverse (5'-CGGGGTACCGCGGATACATATTTGAATGTATTTAG-3') (SEQ ID NO:205) primers, 1 U Phusion High Fidelity DNA polymerase (NEB), and 50 ng pBADals-ilvCD and pBADalsS-ilvCD in 50 µl, respectively.

To remove an internal SphI restriction enzyme site form leuC, overlap PCR was carried out. The front and bottom halves of DNA fragment 3 (for leuABCD), fragment 4 (for leuABCD2), and fragment 5 (for leuABCD4) encoding araBAD promoter, leuA, leuB, leuC, and leuD of *E. coli* BL21 (DE3) were amplified separately by polymerase chain reaction (PCR): 98° C. for 10 sec, 60° C. for 15 sec, and 72° C. for 4 min, repeated 30 times. The reaction mixture contained 1× Phusion buffer (NEB), 2 mM dNTP, 0.5 µM forward (5'-AAGGAAAAAAGCGGCCGCACTTTTCATACTCCCGCCATTCAG-3') (SEQ ID NO:206) for front and (5'-CAAAGGCCGTCTGCACGCGCCGAAAGGCAAA-3') (SEQ ID NO:207) for back halves) and reverse (5'-TTTGCCTTTCGGCGCGTGCAGACGGCCTTTG-3') (SEQ ID NO:208) for front and (5'-ACATGCATGCCGTTTGATGACGTGGACGATAGCGG-3') (SEQ ID NO:209) for bottom halves, 1 U Phusion High Fidelity DNA polymerase (NEB), and 50 ng pBADleuABCD, pBADleuABCD2, and pBADleuABCD4 in 50 µl, respectively. The amplified DNA fragments were gel purified and eluted into 30 ul of EB buffer (Qiagen). 5 ul from each DNA solution was combined and each DNA fragment was spliced by another round of PCR: 98° C. for 10 sec, 60° C. for 15 sec, and 72° C. for 4 min, repeated 30 times. The reaction mixture contained 1× Phusion buffer (NEB), 2 mM dNTP, 0.5 µM forward (5'-AAGGAAAAAAGCGGCCGCACTTTTCATACTCCCGCCATTCAG-3') (SEQ ID NO:210) and reverse (5'-ACATGCATGCCGTTTGATGACGTGGACGATAGCGG-3') (SEQ ID NO:211) primers, 1 U Phusion High Fidelity DNA polymerase (NEB). The resulting fragment 3, 4, and 5 were digested with SphI and NotI and ligated into both fragment 1 and 2 pre-digested with the same restriction enzymes.

Construction of pBADaroG-tktA-aroBDE.

The DNA fragments encoding aroG, tktA, aroB, aroD, and aroE of *Escherichia coli* BL21(DE3) were amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CCCGAGCTCAGGAGGATATATATATGAATTATCAGAACGACGATTTAC-3') (SEQ ID NO:212) for aroG, (5'-GCGTCGCGGGTAAGGAGGAAAATTTTATGTCCTCACGTAAAGAGCTTGCC-3') (SEQ ID NO:213) for tktA, (5'-GAACTGCTGTAAGGAGGTTAAAATTATGGAGAGGATTGTCGTTACTCTCG-3') (SEQ ID NO:214) for aroB, }(5'-CAATCAGCGTAAGGAGGTATATATAATGAAAACCGTAACTGTAAAAGATC-3') (SEQ ID NO:215) for aroD, and (5'-TACACCAGGCATAAGGAGGAATTAATTATGGAAACCTATGCTGTTTTTGG-3') (SEQ ID NO:216) for aroE and reverse (5'-TACGTGAGGACATAAAATTTTCCTCCTTACCCGCGACGCGCTTTTACTGC-3') (SEQ ID NO:217) for aroG, (5'-CAATCCTCTCCATAATTTTAACCTCCTTACAGCAGTTCTTTTGCTTTCGC-3') (SEQ ID NO:218) for tktA, (5'-CAATCAGCGTAAGGAGGTATATATAAT- GAAAACCGTAACTGTAAAAGATC-3') (SEQ ID NO:219) for aroB, (5'-TACGGTTTTCATTATATATACCTC-CTTACGCTGATTGACAATCGGCAATG-3') (SEQ ID NO:220) for aroD, and (5'-AC ATGCATGCTTACGCGGACAATTCCTCCTGCAA-3') (SEQ ID NO:221) for aroE, 1 U Phusion High Fidelity DNA polymerase (NEB), and 50 ng *Escherichia coli* BL21(DE3) genome in 50 µl, respectively. The amplified DNA fragments were gel purified and eluted into 30 ul of EB buffer (Qiagen). 5 ul from each DNA solution was combined and each DNA fragment was spliced by another round of PCR: 98° C. for 10 sec, 60° C. for 15 sec, and 72° C. for 3 min, repeated 30 times. The reaction mixture contained 1×Phusion buffer (NEB), 2 mM dNTP, 0.5 µM forward (5'-CCC GAGCTCAGGAGGATATATATATGAATTATCAGAACG ACGATTTAC-3') (SEQ ID NO:222) and reverse (5'-AC ATGCATGCTTACGCGGACAATTCCTCCTGCAA-3') (SEQ ID NO:223) primers, 1 U Phusion High Fidelity DNA polymerase (NEB). The spliced fragment was digested with SacI and SphI and ligated into pBAD33 pre-digested with the same restriction enzymes.

Construction of pBADpheA-aroLAC.

The DNA fragments encoding pheA, aroL, aroA, and aroC of *Escherichia coli* DH10 were amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CCCGAGCTCAGGA GGATATATATATGACATCGGAAAACCCGTTACTGG-3') (SEQ ID NO:224) for pheA, (5'-GATCCAACCTAAG-GAGGAAAATTTTATGACACAAC-CTCTTTTTCTGATCG-3') (SEQ ID NO:225) for aroL, (5'-GATCAATTGTTAAGGAGGTATATATAATGGAATCCCT GACGTTACAACCC-3') (SEQ ID NO:226) for aroA, and (5'-CAGGCAGCCTAAGGAGGAATTAATTATG-GCTGGAAACACAATTGGACAAC-3') (SEQ ID NO:227) for aroC and reverse (5'-AGGTTGTGTCATAAAATTTTC-CTCCTTAGGTTGGATCAACAGGCACTACG-3') (SEQ ID NO:228) for pheA, (5'-CAGGGATTCCATTATATATAC-CTCCTTAACAATTGATCGTCTGTGCCAGG-3') (SEQ ID NO:229) for aroL, (5'-GTTTCCAGCCATAATTAATTC-CTCCTTAGGCTGCCTGGCTAATCCGCGCC-3') (SEQ ID NO:230) for aroA, and (5'-AC ATGCATGCTTACCAGCGTGGAATATCAGTCTTC-3') (SEQ ID NO:231) for aroC primers, 1 U Phusion High Fidelity DNA polymerase (NEB), and 50 ng *Escherichia coli* BL21(DE3) genome in 50 µl, respectively. The amplified DNA fragments were gel purified and eluted into 30 ul of EB buffer (Qiagen). 5 ul from each DNA solution was combined and each DNA fragment was spliced by another round of PCR: 98° C. for 10 sec, 60° C. for 15 sec, and 72° C. for 4 min, repeated 30 times. The reaction mixture contained 1× Phusion buffer (NEB), 2 mM dNTP, 0.5 µM forward (5'-CC CGAGCTCAGGAGGATATATATATGACATCGGAAAA CCCGTTACTGG-3') (SEQ ID NO:232) and reverse (5'-AC ATGCATGCTTACCAGCGTGGAATATCAGTCTTC-3') (SEQ ID NO:233) primers, 1 U Phusion High Fidelity DNA polymerase (NEB). The spliced fragment was digested with SacI and SphI and ligated into pBAD33 pre-digested with the same restriction enzymes.

Construction of pBADtyrA-aroLAC.

The DNA fragments encoding pheA, aroL, aroA, and aroC of *Escherichia coli* DH10 were amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CCCGAGCTCAGGAGGATATATATATGG TTGCTGAATTGACCGCATTAC-3') (SEQ ID NO:234) for tyrA, (5'-AATCGCCAGTAAGGAGGAAAATTTTAT-GACACAACCTCTTTTTCTGATCG-3') (SEQ ID NO:235) for aroL, (5'-GATCAATTGTTAAGGAGG-TATATATAATGGAATCCCTGACGTTACAACCC-3') (SEQ ID NO:236) for aroA, and (5'-CAGGCAGCCTAAG-GAGGAATTAATTATGGCTGGAAACA-CAATTGGACAAC-3') (SEQ ID NO:237) for aroC, and reverse (5'-GAGGTTGTGTCATAAAATTTTCCTCCT-TACTGGCGATTGTCATTCGCCTG-3') (SEQ ID NO:238) for tyrA, (5'-CAGGGATTCCATTATATATACCTCCT-TAACAATTGATCGTCTGTGCCAGG-3') (SEQ ID NO:239) for aroL, (5'-GTTTCCAGCCATAATTAATTC-CTCCTTAGGCTGCCTGGCTAATCCGCGCC-3') (SEQ ID NO:240) for aroA, and (5'-AC ATGCATGCTTACCAGCGTGGAATATCAGTCTTC-3') (SEQ ID NO:241) for aroC, 1 U Phusion High Fidelity DNA polymerase (NEB), and 50 ng *Escherichia coli* BL21(DE3) genome in 50 µl, respectively. The amplified DNA fragments were gel purified and eluted into 30 ul of EB buffer (Qiagen). 5 ul from each DNA solution was combined and each DNA fragment was spliced by another round of PCR: 98° C. for 10 sec, 60° C. for 15 sec, and 72° C. for 4 min, repeated 30 times. The reaction mixture contained 1× Phusion buffer (NEB), 2 mM dNTP, 0.5 µM forward (5'-CCC GAGCTCAGGAGGATATATATATGGTTGCTGAATTGA CCGCATTAC-3') (SEQ ID NO:242) and reverse (5'-AC ATGCATGCTTACCAGCGTGGAATATCAGTCTTC-3') (SEQ ID NO:243) primers, 1 U Phusion High Fidelity DNA polymerase (NEB). The spliced fragment was digested with SacI and SphI and ligated into pBAD33 pre-digested with the same restriction enzymes.

Construction of pBADpheA-aroLAC-aroG-tktA-aroBDE and pBADtyrA-aroLAC-aroG-tktA-aroBDE.

A DNA fragment 1 (for pheA) and 2 (for tyrA) encoding chloramphenicol acetyltransferase (CAT), P15 origin of replication, araBAD promoter, pheA or tyrA, aroL, aroA, aroC of *Escherichia coli* DH10B and a DNA fragment 3 encoding araBAD promoter, aroG, tktA, aroB, aroD, and aroE of *Escherichia coli* DH10B were amplified separately by polymerase chain reaction (PCR): 98° C. for 10 sec, 60° C. for 15 sec, and 72° C. for 4 min, repeated 30 times. The reaction mixture contained 1× Phusion buffer (NEB), 2 mM dNTP, 0.5 µM forward (5'-AAGGAAAAAA GCGGCCGCCCCTGAACCGACGACCGGGTCG-3') (SEQ ID NO:244) for fragment 1 and 2 and (5'-GC TCTAGAACTTTTCATACTCCCGCCATTCAG-3') (SEQ ID NO:245) for fragment 3, and reverse (5'-GC TCTAGAGCGGATACATATTTGAATGTATTTAG-3') (SEQ ID NO:246) for fragment 1 and 2 and (5'-AAG-GAAAAAA GCGGCCGCGCGGATACATATTTGAATGTATTTAG-3') (SEQ ID NO:247) for fragment 3, 1 U Phusion High Fidelity DNA polymerase (NEB), and 50 ng pBADpheA-aroLAC, pBADtyrA-aroLAC, and pBADaroG-tktA-aroBDE in 50 µl, respectively. Amplified DNA fragments 1 and 2 were digested with NotI and XbaI and ligated into fragment 3 pre-digested with the same restriction enzymes.

Construction of pTrcBAL.

A DNA sequence encoding benzaldehyde lyase (bal) of *Pseudomonas fluorescens* of its codon usage optimized for over-expression in *E. coli* was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CATGCCATGGCTATGATTACTGGTGG-3') (SEQ ID NO:248) and reverse (5'-CCCC GAGCTCTTACGCGCCGGATTGGAAATACA-3') (SEQ ID NO:249) primers, 1 U Phusion High Fidelity DNA polymerase (NEB), and 50 ng pETBAL in 50 µl. Amplified DNA fragment was digested with NcoI and SacI and ligated into pTrc99A pre-digested with the same restriction enzymes.

Construction of pTrcAdhE2.

A DNA sequence encoding Co-A linked alcohol/aldehyde dehydrogenase (adhE2) of *Clostridium acetobutyricum* ATCC824 was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CATGCCATGGCCAAAGTTACAAATCAAAAAG-3') (SEQ ID NO:250) and reverse (5'-C GAGCTCTTAAAATGATTTTATATAGATATCC-3') (SEQ ID NO:251) primers, 1 U Phusion High Fidelity DNA polymerase (NEB), and 50 ng *Clostridium acetobutyricum* ATCC824 genome in 50 µl. Amplified DNA fragment was digested with NcoI and SacI and ligated into pTrc99A pre-digested with the same restriction enzymes.

Construction of pTrcAdh2.

A DNA sequence encoding alcohol dehydrogenase (adh2) of *Saccharomyces cerevisiae* was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CATG CCATGGGTATTCCAGAAACTCAAAAAG-3') (SEQ ID NO:252) and reverse (5'-CCC GAGCTCTTATTTAGAAGTGTCAACAACG-3') (SEQ ID NO:253) primers, 1 U Phusion High Fidelity DNA polymerase (NEB), and 50 ng genome of *Saccharomyces cerevisiae* in 50 µl. Amplified DNA fragment was digested with NcoI and SacI and ligated into pTrc99A pre-digested with the same restriction enzymes.

Construction of pTrcBALD.

A DNA sequence encoding CoA-linked aldehyde dehydrogenase (ald) of *Clostridium beijerinckii* was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CCCCGAGCTCAGGAGG ATATACATAT-GAATAAAGACACACTAATACC-3') (SEQ ID NO:254) and reverse (5'-CCC AAGCTTAGCCGGCAAGTACACATCTTC-3') (SEQ ID NO:255) primers, 1 U Phusion High Fidelity DNA polymerase (NEB), and 50 ng pETBAL in 50 µl. Amplified DNA fragment was digested with SacI and HndIII and ligated into pTrcBAL pre-digested with the same restriction enzymes.

Construction of pTrcBALK.

A DNA sequence encoding ketoisovalerate decarboxylase (kivd) of *Lactococcus lavtis* was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CCCGAGCTCAGGAGGATATATATATGTA TACAGTAGGAGATTACC-3') (SEQ ID NO:256) and reverse (5'-GC TCTAGATTATGATTTATTTTGTTCAGCAAAT-3') (SEQ ID NO:257) primers, 1 U Phusion High Fidelity DNA polymerase (NEB), and 50 ng pETBAL in 50 µl. Amplified DNA fragment was digested with SacI and XbaI and ligated into pTrcBAL pre-digested with the same restriction enzymes.

Construction of pTrcAdh-Kivd.

A DNA sequence encoding ketoisovalerate decarboxylase (kivd) of *Lactococcus lavtis* was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CCCGAGCTCAGGAGGATATATATATG TATACAGTAGGAGATTACC-3') (SEQ ID NO:258) and reverse (5'-GC TCTAGATTATGATTTATTTTGTTCAGCAAAT-3') (SEQ ID NO:259) primers, 1 U Phusion High Fidelity DNA polymerase (NEB), and 50 ng pETBAL in 50 µl. Amplified DNA fragment was digested with SacI and XbaI and ligated into pTrcAdh2 pre-digested with the same restriction enzymes.

Construction of pTrcBAL-DDH-2ADH.

To remove internal NcoI site, overlap PCR was carried out. DNA fragments encoding front and bottom halves of meso-2,3-butanedioldehydrogenase (ddh) of *Klebsiella pneumoniae* subsp. *pneumoniae* MGH 78578 and secondary alcohol dehydrogenase (2adh) of *Pseudomanas fluorescens* were amplified separately by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-C GAGCTCAGGAGGATATATATATGAAAAAAGTCGCA CTTGTTACCG-3') (SEQ ID NO:260) for front half of ddh, (5'-GGCCGGCGGCCGCGCGATGGCGGTGAAAGTG-3') (SEQ ID NO:261) for bottom half of ddh, (5'-AAC-TAATCTAGAGGAGGATATATATATGAG-CATGACGTTTTCCGGCCAGG-3') (SEQ ID NO:262) for front half of 2adh, and (5'-CCTTGCGGAGGGCTCGATG-GATGAGTTCGAC-3') (SEQ ID NO:263) for bottom half of 2adh, and reverse (5'-CACTTTCACCGCCATCGCGCGGC-CGCCGGCC-3') (SEQ ID NO:264) for front half of ddh, (5'-GCTCATATATATATCCTCCTCTAGATT-AGTTAAACACCATCCCGCCGTCG-3') (SEQ ID NO:265) for bottom half of ddh, (5'-GTCGAACTCATCCATCGAGC-CCTCCGCAAGG-3') (SEQ ID NO:266) for front half of 2adh, and (5'-CCC AAGCTTAGATCGCGGTGGCCCCGCCGTCG-3') (SEQ ID NO:267) for bottom half of 2adh, 1 U Phusion High Fidelity DNA polymerase (NEB), and 50 ng *Kiebsiella pneumoniae* subsp. *pneumoniae* MGH 78578 for ddh and *Pseudomanas fluorescens* genome for 2adh in 50 µl, respectively. The amplified DNA fragments were gel purified and eluted into 30 ul of EB buffer (Qiagen). 5 ul from each DNA solution was combined and each DNA fragment was spliced by another round of PCR: 98° C. for 10 sec, 60° C. for 15 sec, and 72° C. for 2 min, repeated 30 times. The reaction mixture contained 1× Phusion buffer (NEB), 2 mM dNTP, 0.5 µM forward (5'-CGAGCTCAGGAGGATATATATATGAAA AAAGTCGCACTTGTTACCG-3') (SEQ ID NO:268) and reverse (5'-CCC AAGCTTAGATCGCGGTGGCCCCGCCGTCG-3') (SEQ ID NO:269) primers, 1 U Phusion High Fidelity DNA polymerase (NEB). The spliced fragment was digested with SacI and HindIII and ligated into pTrcBAL pre-digested with the same restriction enzymes.

Construction of pBBRPduCDEGH.

A DNA sequence encoding propanediol dehydratase medium (pduD) and small (pdue) subunits and propanediol dehydratase reactivation large (pduG) and small (pduH) subunits of *Klebsiella pneumoniae* subsp. *pneumoniae* MGH 78578 was amplified by polymerase chain reaction (PCR): 98° C. for 10 sec, 60° C. for 15 sec, and 72° C. for 2 min, repeated 30 times. The reaction mixture contained 1× Phusion buffer (NEB), 2 mM dNTP, 0.5 µM forward (5'-GC TCTAGAGGAGGATTTAAAAATGGAAATTAACGAAA CGCTGC-3') (SEQ ID NO:270) and reverse (5'-TCC CCGCGGTTAAGCATGGCGATCCCGAAATGGAATCC CTTTGAC-3') (SEQ ID NO:271) primers, 1 U Phusion High Fidelity DNA polymerase (NEB), and 50 ng *Klebsiella pneumoniae* subsp. *pneumoniae* MGH 78578 in 50 µl. Amplified DNA fragment was digested with SacII and XbaI and ligated into pTrc99A pre-digested with the same restriction enzymes to form pBBRPduDEGH.

A DNA sequence encoding propanediol dehydratase large subunit (pduC) of *Klebsiella pneumoniae* subsp. *pneumoniae* MGH 78578 was amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward (5'-CCG CTCGAGGAGGATATATATATGAGATCGAAAAGATTT GAAGC-3') (SEQ ID NO:272) and reverse (5'-GC TCTAGATTAGCCAAGTTCATTGGGATCG-3') (SEQ ID NO:273) primers, 1 U Phusion High Fidelity DNA polymerase (NEB), and 50 ng *Kiebsiella pneumoniae* subsp. *pneumoniae* MGH 78578 in 50 µl. Amplified DNA fragment was digested with XhoI and XbaI and ligated into pBBRPduDEGH pre-digested with the same restriction enzymes.

Construction of pTrcIpdc-Par.

A DNA sequence encoding indole-3-pyruvate (ipdc) of *Azospirillum brasilense* and phenylethanol reductase (par) of *Rhodococcus* sp. ST-10 were amplified by polymerase chain reaction (PCR): 98° C. for 10 sec, 60° C. for 15 sec, and 72° C. for 1 min, repeated 30 times. The reaction mixture contained 1× Phusion buffer (NEB), 2 mM dNTP, 0.5 µM forward primers (5'-CATG CCATGGGACTGGCTGAGGCACTGCTGC-3' (SEQ ID NO:314) for ipdc and 5'-CGAGCTCAGGAGGA TATATATATGAAAGCTATCCAGTACACCCGTAT-3' (SEQ ID NO:315) for par, and reverse primers (5'-CGAGCTCTTATTCGCGCGGTGCCGCGTGCAGG-3' (SEQ ID NO:316) for ipdc and 5'-GC TCTAGATTACAGGCCCGGAACCACAACGGCGC-3' (SEQ ID NO:317) for par, 1 U Phusion High Fidelity DNA polymerase (NEB), and 50 ng pTrcIpdc and pTrcPar, respectively, in 50 µl. Amplified DNA fragment of ipdc and par were digested with NcoI/SacI and SacI/XbaI, respectively, and were ligated into pTrc99A pre-digested with NcoI and XbaI.

Testing and Results:

To test the butyraldehyde biosynthesis pathway, DH10B harboring pBADButP-atoB/pTrcBALD and pBADButP-atoB-ALD/pTrcB2DH/pBBRpduCDEGH were grown overnight in LB media containing 50 ug/ml chroramphenicol (Cm$^{50}$) and 100 ug/ml ampicillin (Amp$^{100}$) at 37 C, 200 rpm. An aliquot of each seed culture was inoculated into fresh TB media containing Cm$^{50}$ and Amp$^{100}$ and was grown in incubation shaker at 37 C, 200 rpm. Three hours after inoculation, the cultures were induced with 13.3 mM arabinose and 1 mM IPTG and were grown for overnight. 700 ul of this culture was extracted with equal volume of ethylacetate and analyzed by GC-MS.

Figure 8A:
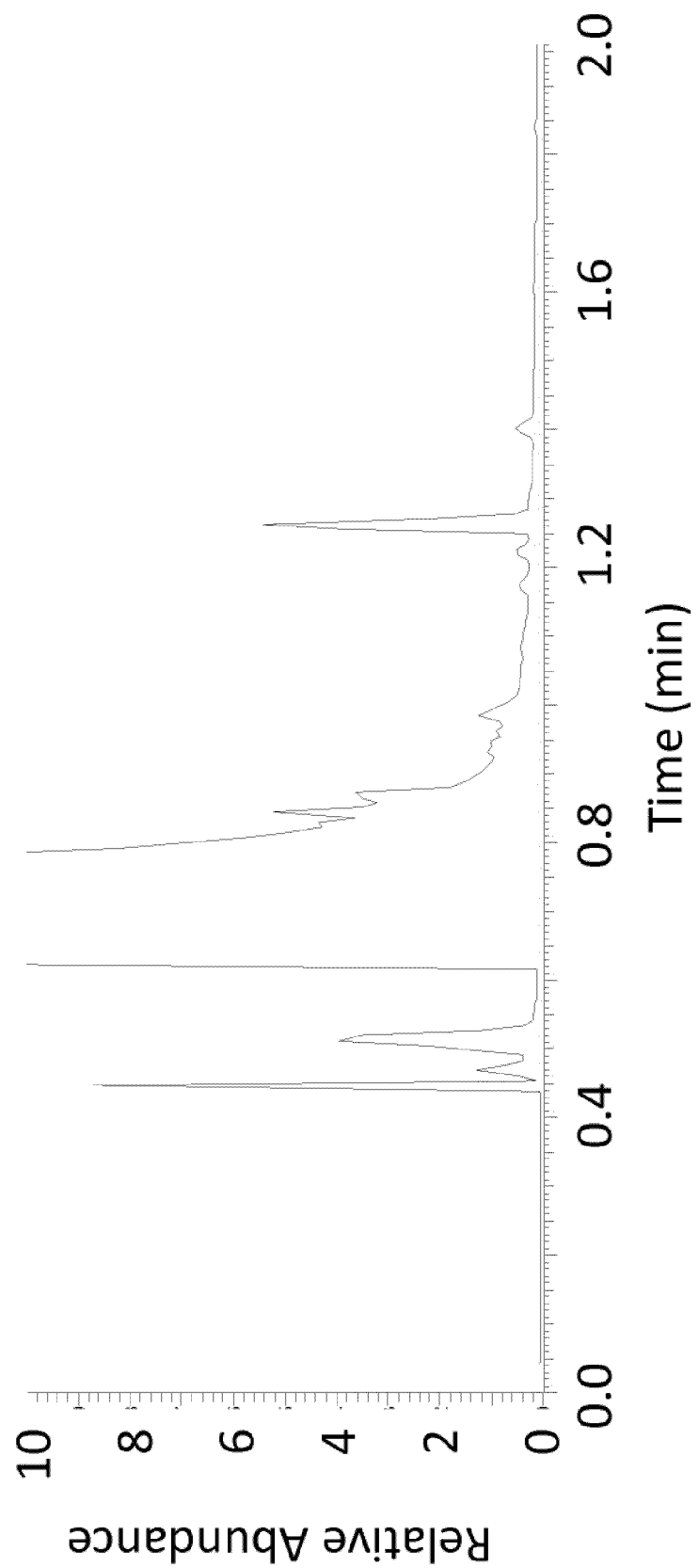
FIG. 8 shows the GC-MS chromatogram results for the control sample (FIG. 8A) and for isobutyraldehyde, 3-methylpentanol, and 2-methylpentanal production from pBAD-alsS-ilvCD-leuABCD2 and pTrcBALK (FIG. 8B).
Figure 8B:
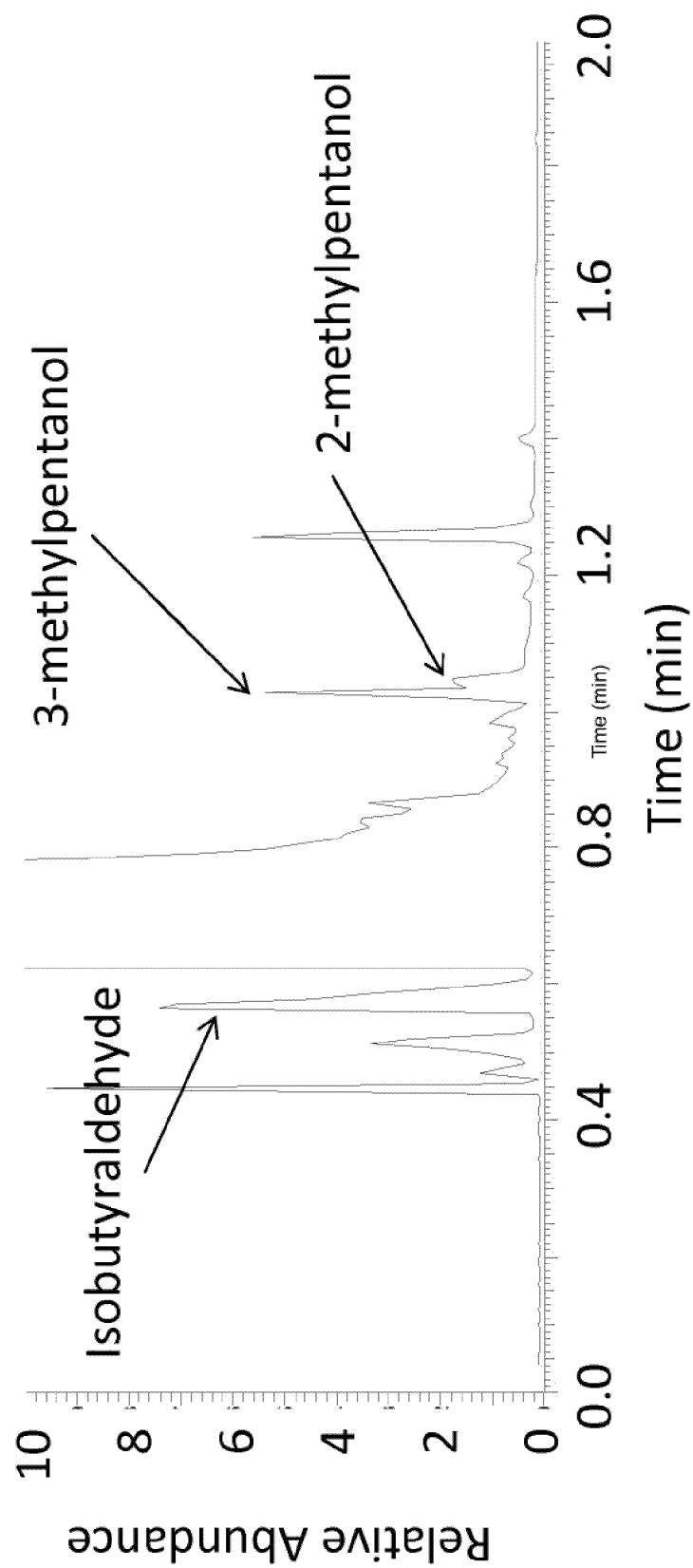

To test the isobutyeraldehyde biosynthesis pathway, DH10B cells harboring pBADals-ilvCD/pTrcBALK or pBADalsS-ilvCD/pTrcBALK were grown overnight in LB media containing 50 ug/ml chroramphenicol (Cm$^{50}$) and 100 ug/ml ampicillin (Amp$^{100}$) at 37 C, 200 rpm. An aliquot of each seed culture was inoculated into fresh TB media containing Cm$^{50}$ and Amp$^{100}$ and was grown in incubation shaker at 37 C, 200 rpm. Three hours after inoculation, the cultures were induced with 13.3 mM arabinose and 1 mM IPTG and were grown for overnight. 700 ul of this culture was extracted with equal volume of ethylacetate and analyzed by GC-MS for the production of isobutyraldehyde. FIG. 8B shows the production of isobutanal from these cultures.

To test the 3-methylbutyraldehyde and 2-methylbutyraldehyde biosynthesis pathways, DH10B harboring pBADals-ilvCD-LeuABCD/pTrcBALK, pBADals-ilvCD-LeuABCD2/pTrcBALK, pBADals-ilvCD-LeuABCD/pTrcBALK4, pBADalsS-LeuABCD/pTrcBALK, pBADalsS-LeuABCD2/pTrcBALK, or pBADalsS-LeuABCD4/pTrcBALK were grown overnight in LB media containing 50 ug/ml chroramphenicol (Cm$^{50}$) and 100 ug/ml ampicillin (Amp$^{100}$) at 37 C, 200 rpm. An aliquot of each seed culture was inoculated into fresh TB media containing Cm$^{50}$ and Amp$^{100}$ and was grown in incubation shaker at 37 C, 200 rpm. Three hours after inoculation, the cultures were induced with 13.3 mM arabinose and 1 mM IPTG and were grown for overnight. 700 ul of this culture was extracted with equal volume of ethylacetate and analyzed by GC-MS. The production of 2-isovaleralcohol (2-methylpental) and 3-isovaleralcohol (3-methylpentanal) was monitored because 3-isovaleraldehyde and 2-isovaleraldehyde are spontaneously converted to their corresponding alcohols. FIG. 8B shows the production of 2-methylpental and 3-methylpentanal from these cultures.

Figure 9A:
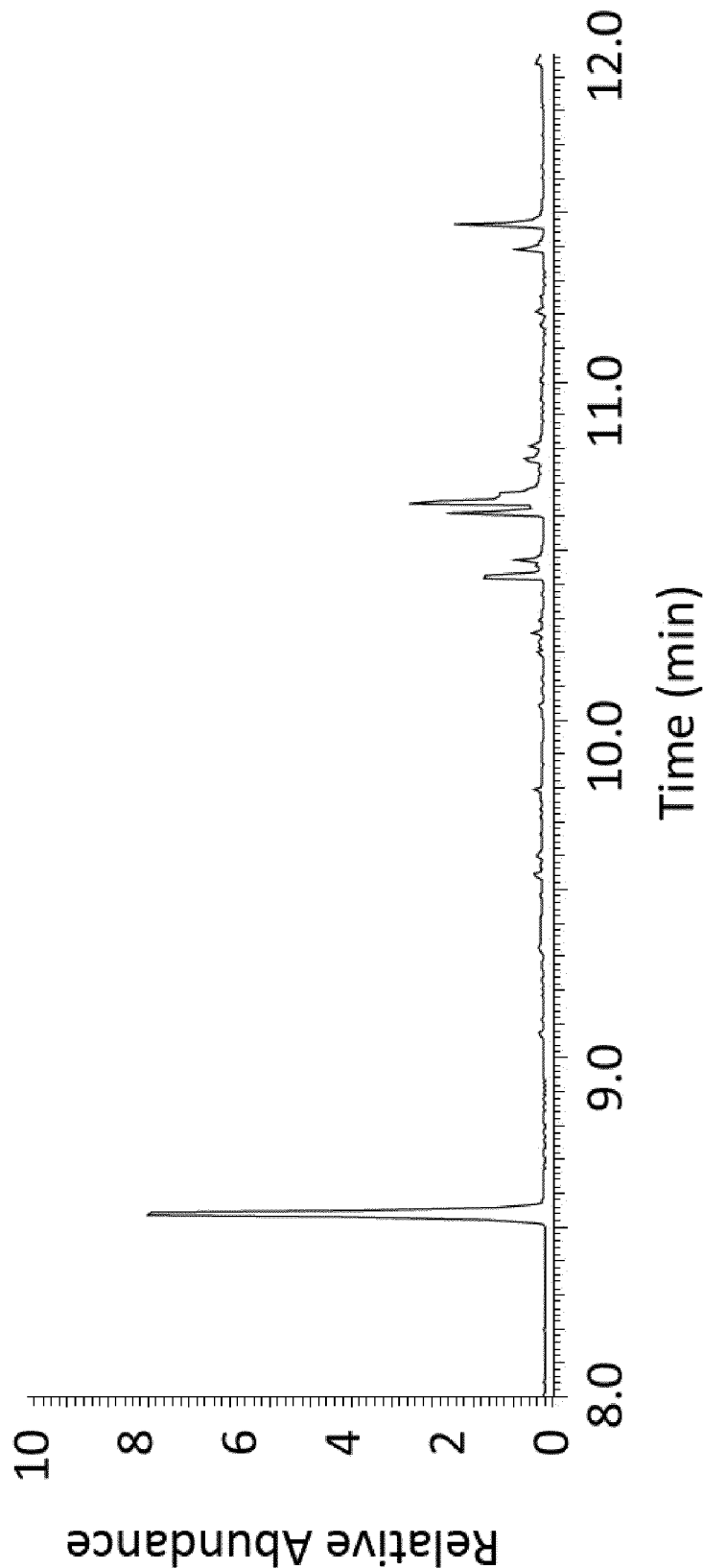
FIG. 9 shows the GC-MS chromatogram results for the control sample (FIG. 9A) and for 4-hydroxyphenylethanol and indole-3-ethanol production from pBADtyrA-aroLAC-aroG-tktA-aroBDE and pTrcBALK (FIG. 9B).
Figure 9B:
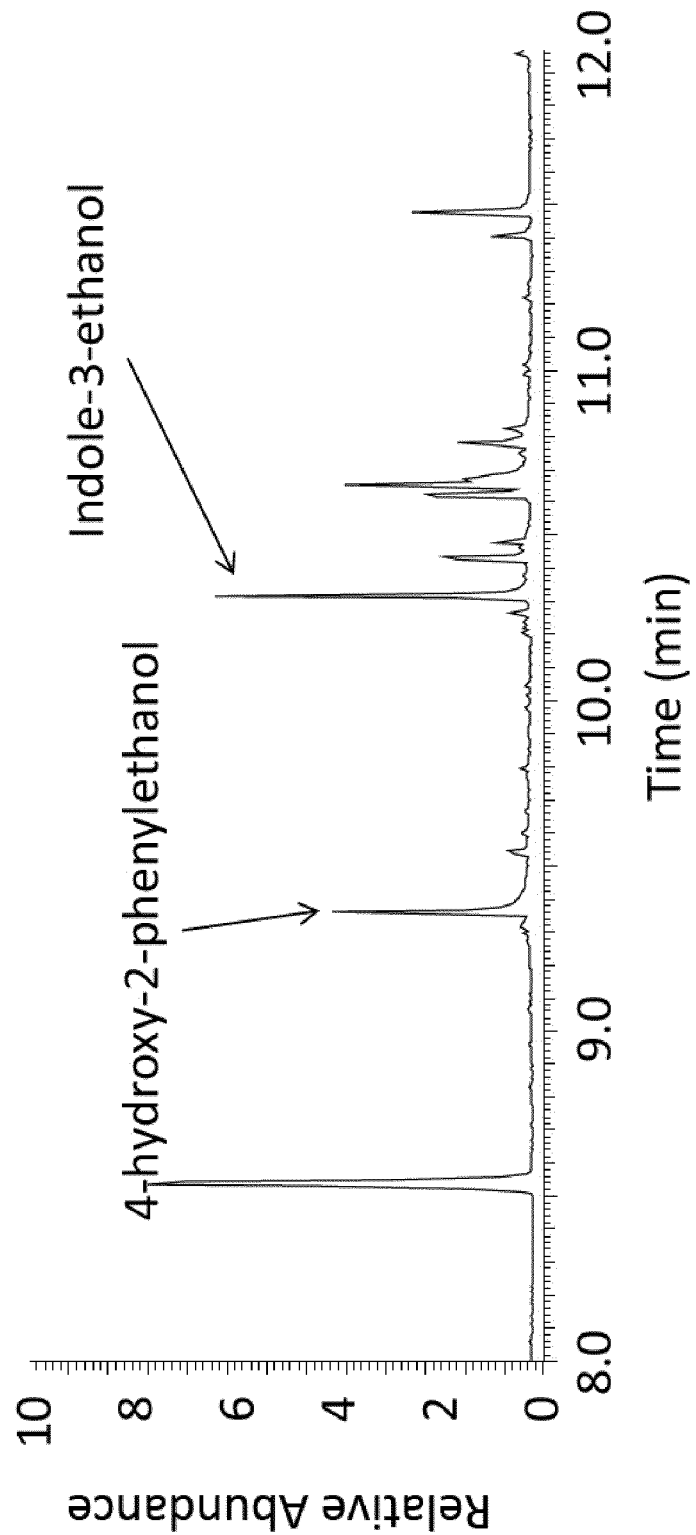
Figure 10A:
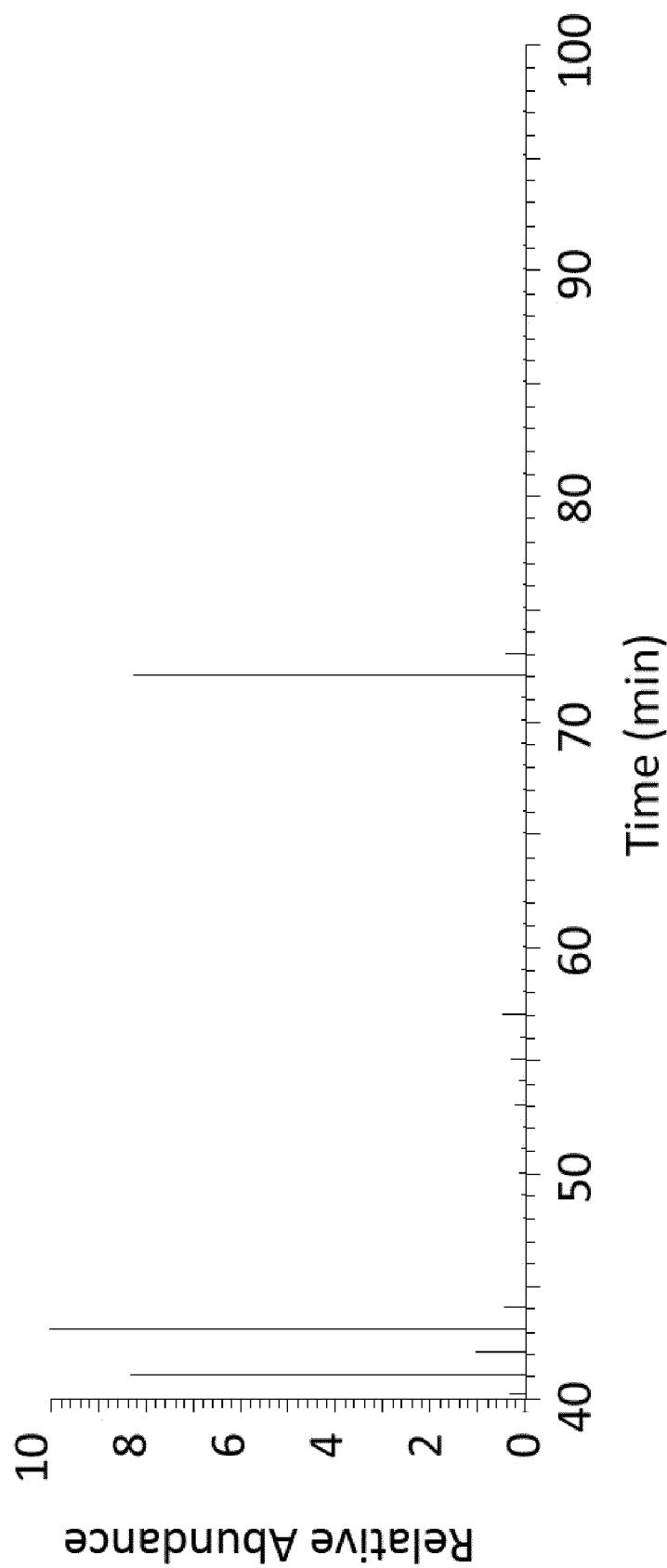
FIG. 10 shows the mass spectrometry results for isobutanal (FIG. 10A), 3-methylpentanol (FIG. 10B), and 2-methylpentanol (FIG. 10C).
Figure 10B:
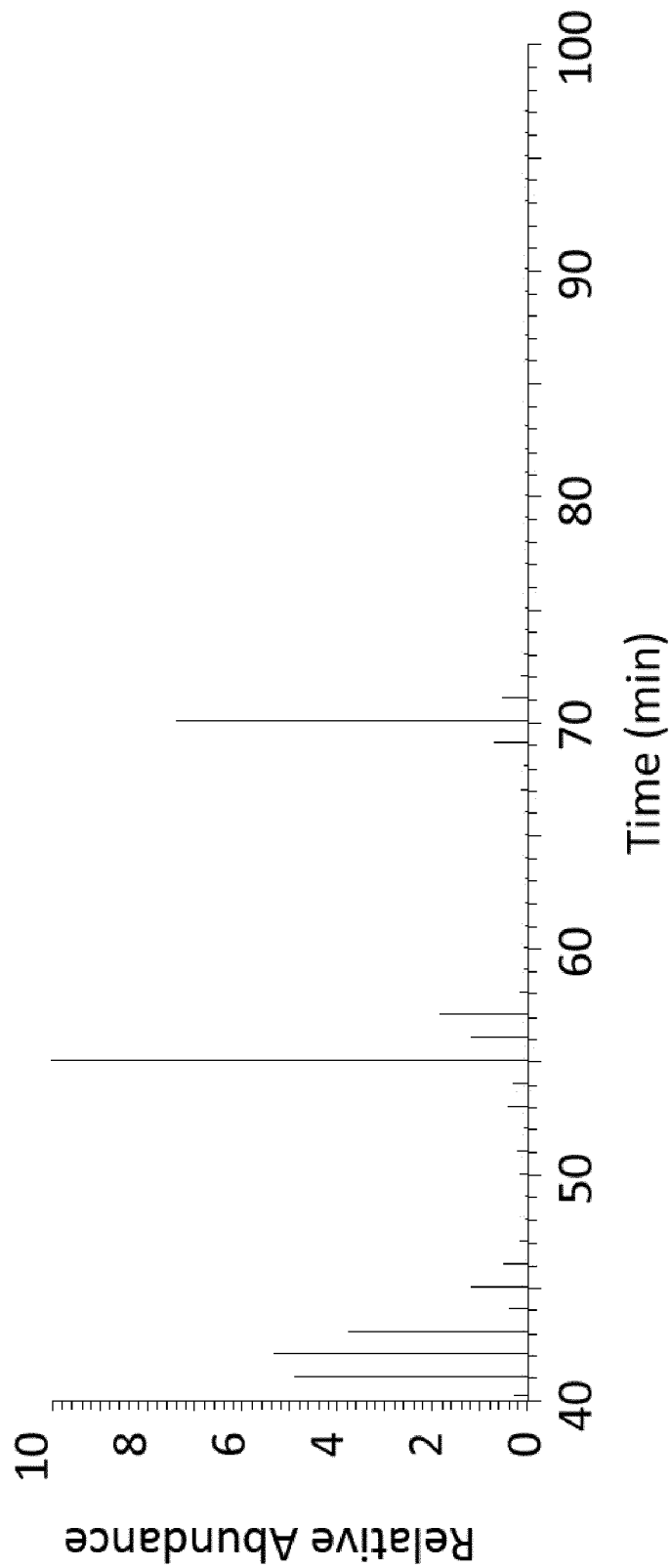
Figure 10C:
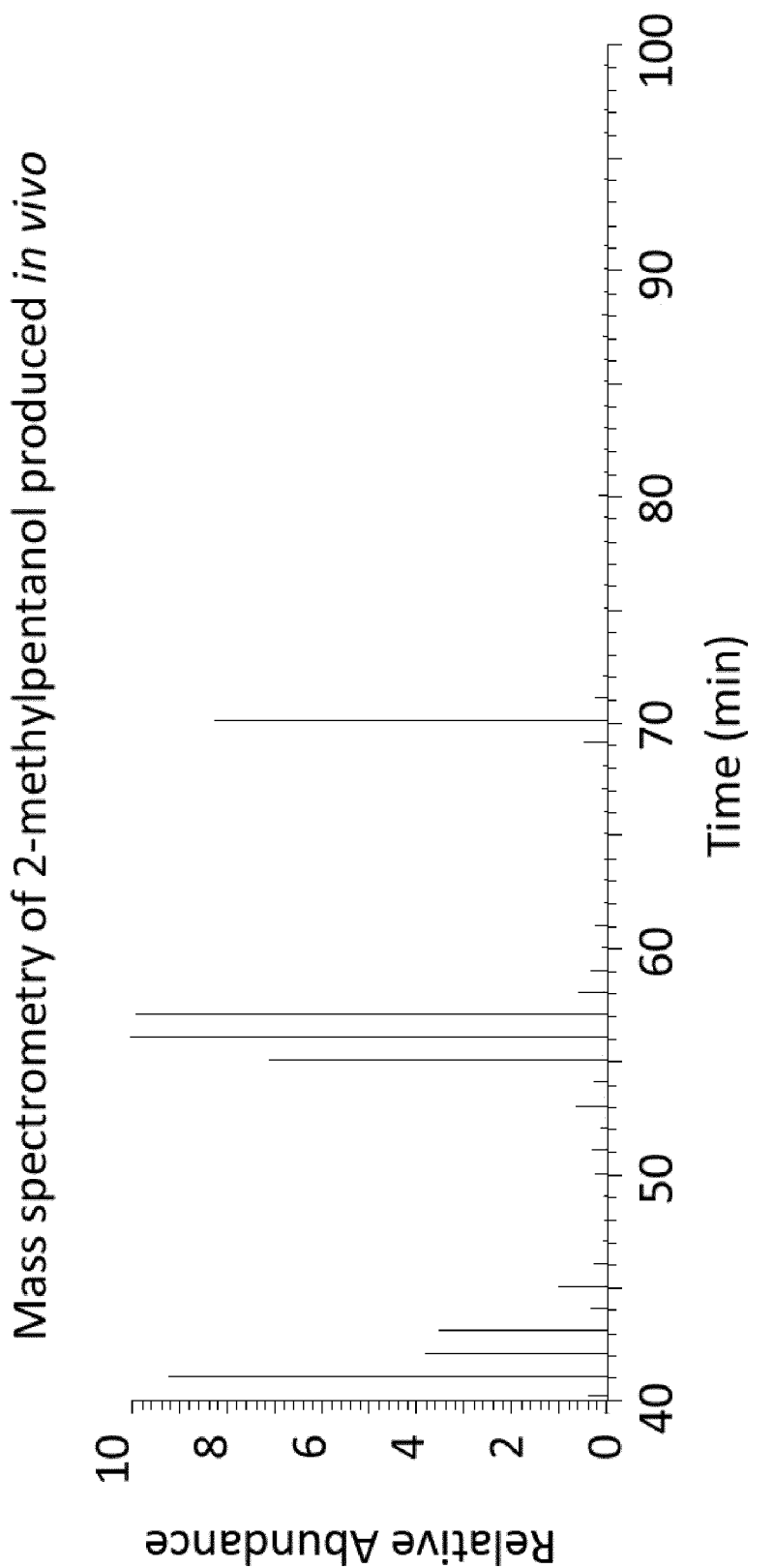
Figure 11A:
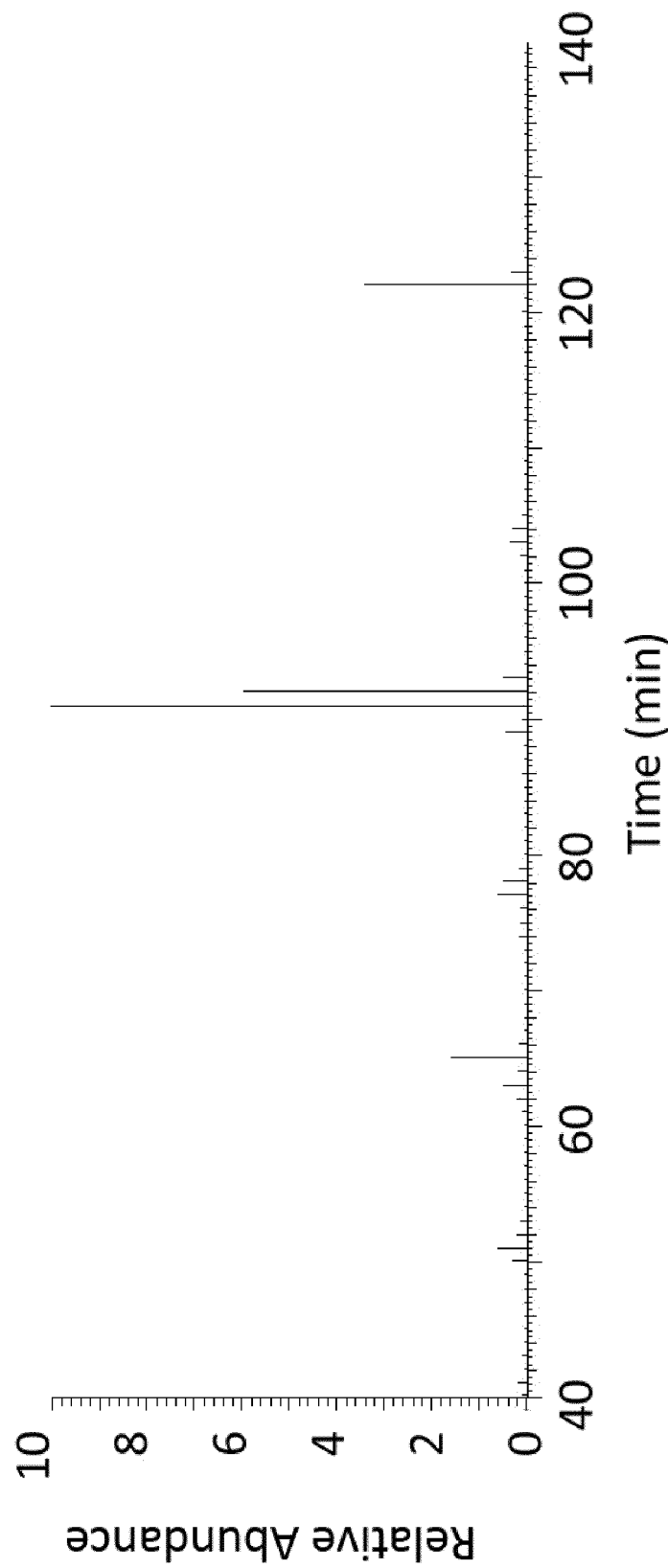
FIG. 11 shows the mass spectrometry results for phenylethanol (FIG. 11A), 4-hydroxyphenylethanol (FIG. 11B), and indole-3-ethanol (FIG. 11C).
Figure 11C:
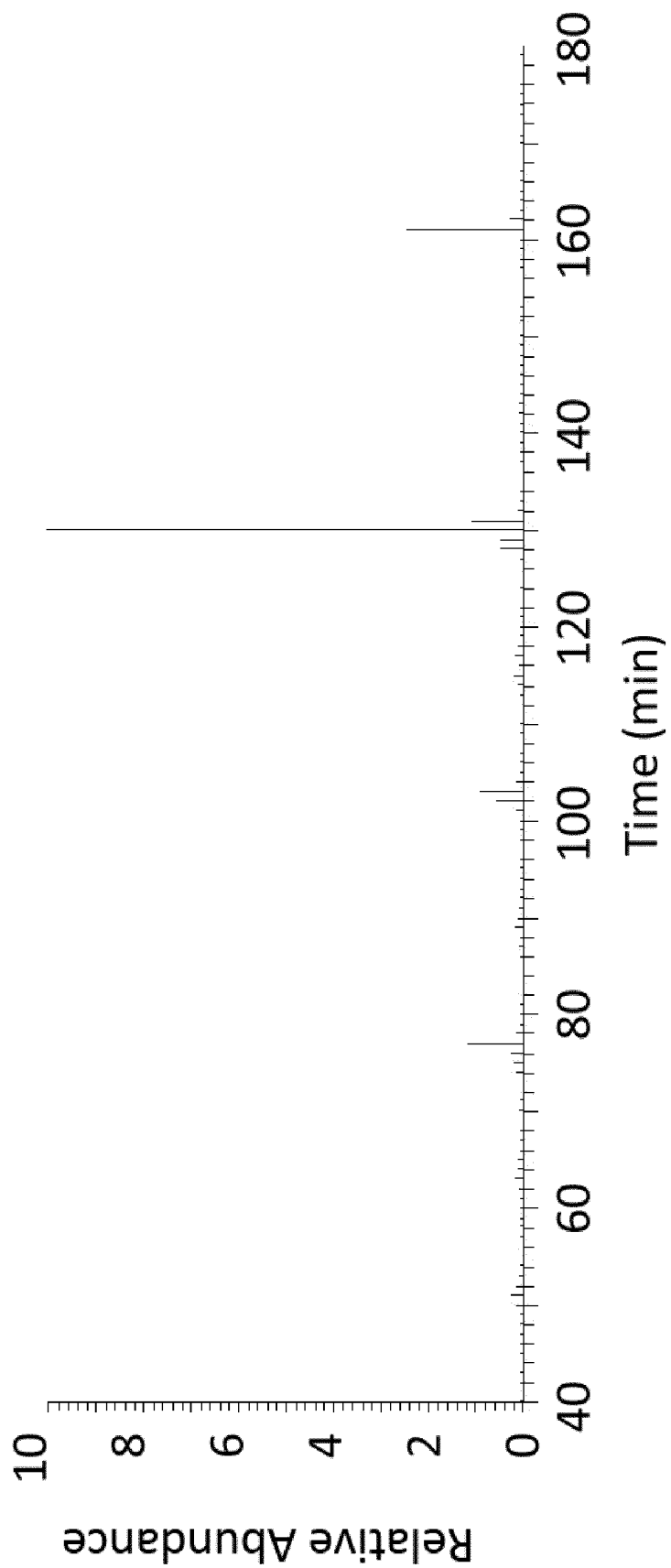

To test the phenylacetoaldehyde and 4-hydroxyphenylacetoaldehyde biosynthesis pathways, DH10B cells harboring pBADpheA-aroLAC/pTrcBALK, pBADtyrA-aroLAC/pTrcBALK, pBADaroG-tktA-aroBDE/pTrcBALK, pBADpheA-aroLAC-aroG-tktA-aroBDE/pTrcBALK, and pBADpheA-aroLAC-aroG-tktA-aroBDE/pTrcBALK were grown overnight in LB media containing 50 ug/ml chroramphenicol (Cm$^{50}$) and 100 ug/ml ampicillin (Amp$^{100}$) at 37 C, 200 rpm. An aliquot of each seed culture was inoculated into fresh TB media containing Cm$^{50}$ and Amp$^{100}$ and was grown in incubation shaker at 37 C, 200 rpm. Three hours after inoculation, the cultures were induced with 13.3 mM arabinose and 1 mM IPTG and were grown for overnight. 700 ul of this culture was extracted with equal volume of ethylacetate and analyzed by GC-MS. The production of phenylacetoaldehyde, 4-hydroxyphenylaldehyde and their corresponding alcohols were monitored using GC-MS. FIG. 9B shows the production of 4-hydroxyphenylethanol from these cultures.

To test the 2-phenylethanol, 2-(4-hydroxyphenyl)ethanol, and 2-(indole-3) ethanol biosynthesis pathways, DH10B harboring pBADpheA-aroLAC-aroG-tktA-aroBDE/pTrcBALK, pBADpheA-aroLAC-aroG-tktA-aroBDE/pTrcBALK, pBADpheA-aroLAC-aroG-tktA-aroBDE/pTrcAdh2-Kivd, pBADpheA-aroLAC-aroG-tktA-aroBDE/pTrcAdh2-Kivd, pBADpheA-aroLAC-aroG-tktA-aroBDE/pTrcIpdc-Par, and pBADpheA-aroLAC-aroG-tktA-aroBDE/pTrcIpdc-Par were grown overnight in LB media containing 50 ug/ml chroramphenicol (Cm$^{50}$) and 100 ug/ml ampicillin (Amp$^{100}$) at 37 C, 200 rpm. An aliquot of each seed culture was inoculated into fresh TB media containing Cm$^{50}$ and Amp$^{100}$ and was grown in incubation shaker at 37 C, 200 rpm. Three hours after inoculation, the cultures were induced with 13.3 mM arabinose and 1 mM IPTG and were grown for overnight to a week. 700 ul of this culture was extracted with equal volume of ethylacetate and analyzed by GC-MS. The results are detailed below.

Figure 42A:
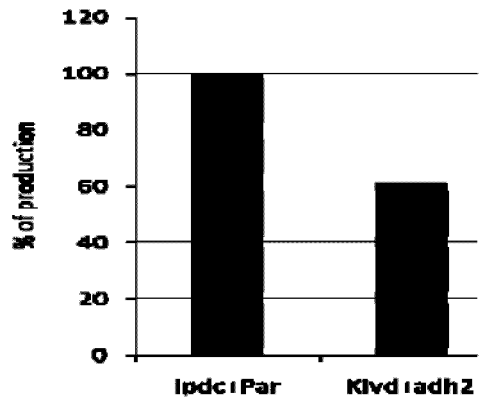
FIG. 42 shows the production of 2-phenyl ethanol (FIG. 42A), 2-(4-hydroxyphenyl)ethanol (FIG. 42B), and 2-(indole-3-)ethanol (FIG. 42C) at 24 hours from the recombinant microorganisms described in Example 4, which comprise functional 2-phenylethanol, 2-(4-hydroxyphenyl)ethanol, and 2-(indole-3-)ethanol biosynthesis pathways.
Figure 42B:
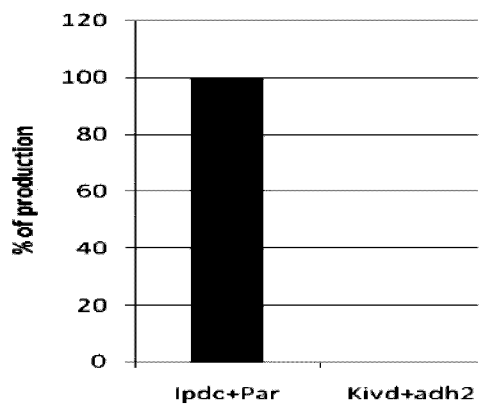
Figure 42C:
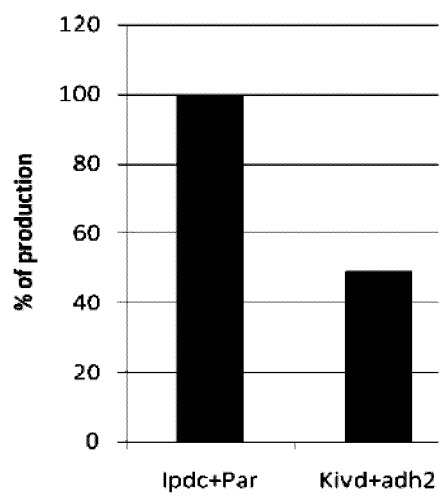

The production of 2-phenylethanol, 2-(4-hydroxyphenyl) ethanol and/or 2-(indole-3-)ethanol was monitored using GC-MS. FIG. 42A shows the production of 2-phenylethanol from these cultures at 24 hours. FIG. 42B shows the production of 2-(4-hydroxyphenyl)ethanol from these cultures at 24 hours. FIG. 42C shows the production of 2-(indole-3-)ethanol from these cultures at 24 hours.

Figure 43A:
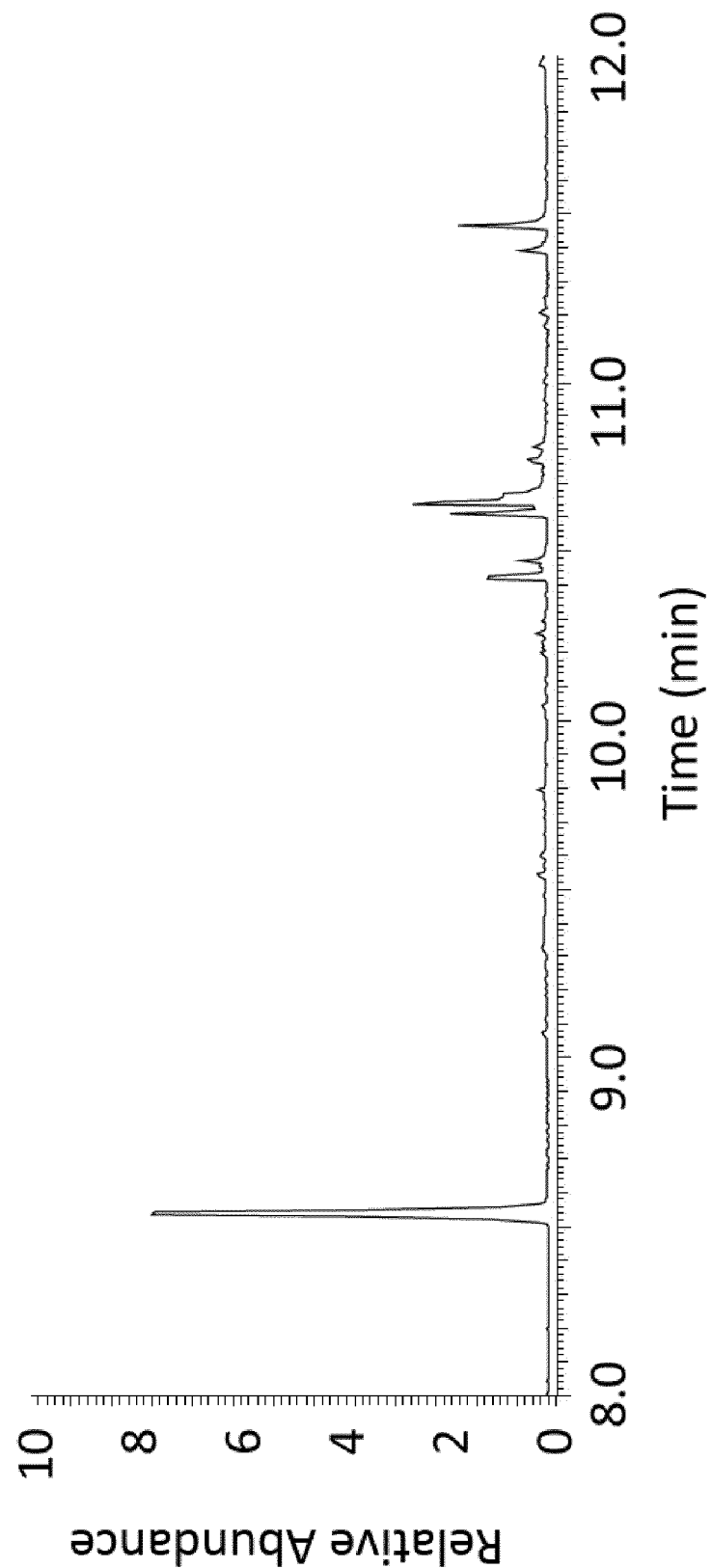
FIG. 43A shows the negative control cells (pBAD33 and pTrc99A).
Figure 43B:
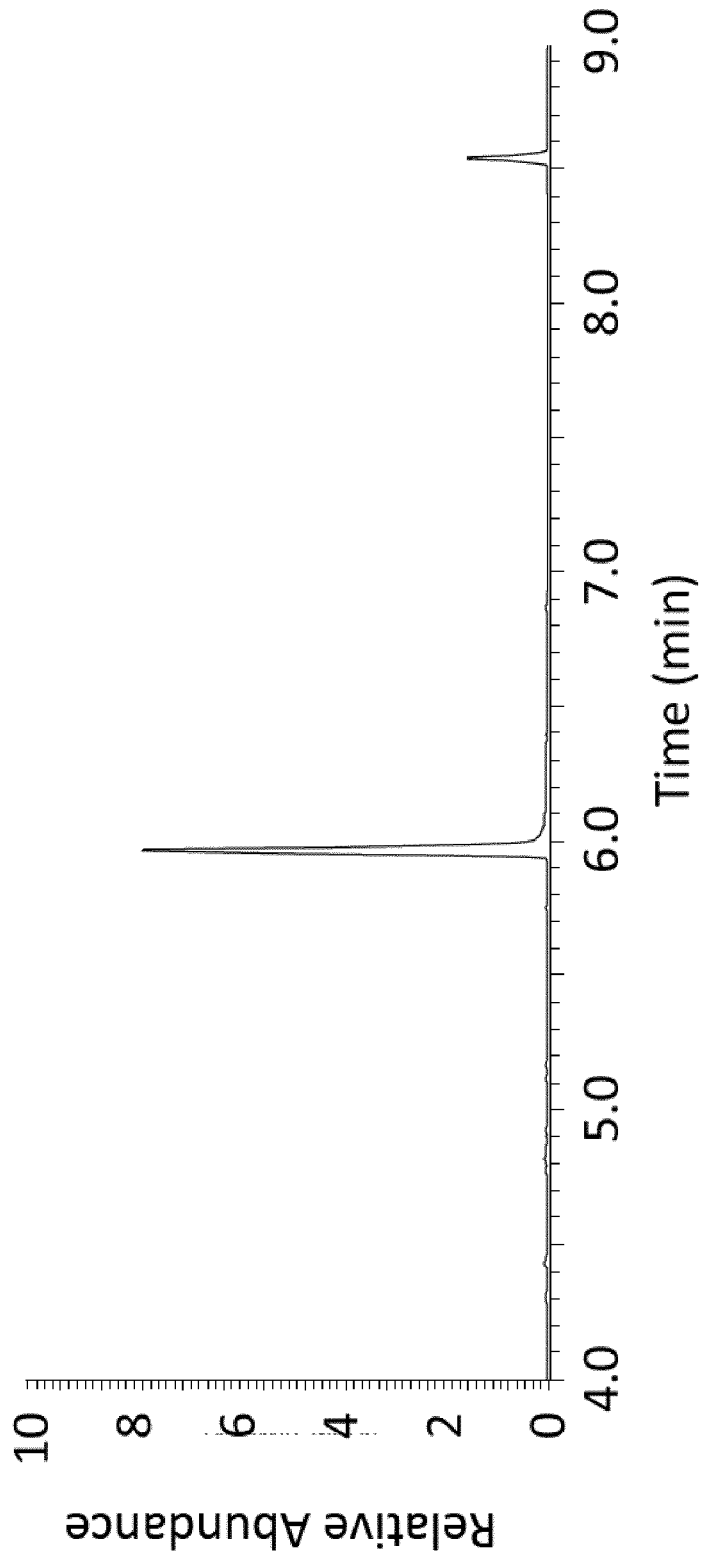
FIG. 43 shows the GC-MS chromatogram results that confirm the production of 2-phenyl ethanol (FIG. 43B) at one week from the recombinant microorganisms described in Example 4 (pBADpheA-aroLAC-aroG-tktA-aroBDE and pTrcBALK).
Figure 44:
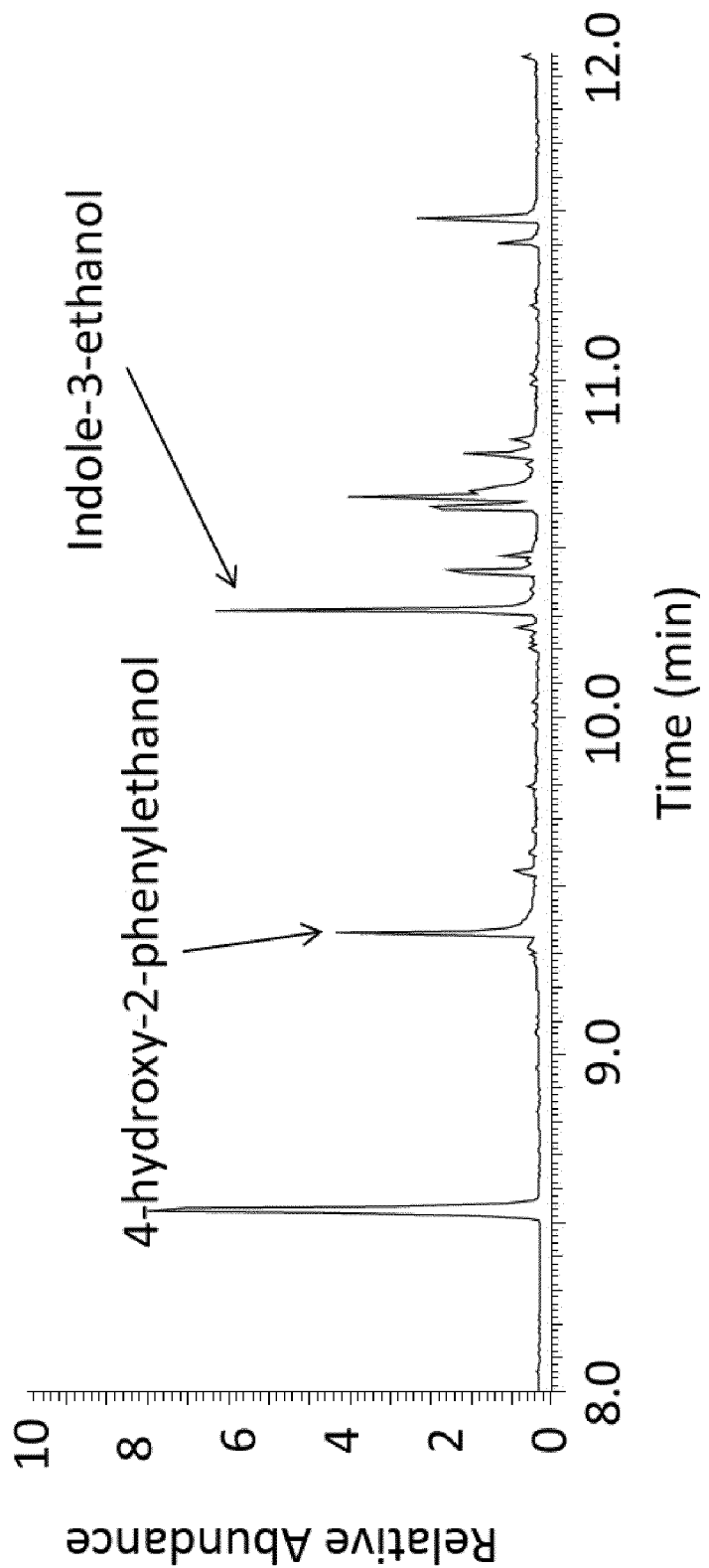
FIG. 44 shows the GC-MS chromatogram results that confirm the production of 2-(4-hydroxyphenyl)ethanol (9.36 min) and 2-(indole-3) ethanol (10.32 min) at one week from the recombinant microorganisms described in Example 4 (pBADtyrA-aroLAC-aroG-tktA-aroBDE and pTrcBALK).

FIG. 43A shows the GC-MS chromatogram for control (pBAD33 and pTrc99A) at one week. FIG. 43B shows the GC-MS chromatogram for 2-phenylethanol (5.97 min) production from pBADpheA-aroLAC-aroG-tktA-aroBDE and pTrcBALK at one week. FIG. 44 shows the GC-MS chromatogram for 2-(4-hydroxyphenyl)ethanol (9.36 min) and 2-(indole-3) ethanol (10.32 min) production from pBAD-tyrA-aroLAC-aroG-tktA-aroBDE and pTrcBALK at one week.

Example 5

Isolation and Biological Activity of Diol Dehydrogenases

Available substrates such as 3-hydroxy-2-butanone (acetoin), 4-hydroxy-3-hexanone (propioin), 5-hydroxy-4-octanone (butyroin), 6-hydroxy-5-decanone (valeroin), and 1,2-cyclopentanediol were used to measure the ability of diol dehydrogenases (ddh) to catalyze the reduction of large saturated α-hydroxyketones to produce a diol. All reagents were purchased from Sigma-Aldrich Co. and TCI America, unless otherwise stated.

For cloning and isolation of DDH polypeptides, genomic DNA from several species of bacteria were obtained from ATCC (Lactobaccilus brevis ATCC 367, Pseudomanas putida KT2440, and *Kiebsiella pneumoniae* MGH78578), PCR-amplified (using Phusion with polymerase with 1× Phusion buffer, 0.2 mM dNTP, 0.5 µL Phusion enzyme, 1.5 µM primers, and 20 pg template DNA in a 50 µL reaction) utilizing the following protocol: 30 cylces, 98° C./10 secs (denaturing), 60° C./15 secs (annealing), 72° C./30 secs (elongation). Polymerase chain reaction products were then digested using restriction enzymes NdeI and BamHI, then ligated into NdeI/BamHI digested pET28 vectors. Vectors containing ddh clones were transformed into BL21(DE3) competent cells for protein expression. Single colony was innoculated into LB media, and expression of 6×His-tagged proteins of interest was induced at $OD_{600}$=0.6 with 0.1 mM IPTG. Expression was allowed to proceed for 15 hours at 22° C. The 6×His-tagged enzymes were purified using Ni-NTA spin columns following suggested protocols by QIAGEN, yelding purified protein concentrations in the range of 1.1-6.5 mg/mL (determined by Bradford assay).

Diol dehydrogenase ddh 1 was isolated from *Lactobaccilus brevis* ATCC 367, diol dehydrogenase ddh2 was isolated from *Pseudomonas putida* KT2440, and diol dehydrogenase ddh3 was isolated from *Klebsiella pneumoniae* MGH78578. The nucleotide sequence encoding and polypeptide sequence of ddh 1 are shown in SEQ ID NOS:97 and 98, respectively; nucleotide sequence encoding and polypeptide sequence of ddh2 are shown in SEQ ID NOS:99 and 100, respectively; and nucleotide sequence encoding and polypeptide sequence of ddh3 are shown in SEQ ID NOS: 101 and 102, respectively.

Reactions to measure biological activity of DDH polypeptides were performed in a final volume of 200 µL as follows: 25 mM substrate, 0.04 mg/mL DDH polypeptide, 0.25 mg/mL nicotinamide cofactor, 200 mM imidazole, 14 mM Tris-HCl, and 1.5% by volume DMSO. Biological activity was assayed using a Molecular Devices Thermomax 96 well plate reader, monitoring absorbance at 340 nm, which corresponds to NADH or NADPH concentration. For the kinetic studies, 0.04 mg/mL DDH polypeptide, 0.25 mg/mL NADH, 20 mM Tris HCl Buffer pH 6.5(red) or 9.0(ox), T=25 C, 100 uL total volume was used.

Figure 12A:
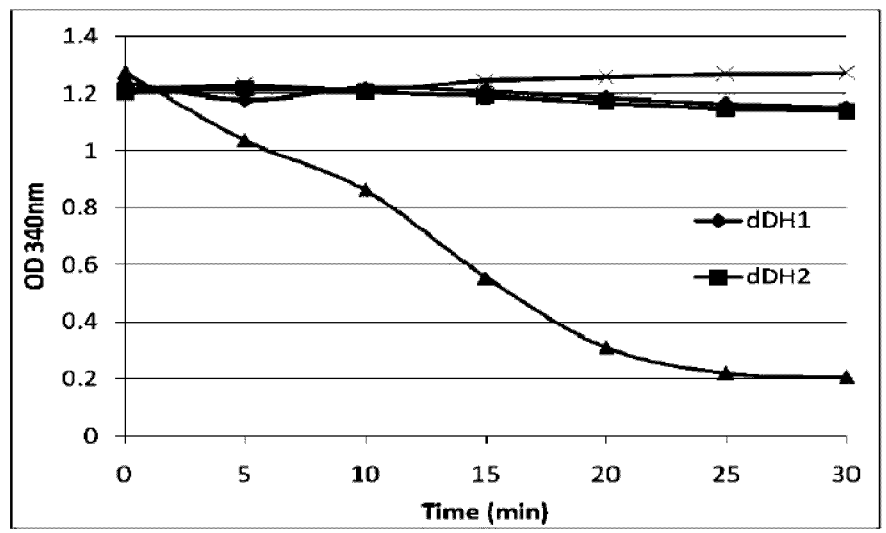
FIG. 12A shows the reduction of butyroin by ddh1, ddh2, and ddh3 as monitored by NADH consumption.
Figure 12B:
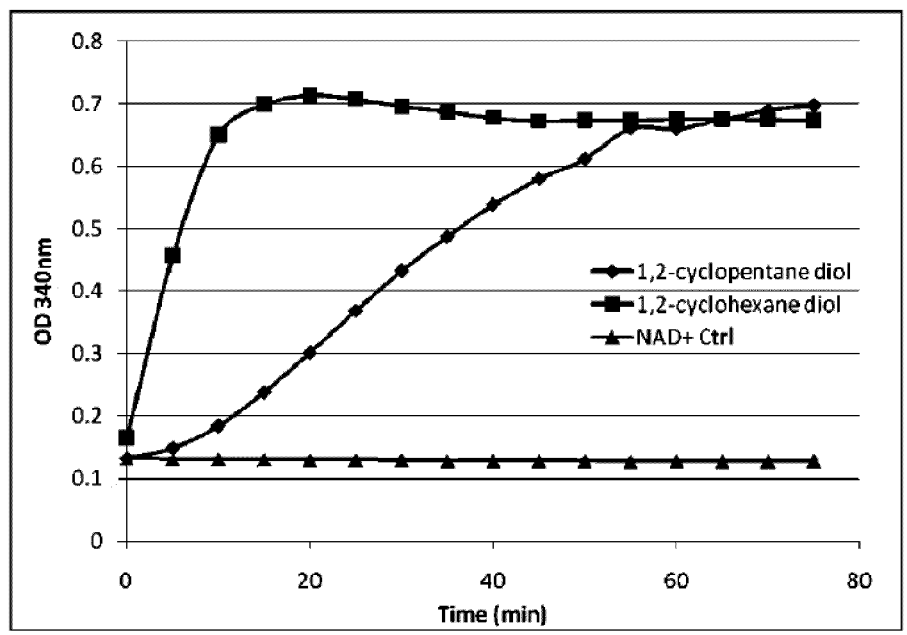
FIG. 12B shows the oxidation activity of ddh3 towards 1,2-cyclopentanediol and 1,2-cyclohexanediol as measured by NADH production.

FIG. 12A shows the biological activity of ddh1, ddh2, and ddh3 using butyroin as a substrate (triangles represent ddh3 activity). FIG. 12B shows the oxidation activity of ddh3 towards 1,2-cyclopentanediol and 1,2-cyclohexanediol as measured by NADH production. FIG. 13 summarizes the results of kinetic studies for various substrates in the oxidation reactions catalyzed by the DDH polypeptides. These reactions were NAD+ dependent.

Example 6

Sequential In Vivo Biological Activity of CC-Ligases (Lyases) and Diol Dehydrogenases The ability of a C—C lyase and a diol hydrogenase to perform the following sequential reaction was tested in *E. coli*:

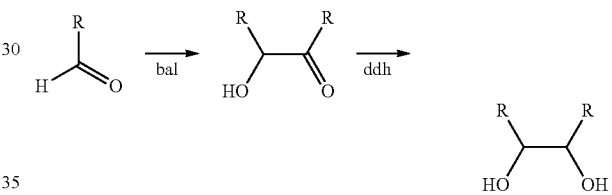

For α-hydroxyketone and diol production, a pathway comprising a benzaldehyde lyase (bal) gene isolated from *Pseudomonas fluorescens* (codon usage was optimized for *E. coli* protein expression) and meso-2,3-butanediol dehydrogenase (ddh) gene isolated from *Kiebsiella pneumoniae* subsp. *pneumoniae* MGH 78578 was constructed in *E. coli* and tested for its ability to condensate the substrates detailed below in Table 2 (e.g., acetoaldehyde, propionaldehyde, butyraldehyde, isobutyraldehyde, 2-methyl-butyraldehyde, 3-methyl-butyraldehyde, phenylacetaldehyde, and 4-hydroxyphenylacetaldehyde, or their corresponding alcohols) to form α-hydroxyketone and the corresponding diol in vivo. The production of various α-hydroxyketones and diols was monitored by gas chromatography-mass spectrometry (GC-MS).

TABLE 2

Summary of substrates and products.

| Substrate | Produced α-hydroxyketone | Produced diol | FIGS. |
|---|---|---|---|
| Butanal | 5-Hydroxy-4-octanone | 4,5-Octanonediol | 17A & B |
| n-Pentanal | 6-Hydroxy-5-decanone | 5,6-Decanediol | 18A & B |
| 3-Methylbutanal | 2,7-Dimethyl-5-hydroxy-4-octanone | 2,7-Dimethyl-4,5-octanediol | 19A & B |
| n-Hexanal | 7-Hydroxy-6-dodecanone | 6,7-dodecanediol | 20A & B |
| 4-Methylpentanal | 2,9-Dimethyl-6-hydroxy-5-decanone | 2,9-Dimethyl-5,6-decanediol | 21A & B |
| n-Octanal | 9-Hydroxy-8-hexadecanone | 8,9-hexadecanediol | 22 |
| Acetaldehyde | 3-Hydroxy-2-butanone | 2,3-Butanediol | 23 |

TABLE 2-continued

Summary of substrates and products.

| Substrate | Produced α-hydroxyketone | Produced diol | FIGS. |
|---|---|---|---|
| n-Propanal | 4-Hydroxy-3-hexanone | 3,4-Hexanediol | 24A & B |
| Phenylacetoaldehyde | 1,4-Diphenyl-3-hydroxy-2-butanone | 1,4-Diphenyl-2,3-butanediol | 25 |

For Analysis of ≦C10.

E. coli harboring pTrcBAL-DDH-2ADH was grown for overnight in LB media containing 50 ug/ml Kanamycine (Km). This seed culture was innoculated into M9 media containing 3% (v/v) glycerol, 0.5% (g/v) and 50 ug/ml Km. 10 mL cultures were grown to $O.D._{600}$=0.7, then cultures were induced with 0.5 mM IPTG. The cells were allowed to express the enzymes of interest for 3 hours before various aldehydes were added to a concentration of 5-10 mM. After addition of aldehydes, the cultures were capped and incubated at 37° C. with shaking for 72 hours. Cultures were extracted with 2 mL ethyl acetate, and analyzed on GC-MS using the following protocol:
  1 μL injection w/50:1 split
  Inlet temperature—150° C.
  Initial oven temperature—50° C.
  Temperature Ramp 1—10° C./min to 150° C.
  Temperature Ramp 2—50° C./min to 300° C.
  GC to MS transfer temp—250° C.
  MS detection—full scan MW 35-200

For Analysis of ≧C12.

E. coli DH10B strains harboring pTrc99A (Ctrl vector) or pTrcBAL were inoculated into 0.75×M9/0.5% LB containing 0.1 mM $CaCl_2$, 2 mM $MgSO_4$, 1 mM KCl, 1% galacturonate, 5 μg/mL thiamine, Amp. The cultures were grown up to an optical density (600 n nm) of 0.8 and induced with 0.25 mM IPTG. The cells were allowed to express the proteins for 2.5 hours at 37° C., then aldehyde substrate was added to a concentration of 5 mM, the culture vial was capped tightly and incubated for 72 hours at 37° C. w/shaking 200 rpm. 1 mL of the final culture was extracted with 0.75 mL of ethyl acetate, centrifuged facilitate phase separation, then analyzed via GCMS using the following method.
  1 μL injection w/50:1 split
  Inlet temperature—250° C.
  Initial oven temperature—50° C.
  Temperature Ramp 1—10° C./min to 125° C.
  Temperature Ramp 2—30° C./min to 300° C.
  Final Temperature 300° C.—1 minute
  GC to MS transfer temp—250° C.
  MS detection—full scan MW 40-260.

Figure 17A:
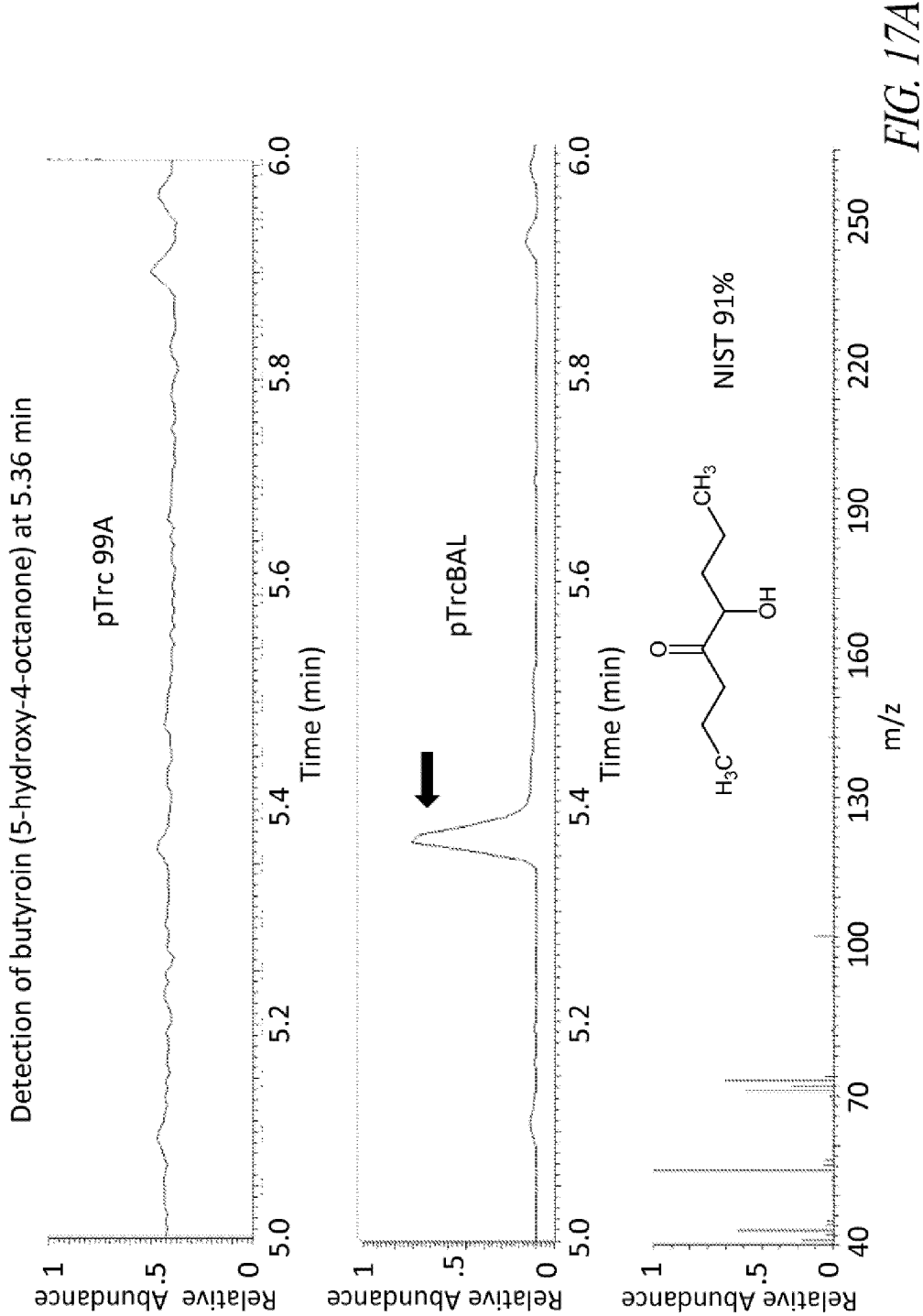
FIG. 17A shows the detection of butyroin (5-hydroxy-4-octanone) at 5.36 minutes.
Figure 17B:
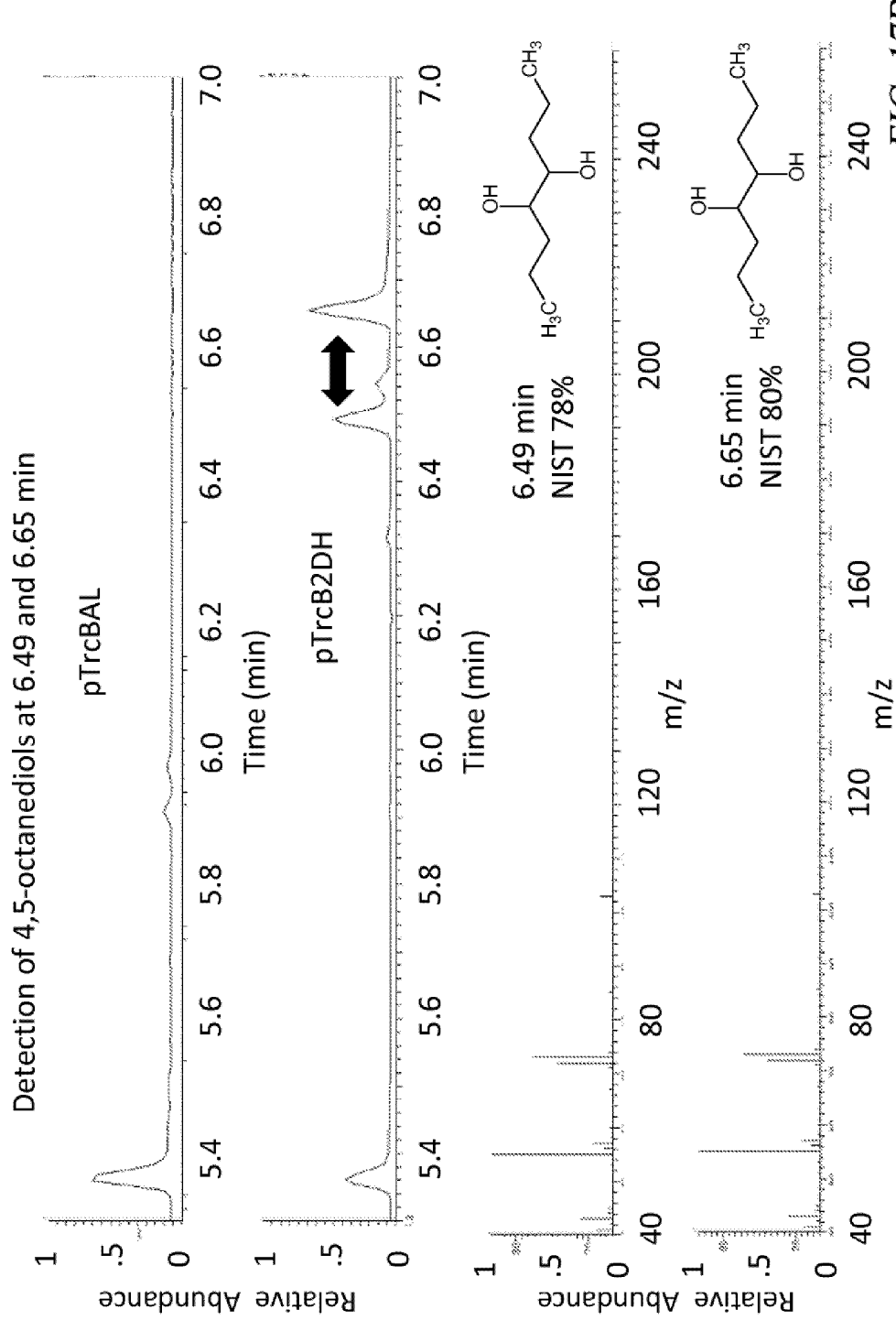
FIG. 17B shows the detection of 4,5-octanediol at 6.49 and 6.65 minutes.
Figure 18A:
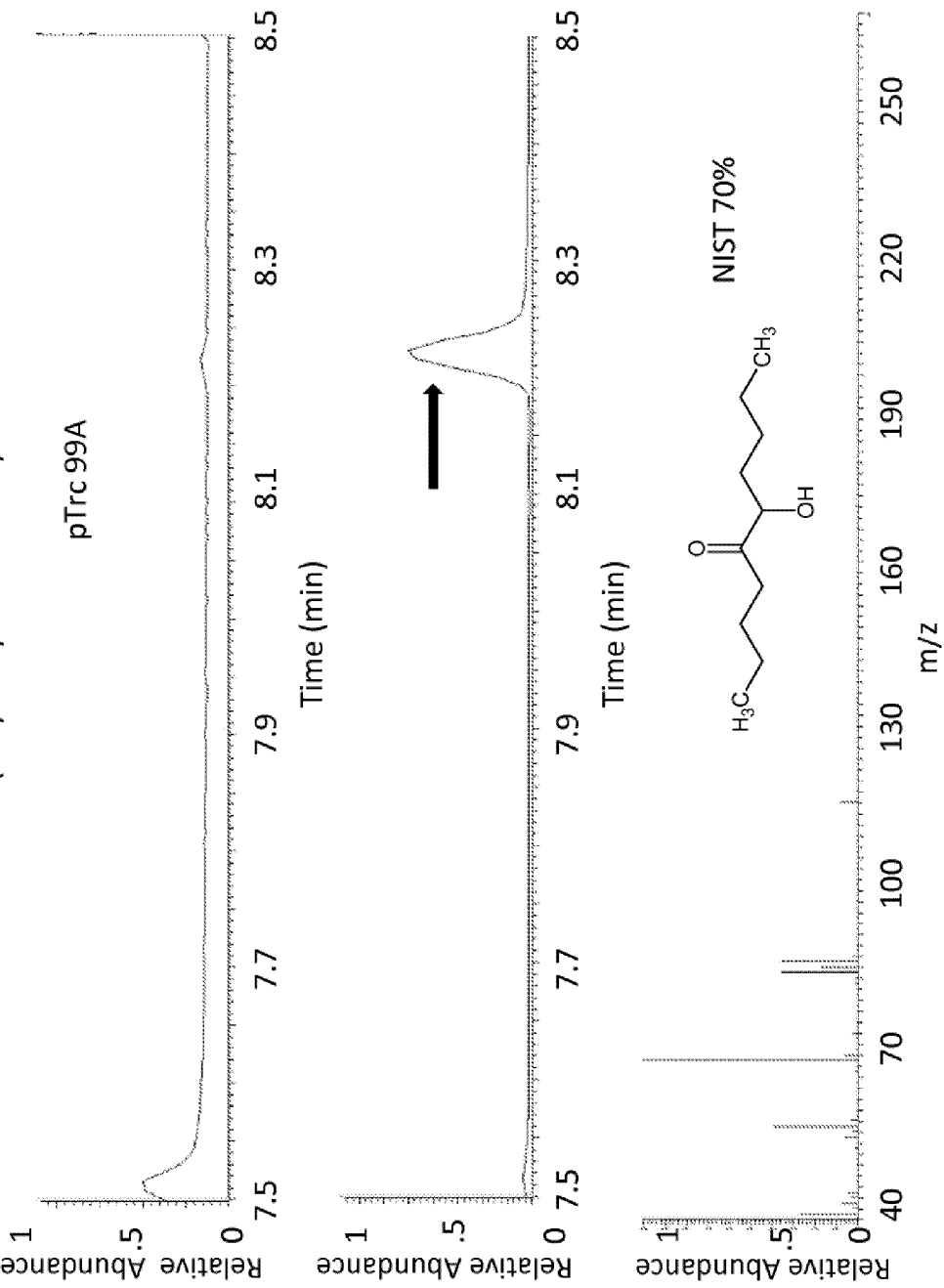
FIG. 18A shows the detection of valeroin (6-hydroxy-5-decanone) at 8.22 minutes.
Figure 18B:
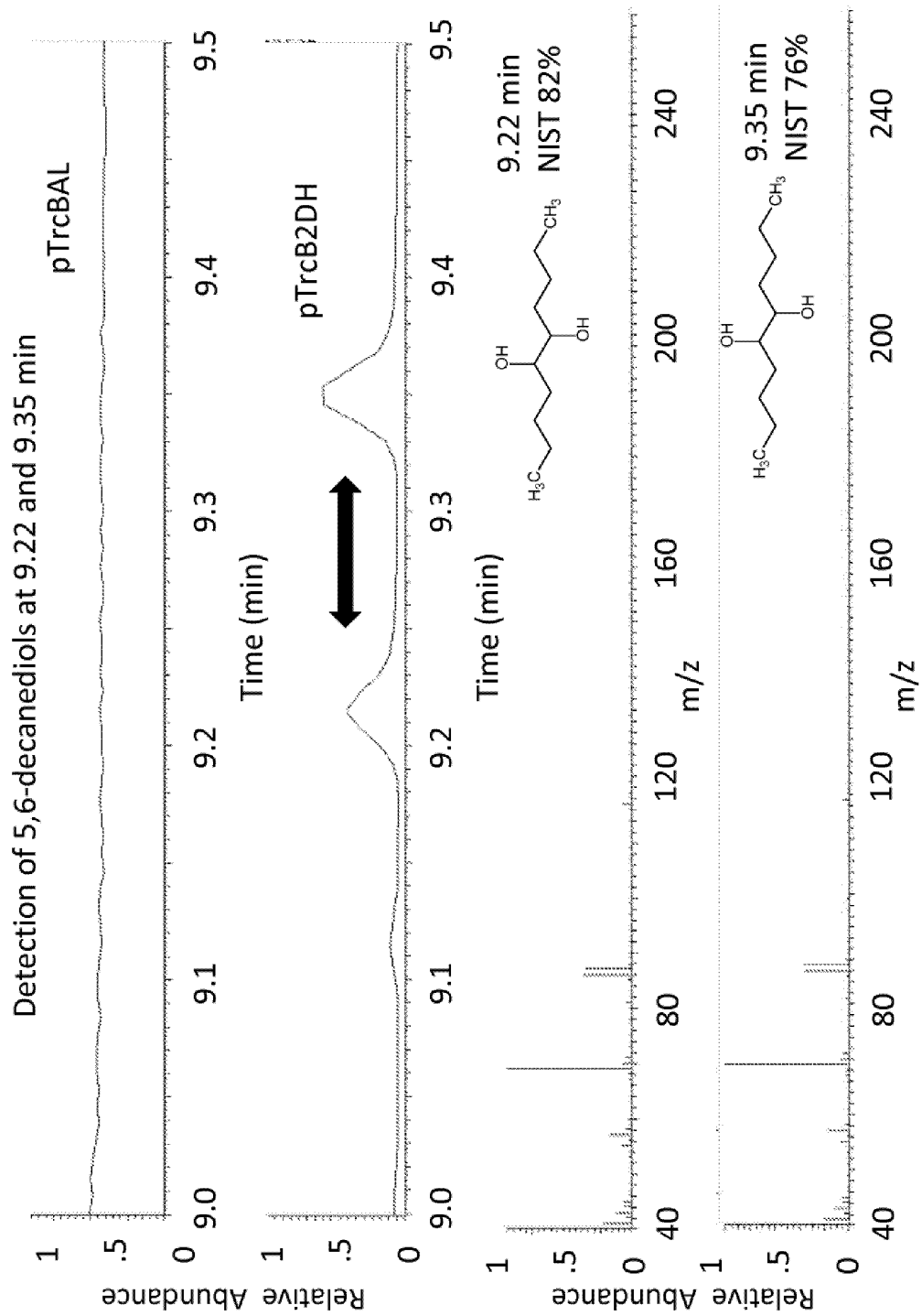
FIG. 18B shows the detection of 5,6 decanediol at 9.22 and 9.35 minutes.
Figure 19A:
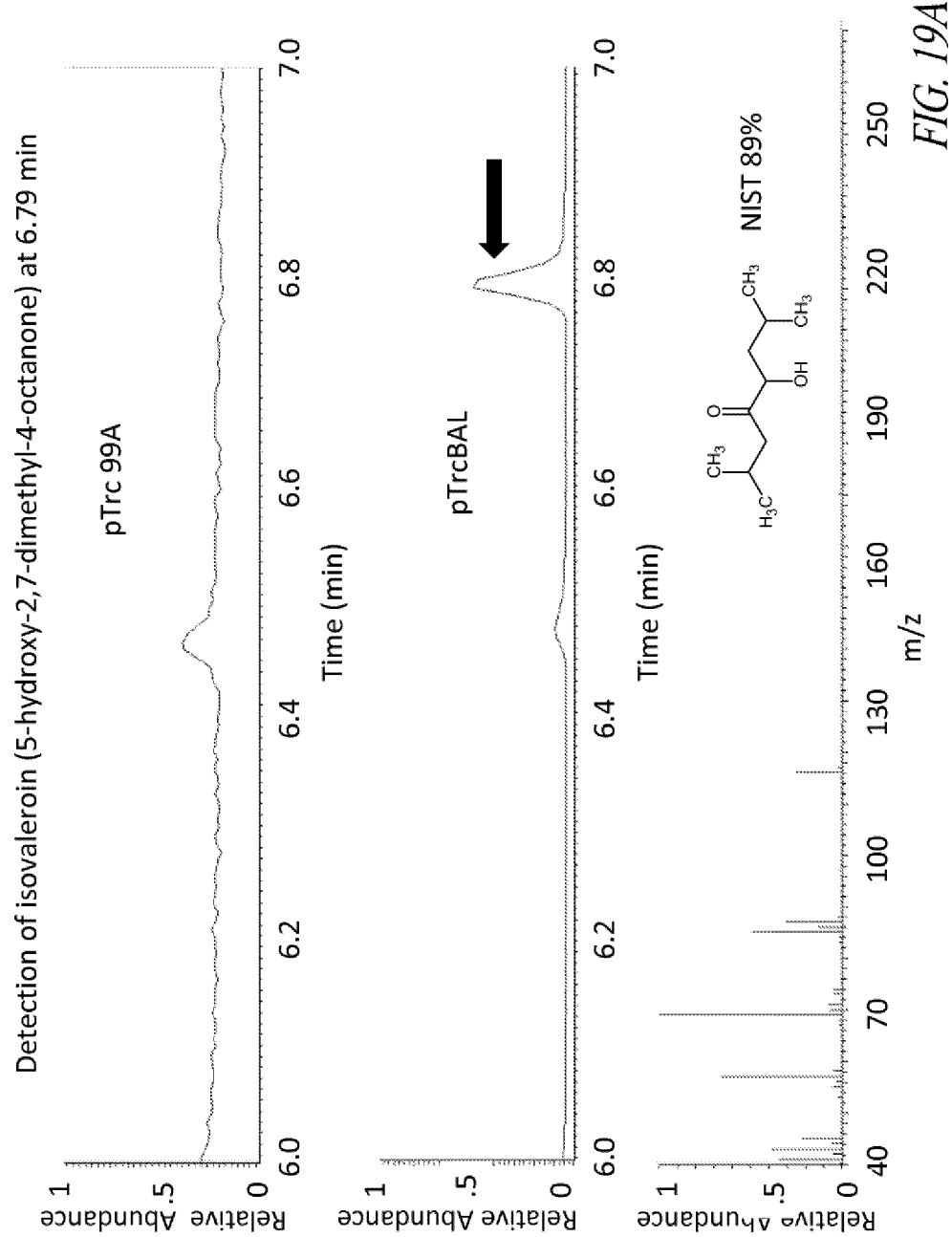
FIG. 19A shows the detection of isoveraloin (2,7-dimethyl-5-hydroxy-4-octanone) at 6.79 minutes.
Figure 19B:
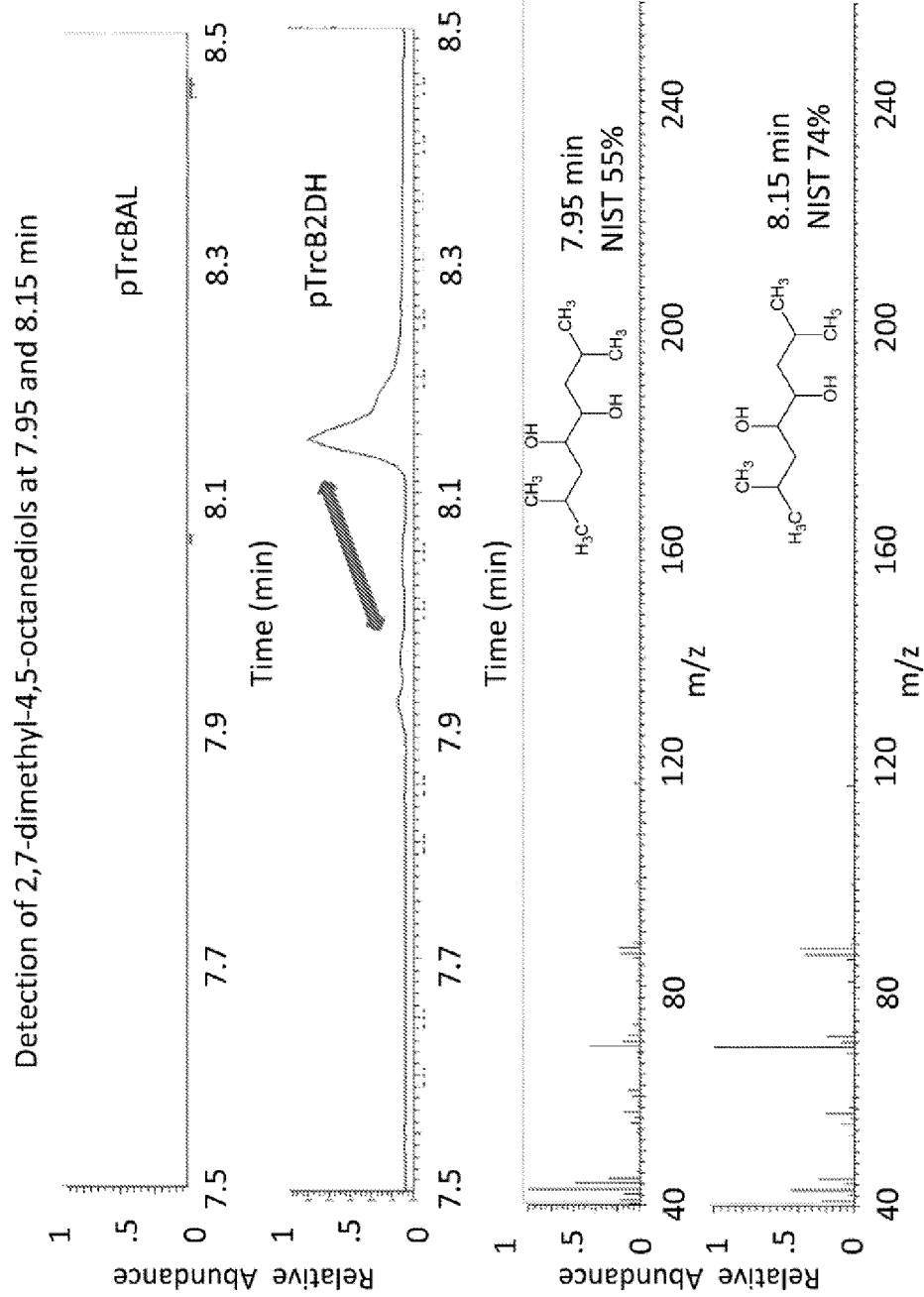
FIG. 19B shows the detection of 2,7-dimethyl-4,5-octanediol at 7.95 and 8.15 minutes.
Figure 20A:
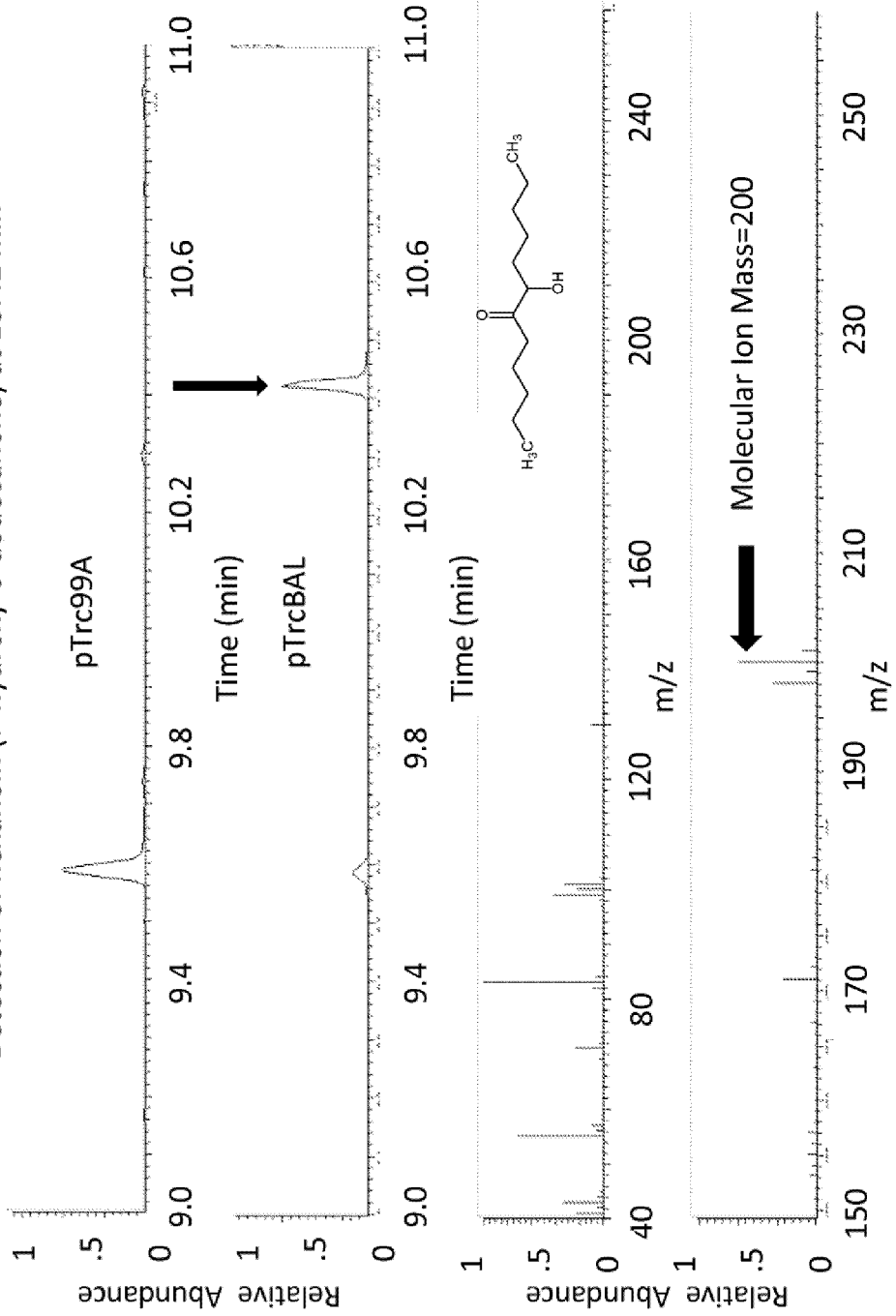
FIG. 20A shows the detection of hexanoin (7-hydroxy-6-decanone) at 10.42 minutes.
Figure 20B:
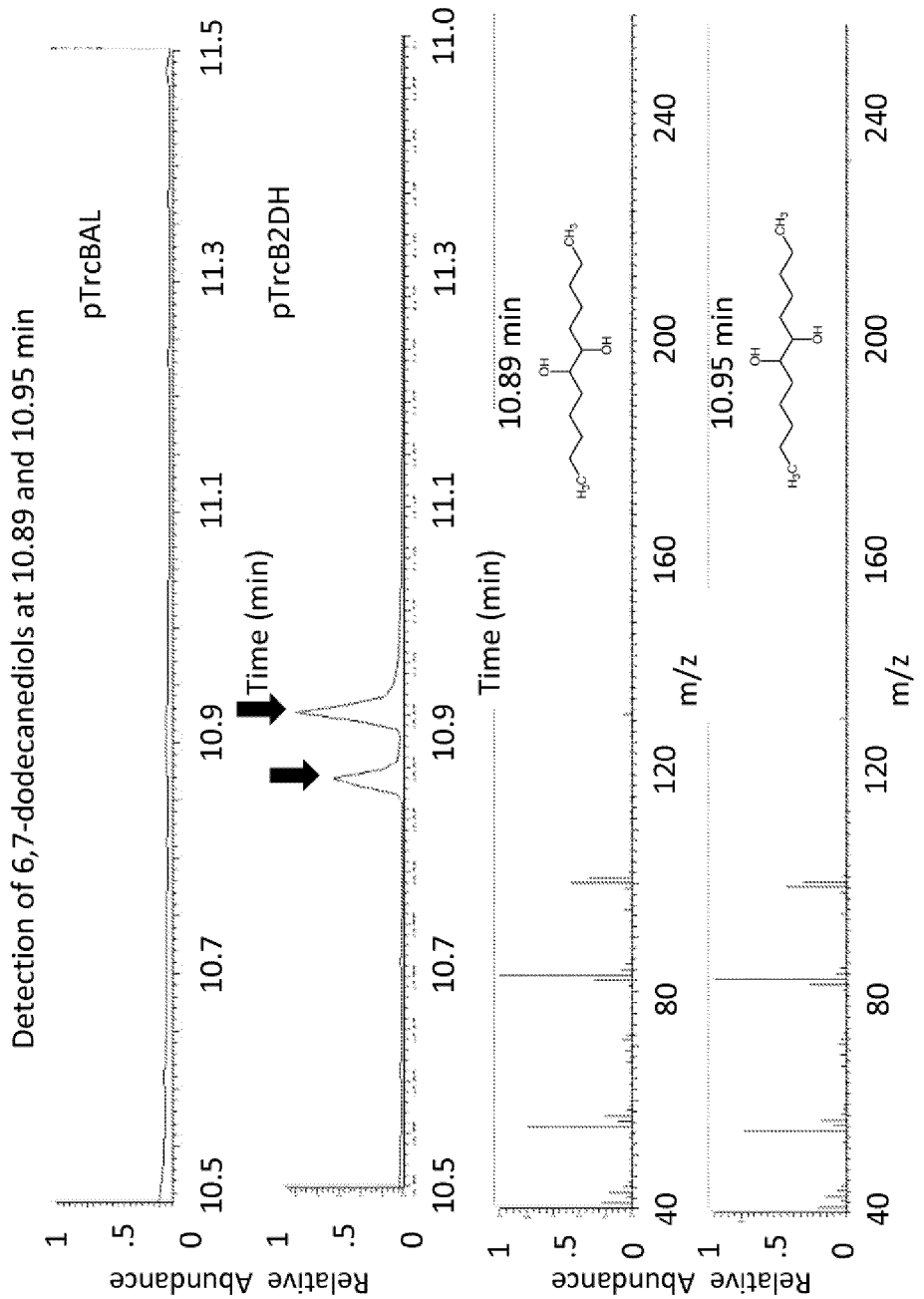
FIG. 20B shows the detection of 6,7 dodecanediol at 10.89 and 10.95 minutes.
Figure 21B:
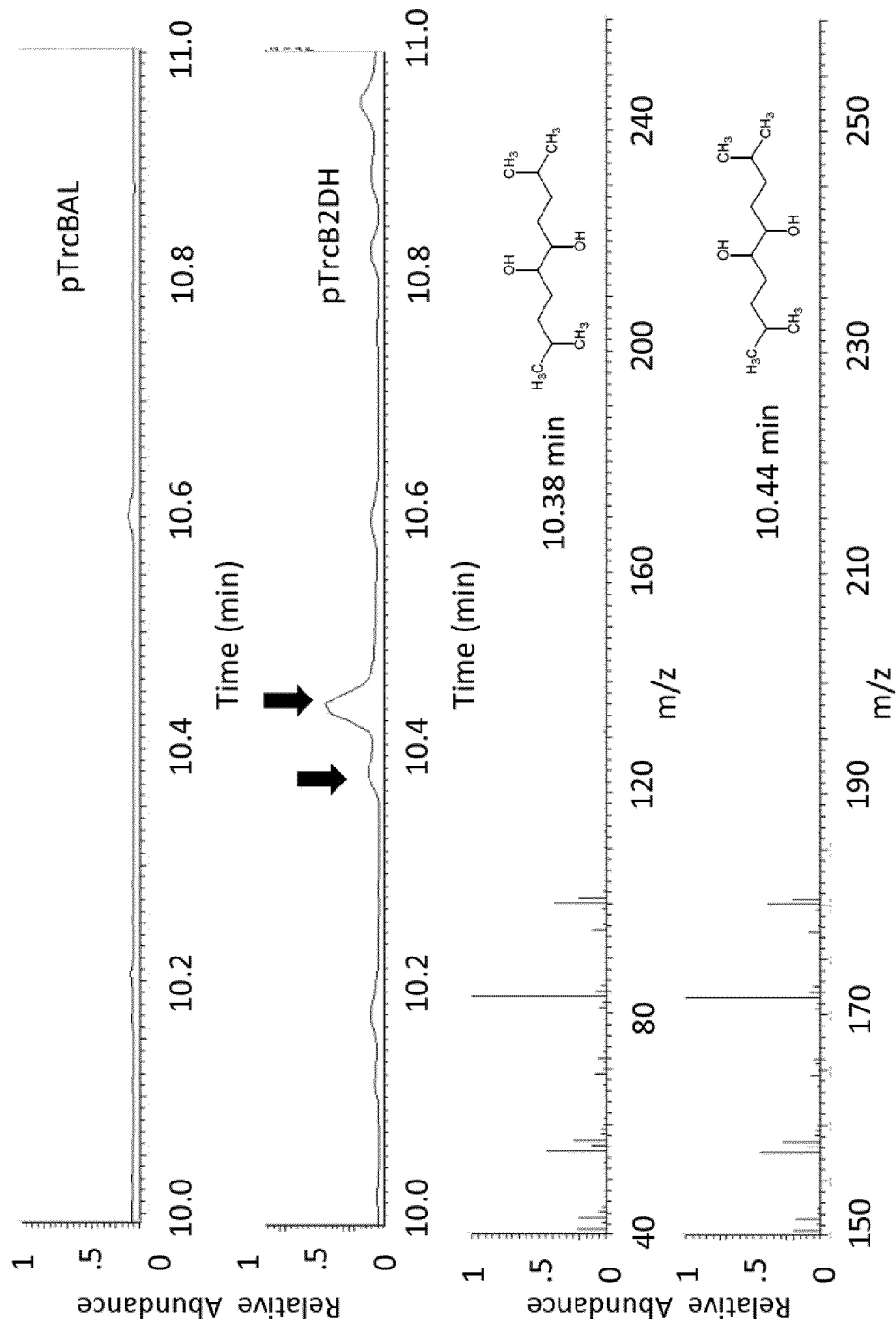
FIG. 21B shows the detection of 2,9-dimethyl-5,6-decanediol at 10.38 and 10.44 minutes.
Figure 22:
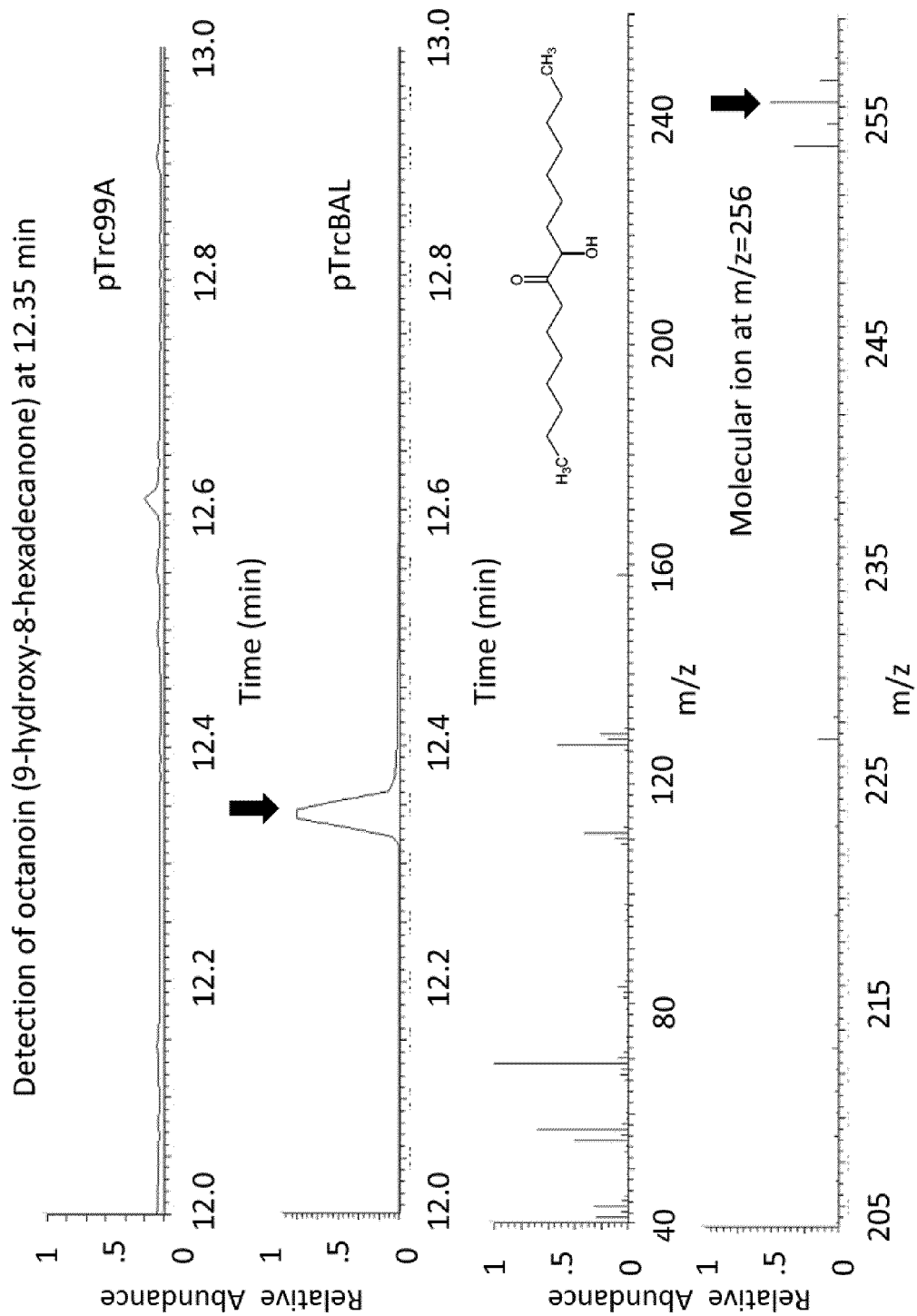
FIG. 22 shows the in vivo biological activity of a benzaldehyde lyase (bal) gene isolated from *Pseudomonas fluorescens* (codon usage was optimized for *E. coli* protein expression) and a ddh gene isolated from *Klebsiella pneumoniae* subsp. *pneumoniae* MGH 78578 (DDH3). This Figure illustrates the conversion of n-octanal into 9-hydroxy-8-hexadecanone by showing the detection of detection of octanoin (9-hydroxy-8-hexadecanone) at 12.35 minutes.
Figure 24A:
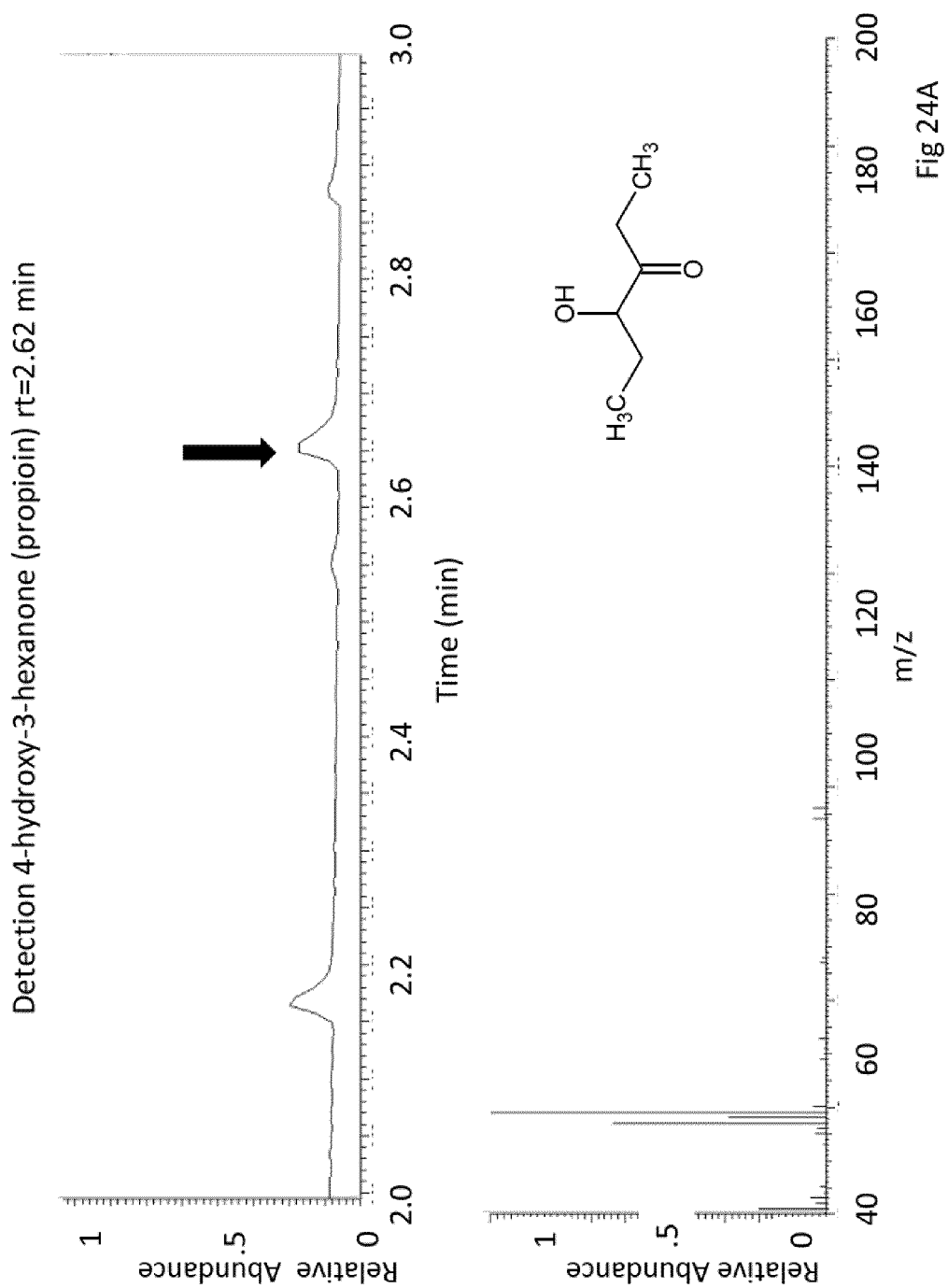
FIG. 24A shows the detection of propioin (4-hydroxy-3-hexanone) at rt=2.62 minutes.
Figure 24B:
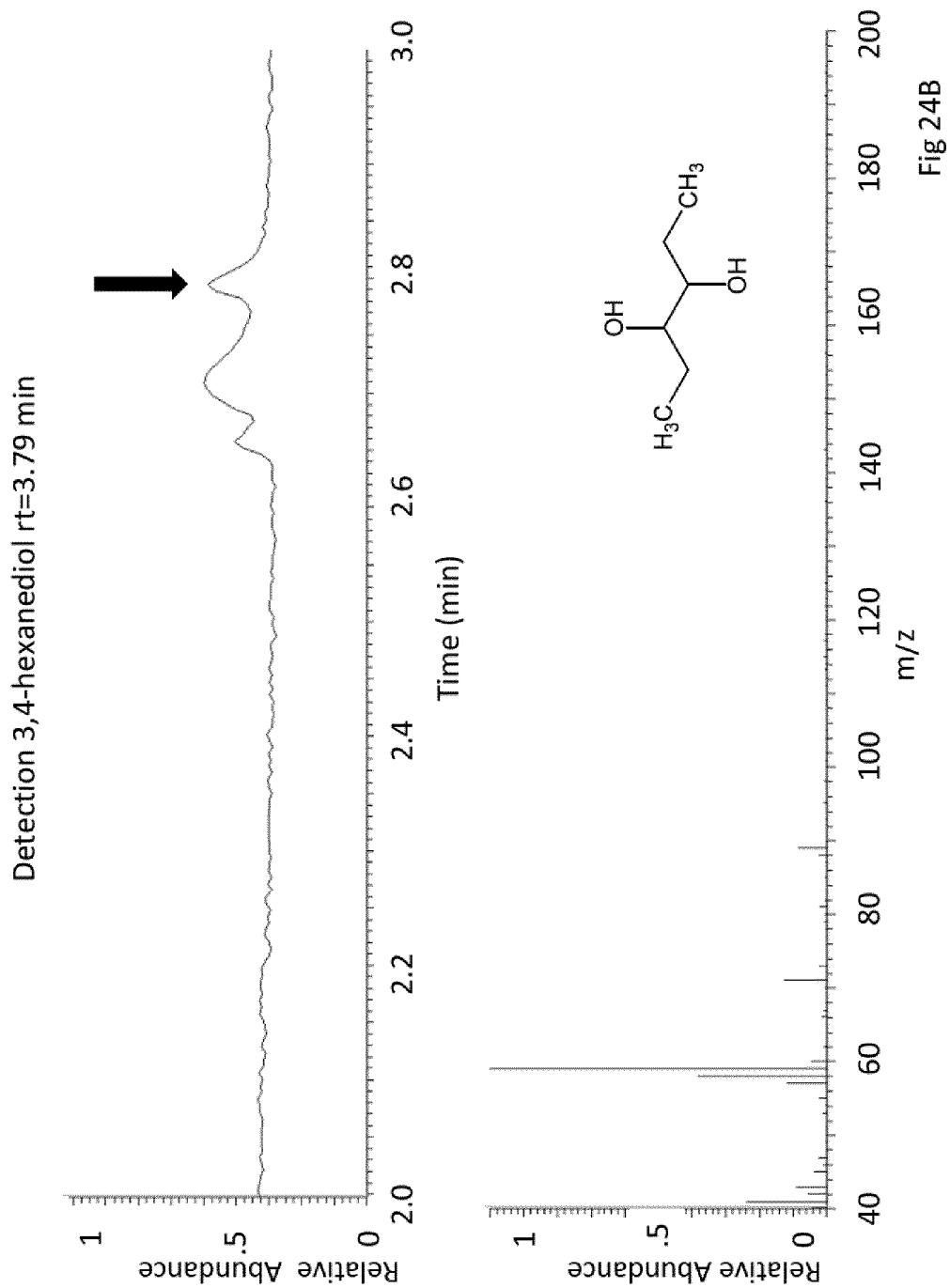
FIG. 24B shows the detection of 3,4-hexanediol at rt=3.79 minutes.
Figure 25:
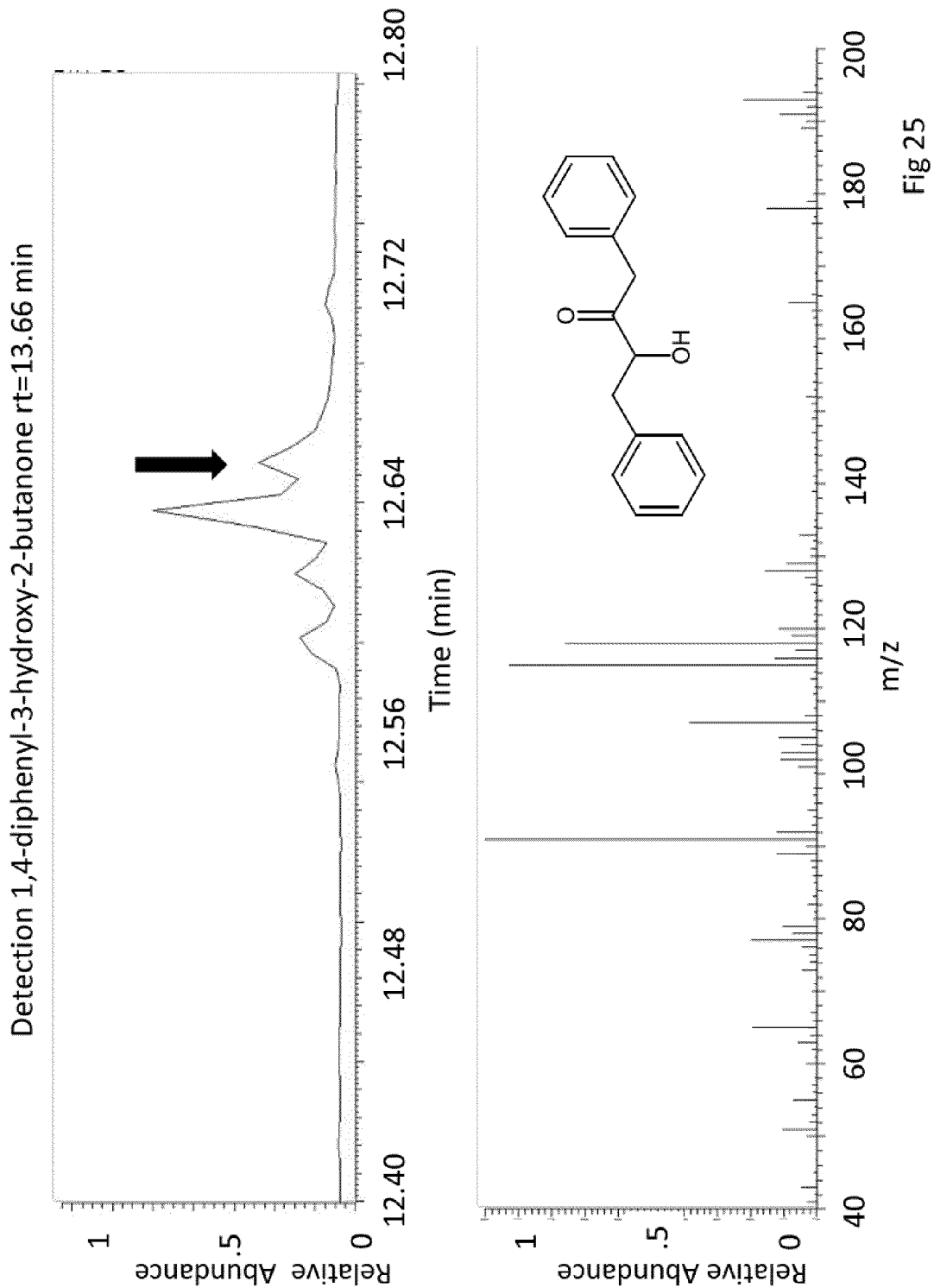
FIG. 25 the in vivo biological activity of a benzaldehyde lyase (bal) gene isolated from *Pseudomonas fluorescens* (codon usage was optimized for *E. coli* protein expression) and a ddh gene isolated from *Klebsiella pneumoniae* subsp. *pneumoniae* MGH 78578 (DDH3). This Figure illustrates the conversion of phenylacetoaldehyde into 1,4-diphenyl-3-hydroxy-2-butanone by showing the detection of 1,4-diphenyl-3-hydroxy-2-butanone at rt=13.66 minutes.

The results are depicted in FIGS. 17 through 25. FIG. 17 shows the sequential conversion of butanal into 5-hydroxy-4-octanone and then 4,5-octanonediol. FIG. 18 shows the sequential conversion of n-pentanal into 6-hydroxy-5-decanone and then 5,6-decanediol. FIG. 19 shows the conversion of 3-methylbutanal into 2,7-dimethyl-5-hydroxy-4-octanone and then 2,7-Dimethyl-4,5-octanediol. FIG. 20 shows the sequential conversion of n-hexanal into 7-hydroxy-6-dodecanone and then 6,7-dodecanediol. FIG. 21 shows the conversion of 4-methylpentanal into 2,9-dimethyl-6-hydroxy-5-decanone and then 2,9-dimethyl-5,6-decanediol. FIG. 22 shows the conversion of n-octanal into 9-hydroxy-8-hexadecanone. FIG. 23 shows the conversion of acetaldehyde into 3-hydroxy-2-butanone. FIG. 24 shows the sequential conversion of n-propanal into 4-hydroxy-3-hexanone and then 3,4-hexanediol. FIG. 25 shows the conversion of phenylacetoaldehyde into 1,4-diphenyl-3-hydroxy-2-butanone.

Similar to above, a pathway comprising a benzaldehyde lyase (bal) gene isolated from *Pseudomonas fluorescens* (codon usage was optimized for E. coli protein expression) was constructed in E. coli and tested for its ability to catalyze the production of various α-hydroxyketones. The results, which show the broad spectrum of C—C ligase activity for the bal gene tested, are set forth in FIG. 48 through FIG. 55.

Example 7

Sequential Biological Activity of Diol Dehydrogenases and Diol Dehydratases

To test the sequential biological activity of diol dehydrogenases and diol dehydratases in a dehydration and reduction pathway, butyroin was used as a substrate in a sequential reaction to produce 4-octanone. The enzyme diol dehydrogenase (e.g., ddh) catalyzes the reversible reduction and oxidation of α-hydroxy ketones and its corresponding diol, such as 5-hydroxy-4-octanone and 4,5-octanediol, and the enzyme diol dehydratase (e.g., pduCDE) catalyzes the irreversible dehydration of diols, such as 4,5-octanediol.

Diol dehydrogenase ddh from *Kiebsiella pneumoniae* MGH 78578 and diol dehydratase pduCDE from *Kiebsiella pneumoniae* MGH 78578 were cloned into a bacterial expression vector and expressed and purified on a Ni-NTA column, as described in Example X except that 1 mM of 1,2-propanediol was added at all time during the expression and purification of diol dehydratase. The large, medium, and small subunits of the pduCDE polyeptide are encoded by the nucleotide sequences of SEQ ID NOs:103, 105, and 107, respectively, and the polypeptide sequence are set forth in SEQ ID NOs: 104, 106, and 108, respectively.

The ddh3 and pduCDE polypeptides were incubated with butyroin and their appropriate cofactors, then assayed using gas chromatography-mass spectrometry (GC-MS) for their ability to perform sequential reactions resulting in the product 4-octanone. Reaction conditions are given in Table 3 below. The reaction mixture was incubated at 37° C. for 40 hours in a 0.6 mL eppendorf tube with minimal head space. The reaction product was extracted with an equivalent volume of ethyl acetate, stored in a glass vial, and sent to Thermo Fischer Scientific Instruments Division for compositional analysis by GC-MS.

TABLE 3

Reaction Conditions

| Rxn Component | Concentration |
|---|---|
| 5-hydroxy-4-octanone (butyroin) | 8.4 mM |
| Adenosylcobalamin (coenzyme $B_{12}$) | 33.5 μM |
| KCl | 9.6 mM |
| NADH | 18 mM |

TABLE 3-continued

Reaction Conditions

| Rxn Component | Concentration |
|---|---|
| dDH3 enzyme | 0.19 mg/mL |
| dDOH1 enzyme mix | 0.15 mg/mL |
| Reaction Buffer | 10 mM Tris HCl pH 7.0 |

FIG. 26A shows GC-MS data which confirms the presence of 4,5-octanediol in the sample extraction. The mass-spectra of the peaks, retention time, at 5.36 was identified as butyroin (substrate), and at 6.01, 6.09, and 6.12 min were identified as different isomers of 4,5-octanediol. This compound is the expected product resulting from the reduction of butyroin by ddh3.

Figure 26B:
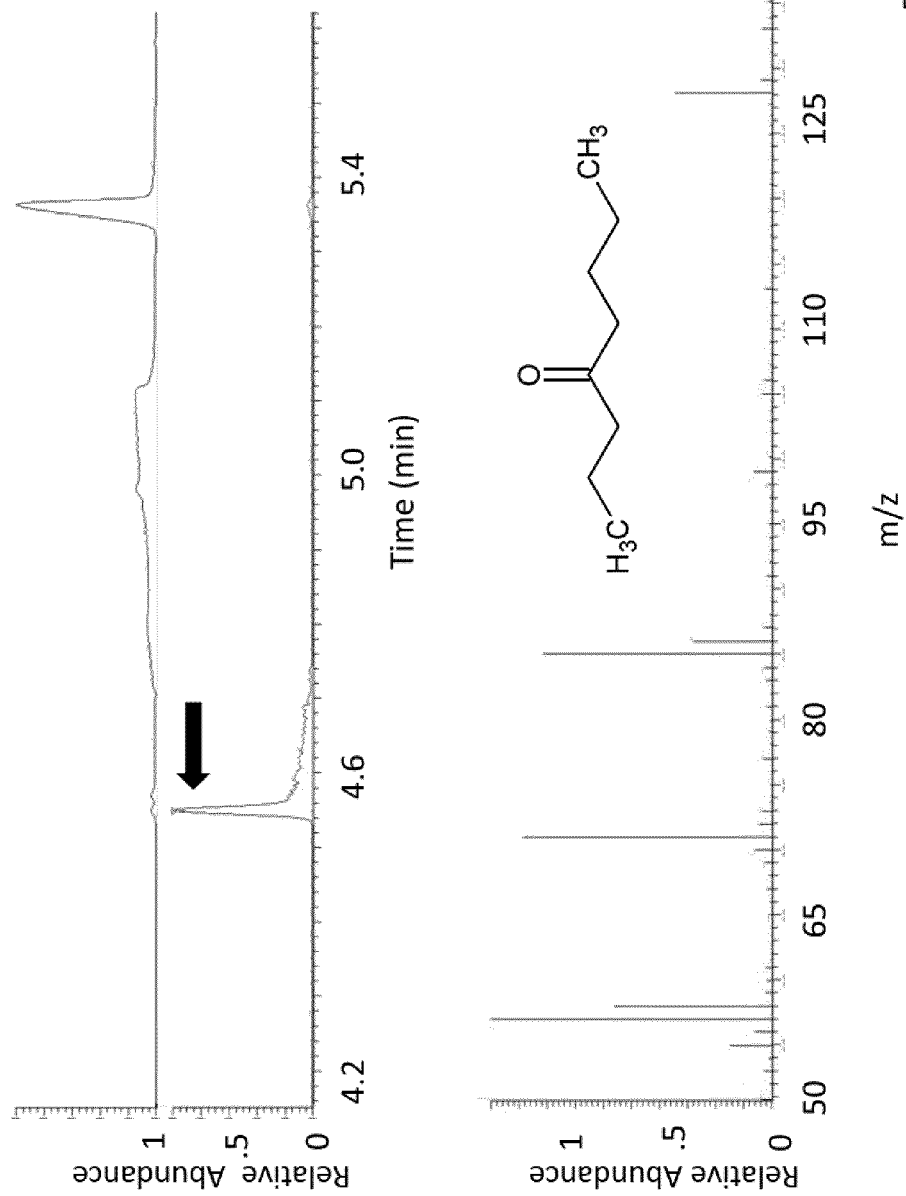
FIG. 26B shows GC-MS data confirming the presence of 4-octanone in the sample extraction, which is the expected product resulting from the sequential dehydrogenation of butyroin and dehydration of 4,5-octanediol by ddh3 and pduCDE, respectively.

FIG. 26B shows GC-MS data confirming the presence of 4-octanone in the sample extraction. The mass-spectra of the peak, retention time, at 4.55 was identified as 4-octanone. This compound is the expected product resulting from the sequential dehydrogenation of butyroin and dehydration of 4,5-octanediol by ddh3 and pduCDE, respectively.

Figure 27A:
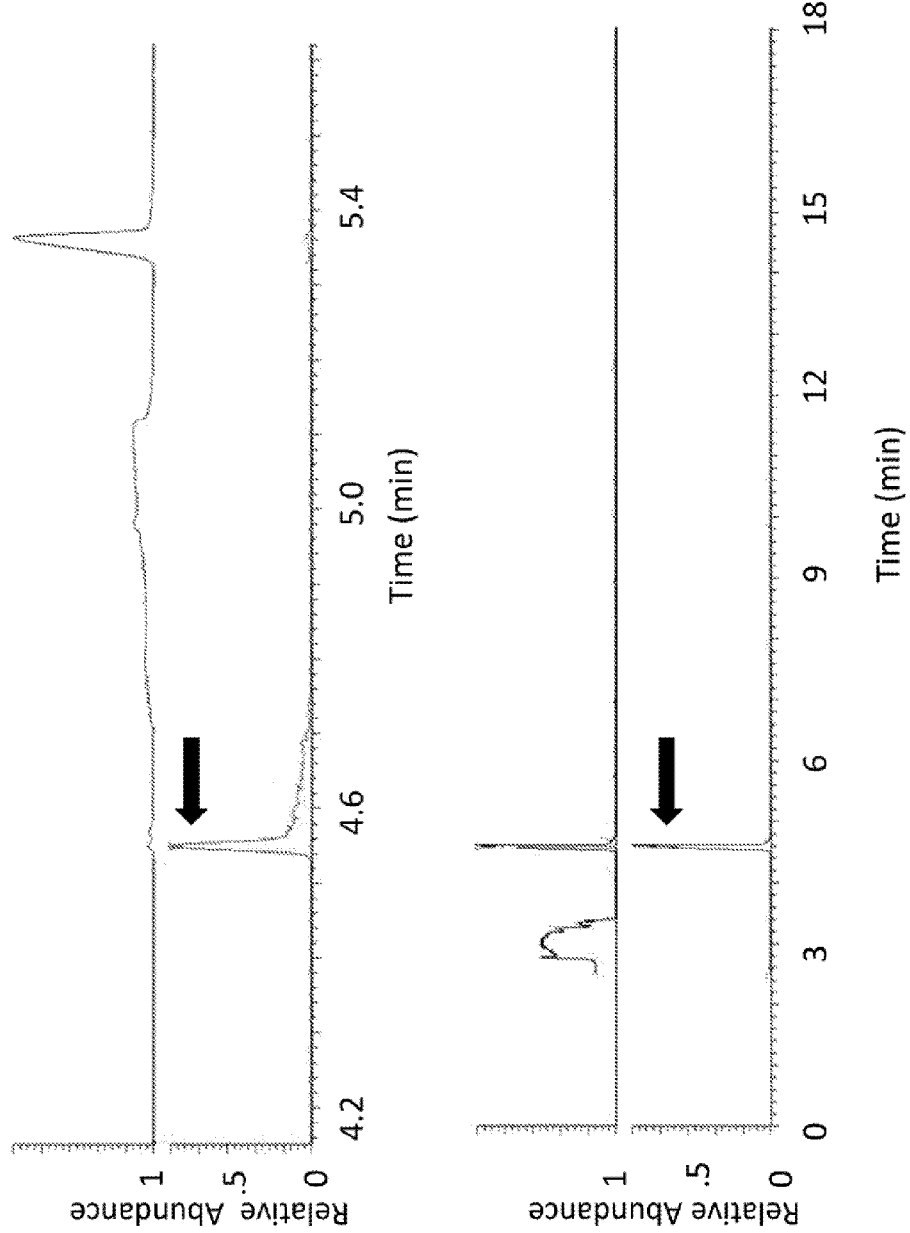
FIGS. 27A and 27B show comparisons between the sample extraction gas chromatograph/mass spectrum and the 4-octanone standard gas chromatograph/mass spectrum, confirming that 4-octanone was produced from butyroin using the enzymes diol dehydrogenase (ddh3) and a diol dehydratase (pduCDE).
Figure 27B:
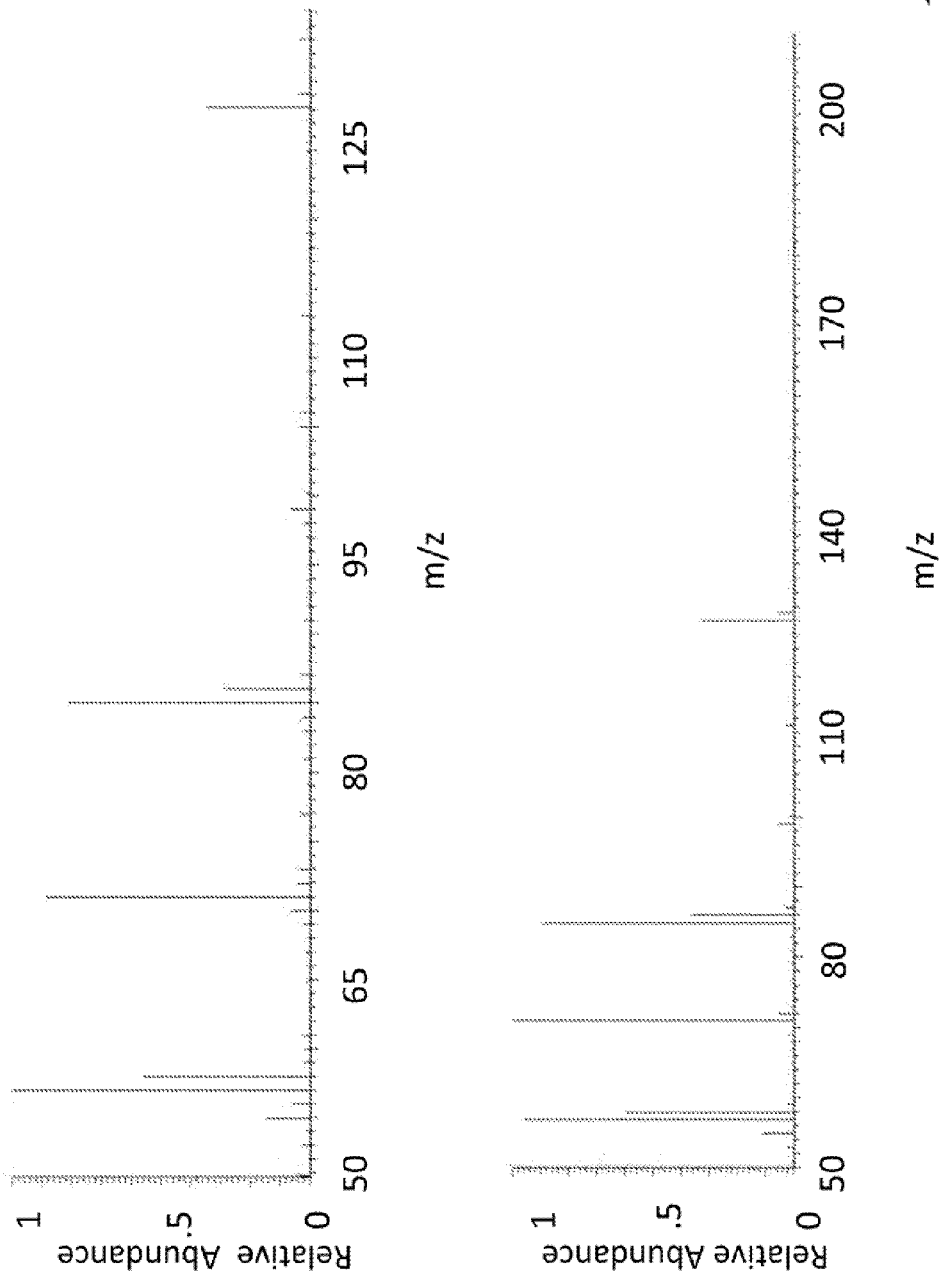

FIGS. 27A and 27B show comparisons between the sample extraction gas chromatograph/mass spectrum and the 4-octanone standard gas chromatograph/mass spectrum. These results demonstrate that 4-octanone was produced from butyroin using the enzymes diol dehydrogenase (ddh3) and a diol dehydratase (pduCDE). GC-MS analysis of the incubated reaction mixture confirmed starting material, intermediate and product, demonstrating that these enzymes can be reappropriated for these specific substrates.

Example 8

Isolation and Biological Activity of Secondary Alcohol Dehydrogenases

Substrates such as 4-octanone, 2,7-dimethyl-4-octanone, cyclopentanone and corresponding alcohols were utilized to measure the ability of secondary alcohol dehydrogenases (2ADHs) to catalyze the reduction of large saturated ketones to secondary alcohols. An example of a reaction catalyzed by secondary alcohol dehydrogenases is illustrated below (reduction of 4-octanone to 4-octanol is shown):

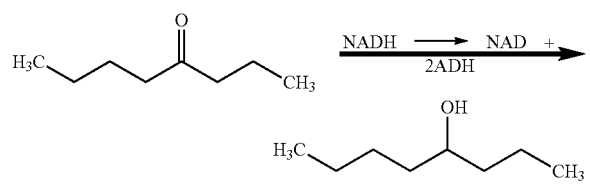

All enzymes and reagents were purchased from New England Biolabs and Sigma, respectively, unless otherwise stated.

Various secondary alcohol dehydrogenases (2ADHs) were isolated from *Pseudomonas putida* KT2440, *Pseudomonas fluorescens* Pf-5, and *Klebsiella pneumoniae* MGH 78578. All vectors were transformed in BL21(DE3) competent cells and expression of the genes encoding the proteins of interest was induced with IPTG (via the T7 promoter). The cells were lysed, proteins were extracted and then purified on Ni-NTA columns. Final protein concentration in the Ni-NTA eluate was diluted to 0.15 mg/mL prior to assays.

NADPH/NADPH consumption and production assays were performed using a THERMOmax microplate reader in the kinetic mode, monitoring the NADPH absorbance peak at 340 nm until the reaction reached equilibrium. In the assay described in Table 2, 2ADH-2, 2ADH-5, 2ADH-8, and 2ADH-10 were tested for their ability to either catalyze the oxidation of 4-octanol or catalyze the reduction of 4-octanone. These reaction conditions are found in Table 4 below.

TABLE 4

Reaction Conditions for Various Enzyme Assays

| Reaction Component | Final Concentration |
|---|---|
| NADH Production Assay (30° C.) | |
| 2ADH enzyme | Approx. 0.058 μg/μL |
| 4-octanol | 5.55 mM |
| NAD+ | Approx. 1.4 μg/μL |
| Imidizole (from Elution Buffer) | Approx. 280 mM |
| NADH Consumption Assay (30° C.) | |
| 2ADH enzyme | Approx. 0.075 μg/μL |
| 4-octanone | 5.0 mM |
| NADH | Approx. 0.25 μg/μL |
| Imidizole (from Elution Buffer) | Approx. 250 mM |
| NADPH Production Assay (30° C.) | |
| 2ADH enzyme | Approx. 0.058 μg/μL |
| 4-octanol | 5.55 mM |
| NADP+ | Approx. 1.4 μg/μL |
| Imidizole (from Elution Buffer) | Approx. 280 mM |

Further testing was performed, as described in Tables 5 below, in which 2ADH-2, 2ADH-11, 2ADH-12, 2ADH-13, 2ADH-14, 2ADH-15, 2ADH-16, 2ADH-17, and 2ADH-18 were tested for their ability to either catalyze the oxidation of 4-octanol, 2,7-dimethyl-4-octanonol, or cyclopentanol, or catalyze the reduction of 4-octanone, 2,7-dimethyl-4-octanonone, or cyclopentanone.

TABLE 5

| Rxn Component | Final Concentration |
|---|---|
| Rxn Components for NADPH Consumption Assays (Reduction) | |
| Substrate | 25 mM |
| Enzyme | 0.04 mg/mL |
| Nicotinamide cofactor | 0.25 mg/mL |
| Imidizole | 200 mM |
| Tris HCl | 14 mM |
| DMSO | 1.5% by volume |
| Total Volume | 200 μL |
| Rxn Components for NAD(P)H Production Assays (Oxidation) | |
| Substrate | 5 mM |
| Enzyme | 0.04 mg/mL |
| Nicotinamide cofactor | 0.25 mg/mL |
| Imidizole | 200 mM |
| Tris HCl | 14 mM |
| Rxn Components for NAD(P)H Production Assay using 2,7-dimethyl-4-octanone as a substrate | |
| Substrate | 50 mM |
| Enzyme | 0.08 mg/mL |
| Nicotinamide cofactor | 0.25 mg/mL |
| Imidizole | 200 mM |
| Tris HCl | 14 mM |
| DMSO | 3% by volume |

Figure 30A:
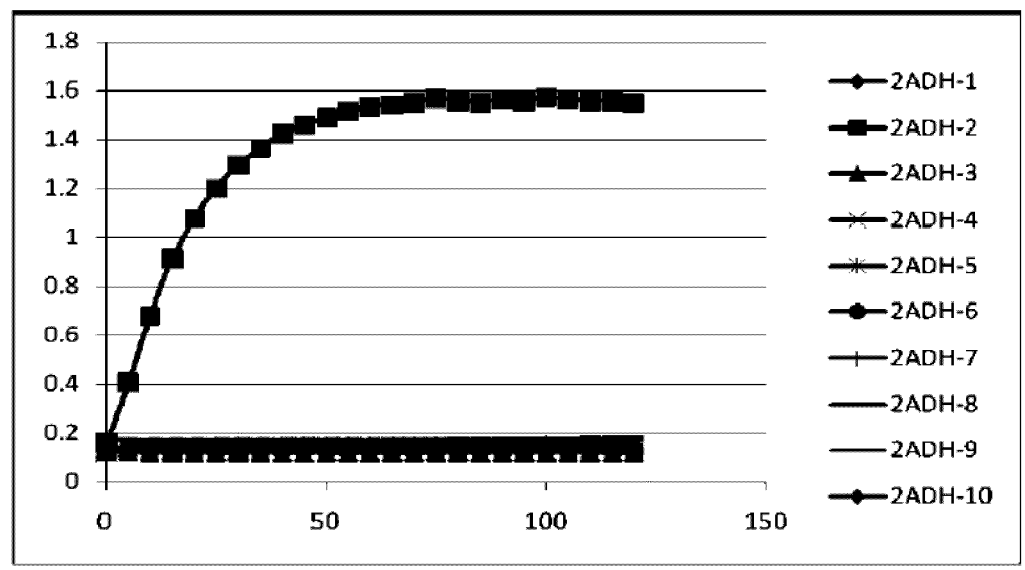
FIG. 30 shows the oxidation of 4-octanol by secondary alcohol dehydrogenases as monitored by NADH production (FIG. 30A) and NADPH production (FIG. 30B).
Figure 30B:
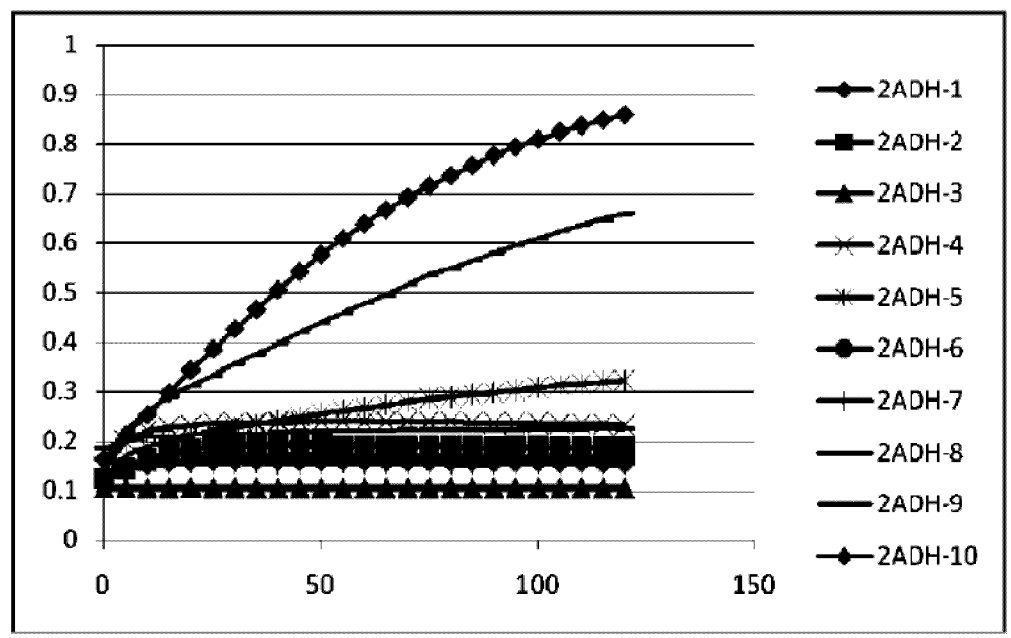

FIG. 30A shows the results from the NADH Production Assay of Table 3, in which 2ADH-2 catalyzes the oxidation of 4-octanol in the presence of NAD+, as measured by NADH production. FIG. 30B shows the results of the NADPH Production Assay of Table 3, in which 2ADH-5, 2ADH-8, and 2ADH-10 catalyze the oxidation of 4-octanol in the presence of NADP+, as measured by NADPH production.

Figure 31A:
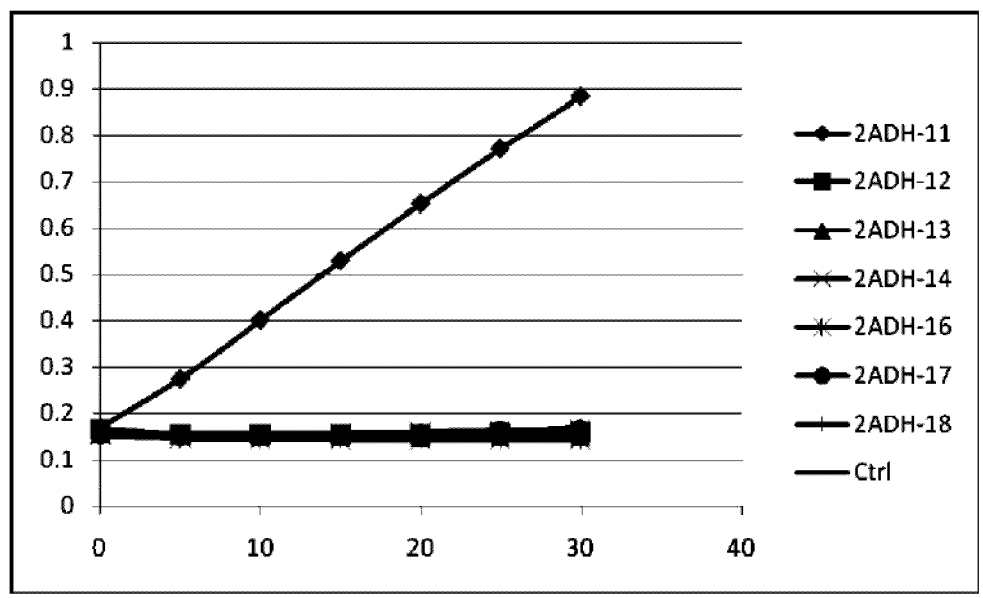
FIG. 31 shows the oxidation of 4-octanol by secondary alcohol dehydrogenases as monitored by NADH production (FIG. 31A) and NADPH production (FIG. 31B).
Figure 31B:
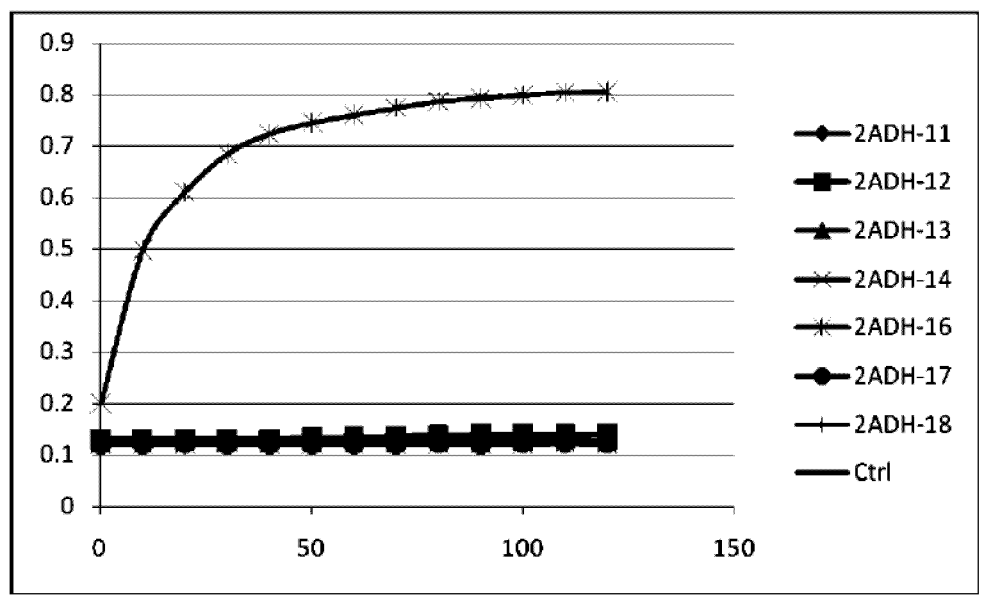

FIG. 31 shows the oxidation of 4-octanol by 2ADH-11 (FIG. 31A) and 2ADH-16 (FIG. 31B), as measured by NADH and NADPH production, respectively. FIG. 32 shows the oxidation of 2,7-dimethyloctanol by 2ADH-11 and others (FIG. 32A) and 2ADH-16 (FIG. 32B), as measured by NADH and NADPH production, respectively.

Figure 33A:
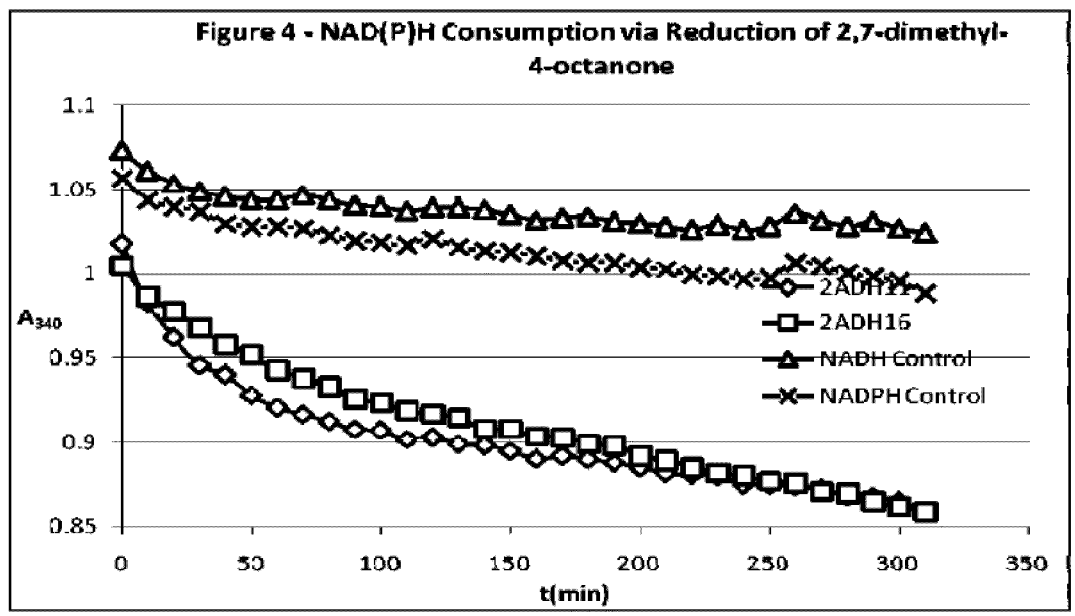
FIG. 33A shows the reduction of 2,7-dimethyl-4-octanone as measured by NADPH consumption.
Figure 33B:
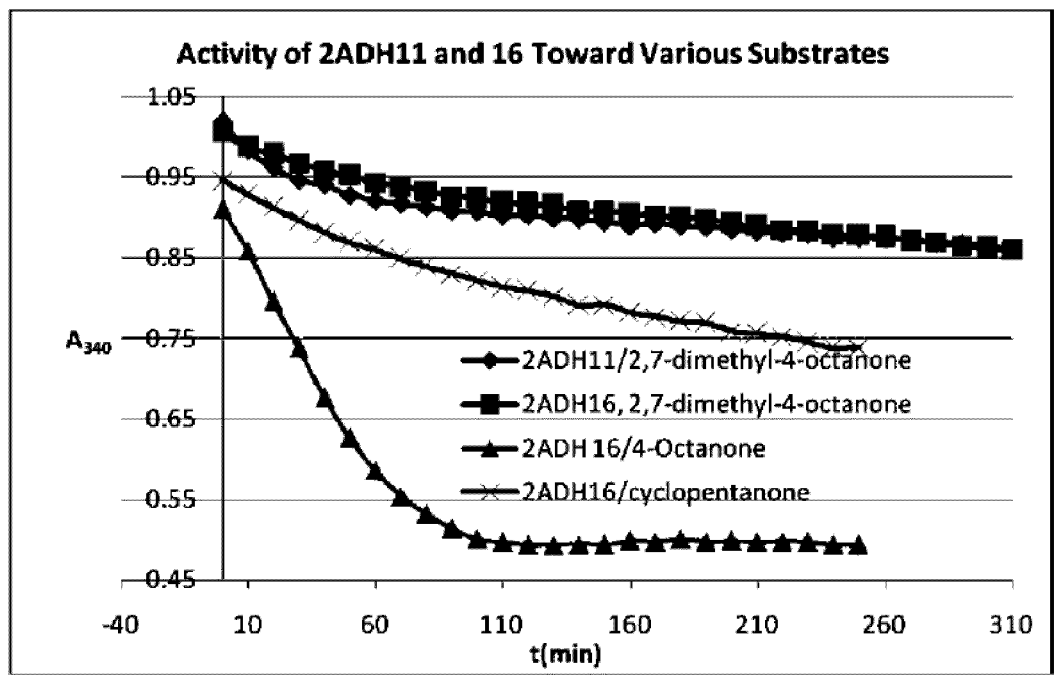
FIG. 33B shows the reduction of 2,7-dimethyl-4-octanone, 4-octanone, and cyclolypentanone.
Figure 34A:
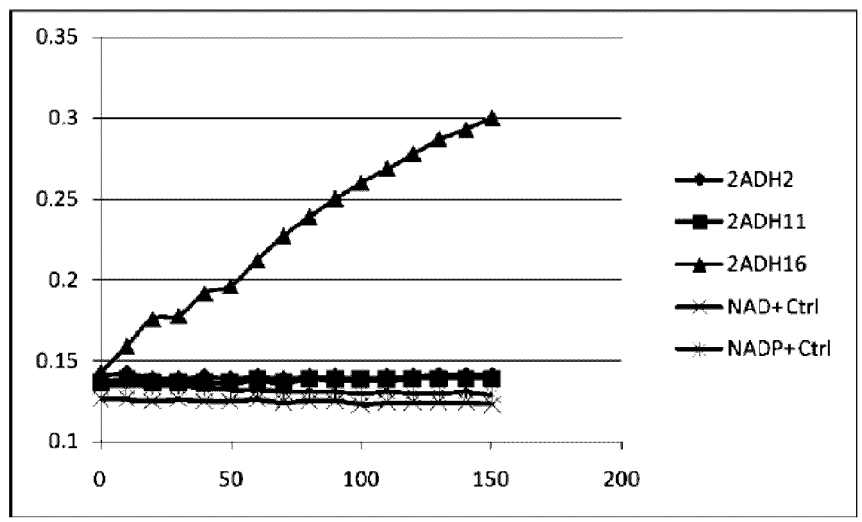
FIG. 34A shows the oxidation of cyclopentanol as monitored by NADH or NADPH formation.
Figure 34B:
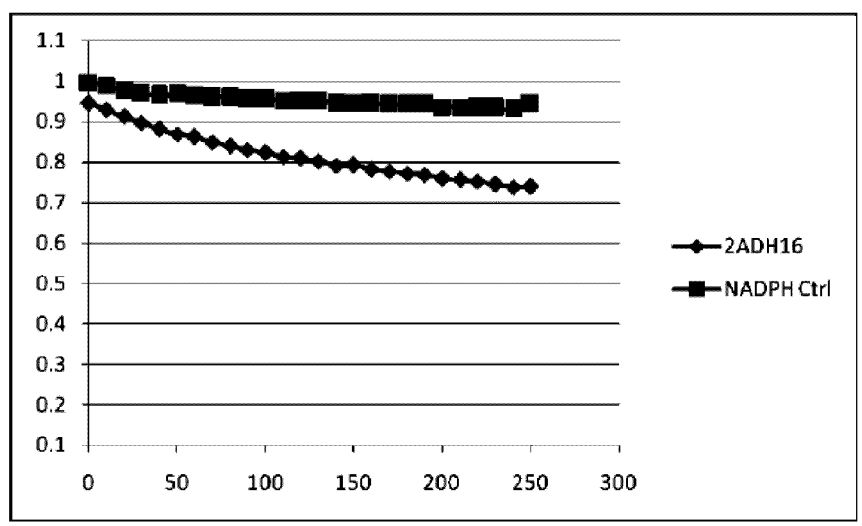
FIG. 34B shows the reduction of cyclopentanol as monitored by NADPH consumption.

FIG. 33A shows the reduction of 2,7-dimethyl octanol by 2ADH 11 and 2ADH16 as monitored by NADPH consumption. FIG. 33B shows the reduction activity of both 2ADH11 and 2ADH16 towards various substrates. FIG. 34 shows the oxidation (FIG. 34A) and reduction (FIG. 34B) of cyclopentanol by 2ADH-16.

Similar to above, kinetic testing for both oxidation and reduction reactions was performed on various substrates using 2ADH-16. The conditions for these studies were as follows: 0.04 mg/mL enzyme, 0.25 mg/mL cofactor, 20 mM Tris HCl Buffer pH 6.5(red) or 9.0(ox), T=25 C, 100 uL total volume was used. The calculated rate constants for the reduction reactions, along with the structures of the substrates, are summarized in FIG. 35. The calculated rate constants for the oxidation reactions, along with the structures of the substrates, are summarized in FIG. 36. These results show that 2ADH-16 is capable of catalyzing both the oxidation and reduction of a wide variety of substrates.

Example 9

Isolation and In Vitro and In Vivo Activity of Coenzyme B 12 Independent Diol Dehydratases Substrates such as 1,2-propanediol, meso-2,3-butanediol, and trans-1,2-cyclopentanediol were utilized to test both the in vitro and in vivo biological activity of a B12 independent diol dehydratase in a dehydration and reduction pathway. Diol dehydratases catalyzes the irreversible dehydration of diols, such as 1,2-propanediol.

For in vitro activity, E. coli BL21(DE3) harboring pETPduCDE (diol dehydratase subunits) was inoculated into 100 mL LB media, grown to $OD_{600}$=0.7, induced with 0.15 mM IPTG, and incubated for 22 hours at 22° C. The cells were lysed and proteins of interest were purified on a Ni-NTA spin column. Purification of all three dehydratase subunits was accomplished by adding 5 mM 1,2-propanediol to the lysis and wash buffers. The Ni-NTA purification yielded approximately 660 µL of protein mixture at a concentration of 2.2 mg/mL. Protein concentration assays were conducted using a Bradford reagent protocol.

The purified PduCDE was used to set up in vitro diol dehydratase reactions. Three assays were conducted with 1,2-propanediol and meso-2,3-butanediol. Control reactions were also set up with elution buffer added in place of purified PduCDE. In vitro reactions were conducted under semianaerobic conditions in 2 mL screw cap glass vials. Reaction components and concentrations are given in Table 6.

TABLE 6

Reaction conditions for $B_{12}$ dependent DDOH in vitro assay

| Rxn Component | Concentration |
| --- | --- |
| Diol substrate | 10 mM |
| Adenosylcobalamin ($B_{12}$) | 100 µg/mL |
| KCl | 10 mM |

TABLE 6-continued

Reaction conditions for $B_{12}$ dependent DDOH in vitro assay

| Rxn Component | Concentration |
| --- | --- |
| dOH1 enzyme mix | 0.08 mg/mL |
| Reaction Buffer | 10 mM Tris HCl pH 7.5 |

After 48 hours, 1 mL of the reaction mixture was extracted with 0.5 mL of either ethylacetate or hexanol and analyzed by GCMS.

The following GCMS protocol was used for all experiments:
1 µL injection w/50:1 split
Inlet temperature—250° C.
Initial oven temperature—50° C.
Temperature Ramp 1—10° C./min to 125° C.
Temperature Ramp 2—30° C./min to 300° C.
Final Temperature 300° C.—1 minute
GC to MS transfer temp—250° C.
MS detection—full scan MW 40-260

Figure 45A:
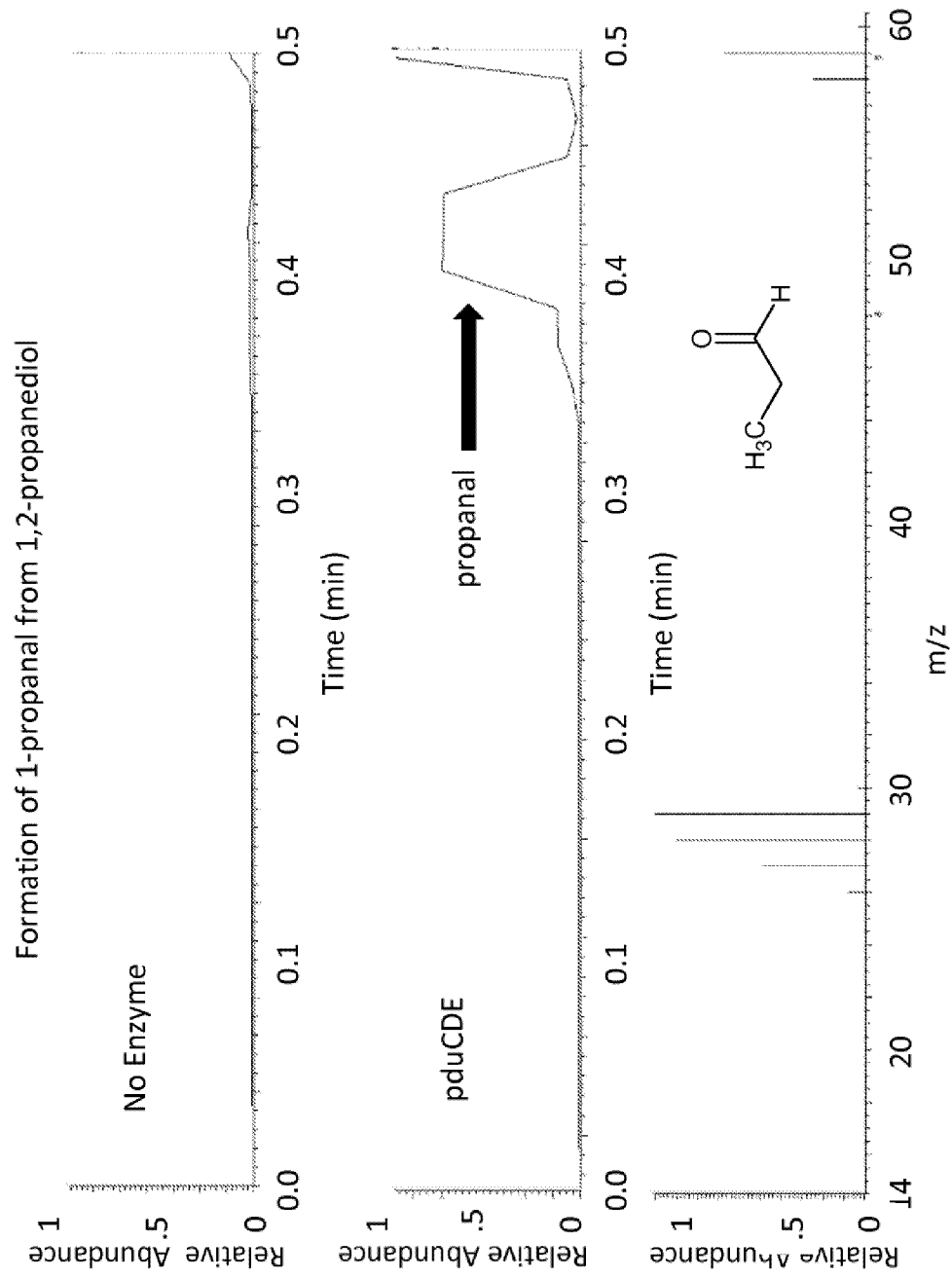
FIG. 45 confirms both the formation of 1-propanal from 1,2-propanediol (FIG. 45A), and the formation of 2-butanone from meso-2,3-butanediol (FIG. 45B), both of which were catalyzed in vitro by an isolated B12 independent diol dehydratase, as described in Example 9.
Figure 45B:
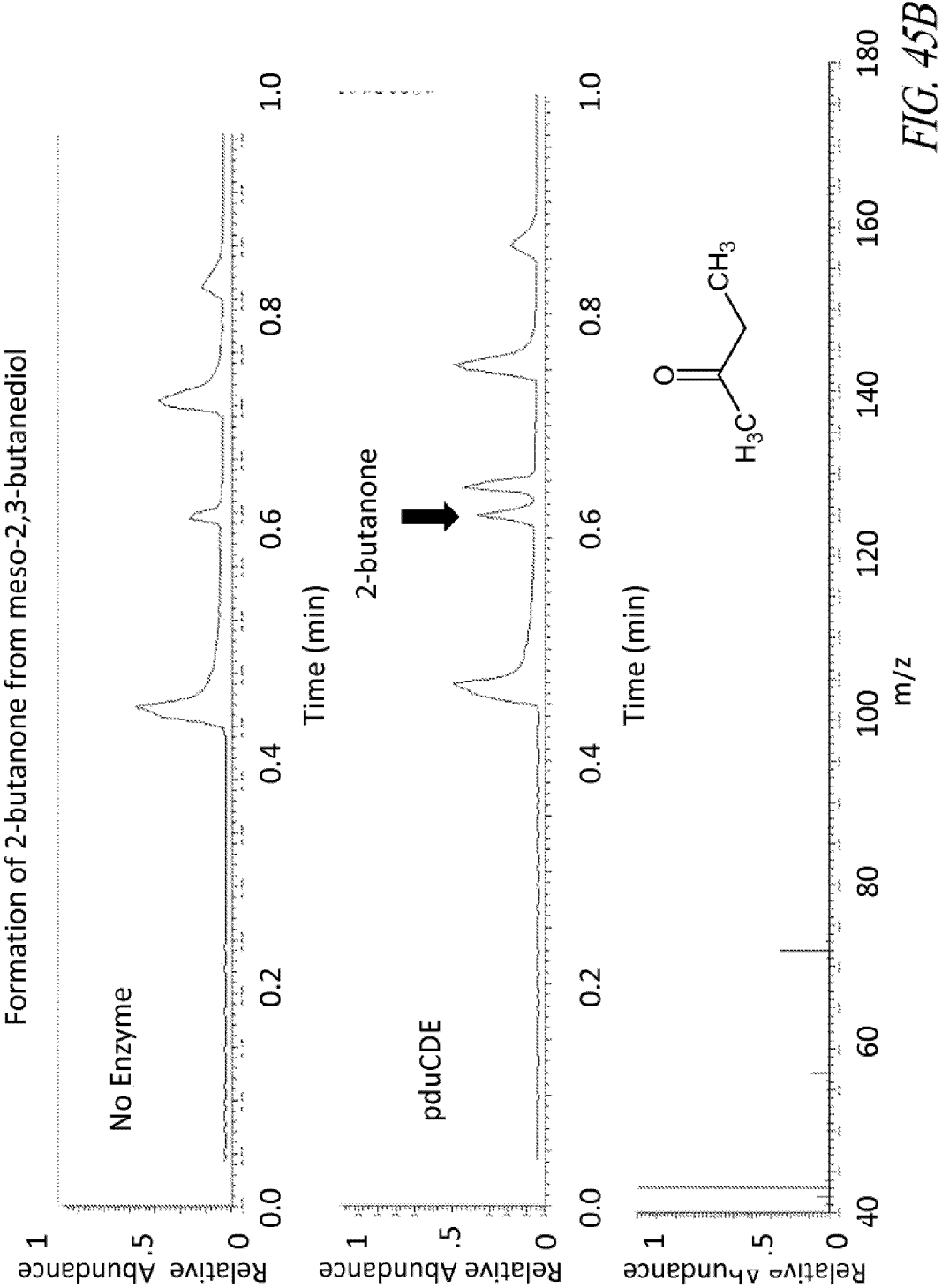

The results are shown in FIG. 45. FIG. 45A confirms the formation of 1-propanal from 1,2-propanediol, and FIG. 45B confirms the formation of 2-butanone from meso-2,3-butanediol, both of which were catalyzed by B12 independent diol dehydratase.

For in vivo activity, the pBBRDhaB1/2 plasmid was constructed as follows: the DNA sequence encoding B12-independent glycerol dehydratase (dhaB1) and activator (dhaB2) of Clostridium butyricum was amplified by polymerase chain reaction (PCR): 98° C. for 10 sec, 60° C. for 15 sec, and 72° C. for 2 min for dhaB1 and 1 min for dhaB2, repeated 30 times. The reaction mixture contained 1× Phusion buffer (NEB), 2 mM dNTP, 0.5 µM forward primers (5'-CCG CTCGAGGAGGATATATATATGATTTCTAAAGGCTTTA GCACCC-3' (SEQ ID NO:318) for dhaB1 and 5'-ACGT-GATGTAATCTAGAGGAGGATATATATATGAGCAAA GAAATTAAAGG-3' (SEQ ID NO:319) for dhaB2, and reverse primers (5'-TCTTTGCTCATATATATATCCTCC TCTAGATTACATCACGTGTTCAGTAC-3' (SEQ ID NO:320) for dhaB1 and 5'-C GAGCTCTTATTCGGCGCCAATGGTGCACGGG-3' (SEQ ID NO:321) for dhaB2, 1 U Phusion High Fidelity DNA polymerase (NEB), and 50 ng pETdhaB1 and pETdhaB2, respectively, in 50 µl. Amplified fragments were gel purified and spliced by another round of PCR: 98° C. for 10 sec, 60° C. for 15 sec, and 72° C. for 2.5 min, repeated 30 times. The reaction mixture contained 1× Phusion buffer (NEB), 2 mM dNTP, 0.5 µM forward (5'-CCG CTCGAGGAGGATATATATATGATTTCTAAAGGCTTTA GCACCC-3') (SEQ ID NO:322) and reverse primers (5'-C GAGCTCTTATTCGGCGCCAATGGTGCACGGG-3') (SEQ ID NO:323), 1 U Phusion High Fidelity DNA polymerase (NEB), and 50 ng each fragment in 50 µl. Amplified DNA fragment was digested with XhoI and SacI and ligated into pBBR1MCS-2 pre-digested with the same restriction enzymes.

Two strains of E. coli DH10B harboring pBBR1MCS-2 or pBBRDhaB1/2 into TB media without glycerol were innoculated. Cultures were grown to $OD_{600}$=0.5 and the substrates 1,2-propanediol, meso-2,3-butanediol, and trans-1,2-cyclopentanediol were added to separate cultures to a concentration of 10 mM. 5 ug/ml of co-enzyme S-adenosylmethionine was added before the culture is transferred to anaerobic environment. The cultures were incubated at 37 C for 48 hrs.

Figure 46A:
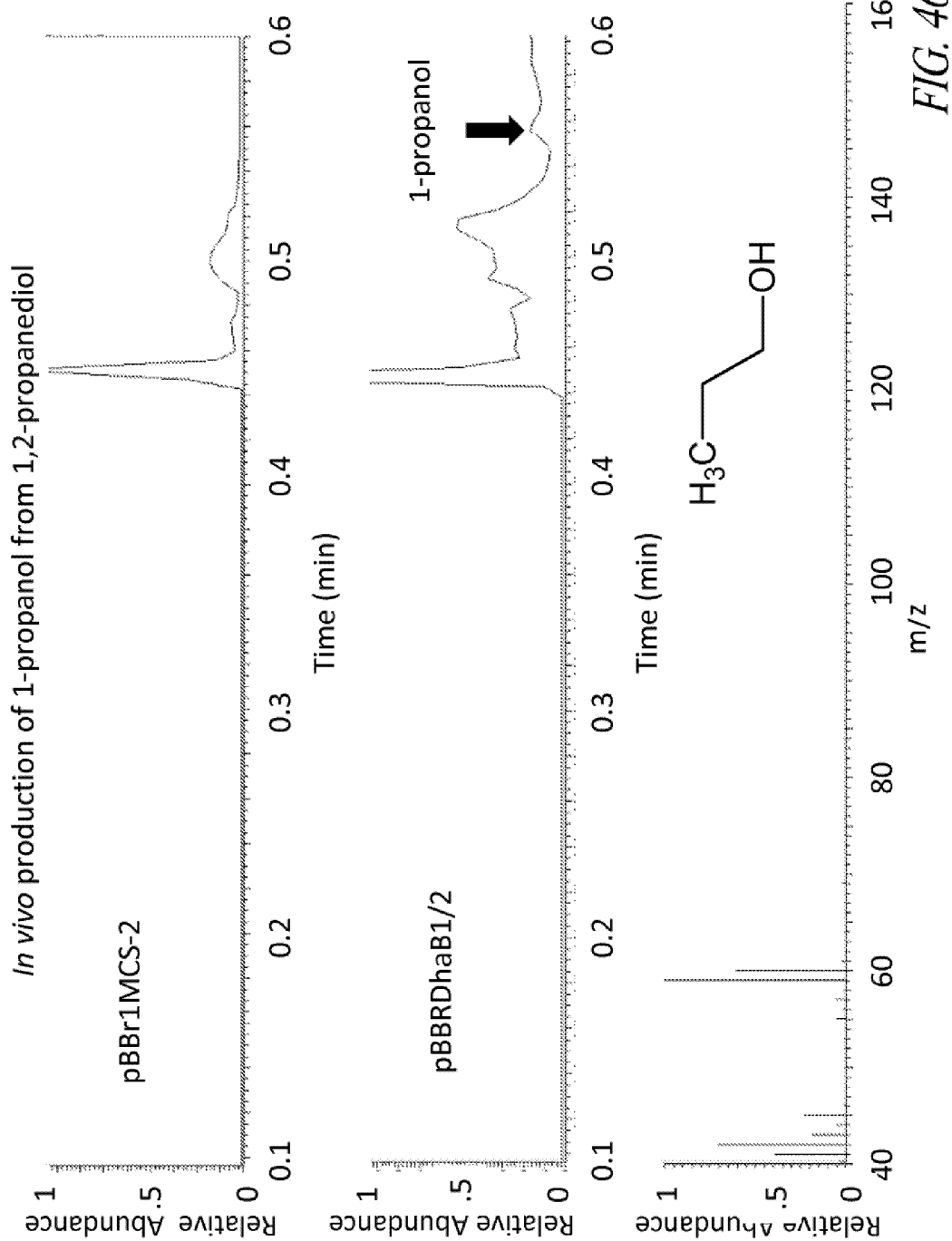
FIG. 46A shows the in vivo production of 1-propanol from 1,2-propanediol.
Figure 46B:
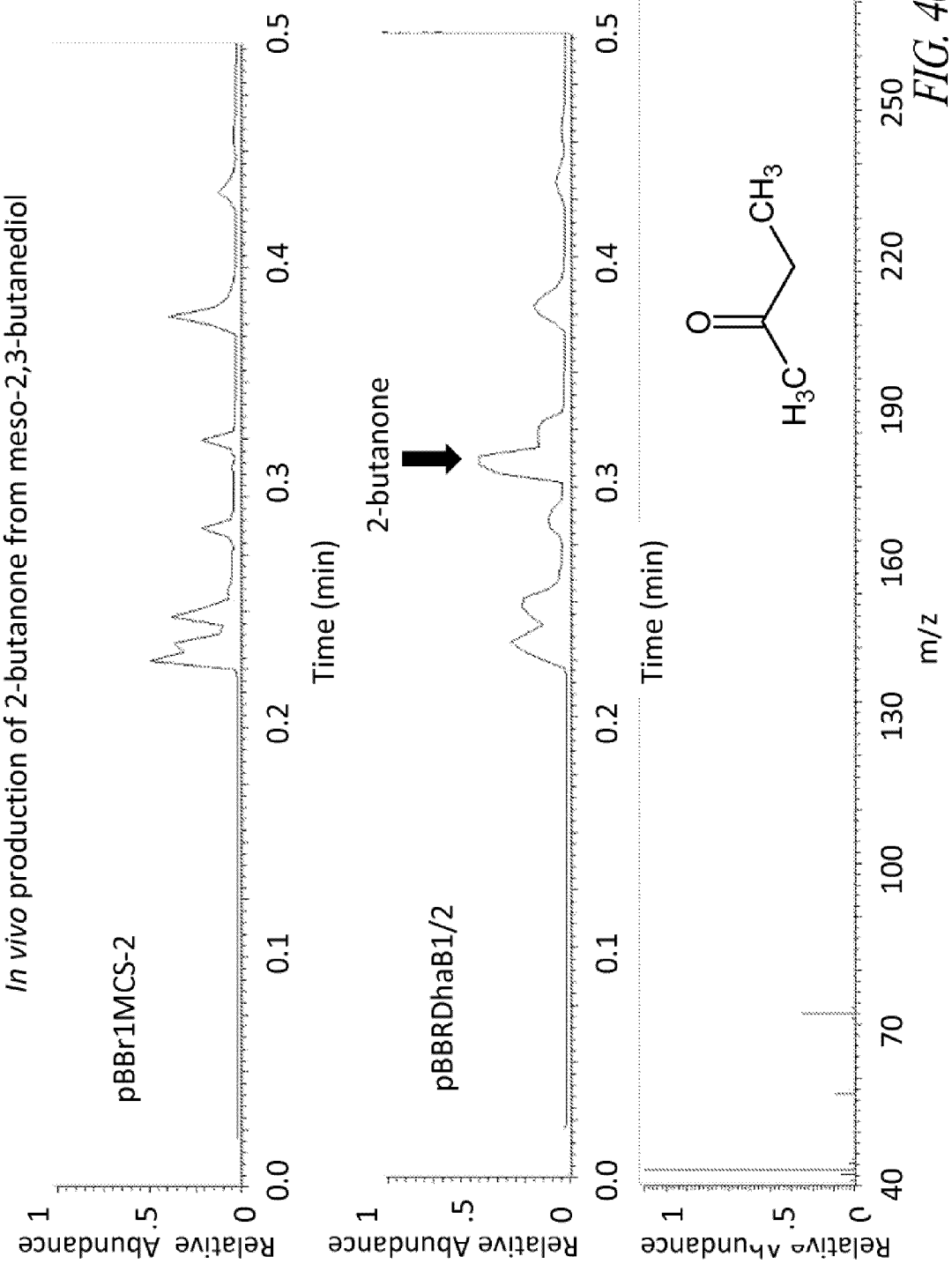
FIG. 46B shows the in vivo production of 2-butanol from meso-2,3 butanediol.
Figure 46C:
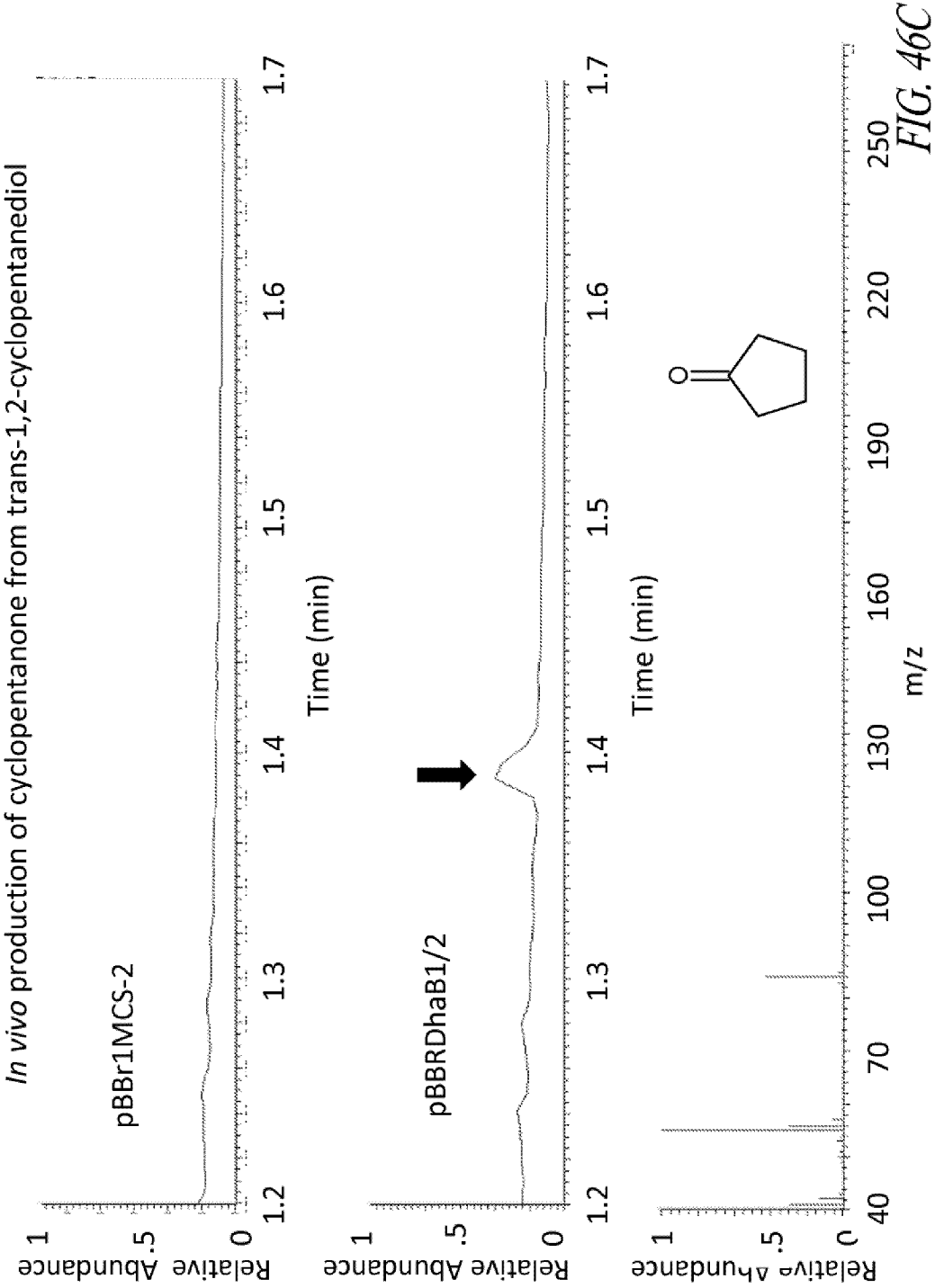
FIG. 46C shows the in vivo production of cyclopentanone from trans-1,2-cyclopentanediol. These experiments were performed as described in Example 9.

After 48 hours, 1 mL of culture was extracted with 0.5 mL of ethylacetate or hexanol and analyzed by GCMS, as described above. The results are shown in FIG. 46. FIG. 46A shows the in vivo production of 1-propanol from 1,2-propanediol. FIG. 46B shows the in vivo production of 2-butanol from meso-2,3 butanediol. FIG. 46C shows the in vivo production of cyclopentanone from trans-1,2-cyclopentanediol.

Example 10

Identification of Secreted Alginate Lyase and Genomic Regions Sufficient for Growth on Alginate as a Sole Source of Carbon To identify secreted or external alginate lyases, and to identify genomic regions from *Vibrio splendidus* that are sufficient to confer growth in alginate as a sole source of carbon, the following clones were made using the gateway system from Invitrogen (Carlsbad, Calif.). First, entry vectors were made by TOPO cloning PCR fragments into pENTR/D/TOPO. PCR fragments were generated using *Vibrio splendidus* B01 genomic DNA as a template and amplified with the following primer pairs:

Vs24214-24249: genomic region corresponding to gene id between V12B01__24214 and V12B01__24249 (see Example 1).

TABLE 7

| 24214 F | cacc caagcgatagtttatatagcgt (SEQ ID NO: 324) |
|---|---|
| 24249 R | gaaatgaacggatattacgt (SEQ ID NO: 325) |

Vs24189-24209; genomic region corresponding to gene id between V12B01__24189 and V12B01__24209 (see Example 1).

TABLE 8

| 24189 R | cggaacaggtgattgtggt | (SEQ ID NO: 326) |
|---|---|---|
| 24209 F | cacc gcccacttcaagatgaagctgt | (SEQ ID NO: 327) |

Vs24214-24239; genomic region corresponding to gene id between V12B01__24214 and V12B01__24239 (see Example 1).

TABLE 9

| 24214 F | cacc caagcgatagtttatatagcgt | (SEQ ID NO: 328) |
|---|---|---|
| 24239 R_1 | gtggctaagtacatgccggt | (SEQ ID NO: 329) |

The entry vectors were recombined with the destination vector pET-DEST42 (Invitrogen) using the LR recombinase enzyme (Invitrogen). These destination vectors were then put into electrocompetent DH10B or BL21 cells.

The alginate lyase clones were then made by digesting (using enzymes Nde I and Bam HI) the PCR products that were generated using *Vibrio splendidus* 12B01 genomic DNA as a template and amplified with the following primer pairs:

TABLE 10

| 24214 ndeF | GGAATTC CAT atgacaaagaatatgacgactaaac (SEQ ID NO: 330) for forward primer for V12B01_24214 |
|---|---|
| 24214 bamR | CG GGATCC ttattatttcccctgccctgcagt (SEQ ID NO: 331) for reverse primer for V12B01_24214 |
| 24219 ndeF | GGAATTC CAT atgagctatcaaccacttttac (SEQ ID NO: 332) for forward primer for V12B01_24219 |
| 24219 bamR | CG GGATCC ttacagttgagcaaatgatcc (SEQ ID NO: 333) for reverse primer for V12B01_24219 |

The digested PCR products were then ligated into cut pET28 vector. Certain of the cloned genomic regions of *Vibrio splendidus* B01 were tested for the presence of secreted alginate lyases, and the above-described constructs were tested in various combinations for the ability to confer growth on alginate as a sole source of carbon.

Figure 47:
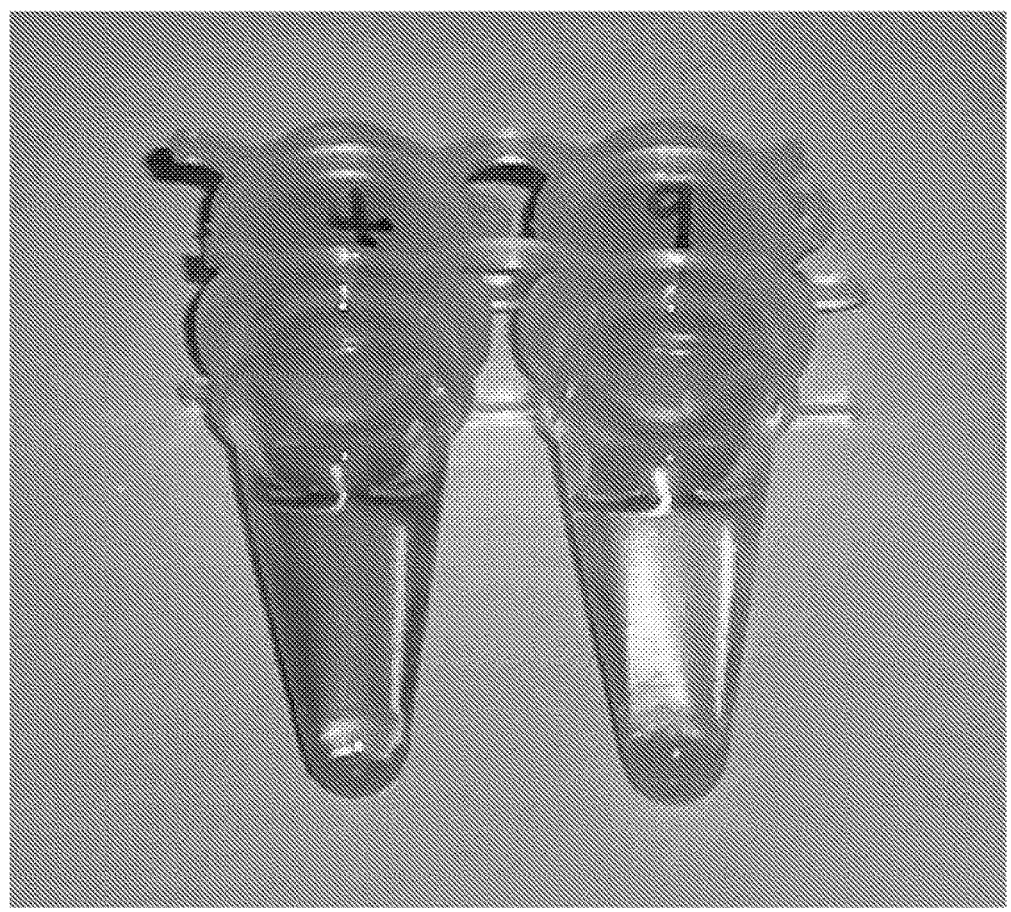
FIG. 47 shows the results of the TBA assay, as performed in Example 10. The left tube in FIG. 47 represents media taken from an overnight culture of cells expressing Vs24254, showing secretion of an alginate lyase, while the right hand tube shows the TBA reaction using media from cells expressing Vs24259 (negative control). The lack of pink coloration in the negative control indicates that little or no cleavage of the alginate polymer has occurred.
Figure 48A:
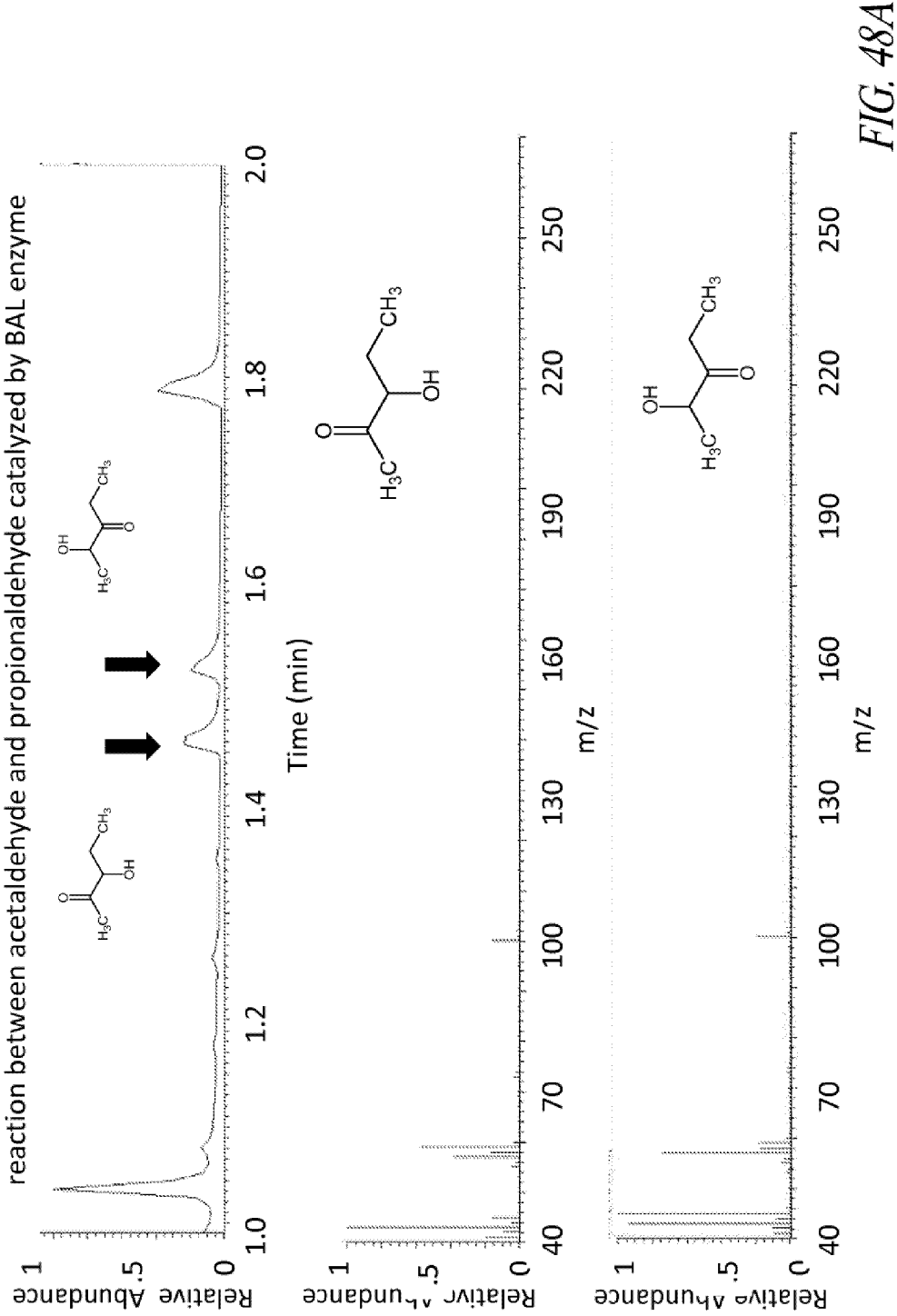
FIG. 48 shows the in vivo biological activity of a C—C ligase isolated from *Pseudomonas fluorescens* and cloned into *E. coli*. The GC-MS chromatogram results show that codon-optimized benzaldehyde lyase (BAL) catalyzed the in vivo production of 3-hydroxy-2-pentanone and 2-hydroxy-3-pentanone from a ligation reaction between acetaldehyde and propionaldehyde (FIG. 48A), and catalyzed the in vivo production of 4-hydroxy-3-heptanone and 3-hydroxy-4-heptanone from a ligation reaction between propionaldehyde and butyraldehyde (FIG. 48B).
Figure 48B:
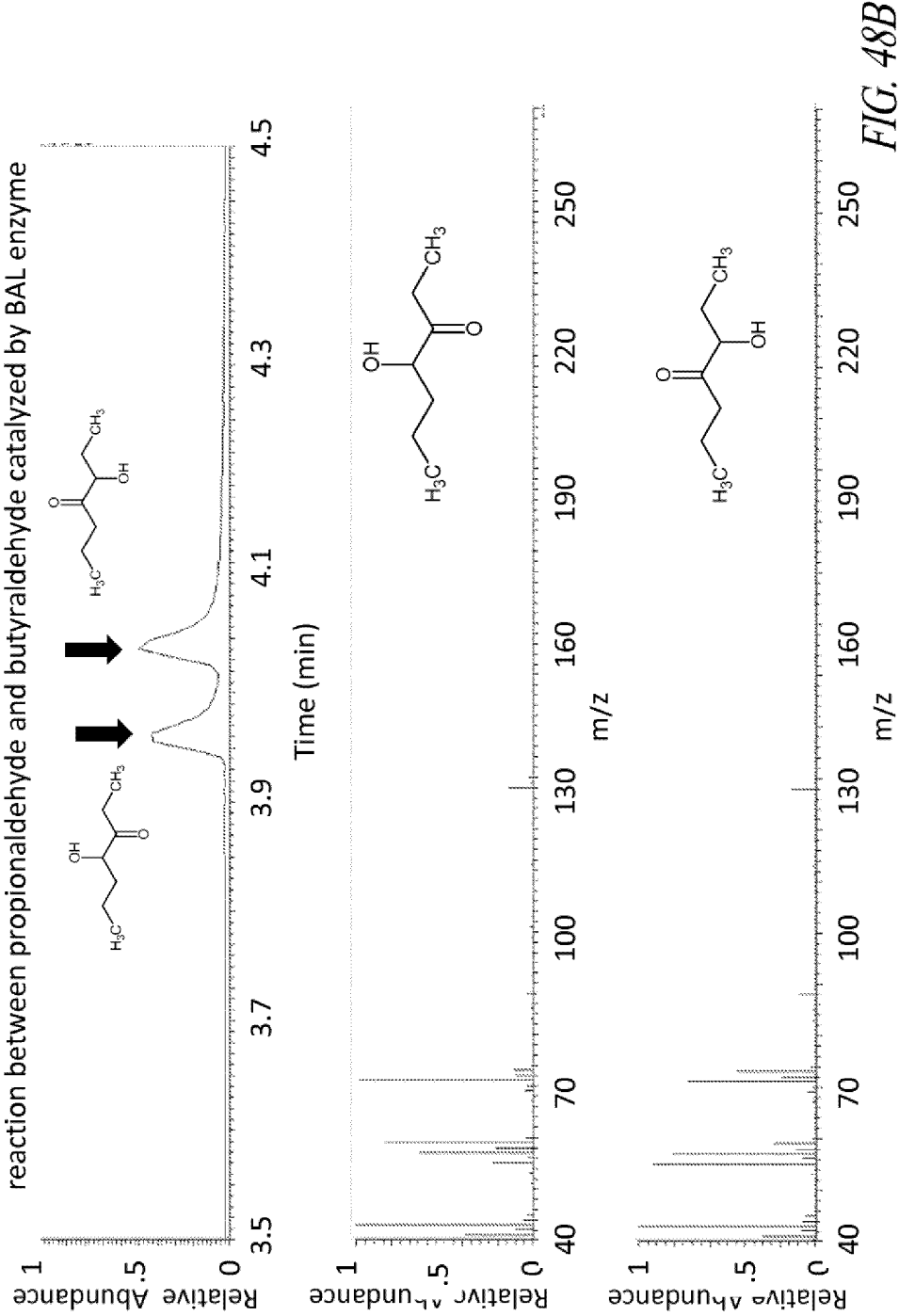
Figure 49B:
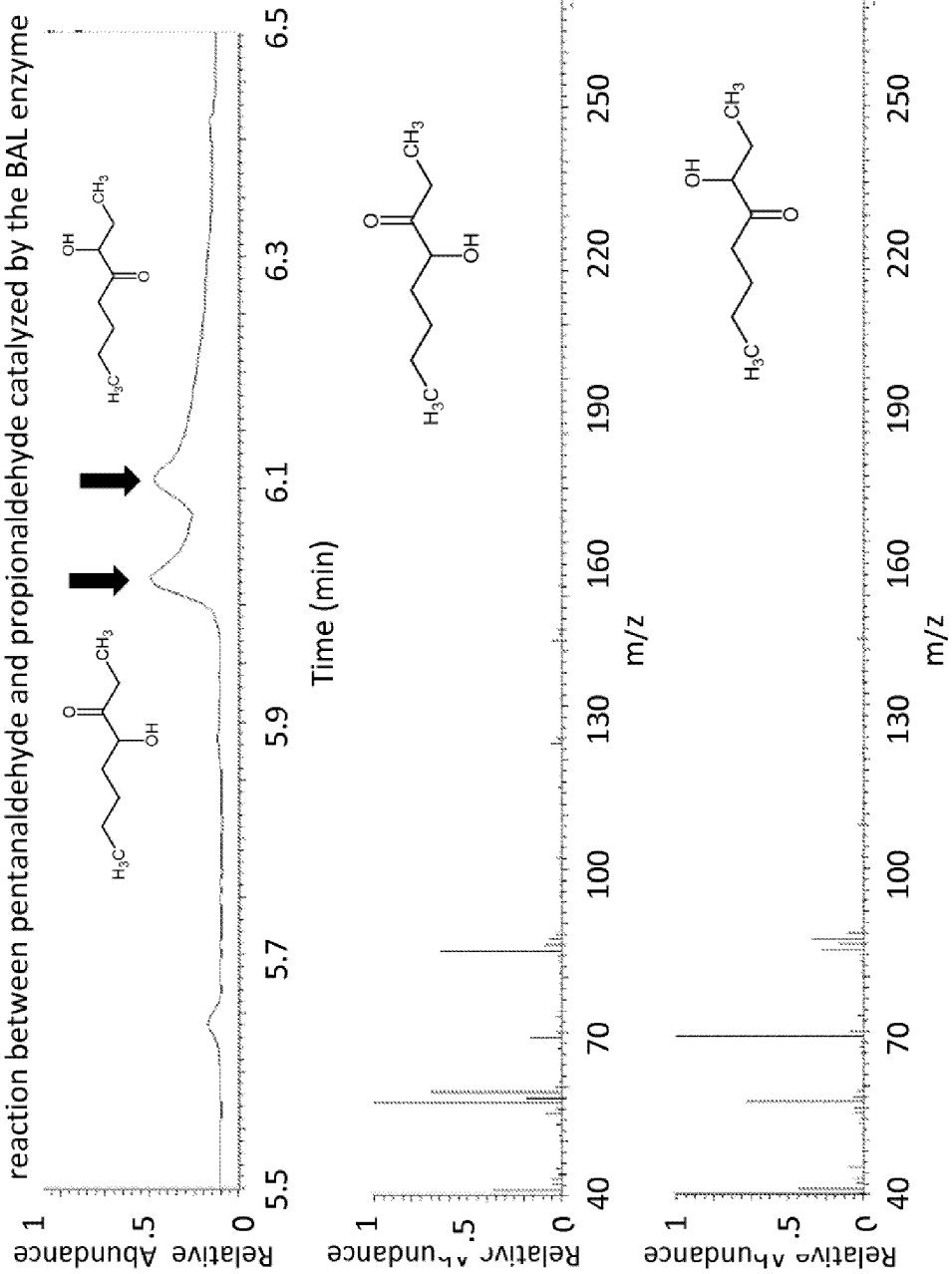
FIG. 49 shows the in vivo biological activity of a C—C ligase isolated from *Pseudomonas fluorescens* and cloned into *E. coli*. The GC-MS chromatogram results show that codon-optimized BAL catalyzed the in vivo production of 3-hydroxy-2-heptanone from a ligation reaction between acetaldehyde and pentanal (FIG. 49A), and catalyzed the in vivo production of 4-hydroxy-3-octanone and 3-hydroxy-4-octanone from a ligation reaction between pentanal and propionaldehyde (FIG. 49B).
Figure 50A:
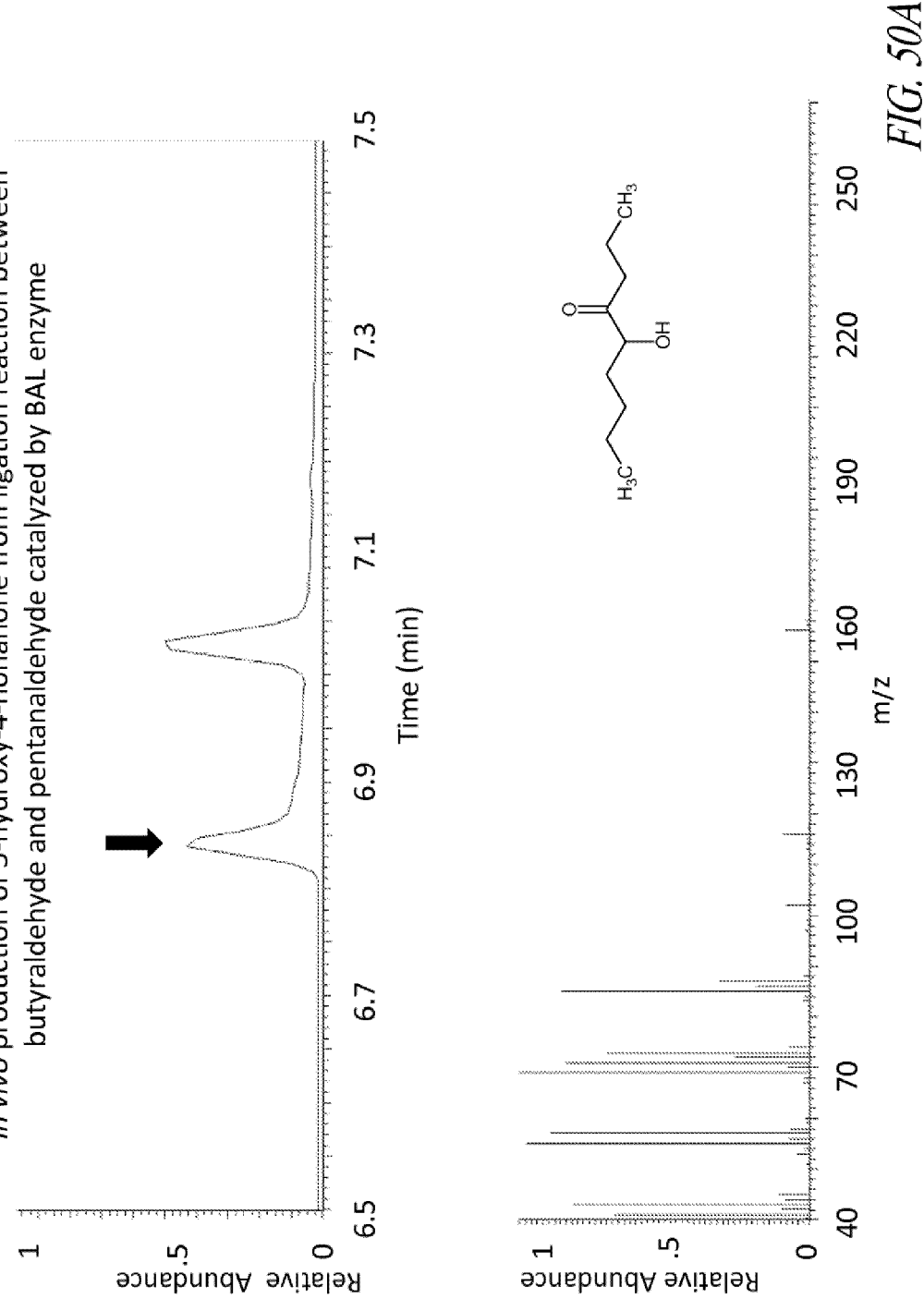
FIG. 50 shows the in vivo biological activity of a C—C ligase isolated from *Pseudomonas fluorescens* and cloned into *E. coli*. The GC-MS chromatogram results show that codon-optimized BAL catalyzed the in vivo production of 5-hydroxy-4-nonanone from ligation reaction between butyraldehyde and pentanal (FIG. 50A), and catalyzed the in vivo production of 2-methyl-5-hydroxy-4-decanone and 2-methyl-4-hydroxy-5-decanone from ligation reaction between hexanal and 3-methylbutyraldehyde (FIG. 50B).
Figure 50B:
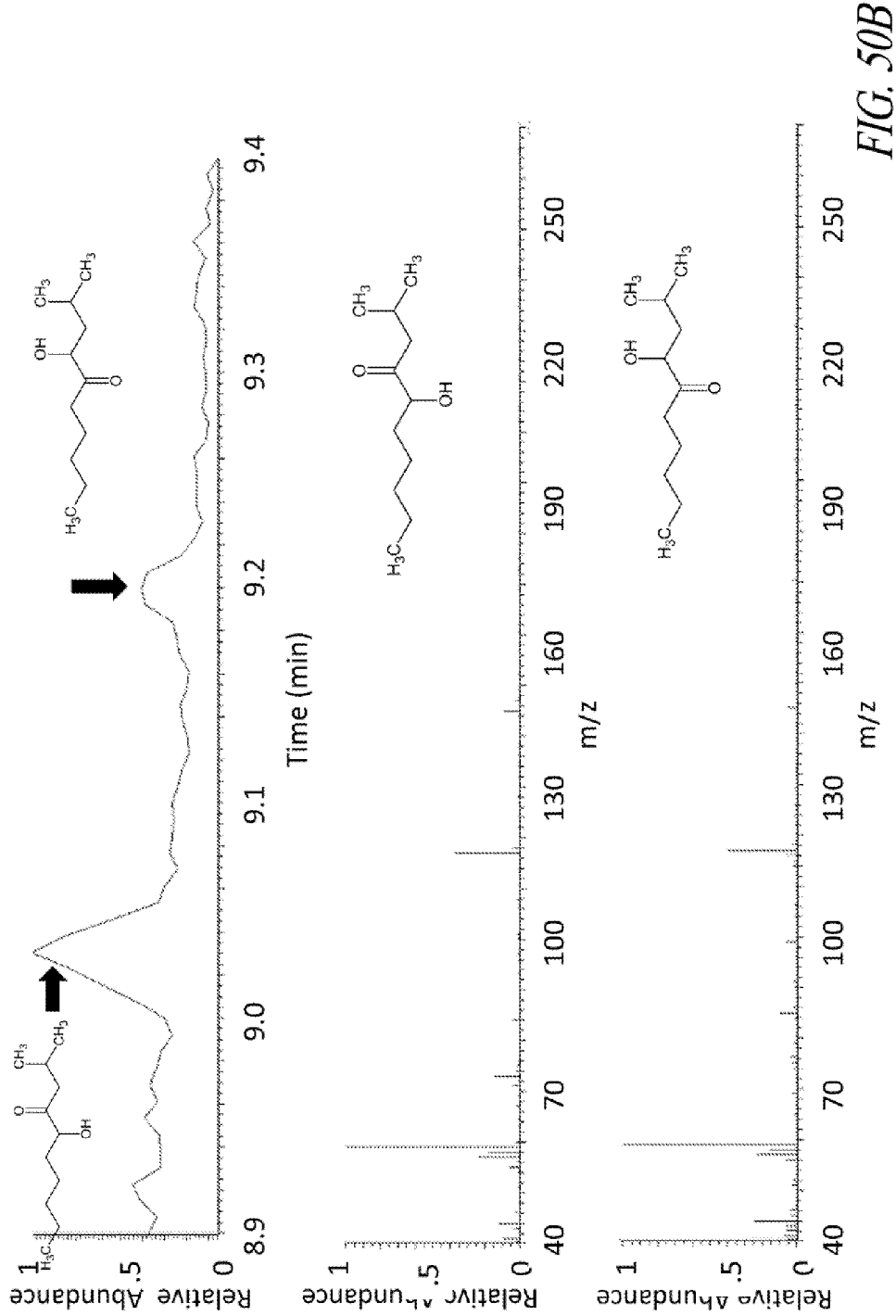
Figure 54B:
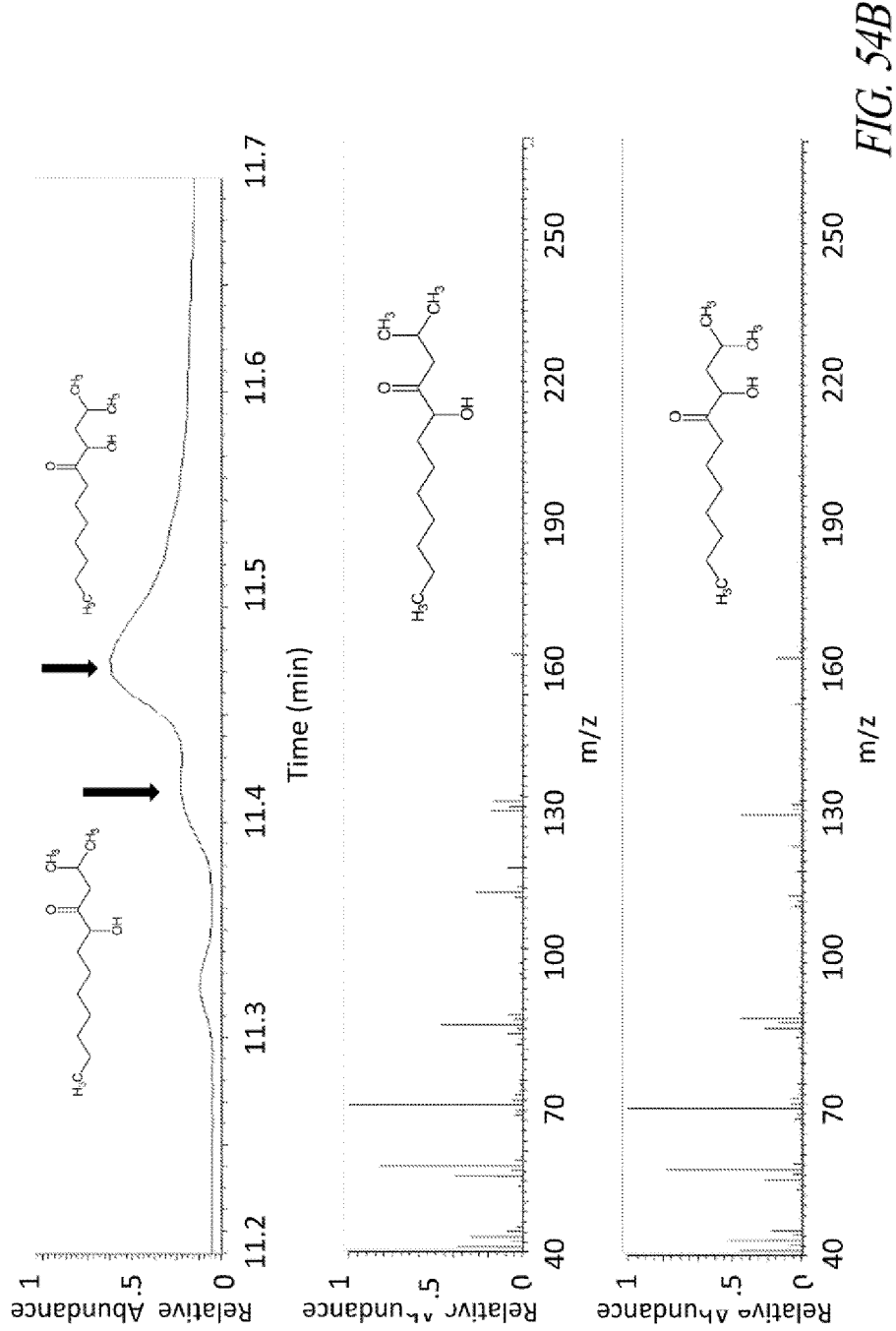
FIG. 54 shows the in vivo biological activity of a C—C ligase isolated from *Pseudomonas fluorescens* and cloned into E. coli. The GC-MS chromatogram results show that codon-optimized BAL catalyzed the in vivo production of 6-hydroxy-5-tridecanone (FIG. 54A) from ligation reaction between octanal and pentanal, and catalyzed the in vivo production of 2-methyl-5-hydroxy-4-dodecanone and 2-methyl-4-hydroxy-5-decanone from a ligation reaction between octanal and 3-methylbutyraldehyde (FIG. 54B).

The Vs24254 (SEQ ID NO: 32) region of *Vibro spendidus* encodes a functional external alginate lyase. BL21 cells expressing Vs24254 from the pET28 vector were capable of breaking down alginate in the growth medium. When grown on LB+2% alginate+0.1 mM Isopropyl β3-D-1-thiogalacto-pyranoside (IPTG), only cells expressing the Vs24254 gene give a positive TBA assay result of pink color. This assay was performed by spinning down an overnight culture grown on the above mentioned media. The media was then mixed in a 1:1 ratio with 0.8% thiobarbituric acid (TBA), heated for 10 min at 99 degrees Celsius, and assayed for pink coloration. FIG. 47 shows the results of this assay. The left tube in FIG. 47 represents media taken from an overnight culture of cells expressing Vs24254, while the right hand tube shows the TBA reaction using media from cells expressing Vs24259 (negative control). The lack of pink coloration in the negative control indicates that little or no cleavage of the alginate polymer has occurred. Wildtype *E. coli* cells not expressing any recombinant proteins show the same coloration as the negative control Vs24259 (data not shown).

To test the ability of recombinant *E. coli* to grow on alginate as a sole source of carbon, transformed cells were grown for 19 hours at 30 degrees Celsius with mild shaking in a 96-well plate. Each well held 222 μl of minimal media (see growth conditions for explanation of minimal media) with the 0.66% carbon source in the form of either degraded alginate or glucose (positive control for growth). All cells were either BL21 with no plasmid (BL21—negative control), one plasmid (Da or 3a), or two plasmids (Dk3a and Da3k). The plasmids are indicated by the lower case letter: "a" refers to the plasmid backbone pET-DEST42 and "k" refers to the pENTR/D/TOPO backbone. "D" indicates that the plasmid contains the genomic region Vs24214-24249, while "3" indicates that the plasmid contains the genomic region Vs24189-24209. Thus, Da would be pET-DEST42-Vs24214-24249, Da3k would be pET-DEST42-Vs24214-24249 and pENTR/D/TOPO-Vs24189-24209 and so on.

Figure 56A:
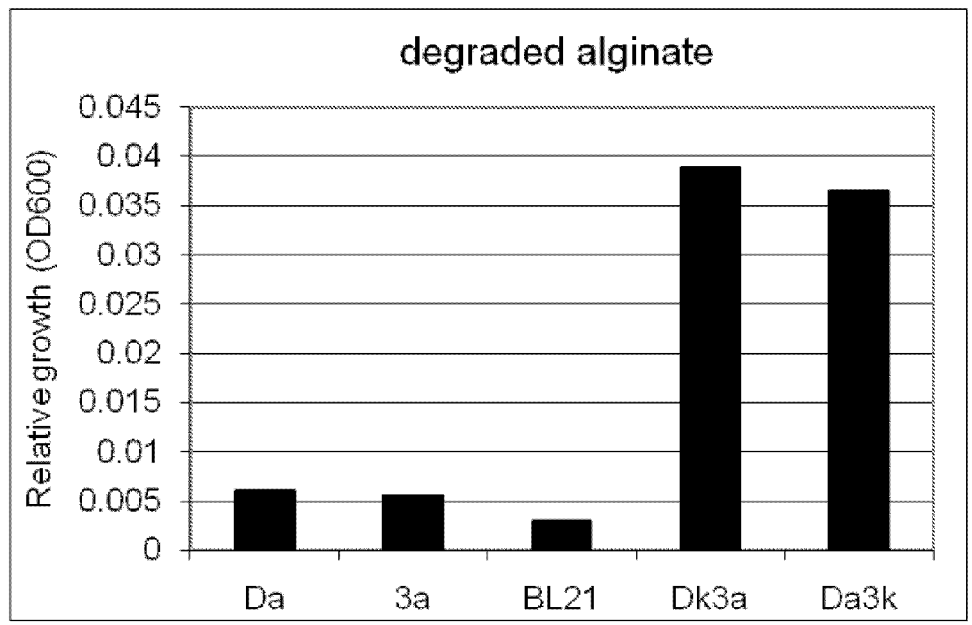
FIG. 56 shows the growth of recombinant E. coli on alginate as a sole source of carbon (FIG. 56A), as described in Example 10. Growth on glucose (FIG. 56B) provides a positive control. The cells were transformed with either no plasmid (BL21—negative control), one plasmid (e.g., Da or 3a), or two plasmids (e.g., Dk3a and Da3k). The plasmids are indicated by the lower case letter: "a" refers to the pET-DEST42 plasmid backbone and "k" refers to the pENTR/D/TOPO backbone. "D" indicates that the plasmid contains the genomic region Vs24214-24249, while "3" indicates that the plasmid contains the genomic region Vs24189-24209. Thus, Da would be pET-DEST42-Vs24214-24249, Da3k would be pET-DEST42-Vs24214-24249 and pENTR/D/TOPO-Vs24189-24209 and so on. These results show that the combined genomic regions Vs24214-24249 and Vs24189-24209 are sufficient to confer on E. coli the ability to grow on alginate as a sole source of carbon.
Figure 56B:
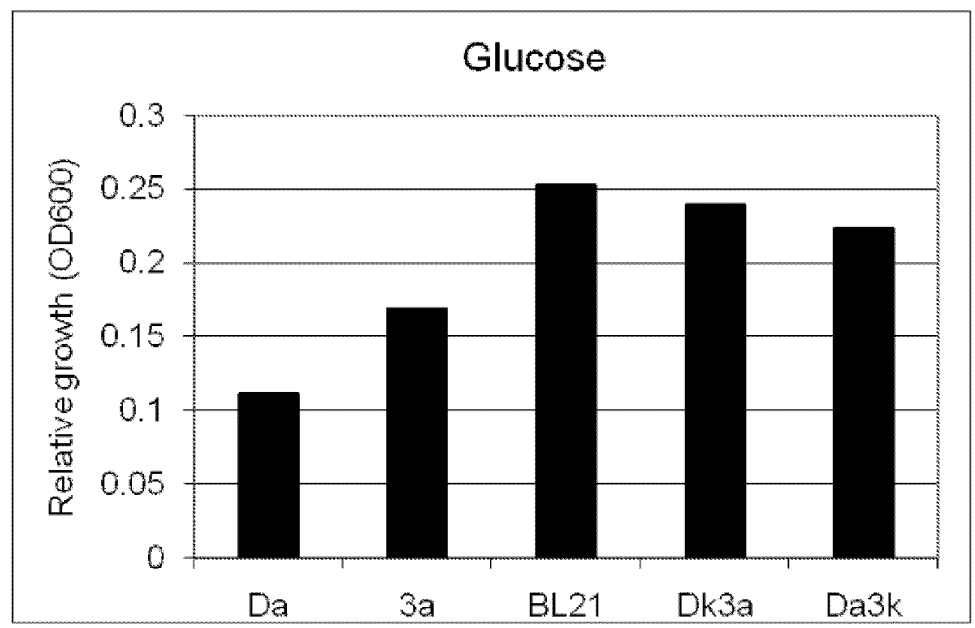

As shown in FIG. 56A, the two vector-constructs pET-DEST42-Vs24214-24249 and pENTR/D/TOPO-Vs24189-24209 when combined in *E. coli* confer growth on degraded alginate as the sole carbon source. This same result is be observed when these genomic inserts are switched into the opposite vector (pET-DEST42-Vs24189-24209 and pENTR/D/TOPO-Vs24214-24249). FIG. 56B shows growth on glucose as a positive control. Thus, the combined genomic regions of Vs24214-24249 and Vs24189-24209 from Vibro splendidus were sufficient to confer on *E. coli* the ability to grown on alginate as a sole source of carbon.

Example 11

Production of Ethanol from Alginate

The ability of recombinant *E. coli* to produce ethanol by growing on alginate on a source of carbon was tested. To generate recombinant *E. coli*, DNA sequences encoding pyruvate decarboxylase (pdc), and two alcohol dehydrogenase (adhA and adhB) of *Zymomonas mobilis* were amplified by polymerase chain reaction (PCR). These amplified fragments were gel purified and spliced together by another round of PCR. The final amplified DNA fragment was digested with BamHI and XbaI ligated into pBBR1MCS-2 pre-digested with the same restriction enzymes. The resulting plasmid is referred to as pBBRPdc-AdhA/B.

Figure 57:
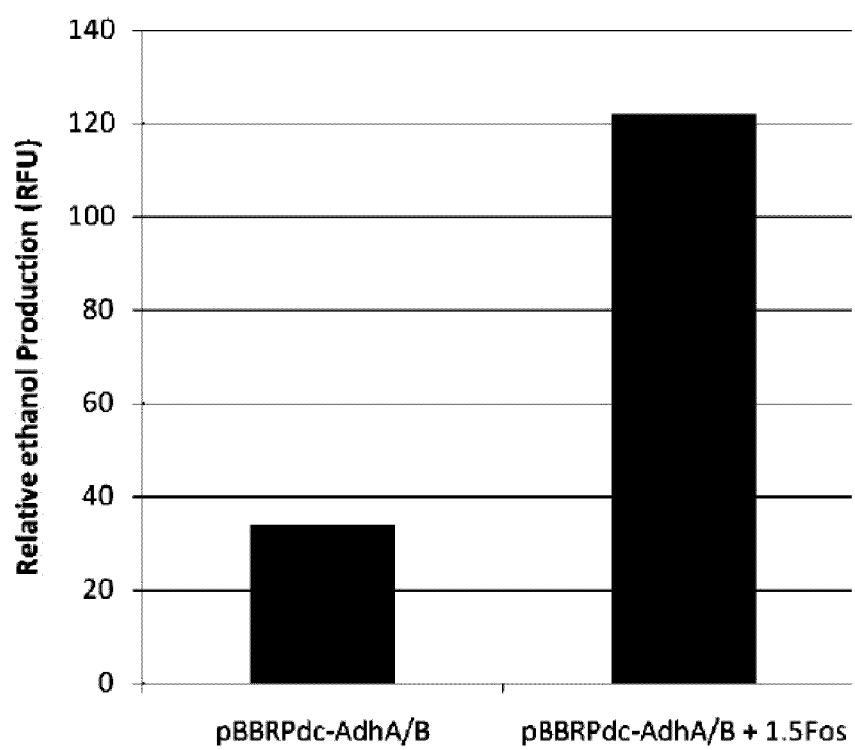
FIG. 57 shows the production of ethanol by E. coli growing on alginate, as performed in Example 11. E. coli was transformed with either pBBRPdc-AdhA/B or pBBRPdc-AdhA/B+1.5 FOS and allowed to grow in m9 media containing alginate.

*E. coli* was transformed with either pBBRPdc-AdhA/B or pBBRPdc-AdhA/B+1.5 Fos (fosmid clone containing genomic region between VI 2B01__24189 and V12B01__24249; these sequences confer on *E. coli* the ability to use alginate as a sole source of carbon, see Examples 1 and 10), grown in m9 media containing alginate, and tested for the production of ethanol. The results are shown in FIG. 57, which demonstrates that the strain harboring pBBRPdc-AdhA/B+1.5 FOS showed significantly higher ethanol production when growing on alginate. These results indicate that the pBBRPdc-AdhA/B+1.5 FOS was able to utilize alginate as a source of carbon in the production of ethanol.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The following publications are herein incorporated by reference in their entirety.
1. T. Y. Wong, L. A. Preston, N. L. Schiller, *Annu Rev Microbiol* 54, 289 (2000).
2. W. Hashimoto, O. Miyake, A. Ochiai, K. Murata, *J Biosci Bioeng* 99, 48 (January, 2005).
3. M. Yamasaki, K. Ogura, W. Hashimoto, B. Mikami, K. Murata, *J Mol Biol* 352, 11 (Sep. 9, 2005).
4. M. Yamasaki et al., *Acta Crystallogr Sect F Struct Biol Cryst Commun* 61, 288 (Mar. 1, 2005).
5. O. Miyake, A. Ochiai, W. Hashimoto, K. Murata, *J Bacteriol* 186, 2891 (May, 2004).
6. O. Miyake, W. Hashimoto, K. Murata, *Protein Expr Purif* 29, 33 (May, 2003).
7. H. J. Yoon, B. Mikami, W. Hashimoto, K. Murata, *J Mol Biol* 290, 505 (Jul. 9, 1999).
8. H. J. Yoon, W. Hashimoto, O. Miyake, K. Murata, B. Mikami, *J Mol Biol* 307, 9 (Mar. 16, 2001).
9. W. Hashimoto, O. Miyake, K. Momma, S. Kawai, K. Murata, *J Bacteriol* 182, 4572 (August, 2000).
10. H. J. Yoon et al., *Protein Expr Purif* 19, 84 (June, 2000).
11. T. Osawa, Y. Matsubara, T. Muramatsu, M. Kimura, Y. Kakuta, *J Mol Biol* 345, 1111 (Feb. 4, 2005).
12. A. Ochiai, W. Hashimoto, K. Murata, *Res Microbiol* 157, 642 (September, 2006).
13. F. J. Mergulhao, D. K. Summers, G. A. Monteiro, *Biotechnol Adv* 23, 177 (May, 2005).
14. J. H. Choi, S. Y. Lee, *Appl Microbiol Biotechnol* 64, 625 (June, 2004).
15. M. P. DeLisa, D. Tullman, G. Georgiou, *Proc Natl Acad Sci USA* 100, 6115 (May 13, 2003).
16. N. Blaudeck, G. A. Sprenger, R. Freudl, T. Wiegert, *J Bacteriol* 183, 604 (January, 2001).
17. N. Pradel et al., *Biochem Biophys Res Commun* 306, 786 (Jul. 4, 2003).
18. L. Masip et al, *Science* 303, 1185 (Feb. 20, 2004).
19. C. M. Barrett, N. Ray, J. D. Thomas, C. Robinson, A. Bolhuis, *Biochem Biophys Res Commun* 304, 279 (May 2, 2003).
20. R. Binet, S. Letoffe, J. M. Ghigo, P. Delepelaire, C. Wandersman, *Folia Microbiol (Praha)* 42, 179 (1997).
21. I. Gentschev, G. Dietrich, W. Goebel, *Trends Microbiol* 10, 39 (January, 2002).
22. V. Koronakis, *FEBS Lett* 555, 66 (Nov. 27, 2003).
23. J. Jose, *Appl Microbiol Biotechnol* 69, 607 (February, 2006).
24. J. Jose, D. Betscheider, D. Zangen, *Anal Biochem* 346, 258 (Nov. 15, 2005).
25. M. Ashiuchi, H. Misono, *Appl Microbiol Biotechnol* 59, 9 (June, 2002).
26. J. Narita et al., *Appl Microbiol Biotechnol* 70, 564 (May, 2006).
27. Y. Aso et al., *Nat Biotechnol* 24, 188 (February, 2006).
28. W. Hashimoto et al., *Biosci Biotechnol Biochem* 69, 673 (April, 2005).
29. A. E. Lagarde, F. R. Stoeber, *J Bacteriol* 129, 606 (February, 1977).
30. M. A. Mandrand-Berthelot, P. Ritzenthaler, M. Mata-Gilsinger, *J Bacteriol* 160, 600 (November, 1984).
31. J. Pouyssegur, F. Stoeber, *J Bacteriol* 117, 641 (February, 1974).
32. J. Preiss, G. Ashwell, *J Biol Chem* 237, 309 (February, 1962).
33. J. Preiss, G. Ashwell, *J Biol Chem* 237, 317 (February, 1962).
34. G. M. Bird, P. Haas, *Biochemical Journal* 25, 403 (1931).
35. L. H. Cretcher, W. L. Nelson, *Science* 67, 537 (May 25, 1928).
36. W. L. Nelson, L. H. Cretcher, *Journal of the American Chemical Society* 51, 1914 (1929).
37. W. L. Nelson, L. H. Cretcher, *Journal of the American Chemical Society* 52, 2130 (1930).
38. W. L. Nelson, L. H. Cretcher, *Journal of the American Chemical Society* 54, 3409 (1932).
39. E. Schoeffel, K. P. Link, *Journal of Biological Chemistry* 95, 213 (1932).
40. E. Schoeffel, K. P. Link, *Journal of Biological Chemistry* 100, 397 (1933).
41. H. A. Spoehr, *Archive of Biochemistry* 14, 153 (1947).
42. J. J. Farmer, 3rd, R. G. Eagon, *J Bacteriol* 97, 97 (January, 1969).
43. R. L. Anderson, D. P. Allison, *J Biol Chem* 240, 2367 (June, 1965).
44. W. J. Lennarz, R. J. Light, K. Bloch, *Proc Natl Acad Sci USA* 48, 840 (May, 1962).

45. S. A. Graham, *Crit Rev Food Sci Nutr* 28, 139 (1989).
46. E. Wiberg, P. Edwards, J. Byrne, S. Stymne, K. Dehesh, *Planta* 212, 33 (December, 2000).
47. L. Yuan, T. A. Voelker, D. J. Hawkins, *Proc Natl Acad Sci USA* 92, 10639 (Nov. 7, 1995).
48. K. Dehesh, A. Jones, D. S. Knutzon, T. A. Voelker, *Plant J* 9, 167 (February, 1996).
49. K. Dehesh, P. Edwards, T. Hayes, A. M. Cranmer, J. Fillatti, *Plant Physiol* 110, 203 (January, 1996).
50. K. M. Mayer, J. Shanklin, *BMC Plant Biol* 7, 1 (2007).
51. J. K. Jha et al., *Plant Physiol Biochem* 44, 645 (November-December, 2006).
52. B. S. Schutt, M. Brummel, R. Schuch, F. Spener, *Planta* 205, 263 (June, 1998).
53. K. Dehesh, P. Edwards, J. Fillatti, M. Slabaugh, J. Byrne, *Plant J* 15, 383 (August, 1998).
54. J. M. Leonard, S. J. Knapp, M. B. Slabaugh, *Plant J* 13, 621 (March, 1998).
55. M. Vedadi, R. Szittner, L. Smillie, E. Meighen, *Biochemistry* 34, 16725 (Dec. 26, 1995).
56. M. O. Park, *J Bacteriol* 187, 1426 (February, 2005).
57. M. O. Park, K. Heguri, K. Hirata, K. Miyamoto, *J Appl Microbiol* 98, 324 (2005).
58. M. O. Park, M. Tanabe, K. Hirata, K. Miyamoto, *Appl Microbiol Biotechnol* 56, 448 (August, 2001).
59. M. Morikawa, T. Twasa, S. Yanagida, T. Imanaka, *Journal of Fermentation and Bioengineering* 85, 243 (1998).
60. M. Dennis, P. E. Kolattukudy, *Proc Natl Acad Sci USA* 89, 5306 (Jun. 15, 1992).
61. T. M. Cheesbrough, P. E. Kolattukudy, *J Biol Chem* 263, 2738 (Feb. 25, 1988).
62. M. C. Chang, R. A. Eachus, W. Trieu, D. K. Ro, J. D. Keasling, *Nat Chem Biol* 3, 274 (May, 2007).
63. R. J. Porra, B. D. Ross, *Biochem J* 94, 557 (March, 1965).
64. X. Chen, W. Guo, L. Zhao, Q. Fu, Y. Ma, *J Phys Chem A* 111, 3566 (May 10, 2007).
65. L. Zhao, W. Guo, R. Zhang, S. Wu, X. Lu, *Chemphyschem* 7, 1345 (Jun. 12, 2006).
66. L. Zhao, R. Zhang, W. Guo, S. Wu, X. Lu, *Chemical Physics Letters* 414, 28 (2005).
67. G. Gorgen, W. Boland, *Eur J Biochem* 185, 237 (Nov. 6, 1989).
68. P. Ney, W. Boland, *Eur J Biochem* 162, 203 (Jan. 2, 1987).
69. Z. L. Boynton, G. N. Bennett, F. B. Rudolph, *Appl Environ Microbiol* 62, 2758 (August, 1996).
70. R. T. Yan, J. S. Chen, *Appl Environ Microbiol* 56, 2591 (September, 1990).
71. R. V. Nair, G. N. Bennett, E. T. Papoutsakis, *J Bacteriol* 176, 871 (February, 1994).
72. D. P. Wiesenbom, F. B. Rudolph, E. T. Papoutsakis, *Appl Environ Microbiol* 55, 317 (February, 1989).
73. D. K. Thompson, J. S. Chen, *Appl Environ Microbiol* 56, 607 (March, 1990).
74. M. G. Hartmanis, *J Biol Chem* 262, 617 (Jan. 15, 1987).
75. K. X. Huang, S. Huang, F. B. Rudolph, G. N. Bennett, *J Mol Microbiol Biotechnol* 2, 33 (January, 2000).
76. L. Fontaine et al., *J Bacteriol* 184, 821 (February, 2002).
77. B. McMahon, M. E. Gallagher, S. G. Mayhew, *FEMS Microbiol Lett* 250, 121 (Sep. 1, 2005).
78. M. Li, S. Yao, S. K., *Microbial Biotechnology* 23, 573 (2007).
79. T. B. Causey, S. Zhou, K. T. Shanmugam, L. O. Ingram, *Proc Natl Acad Sci USA* 100, 825 (Feb. 4, 2003).
80. D. E. Chang, S. Shin, J. S. Rhee, J. G. Pan, *J Bacteriol* 181, 6656 (November, 1999).
81. C. R. Dittrich, R. V. Vadali, G. N. Bennett, K. Y. San, *Biotechnol Prog* 21, 627 (March-April, 2005).
82. H. Lin, N. M. Castro, G. N. Bennett, K. Y. San, *Appl Microbiol Biotechnol* 71, 870 (August, 2006).
83. U. Schorken, G. A. Sprenger, *Biochim Biophys Acta* 1385, 229 (Jun. 29, 1998).
84. G. A. Sprenger, M. Pohl, *Journal of Molecular Catalysis B: Enzymatic* 6, 145 (1999).
85. G. A. Sprenger, M. Pohl, *Journal of Molecular Catalysis B: Enzymic* 6, 145 (1999).
86. B. Gonzalez, R. Vicuna, *J Bacteriol* 171, 2401 (May, 1989).
87. P. Hinrichsen, I. Gomez, R. Vicuna, *Gene* 144, 137 (Jun. 24, 1994).
88. E. Janzen et al., *Bioorg Chem* 34, 345 (December, 2006).
89. M. M. Kneen, I. D. Pogozheva, G. L. Kenyon, M. J. McLeish, *Biochim Biophys Acta* 1753, 263 (Dec. 1, 2005).
90. K. Yamada-Onodera, A. Nakajima, Y. Tani, *J Biosci Bioeng* 102, 545 (December, 2006).
91. K. Yamada-Onodera, M. Fukui, Y. Tani, *J Biosci Bioeng* 103, 174 (February, 2007).
92. T. Tobimatsu, M. Azuma, S. Hayashi, K. Nishimoto, T. Toraya, *Biosci Biotechnol Biochem* 62, 1774 (September, 1998).
93. T. Tobimatsu et al., *J Biol Chem* 271, 22352 (Sep. 13, 1996).
94. T. Toraya, T. Shirakashi, T. Kosuga, S. Fukui, *Biochem Biophys Res Commun* 69, 475 (Mar. 22, 1976).
95. M. Yamanishi et al., *Eur J Biochem* 269, 4484 (September, 2002).
96. J. R. O'Brien et al., *Biochemistry* 43, 4635 (Apr. 27, 2004).
97. C. Raynaud, P. Sarcabal, I. Meynial-Salles, C. Croux, P. Soucaille, *Proc Natl Acad Sci USA* 100, 5010 (Apr. 29, 2003).
98. B. Ludwig, A. Akundi, K. Kendall, *Appl Environ Microbiol* 61, 3729 (October, 1995).
99. S. X. Xie, J. Ogawa, S. Shimizu, *Biosci Biotechnol Biochem* 63, 1721 (October, 1999).
100. T. Zelinski, J. Peters, M. R. Kula, *J Biotechnol* 33, 283 (Apr. 15, 1994).
101. M. C. Hunt, A. Rautanen, M. A. Westin, L. T. Svensson, S. E. Alexson, *Faseb J* 20, 1855 (September, 2006).
102. M. A. Westin, S. E. Alexson, M. C. Hunt, *J Biol Chem* 279, 21841 (May 21, 2004).
103. M. A. Westin, M. C. Hunt, S. E. Alexson, *J Biol Chem* 280, 38125 (Nov. 18, 2005).
104. H. Iwaki, Y. Hasegawa, S. Wang, M. M. Kayser, P. C. Lau, *Appl Environ Microbiol* 68, 5671 (November, 2002).

The invention claimed is:

1. A method of producing 2-keto-3-deoxy D-gluconate (KDG), comprising:
    a) providing 4-deoxy-L-erythro-5-hexoseulose uronic acid (DEHU);
    b) providing recombinant DEHU hydrogenase wherein said DEHU hydrogenase comprises SEQ ID NO:92; and
    c) contacting said DEHU with said recombinant DEHU hydrogenase whereby said DEHU is converted to KDG by said recombinant DEHU hydrogenase.

2. The method of claim 1 wherein said KDG is produced in a microorganism.

3. The method of claim 2 wherein the microorganism is yeast.

4. The method of claim 2 wherein the microorganism is E. Coli.

5. The method of claim 2 wherein said KDG is converted to a commodity chemical in the microorganism.

* * * * *